(12) United States Patent
Shiro et al.

(10) Patent No.: US 9,040,516 B2
(45) Date of Patent: May 26, 2015

(54) URACIL DERIVATIVE AND USE THEREOF FOR MEDICAL PURPOSES

(75) Inventors: Tomoya Shiro, Suita (JP); Masanori Tobe, Suita (JP); Katsumi Kubota, Osaka (JP); Yosuke Takanashi, Osaka (JP); Tomoaki Nakamura, Osaka (JP); Toshihiko Sone, Osaka (JP)

(73) Assignee: SUMITOMO DAINIPPON PHARMA CO., LTD., Osaka (JP)

( * ) Notice: Subject to any disclaimer, the term of this patent is extended or adjusted under 35 U.S.C. 154(b) by 0 days.

(21) Appl. No.: 14/236,571

(22) PCT Filed: Jul. 31, 2012

(86) PCT No.: PCT/JP2012/069485
§ 371 (c)(1),
(2), (4) Date: Jan. 31, 2014

(87) PCT Pub. No.: WO2013/018804
PCT Pub. Date: Feb. 7, 2013

(65) Prior Publication Data
US 2014/0179670 A1    Jun. 26, 2014

(30) Foreign Application Priority Data

Aug. 1, 2011    (JP) .................................. 2011-168168

(51) Int. Cl.

| | | |
|---|---|---|
| A61K 31/505 | (2006.01) | |
| A61K 31/4015 | (2006.01) | |
| A61K 31/497 | (2006.01) | |
| A61K 31/535 | (2006.01) | |
| A61K 31/54 | (2006.01) | |
| C07D 401/04 | (2006.01) | |
| C07D 403/14 | (2006.01) | |
| C07D 413/14 | (2006.01) | |
| C07D 417/14 | (2006.01) | |
| C07D 403/04 | (2006.01) | |
| C07D 401/14 | (2006.01) | |
| C07D 405/14 | (2006.01) | |
| C07D 409/14 | (2006.01) | |

(52) U.S. Cl.
CPC ............ *C07D 403/04* (2013.01); *C07D 401/14* (2013.01); *C07D 405/14* (2013.01); *C07D 413/14* (2013.01); *C07D 401/04* (2013.01); *C07D 403/14* (2013.01); *C07D 409/14* (2013.01); *C07D 417/14* (2013.01)

(58) Field of Classification Search
CPC ............................ C07D 239/02; A61K 31/505
USPC ........................................ 514/269; 544/316
See application file for complete search history.

(56) References Cited

U.S. PATENT DOCUMENTS

| 6,107,297 A | 8/2000 | Kindon et al. |
|---|---|---|
| 7,713,998 B2 | 5/2010 | Nakai et al. |
| 2006/0035938 A1 | 2/2006 | Bladh et al. |

(Continued)

FOREIGN PATENT DOCUMENTS

| JP | 2001-509506 A | 7/2001 |
|---|---|---|
| JP | 2006-513261 A | 4/2006 |
| WO | WO 2004/043924 A1 | 5/2004 |

(Continued)

OTHER PUBLICATIONS

Bioorganic & Medicinal Chemistry vol. 11, Issue 23, Nov. 17, 2003, pp. 4933-4940 Structure and activity relationships of novel uracil derivatives as topical anti-inflammatory agents. Yoshiaki et al.*
A. Dirksen et al.; Exploring the role of CT densitometry: a randomised study of augmentation therapy . . . ; Eur. Respir. J. 2009; 33; pp. 1345-1353.
International Preliminary Report on Patentability issued in PCT/JP2012/069485, (2012).

(Continued)

*Primary Examiner* — James O Wilson
*Assistant Examiner* — Ebenezer O Sackey
(74) *Attorney, Agent, or Firm* — Birch, Stewart, Kolasch & Birch, LLP

(57) ABSTRACT

The present invention provides: an uracil derivative represented by general formula (I) or a physiologically acceptable salt thereof (in the formula, $R^1$ represents a hydrogen atom, a $C_{1-10}$ alkyl group, a $C_{2-6}$ alkene group or a 3- to 6-membered saturated or 4- to 6-membered unsaturated aliphatic ring group which may contain 1 to 2 hetero atoms independently selected from the group consisting of N, O and S; $R^2$ represents a hydrogen atom, a halogen atom, a cyano group, —NR-$^cR^d$, —N=CHN(CH$_3$)$_2$, or an $C_{1-3}$ alkyl group; $Ar^1$ and $Ar^2$ independently represent a 5- to 6-membered aromatic ring group which may contain 1 to 3 hetero atoms independently selected from the group consisting of N, O and S; and L represents a 6-membered aromatic ring group which may contain 1 to 4 nitrogen atoms, a pyrazole group, a triazole group, or an imidazole group); and a therapeutic agent or prophylactic agent for various inflammatory diseases associated with elastase, comprises the compound or the like as an active ingredient.

(I)

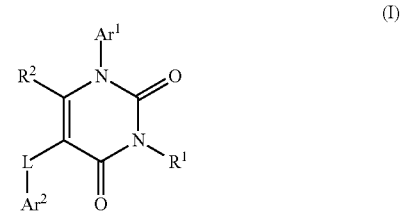

20 Claims, No Drawings

(56) References Cited

U.S. PATENT DOCUMENTS

2007/0043036 A1    2/2007    Hansen et al.
2010/0063104 A1    3/2010    Nakai et al.

FOREIGN PATENT DOCUMENTS

| | | |
|---|---|---|
| WO | WO 2005/026124 A1 | 3/2005 |
| WO | WO 2006/051826 A1 | 5/2006 |
| WO | WO 2007/040208 A1 | 4/2007 |

OTHER PUBLICATIONS

European Search Report dated Feb. 27, 2015 for Application No. 12820213.2.

Hiroyuki Ohbayashi, "Current synthetic inhibitors of human neutrophil elastase in 2005", Expert Opinion on Therapeutic Patents, Informa Healthcare, GB, vol. 15, No. 7, Jan. 1, 2005, pp. 759-771.

* cited by examiner

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: substrate of elastase, MeO-Suc-peptide-AMC

<400> SEQUENCE: 1

Ala Ala Pro Val
1

URACIL DERIVATIVE AND USE THEREOF FOR MEDICAL PURPOSES

TECHNICAL FIELD

The present invention provides a novel uracil derivative useful as medicament showing an elastase inhibitory activity. More specifically, the present invention provides a novel uracil derivative useful as a prophylactic agent and/or a therapeutic agent for various diseases associated with elastase such as inflammatory disease.

BACKGROUND ART

Human neutrophil elastase (hereinafter, sometimes referred to as solely "elastase") is one kind of serine protease having a molecular weight of about 30 KDa and is stored in azurophilic granules of neutrophil. In physiological states, elastase takes, inside of neutrophils, a role for rapid digestion or degradation of phagocytized bacteria or exogenous materials, and takes, outside of neutrophils, roles for degradation of elastin, collagen (type III, type IV), proteoglycan, fibronectin which constitute interstitium of biological connective tissues such as lung, cartilage, blood vessel wall and skin, and for maintenance of tissue homeostasis.

In vivo, endogenous elastase-inhibiting proteins are existed. Among them, best known one is α1-antitrypsin (α1-AT), and patients with genetic defect of α1-AT are known to present chronic obstructive pulmonary disease (COPD) like-symptoms (see Non-Patent Literature-1). Like this case, when an imbalance occurs between endogenous elastase-inhibiting proteins and elastase, or when excess elastase is released due to pathological states such as inflammatory disease, it has been thought that elastase destroys normal tissues actively to cause various pathological conditions.

The diseases in which elastase is suggested to associate with pathological conditions include, for example, chronic obstructive pulmonary disease (COPD), pulmonary cystic fibrosis, emphysema, adult respiratory distress syndrome (ARDS), acute lung injury (ALI), idiopathic interstitial pneumonia (IIP), chronic interstitial pneumonia, chronic bronchitis, chronic airway infection, diffuse panbronchiolitis, bronchiectasis, asthma, pancreatitis, nephritis, hepatic failure, chronic rheumatoid arthritis, arthrosclerosis, osteoarthritis, psoriasis, periodontitis, atherosclerosis, rejection of organ transplantation, premature rupture of membrane, bullosa, shock, sepsis, systemic lupus erythematodes (SLE), Crohn disease, disseminated intravascular coagulation (DIC), ischemia-reperfusion induced-tissue injury, corneal scar tissue formation, myelitis, lung squamous cell carcinoma, pulmonary adenocarcinoma, lung cancers such as non-small cell lung cancer, breast cancer, liver cancer, bladder cancer, colorectal cancer, skin cancer, pancreas cancer, glioma and the others. Thus, an agent showing inhibitory activity for elastase is useful for treatment or prophylaxis of diseases associated with elastase.

With such an expectation, various elastase inhibitors have been reported. For example, Patent Literature-1 discloses 2-pyridone derivatives as neutrophil elastase inhibitor. In claim 1 of the Claims of the Literature, the compounds represented by the following general formula (A-1) (corresponding to formula I of said publication document) are described.

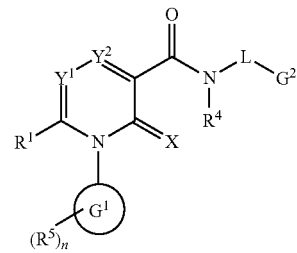

(A-1)

In the formula, variables are defined as follows:
[wherein,
X represents O . . . ;
$Y^1$ represents N . . . ; and when $R^1$ represents OH, $Y^1$ may also, in the tautomeric form, represent $NR^6$;
$Y^2$ represents $CR^3$;
$R^1$ represents . . . , when $Y^1$ represents N, $R^1$ may also represent OH;
. . . ]

If the above-mentioned definitions of X, $Y^1$, $Y^2$ and $R^1$ are assigned to said formula (A-1), the formula (A-1) can be replaced by the following formula (A-2). Here, though there may be the compounds containing uracil backbone, they are clearly different in structure from the present compounds below-mentioned.

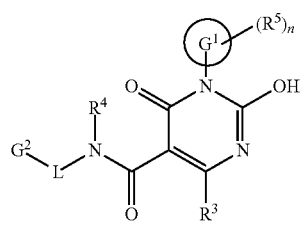

(A-2)

Also, as compound showing p38 MAP kinase inhibitory activity, in each claim 1 of the Claims of Patent Literature-2 and Patent Literature-3 the compounds represented by the following general formula (A-3) (corresponding to formula I of said publication documents) are described.

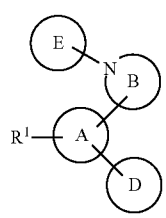

(A-3)

[wherein,
ring A represents a 5-membered mono-ring hetero ring which contains 1 to 3 atom(s) selected from the group consisting of oxygen atom, nitrogen atom and sulfur atom as a hetero atom, and which may have a further substituent(s);
ring B represents an optionally substituted hetero ring containing at least one nitrogen atom;

ring D represents an optionally substituted cyclic group;

ring E represents an optionally substituted cyclic group; and

R$^1$ represents a substituent which contains nitrogen atom(s) having basicity] (see Patent Literature-2); and

[wherein ring A represents a 5-membered mono-ring hetero ring which contains 1 to 3 atom(s) selected from the group consisting of an oxygen atom, a nitrogen atom and a sulfur atom, and which may have a further substituent(s);

ring B represents a hetero ring which may be substituted and may contain 1 to 3 atom(s) selected from the group consisting of an oxygen atom, a nitrogen atom and a sulfur atom in addition to the described nitrogen atom;

ring D represents a ring group which may be substituted;

ring E represents an optionally substituted cyclic group;

R$^1$ represents a neutral group or an acidic group which contains an oxygen atom(s) and/or a sulfur atom(s)] (see Patent Literature-3).

However, in the compounds described specifically in Patent Literatures-2 and 3, a position of a substituent R$^1$ that is substituted on five membered ring A is a 4$^{th}$-position counting sequentially from the position binding to ring B, then ring D, while in the present compounds, ring A (corresponding to L of formula (I) described herein) is unsubstituted and a position of a substituent on ring A (corresponding to L of formula (I) described herein) is a 5$^{th}$-position, which are different each other in structure.

RELATED ART DOCUMENTS

Patent Documents

[Patent Literature-1]: WO 2004/043924 pamphlet
[Patent Literature-2]: WO 2006/051826 pamphlet
[Patent Literature-3]: WO 2007/040208 pamphlet Non-Patent Documents

[Non-patent Literature-1]: Eur. Respir. J. 2009, 33, 1345-1353

DISCLOSURE OF INVENTION

Problems to be Solved by Invention

An object of the present invention is to provide a therapeutic agent for various inflammatory diseases associated with elastase.

Means to Solve Problems

The present inventors have intensively studied and as a result, they have found out that the novel compounds represented by the following formula (I) show an elastase inhibitory activity, and have therefore completed the present invention. According to the present invention, uracil derivatives represented by the following formula (I) (hereinafter, sometimes referred to as "Present compound") is provided.

A compound represented by formula (I) or physiologically acceptable salts thereof:

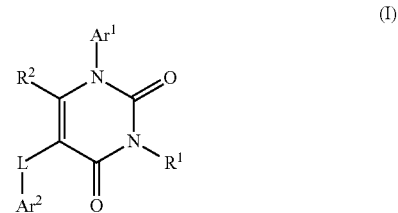

(I)

[wherein

R$^1$ represents a hydrogen atom, a C$_{1-10}$ alkyl group, a C$_{2-6}$ alkene group or a three to six-membered saturated- or four to six-membered unsaturated-aliphatic ring group optionally containing one to two heteroatoms independently selected from the group consisting of N, O and S, said alkyl group and said alkene group for R$^1$ may be optionally substituted at substitutable positions with one or multiple substituents selected from the group consisting of Substituent List 1:

(1) hydroxy group,
(2) halogen atom,
(3) cyano group,
(4) C$_{1-6}$ alkoxy group (said alkoxy group may be optionally substituted at substitutable positions with
    hydroxy group,
    halogen atom,
    cyano group,
    —C(=O)OR$^b$,
    —C(=O)NR$^c$R$^d$,
    five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$C(=O)NR$^c$R$^d$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
    three to six-membered saturated- or four to six-membered unsaturated-aliphatic ring group each optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$C(=O)NR$^c$R$^d$ group, —NR$^a$S(=O)$_m$R$^b$ group, —C(=O)OR$^b$ group, —C(=O)NR$^c$R$^d$ group, —NR$^c$R$^d$ group or oxo group), (5) C$_{1-6}$ alkylthio group (said alkylthio group may be optionally substituted at substitutable positions with
    hydroxy group,
    halogen atom,
    cyano group,
    —C(=O)OR$^b$,
    —C(=O)NR$^c$R$^d$,
    five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$C(=O)NR$^c$R$^d$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or three to six-membered saturated- or four to six-membered unsaturated-aliphatic ring group each optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O) R$^b$ group, —NR$^a$C(=O)NR$^c$R$^d$ group, —NR$^a$S(=O)$_m$R$^b$ group, —C(=O)OR$^b$ group, —C(=O)NR$^c$R$^d$ group, —NR$^c$R$^d$ group or oxo group), (6) five to six-membered aromatic ring group optionally containing one to four heteroatoms independently selected from the group consisting of N, O and S (said aromatic ring group may be substituted at substitutable positions with $C_{1-3}$ alkyl group optionally substituted with hydroxy or halogen,
$C_{1-3}$ alkoxy group optionally substituted with hydroxy or halogen,
hydroxy group,
halogen atom,
cyano group,
—NR$^a$C(=O)R$^b$,
—NR$^a$C(=O)NR$^c$R$^d$,
—NR$^a$S(=O)$_m$R$^b$,
—C(=O)OR$^b$,
—C(=O)NR$^c$R$^d$,
—S(=O)$_m$NR$^c$R$^d$,
—S(=O)$_m$R$^b$ or
—NR$^c$R$^d$), (7) three to six-membered saturated- or four to six-membered unsaturated-aliphatic ring group each optionally containing one to two heteroatoms independently selected from the group consisting of N, O and S (said aliphatic ring group may be optionally substituted at substitutable positions with $C_{1-3}$ alkyl group (said alkyl group may be optionally substituted with hydroxy, halogen, cyano, —NR$^a$C(=O) R$^b$, —NR$^a$C(=O)NR$^c$R$^d$, —NR$^a$S(=O)$_m$R$^b$, —C(=O)OR$^b$, —C(=O)NR$^c$R$^d$ or —NR$^c$R$^d$),
$C_{1-3}$ alkoxy group optionally substituted with hydroxy or halogen,
hydroxy group,
halogen atom,
cyano group,
—NR$^a$C(=O)R$^b$,
—NR$^a$C(=O)NR$^c$R$^d$
—NR$^a$S(=O)$_m$R$^b$,
—C(=O)OR$^b$,
—C(=O)NR$^c$R$^d$,
—C(=O)R$^b$,
—S(=O)$_m$NR$^c$R$^d$,
—S(=O)$_m$R$^b$,
—NR$^c$R$^d$ or
oxo group), (8) —NR$^a$R$^e$ group,
(9) —OC(=O)NR$^c$R$^d$ group,
(10) —C(=O)R$^f$ group,
(11) —S(=O)$_m$R$^g$ group,
(12) thiol group,
(13) nitro group and
(14) —OR$^e$ group, said three to six-membered saturated- or four to six-membered unsaturated-aliphatic ring group for R$^1$ may be optionally substituted at substitutable positions with one or multiple substituents selected from the group consisting of Substituent List 2:

(1) hydroxy group,
(2) halogen atom,
(3) cyano group,
(4) $C_{1-6}$ alkyl group (said alkyl group may be optionally substituted at substitutable positions with
hydroxy group,
halogen atom,
cyano group,
five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or three- to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O) OR$^b$ group, —C(=O)NR$^c$R$^d$ group, —NR$^c$R$^d$ group or oxo group), (5) $C_{1-6}$ alkoxy group (said alkoxy group may be optionally substituted at substitutable positions with
hydroxy group,
halogen atom,
cyano group,
five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or a —NR$^c$R$^d$ group) or three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O) OR$^b$ group, —C(=O)NR$^c$R$^d$ group, —NR$^c$R$^d$ group or oxo group), (6) $C_{1-6}$ alkylthio group (said alkylthio group may be optionally substituted at substitutable positions with
  hydroxy group,
  halogen atom,
  cyano group,
  five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
  three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group), (7) five to six-membered aromatic ring group optionally containing one to four heteroatoms independently selected from the group consisting of N, O and S (said aromatic ring group may be optionally substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —NR$^a$C(=O)R$^b$,
  —NR$^a$S(=O)$_m$R$^b$,
  —C(=O)OR$^b$,
  —C(=O)NR$^c$R$^d$,
  —S(=O)$_m$NR$^c$R$^d$,
  —S(=O)$_m$R$^b$ or
  —NR$^c$R$^d$), (8) three to six-membered saturated aliphatic ring group optionally containing one to two heteroatoms independently selected from the group consisting of N, O and S (said aliphatic ring group may be optionally substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —NR$^a$C(=O)R$^b$,
  —NR$^a$S(=O)$_m$R$^b$,
  —C(=O)OR$^b$,
  —C(=O)NR$^c$R$^d$,
  —NR$^c$R$^d$ or
  oxo group), (9) —NR$^a$R$^e$ group,
(10) —OC(=O)NR$^c$R$^d$ group,
(11) —C(=O)R$^f$ group,
(12) —S(=O)$_m$R$^g$ group,
(13) thiol group,
(14) oxo group,
(15) nitro group,
(16) —NR$^a$C(=O)R$^b$ group,
(17) —NR$^a$C(=O)NR$^c$R$^d$ group,
(18) —NR$^a$S(=O)$_m$R$^b$ group,
(19) —C(=O)OR$^b$ group and
(20) —C(=O)NR$^c$R$^d$ group, R$^2$ represents a hydrogen atom, a halogen atom, a cyano group, a —NR$^c$R$^d$ group, a —N=CHN(CH$_3$)$_2$ group or a $C_{1-3}$ alkyl group (said alkyl group may be optionally substituted with hydroxy, halogen, —NR$^c$R$^d$, —OR$^a$ or —OC(=O)R$^a$), Ar$^1$ represents a five to six-membered aromatic ring group optionally containing one to three heteroatoms independently selected from the group consisting of N, O and S (said aromatic ring group is substituted at substitutable positions with $C_{1-6}$ alkyl group optionally substituted with hydroxy or halogen, $C_{1-3}$ alkoxy group optionally substituted with hydroxy or halogen, hydroxy group, halogen atom, cyano group, nitro group, phenyl group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O) R$^a$ group, —S(=O)$_m$NR$^c$R$^d$ group, —S(=O)$_n$R$^h$ group or —NR$^c$R$^d$ group), L represents a six membered aromatic ring group optionally containing one to four nitrogen atoms, a Pyr-1 group of the following formula, a Tri-1 group of the following formula or an Imi-1 group of the following formula:

(in each formula,
the bond 1 represents a binding to uracil ring, the bond 2 represents a binding to Ar$^2$, and the Z$^1$, Z$^2$ and Z$^3$ represents independently of each other a halogen atom, a —C(=O)NR$^c$R$^d$ group, a —C(=O)OR$^a$ group, a nitro group, a hydroxy group, a —NR$^c$R$^d$ group, a —NR$^a$C(=O)R$^b$ group, a hydrogen atom, a $C_{1-6}$ alkyl group or a $C_{2-6}$ alkene group, and said alkyl group and said alkene group may independently of each other be optionally substituted with halogen, hydroxy, —NR$^c$R$^d$, —C(=O)NR$^c$R$^d$ or —C(=O)OR$^a$), wherein, when L represents a six membered aromatic ring group, the L may be optionally substituted at substitutable positions with halogen, —C(=O)NR$^c$R$^d$, —C(=O)OR$^a$, hydroxy, —NR$^c$R$^d$, nitro, —NR$^a$C(=O)R$^b$, C$_{1-6}$ alkyl or C$_{2-6}$ alkene, and said alkyl and said alkene may independently of each other be optionally substituted with halogen, hydroxy, —NR$^c$R$^d$, —C(=O)NR$^c$R$^d$ or —C(=O)OR$^a$, Ar$^2$ represents a five to six-membered aromatic ring group optionally containing one to three heteroatoms independently selected from the group consisting of N, O and S (said aromatic ring group is substituted at one or more substitutable positions with C$_{1-6}$ alkyl group optionally substituted with hydroxy, cyano or halogen, C$_{1-3}$ alkoxy group optionally substituted with hydroxy or halogen, hydroxy group, halogen atom, cyano group, nitro group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O) R$^a$ group, —S(=O)$_m$NR$^c$R$^d$ group, —S(=O)$_n$R$^h$ group or —NR$^c$R$^d$ group), R$^a$ represents a hydrogen atom or a C$_{1-6}$ alkyl group optionally substituted with hydroxy or halogen, R$^b$ represents a hydrogen atom, a C$_{1-6}$ alkyl group optionally substituted with hydroxy or halogen, a benzyl group optionally substituted with methoxy or nitro, or a C$_{3-6}$ cycloalkyl group optionally substituted with hydroxy or halogen, R$^c$ and R$^d$ represents independently of each other a hydrogen atom, or a C$_{1-3}$ alkyl group optionally substituted with hydroxy or halogen, or alternatively combine each other together with N to which they are attached and optionally together with further one to two heteroatoms independently selected from the group consisting of N, O and S to represent a four to six-membered saturated or unsaturated aliphatic ring group (said aliphatic ring group may be optionally substituted at substitutable positions with C$_{1-6}$ alkyl, hydroxy, halogen or oxo), R$^e$ represents a hydrogen atom, a C$_{1-6}$ alkyl group (said alkyl group may be optionally substituted with hydroxy, cyano, halogen, C$_{1-3}$ alkoxy or —NR$^c$R$^d$), an -A group, a —C(=O)-A group, a C$_{1-6}$ alkylcarbonyl group (the alkyl moiety of said alkylcarbonyl group may be optionally substituted with hydroxy, halogen, cyano, C$_{1-3}$ alkoxy or —NR$^c$R$^d$), a C$_{1-6}$ alkoxycarbonyl group (the alkyl moiety of said alkoxycarbonyl group may be optionally substituted with hydroxy or halogen), a —C(=O)NR$^c$R$^d$ group or a —S(=O)$_m$R$^b$ group, R$^f$ represents a hydrogen atom, a hydroxy group, a C$_{1-6}$ alkyl group (said alkyl group may be optionally substituted with hydroxy, cyano, halogen, C$_{1-3}$ alkoxy or —NR$^c$R$^d$), a C$_{1-3}$ alkoxy group (said alkoxy group may be optionally substituted with phenyl optionally substituted with methoxy or nitro, hydroxy group, cyano group, halogen atom, C$_{1-3}$ alkoxy group or —NR$^c$R$^d$ group), an -A group or a —NR$^a$R$^i$ group, R$^g$ represents a hydroxy group, a C$_{1-6}$ alkyl group (said alkyl group may be optionally substituted with hydroxy, cyano, halogen, C$_{1-3}$ alkoxy or —NR$^c$R$^d$), an -A group or a —NR$^a$R$^i$ group, R$^h$ represents a C$_{1-6}$ alkyl group optionally substituted with hydroxy or halogen, R$^i$ represents a hydrogen atom, a C$_{1-6}$ alkyl group (said alkyl group may be optionally substituted with hydroxy, cyano, halogen, C$_{1-3}$ alkoxy, C$_{3-6}$ cycloalkyl or —NR$^c$R$^d$), an -A group, a —C(=O)R$^b$ group, a —C(=O)A group or a C$_{1-6}$ alkyl carbonyl group (the alkyl moiety of said alkylcarbonyl group may be optionally substituted with hydroxy, halogen, cyano, C$_{1-3}$ alkoxy or —NR$^c$R$^d$), A represents a five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —C(=O)OH group or —NR$^c$R$^d$ group) or a three to six-membered saturated- or four to six-membered unsaturated-aliphatic ring group each optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —C(=O)OH group, —NR$^c$R$^d$ group or oxo group), m represents an integer of one (1) or two (2) and n represents an integer of zero (0) to two (2)].

The compound according to [1] or physiologically acceptable salts thereof wherein R$^1$ represents a hydrogen atom, a C$_{1-10}$ alkyl group, a C$_{2-6}$ alkene group or a three to six-membered saturated- or four to six-membered unsaturated-aliphatic ring group each optionally containing one to two heteroatoms independently selected from the group consisting of N, O and S, said alkyl group and said alkene group for R$^1$ may be optionally substituted at substitutable positions with one or multiple substituents selected from the group consisting of Substituent List 3:

(1) hydroxy group,
(2) halogen atom,
(3) cyano group,
(4) C$_{1-6}$ alkoxy group (said alkoxy group may be optionally substituted at substitutable positions with
    hydroxy group,
    halogen atom,
    cyano group,
    five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or three to six-membered saturated aliphatic ring group optionally containing one to two heteroatoms independently selected from the group consisting of N, O and S (said aliphatic ring group may be optionally at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group), (5) C$_{1-6}$ alkylthio group (said alkylthio group may be optionally substituted at substitutable positions with hydroxy group, halogen atom, cyano group, five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or three to six-membered saturated aliphatic ring group optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group), (6) five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$, —NR$^a$S(=O)$_m$R$^b$, —C(=O)OR$^b$, —C(=O)NR$^c$R$^d$, —S(=O)$_m$NR$^c$R$^d$, —S(=O)$_m$R$^b$ or —NR$^c$R$^d$), (7) three to six-membered saturated aliphatic ring group optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkyl group optionally substituted with hydroxy or halogen, hydroxy group, halogen atom, cyano group, —NR$^a$C(=O)R$^b$, —NR$^a$S(=O)$_m$R$^b$, —C(=O)OR$^b$, —C(=O)R$^b$, —C(=O)NR$^c$R$^d$, —NR$^c$R$^d$ or oxo group), (8) —NR$^a$R$^e$ group, (9) —OC(=O)NR$^c$R$^d$ group,

(10) —C(=O)R$^f$ group,

(11) —S(=O)$_m$R$^g$ group and

(12) thiol group, said three to six-membered saturated- or four to six-membered unsaturated-aliphatic ring group for R$^1$ may be optionally substituted at substitutable positions with one or multiple substituents selected from the group consisting of Substituent List 4:

(1) hydroxy group, (2) halogen atom, (3) cyano group, (4) C$_{1-6}$ alkyl group (said alkyl group may be optionally substituted at substitutable positions with hydroxy group, halogen atom, cyano group, five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(O)$_m$R$^b$ group or —NR$^c$R$^d$ group) or three to six-membered saturated aliphatic ring group optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group), (5) C$_{1-6}$ alkoxy group (said alkoxy group may be optionally substituted at substitutable positions with hydroxy group, halogen atom, cyano group, five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group), (6) $C_{1-6}$ alkylthio group (said alkylthio group may be optionally substituted at substitutable positions with
  hydroxy group,
  halogen atom,
  cyano group,
  five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
  three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group), (7) five to six-membered aromatic ring group optionally containing one to four heteroatoms independently selected from the group consisting of N, O and S (said aromatic ring group may be optionally substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —NR$^a$C(=O)R$^b$,
  —NR$^a$S(=O)$_m$R$^b$,
  —C(=O)OR$^b$,
  —C(=O)NR$^c$R$^d$,
  —S(=O)$_m$NR$^c$R$^d$,
  —S(=O)$_m$R$^b$ or
  —NR$^c$R$^d$), (8) three to six-membered saturated aliphatic ring group optionally containing one to two heteroatoms independently selected from the group consisting of N, O and S (said aliphatic ring group may be optionally substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —NR$^a$C(=O)R$^b$,
  —NR$^a$S(=O)$_m$R$^b$,
  —C(=O)OR$^b$,
  —C(=O)NR$^c$R$^d$,
  —NR$^c$R$^d$ or
  oxo group),
(9) —NR$^a$R$^e$ group,
(10) —OC(=O)NR$^c$R$^d$ group,
(11) —C(=O)R$^f$ group,
(12) —S(=O)$_m$R$^g$ group,
(13) thiol group and
(14) oxo group, R$^2$ represents a hydrogen atom, a halogen atom, a cyano group, a —NR$^c$R$^d$ group, a —N=CHN(CH$_3$)$_2$ group or a $C_{1-3}$ alkyl group (said alkyl group may be optionally substituted with hydroxy, halogen, —NR$^c$R$^d$, —OR$^a$ or —OC(=O)R$^a$), Ar$^1$ represents a benzene ring or a pyridine ring (said benzene ring and said pyridine ring are independently of each other substituted at one or multiple substitutable positions with $C_{1-6}$ alkyl group optionally substituted with hydroxy or halogen, $C_{1-3}$ alkoxy group optionally substituted with hydroxy or halogen, hydroxy group, halogen atom, cyano group, nitro group, phenyl group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O)R$^a$ group, —S(=O)$_m$NR$^c$R$^d$ group, —S(=O)$_n$R$^h$ group or —NR$^c$R$^d$ group), L represents a six-membered aromatic ring group optionally containing one to four nitrogen atoms, a Pyr-1 group of the following formula, a Tri-1 group of the following formula or an Imi-1 group of the following formula:

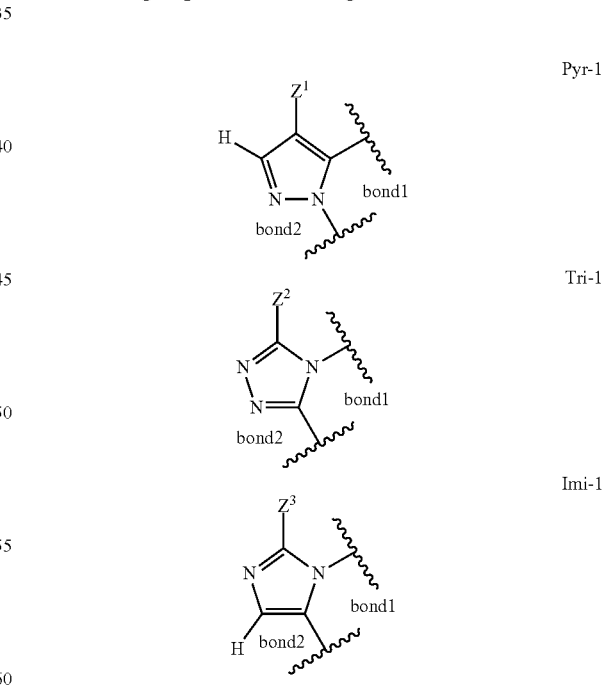

(in each formula, the bond 1 represents a binding to uracil ring, the bond 2 represents a binding to Ar$^2$, and the Z$^1$, Z$^2$ and Z$^3$ represent independently of each other a halogen atom, a —C(=O)NR$^c$R$^d$ group, a —C(=O)OR$^a$ group, a nitro group, a hydroxy group, a —NR$^c$R$^d$ group, a —NR$^a$C(=O)R$^b$ group, a hydrogen atom, a $C_{1-6}$ alkyl group or a $C_{2-6}$ alkene group, and said alkyl group and said alkene group may independently of each other be optionally substituted with halogen, hydroxy, —NR$^c$R$^d$, —C(=O)NR$^c$R$^d$ or —C(=O)OR$^a$), wherein, when L represents a six-membered aromatic ring group, the L may be optionally substituted at substitutable positions with halogen, —C(=O)NR$^c$R$^d$, —C(=O)OR$^a$, hydroxy, —NR$^c$R$^d$, nitro, —NR$^a$C(=O)R$^b$, C$_{1-6}$ alkyl group or C$_{2-6}$ alkene group, and said alkyl group and said alkene group may independently of each other be optionally substituted at substitutable positions with halogen, hydroxy, —NR$^c$R$^d$, —C(=O)NR$^c$R$^d$ or —C(=O)OR$^a$;

Ar$^2$ represents a benzene ring or a pyridine ring (said benzene ring and said pyridine ring are independently of each other substituted at one or multiple substitutable positions with C$_{1-6}$ alkyl group optionally substituted with hydroxy or halogen, C$_{1-3}$ alkoxy group optionally substituted with hydroxy or halogen, hydroxy group, halogen atom, cyano group, nitro group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O)R$^a$ group, —S(=O)$_m$NR$^c$R$^d$ group, —S(=O)$_n$R$^h$ group or —NR$^c$R$^d$ group), R$^a$ represents a hydrogen atom or a C$_{1-6}$ alkyl group optionally substituted with hydroxy or halogen, R$^b$ represents a hydrogen atom, a C$_{1-6}$ alkyl group optionally substituted with hydroxy or halogen or a benzyl group optionally substituted with methoxy or nitro, R$^c$ and R$^d$ represent independently of each other a hydrogen atom or a C$_{1-3}$ alkyl group optionally substituted with hydroxy or halogen, or alternatively combine each other together with N to which they are attached and optionally together with further one to two heteroatoms independently selected from the group consisting of N, O and S to represent a four to six-membered saturated aliphatic ring group (said aliphatic ring group may be optionally substituted at substitutable positions with C$_{1-6}$ alkyl, hydroxy or halogen), R$^e$ represents
a hydrogen atom,
a C$_{1-6}$ alkyl group (said alkyl group may be optionally substituted with hydroxy, cyano, halogen, C$_{1-3}$ alkoxy or —NR$^c$R$^d$),
an -A group,
a —C(=O)-A group,
a C$_{1-6}$ alkylcarbonyl group (the alkyl moiety of said alkylcarbonyl group may be optionally substituted with hydroxy, halogen, cyano, C$_{1-3}$ alkoxy or —NR$^c$R$^d$),
a C$_{1-6}$ alkoxycarbonyl group (the alkyl moiety of said alkoxycarbonyl group may be optionally substituted with hydroxy or halogen),
a —C(=O)NR$^c$R$^d$ group or
a —S(=O)$_m$R$^b$ group,
R$^f$ represents
a hydrogen atom,
a hydroxy group,
a C$_{1-6}$ alkyl group (said alkyl group may be optionally substituted with hydroxy, cyano, halogen, C$_{1-3}$ alkoxy or —NR$^c$R$^d$),
a C$_{1-3}$ alkoxy group (said alkoxy group may be optionally substituted with phenyl group optionally substituted with methoxy or nitro, hydroxy group, cyano group, halogen atom, C$_{1-3}$ alkoxy group or —NR$^c$R$^d$ group),
an -A group or
a —NR$^a$R$^i$ group, R$^g$ represents
a hydroxy group,
a C$_{1-6}$ alkyl group (said alkyl group may be optionally substituted with hydroxy, cyano, halogen, C$_{1-3}$ alkoxy or —NR$^c$R$^d$),
an -A group or
a —NR$^a$R$^i$ group,
R$^h$ represents a C$_{1-6}$ alkyl group optionally substituted with hydroxy or halogen,
R$^i$ represents
a hydrogen atom,
a C$_{1-6}$ alkyl group (said alkyl group may be optionally substituted with hydroxy, cyano, halogen, C$_{1-3}$ alkoxy or —NR$^c$R$^d$),
an -A group,
a —C(=O)A group,
a C$_{1-6}$ alkylcarbonyl group (the alkyl moiety of said alkylcarbonyl group may be optionally substituted with hydroxy, halogen, cyano, C$_{1-3}$ alkoxy or —NR$^c$R$^d$),
A represents
a five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —C(=O)OH group or —NR$^c$R$^d$ group) or
a three to six-membered saturated aliphatic ring group optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —C(=O)OH group, —NR$^c$R$^d$ group or oxo group),
m represents an integer of 1 or 2 and
n represents an integer of zero (0) to two (2).

[3]
The compound according to [1] or [2] or physiologically acceptable salts thereof wherein R$^1$ represents a C$_{1-10}$ alkyl group (said alkyl group may be optionally substituted with one or multiple substituents described in Substituent List 3), a C$_{2-6}$ alkene group (said alkene group may be optionally substituted with one or multiple substituents described in Substituent List 3) or a three to six-membered saturated- or four to six-membered unsaturated-aliphatic ring group each optionally containing one to two heteroatoms independently selected from the group consisting of N, O and S (said aliphatic ring group may be optionally substituted with one or multiple substituents described in Substituent List 4).

[4]
The compound according to any one of [1] to [3] or a physiologically acceptable salts thereof wherein R$^2$ represents a hydrogen atom, a —NR$^c$R$^d$ group, a —N=CHN(CH$_3$)$_2$ group or a C$_{1-3}$ alkyl group (said alkyl group may be optionally substituted with hydroxy, halogen, —NR$^c$R$^d$, —OR$^a$ or —OC(=O)R$^a$).

[5]
The compound according to any one of [1] to [4] or physiologically acceptable salts thereof, wherein Ar$^1$ represents a benzene ring or a pyridine ring (said benzene ring and said pyridine ring are independently of each other substituted at one to three substitutable positions with C$_{1-6}$ alkyl group optionally substituted with hydroxy or halogen, C$_{1-3}$ alkoxy group optionally substituted with hydroxy or halogen, hydroxy group, halogen atom, cyano group, nitro group, phenyl group, —C(=O)NR$^c$R$^d$ group, —C(=O)OR$^a$ group, —C(=O)R$^a$ group, —S(=O)$_n$R$^h$ group or —NR$^c$R$^d$ group.

[6]

The compound according to any one of [1] to [5] or a physiologically acceptable salts thereof, wherein Ar$^1$ represents an Ar$^1$-1 group of the following formula:

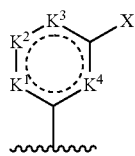

Ar$^1$-1

(in the formula,

K$^1$, K$^2$, K$^3$ and K$^4$ represent all carbon atoms for benzene ring, or only one nitrogen atom and the remaining carbon atoms for pyridine ring, and X represents a C$_{1-6}$ alkyl group optionally substituted with hydroxy or halogen, a C$_{1-3}$ alkoxy group optionally substituted with hydroxy or halogen, a hydroxy group, a halogen atom, a cyano group, a nitro group, a phenyl group, a —C(=O)NR$^c$R$^d$ group, a —C(=O)OR$^a$ group, a —C(=O)R$^a$ group, a —S(=O)$_n$R$^h$ group or a —NR$^c$R$^d$ group;

said benzene ring and said pyridine ring may be optionally substituted at one to two substitutable positions of K$^1$ to K$^4$ with C$_{1-6}$ alkyl group optionally substituted with hydroxy or halogen, C$_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group.

[7]

The compound according to any one of [1] to [6] or physiologically acceptable salts thereof wherein Ar$^2$ represents a benzene ring or a pyridine ring (said benzene ring and said pyridine ring are independently of each other substituted at one to three substitutable positions with C$_{1-6}$ alkyl group optionally substituted with hydroxy or halogen, C$_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group.

[8]

The compound according to any one of [1] to [7] or physiologically acceptable salts thereof wherein Ar$^2$ represents an Ar$^2$-1 group of the following formula:

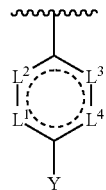

Ar$^2$-1

(in the formula,

L$^1$, L$^2$, L$^3$ and L$^4$ represents all carbon atoms for benzene ring, or only one nitrogen atom and the remaining carbon atoms for pyridine ring, and Y represents a C$_{1-6}$ alkyl group optionally substituted with hydroxy or halogen, a C$_{1-3}$ alkoxy group optionally substituted with hydroxy or halogen, a hydroxy group, a halogen atom, a cyano group, a nitro group, a —C(=O)NR$^c$R$^d$ group, a —C(=O)OR$^a$ group, a —C(=O)R$^a$ group, a —S(=O)$_n$R$^h$ group or a —NR$^c$R$^d$ group, said benzene ring and said pyridine ring may be optionally substituted at one to two substitutable positions of L$^1$ to L$^4$ with C$_{1-6}$ alkyl group optionally substituted with hydroxy or halogen, or C$_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group).

[9]

The compound according to any one of [1] to [8] or physiologically acceptable salts thereof wherein the formula (I) represents the following formula (I'):

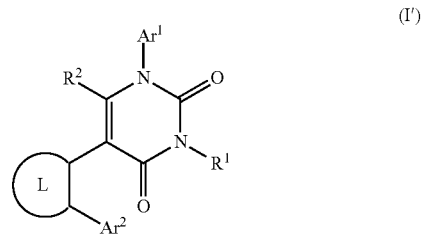

(I')

(in the formula,

L represents a benzene ring or a pyridine ring, and the position on which said benzene ring and said pyridine ring are attached to the uracil ring is an or to position to the position on which said benzene ring and the pyridine ring are attached to the Ar$^2$;

said benzene ring and the pyridine ring may independently of each other be optionally substituted with C$_{1-6}$ alkyl group optionally substituted with one or multiple substituents selected from the group consisting of halogen, hydroxy, —NR$^c$R$^d$, —C(=O)NR$^c$R$^d$ and —C(=O)OR$^a$, halogen atom, —C(=O)NR$^c$R$^d$ group, —C(=O)OR$^a$ group, —NR$^c$R$^d$ group, nitro group or —NR$^a$C(=O)R$^b$ group).

[10]

The compound according to any one of [1] to [9] or physiologically acceptable salts thereof wherein L represents an unsubstituted benzene ring or an unsubstituted pyridine ring.

[11]

The compound according to any one of [1] to [8] or physiologically acceptable salts thereof wherein the L represents a group of Pyr-1, Tri-1 or Imi-1, and the Z$^1$, Z$^2$ and Z$^3$ represent a hydrogen atom.

[12]

The compound according to any one of [1] to [8] or physiologically acceptable salts thereof wherein the L represents a group of Pyr-1, Tri-1 or Imi-1, and the Z$^1$, Z$^2$ and Z$^3$ represent independently of each other a C$_{1-6}$ alkyl group optionally substituted with —NR$^c$R$^d$ or halogen, a halogen atom, a —NR$^c$R$^d$ group or a nitro group.

[13]

The compound according to any one of [1] to [8] or physiologically acceptable salts thereof wherein the L represents a group of Pyr-1, Tri-1 or Imi-1, and the Z$^1$, Z$^2$ and Z$^3$ represent independently of each other a C$_{1-6}$ alkyl group optionally substituted with —C(=O)NR$^c$R$^d$, a —C(=O)NR$^c$R$^d$ group or a —NR$^a$C(=O)R$^b$ group.

[14]

The compound according to any one of [1] to [8] or physiologically acceptable salts thereof wherein the L represents a group of Pyr-1, Tri-1 or Imi-1, and the $Z^1$, $Z^2$ and $Z^3$ represent independently of each other a $C_{1-6}$ alkyl group optionally substituted with hydroxy or —C(=O)OR$^a$, a hydroxy group or a —C(=O)OR$^a$ group.

[15]

The compound according to any one of [1] to [14] or physiologically acceptable salts thereof wherein $R^1$ represents a $C_{1-10}$ alkyl group optionally substituted at substitutable positions with one or multiple substituents described in Substituent List 3, or a three to six-membered saturated aliphatic ring group optionally containing one to two heteroatoms independently selected from the group consisting of N, O and S that may be optionally substituted at substitutable positions with one or multiple substituents described in Substituent List 4.

[16]

The compound according to any one of [1] to [15] or physiologically acceptable salts thereof wherein
$R^1$ represents a $C_{1-10}$ alkyl group (said alkyl group may be optionally substituted at substitutable positions with one or multiple substituents selected from the group consisting of Substituent List 5:
(1) hydroxy group,
(2) halogen atom,
(3) cyano group,
(4) $C_{1-6}$ alkoxy group (said alkoxy group may be optionally substituted at substitutable positions with
  hydroxy group,
  halogen atom,
  cyano group,
  three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group),
(5) $C_{1-6}$ alkylthio group (said alkylthio group may be optionally substituted at substitutable positions with
  hydroxy group,
  halogen atom,
  cyano group,
  three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group),
(6) five to six-membered aromatic ring group optionally containing one to four heteroatoms independently selected from the group consisting of N, O and S (said aromatic ring group may be optionally substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —NR$^a$C(=O)R$^b$,
  —NR$^a$S(=O)$_m$R$^b$,
  —C(=O)OR$^b$,
  —C(=O)NR$^c$R$^d$,
  —S(=O)$_m$NR$^c$R$^d$,
  —S(=O)$_m$R$^b$ or
  —NR$^c$R$^d$),
(7) three to six-membered saturated aliphatic ring group optionally containing one to two heteroatoms independently selected from the group consisting of N, O and S (said aliphatic ring group may be optionally substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —NR$^a$C(=O)R$^b$,
  —NR$^a$S(=O)$_m$R$^b$,
  —C(=O)OR$^b$,
  —C(=O)NR$^c$R$^e$,
  —C(=O)R$^b$,
  —NR$^c$R$^d$ or
  oxo group),
(8) —NR$^a$R$^e$ group,
(9) —OC(=O)NR$^c$R$^d$ group,
(10) —C(=O)R$^f$ group,
(11) —S(=O)$_m$R$^g$ group and
(12) thiol group.

[17]

The compound according to any one of [1] to [16] or physiologically acceptable salts thereof wherein
$R^1$ represents a $C_{1-10}$ alkyl group (said alkyl group may be optionally substituted at substitutable positions with one to three substituents selected from the group consisting of Substituent List 6:
(1) hydroxy group,
(2) halogen atom,
(3) cyano group,
(6) five to six-membered aromatic ring group optionally containing one to four heteroatoms independently selected from the group consisting of N, O and S (said aromatic ring group may be optionally substituted at substitutable positions with
  $C_{1-3}$ alkyl group optionally substituted with one or multiple substituents selected from the group consisting of hydroxy and halogen,
  $C_{1-3}$ alkoxy group optionally substituted with one or multiple substituents selected from the group consisting of hydroxy and halogen,
  hydroxy group,
  halogen atom,
  cyano group,
  —NR$^a$C(=O)R$^b$,
  —NR$^a$S(=O)$_m$R$^b$,
  —C(=O)OR$^b$,
  —C(=O)NR$^c$R$^d$,
  —S(=O)$_m$NR$^c$R$^d$,
  —S(=O)$_m$R$^b$ or
  —NR$^c$R$^d$), (7) three to six-membered saturated aliphatic ring group optionally containing one to two heteroatoms independently selected from the group consisting of N, O and S (said aliphatic ring group may be optionally substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —NR$^a$C(=O)R$^b$,
  —NR$^a$S(=O)$_m$R$^b$,
  —C(=O)OR$^b$,
  —C(=O)NR$^c$R$^d$,
  —C(=O)R$^b$,
  —NR$^c$R$^d$ or
  oxo group),
(8) —NR$^a$R$^e$ group, and
(10) —C(=O)R$^f$ group.

[18]

The compound according to any one of [1] to [15] or physiologically acceptable salts thereof wherein
R$^1$ represents a three to six-membered saturated aliphatic ring group optionally containing one to two heteroatoms independently selected from the group consisting of N, O and S that may be optionally substituted at substitutable positions with one or multiple substituents described in Substituent List 4.

[19]

The compound according to any one of [1] to [15] and [18] or physiologically acceptable salts thereof wherein
R$^1$ represents a three to six-membered saturated aliphatic ring group optionally containing one to two heteroatoms independently selected from the group consisting of N, O and S (said aliphatic ring group may be optionally substituted at substitutable positions with one or multiple substituents selected from the group consisting of
Substituent List 7:
  (1) hydroxy group,
  (2) halogen atom,
  (3) cyano group,
  (4) $C_{1-6}$ alkyl group (said alkyl group may be optionally substituted at substitutable positions with
    hydroxy group,
    halogen atom,
    cyano group,
    five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group), or
    three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group),
  (5) $C_{1-6}$ alkoxy group (said alkoxy group may be optionally substituted at substitutable positions with
    hydroxy group,
    halogen atom,
    cyano group,
    five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
    three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group),
  (7) five to six-membered aromatic ring group optionally containing one to four heteroatoms independently selected from the group consisting of N, O and S (said aromatic ring group may be optionally substituted at substitutable positions with
    $C_{1-3}$ alkyl group optionally substituted with hydroxy or halogen,
    $C_{1-3}$ alkoxy group optionally substituted with hydroxy or halogen,
    hydroxy group,
    halogen atom,
    cyano group,
    —NR$^a$C(=O)R$^b$,
    —NR$^a$S(=O)$_m$R$^b$,
    —C(=O)OR$^b$,
    —C(=O)NR$^c$R$^d$,
    —S(=O)$_m$NR$^c$R$^d$,
    —S(=O)$_m$R$^b$ or
    —NR$^c$R$^d$),
  (8) three to six-membered saturated aliphatic ring group optionally containing one to two heteroatoms independently selected from the group consisting of N, O and S (said aliphatic ring group may be optionally substituted at substitutable positions with
    $C_{1-3}$ alkyl group optionally substituted with hydroxy or halogen,
    $C_{1-3}$ alkoxy group optionally substituted with hydroxy or halogen,
    hydroxy group,
    halogen atom,
    cyano group,
    —NR$^a$C(=O)R$^b$,
    —NR$^a$S(=O)$_m$R$^b$,
    —C(=O)OR$^b$,
    —C(=O)NR$^c$R$^d$,
    —NR$^c$R$^d$ or
    oxo group), (9) —NR$^a$R$^e$ group,
(10) —OC(=O)NR$^c$R$^d$ group,
(11) —C(=O)R$^f$ group,
(12) —S(=O)$_m$R$^g$ group and
(14) oxo group.

[20]
The compound according to any one of [1] to [15], [18] and [19] or physiologically acceptable salts thereof wherein R$^1$ represents a three to six-membered saturated aliphatic ring group optionally containing one to two heteroatoms independently selected from the group consisting of N, O and S that may be optionally substituted with one or multiple substituents described in Substituent List 7, and said aliphatic ring group represents C$_{3-6}$ saturated carbocycle, aziridine, azetidine, pyrrolidine, piperidine, oxetane, tetrahydrofuran, tetrahydropyran, morpholine or piperazine.

[21]
The compound according to any one of [1] to [20] or physiologically acceptable salts thereof, wherein
R$^a$ represents a hydrogen atom or a C$_{1-6}$ alkyl group optionally substituted with hydroxy or fluorine,
R$^b$ represents a C$_{1-6}$ alkyl group optionally substituted with hydroxy or fluorine,
R$^c$ and R$^d$ represent independently of each other a hydrogen atom or a C$_{1-3}$ alkyl group optionally substituted with hydroxy or fluorine, or alternatively combine each other together with N (nitrogen atom) to which they are attached and optionally together with further O (oxygen atom) to represent a four to six-membered saturated aliphatic ring group (said aliphatic ring group may be optionally substituted at substitutable positions with hydroxy or fluorine),
R$^e$ represents a C$_{1-6}$ alkyl group (said alkyl group may be optionally substituted with hydroxy, cyano, fluorine, C$_{1-3}$ alkoxy or —NR$^c$R$^d$), an -A group, a —C(=O)-A group, a C$_{1-6}$ alkylcarbonyl group (the alkyl moiety of said alkylcarbonyl group may be optionally substituted with hydroxy, fluorine, cyano, C$_{1-3}$ alkoxy or —NR$^c$R$^d$), a —C(=O)NR$^c$R$^d$ group or a —S(=O)$_m$R$^b$ group,
R$^f$ represents a hydroxy group, a C$_{1-3}$ alkyl group (said alkyl group may be optionally substituted with hydroxy, cyano, fluorine or —NR$^c$R$^d$) or a —NR$^a$R$^i$ group,
R$^g$ represents a hydroxy group or a C$_{1-3}$ alkyl group (said alkyl group may be optionally substituted with hydroxy, cyano, fluorine or —NR$^c$R$^d$) or a —NR$^a$R$^i$ group,
R$^h$ represents a C$_{1-3}$ alkyl group optionally substituted with hydroxy or fluorine,
R$^i$ represents a C$_{1-6}$ alkyl group (said alkyl group may be optionally substituted with fluorine or —NR$^c$R$^d$), an -A group, a —C(=O)-A group or a C$_{1-6}$ alkyl carbonyl group (the alkyl moiety of said alkylcarbonyl group may be optionally substituted with fluorine or —NR$^c$R$^d$),
A represents
an aromatic ring group selected from the group consisting of phenyl, imidazolyl, pyridyl, oxazolyl, isoxazolyl, pyrazolyl, thiazolyl, isothiazolyl and tetrazolyl (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —C(=O)OH group or —NR$^c$R$^d$ group) or
an aliphatic ring group selected from the group consisting of cyclopropyl, cyclobutyl, cyclopentyl, cyclohexyl, pyranyl, azetidinyl, pyrrolidinyl, piperidinyl, piperazinyl and morpholinyl (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —C(=O)OH group, —NR$^c$R$^d$ group or oxo group), and
m represents 1 or 2.

[22]
The compound according to any one of [1] to [8], [15] and [21] or physiologically acceptable salts thereof, wherein the formula (I) represents the following formula (I″):

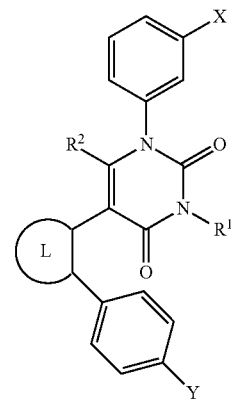

(I″)

[wherein,
L represents a benzene ring (wherein, the position on which said benzene ring is attached to the uracil ring is an orto position to the position on which said benzene ring is attached to the Ar$^2$, and said benzene ring may be optionally substituted at substitutable positions with C$_{1-6}$ alkyl group optionally substituted with hydroxy or halogen, —C(=O)NR$^c$R$^d$ group or —C(=O)OH group), or a group of Pyr-1 or Tri-1 of the following formula:

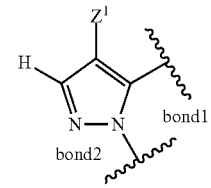

Pyr-1

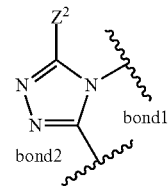

Tri-1

(in each formula,
the bond 1 represents a binding to uracil ring, the bond 2 represents a binding to Ar$^2$, and the Z$^1$ and Z$^2$ represent independently of each other a C$_{1-6}$ alkyl group optionally substituted with a halogen atom, a hydroxy group, a —NR$^c$R$^d$ group, —C(=O)NR$^c$R$^d$ or —C(=O)OH group, a halogen atom, a —C(=O)NR$^c$R$^d$ group, a —C(=O)OH group, a —NR$^c$R$^d$ group or a hydrogen atom),
R$^1$ represents
a C1-10 alkyl group (said alkyl group may be optionally substituted at substitutable positions with one to three substituents selected from the group consisting of (1) hydroxy group,
(2) halogen atom,
(4) $C_{1-6}$ alkoxy group (said alkoxy group may be substituted at substitutable positions with
   hydroxy group,
   halogen atom,
   five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom or —C(=O)OH group) or
   three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, —C(=O)OR$^b$ group, —C(=O)NR$^c$R$^d$ group or oxo group),
(6) five to six-membered aromatic ring group optionally containing one to four heteroatoms independently selected from the group consisting of N, O and S (said aromatic ring group may be optionally substituted at substitutable positions with
   $C_{1-3}$ alkyl group optionally substituted with hydroxy or halogen,
   $C_{1-3}$ alkoxy group optionally substituted with hydroxy or halogen,
   hydroxy group,
   halogen atom or
   —C(=O)OR$^b$),
(7) three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, —C(=O)OR$^b$ group, —C(=O)NR$^c$R$^d$ group, —C(=O)R$^b$ group or oxo group) and
(8) —NR$^a$R$^e$ group)
or
a three to six-membered saturated aliphatic ring group optionally containing one to two heteroatoms independently selected from the group consisting of N and O (said aliphatic ring group may be optionally substituted at substitutable positions with one or multiple substituents selected from the group consisting of
   (1) hydroxy group,
   (2) halogen atom,
   (3) cyano group,
   (4) $C_{1-6}$ alkyl group (said alkyl group may be optionally substituted at substitutable positions with hydroxy or halogen),
   (5) $C_{1-6}$ alkoxy group (said alkoxy group may be optionally substituted at substitutable positions with hydroxy or halogen),
   (9) —NR$^a$R$^e$ group,
   (10) —OC(=O)NR$^c$R$^d$ group,
   (11) —C(=O)R$^f$ group,
   (12) —S(=O)$_m$R$^g$ group and
   (14) oxo group, $R^2$ represents a halogen atom, a —NR$^c$R$^d$ group, or a $C_{1-3}$ alkyl group optionally substituted with —OR$^a$ or —OC(=O)R$^a$, X represents a $C_{1-3}$ alkyl group optionally substituted with one or multiple fluorine atoms or a nitro group, Y represents a cyano group, a chlorine atom or a nitro group, $R^a$ represents a hydrogen atom, or a $C_{1-3}$ alkyl group optionally substituted with hydroxy or fluorine, $R^b$ represents a $C_{1-3}$ alkyl group optionally substituted with one to three fluorine atoms, $R^c$ and $R^d$ represent independently of each other a $C_{1-3}$ alkyl group optionally substituted with fluorine or a hydrogen atom, or alternatively combine each other together with N to which they are attached to represent pyrrolidine or piperidine, $R^e$ represents a $C_{1-6}$ alkyl group (said alkyl group may be optionally substituted with fluorine or —NR$^c$R$^d$), an -A group, a —C(=O)-A group, a $C_{1-6}$ alkylcarbonyl group (the alkyl moiety of said alkylcarbonyl group may be optionally substituted with fluorine or —NR$^c$R$^d$) or a —S(=O)$_2$R$^b$ group, $R^f$ represents a hydroxy group or a —NR$^a$R$^i$ group, $R^g$ represents a $C_{1-3}$ alkyl group, $R^h$ represents a $C_{1-3}$ alkyl group optionally substituted with fluorine, $R^i$ represents a $C_{1-3}$ alkyl group (said alkyl group may be optionally substituted with fluorine or —NR$^c$R$^d$) or an -A group, A represents an aliphatic ring group selected from the group consisting of cyclopropyl, cyclobutyl, cyclopentyl, cyclohexyl, azetidinyl, pyrrolidinyl, piperidinyl, piperazinyl and morpholinyl (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —C(=O)OH group, —NR$^c$R$^d$ group or oxo group) and m represents 2].

[23]
The compound according to any one of [1] to [8], [15] and [21] to [22] or physiologically acceptable salts thereof wherein the $Z^1$ and $Z^2$ represent a hydrogen atom.

[24]
A compound represented by formula (I) or physiologically acceptable salts thereof:

$$\text{(I)}$$

[wherein
$R^1$ represents a hydrogen atom, a $C_{1-10}$ alkyl group, a $C_{2-6}$ alkene group or a three to six-membered saturated- or four to six-membered unsaturated-aliphatic ring group optionally containing one to two heteroatoms independently selected from the group consisting of N, O and S, said alkyl group and said alkene group for $R^1$ may be optionally substituted at substitutable positions with one or multiple substituents selected from the group consisting of Substituent List 1:
 (1) hydroxy group,
 (2) halogen atom,
 (3) cyano group,
 (4) $C_{1-6}$ alkoxy group (said alkoxy group may be optionally substituted at substitutable positions with
  hydroxy group,
  halogen atom,
  cyano group,
  —C(=O)OR$^b$,
  —C(=O)NR$^c$R$^d$,
   five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$C(=O)NR$^c$R$^d$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
   three to six-membered saturated- or four to six-membered unsaturated-aliphatic ring group each optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$C(=O)NR$^c$R$^d$ group, —NR$^a$S(=O)$_m$R$^b$ group, —C(=O)OR$^b$ group, —C(=O)NR$^c$R$^d$ group, —NR$^c$R$^d$ group or oxo group),
 (5) $C_{1-6}$ alkylthio group (said alkylthio group may be optionally substituted at substitutable positions with
  hydroxy group,
  halogen atom,
  cyano group,
  —C(=O)OR$^b$,
  —C(=O) NR$^c$R$^d$,
   five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$C(=O)NR$^c$R$^d$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
   three to six-membered saturated- or four to six-membered unsaturated-aliphatic ring group each optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$C(=O)NR$^c$R$^d$ group, —NR$^a$S(=O)$_m$R$^b$ group, —C(=O)OR$^b$ group, —C(=O)NR$^c$R$^d$ group, —NR$^c$R$^d$ group or oxo group),
 (6) five to six-membered aromatic ring group optionally containing one to four heteroatoms independently selected from the group consisting of N, O and S (said aromatic ring group may be substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —NR$^a$C(=O)R$^b$,
  —NR$^a$C(=O)NR$^c$R$^d$,
  —NR$^a$S(=O)$_m$R$^b$,
  —C(=O)OR$^b$,
  —C(=O)NR$^c$R$^d$,
  —S(=O)$_m$NR$^c$R$^d$,
  —S(=O)$_m$R$^b$ or
  —NR$^c$R$^d$),
 (7) three to six-membered saturated- or four to six-membered unsaturated-aliphatic ring group each optionally containing one to two heteroatoms independently selected from the group consisting of N, O and S (said aliphatic ring group may be optionally substituted at substitutable positions with
  $C_{1-3}$ alkyl group (said alkyl group may be optionally substituted with hydroxy, halogen, cyano, —NR$^a$C(=O)R$^b$, —NR$^a$C(=O)NR$^c$R$^d$, —NR$^a$S(=O)$_m$R$^b$, —C(=O)OR$^b$, C(=O)NR$^c$R$^d$ or —NR$^c$R$^d$),
  $C_{1-3}$ alkoxy group optionally substituted with hydroxy or halogen,
  hydroxy group,
  halogen atom,
  cyano group,
  —NR$^a$C(=O)R$^b$,
  —NR$^a$C(=O)NR$^c$R$^d$,
  —NR$^a$S(=O)$_m$R$^b$,
  —C(=O)OR$^b$,
  —C(=O)NR$^c$R$^d$,
  —C(=O)R$^b$,
  —S(=O)$_m$NR$^c$R$^d$,
  —S(=O)$_m$R$^b$,
  —NR$^c$R$^d$ or
  oxo group),
 (8) —NR$^a$R$^e$ group,
 (9) —OC(=O)NR$^c$R$^d$ group,
 (10) —C(=O)R$^f$ group,
 (11) —S(=O)$_m$R$^g$ group,
 (12) thiol group,
 (13) nitro group and
 (14) —OR$^e$ group,
 said three to six-membered saturated- or four to six-membered unsaturated-aliphatic ring group for R$^1$ may be optionally substituted at substitutable positions with one or multiple substituents selected from the group consisting of
Substituent List 2:
 (1) hydroxy group,
 (2) halogen atom,
 (3) cyano group,
 (4) $C_{1-6}$ alkyl group (said alkyl group may be optionally substituted at substitutable positions with
  hydroxy group,
  halogen atom,
  cyano group,
   five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or three- to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group), (5) $C_{1-6}$ alkoxy group (said alkoxy group may be optionally substituted at substitutable positions with
  hydroxy group,
  halogen atom,
  cyano group,
  five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or a —NR$^c$R$^d$ group) or
  three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group), (6) $C_{1-6}$ alkylthio group (said alkylthio group may be optionally substituted at substitutable positions with
  hydroxy group,
  halogen atom,
  cyano group,
  five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
  three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group), (7) five to six-membered aromatic ring group optionally containing one to four heteroatoms independently selected from the group consisting of N, O and S (said aromatic ring group may be optionally substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —NR$^a$C(=O)R$^b$,
  —NR$^a$S(=O)$_m$R$^b$,
  —C(=O)OR$^b$,
  —C(=O)NR$^c$R$^d$,
  —S(=O)$_m$NR$^c$R$^d$,
  —S(=O)$_m$R$^b$ or
  —NR$^c$R$^d$), (8) three to six-membered saturated aliphatic ring group optionally containing one to two heteroatoms independently selected from the group consisting of N, O and S (said aliphatic ring group may be optionally substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —NR$^a$C(=O)R$^b$,
  —NR$^a$S(=O)$_m$R$^b$,
  —C(=O)OR$^b$,
  —C(=O)NR$^c$R$^d$,
  —NR$^c$R$^d$ or
  oxo group), (9) —NR$^a$R$^e$ group,
(10) —OC(=O)NR$^c$R$^d$ group,
(11) —C(=O)R$^f$ group,
(12) —S(=O)$_m$R$^g$ group,
(13) thiol group,
(14) oxo group,
(15) nitro group,
(16) —NR$^a$C(=O)R$^b$ group,
(17) —NR$^a$C(=O)NR$^c$R$^d$ group,
(18) —NR$^a$S(=O)$_m$R$^b$ group,
(19) —C(=O)OR$^b$ group and
(20) —C(=O)NR$^c$R$^d$ group, R$^2$ represents a hydrogen atom, a halogen atom, a cyano group, a —NR$^c$R$^d$ group, a —N=CHN(CH$_3$)$_2$ group or a $C_{1-3}$ alkyl group (said alkyl group may be optionally substituted with hydroxy, halogen, —NR$^c$R$^d$, —OR$^a$ or —OC(=O)R$^a$), Ar$^1$ represents a five to six-membered aromatic ring group optionally containing one to three heteroatoms independently selected from the group consisting of N, O and S (said aromatic ring group is substituted at substitutable positions with $C_{1-6}$ alkyl group optionally substituted with hydroxy or halogen, $C_{1-3}$ alkoxy group optionally substituted with hydroxy or halogen, hydroxy group, halogen atom, cyano group, nitro group, phenyl group, —NR$^a$C(=O)R$^h$ group, —NR$^a$S (=O)$_m$R$^h$ group, —NR$^a$C(=O)NR$^c$R$^d$ group, —C(=O) NR$^c$R$^d$ group, —C(=O)OR$^a$ group, —C(=O) R$^a$ group, —S(=O)$_m$NR$^c$R$^d$ group, —S(=O)$_n$R$^h$ group or —NR$^c$R$^d$ group), L represents a six membered aromatic ring group optionally containing one to four nitrogen atoms, a Pyr-1 group of the following formula, a Tri-1 group of the following formula or an Imi-1 group of the following formula:

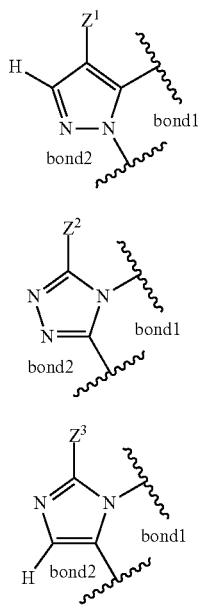

(in each formula, the bond 1 represents a binding to uracil ring, the bond 2 represents a binding to Ar$^2$, and the Z$^1$, Z$^2$ and Z$^3$ represent independently of each other a cyano group, a halogen atom, a —C(=O)NR$^c$R$^d$ group, a —C(=O)OR$^{b2}$ group, a —CHO group, a nitro group, a hydroxy group, a —NR$^c$R$^d$ group, a —NR$^a$C(=O)R$^h$ group, a hydrogen atom, a —S(=O)$_m$NR$^{c2}$R$^{d2}$ group, a —S(=O)$_m$NR$^a$C(=O)R$^{b3}$ group, a —S(=O)$_m$NR$^a$C(=O)OR$^{b4}$ group, a —S(=O)$_m$N-R$^a$C(=O)NR$^a$R$^{b3}$ group, a —S(=O)$_m$R$^{g2}$ group, a —S—R$^{g3}$ group, a three to six-membered saturated aliphatic ring group optionally containing one to two heteroatoms independently selected from the group consisting of N, O and S, a C$_{1-6}$ alkyl group or a C$_{2-6}$ alkene group, and said alkyl group and an alkene group may independently of each other be optionally substituted with halogen, hydroxy, —NR$^c$R$^d$, —C(=O)NR$^c$R$^d$, —NR$^a$S(=O)$_m$R$^h$ or —C(=O)OR$^a$, and said saturated aliphatic ring group may be optionally substituted with hydroxy, halogen, C$_{1-6}$ alkyl, C$_{1-3}$ alkoxy, —C(=O)OR$^a$, —C(=O)R$^a$ or —NR$^a$R$^b$), wherein, when L represents a six-membered aromatic ring group, the L may be optionally substituted at substitutable positions with halogen, —C(=O)NR$^c$R$^d$, —C(=O)OR$^a$, hydroxy, —NR$^c$R$^d$, nitro, —NR$^a$C(=O)R$^b$, C$_{1-6}$ alkyl or C$_{2-6}$ alkene, and said alkyl and said alkene may independently of each other be optionally substituted with halogen, hydroxy, —NR$^c$R$^d$, —C(=O)NR$^c$R$^d$ or —C(=O)OR$^a$, Ar$^2$ represents a five to six-membered aromatic ring group optionally containing one to three heteroatoms independently selected from the group consisting of N, O and S (said aromatic ring group is substituted at one or more substitutable positions with C$_{1-6}$ alkyl group optionally substituted with hydroxy, cyano or halogen, C$_{1-3}$ alkoxy group optionally substituted with hydroxy or halogen, hydroxy group, halogen atom, cyano group, nitro group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O)R$^a$ group, —S(=O)$_m$NR$^c$R$^d$ group, —S(=O)$_n$R$^h$ group or —NR$^c$R$^d$ group), R$^a$ represents a hydrogen atom or a C$_{1-6}$ alkyl group (said alkyl group may be optionally substituted with hydroxy or halogen), R$^b$ represents a hydrogen atom, a C$_{1-6}$ alkyl group optionally substituted with hydroxy or halogen, a benzyl group optionally substituted with methoxy or nitro, or a C$_{3-6}$ cycloalkyl group optionally substituted with hydroxy or halogen, R$^{b2}$ represents a hydrogen atom, a C$_{1-6}$ alkyl group (said alkyl group may be optionally substituted with hydroxy, —NR$^a$R$^b$ or halogen), a benzyl group (said benzyl group may be optionally substituted with methoxy or nitro) or a C$_{3-6}$ cycloalkyl group (said cycloalkyl group may be optionally substituted with hydroxy or halogen), R$^{b3}$ represents a hydrogen atom, a phenyl group (said phenyl group may be optionally substituted with halogen), a C$_{1-6}$ alkyl group (said alkyl group may be optionally substituted with hydroxy or halogen) or a C$_{3-6}$ cycloalkyl group (said cycloalkyl group may be optionally substituted with hydroxy or halogen), R$^{b4}$ represents a hydrogen atom, a phenyl group (said phenyl group may be optionally substituted with halogen), a C$_{1-6}$ alkyl group (said alkyl group may be optionally substituted with hydroxy or halogen), a C$_{3-6}$ cycloalkyl group (said cycloalkyl group may be optionally substituted with hydroxy or halogen) or an 2-isopropyl-5-methylcyclohexyl, R$^c$ and R$^d$ represent independently of each other a hydrogen atom or a C$_{1-3}$ alkyl group optionally substituted with C$_{1-3}$ alkoxy, cyano, hydroxy or halogen, or alternatively may combine each other together with N to which they are attached and optionally together with further one to two heteroatoms independently selected from the group consisting of N, O and S to represent a four to six-membered saturated or unsaturated aliphatic ring group (said aliphatic ring group may be optionally substituted at substitutable positions with C$_{1-6}$ alkyl group (said alkyl group may be optionally substituted with hydroxy, —NR$^a$R$^b$, —NR$^a$C(=O)OR$^h$ or —NR$^a$C(=O)R$^h$), C$_{1-3}$ alkoxy group, —NR$^a$R$^b$ group, —NR$^a$C(=O)OR$^h$ group, —NR$^a$C(=O) R$^h$ group, —C(=O)OR$^a$ group, hydroxy group, halogen atom or oxo group), R$^{c2}$ and R$^{d2}$ represent independently of each other a hydrogen atom or a C$_{1-3}$ alkyl group (said alkyl group may be optionally substituted with phenyl group optionally substituted with methoxy, —NR$^a$R$^b$ group, —NR$^a$(C=O)OR$^h$ group, —NR$^a$C(=O)R$^h$ group, C$_{1-3}$ alkoxy group, cyano group, hydroxy group or halogen atom), or alternatively may combine each other together with N to which they are attached and optionally together with further one to two heteroatoms independently selected from the group consisting of N, O and S to represent a four to six-membered saturated or unsaturated aliphatic ring group (said aliphatic ring group may be optionally substituted at substitutable positions with C$_{1-6}$ alkyl group, C$_{1-3}$ alkoxy group, —NR$^a$R$^b$ group, —NR$^a$C(=O)OR$^h$ group, —NR$^a$C(=O)R$^h$ group, —C(=O)OR$^a$ group, hydroxy group, halogen atom or oxo group), $R^e$ represents
a hydrogen atom,
a $C_{1-6}$ alkyl group (said alkyl group may be optionally substituted with hydroxy, cyano, halogen, $C_{1-3}$ alkoxy or —$NR^cR^d$),
an -A group,
a —C(=O)-A group,
a $C_{1-6}$ alkylcarbonyl group (the alkyl moiety of said alkylcarbonyl may be optionally substituted with hydroxy, halogen, cyano, $C_{1-3}$ alkoxy or —$NR^cR^d$),
a $C_{1-6}$ alkoxycarbonyl group (the alkyl moiety of said alkoxycarbonyl group may be optionally substituted with hydroxy or halogen),
a —C(=O)$NR^cR^d$ group or
a —S(=O)$_m R^b$ group,
$R^f$ represents
a hydrogen atom,
a hydroxy group,
a $C_{1-6}$ alkyl group (said alkyl group may be optionally substituted with hydroxy, cyano, halogen, $C_{1-3}$ alkoxy or —$NR^cR^d$),
a $C_{1-3}$ alkoxy group (said alkoxy group may be optionally substituted with phenyl group optionally substituted with methoxy or nitro, hydroxy group, cyano group, halogen atom, $C_{1-3}$ alkoxy group or —$NR^cR^d$ group),
an -A group or
a —$NR^aR^i$ group,
$R^g$ represents
a hydroxy group,
a chlorine atom,
a $C_{1-6}$ alkyl group (said alkyl group may be optionally substituted with hydroxy, cyano, halogen, $C_{1-3}$ alkoxy or —$NR^cR^d$),
an -A group or
a —$NR^aR^i$ group,
$R^{g2}$ represents
a hydroxy group,
a chlorine atom,
a $C_{1-6}$ alkyl group (said alkyl group may be optionally substituted with hydroxy, cyano, halogen, $C_{1-3}$ alkoxy or —$NR^cR^d$) or
an -A group,
$R^{g3}$ represents
a $C_{1-6}$ alkyl group (said alkyl group may be optionally substituted with hydroxy, cyano, halogen, $C_{1-3}$ alkoxy or $NR^cR^d$) or
an -A group,
$R^b$ represents a $C_{1-6}$ alkyl optionally substituted with hydroxy or halogen,
$R^i$ represents
a hydrogen atom,
a $C_{1-6}$ alkyl group (said alkyl group may be optionally substituted with hydroxy, cyano, halogen, $C_{1-3}$ alkoxy, $C_{3-6}$ cycloalkyl or —$NR^cR^d$),
an -A group,
a —C(=O)$R^h$ group,
a —C(=O)A group or
a $C_{1-6}$ alkylcarbonyl group (the alkyl moiety of said alkylcarbonyl group may be optionally substituted with hydroxy, halogen, cyano, $C_{1-3}$ alkoxy or —$NR^cR^d$),
A represents
a five to six-membered aromatic ring group optionally containing one to four heteroatoms independently selected from the group consisting of N, O and S (said aromatic group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —C(=O)OH group or —$NR^cR^d$ group),
a three to six-membered saturated- or four to six-membered unsaturated-aliphatic ring group each optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —C(=O)OH group, —$NR^cR^d$ group or oxo group),
m represents an integer of 1 or 2 and
n represents an integer of 0 to 2].
[25]
The compound according to [24] or physiologically acceptable salts thereof, wherein
L represents
a six membered unsubstituted aromatic ring group optionally containing 1 to 2 nitrogen atoms, a Pyr-1 group of the following formula or a Tri-1 group of the following formula:

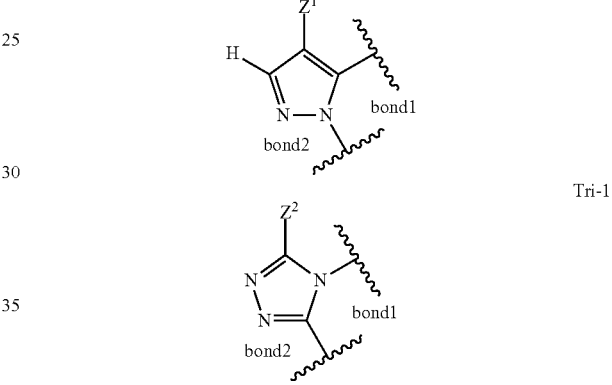

(in each formula,
the bond 1 represents a binding to uracil ring, the bond 2 represents a binding to $Ar^2$, and the $Z^1$ and $Z^2$ represent independently of each other a cyano group, a halogen atom, a —C(=O)$NR^cR^d$ group, a —C(=O)$OR^{b2}$ group, a —CHO group, a nitro group, a hydroxy group, a —$NR^cR^d$ group, a —$NR^aC$(=O)$R^h$ group, a hydrogen atom, a —S(=O)$_m NR^{c2}R^{d2}$ group, a —S(=O)$_m NR^aC$(=O)$R^{b3}$ group, a —S(=O)$_m NR^aC$(=O)$OR^{b4}$ group, a —S(=O)$_m N$-$R^aC$(=O)$NR^aR^{b3}$ group, a —S(=O)$_m R^{g2}$ group, a —S—$R^{g3}$ group, a three to six-membered saturated aliphatic ring group optionally containing one to two heteroatoms independently selected from the group consisting of N, O and S (said saturated aliphatic ring group may be optionally substituted with hydroxy, halogen, $C_{1-6}$ alkyl, $C_{1-3}$ alkoxy, —C(=O)$OR^a$, —C(=O)$R^a$ or —$NR^aR^b$), a $C_{1-6}$ alkyl group or a $C_{2-6}$ alkene group (said alkyl group and said alkene group may independently of each other be optionally substituted with halogen, hydroxy, —$NR^cR^d$, —C(=O)$NR^cR^d$, —$NR^aS$(=O)$_m R^h$ or —C(=O)$OR^a$).
[26]
The compound according to [24] or [25] or physiologically acceptable salts thereof, wherein
$Z^1$ and $Z^2$ represent independently of each other a cyano group, a halogen atom, a —C(=O)$NR^cR^d$ group, a —C(=O)$OR^{b2}$ group, a —CHO group, a nitro group, a —$NR^aC$(=O)$R^b$ group, a hydrogen atom, a —S(=O)$_m NR^{c2}R^{d2}$ group, a —S(=O)$_m NR^aC$(=O)$R^{b3}$ group, a —S(=O)$_m NR^aC$(=O)

OR$^{b4}$ group, a —S(=O)$_m$NR$^a$C(=O)NR$^a$R$^{b3}$ group, a —S(=O)$_m$R$^{g2}$ group, a three to six-membered saturated aliphatic ring group optionally containing one to two heteroatoms independently selected from the group consisting of N, O and S (said saturated aliphatic ring group may be optionally substituted with halogen, C$_{1-6}$ alkyl, —C(=O)OR$^a$ or —C(=O)R$^a$) or a C$_{1-6}$ alkyl group (said alkyl group may be optionally substituted with halogen, —C(=O)NR$^c$R$^d$, —NR$^a$S(=O)$_m$R$^h$, —C(=O)NR$^c$R$^d$ or —C(=O)OR$^a$).

[27]

The compound according to any one of [24] to [26] or physiologically acceptable salts thereof wherein Ar$^1$ represents a benzene ring or a pyridine ring (said benzene ring and said pyridine ring are independently of each other substituted at one to three substitutable positions with C$_{1-6}$ alkyl group optionally substituted with hydroxy or halogen, C$_{1-3}$ alkoxy group optionally substituted with hydroxy or halogen, hydroxy group, halogen atom, cyano group, nitro group, phenyl group, —C(=O)NR$^c$R$^d$ group, —C(=O)OR$^a$ group, —C(=O)R$^a$ group, —S(=O)$_n$R$^h$ group or —NR$^c$R$^d$ group), and Ar$^2$ represent a benzene ring or a pyridine ring (said benzene ring and said pyridine ring are substituted independently of each other at one to three substitutable positions with C$_{1-6}$ alkyl group optionally substituted with hydroxy or halogen, C$_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group).

[28]

The compound according to any one of [24] to [27] or physiologically acceptable salts thereof wherein Ar$^1$ represents the following formula of Ar$^1$-1:

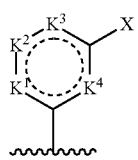

Ar$^1$-1

(in the formula, K$^1$, K$^2$, K$^3$ and K$^4$ represent all carbon atoms for benzene ring, or only one nitrogen atom and the remaining carbon atoms for pyridine ring, and X represents a C$_{1-6}$ alkyl group optionally substituted with hydroxy or halogen, a C$_{1-3}$ alkoxy group optionally substituted with hydroxy or halogen, a hydroxy group, a halogen atom, a cyano group, a nitro group, a phenyl group, a —C(=O)NR$^c$R$^d$ group, a —C(=O)OR$^a$ group, a —C(=O) R$^a$ group, a —S(=O)$_n$R$^h$ group or a —NR$^c$R$^d$ group, said benzene ring and said pyridine ring may be optionally substituted at one to two substitutable positions of K$^1$ to K$^4$ with further C$_{1-6}$ alkyl group optionally substituted with hydroxy or halogen, C$_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group), Ar$^2$ represents the following formula Ar$^2$-1:

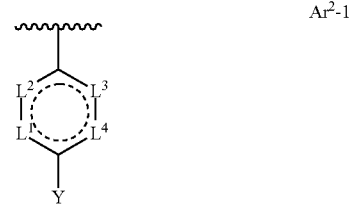

Ar$^2$-1

(in the formula, L$^1$, L$^2$, L$^3$ and L$^4$ represent all carbon atoms for benzene ring, or only one nitrogen atom and the remaining carbon atoms for pyridine ring, and Y represents a C$_{1-6}$ alkyl group optionally substituted with hydroxy or halogen, a C$_{1-3}$ alkoxy group optionally substituted with hydroxy or halogen, a hydroxy group, a halogen atom, a cyano group, a nitro group, a —C(=O)NR$^c$R$^d$ group, a —C(=O)OR$^a$ group, a —C(=O)R$^a$ group, a —S(=O)$_n$R$^h$ group or a —NR$^c$R$^d$ group, said benzene ring and said pyridine ring may be optionally substituted at one to two substitutable positions of L$^1$ to L$^4$ with further C$_{1-6}$ alkyl group optionally substituted with hydroxy or halogen, C$_{1-3}$ alkoxy group optionally substituted with hydroxy or halogen, hydroxy group, halogen atom, cyano group, nitro group, —C(=O)NR$^c$R$^d$ group, —C(=O) OR$^a$ group, —C(=O)R$^a$ group, —S(=O)$_n$R$^h$ group or —NR$^c$R$^d$ group).

[29]

The compound according to any one of [24] to [28] or physiologically acceptable salts thereof wherein R$^2$ represents a —NR$^c$R$^d$ group, a —N=CHN(CH$_3$)$_2$ group or a C$_{1-3}$ alkyl group (said alkyl group may be optionally substituted with hydroxy, halogen, —NR$^c$R$^d$, —OR$^a$ or —OC(=O)R$^a$).

[30]

The compound according to any one of [24] to [29] or physiologically acceptable salts thereof, wherein R$^a$ represents a hydrogen atom or a C$_{1-6}$ alkyl group optionally substituted with hydroxy or halogen, R$^b$ represents a C$_{1-6}$ alkyl group optionally substituted with hydroxy or halogen, R$^{b2}$ represents a hydrogen atom, a C$_{1-6}$ alkyl group (said alkyl group may be optionally substituted with hydroxy, —NR$^a$R$^b$ or fluorine) or a C$_{3-6}$ cycloalkyl group (said cycloalkyl group may be optionally substituted with hydroxy or fluorine), R$^{b3}$ represents a hydrogen atom, a phenyl group (said phenyl group may be optionally substituted with fluorine or chlorine), a C$_{1-6}$ alkyl group (said alkyl group may be optionally substituted with hydroxy or fluorine) or a C$_{3-6}$ cycloalkyl group (said cycloalkyl group may be optionally substituted with hydroxy or fluorine), R$^{b4}$ represents a hydrogen atom, a phenyl group (said phenyl group may be optionally substituted with fluorine or chlorine), a C$_{1-6}$ alkyl group (said alkyl group may be optionally substituted with hydroxy or fluorine), a C$_{3-6}$ cycloalkyl group (said cycloalkyl group may be optionally substituted with hydroxy or fluorine) or an 2-isopropyl-5-methylcyclohexyl, R$^c$ and R$^d$ represent independently of each other a hydrogen atom or a C$_{1-3}$ alkyl group (said alkyl group may be optionally substituted with C$_{1-3}$ alkoxy, cyano, hydroxy or fluorine), or alternatively may combine each other together with N to which they are attached and optionally together with further one to two heteroatoms independently selected from the group consisting of N, O and S to represent a four to six-membered saturated aliphatic ring group (said aliphatic ring group may be optionally substituted at substitutable positions with $C_{1-6}$ alkyl group (said alkyl group may be optionally substituted with hydroxy, —$NR^aR^b$, —$NR^aC(=O)OR^h$ or —$NR^aC(=O)R^h$), $C_{1-3}$ alkoxy group, —$NR^aR^b$ group, —$NR^aC(=O)OR^a$ group, —$NR^aC(=O)R^a$ group, —$C(=O)OR^a$ group, hydroxy group, fluorine atom or oxo group), $R^{c2}$ an $R^{d2}$ represent independently of each other a hydrogen atom or a $C_{1-3}$ alkyl group (said alkyl group may be optionally substituted with phenyl group optionally substituted with methoxy, —$NR^aR^b$ group, —$NR^a(C=O)OR^h$ group, —$NR^aC(=O)R^h$ group, $C_{1-3}$ alkoxy group, cyano group, hydroxy group or fluorine atom), or alternatively combine each other together with N to which they are attached and optionally together with further one to two heteroatoms independently selected from the group consisting of N, O and S to represent a four to six-membered saturated aliphatic ring group (said aliphatic ring group may be optionally substituted at substitutable positions with $C_{1-6}$ alkyl, $C_{1-3}$ alkoxy, —$NR^aR^b$, —$NR^aC(=O)OR^h$, —$NR^aC(=O) R^h$, —$C(=O)OR^a$, hydroxy, fluorine or oxo), $R^e$ represents a $C_{1-6}$ alkyl group (said alkyl group may be optionally substituted with hydroxy or fluorine), an -A group, a $C_{1-6}$ alkylcarbonyl group (the alkyl moiety of said alkylcarbonyl group may be optionally substituted with hydroxy or fluorine) or a —$S(=O)_2R^b$ group, $R^f$ represents a hydroxy group, an -A group or an —$NR^aR^i$ group, $R^g$ represents a hydroxy group, a $C_{1-3}$ alkyl group (said alkyl group may be optionally substituted with hydroxy, fluorine or —$NR^cR^d$), a chlorine atom, an -A group or a —$NR^aR^i$ group, $R^{g2}$ represents a hydroxy group, a $C_{1-3}$ alkyl group (said alkyl group may be optionally substituted with hydroxy or fluorine), a chlorine atom or an -A group, $R^{g3}$ represents a $C_{1-6}$ alkyl group (said alkyl group may be optionally substituted with hydroxy, fluorine or —$NR^cR^d$), $R^h$ represents a $C_{1-3}$ alkyl group optionally substituted with hydroxy or fluorine, $R^i$ represents a $C_{1-6}$ alkyl group (said alkyl group may be optionally substituted with hydroxy, $C_{1-3}$ alkoxy or fluorine) or an -A group, A represents an aromatic ring group selected from the group consisting of phenyl, pyridyl and tetrazolyl (said aromatic ring group may be optionally substituted at substitutable positions with hydroxy or fluorine) or an aliphatic ring group selected from the group consisting of cyclopropyl, cyclobutyl, cyclopentyl, cyclohexyl, pyranyl, azetidinyl, pyrrolidinyl, piperidinyl, piperazinyl and morpholinyl (said aliphatic ring group may be optionally substituted at substitutable positions with $C_{1-3}$ alkyl, $C_{1-3}$ alkoxy, hydroxy, fluorine, —$NR^cR^d$ or oxo), and m represents an integer of 1 or 2.

[31]

The compound according to any one of [24] to [30] or physiologically acceptable salts thereof wherein $R^1$ represents a $C_{1-10}$ alkyl group (said alkyl group may be substituted at substitutable positions with one to three substituents selected from the group consisting of Substituent List 8:

(1) hydroxy group,
(2) halogen atom,
(3) cyano group,
(7) three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen,
$C_{1-3}$ alkoxy group optionally substituted with hydroxy or halogen,
hydroxy group,
halogen atom,
cyano group,
—$NR^aC(=O)R^b$,
—$NR^aS(=O)_mR^b$,
—$C(=O)OR^b$,
—$C(=O)NR^cR^d$,
—$C(=O)R^b$,
—$NR^cR^d$ or
oxo group),
(8) —$NR^aR^e$ group,
(10) —$C(=O)R^f$ group,
(11) —$S(=O)_mR^g$ group, and
(12) thiol group, or a three to six-membered saturated aliphatic ring group optionally containing one to two heteroatoms independently selected from the group consisting of N, O and S (said aliphatic ring group may be optionally substituted at substitutable positions with one or multiple substituents selected from the group consisting of Substituent List 9:

(1) hydroxy group,
(2) halogen atom,
(3) cyano group,
(4) $C_{1-6}$ alkyl group (said alkyl group may be optionally substituted at substitutable positions with
hydroxy group,
halogen atom,
cyano group,
five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —$NR^aC(=O)R^b$ group, —$NR^aS(=O)_mR^b$ group, —$C(=O)OR^b$ group, —$C(=O)NR^cR^d$ group, —$S(=O)_mNR^cR^d$ group, —$S(=O)_mR^b$ group or —$NR^cR^d$ group) or
three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —$NR^aC(=O)R^b$ group, —$NR^aS(=O)_mR^b$ group, —$C(=O)OR^b$ group, —$C(=O)NR^cR^d$ group, —$NR^cR^d$ group or oxo group),
(5) $C_{1-6}$ alkoxy group (said alkoxy group may be optionally substituted at substitutable positions with
hydroxy group,
halogen atom,
cyano group,
five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or a —NR$^c$R$^d$ group) or three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group),

(11) —C(=O)R$^f$ group,
(12) —S(=O)$_m$R$^g$ group, and
(14) oxo group.

[32]
The compound according to any one of [24] to [31] or physiologically acceptable salts thereof wherein
R$^1$ represents
a $C_{1-10}$ alkyl group (said alkyl group may be substituted at substitutable positions with one to three substituents selected from the group consisting of
Substituent List 10:
(1) hydroxy group,
(2) halogen atom,
(7) three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy, halogen, —C(=O)OR$^b$, —C(=O)NR$^c$R$^d$, —C(=O)R$^b$ or oxo group),
(8) —NR$^a$R$^e$ group, and
(11) —S(=O)$_2$R$^g$ group)
or
a three to six-membered saturated aliphatic ring group optionally containing one to two heteroatoms independently selected from the group consisting of N and O (said aliphatic ring group may be optionally substituted at substitutable positions with one or multiple substituents selected from the group consisting of
Substituent List 11:
(1) hydroxy group,
(2) halogen atom,
(4) $C_{1-6}$ alkyl group (said alkyl group may be optionally substituted at substitutable positions with hydroxy or halogen),
(9) —NR$^a$R$^e$ group,
(11) —C(=O)R$^f$ group and
(14) oxo group.

[33]
The compound according to any one of [24] to [32] or physiologically acceptable salts thereof wherein L represents a Pyr-1 group.

[34]
The compound according to any one of [24] to [33] or physiologically acceptable salts thereof wherein
the formula (I) represents the following formula (I'''):

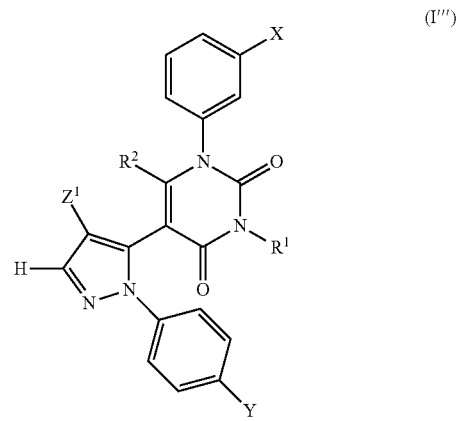

(wherein, Z$^1$ represents a cyano group, a halogen atom, a —C(=O)NR$^c$R$^d$ group, a —C(=O)OR$^{b2}$ group, a hydrogen atom, a —S(=O)$_2$NR$^{c2}$R$^{d2}$ group, a —S(=O)$_2$NR$^a$C(=O)R$^{b3}$ group, a —S(=O)$_2$NR$^a$C(=O)OR$^{b4}$ group, a —S(=O)$_2$NR$^a$C(=O)NR$^a$R$^{b3}$ group or a S(=O)$_2$R$^g$ group, X represents a $C_{1-3}$ alkyl group optionally substituted one or multiple fluorine atoms or a nitro group, and Y represents a cyano group, a chlorine atom or a nitro group).

[35]
The compound according to [34] or physiologically acceptable salts thereof wherein
Z$^1$ represents a —C(=O)NR$^c$R$^d$ group, a —C(=O)OR$^{b2}$ group, a —S(=O)$_2$NR$^{c2}$R$^{d2}$ group, a —S(=O)$_2$NR$^{a2}$C(=O)R$^{b3}$ group, a —S(=O)$_2$NR$^a$C(=O)OR$^{b4}$ group, a —S(=O)$_2$NR$^a$C(=O)NR$^a$R$^{b3}$ group, a S(=O)$_2$R$^g$ group, an iodine atom, a bromine atom or a chlorine atom, and R$^2$ represents a $C_{1-3}$ alkyl group optionally substituted with hydroxy.

[36]
The compound according to [1] or [24] selected from the following Group or physiologically acceptable salts thereof,
Group:
4-[5-[3,6-Dimethyl-2,4-dioxo-1-(3-trifluoromethylphenyl)-1,2,3,4-tetrahydropyrimidin-5-yl]-1H-pyrazol-1-yl]benzonitrile,
4-[5-[6-Methyl-2,4-dioxo-3-propyl-1-(3-trifluoromethylphenyl)-1,2,3,4-tetrahydropyrimidin-5-yl]-1H-pyrazol-1-yl]benzonitrile,
4-(5-(3-Ethyl-6-methyl-2,4-dioxo-1-(3-(trifluoromethyl)phenyl)-1,2,3,4-tetrahydropyrimidin-5-yl)-1H-pyrazol-1-yl)benzonitrile,
4-[5-[1-(3-Chlorophenyl)-3,6-dimethyl-2,4-dioxo-1,2,3,4-tetrahydropyrimidin-5-yl]-1H-pyrazol-1-yl]benzonitrile,
4-(5-(3,6-Dimethyl-2,4-dioxo-1-m-tolyl-1,2,3,4-tetrahydropyrimidin-5-yl)-1H-pyrazol-1-yl)benzonitrile,
4-(5-(3-Isopropyl-6-methyl-2,4-dioxo-1-(3-(trifluoromethyl)phenyl)-1,2,3,4-tetrahydropyrimidin-5-yl)-1H-pyrazol-1-yl)benzonitrile,
4-(5-(6-Ethyl-3-methyl-2,4-dioxo-1-(3-(trifluoromethyl)phenyl)-1,2,3,4-tetrahydropyrimidin-5-yl)-1H-pyrazol-1-yl)benzonitrile, (R)-4-(5-(3-(1-Hydroxypropan-2-yl)-6-methyl-2,4-dioxo-1-(3-(trifluoromethyl)phenyl)-1,2,3,4-tetrahydropyrimidin-5-yl)-1H-pyrazol-1-yl)benzonitrile, 4-(4-(3-Isopropyl-6-methyl-2,4-dioxo-1-(3-(trifluoromethyl)phenyl)-1,2,3,4-tetrahydropyrimidin-5-yl)-4H-1,2,4-triazol-3-yl)benzonitrile, (S)-4-(5-(2,4-Dioxo-3-(5-oxopyrrolidin-3-yl) 1-(3-(trifluoromethyl)phenyl)-1,2,3,4-tetrahydropyrimidin-5-yl)-1H-pyrazol-1-yl)benzonitrile, 1-(4-Cyanophenyl)-5-(3-isopropyl-6-methyl-2,4-dioxo-1-(3-(trifluoromethyl)phenyl)-1,2,3,4-tetrahydropyrimidin-5-yl)-1H-pyrazole-4-carboxamide, 4-(Dimethylamino)butyl 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-carboxylate, (±)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonaic acid, (+)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonaic acid, (−)-1-(4-Cyanophenyl)-5-(3,6-dimethyl-2,4-dioxo-1-(3 trifluoromethylphenyl)-1,2,3,4-tetrahydropyrimidin-5-yl)-1H-pyrazole-4-sulfonaic acid, (±)-1-(4-Cyanophenyl)-5-(3,6-dimethyl-2,4-dioxo-1-(3 trifluoromethylphenyl)-1,2,3,4-tetrahydropyrimidin-5-yl)-1H-pyrazole-4-sulfonamide, (−)-1-(4-Cyanophenyl)-5-(3,6-dimethyl-2,4-dioxo-1-(3 trifluoromethylphenyl)-1,2,3,4-tetrahydropyrimidin-5-yl)-1H-pyrazole-4-sulfonamide, (+)-1-(4-Cyanophenyl)-5-(3,6-dimethyl-2,4-dioxo-1-(3 trifluoromethylphenyl)-1,2,3,4-tetrahydropyrimidin-5-yl)-1H-pyrazole-4-sulfonamide, (+)-1-(4-Cyanophenyl)-5-(3,6-dimethyl-2,4-dioxo-1-(3 trifluoromethylphenyl)-1,2,3,4-tetrahydropyrimidin-5-yl)-1H-pyrazole-4-sulfonamide.0.5 IPA solvates, (±)-1-(4-Cyanophenyl)-5-(3-ethyl-6-methyl-2,4-dioxo-trifluoromethylphenyl)-1,2,3,4-tetrahydropyrimidin-5-yl)-1H-pyrazole-4-sulfonamide, (+)-1-(4-Cyanophenyl)-5-(3-ethyl-6-methyl-2,4-dioxo-trifluoromethylphenyl)-1,2,3,4-tetrahydropyrimidin-5-yl)-1H-pyrazole-4-sulfonamide, N-(1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-ylsulfonyl)pivalamine, Butyl 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-ylsulfonylcarbamate, N-(1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-ylsulfonyl)benzamide, 1-(4-Cyanophenyl)-5-(3,6-dimethyl-2,4-dioxo-1-(3-trifluoromethylphenyl)-1,2,3,4-tetrahydropyrimidin-5-yl)-N-(ethylcarbonyl)-1H-pyrazole-4-sulfonamide, (±)-4-(5-(3,6-Dimethyl-2,4-dioxo-1-(3-trifluoromethylphenyl)-1,2,3,4-tetrahydropyrimidin-5-yl-4-(methylsulfonyl)-1H-pyrazol-1-yl)benzonitrile, (+)-4-(5-(3,6-Dimethyl-2,4-dioxo-1-(3-trifluoromethylphenyl)-1,2,3,4-tetrahydropyrimidin-5-yl-4-(methylsulfonyl)-1H-pyrazol-1-yl)benzonitrile, (±)-4-(5-(3-Isopropyl-6-methyl-2,4-dioxo-1-(3-trifluoromethylphenyl)-1,2,3,4-tetrahydropyrimidin-5-yl-4-(methylsulfonyl)-1H-pyrazol-1-yl)benzonitrile, 4-(5-(3-Ethyl-6-methyl-2,4-dioxo-1-(3-trifluoromethylphenyl)-1,2,3,4-tetrahydropyrimidin-5-yl)-4-(2-hydroxypropan-2-yl)-1H-pyrazol-1-yl)benzonitrile, (R)-4-(5-(6-Methyl-2,4-dioxo-3-(pyrrolidin-3-yl)-1-(3-trifluoromethylphenyl)-1,2,3,4-tetrahydropyrimidin-5-yl)-1H-pyrazol-1-yl)benzonitrile, 4-(5-(3,6-Dimethyl-2,4-dioxo-1-(3-trifluoromethylphenyl)-1,2,3,4-tetrahydropyrimidin-5-yl)-4-fluoro-1H-pyrazol-1-yl)benzonitrile, 4-(4-Chloro-5-(3,6-dimethyl-2,4-dioxo-1-(3-trifluoromethylphenyl)-1,2,3,4-tetrahydropyrimidin-5-yl)-1H-pyrazol-1-yl)benzonitrile, 1-(4-Cyanophenyl)-5-(3,6-dimethyl-2,4-dioxo-1-(3-trifluoromethyl)-1,2,3,4-tetrahydropyrimidin-5-yl)-1H-pyrazole-4-carbonitrile, (R)-4-(5-(6-Methyl-3-(methanesulfonyl)propan-2-yl)-2,4-dioxo-3-(1-oxopropane-2-yl)-1-(3-trifluoromethylphenyl)-1,2,3,4-tetrahydropyrimidin-5-yl)-1H-pyrazol-1-yl)benzonitrile, (R)-2-(5-(1-(4-Cyanophenyl)-1H-pyrazol-5-yl)-4-methyl-2,6-dioxo-3-(3-trifluoromethylphenyl)-2,3-dihydropyrimidin-1(6H)-yl)propane-1-sulfonamide and 5-(4-Cyanophenyl)-4-(3-ethyl-6-methyl-2,4-dioxo-1-(3-trifluoromethylphenyl)-1,2,3,4-tetrahydropyrimidin-5-yl)-4H-1,2,4-triazole-3-carboxamide.

[37]

A pharmaceutical composition comprising the compound according to any one of [1] to [36] or physiologically acceptable salts thereof as active ingredient and a pharmaceutical carrier.

[38]

An esterase inhibitor comprising the compound according to any one of [1] to [36] or physiologically acceptable salts thereof as active ingredient.

[39]

An agent for treatment or prophylaxis of inflammatory diseases comprising the compound according to any one of [1] to [36] or physiologically acceptable salts thereof.

[40]

An agent for treatment or prophylaxis of diseases required for elastase inhibitory activity comprising the compound according to any one of [1] to [36] or physiologically acceptable salts thereof.

Also, the present application provides the following aspects:

[41]

Use of the compound according to any one of [1] to [36] or physiologically acceptable salts thereof in a preparation of medicine for treatment or prophylaxis of inflammatory diseases.

[42]

A pharmaceutical composition for use in treatment or prophylaxis of inflammatory diseases comprising the compound according to any one of [1] to [36] or physiologically acceptable salts thereof as active ingredient.

[43]

A method for treatment or prophylaxis of inflammatory diseases which comprises administering a therapeutically effective amount of the compound according to any one of [1] to [36] or physiologically acceptable salts thereof into a patient in need thereof.

Effect of Invention

The present invention can provide compounds showing elastase inhibitory activity, and thereby can provide a therapeutic agent or a prophylactic agent for diseases associated with elastase such as inflammatory diseases. The diseases in which elastase is suggested to associate with pathological conditions include, for example, chronic obstructive pulmonary disease (COPD), pulmonary cystic fibrosis, emphysema, adult respiratory distress syndrome (ARDS), acute lung injury (ALI), idiopathic interstitial pneumonia (IIP) including idiopathic pulmonary fibrosis (IPF), chronic interstitial pneumonia, chronic bronchitis, chronic airway infection, diffuse panbronchiolitis, bronchiectasis, asthma, pancreatitis, nephritis, hepatic failure, chronic rheumatoid arthritis, arthrosclerosis, osteoarthritis, psoriasis, periodontitis, atherosclerosis, rejection of organ transplantation, premature rupture of membrane, bullosa, shock, sepsis, systemic lupus erythematodes (SLE), Crohn disease, disseminated intravascular coagulation (DIC), ischemia-reperfusion induced-tissue injury, corneal scar tissue formation, myelitis, lung squamous cell carcinoma, pulmonary adenocarcinoma, lung cancers such as non-small cell lung cancer, breast cancer, liver cancer, bladder cancer, colorectal cancer, skin cancer, pancreas cancer, glioma and the others.

MODE FOR CARRYING OUT THE INVENTION

Hereinafter, the compounds represented by formula (I) of the present invention are further explained.

A term "physiologically acceptable salts of compounds represented by formula (I)" means acid additional physiologically acceptable salts of compounds of formula (I) that contain any groups capable of forming acid addition salts in a structure thereof, or base additional physiologically acceptable salts of compounds of formula (I) that contain any groups capable of forming base addition salts in a structure thereof.

Specific examples of acid addition salts include salts with inorganic acids (such as hydrochloride, hydrobromide, hydroiodide, sulfate, perchlorate and phosphate); salts with organic acids (such as oxalate, malonate, maleate, fumarate, lactate, malate, citrate, tartrate, benzoate, trifluoroacetate, acetate, methanesulfonate, p-toluenesulfonate and trifluoromethanesulfonate); as well as salts with amino acids (such as glutamate and aspartate). Specific examples of base addition salts include salts with alkali metal or alkaline-earth metals (such as sodium salt, potassium salt and calcium salt); salts with organic bases (such as pyridine salts and triethylamine salts); as well as salts with amino acids (such as lysine salts and arginine salts).

The compound of formula (I) and salts thereof may exist in forms of hydrates and/or solvates, and thus these hydrates and/or solvates may be also encompassed in the present compounds. That is to say, "Present compound" encompasses, in addition to the above-mentioned compounds of formula (I) and physiologically acceptable salts thereof, the hydrates and/or solvates thereof.

Also, the compound of formula (I) may contain one or more asymmetric carbon atoms and may form geometric isomer or axial chirality (i.e., atropisomer), and can thus exist as several kinds of stereoisomers. In the present invention, the compounds of formula (I) of the present invention encompass each of the stereoisomer, and mixtures and racemates thereof.

Also, the compounds of formula (I) may be labeled with one or more isotopes (such as $^3$H, $^{14}$C, $^{35}$S and so on). Also, the deuterium exchange product wherein any one or two or more $^1$H(s) is/are exchanged to $^2$H (D) in the compounds represented by formula (I) are also encompassed in the compounds represented by these general formulae respectively.

Herein, the number of substituents in the certain group defined by "(may be) optionally substituted" or "substituted" should not be specifically limited as long as the group can be substituted and includes, for example one to multiple. Also, when the number of the substituents is multiple, each of the substituents may be the same or different from each other.

Specifically, the term "said aromatic ring group may be optionally substituted at one or more substitutable positions with $C_{1-6}$ alkyl group optionally substituted with hydroxy or halogen, $C_{1-3}$ alkoxy group optionally substituted with hydroxy or halogen, hydroxy group, halogen atom, cyano group, nitro group, phenyl group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O)R$^a$ group, —S(=O)$_m$NR$^c$R$^d$ group, —S(=O)$_n$R$^h$ group or —NR$^c$R$^d$ group" means, for example, that "said aromatic ring group is substituted at substitutable positions with $C_{1-6}$ alkyl group optionally substituted with hydroxy or halogen, hydroxy group, halogen atom or cyano group", and the above-mentioned descriptions may be changed to "said aromatic ring group is substituted at substitutable positions with one or more same or different substituents selected from the group consisting of $C_{1-6}$ alkyl group optionally substituted with hydroxy or halogen, $C_{1-3}$ alkoxy group optionally substituted with hydroxy or halogen, hydroxy group, halogen atom, cyano group, nitro group, phenyl group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O)R$^a$ group, —S(=O)$_m$NR$^c$R$^d$ group, —S(=O)$_n$R$^h$ group and —NR$^c$R$^d$ group. Also, the explanations for each group may apply to the case where the group is a part/moiety or a substituent of other group unless otherwise specified.

The terms described herein are explained below.

The term "alkyl" used herein means a straight or branched saturated hydrocarbon group, and the term "$C_{1-3}$ alkyl", "$C_{1-6}$ alkyl" and "$C_{1-10}$ alkyl" means an alkyl group having 1 to 3 carbon atoms, 1 to 6 carbon atoms, or 1 to 10 carbon atoms respectively. For specific examples thereof, examples of "$C_{1-3}$ alkyl group" include methyl, ethyl, propyl, isopropyl and the others, examples of "$C_{1-6}$ alkyl group" include in addition to the above-mentioned groups, butyl, isobutyl, sec-butyl, tert-butyl, pentyl, isopentyl, neopentyl, hexyl and the others, and examples of "$C_{1-10}$ alkyl group" include in addition to the above-mentioned groups, octyl, nonyl, decyl and the others, and said alkyl may be straight or branched. Preferably, examples of "$C_{1-3}$ alkyl group" include methyl, ethyl, propyl and isopropyl, examples of "$C_{1-6}$ alkyl group" include methyl, ethyl, propyl, isopropyl, butyl, tert-butyl, pentyl and hexyl, and examples of "$C_{1-10}$ alkyl group" include methyl, ethyl, propyl, isopropyl, butyl, pentyl, hexyl, heptyl, octyl and nonyl.

The alkyl part of "$C_{1-6}$ alkylthio" used herein is the same as defined in the above-mentioned "$C_{1-6}$ alkyl", and specific examples of "$C_{1-6}$ alkylthio" include methylthio, ethylthio, propylthio, isopropylthio, tert-butylthio and the others, and preferably include methylthio and ethylthio.

The alkyl part of "$C_{1-6}$ alkylcarbonyl" used herein is the same as defined in the above-mentioned "$C_{2-6}$ alkyl", and specific examples of "$C_{1-6}$ alkylcarbonyl" include methylcarbonyl, ethylcarbonyl, propylcarbonyl, isopropylcarbonyl, butylcarbonyl, tert-butylcarbonyl (pivaloyl) and the others, and preferably include methylcarbonyl, ethylcarbonyl, propylcarbonyl, isopropylcarbonyl and tert-butylcarbonyl.

The term "$C_{3-6}$ cycloalkyl" used herein means a ring saturated or unsaturated hydrocarbon group having 3 to 6 carbon atoms, preferably means ring saturated hydrocarbon group, and include, for example, cyclopentene, cyclohexene, cyclopropane, cyclobutane, cyclopentane and cyclohexane. Preferred examples thereof include cyclopropane, cyclobutane and cyclopentane.

The term "$C_{3-6}$ saturated carbocycle" used herein a ring saturated hydrocarbon group having 3 to 6 carbon atoms, and include cyclopropane, cyclobutane, cyclopentane and cyclohexane. Preferred examples thereof include cyclopropane, cyclobutane and cyclopentane.

The "$C_{2-6}$ alkene group" used herein means a straight or branched unsaturated hydrocarbon group having 2 to 6 carbon atoms, and include ethene, 1-propylene, 2-propylene, isopropylene, 1-butene, 2-butene, 3-butene, 1-pentene, 2-pentene, 3-pentene, 4-pentene, 1-hexene, 2-hexene, 3-hexene, 4-hexene, 5-hexene, 2-methyl-3-butene, 2-methyl-2-pentene, 3-methyl-2-pentene and the others. Preferred examples thereof include ethene, 2-propylene and 2-butene.

The term "halogen atom" used herein include fluorine atom, chlorine atom, bromine atom and iodine atom. Preferred examples thereof include fluorine atom, chlorine atom and bromine atom.

The term "alkoxy" used herein means a group wherein the alkyl group is attached to an oxygen atom, and the "alkyl" part is the same as defined in the above-mentioned "alkyl". Specific examples of the "$C_{1-3}$ alkoxy group" include methoxy, ethoxy, n-propoxy and isopropoxy, and specific examples of the "$C_{1-6}$ alkoxy" include in addition to the above-mentioned groups, n-butoxy, isobutoxy, sec-butoxy, tert-butoxy, pentyloxy hexyloxy and the others. Preferred examples thereof include methoxy, ethoxy, n-propoxy, isopropoxy and n-butoxy.

The term "$C_{1-6}$ alkoxycarbonyl" used herein means a group wherein the $C_{1-6}$ alkoxy group is attached to a carbonyl group, and specific examples of the "$C_{1-6}$ alkoxycarbonyl" include methoxycarbonyl, ethoxycarbonyl, propoxycarbonyl, isopropoxycarbonyl, butoxycarbonyl, tert-butoxycarbonyl and the others, and preferably include methoxycarbonyl, ethoxycarbonyl, propoxycarbonyl, isopropoxycarbonyl and tert-butoxycarbonyl.

The term "five to six-membered aromatic ring group optionally containing one to three heteroatoms independently selected from the group consisting of N, O and S" used herein means a phenyl group and a mono-ring five to six-membered aromatic heteroring group consisting of carbon atoms as well as one to three heteroatoms independently selected from the group consisting of nitrogen atom, oxygen atom and sulfur atom. Specific examples thereof include phenyl, thienyl, furyl, pyrrolyl, imidazolyl, pyridyl, pyrazinyl, oxazolyl, isoxazolyl, pyrazolyl, thiazolyl, isothiazolyl, pyrimidinyl, oxadiazolyl, thiadiazolyl, pyridazinyl, triazolyl and the others. Preferred examples thereof include phenyl, pyridyl, pyrazinyl and triazolyl.

The term "five to six-membered aromatic ring group optionally containing one to four heteroatoms independently selected from the group consisting of N, O and S" used herein means a phenyl group and a mono-ring five to six-membered aromatic heteroring group consisting of carbon atoms as well as one to four heteroatoms independently selected from the group consisting of nitrogen atom, oxygen atom and sulfur atom. Specific examples thereof include in addition to the above-mentioned specific examples for "five to six-membered aromatic ring group optionally containing one to three heteroatoms independently selected from the group consisting of N, O and S", tetrazolyl and the others. Preferred examples thereof include phenyl, pyridyl, pyrazinyl and triazolyl.

The "six-membered aromatic ring group optionally containing one to four nitrogen atoms" used herein means a phenyl group and a mono-ring six-membered aromatic heteroring group consisting of carbon atoms as well as one to four nitrogen atoms, and specific examples thereof include phenyl, pyridyl, pyrimidinyl, triazinyl, tetrazinyl and the others. Preferred examples thereof include phenyl and pyridyl.

The term "six-membered aromatic ring group optionally containing one to two nitrogen atoms" used herein means a phenyl group and a mono-ring six-membered aromatic heteroring group consisting of carbon atoms as well as one to two nitrogen atoms, and specific examples thereof include phenyl, pyridyl and pyrimidinyl. Preferred specific examples thereof include phenyl and pyridyl.

The term "three to six-membered saturated aliphatic ring group optionally containing one to two heteroatoms independently selected from the group consisting of N, O and S" used herein means a mono-ring saturated hydrocarbon aliphatic ring group having three to six carbon atoms, as well as a mono-ring saturated heteroaliphatic ring group containing one to two same or different atoms selected from nitrogen atom, oxygen atom and sulfur atom. The above-mentioned nitrogen atom, oxygen atom and sulfur atom are all ring-constituting atoms. Specific examples thereof include cyclopropyl, cyclobutyl, cyclopentyl, cyclohexyl, tetrahydropyranyl, azetidinyl, pyrrolidinyl, imidazolidinyl, pyrazolidinyl, piperidinyl, piperazinyl, morpholinyl, thiomorpholinyl, oxazolidinyl, thiazolidinyl, isoxazolidinyl, isothiazolidinyl, tetrahydrofuranyl and the others. Preferred examples include cyclopropyl, cyclobutyl, cyclopentyl, cyclohexyl, azetidinyl, pyrrolidinyl, piperidinyl, piperazinyl, morpholinyl, thiomorpholinyl, oxazolidinyl, isoxazolidinyl and tetrahydrofuranyl.

The term "four to six-membered unsaturated aliphatic ring group optionally containing one to two heteroatoms independently selected from the group consisting of N, O and S" used herein means a mono-ring unsaturated hydrocarbon aliphatic ring group having four to six carbon atoms, as well as a four to six-membered unsaturated heteroaliphatic ring group containing one to two same or different atoms selected from nitrogen atom, oxygen atom and sulfur atom. The above-mentioned nitrogen atom, oxygen atom and sulfur atom are all ring-constituting atoms. Specific examples thereof include cyclobutenyl, cyclopentenyl, cyclohexenyl, dihydropyranyl, dihydrofuranyl, pyrrolinyl, imidazolinyl, pyrazolynlyl, oxazolinyl, thiazolinyl, dihydropyridinyl, tetrahydropyridinyl and the others. Preferred specific examples thereof include cyclobutenyl, cyclopentenyl, dihydropyranyl and tetrahydropyridyl.

The term "combine each other together with N (nitrogen atom) to which they are attached and optionally together with further one to two heteroatoms independently selected from the group consisting of N, O and S to represent four to six-membered saturated aliphatic ring group" used herein means a formation of a four to six-membered saturated heteroaliphatic ring group containing one nitrogen atom and optionally containing further one to two heteroatoms selected from nitrogen atom, oxygen atom and sulfur atom. Specific examples thereof include azetidinyl, pyrrolidinyl, piperidinyl, morpholinyl, thiomorpholinyl, piperazinyl and the others. Preferred examples thereof include azetidinyl, pyrrolidinyl, piperidinyl, morpholinyl and piperazinyl.

The term "combine each other together with nitrogen atom to which they are attached and optionally together with further one to two heteroatoms independently selected from the group consisting of N, O and S to represent four to six-membered unsaturated aliphatic ring group" used herein means a formation of a four to six-membered unsaturated heteroaliphatic ring group containing one nitrogen atom and optionally containing further one to two heteroatoms selected from nitrogen atom, oxygen atom and sulfur atom. Specific examples thereof include tetrahydropyridyl, dihydropyrrolyl and the others. Preferred examples thereof include tetrahydropyridyl.

The term "three to six-membered saturated aliphatic ring group optionally containing one to two heteroatoms independently selected from the group consisting of N and O" used herein means a mono-ring saturated hydrocarbon aliphatic ring group having three to six carbon atoms as well as a three to six-membered saturated heteroaliphatic ring group containing one to two heteroatoms selected from nitrogen atom and oxygen atom. Specific examples thereof include cyclopropyl, cyclobutyl, cyclopentyl, cyclohexyl, tetrahydrofuranyl, tetrahydropyranyl, azetidinyl, pyrrolidinyl, piperidinyl, morpholinyl, piperazinyl and the others. Preferred examples thereof include cyclopropyl, cyclobutyl, cyclopentyl, cyclohexyl, tetrahydrofuranyl, tetrahydropyranyl, azetidinyl, pyrrolidinyl, piperidinyl, morpholinyl and piperazinyl.

The term "saturated aliphatic ring group substituted with alkyl group" used herein means the above-mentioned saturated aliphatic ring group wherein one, two or more (for example, one to three) hydrogen atoms are substituted with the above-mentioned alkyl group. Specific examples thereof include dimethylcyclopropyl, methylcyclobutyl, dimethylcyclobutyl, methylcyclopentyl, dimethylcyclopentyl, methylazetidinyl, methylpyrrolidinyl, methylpiperidinyl, methylpiperazinyl, ethylpiperazinyl, propylmorpholinyl and the others. Preferred examples thereof include dimethylcyclobutyl, dimethylcyclopentyl, methylazetidinyl, methylpyrrolidinyl, methylpiperidinyl, methylpiperazinyl, ethylpiperazinyl, propylmorpholinyl and the others.

The term "unsaturated aliphatic ring group substituted with alkyl group" used herein means the above-mentioned saturated aliphatic ring group wherein one, two or more (for example, one to three) hydrogen atoms are substituted with the above-mentioned alkyl group. Specific examples thereof include methylcyclobutenyl, dimethylcyclobutenyl, methylcyclopentenyl, dimethylcyclopentenyl, methyltetrahydropyridyl, ethyltetrahydropyridyl, propyltetrahydropyridyl and the others. Preferred examples thereof include methylcyclopentenyl, methyltetrahydropyridyl, ethyltetrahydropyridyl and the others.

The term "combine each other together with nitrogen atom to which they are attached and optionally together with further oxygen atom to represent four to six-membered saturated aliphatic ring group" used herein means a formation of a four to six-membered saturated heteroaliphatic ring group containing one nitrogen atom and optionally containing further one or more oxygen atoms. Specific examples thereof include azetidinyl, pyrrolidinyl, piperidinyl, morpholinyl and the others. Preferred examples thereof include azetidinyl, pyrrolidinyl, piperidinyl and morpholinyl.

The term "alkyl group substituted with halogen atom" used herein means the above-mentioned alkyl group wherein one, two or more (for example, one to five, preferably one to three) hydrogen atoms are substituted with halogen atoms. Specific examples thereof include fluoromethyl, difluoromethyl, trifluoromethyl, 2,2,2-trifluoroethyl, 1,1-difluoroethyl, 1-methyl-2,2,2-trifluoroethyl, 3,3,3-trifluoropropyl, 4,4,4-trifluorobutyl, chloromethyl, chloroethyl, chloropropyl, chlorobutyl, bromomethyl, bromoethyl, bromopropyl, bromobutyl, iodomethyl, iodoethyl, iodopropyl, iodobutyl and the others. Preferred examples include fluoromethyl, difluoromethyl, trifluoromethyl, 2,2,2-trifluoroethyl and 1,1-difluoroethyl The term "alkoxy group substituted with halogen atom" used herein means the above-mentioned alkoxy group wherein one, two or more (for example, one to five, preferably one to three) hydrogen atoms are substituted with halogen atom. Specific examples thereof include fluoromethoxy, difluoromethoxy, trifluoromethoxy, 2,2,2-trifluoroethoxy, 1,1-difluoroethoxy, 1-methyl-2,2,2-trifluoroethoxy, 3,3,3-trifluoropropoxy, 4,4,4-trifluorobutoxy, chloromethoxy, chloroethoxy, chloropropoxy, chlorobutoxy, bromoethoxy, bromopropoxy, bromobutoxy, iodoethoxy, iodopropoxy, iodobutoxy and the others. Preferred examples include fluoromethoxy, difluoromethoxy, trifluoromethoxy, 2,2,2-trifluoroethoxy and 1,1-difluoroethoxy.

The term "alkylthio group substituted with halogen atom" used herein means the above-mentioned alkylthio group wherein one, two or more (for example, one to five, preferably one to three) hydrogen atoms are substituted with halogen atoms. Specific examples thereof include trifluoromethylthio, 2,2,2-trifluoroethylthio, 2-fluoroethylthio, 3-fluoropropylthio, 3,3,3-trifluoropropylthio and the others. Preferred examples include trifluoromethylthio and 2,2,2-trifluoroethylthio.

The term "alkylcarbonyl group substituted with halogen atom" used herein means the above-mentioned alkylcarbonyl group wherein one, two or more (for example, one to five, preferably one to three) hydrogen atoms are substituted with halogen atoms. Specific examples thereof include trifluoromethylcarbonyl, 2-fluoroethylcarbonyl, 2,2,2-trifluoroethylcarbonyl, 3,3,3-trifluoropropylcarbonyl and the others. Preferred examples thereof include trifluoromethylcarbonyl, 2-fluoroethylcarbonyl and 2,2,2-trifluoroethylcarbonyl.

The term "alkoxycarbonyl group substituted with halogen atom" used herein means the above-mentioned alkoxycarbonyl group wherein one, two or more (for example, one to five, preferably one to three) hydrogen atom are substituted with halogen atoms. Specific examples thereof include trifluoromethoxycarbonyl, 2-fluoroethoxycarbonyl, 2,2,2-trifluoroethoxycarbonyl, 3,3,3-trifluoropropoxycarbonyl and the others. Preferred examples thereof include trifluoromethoxycarbonyl, 2-fluoroethoxycarbonyl and 2,2,2-trifluoroethoxycarbonyl.

The term "aromatic ring group substituted with halogen atom" used herein means the above-mentioned aromatic ring group substituted with one to three substituents selected from the group consisting of fluorine atom, chlorine atom, bromine atom and iodine atom.

The term "saturated aliphatic ring group substituted with halogen atom" used herein means a mono-ring saturated aliphatic ring group substituted with one to three substituents selected from the group consisting of fluorine atom, chlorine atom, bromine atom and iodine atom. Specific examples thereof include fluorocyclopropyl, difluorocyclopropyl, fluorocyclobutyl, difluorocyclobutyl, chlorocyclobutyl, dichlorocyclobutyl, fluorocyclopentyl, difluorocyclopentyl, chlorocyclopentyl, fluorocyclohexyl, difluorocyclohexyl, fluoroazetidinyl, difluoroazetidinyl, difluoropyrrolidinyl, difluoropiperidinyl, difluoromorpholinyl and the others. Preferred examples thereof include fluorocyclopropyl, difluorocyclopropyl, fluorocyclobutyl, difluorocyclobutyl, difluorocyclopentyl, difluoroazetidinyl and difluoropyrrolidinyl.

The term "unsaturated aliphatic ring group substituted with halogen atom" used herein means a mono-ring four to six-membered unsaturated aliphatic ring group substituted with one to three substituents selected from the group consisting of fluorine atom, chlorine atom, bromine atom and iodine atom. Specific examples thereof include fluorocyclobutenyl, difluorocyclobutenyl, chlorocyclobutenyl, dichlorocyclobutenyl, fluorocyclopentenyl, difluorocyclopentenyl, chlorocyclopentenyl, fluorocyclohexenyl, difluorocyclohexenyl, difluorotetrahydropyridyl and the others. Preferred examples include fluorocyclobutenyl, difluorocyclobutenyl and difluorocyclopentenyl.

The term "alkyl group substituted with hydroxy group" used herein means the above-mentioned alkyl group wherein one, two or more (for example, one to five, preferably one to three) hydrogen atoms are substituted with hydroxy groups. Specific examples thereof include hydroxymethyl, 2-hydroxyethyl, 2-hydroxypropyl, 3-hydroxypropyl, 1,3-dihydroxypropyl, 2,3-dihydroxypropyl, 2-hydroxybutyl, 3-hydroxybutyl, 4-hydroxybutyl, 2,3-dihydroxybutyl, 3,4-dihydroxybutyl, 2,4-dihydroxybutyl, 2-hydroxypentyl, 3-hydroxypentyl, 4-hydroxypentyl, 5-hydroxypentyl, 2,5-dihydroxypentyl, 3,5-dihydroxypentyl, 2-hydroxyhexyl, 3-hydroxyhexyl, 4-hydroxyhexyl, 5-hydroxyhexyl, 6-hydroxyhexyl, 2,6-dihydroxyhexyl, 3,6-dihydroxyhexyl, 4,6-dihydroxyhexyl, 2-hydroxyisopropyl, 2-hydroxysec-butyl, 3-hydroxy-sec-butyl, 2-hydroxy-tert-butyl, 3-methyl-5-hydroxypentyl, 3-methyl-3-hydroxypentyl, 4-methyl-5-hydroxypentyl, 4-methyl-4-hydroxypentyl, 4-methyl-3-hydroxypentyl and the others. Preferred examples thereof include hydroxymethyl, 2-hydroxyethyl, 2-hydroxypropyl, 1-hydroxy-2-propyl, 3-hydroxypropyl and 1,3-dihydroxy-2-propyl.

The term "alkoxy group substituted with hydroxy group" used herein means the above-mentioned alkoxy group wherein one, two or more (for example, one to five, preferably one to two) hydrogen atoms are substituted with hydroxy groups. Specific examples thereof include 2-hydroxyethoxy, 2-hydroxypropoxy, 3-hydroxypropoxy, 1,3-dihydroxypropoxy, 2,3-dihydroxypropoxy, 2-hydroxybutoxy, 3-hydroxybutoxy, 4-hydroxybutoxy, 2,3-dihydroxybutoxy, 3,4-dihydroxybutoxy, 2,4-dihydroxybutoxy, 2-hydroxypentyloxy, 3-hydroxypentyloxy, 4-hydroxypentyloxy, 5-hydroxypentyloxy, 2,5-hydroxypentyloxy, 3,5-hydroxypentyloxy, 2-hydroxyhexyloxy, 3-hydroxyhexyloxy, 4-hydroxyhexyloxy, 5-hydroxyhexyloxy, 6-hydroxyhexyloxy, 2,6-dihydroxyhexyloxy, 3,6-dihydroxyhexyloxy, 4,6-dihydroxyhexyloxy, 1-hydroxy-2-propoxy, 2-hydroxy-2-butoxy, 3-hydroxy-2-butoxy, 3-methyl-5-hydroxypentyloxy, 3-methyl-3-hydroxypentyloxy, 4-methyl-5-hydroxypentyloxy, 4-methyl-4-hydroxypentyloxy, 4-methyl-3-hydroxypentyloxy and the others. Preferred examples thereof include 2-hydroxyethoxy, 2-hydroxypropoxy, 1-hydroxy-2-propoxy, 3-hydroxypropoxy and 1,3-dihydroxy-2-propoxy.

The term "alkylthio group substituted with hydroxy group" used herein means the above-mentioned alkylthio group wherein one, two or more (for example, one to five, preferably one to two hydrogen atoms are substituted with hydroxy groups. Specific examples thereof include 2-hydroxyethylthio, 2-hydroxy-1-propylthio, 3-hydroxy-1-propylthio, 1-hydroxy-2-propylthio and the others. Preferred examples thereof include 2-hydroxyethylthio, 3-hydroxy-1-propylthio and 1-hydroxy-2-propylthio.

The term "alkylcarbonyl group substituted with hydroxy group" used herein means the above-mentioned alkylcarbonyl group wherein one, two or more (for example, one to five, preferably one to two hydrogen atoms are substituted with hydroxy groups. Specific examples thereof include hydroxymethylcarbonyl, hydroxyethylcarbonyl, hydroxypropylcarbonyl, hydroxyisopropylcarbonyl, hydroxybutylcarbonyl and the others. Preferred examples thereof include hydroxymethylcarbonyl, hydroxyethylcarbonyl, hydroxypropylcarbonyl and hydroxybutylcarbonyl.

The term "alkoxycarbonyl group substituted with hydroxy group" used herein means the above-mentioned alkoxycarbonyl group wherein one, two or more (for example, one to five, preferably one to two hydrogen atoms are substituted with hydroxy groups. Specific examples thereof include hydroxyethoxycarbonyl, hydroxypropoxycarbonyl, hydroxyisopropoxycarbonyl, hydroxybutoxycarbonyl and the others. Preferred examples thereof include hydroxyethoxycarbonyl, hydroxypropoxycarbonyl and hydroxyisopropoxycarbonyl.

The term "aromatic ring group substituted with hydroxy group" used herein means the above-mentioned aromatic ring group wherein one, two or more (for example, one to two) hydrogen atoms are substituted with hydroxy groups.

The term "saturated aliphatic ring group substituted with hydroxy group" used herein means the above-mentioned saturated aliphatic ring group wherein one, two or more (for example, one to two) hydrogen atoms are substituted with hydroxy groups. Specific examples thereof include hydroxycyclopropyl, hydroxycyclobutyl, hydroxycyclopentyl, hydroxycyclohexyl, hydroxyazetidinyl, hydroxypyrrolidinyl, hydroxypiperidinyl and the others. Preferred examples thereof include hydroxycyclopropyl, hydroxycyclobutyl, hydroxycyclopentyl, hydroxyazetidinyl and hydroxypyrrolidinyl.

The term "unsaturated aliphatic ring group substituted with hydroxy group" used herein means the above-mentioned unsaturated aliphatic ring group wherein one, two or more (for example, one to two) hydrogen atoms are substituted with hydroxy groups. Specific examples thereof include hydroxycyclobutenyl, hydroxycyclopentenyl, hydroxycyclohexenyl, hydroxytetrahydropyridyl and the others. Preferred examples thereof include hydroxycyclopentenyl and hydroxycyclohexenyl.

The term "aromatic ring group substituted with alkyl group" used herein means the above-mentioned aromatic ring group wherein one, two or more (for example, one to two) hydrogen atoms are substituted with alkyl groups.

The term "aromatic ring group substituted with cyano group" used herein means the above-mentioned aromatic ring group wherein one, two or more (for example, one to two) hydrogen atoms are substituted with cyano groups.

The term "alkyl group substituted with cyano group" used herein means the above-mentioned alkyl group wherein one, two or more (for example, one to two) hydrogen atoms are substituted with cyano groups. Specific examples thereof include cyanomethyl, cyanoethyl, cyanopropyl, cyanoisopropyl, cyanobutyl, cyanoisobutyl, cyanopentyl, cyanohexyl, cyanooctyl, cyanononyl, cyanodecyl and the others. Preferred examples thereof include cyanomethyl, 2-cyanoethyl, 1-cyanoethyl, 3-cyanopropyl, 1-cyano-2-propyl and 4-cyanobutyl.

The term "alkoxy group substituted with cyano group" means the above-mentioned alkoxy group wherein one, two or more (for example, one to two) hydrogen atoms are substituted with cyano groups. Specific examples thereof include cyanomethoxy, cyanoethoxy, cyanopropoxy, cyanoisopropoxy, cyanobutoxy, cyanopentyloxy, cyanohexyloxy, cyanooctyloxy, cyanononyloxy, cyanodecyloxy and the others. Preferred examples thereof include cyanomethoxy, 2-cyanoethoxy, 3-cyanopropoxy, 1-cyano-2-propoxy and 4-cyanobutoxy.

The term "alkylthio group substituted with cyano group" used herein means the above-mentioned alkylthio group wherein one, two or more (for example, one to two) hydrogen atoms are substituted with cyano groups. Specific examples thereof include 2-cyanoethylthio, 2-cyano-1-propylthio, 3-cyano-1-propylthio, 1-cyano-2-propylthio and the others. Preferred examples thereof include 2-cyanoethylthio, 3-cyano-1-propylthio and 1-cyano-2-propylthio.

The term "alkylcarbonyl group substituted with cyano group" used herein means the above-mentioned alkylcarbonyl group wherein one, two or more (for example, one to two)

hydrogen atoms are substituted with cyano groups. Specific examples thereof include cyanomethylcarbonyl, cyanoethylcarbonyl, cyanopropylcarbonyl, cyanoisopropylcarbonyl, cyanobutylcarbonyl, cyanopentylcarbonyl, cyanohexylcarbonyl and the others. Preferred examples thereof include cyanomethylcarbonyl, cyanoethylcarbonyl, cyanopropylcarbonyl, cyanoisopropylcarbonyl and cyanobutylcarbonyl.

The term "saturated aliphatic ring group substituted with cyano group" used herein means the above-mentioned saturated aliphatic ring group wherein one, two or more (for example, one to two) hydrogen atoms are substituted with cyano groups. Specific examples thereof include cyanocyclobutyl, cyanocyclopentyl, cyanocyclohexyl, cyanopyrrolidinyl, cyanopiperidinyl, cyanopiperazinyl, cyanomorpholinyl, cyanotetrahydrofuranyl and the others. Preferred examples thereof include cyanocyclobutyl, cyanocyclopentyl, cyanocyclohexyl, cyanopyrrolidinyl and cyanopiperidinyl.

The term "unsaturated aliphatic ring group substituted with cyano group" used herein means the above-mentioned unsaturated aliphatic ring group wherein one, two or more (for example, one to two) hydrogen atoms are substituted with cyano groups. Specific examples thereof include cyanocycloobutenyl, cyanocyclopentenyl, cyanocyclohexenyl, cyanodihydropyranyl, cyanodihydrofuranyl, cyanodihydropyridyl, cyanotetrahydropyridyl and the others. Preferred examples thereof include cyanocyclopentenyl, cyanocyclohexenyl, cyanodihydropyridyl and cyanotetrahydropyridyl.

The term "alkyl group substituted with alkoxy group" used herein means the above-mentioned alkyl group wherein one, two or more (for example, one to three) hydrogen atoms are substituted with the above-mentioned alkoxy groups. Specific examples thereof include methoxyethyl, ethoxyethyl, propoxyethyl, isopropoxyethyl, methoxypropyl, ethoxypropyl, propoxypropyl, isopropoxypropyl, methoxyisopropyl, ethoxyisopropyl, propoxyisopropyl, isopropoxyisopropyl, methoxybutyl, ethoxybutyl, propoxybutyl, isopropoxybutyl, methoxyisobutyl, ethoxyisobutyl, propoxyisobutyl, isopropoxyisobutyl and the others. Preferred examples thereof include methoxyethyl, ethoxyethyl, propoxyethyl, isopropoxyethyl, methoxypropyl and ethoxypropyl.

The term "aromatic group substituted with alkoxy group" means the above-mentioned aromatic group wherein one, two or more (for example, one to three) hydrogens are substituted with the above-mentioned alkoxy groups.

The term "alkylcarbonyl group substituted with alkoxy group" used herein means the above-mentioned alkylcarbonyl group wherein one, two or more (for example, one to three) hydrogen atoms are substituted with the above-mentioned alkoxy groups. Specific examples thereof include methoxymethylcarbonyl, ethoxymethylcarbonyl, methoxyethylcarbonyl, ethoxyethylcarbonyl, methoxypropylcarbonyl, methoxyisopropylcarbonyl and the others. Preferred examples thereof include methoxymethylcarbonyl, ethoxymethylcarbonyl, methoxyethylcarbonyl and ethoxyethylcarbonyl.

The term "saturated aliphatic ring group substituted with alkoxy group" means the above-mentioned saturated aliphatic ring group wherein one, two or more (for example, one to three) hydrogen atoms are substituted with the above-mentioned alkoxy groups. Specific examples thereof include methoxycyclopropyl, ethoxycyclopropyl, methoxycyclobutyl, ethoxycyclobutyl, methoxycyclopentyl, methoxycyclohexyl, methoxytetrahydropyranyl, methoxypyrrolidinyl, methoxypiperidinyl, methoxytetrahydrofuranyl, methoxyazetidinyl, ethoxyazetidinyl, methoxypyrrolidinyl, ethoxypyrrolidinyl, methoxypiperidinyl and the others. Preferred examples thereof include methoxycyclopropyl, ethoxycyclopropyl, methoxycyclobutyl, ethoxycyclobutyl, methoxycyclopentyl, methoxycyclohexyl and methoxyazetidinyl.

The term "unsaturated aliphatic ring group substituted with alkoxy group" used herein means the above-mentioned unsaturated aliphatic ring group wherein one, two or more (for example, one to three) hydrogen atoms are substituted with the above-mentioned alkoxy groups. Specific examples thereof include methoxycyclobutenyl, methoxycyclopentenyl, methoxycyclohexenyl, ethoxycyclobutenyl, ethoxycyclopentenyl, ethoxycyclohexenyl, methoxydihydropyranyl, methoxydihydrofuranyl, methoxytetrahydropyridinyl and the others.

The term "alkyl group substituted with optionally substituted aromatic ring group" used herein means the above-mentioned alkyl group wherein one, two or more hydrogen atoms are substituted with "optionally substituted aromatic ring group". Specific examples thereof include an alkyl group having one to six carbon atoms wherein any hydrogen atoms are substituted with optionally substituted aromatic ring groups such as phenyl, pyridyl, oxazolyl, thiazolyl and pyrazolyl. Specific examples of substituents of said optionally substituted aromatic ring group include methoxy, methanesulfonyl, dimethylamino, cyano and the others.

The term "alkoxy group substituted with optionally substituted aromatic ring group" used herein means a group wherein the above-mentioned "alkyl group substituted with optionally substituted aromatic ring group" is attached to an oxygen atom.

The term "alkylthio group substituted with optionally substituted aromatic ring group" used herein means a group wherein the above-mentioned alkyl group substituted with optionally substituted aromatic ring group is attached to a sulfur atom.

The term "saturated aliphatic ring group substituted with oxo group" used herein means the above-mentioned saturated aliphatic ring group wherein one to two hydrogen atoms are replaced with oxo groups. Specific examples thereof include 2-oxocyclopentyl, 3-oxocyclopentyl, 2-oxocyclohexyl, 3-oxocyclohexyl, 4-oxocyclohexyl, 2-oxopyrrolidinyl, 3-oxopyrrolidinyl, 2,5-dioxopyrrolidinyl, 2-oxopiperidinyl, 3-oxopiperidinyl, 4-oxopiperidinyl, 2,6-dioxopiperidinyl, 2-oxopiperazinyl, 3-oxopiperazinyl, 2-oxomorpholinyl, 2-oxothiomorpholinyl, oxoimidazolidinyl, dioxoimidazolidinyl, oxazolidinyl, dioxazolidinyl, dioxothiazolidinyl and the others. Preferred examples thereof include 4-oxocyclohexyl, 2-oxopyrrolidinyl, 3-oxopyrrolidinyl, 2-oxopiperazinyl and 3-oxopiperazinyl.

The term "unsaturated aliphatic ring group substituted with oxo group" used herein means the above-mentioned unsaturated aliphatic ring group wherein one to two oxo hydrogen atoms are replaced with oxo groups. Specific examples thereof include oxocyclopentenyl, oxocyclohexenyl, oxopyrrolinyl, oxoimidazolinyl, oxo-oxazolidinyl, oxothiazolinyl, oxodihydropyridinyl, oxotetrahydropyridinyl and the others. Preferred examples thereof include oxopyrrolinyl, oxoimidazolinyl, oxodihydropyridinyl and oxotetrahydropyridinyl.

Any groups other than the above-mentioned groups are defined and exemplified similarly to the above-mentioned exemplification. Also, the term "aliphatic ring group" means an alicyclic group.

Each group used herein is explained.

Hereinafter, any groups described in formula (I) are explained.

$R^a$ represents a hydrogen atom or a $C_{1-6}$ alkyl optionally substituted with hydroxy group or halogen atom, preferably a hydrogen atom or a $C_{1-3}$ alkyl group optionally substituted with hydroxy group or fluorine atom, and more preferably a hydrogen atom, methyl, ethyl, trifluoromethyl, difluoromethyl, hydroxymethyl or hydroxyethyl.

$R^b$ represents a hydrogen atom, a $C_{1-6}$ alkyl optionally substituted with hydroxy group or halogen atom, a benzyl group optionally substituted with methoxy group or nitro group or a $C_{3-6}$ cycloalkyl group optionally substituted with hydroxy group or halogen atom, preferably a hydrogen atom, a $C_{1-6}$ alkyl group optionally substituted with hydroxy group or halogen atom or a benzyl group optionally substituted with methoxy group or nitro group, and more preferably a hydrogen atom or a $C_{1-3}$ alkyl group optionally substituted with hydroxy group or fluorine atom.

Also, $R^b$ represents preferably a $C_{1-6}$ alkyl group optionally substituted with hydroxy group or halogen atom, more preferably a $C_{1-3}$ alkyl group optionally substituted with hydroxy group or fluorine atom.

$R^{b2}$ represents a hydrogen atom, a $C_{1-6}$ alkyl group (said alkyl group may be optionally substituted with hydroxy group, —$NR^aR^b$ or halogen atom), a benzyl group (said benzyl group may be optionally substituted with methoxy group or nitro group) or a $C_{3-6}$ cycloalkyl group (said cycloalkyl group may be optionally substituted with hydroxy group or halogen atom), preferably a hydrogen atom, a $C_{1-6}$ alkyl group (said alkyl group may be optionally substituted with hydroxy group, —$NR^aR^b$ or fluorine atom) or a $C_{3-6}$ cycloalkyl group (said cycloalkyl group may be optionally substituted with hydroxy group or fluorine atom), more preferably a hydrogen atom or a $C_{1-6}$ alkyl group (said alkyl group may be optionally substituted with hydroxy group or —$NR^aR^b$).

$R^{b3}$ represents a hydrogen atom, a phenyl group (said phenyl group may be optionally substituted with halogen atom), a $C_{1-6}$ alkyl group (said alkyl group may be optionally substituted with hydroxy group or halogen atom) or a $C_{3-6}$ cycloalkyl group (said cycloalkyl group may be optionally substituted with hydroxy group or halogen atom), preferably a hydrogen atom, a phenyl group (said phenyl group may be optionally substituted with fluorine atom or chlorine atom), a $C_{1-6}$ alkyl group (said alkyl group may be optionally substituted with hydroxy group or fluorine atom), or a $C_{3-6}$ cycloalkyl group (said cycloalkyl group may be optionally substituted with hydroxy group or fluorine atom), and more preferably a $C_{1-6}$ alkyl group (said alkyl group may be optionally substituted with hydroxy group) or a $C_{3-6}$ cycloalkyl group (said cycloalkyl group may be optionally substituted with hydroxy group).

$R^{b4}$ represents a hydrogen atom, a phenyl group (said phenyl group may be optionally substituted with halogen atom), a $C_{1-6}$ alkyl group (said alkyl group may be optionally substituted with hydroxy group or halogen atom), a $C_{3-6}$ cycloalkyl group (said cycloalkyl group may be optionally substituted with hydroxy group or halogen atom) or an 2-isopropyl-5-methylcyclohexyl, preferably a hydrogen atom, a phenyl group (said phenyl group may be optionally substituted with fluorine atom or chlorine atom), a $C_{1-6}$ alkyl group (said alkyl group may be optionally substituted with hydroxy group or fluorine atom), a $C_{3-6}$ cycloalkyl group (said cycloalkyl group may be optionally substituted with hydroxy group or fluorine atom) or an 2-isopropyl-5-methylcyclohexyl, more preferably a phenyl group (said phenyl group may be optionally substituted with fluorine atom or chlorine atom), a $C_{1-6}$ alkyl group (said alkyl group may be optionally substituted with hydroxy group or fluorine atom) or a $C_{3-6}$ cycloalkyl group (said cycloalkyl group may be optionally substituted with hydroxy group or fluorine atom), further more preferably a $C_{1-6}$ alkyl group (said alkyl group may be optionally hydroxy group) or a $C_{3-6}$ cycloalkyl group (said cycloalkyl group may be optionally substituted with hydroxy group).

$R^c$ and $R^d$ represent independently of each other a hydrogen atom, or a $C_{1-3}$ alkyl group optionally substituted with an $C_{1-3}$ alkoxy group, cyano group, hydroxy group or halogen atom, or alternatively combine each other together with N to which they are attached and optionally together with further one to two heteroatoms independently selected from the group consisting of N, O and S to represent four to six-membered saturated or unsaturated aliphatic ring group (said aliphatic ring group may be optionally substituted at substitutable positions with $C_{1-6}$ alkyl group (said alkyl group may be optionally substituted with hydroxy, —$NR^aR^b$, —$NR^aC(=O)OR^h$, or $NR^aC(=O)R^h$), $C_{1-3}$ alkoxy group, —$NR^aR^b$ group, —$NR^aC(=O)OR^h$ group, —$NR^aC(=O)R^h$ group, —$C(=O)OR^a$ group, hydroxy group, halogen atom or oxo group), preferably $R^c$ and $R^d$ represent independently of each other a hydrogen atom or a $C_{1-3}$ alkyl group optionally substituted with hydroxy group or fluorine atom, or alternatively combine each other together with one to two heteroatoms independently selected from the group consisting of N and O to represent a four to six-membered saturated heteroaliphatic ring group (said aliphatic ring group may be optionally substituted at substitutable positions with $C_{1-3}$ alkyl group, hydroxy group, fluorine atom or oxo group), and more preferably $R^c$ and $R^d$ represent independently of each other a hydrogen atom or a $C_{1-3}$ alkyl group optionally substituted with hydroxy group or fluorine atom, or alternatively combine each other to represent a saturated heteroaliphatic ring group selected from the group consisting of azetidine, pyrrolidine, piperidine, piperazine and morpholine (said aliphatic ring group may be optionally substituted at substitutable positions with $C_{1-3}$ alkyl group, hydroxy group or fluorine atom), also, preferably, $R^c$ and $R^d$ represent independently of each other a hydrogen atom or a $C_{1-3}$ alkyl group (said alkyl group may be optionally substituted with $C_{1-3}$ alkoxy group, cyano group, hydroxy group or fluorine atom), or alternatively combine each other together with N to which they are attached and optionally together with further one to two heteroatoms independently selected from the group consisting of N, O and S to represent a four to six-membered saturated aliphatic ring group (said aliphatic ring group may be optionally substituted at substitutable positions with $C_{1-6}$ alkyl group (said alkyl group may be optionally substituted with hydroxy, —$NR^aR^b$, —$NR^aC(=O)OR^h$ or —$NR^aC(=O)R^h$), $C_{1-3}$ alkoxy group, —$NR^aR^b$ group, —$NR^aC(=O)OR^h$ group, —$NR^aC(=O)R^h$ group, —$C(=O)OR^a$ group, hydroxy group, fluorine atom or oxo group), more preferably, $R^c$ and $R^d$ represent independently of each other a hydrogen atom or a $C_{1-3}$ alkyl group (said alkyl group may be optionally substituted with methoxy, cyano, hydroxy or fluorine) or alternatively combine each other to represent a saturated heteroaliphatic ring group selected from the group consisting of azetidine, pyrrolidine, piperidine, piperazine and morpholine (said aliphatic ring group may be optionally substituted at substitutable positions with $C_{1-6}$ alkyl group (said alkyl group may be optionally substituted with hydroxy, —$NR^aR^b$ or —$NR^aC(=O)R^h$), methoxy group, —$NR^aR^b$ group, —$NR^aC(=O)R^h$ group, hydroxy group, fluorine atom or oxo group).

$R^{c2}$ and $R^{d2}$ represent independently of each other a hydrogen atom or a $C_{1-3}$ alkyl group (said alkyl group may be optionally substituted with phenyl group optionally substituted with methoxy, —$NR^aR^b$ group, —$NR^aC(=O)OR^h$ group, —$NR^aC(=O)R^h$ group, $C_{1-3}$ alkoxy group, cyano group, hydroxy group or halogen atom), or alternatively combine each other together with N to which they are attached and optionally together with further one to two heteroatoms independently selected from the group consisting of N, O and S to represent a four to six-membered saturated or unsaturated aliphatic ring group (said aliphatic ring group may be optionally substituted at substitutable positions with $C_{1-6}$ alkyl group, $C_{1-3}$ alkoxy group, —$NR^aR^b$ group, —$NR^aC(=O)OR^h$ group, —$NR^aC(=O)R^h$ group, —$C(=O)OR^a$ group, hydroxy group, halogen atom or oxo group), preferably, $R^{c2}$ and $R^{d2}$ represent independently of each other to represent a hydrogen atom or a $C_{1-3}$ alkyl group (said alkyl group may be optionally substituted with phenyl group optionally substituted with methoxy, —$NR^aR^b$ group, —$NR^a(C=O)OR^h$ group, —$NR^aC(=O)R^h$ group, $C_{1-3}$ alkoxy group, cyano group, hydroxy group or fluorine atom), or alternatively combine each other together with N to which they are attached and optionally together with further one to two heteroatoms independently selected from the group consisting of N, O and S to represent a four to six-membered saturated aliphatic ring group (said aliphatic ring group may be optionally substituted at substitutable positions with $C_{1-6}$ alkyl group, $C_{1-3}$ alkoxy group, —$NR^aR^b$ group, —$NR^aC(=O)OR^h$ group, —$NR^aC(=O)R^h$ group, —$C(=O)OR^a$ group, hydroxy group, fluorine atom or oxo group), more preferably, $R^{c2}$ and $R^{d2}$ represent independently of each other a hydrogen atom or a $C_{1-3}$ alkyl group (said alkyl group may be optionally substituted with —$NR^aR^b$, —$NR^aC(=O)R^h$, methoxy, cyano, hydroxy or fluorine) or alternatively combine each other to represent a saturated heteroaliphatic ring group selected from the group consisting of azetidine, pyrrolidine, piperidine, piperazine, morpholine, oxazolidine and imidazolidine (said aliphatic ring group may be optionally substituted at substitutable positions with methoxy, —$NR^aR^b$, —$NR^aC(=O)R^h$, hydroxy, fluorine or oxo).

$R^e$ represents a hydrogen atom, a $C_{1-6}$ alkyl group (said alkyl group may be optionally substituted with hydroxy group, cyano group, halogen atom, $C_{1-3}$ alkoxy group or —$NR^cR^d$ group), an -A group, a —$C(=O)$-A group, a $C_{1-6}$ alkylcarbonyl group (the alkyl moiety of said alkylcarbonyl group may be optionally substituted with hydroxy group, halogen atom, cyano group, $C_{1-3}$ alkoxy group or —$NR^cR^d$ group), a $C_{1-6}$ alkoxycarbonyl group (the alkyl moiety of said alkoxycarbonyl group may be optionally substituted with hydroxy group or halogen atom), —$C(=O)NR^cR^d$ group or —$S(=O)_mR^b$ group, preferably, represents a $C_{1-6}$ alkyl group (said alkyl group may be optionally substituted with hydroxy group, cyano group, fluorine atom, $C_{1-3}$ alkoxy group, or —$NR^cR^d$ group), an -A group, a —$C(=O)$-A group, a $C_{1-6}$ alkylcarbonyl group (the alkyl moiety of the alkylcarbonyl group may be optionally substituted with hydroxy group or halogen atom), a —$C(=O)NR^cR^d$ group or a —$S(=O)_mR^b$ group, more preferably, represent a $C_{1-6}$ alkyl group (said alkyl group may be optionally substituted with hydroxy group or fluorine atom), an -A group, a $C_{1-6}$ alkylcarbonyl group (the alkyl moiety of said alkylcarbonyl group may be optionally substituted with hydroxy group or fluorine atom) or a —$S(=O)_2R^b$ group.

$R^f$ represents a hydrogen atom, a hydroxy group, a $C_{1-6}$ alkyl group (said alkyl group may be optionally substituted with hydroxy group, cyano group, halogen atom group, $C_{1-3}$ alkoxy group or —$NR^cR^d$ group), a $C_{1-3}$ alkoxy group (said alkoxy group may be optionally substituted with phenyl group optionally substituted with methoxy or nitro, hydroxy group, cyano group, halogen atom, $C_{1-3}$ alkoxy group or —$NR^cR^d$ group), an -A group or a —$NR^aR^i$ group; preferably, represents a hydrogen atom, a hydroxy group, a $C_{1-3}$ alkyl group, a $C_{1-3}$ alkoxy group, an -A group or a —$NR^aR^i$ group; and more preferably, represents a hydroxy group, an -A group or a —$NR^aR^i$ group.

$R^g$ represents a hydroxy group, a chlorine atom, a $C_{1-6}$ alkyl group (said alkyl group may be optionally substituted with hydroxy group, cyano group, halogen atom, $C_{1-3}$ alkoxy group or —$NR^cR^d$ group), an -A group or a —$NR^aR^i$ group; preferably, represents a chlorine atom, a $C_{1-6}$ alkyl group (said alkyl group may be optionally substituted with hydroxy group, cyano group or fluorine atom), an -A group or a —$NR^aR^i$ group; and more preferably, represents a $C_{1-3}$ alkyl group (said alkyl group may be optionally substituted with cyano group or fluorine atom), an -A group or a —$NR^aR^i$ group.

Also, $R^g$ represents preferably a hydroxy group, a $C_{1-3}$ alkyl group (said alkyl group may be optionally substituted with hydroxy group, fluorine atom, or —$NR^cR^d$ group), a chlorine atom, an -A group or a —$NR^aR^i$ group.

$R^{g2}$ represents a hydroxy group, a chlorine atom, a $C_{1-6}$ alkyl group (said alkyl group may be optionally substituted with hydroxy group, cyano group, halogen atom, $C_{1-3}$ alkoxy group or —$NR^cR^d$ group) or an -A group; preferably represents a hydroxy group or a $C_{1-3}$ alkyl group (said alkyl group may be optionally substituted with hydroxy group or fluorine atom), a chlorine atom or an -A group; and more preferably represents a hydroxy group or a $C_{1-3}$ alkyl group (said alkyl group may be optionally substituted with hydroxy group or fluorine atom).

$R^{g3}$ represents a $C_{1-6}$ alkyl group (said alkyl group may be optionally substituted with hydroxy group, cyano group, halogen atom, $C_{1-3}$ alkoxy group or —$NR^cR^d$ group) or an -A group; preferably represent a $C_{1-6}$ alkyl group (said alkyl group may be optionally substituted with hydroxy group, fluorine atom or —$NR^cR^d$ group).

$R^h$ represents a $C_{1-6}$ alkyl group optionally substituted with hydroxy group or halogen atom, preferably a $C_{1-3}$ alkyl group optionally substituted with hydroxy group or fluorine atom, and more preferably methyl, ethyl or trifluoroethyl.

$R^i$ represents a hydrogen atom or a $C_{1-6}$ alkyl group (said alkyl group may be optionally substituted with hydroxy group, cyano group, halogen atom, $C_{1-3}$ alkoxy group, $C_{3-6}$ cycloalkyl group or —$NR^cR^d$ group), an -A group, a —$C(=O)R^b$ group, a —$C(=O)R^h$ group, a —$C(=O)$A group or a $C_{1-6}$ alkylcarbonyl group (the alkyl moiety of the alkylcarbonyl group may be optionally substituted with hydroxy group, halogen atom, cyano group, $C_{1-3}$ alkoxy group or —$NR^cR^d$ group); preferably represents a hydrogen atom or a $C_{1-6}$ alkyl group (said alkyl group may be optionally substituted with hydroxy group, cyano group, fluorine atom, $C_{1-3}$ alkoxy group, $C_{3-6}$ cycloalkyl group or —$NR^cR^d$ group) or an -A group; more preferably represent a $C_{1-6}$ alkyl group (said alkyl group may be optionally substituted with hydroxy group, $C_{1-3}$ alkoxy group or fluorine atom) or an -A group.

A represents a five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —$C(=O)OH$ group or —$NR^cR^d$ group) or a three to six-membered saturated or four to six-membered unsaturated-aliphatic ring group each optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —C(=O)OH group, —NR$^c$R$^d$ group or an oxo group), preferably, represents an optionally substituted aromatic ring group selected from the group consisting of phenyl, imidazolyl, pyridyl, pyrazinyl, oxazolyl, isoxazolyl, pyrazolyl, thiazolyl, isothiazolyl, pyrimidinyl, oxadiazolyl, thiadiazolyl, triazolyl and tetrazolyl (said aromatic ring group may be optionally substituted with $C_{1-3}$ alkyl group optionally substituted with hydroxy or halogen, $C_{1-3}$ alkoxy group optionally substituted with hydroxy or halogen, hydroxy group, halogen atom, cyano group, —C(=O)OH group or —NR$^c$R$^d$ group) or an optionally substituted saturated aliphatic ring group selected from the group consisting of cyclopropyl, cyclobutyl, cyclopentyl, cyclohexyl, pyranyl, azetidinyl, pyrrolidinyl, piperidinyl, pyrrolinyl, dihydropyridinyl and tetrahydropyridinyl (said aliphatic ring group may be optionally substituted with $C_{1-3}$ alkyl group optionally substituted with hydroxy or halogen, $C_{1-3}$ alkoxy group optionally substituted with hydroxy or halogen, hydroxy group, halogen atom, cyano group, —C(=O)OH group, —NR$^c$R$^d$ group or oxo group), and more preferably, represents aromatic heterocyclic group selected from the group consisting of imidazolyl, oxazolyl, isoxazolyl, pyrazolyl, thiazolyl, isothiazolyl, oxadiazolyl, thiadiazolyl, triazolyl and tetrazolyl (said aromatic heterocyclic group may be optionally substituted with $C_{1-3}$ alkyl group optionally substituted with hydroxy or fluorine, $C_{1-3}$ alkoxy group optionally substituted with hydroxy or fluorine, hydroxy group, fluorine atom, cyano group, —C(=O)OH group or —NR$^c$R$^d$ group) or a saturated aliphatic ring group selected from the group consisting of cyclopropyl, cyclobutyl, cyclopentyl, cyclohexyl, pyranyl, azetidinyl, pyrrolidinyl and piperidinyl (said aliphatic ring group may be optionally substituted with $C_{1-3}$ alkyl group optionally substituted with hydroxy or fluorine, $C_{1-3}$ alkoxy group optionally substituted with hydroxy or fluorine, hydroxy group, fluorine atom, cyano group, —C(=O)OH group, —NR$^c$R$^d$ group or oxo group), further more preferably represents a saturated aliphatic ring group selected from the group consisting of cyclopropyl, cyclobutyl, cyclopentyl, cyclohexyl, pyranyl, azetidinyl, pyrrolidinyl and piperidinyl (said aliphatic ring group may be optionally substituted with $C_{1-3}$ alkyl group optionally substituted with hydroxy or fluorine, $C_{1-3}$ alkoxy group optionally substituted with hydroxy or fluorine atom, hydroxy group, fluorine atom, cyano group, —C(=O)OH group or —NR$^c$R$^d$ group).

Also, preferably, A represents an aromatic ring group selected from the group consisting of phenyl, pyridyl and tetrazolyl (said aromatic ring group may be optionally substituted at substitutable positions with hydroxy or fluorine), or an aliphatic ring group selected from the group consisting of cyclopropyl, cyclobutyl, cyclopentyl, cyclohexyl, pyranyl, azetidinyl, pyrrolidinyl, piperidinyl, piperazinyl and morpholinyl (said aliphatic ring group may be optionally substituted at substitutable positions with $C_{1-3}$ alkyl group, $C_{1-3}$ alkoxy group, hydroxy group, fluorine atom, —NR$^c$R$^d$ or oxo group).

Preferred one embodiment with respect to a combination of the above-mentioned each group include the followings:

$R^a$ represents a hydrogen atom or a $C_{1-6}$ alkyl group optionally substituted with hydroxy group or halogen atom;

$R^b$ represents a $C_{1-6}$ alkyl group optionally substituted with hydroxy group or halogen atom;

$R^{b2}$ represents a hydrogen atom, a $C_{1-6}$ alkyl group (said alkyl group may be optionally substituted with hydroxy group, —NR$^a$R$^b$ group or fluorine atom) or a $C_{3-6}$ cycloalkyl group (said cycloalkyl group may be optionally substituted with hydroxy group or fluorine atom);

$R^{b3}$ represents a hydrogen atom, a phenyl group (said phenyl group may be optionally substituted with fluorine atom or chlorine atom), a $C_{1-6}$ alkyl group (said alkyl group may be optionally substituted with hydroxy group or fluorine atom) or a $C_{3-6}$ cycloalkyl group (said cycloalkyl group may be optionally substituted with hydroxy group or fluorine atom);

$R^{b4}$ represents a hydrogen atom, a phenyl group (said phenyl group may be optionally substituted with fluorine atom or chlorine atom), a $C_{1-6}$ alkyl group (said alkyl group may be optionally substituted with hydroxy group or fluorine atom), a $C_{3-6}$ cycloalkyl group (said cycloalkyl group may be optionally substituted with hydroxy group or fluorine atom) or a residue of menthol group;

$R^c$ and $R^d$ represent independently of each other a hydrogen atom or a $C_{1-3}$ alkyl group (said alkyl group may be optionally substituted with $C_{1-3}$ alkoxy group, cyano group, hydroxy group or fluorine atom), or alternatively may combine each other together with N to which they are attached and optionally together with further one to two heteroatoms independently selected from the group consisting of N, O and S to form a four to six-membered saturated aliphatic ring group (said aliphatic ring group may be optionally substituted at substitutable positions with $C_{1-6}$ alkyl group (said alkyl group may be optionally substituted with hydroxy group, —NR$^a$R$^b$ group, —NR$^a$C(=O)OR$^h$ group, or NR$^a$C(=O)R$^h$ group), a $C_{1-3}$ alkoxy group, a —NR$^a$R$^b$ group, a —NR$^a$C(=O)OR$^a$ group, a —NR$^a$C(=O) R$^a$ group, a —C(=O)OR$^a$ group, a hydroxy group, a fluorine atom or an oxo group);

$R^{c2}$ and $R^{d2}$ represent independently of each other a hydrogen atom or a $C_{1-3}$ alkyl group (said alkyl group may be optionally substituted with phenyl group optionally substituted with methoxy, —NR$^a$R$^b$ group, —NR$^a$C(=O)OR$^h$ group, —NR$^a$C(=O)R$^h$ group, $C_{1-3}$ alkoxy group, cyano group, hydroxy group or fluorine atom), or alternatively may combine each other together with N to which they are attached and optionally together with further one to two heteroatoms independently selected from the group consisting of N, O and S to form a four to six-membered saturated aliphatic ring group (said aliphatic ring group may be optionally substituted at substitutable positions with $C_{1-6}$ alkyl group, $C_{1-3}$ alkoxy group, —NR$^a$R$^b$ group, —NR$^a$C(=O)OR$^h$ group, —NR$^a$C(=O)R$^h$ group, —C(=O)OR$^a$ group, hydroxy group, fluorine atom or oxo group);

$R^e$ represents a $C_{1-6}$ alkyl group (said alkyl group may be optionally substituted with hydroxy group or fluorine atom), an -A group, a $C_{1-6}$ alkylcarbonyl group (the alkyl moiety of said alkylcarbonyl group may be optionally substituted with hydroxy group or fluorine atom) or a —S(=O)$_2$R$^b$ group;

$R^f$ represents a hydroxy group, an -A group or a —NR$^a$R$^i$ group;

$R^g$ represents a hydroxy group, a $C_{1-3}$ alkyl group (said alkyl group may be optionally substituted with hydroxy group, fluorine atom or —NR$^c$R$^d$ group), a chlorine atom, an -A group or a —NR$^a$R$^i$ group;

$R^{g2}$ represents a hydroxy group or a $C_{1-3}$ alkyl group (said alkyl group may be optionally substituted with hydroxy group or fluorine atom), a chlorine atom or an -A group;

$R^{g3}$ represents a $C_{1-6}$ alkyl group (said alkyl group may be optionally substituted with hydroxy group, fluorine atom or —NR$^c$R$^d$ group);

$R^h$ represents a $C_{1-3}$ alkyl group optionally substituted with hydroxy group or fluorine atom;

$R^i$ represents a $C_{1-6}$ alkyl group (said alkyl group may be optionally substituted with hydroxy group, $C_{1-3}$ alkoxy group or fluorine atom) or an -A group;

A represents an aromatic ring group selected from the group consisting of phenyl, pyridyl and tetrazolyl (said aromatic ring group may be optionally substituted at substitutable positions with hydroxy group or fluorine atom) or an aliphatic ring group selected from the group consisting of cyclopropyl, cyclobutyl, cyclopentyl, cyclohexyl, pyranyl, azetidinyl, pyrrolidinyl, piperidinyl, piperazinyl and morpholinyl (said aliphatic ring group may be optionally substituted at substitutable positions with $C_{1-3}$ alkyl group, $C_{1-3}$ alkoxy group, hydroxy group, fluorine atom, —$NR^cR^d$ group or oxo group); and m is an integer of 1 or 2.

$R^1$ represents a hydrogen atom, a $C_{1-10}$ alkyl group, a $C_{2-6}$ alkene group, or a three to six-membered saturated- or four- to six-membered unsaturated-aliphatic ring group each optionally containing one to two heteroatoms independently selected from the group consisting of N, O and S, wherein said alkyl group and said alkene group may be optionally substituted at substitutable positions with one or multiple substituents selected from the group consisting of Substituent List 1:

(1) hydroxy group,
(2) halogen atom,
(3) cyano group,
(4) $C_{1-6}$ alkoxy group (said alkoxy group may be optionally substituted with
  hydroxy group,
  halogen atom,
  cyano group,
  —$C(=O)OR^b$,
  —$C(=O)NR^cR^d$,
  five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —$NR^aC(=O)R^b$ group, —$NR^aC(=O)NR^cR^d$ group, —$NR^aS(=O)_mR^b$ group, —$C(=O)OR^b$ group, —$C(=O)NR^cR^d$ group, —$S(=O)_mNR^cR^d$ group, —$S(=O)_mR^b$ group or —$NR^cR^d$ group) or
  three to six-membered saturated- or four to six-membered unsaturated-aliphatic ring group each optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —$NR^aC(=O)R^b$ group, —$NR^aC(=O)NR^cR^d$ group, —$NR^aS(=O)_mR^b$ group, —$C(=O)OR^b$ group, —$C(=O)NR^cR^d$ group, —$NR^cR^d$ group or oxo group),
(5) $C_{1-6}$ alkylthio group (said alkylthio group may be optionally substituted at substitutable positions with
  hydroxy group,
  halogen atom,
  cyano group,
  —$C(=O)OR^b$,
  —$C(=O)NR^cR^d$,
  five to six-membered aromatic ring group optionally containing one to four heteroatoms independently selected from the group consisting of N, O and S (said aromatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —$NR^aC(=O)R^b$ group, —$NR^aC(=O)NR^cR^d$ group, —$NR^aS(=O)_mR^b$ group, —$C(=O)OR^b$ group, —$C(=O)NR^cR^d$ group, —$S(=O)_mNR^cR^d$ group, —$S(=O)_mR^b$ group or —$NR^cR^d$ group) or
  three to six-membered saturated- or four to six-membered unsaturated-aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —$NR^aC(=O)R^b$ group, —$NR^aC(=O)NR^cR^d$ group, —$NR^aS(=O)_mR^b$ group, —$C(=O)OR^b$ group, —$C(=O)NR^cR^d$ group, —$NR^cR^d$ group or oxo group),
(6) five to six-membered aromatic ring group optionally containing one to four heteroatoms independently selected from the group consisting of N, O and S (said aromatic ring group may be optionally substituted at substitutable positions with
  $C_{1-3}$ alkyl group optionally substituted with hydroxy or halogen,
  $C_{1-3}$ alkoxy group optionally substituted with hydroxy or halogen,
  hydroxy group,
  halogen atom,
  cyano group,
  —$NR^aC(=O)R^b$,
  —$NR^aC(=O)NR^cR^d$,
  —$NR^aS(=O)_mR^b$,
  —$C(=O)OR^b$,
  —$C(=O)NR^cR^d$,
  —$S(=O)_mNR^cR^d$,
  —$S(=O)_mR^b$ or
  —$NR^cR^d$),
(7) three to six-membered saturated- or four to six-membered unsaturated-aliphatic ring group each optionally containing one to two heteroatoms independently selected from the group consisting of N, O and S (said aliphatic ring group may be optionally substituted at substitutable positions with
  $C_{1-3}$ alkyl group (said alkyl group may be optionally substituted with hydroxy, halogen, cyano, —$NR^aC(=O)R^b$, —$NR^aC(=O)NR^cR^d$, —$NR^aS(=O)_mR^b$, —$C(=O)OR^b$, —$C(=O)NR^cR^d$ or —$NR^cR^d$),
  $C_{1-3}$ alkoxy group optionally substituted with hydroxy or halogen,
  hydroxy group,
  halogen atom,
  cyano group,
  —$NR^aC(=O)R^b$,
  —$NR^aC(=O)NR^cR^d$,
  —$NR^aS(=O)_mR^b$,
  —$C(=O)OR^b$,
  —$C(=O)NR^cR^d$,
  —$C(O)R^b$, —S(=O)$_m$NR$^c$R$^d$,
—S(=O)$_m$R$^b$,
—NR$^c$R$^d$ or
oxo group),
(8) —NR$^a$R$^e$ group,
(9) —OC(=O)NR$^c$R$^d$ group,
(10) —C(=O)R$^f$ group,
(11) —S(=O)$_m$R$^g$ group,
(12) thiol group,
(13) nitro group and
(14) —OR$^e$ group,
wherein said saturated or unsaturated aliphatic ring group may be optionally substituted at substitutable positions with one or multiple substituents selected from the group consisting of
Substituent List 2:
(1) hydroxy group,
(2) halogen atom,
(3) cyano group,
(4) C$_{1-6}$ alkyl group (said alkyl group may be optionally substituted at substitutable positions with
hydroxy group,
halogen atom,
cyano group,
five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ or —NR$^c$R$^d$ group) or
three to six-membered saturated aliphatic ring group optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group),
(5) C$_{1-6}$ alkoxy group (said alkoxy group may be optionally substituted at substitutable positions with
hydroxy group,
halogen atom,
cyano group,
five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$R$^b$ group or —NR$^a$R$^d$ group) or
three to six-membered saturated aliphatic ring group optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group),
(6) C$_{1-6}$ alkylthio group (said alkylthio group may be optionally substituted at substitutable positions with
hydroxy group,
halogen atom,
cyano group,
five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
three to six-membered saturated aliphatic ring group optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group),
(7) five to six-membered aromatic ring group optionally containing one to four heteroatoms independently selected from the group consisting of N, O and S (said aromatic ring group may be optionally substituted at substitutable positions with
C$_{1-3}$ alkyl group optionally substituted with hydroxy or halogen,
C$_{1-3}$ alkoxy group optionally substituted with hydroxy or halogen,
hydroxy group,
halogen atom,
cyano group,
—NR$^a$C(=O)R$^b$,
—NR$^a$S(=O)$_m$R$^b$,
—C(=O)OR$^b$,
—C(=O)NR$^c$R$^d$,
—S(=O)$_m$NR$^c$R$^d$,
—S(=O)$_m$R$^b$ or
—NR$^c$R$^d$),
(8) three- to six-membered saturated aliphatic ring group optionally containing one to two heteroatoms independently selected from the group consisting of N, O and S (said aliphatic ring group may be optionally substituted at substitutable positions with
C$_{1-3}$ alkyl group optionally substituted with hydroxy or halogen,
C$_{1-3}$ alkoxy group optionally substituted with hydroxy or halogen,
hydroxy group,
halogen atom,
cyano group,
—NR$^a$C(=O)R$^b$ group,
—NR$^a$S(=O)$_m$R$^b$ group,
—C(=O)OR$^b$ group, —C(=O)NR$^c$R$^d$ group,
—NR$^c$R$^d$ group or
oxo group),
(9) —NR$^a$R$^e$ group,
(10) —OC(=O)NR$^c$R$^d$ group,
(11) —C(=O)R$^f$ group,
(12) —S(=O)$_m$R$^g$ group,
(13) thiol group,
(14) oxo group,
(15) nitro group,
(16) —NR$^a$C(=O)R$^b$ group,
(17) —NR$^a$C(=O)NR$^c$R$^d$ group,
(18) —NR$^a$S(=O)$_m$R$^b$ group,
(19) —C(=O)OR$^b$ group and
(20) —C(=O)NR$^c$R$^d$ group, R$^1$ represents preferably a C$_{1-10}$ alkyl group or a three to six-membered saturated- or four to six-membered unsaturated-aliphatic ring group each optionally containing one to two heteroatoms independently selected from the group consisting of N, O and S,
wherein
said alkyl group may be optionally substituted at substitutable positions with one substituent or multiple substituents less than three selected from the group consisting of (1) to (14) of Substituent List 1,
said saturated or unsaturated aliphatic ring group may be optionally substituted at substitutable positions with one substituent or multiple substituents less than three selected from the group consisting of (1) to (20) of Substituent List 2, R$^1$ represents more preferably a C$_{1-10}$ alkyl group or a three to six-membered saturated aliphatic ring group optionally containing one to two heteroatoms independently selected from the group consisting of N, O and S,
wherein
said alkyl group may be optionally substituted at substitutable positions with one substituent or multiple substituents less than three selected from the group consisting of (1) to (4) and (6) to (10) of Substituent List 1,
said saturated aliphatic ring group may be optionally substituted at substitutable positions with one substituent or multiple substituents less than three selected from the group consisting of (1) to (4), (7) to (12), (14), (19) and (20) of Substituent List 2, R$^1$ represents further more preferably
a C$_{1-10}$ alkyl group (said alkyl group may be optionally substituted at substitutable positions with one substituent or multiple substituents less than three selected from the group consisting of the followings:
(1) hydroxy group,
(2) fluorine atom,
(3) cyano group,
(4) C$_{1-6}$ alkoxy group (said alkoxy group may be optionally substituted at substitutable positions with
  C$_{1-3}$ alkyl group optionally substituted with hydroxy or fluorine,
  C$_{1-3}$ alkoxy group optionally substituted with hydroxy or fluorine,
  hydroxy group,
  halogen atom,
  cyano group,
  —C(=O)OH,
  —C(=O)NR$^c$R$^d$ or
  —NR$^c$R$^d$),
(6) five-membered aromatic ring group optionally containing one to four heteroatoms independently selected from the group consisting of N, O and S (said aromatic ring group may be optionally substituted at substitutable positions with
  C$_{1-3}$ alkyl group optionally substituted with hydroxy or fluorine,
  C$_{1-3}$ alkoxy group optionally substituted with hydroxy or fluorine,
  hydroxy group,
  halogen atom,
  cyano group,
  —C(=O)OH,
  —C(=O)NR$^c$R$^d$ or
  —NR$^c$R$^d$),
(7) three to six-membered saturated aliphatic ring group optionally containing one to two heteroatoms independently selected from the group consisting of N, O and S (said saturated aliphatic ring group may be optionally substituted at substitutable positions with
  C$_{1-3}$ alkyl group (said alkyl group may be optionally substituted with hydroxy group, fluorine atom, cyano, —C(=O)OH group or —C(=O)NR$^c$R$^d$),
  C$_{1-3}$ alkoxy group optionally substituted with hydroxy or fluorine,
  hydroxy group,
  fluorine atom,
  cyano group,
  —NR$^a$C(=O)R$^b$,
  —NR$^a$C(=O)NR$^c$R$^d$,
  —NR$^a$S(=O)$_m$R$^b$,
  —C(=O)OH,
  —C(=O)NR$^c$R$^d$,
  —NR$^c$R$^d$ or
  oxo group),
(8) —NR$^a$R$^e$ group and
(10) —C(=O)R$^f$ group),
or
a three to six-membered saturated aliphatic ring group optionally containing one to two heteroatoms independently selected from the group consisting of N, O and S (said saturated aliphatic ring group may be optionally substituted at substitutable positions with one substituent or multiple substituents less than three selected from the group consisting of the followings:
(1) hydroxy group,
(2) halogen atom,
(3) cyano group,
(4) C$_{1-6}$ alkyl group (said alkyl group may be optionally substituted at substitutable positions with
  hydroxy group,
  halogen atom,
  cyano group,
  five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
  three to six-membered saturated aliphatic ring group optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C (=O)R$^b$ group, —NR$^a$S(=O)$_m$R$^b$ group, —C(=O)OR$^b$ group, —C(=O)NR$^c$R$^d$ group, —NR$^c$R$^d$ group or oxo group), (7) five to six-membered aromatic ring group optionally containing one to four heteroatoms independently selected from the group consisting of N, O and S (said aromatic ring group may be optionally substituted at substitutable positions with
C$_{1-3}$ alkyl group optionally substituted with hydroxy or halogen,
C$_{1-3}$ alkoxy group optionally substituted with hydroxy or halogen,
hydroxy group,
halogen atom,
cyano group,
—NR$^a$C(=O)R$^b$,
—NR$^a$S(=O)$_m$R$^b$,
—C(=O)OR$^b$,
—C(=O)NR$^c$R$^d$,
—S(=O)$_m$NR$^c$R$^d$,
—S(=O)$_m$R$^b$ or
—NR$^c$R$^d$), (8) three to six-membered saturated aliphatic ring group optionally containing one to two heteroatoms independently selected from the group consisting of N, O and S (said aliphatic ring group may be optionally substituted at substitutable positions with
C$_{1-3}$ alkyl group optionally substituted with hydroxy or halogen,
C$_{1-3}$ alkoxy group optionally substituted with hydroxy or halogen,
hydroxy group,
halogen atom,
cyano group,
—NR$^a$C(=O)R$^b$,
—NR$^a$S(=O)$_m$R$^b$,
—C(=O)OR$^b$,
—C(=O)NR$^c$R$^d$,
—NR$^c$R$^d$ or
oxo group),
(9) —NR$^a$R$^e$ group,
(10) —OC(=O)NR$^c$R$^d$ group,
(11) —C(=O)R$^f$ group,
(12) —S(=O)$_m$R$^g$ group,
(14) oxo group,
(19) —C(=O)OR$^b$ group and
(20) —C(=O)NR$^c$R$^d$ group).

Also, R$^1$ represents preferably a C$_{1-10}$ alkyl group (said alkyl group may be optionally substituted at substitutable positions with one to three substituents selected from the group consisting of
Substituent List 8:
(1) hydroxy group,
(2) halogen atom,
(3) cyano group,
(7) three to six-membered saturated aliphatic ring group optionally containing one to two heteroatoms independently selected from the group consisting of N, O and S (said aliphatic ring group may be optionally substituted at substitutable positions with
C$_{1-3}$ alkyl group optionally substituted with hydroxy or halogen,
C$_{1-3}$ alkoxy group optionally substituted with hydroxy or halogen,
hydroxy group,
halogen atom,
cyano group,
—NR$^a$C(=O)R$^b$,
—NR$^a$S(=O)$_m$R$^b$,
—C(=O)OR$^b$,
—C(=O)NR$^c$R$^d$,
—C(=O)R$^b$,
—NR$^c$R$^d$ or
oxo group),
(8) —NR$^a$R$^e$ group,
(10) —C(=O)R$^f$ group,
(11) —S(=O)$_m$R$^g$ group and
(12) thiol group) or
a three to six-membered saturated aliphatic ring group optionally containing one to two heteroatoms independently selected from the group consisting of N, O and S (said aliphatic ring group may be optionally substituted at substitutable positions with one or multiple substituents selected from the group consisting of
Substituent List 9:
(1) hydroxy group,
(2) halogen atom,
(3) cyano group,
(4) C$_{1-6}$ alkyl group (said alkyl group may be optionally substituted at substitutable positions,
hydroxy group,
halogen atom,
cyano group,
five to six-membered aromatic ring group optionally containing one to four heteroatoms independently selected from the group consisting of N, O and S (said aromatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
three to six-membered saturated aliphatic ring group optionally containing one to two heteroatoms independently selected from the group consisting of N, O and S (said aliphatic ring group may be optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group),
(5) C$_{1-6}$ alkoxy group (said alkoxy group may be optionally substituted at substitutable positions with
hydroxy group,
halogen atom,
cyano group,
five to six-membered aromatic ring group optionally containing one to four heteroatoms independently selected from the group consisting of N, O and S (said aromatic ring group may be optionally substituted at substitutable positions with an C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or —NR$^c$R$^d$ group) or
three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —$NR^aC(=O)R^b$ group, —$NR^aS(=O)_mR^b$ group, —$C(=O)OR^b$ group, —$C(=O)NR^cR^d$ group, —$NR^cR^d$ group or oxo group)),

(11) —$C(=O)R^f$ group,
(12) —$S(=O)_mR^g$ group and
(14) oxo group.

$R^1$ represents more preferably
a $C_{1-10}$ alkyl group (said alkyl may be optionally substituted at substitutable positions with one to three substituents selected from the group consisting of
Substituent List 10:
(1) hydroxy group,
(2) halogen atom,
(7) three to six-membered saturated aliphatic ring group optionally containing one to two heteroatoms independently selected from the group consisting of N, O and S (said aliphatic ring group may be optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, —$C(=O)OR^b$ group, —$C(=O)NR^cR^d$ group, —$C(=O)R^b$ group or oxo group),
(8) —$NR^aR^e$ group and
(11) $S(=O)_2R^g$ group) or
a three to six-membered saturated aliphatic ring group optionally containing one to two heteroatoms independently selected from the group consisting of N and O (said aliphatic ring group may be optionally substituted at substitutable positions with one or multiple substituents selected from the group consisting of
Substituent List 11:
(1) hydroxy group,
(2) halogen atom,
(4) $C_{1-6}$ alkyl group (said alkyl group may be optionally substituted at substitutable positions with hydroxy or halogen),
(9) —$NR^aR^e$ group,
(11) —$C(=O)R^f$ group, and
(14) oxo group).

$R^2$ represents a hydrogen atom, a halogen atom, a cyano group, a —$NR^cR^d$ group, a —$N=CHN(CH_3)_2$ group or a $C_{1-3}$ alkyl group (said alkyl group may be optionally substituted with hydroxy, halogen, —$NR^cR^d$, —$OR^a$ or —$OC(=O)R^a$).

$R^2$ represents preferably a —$NR^cR^d$ group, a —$N=CHN(CH_3)_2$ group or a $C_{2-3}$ alkyl group (said alkyl group may be optionally substituted with hydroxy, halogen, —$NR^cR^d$, —$OR^a$ or —$OC(=O)R^a$).

$R^2$ represents more preferably a hydrogen atom, an amino group or a $C_{1-3}$ alkyl group (said alkyl group may be optionally substituted with hydroxy, halogen, —$NR^cR^d$, —$OR^a$ or —$OC(=O)R^a$), and represents further more preferably a hydrogen atom, an amino group, a methyl group or a hydroxymethyl group.

m represents an integer of one (1) or two (2) and preferably represents 2.

n represents an integer of zero (0) to two (2) and preferably represents 2.

L represents a six-membered aromatic ring group optionally containing one to four nitrogen atoms (said group may be optionally substituted at substitutable positions with halogen, —$C(=O)NR^cR^d$, —$C(=O)OR^a$, hydroxy, —$NR^cR^d$, nitro, —$NR^aC(=O)R^b$, $C_{1-6}$ alkyl or $C_{2-6}$ alkene, wherein said alkyl and said alkene may be optionally substituted independently of each other with halogen, hydroxy, —$NR^cR^d$, —$C(=O)NR^cR^d$ or —$C(=O)OR^a$), a Pyr-1 of the following formula, a Tri-1 of the following formula or an Imi-1 of the following formula:

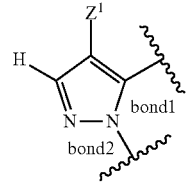
Pyr-1

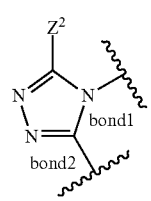
Tri-1

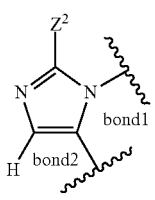
Imi-1

(in each formula, bond 1 represents a binding to uracil ring, bond 2 represents a binding to $Ar^2$, and $Z^1$, $Z^2$ and $Z^3$ represent independently of each other a cyano group, a halogen atom, a —$C(=O)NR^cR^d$ group, —$C(=O)OR^{b2}$ group, —CHO group, a nitro group, a hydroxy group, a —$NR^cR^d$ group, a —$NR^aC(=O)R^h$ group, a hydrogen atom, a —$S(=O)_mNR^{c2}R^{d2}$ group, a —$S(=O)_mNR^aC(=O)R^{b3}$ group, a —$S(=O)_mNR^aC(=O)OR^{b4}$ group, a —$S(=O)_mN-R^aC(=O)NR^aR^{b3}$ group, a —$S(=O)_mR^{g2}$ group, a —$S$—$R^{g3}$ group, a three to six-membered saturated aliphatic ring group optionally containing one to two heteroatoms independently selected from the group consisting of N, O and S, an $C_{1-6}$ alkyl group or a $C_{2-6}$ alkene group, wherein said alkyl group and said alkene group may be optionally substituted independently of each other with halogen, hydroxy, —$NR^cR^d$, —$C(=O)NR^cR^d$, —$NR^aS(=O)_mR^h$ or —$C(=O)OR^a$, and said saturated aliphatic ring group may be optionally substituted with hydroxy, halogen, $C_{1-6}$ alkyl, $C_{1-3}$ alkoxy, —$C(=O)OR^a$, —$C(=O)R^a$ or —$NR^aR^b$)).

Also, in one embodiment, in each formula, bond 1 represents a binding to uracil ring, bond 2 represents a binding to $Ar^2$, and $Z^1$, $Z^2$ and $Z^3$ may be optionally substituted independently of each other with halogen, —$C(=O)NR^cR^d$, —$C(=O)OR^a$, nitro, hydroxy, —$NR^cR^d$, —$NR^aC(=O)R^b$, hydrogen, $C_{1-6}$ alkyl or $C_{2-6}$ alkene, wherein said alkyl and said alkene may be optionally substituted independently of each other with halogen, hydroxy, —$NR^cR^d$, —$C(=O)NR^cR^d$ or —$C(=O)OR^a$).

Preferably, L represents
a six-membered unsubstituted aromatic ring group optionally containing one to two nitrogen atoms, a Pyr-1 of the following formula or a Tri-1 of the following formula:

Pyr-1

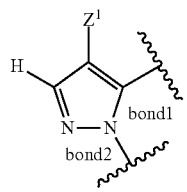

Tri-1

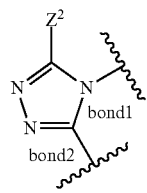

(in each formula, bond 1 represents a binding to uracil ring, bond 2 represents a binding to Ar$^2$, and Z$^1$ and Z$^2$ represent independently of each other a cyano group, a halogen atom, a —C(=O)NR$^c$R$^d$ group, a —C(=O)OR$^{b2}$ group, —CHO group, a nitro group, a hydroxy group, a —NR$^c$R$^d$ group, a —NR$^a$C(=O)R$^h$ group, a hydrogen atom, a —S(=O)$_m$NR$^{c2}$R$^{d2}$ group, a —S(=O)$_m$NR$^a$C(=O)R$^{b3}$ group, a —S(=O)$_m$NR$^a$C(=O)OR$^{b4}$ group, a —S(=O)$_m$NR$^a$C(=O)NR$^a$R$^{b3}$ group, a —S(=O)$_m$R$^{g2}$ group, a —S—R$^{g3}$ group, a three to six-membered saturated aliphatic ring group optionally containing one to two heteroatoms independently selected from the group consisting of N, O and S (said saturated aliphatic ring group may be optionally substituted with hydroxy, halogen, C$_{1-6}$ alkyl, C$_{1-3}$ alkoxy, —C(=O)OR$^a$, —C(=O)R$^a$ or —NR$^a$R$^b$), a C$_{1-6}$ alkyl group or a C$_{2-6}$ alkene group (said alkyl group and said alkene group may be optionally substituted independently of each other with halogen, hydroxy, —NR$^c$R$^d$, —C(=O)NR$^c$R$^d$, —NR$^a$S(=O)$_m$R$^h$, —C(=O)NR$^c$R$^d$ or —C(=O)OR$^a$)).

Preferably, Z$^1$ and Z$^2$ represent independently of each other a cyano group, a halogen atom, a —C(=O)NR$^c$R$^d$ group, a —C(=O)OR$^{b2}$ group, a —CHO group, a nitro group, a —NR$^a$C(=O)R$^b$ group, a hydrogen atom, a —S(=O)$_m$NR$^{c2}$R$^{d2}$ group, a —S(=O)$_m$NR$^a$C(=O)NR$^a$R$^{b3}$ group, a —S(=O)$_m$NR$^a$C(=O)OR$^{b4}$ group, a —S(=O)$_m$NR$^a$C(=O)NR$^a$R$^{b3}$ group, a —S(=O)$_m$R$^{g2}$ group, a three to six-membered saturated aliphatic ring group optionally containing one to two heteroatoms independently selected from the group consisting of N, O and S (said saturated aliphatic ring group may be optionally substituted with halogen, C$_{1-6}$ alkyl, —C(=O)OR$^a$ or —C(=O)R$^a$), or a C$_{1-6}$ alkyl group (said alkyl group may be optionally substituted with halogen, —C(=O)NR$^c$R$^d$, —NR$^a$S(=O)$_m$R$^h$, —C(=O)NR$^c$R$^d$ or —C(=O)OR$^a$).

When L represents a six-membered aromatic ring group optionally containing one to four nitrogen atoms, preferred binding position on said aromatic ring represents a binding manner in which said uracil backbone and said Ar$^2$ are attached to adjacent carbon atoms on the aromatic ring respectively as shown in the following formula (I'):

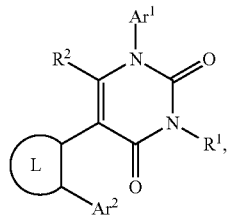

and

L represents preferably a benzene ring group, a pyridine ring group, a group of formula Pyr-1, a group of formula Tri-1 or a group of formula Imi-1, and represents more preferably a benzene ring group, a pyridine ring group, a group of formula Pyr-1 or a group of formula Tri-1. Further more preferably, L represents a group of formula Pyr-1.

Ar$^1$ represents a five to six-membered aromatic ring group optionally containing one to three heteroatoms independently selected from the group consisting of N, O and S (said aromatic ring group is substituted at one or multiple substitutable positions with C$_{1-6}$ alkyl group optionally substituted with hydroxy or halogen, C$_{1-3}$ alkoxy group optionally substituted with hydroxy or halogen, hydroxy group, halogen atom, cyano group, nitro group, phenyl group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O)R$^a$ group, —S(=O)$_m$NR$^c$R$^d$ group, —S(=O)$_n$R$^h$ group or —NR$^c$R$^d$ group), preferably, Ar$^1$ represents a benzene ring or a pyridine ring (said benzene ring and said pyridine ring are independently of each other substituted at one to three substitutable positions independently of each other with C$_{1-6}$ alkyl group optionally substituted with hydroxy or halogen, C$_{1-3}$ alkoxy group optionally substituted with hydroxy or halogen, hydroxy group, halogen atom, cyano group, nitro group, phenyl group, —C(=O)NR$^c$R$^d$ group, —C(=O)OR$^a$ group, —C(=O)R$^a$ group, —S(=O)$_n$R$^h$ group or —NR$^c$R$^d$ group), more preferably, Ar$^1$ represents a benzene ring or a pyridine ring represented by the following formula Ar$^1$-1:

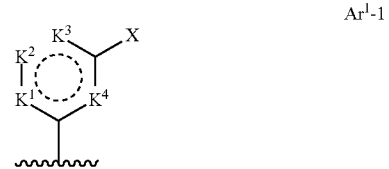

(in the formula, K$^1$, K$^2$, K$^3$ and K$^4$ represent all carbon atoms for benzene ring, or only one nitrogen atom and the remaining carbon atoms for pyridine ring, X represents a C$_{1-6}$ alkyl group optionally substituted with hydroxy or halogen, a C$_{1-3}$ alkoxy group optionally substituted with hydroxy or halogen, a hydroxy group, a halogen atom, a cyano group, a nitro group, a phenyl group, a —C(=O)NR$^c$R$^d$ group, a —C(=O)OR$^a$ group, a —C(=O)R$^a$ group, a —S(=O)$_n$R$^h$ group or a —NR$^c$R$^d$ group, said benzene ring and said pyridine ring may be optionally substituted at one to two substitutable positions of K$^1$ to K$^4$ further with C$_{1-6}$ alkyl group optionally substituted with hydroxy or halogen, C$_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group, further preferably, Ar$^1$ represents a group of the following formula Ar$^1$-10:

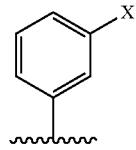

Ar$^1$-10

(in the formula, X represents a C$_{1-3}$ alkyl group optionally substituted with one to three fluorine atoms, a chlorine atom, a cyano group or a nitro group).

Ar$^2$ represents a five to six-membered aromatic ring group optionally containing one to three heteroatoms independently selected from the group consisting of N, O and S (said aromatic ring group is substituted at one or multiple substitutable positions with C$_{1-6}$ alkyl group optionally substituted with hydroxy, cyano or halogen, C$_{1-3}$ alkoxy group optionally substituted with hydroxy or halogen, hydroxy group, halogen atom, cyano group, nitro group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O)R$^a$ group, —S(=O)$_m$NR$^c$R$^d$ group, —S(=O)$_n$R$^h$ group, or —NR$^c$R$^d$ group), preferably, Ar$^2$ represents a benzene ring or a pyridine ring represented by the following formula Ar$^2$-1:

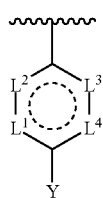

Ar$^2$-1

(in the formula, L$^1$, L$^2$, L$^3$ and L$^4$ represent all carbon atoms for benzene ring, or only one nitrogen atom and the remaining carbon atoms for pyridine ring, Y represents a C$_{1-6}$ alkyl group optionally substituted with hydroxy or halogen, a C$_{1-3}$ alkoxy group optionally substituted with hydroxy or halogen, a hydroxy group, a halogen atom, a cyano group, a nitro group, a —C(=O)NR$^c$R$^d$ group, a —C(=O)OR$^a$ group, a —C(=O)R$^a$ group, a —S(=O)$_n$R$^h$ group or a —NR$^c$R$^d$ group, said benzene ring and said pyridine ring may be optionally substituted at one to two substitutable positions of L$^1$ to L$^4$ further with C$_{1-6}$ alkyl group optionally substituted with hydroxy or halogen, C$_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group, more preferably, Ar$^2$ represents a structure wherein L$^2$ position is unsubstituted or is substituted with C$_{1-6}$ alkyl, C$_{1-3}$ alkoxy, hydroxy, halogen or —S(=O)$_n$R$^h$, further more preferably, Ar$^2$ represents a group of the following formula Ar$^2$-10:

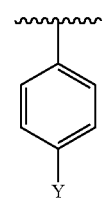

Ar$^2$-10

(in the formula, Y represents a cyano group, a chlorine atom or a nitro group).

One embodiment with respect to a preferred combination of Ar$^1$ and Ar$^2$ include the followings:

Ar$^1$ represents the following formula Ar$^1$-1:

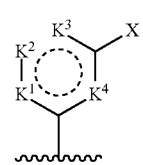

Ar$^1$-1

(in the formula, K$^1$, K$^2$, K$^3$ and K$^4$ represent all carbon atoms for benzene ring, or only one nitrogen atom and the remaining carbon atoms for pyridine ring, X represents a C$_{1-6}$ alkyl group optionally substituted with hydroxy or halogen, a C$_{1-3}$ alkoxy group optionally substituted with hydroxy or halogen, a hydroxy group, a halogen atom, a cyano group, a nitro group, a phenyl group, a —C(=O)NR$^c$R$^d$ group, a —C(=O)OR$^a$ group, a —C(=O)R$^a$ group, a —S(=O)$_n$R$^h$ group or a —NR$^c$R$^d$ group, said benzene ring and said pyridine ring may be optionally substituted at one to two substitutable positions of K$^1$ to K$^4$ further with C$_{1-6}$ alkyl group optionally substituted with hydroxy or halogen, C$_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group);

Ar$^2$ represents the following formula Ar$^2$-1:

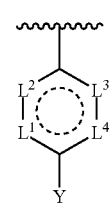

Ar$^2$-1

(in the formula, L$^1$, L$^2$, L$^3$ and L$^4$ represent all carbon atoms for benzene ring, or only one nitrogen atom and the remaining carbon atoms for pyridine ring, Y represents a C$_{1-6}$ alkyl group optionally substituted with hydroxy or halogen, a C$_{1-3}$ alkoxy group optionally substituted with hydroxy or halogen, a hydroxy group, a halogen atom, a cyano group, a nitro group, a —C(=O)NR$^c$R$^d$ group, a —C(=O)OR$^a$ group, a —C(=O)R$^a$ group, a —S(=O)$_n$R$^h$ group or a —NR$^c$R$^d$ group, said benzene ring and said pyridine ring may be optionally substituted at one to two substitutable positions of $L^1$ to $L^4$ further with $C_{1-6}$ alkyl group optionally substituted with hydroxy or halogen, $C_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group).

Examples of preferred compounds as uracil derivatives represented by formula (I) include the compounds wherein the formula (I) represents the following formula (I'''):

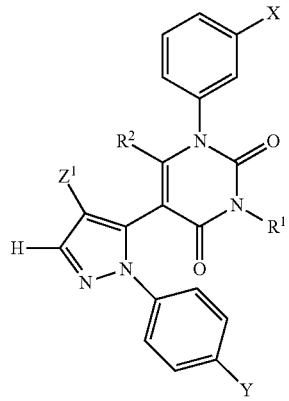

(wherein, $Z^1$ represents a cyano group, a halogen atom, a —C(=O)NR$^c$R$^d$ group, a —C(=O)OR$^{b2}$ group, a hydrogen atom, a —S(=O)$_2$NR$^{c2}$R$^{d2}$ group, a —S(=O)$_2$NR$^a$C(=O)R$^{b3}$ group, a —S(=O)$_2$NR$^a$C(=O)OR$^{b4}$ group, a —S(=O)$_2$NR$^a$C(=O)NR$^a$R$^{b3}$ group or a S(=O)$_2$R$^g$ group, X represents a $C_{1-3}$ alkyl group optionally substituted with one or multiple fluorines or a nitro group, and Y represents a cyano group, a chlorine atom or a nitro group)

or physiologically acceptable salts thereof.

The compounds or physiologically acceptable salts thereof wherein in the above-mentioned formula (I'''), $Z^1$ represents a —C(=O)NR$^c$R$^d$ group, a —C(=O)OR$^{b2}$ group, a —S(=O)$_2$NR$^{c2}$R$^{d2}$ group, a —S(=O)$_2$NR$^{a2}$C(=O)R$^{b3}$ group, a —S(=O)$_2$NR$^a$C(=O)OR$^{b4}$ group, a —S(=O)$_2$NR$^a$C(=O)NR$^a$R$^{b3}$ group, a S(=O))$_2$R$^g$ group, an iodine atom, a bromine atom or a chlorine atom, and $R^2$ represents a $C_{1-3}$ alkyl group optionally substituted with hydroxy, can exist as atropisomer.

Process of Present Compound

The Present compound represented by formula (I) or physiologically acceptable salts thereof is a novel compound, and can be prepared according to the below-mentioned processes, the below-mentioned examples or equivalent processes to known processes.

The compounds obtained by the below-mentioned processes may form salts thereof as long as they do not afford any adverse effect to an intended reaction.

[Process A]

The compounds of formula (I) is prepared according to the below-mentioned processes.

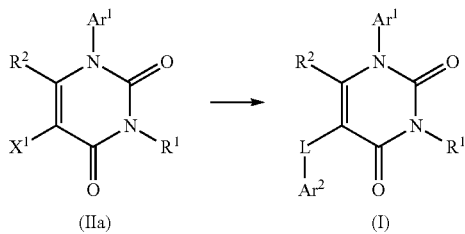

(wherein, $R^1$, $Ar^1$, L, $Ar^2$ and $R^2$ are the same as defined above, and $X^1$ represents halogen atoms (for example, chlorine atom, bromine atom and iodine atom) or an amino group)

[A-1]

When $X^1$ in compound (IIa) represents a halogen atom, the compound (I) can be prepared by performing a coupling reaction on the compound (IIa) with $Z^1$-L-$Ar^2$ (wherein $Z^1$ is a substituent on carbon atom in L ring and represents a metal substituent (for example, boronic acid, boronate ester, organotin, zinc halide, magnesium halide, organosilicon and lithium)) according to a conventional method. For example, the reaction can be achieved by performing a cross-coupling reaction on the compound (IIa) and $Z^1$-L-$Ar^2$ in appropriate solvents or under solvent-free condition in the presence of palladium catalysts (typically, tetrakis(triphenylphosphin)palladium), copper catalysts (typically, copper iodide), nickel catalysts (typically, nickel chloride-1,2-bis(diphenylphosphino)ethane complex), zinc reagents, iron chelating reagents and the others, optionally with an addition of phosphorus ligands (typically, 2,2'-bis(diphenylphosphino)-1,1-binaphthalene or 2-(di-t-butyl)phosphino biphenyl). Such coupling reactions may be carried out in the co-presence of alkali carbonates (for example, sodium carbonate, potassium carbonate or cesium carbonate), alkali phosphates (for example or potassium phosphate), organic bases (for example, triethylamine or diisopropylethylamine), alkali halides (for example, lithium chloride or cesium fluoride), alkali hydroxides (for example, sodium hydroxide) or metal alkoxides (for example, potassium t-butoxide) in addition to the above-mentioned reagents.

[A-2]

Also, when $X^1$ in compound (IIa) represents a halogen atom, the compound (I) can be prepared by converting the $X^1$ in compound (IIa) into coupling reactive group (for example, boronic acid group, zinc halide group, and magnesium halide group) followed by performing a coupling reaction on the resultant compounds with $Z^2$-L-$Ar^2$ (wherein $Z^2$ is a substituent on carbon atom in L ring and represents a halogen atom) according to a conventional method. For example, this reaction can be achieved by reacting the compound (IIa) with boron reagents (typically, bis(pinacolato)diboron reagents) and palladium catalysts (typically, tetrakis(triphenylphosphin)palladium) to prepare boron compounds, by reacting the compound (IIa) with zinc dust and alkyl magnesium reagents to prepare zinc halides, or by reacting the compound (IIa) with magnesium powder to prepare magnesium halides, respectively in appropriate solvents or under solvent-free condition, followed by performing a cross-coupling reaction on the compound (IIa) with $Z^2$-L-$Ar^2$ in the presence of palladium catalysts (typically, tetrakis(triphenylphosphin)palladium or bis(triphenylphosphine)palladium dichloride), copper catalysts (typically, copper iodide), nickel catalysts (typically, nickel chloride-1,2-bis(diphenylphosphino)ethane complex), zinc reagents, iron chelating reagents or the others, optionally with an addition of ligand compounds (for example, phosphorus ligands (typically, 2,2'-bis(diphenylphosphino)-1,1-binaphthalene or 2-(di-t-butyl)phosphino biphenyl) or organoarsenic compounds). Such coupling reactions may be carried out in the co-presence of alkali metal carbonates (for example, sodium carbonate, potassium carbonate or cesium carbonate), alkali phosphates (for example, potassium phosphate), organic bases (for example, triethylamine or diisopropylethylamine), alkali halides (for example, lithium chloride or cesium fluoride), alkali metal hydroxides (for example, sodium hydroxide) or metal alkoxides (for example, potassium t-butoxide) in addition to the above-mentioned reagents.

[A-3]

Also, when $X^1$ in compound (IIa) represents an amino group, the compound (I) can be prepared by performing a cyclization of the compound (IIa) with $Ar^2$'s carbohydrazides (i.e., $Ar^2$—C($=$O)NHNH$_2$) according to a conventional method. For example, the reaction can be achieved by reacting the compound (IIa) with $Ar^2$'s carbohydrazides in appropriate solvents or under solvent-free condition in the presence of N,N-dimethylformamide dimethyl acetal and acetic acid. For example, the compound (I) can be prepared, for example, according to the method described in Org. Lett. 2004, 17(6), 2969-2971 or the like or equivalent methods thereto (see Example 62).

[A-4]

The compound of $Z^1$-L-$Ar^2$ can be prepared by replacing $Z^3$ in the $Z^3$-L-$Ar^2$ (wherein $Z^3$ is a substituent on carbon atom in L ring and represents a halogen atom or a hydrogen atom) with various metal atoms. For example, the reaction can be carried out by reacting $Z^3$-L-$Ar^2$ with diboron reagents (for example, bis(pinacolato)diboron reagent) in the presence of palladium catalysts (typically, tetrakis(triphenylphosphin)palladium) or by reacting $Z^3$-L-$Ar^2$ with alkyl lithium reagents (for example, butyl lithium) followed by reacting the resultant compounds with trialkoxy borane reagents (for example, trimethyl borate reagent), respectively in appropriate solvents or under solvent-free condition to prepare boron reagents; by reacting $Z^3$-L-$Ar^2$ with alkyllithium reagents (for example, butyllithium) followed by reacting the resultant compounds with tin chloride reagents (for example, tributyltin chloride) in appropriate solvents or under solvent-free condition to prepare organotin reagents; by reacting $Z^3$-L-$Ar^2$ with zinc dust or diethylzinc in appropriate solvents or under solvent-free condition to prepare zinc reagents; by reacting $Z^3$-L-$Ar^2$ with magnesium powder in appropriate solvents or under solvent-free condition to prepare organomagnesium reagents; by reacting $Z^3$-L-$Ar^2$ with alkyllithium reagents (for example, butyllithium) followed by the resultant compounds with silicon reagents (for example, chlorotrimethylsilane) to prepare organosilicon reagents, respectively in appropriate solvents or under solvent-free condition; by reacting $Z^3$-L-$Ar^2$ with alkyllithium reagents (for example, butyllithium) in appropriate solvents or under solvent-free condition to prepare organolithium reagents. Alternatively, the compound of $Z^1$-L-$Ar^2$ can be prepared, for example, according to the method described in WO 2007/129962 or the like or equivalent methods thereto.

[A-5]

The compounds of $Z^1$-L-$Ar^2$, $Z^2$-L-$Ar^2$ and $Z^3$-L-$Ar^2$ can be prepared by performing a coupling reaction in Ring L and Ring $Ar^2$ using commercially available starting materials according to the similar methods to those of Process A-1.

[A-6]

Also, the compounds of $Z^1$-L-$Ar^2$, $Z^2$-L-$Ar^2$ and $Z^3$-L-$Ar^2$ can be prepared by performing a substitution reaction in the case where a binding between Ring L and Ring $Ar^2$ in the $Z^1$-L-$Ar^2$, $Z^2$-L-$Ar^2$ and $Z^3$-L-$Ar^2$ is a N—C bond. For example, the reaction can be achieved, for example, by reacting Ring $Ar^2$ containing a halogen atom as substituent with Ring L containing a NH group in the ring in appropriate solvents or under solvent-free condition in the co-presence of alkali carbonates (for example, sodium carbonate, potassium carbonate or cesium carbonate), alkali phosphates (for example or potassium phosphate), organic bases (for example, triethylamine or diisopropylethylamine), alkali metal halides (for example, lithium chloride, cesium fluoride) or alkali metal hydroxides (for example, sodium hydroxide) and the others. Also, the reaction may be achieved by performing a cross-coupling reaction on Ring L and $Z^4$—$Ar^2$ (wherein $Z^4$ is a substituent on carbon atom in $Ar^1$ ring and represents a boronic acid, a boronate ester or a halogen atom) in the presence of palladium catalysts (typically, tetrakis (triphenylphosphin)palladium or palladium acetate), copper catalysts (for example, copper iodide), zinc reagents or iron chelating reagents and the others optionally with an addition of phosphorus catalysts (for example, 2,2'-bis(diphenylphosphino)-1,1-binaphthalene or 2-(di-t-butyl)phosphinobiphenyl) or diamine reagents (typically, 1,2-diaminocyclohexane). Also, such coupling reactions may be carried out in the co-presence of alkali carbonates (for example, sodium carbonate, potassium carbonate or cesium carbonate), alkali metal phosphates (for example, potassium phosphate), organic bases (for example, triethylamine or diisopropylethylamine), alkali halides (for example, lithium chloride or cesium fluoride), alkali hydroxides (for example, sodium hydroxide), metal alkoxides (for example, potassium t-butoxide) or the others, in addition to the above-mentioned reagents. For example, the compounds can be prepared, for example, according to the method described in J. Am. Chem. Soc. 1998, 120, 827-828, J. Am. Chem. Soc. 2001, 123, 7727-7729 or J. Org. Chem. 2002, 67, 1699-1702 or equivalent methods thereto.

Also, in the case where a binding between Ring L and Ring $Ar^2$ in the $Z^1$-L-$Ar^2$, $Z^2$-L-$Ar^2$ and $Z^3$-L-$Ar^2$ is a C—N bond, the compounds of $Z^1$-L-$Ar^2$, $Z^2$-L-$Ar^2$ and $Z^3$-L-$Ar^2$ can be prepared by performing a substitution reaction on a commercially available Ring $Ar^2$ containing a NH group in the ring and a commercially available Ring L containing a halogen atom as substituent according to a conventional method. This reaction can be achieved according to the similar method to those of Process A-6.

Specific examples of solvents to be used for each reaction in Process A should be selected depending on the kind of the starting materials or the kind of reagents used and include, for example, dichloromethane, chloroform, dichloroethane, toluene, tetrahydrofuran, 1,4-dioxane, dimethoxyethane, N,N-dimethylformamide and the others, which may be used alone or as a mixed solvent thereof. The reaction temperature may be varied depending on the kind of starting materials used and the kind of reagents and the others, and includes usually within a range of −40° C. to 150° C., preferably within a range of 0° C. to 120° C., and the reaction may be optionally carried out under pressurized condition.

[Process B]

The compound of formula (I) can be prepared according to the below-mentioned processes.

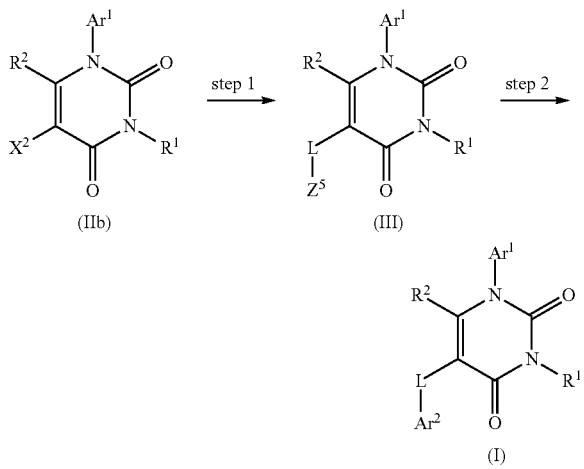

(wherein, $R^1$, $Ar^1$, L, $Ar^2$ and $R^2$ are the same as defined as above, $X^2$ represents a halogen atom (for example, iodine atom or bromine atom), and $Z^5$ represents a hydrogen atom, an amino group or a halogen atom)

[Step 1]

The compound (III) can be prepared by performing a coupling reaction on the compound (IIb) and $Z^1$-L-$Z^5$ (wherein $Z^1$ is the same as defined above, and $Z^5$ represents a hydrogen atom or a halogen atom) according to a conventional method. This reaction can be achieved according to the similar methods to those of Process A-1 (see Reference Examples 189 to 191).

Also, the compounds (III) can be prepared by converting an $X^2$ group in the compound (IIb) into coupling reactive groups (for example, boron compound group, zinc halide group or magnesium halide group) according to the similar methods to those of Process A-2 followed by performing a coupling reaction on the resultant compounds and $Z^2$-L-$Z^5$ (wherein, $Z^2$ and $Z^5$ are the same as defined above).

[Step 2]

When $Z^5$ in the compound (III) represents a halogen atom, compound (I) can be prepared by performing a coupling reaction on the compound (III) and $Z^1$—$Ar^2$ (wherein $Z^1$ is the same as defined above) according to a conventional method. This reaction can be achieved according to the similar methods to those of Process A-1 (see Examples 59 to 61).

Also, when $Z^5$ in the compound (III) represents a hydrogen atom, the compound (I) can be prepared by performing a halogenation of a L group in the compound (III), followed by performing a coupling reaction of the resultant compounds with $Z^1$—$Ar^2$. For example, this halogenation reaction can be achieved by reacting the compound (III) with halogenating agents (for example, N-iodosuccinimide, N-bromosuccinimide, iodine or bromine), and the coupling reaction can be achieved according to the similar method to those of Process A-1.

Also, when $Z^5$ in the compound (III) represents a halogen atom, the compound (I) can be prepared by converting the $Z^5$ group into coupling reactive groups (for example, boron compound group, zinc halide group or magnesium halide group) according to the similar method to those of Process A-2 followed by performing a coupling reaction on the resultant compounds and Ring $Ar^2$ wherein halogen atom is substituted.

Also, when $Z^5$ of the compound (III) represents an amino group, the compound (I) can be also prepared by converting the $Z^5$ group into halogen atom (for example, bromine atom or iodine atom) via Sandmeyer reaction according to a conventional method followed by performing a coupling reaction on the resultant compounds and $Z^1$—$Ar^2$ according to the similar method to those of Process A-1. For example, the Sandmeyer reaction can be achieved by reacting the compound (III) with nitrites (typically, sodium nitrite) and copper halides (typically, copper bromide or copper iodide) in appropriate solvents or under solvent-free condition.

Also, when L group in the compound (III) contains a NH group in the ring, that is, when a NH group is contained as a L-constituting group, the compound (I) can be prepared by performing a substitution reaction or a coupling reaction on the compound (III) and $Z^4$—$Ar^2$ (wherein $Z^4$ is the same as defined above) according to a conventional method. This reaction can be achieved according to the similar method to those of Process A-6.

In the processes, a coupling reaction between $Ar^2$ and L (step 2) can be applied to a coupling reaction in the case of a halogen atom on various substituents for $R^1$ or a halogen atom on $Ar^1$.

Specific examples of solvents to be used for each reaction in Process B should be selected depending on the kind of starting materials and the kind of reagents used and include, for example, dichloromethane, chloroform, dichloroethane, toluene, tetrahydrofuran, 1,4-dioxane, dimethoxyethane, N,N-dimethylformamide and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Process C]

The compound (I) can be prepared according to the below-mentioned processes.

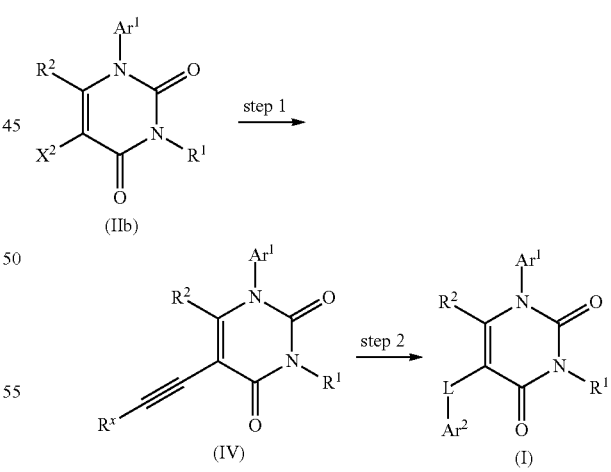

(wherein, $R^1$, $Ar^1$, L, $Ar^2$ and $R^2$ are the same as defined above, $X^2$ represents a halogen atom, $R^x$ represents —C(=O)H or —CH($OR^j$)$_2$ and $R^j$ represents an alkyl group having one to six carbon atoms)

[Step 1]

The compound (IV) can be prepared by performing a coupling reaction on the compound (IIb) and acetylene reagents according to a conventional method. For example, this reaction can be achieved by performing a cross-coupling reaction on the compound (IIb) and various acetylene reagents in appropriate solvents or under solvent-free condition in the co-presence of palladium catalyst (typically, tetrakis(triphenylphosphin)palladium), copper catalyst (typically, copper iodide), alkali carbonates (for example, sodium carbonate, potassium carbonate or cesium carbonate), alkali phosphates (for example, potassium phosphate), organic bases (for example, triethylamine or diisopropylethylamine), alkali halides (for example, lithium chloride or cesium fluoride), alkali hydroxides (for example, sodium hydroxide), metal alkoxides (for example, potassium t-butoxide) and the others (see Reference Example 61, Reference Examples 120-162).

[Step 2]

When $R^x$ in the compound (IV) represents —C(=O)H or —CH(OR$^j$)$_2$, the compound (I) wherein L represents a pyrazole ring can be prepared by performing a cyclization reaction on the compound (IV) according to a conventional method. For example, this reaction can be achieved by reacting the compound (IV) with Ar$_2$—NH—NH$_2$ in appropriate solvents or under solvent-free condition. The above-mentioned hydrazine compounds may be hydrochloride salts thereof, and the reaction may be optionally carried out in the presence of acids (for example, hydrochloric acid) (see Examples 1-29).

Also, this reaction can be achieved by isolating hydrazine compound (as shown in the hydrazine compound of the below-mentioned structure (IV)-1 that produced as a reaction intermediate) followed by performing a cyclization reaction on the resultant compounds. For example, this cyclization reaction can be achieved in the presence of acids (for example, hydrochloric acid or sulfuric acid) or Lewis acids (for example, gold chloride) (see Example 30).

Also, the compound (I) wherein L represents a pyrazole ring can be prepared by performing a cyclization reaction on the compound (IV) and hydrazines according to a conventional method followed by performing a coupling reaction on the resultant compounds and $Z^4$—Ar$^2$ (wherein $Z^4$ is the same as defined above) according to the similar method to those of Process [A-6]. The hydrazines to be used in this reaction may be hydrates or hydrochloride salts thereof and the reaction may be optionally carried out in the presence of acids (for example, hydrochloric acid) or transition metal catalysts (for example, gold(III) chloride).

When Ar$^2$ contains an amino group as a substituent, the compound of Ar$^2$—NH—NH$_2$ can be prepared by converting the amino group into the hydrazine group according to a conventional method. For example, this reaction can be achieved by reacting the compounds with sodium nitrite or nitrite esters in the presence of acids (for example, hydrochloric acid) in appropriate solvents or under solvent-free condition followed by reacting the resultant compounds with reducing agents (for example, tin(II) chloride) (see Reference Example 198).

Specific examples of solvents to be used for each step in Process C should be selected depending on the kind of starting materials and the kind of reagents used and includes, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid, and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Process D]

The compound (I) wherein $R^1$ represents an $C_{1-10}$ alkyl group substituted with C(=O)OH or S(=O)$_m$OH, an $C_{2-6}$ alkene group or a three to six-membered saturated- or four to six-membered unsaturated-aliphatic ring group each optionally containing one to two heteroatoms independently selected from the group consisting of N, O and S [the below-mentioned compound of formula (Ib)], the compounds (I) wherein $R^1$ represents an $C_{1-10}$ alkyl group substituted with C(=O)NR$^c$R$^d$, S(=O)$_m$NR$^c$R$^d$ or C(=O)OR$^b$, an $C_{2-6}$ alkene group or a three to six-membered saturated- or four to six-membered unsaturated-aliphatic ring group each optionally containing one to two heteroatoms independently selected from the group consisting of N, O and S [the below-mentioned compound of formula (Ic)] can be prepared according to the below-mentioned Processes.

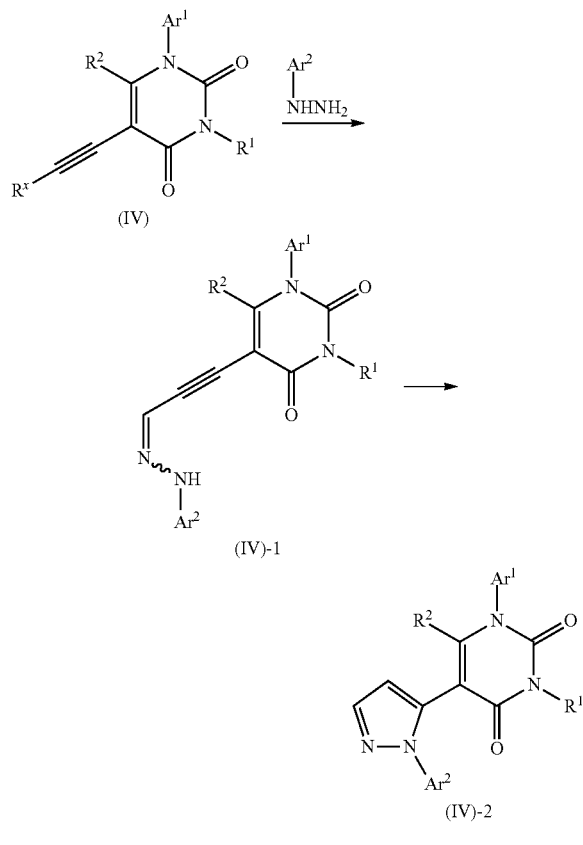

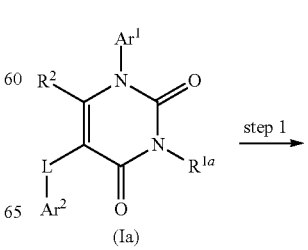

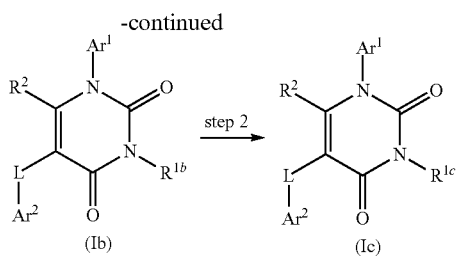

(wherein, $Ar^1$, L, $Ar^2$ and $R^2$ are the same as defined above, $R^{1a}$ represents an $C_{1-10}$ alkyl group substituted with $C(=O)OR^b$ or $S(=O)_mOR^b$, an $C_{2-6}$ alkene group or a three to six-membered saturated- or four to six-membered unsaturated-aliphatic ring group optionally containing one to two heteroatoms independently selected from the group consisting of N, O and S, $R^{1b}$ represents a $C_{1-10}$ alkyl group substituted with —C(=O)OH or —S(=O)$_m$OH, a $C_{2-6}$ alkene group or a three to six-membered saturated- or four to six-membered unsaturated-aliphatic ring group each optionally containing one to two heteroatoms independently selected from the group consisting of N, O and S, $R^{1c}$ represents a $C_{1-10}$ alkyl group substituted with C(=O)NR$^c$R$^d$, S(=O)$_m$NR$^c$R$^d$ or C(=O)OR$^b$, a $C_{2-6}$ alkene group or a three to six-membered saturated- or four to six-membered unsaturated-aliphatic ring group each optionally containing one to two heteroatoms independently selected from the group consisting of N, O and S, and $R^b$, $R^c$, $R^d$ and m are the same as defined above)

[Step 1]

The compound (Ib) can be prepared by performing a hydrolysis reaction on the compound (Ia) according to a conventional method. For example, this reaction can be achieved by performing a hydrolysis reaction in appropriate solvents or under solvent-free condition, under alkaline condition (for example, sodium hydroxide) or acidic condition (for example, hydrochloric acid) (see Examples 73 and 74).

Also, when $R^b$ in the compound (Ia) represents a benzyl group optionally substituted with nitro or methoxy, the compound (Ib) can be prepared by performing a reduction reaction on the compound (Ia) according to a conventional method. For example, this reaction can be achieved by performing the reaction with catalytic reduction reagents (for example, palladium on carbon or palladium hydroxide) in charged states of hydrogen gas or in the presence of ammonium formate in appropriate solvents or under solvent-free condition, by performing the reaction in the presence of acids (for example, trifluoroacetic acid), or by performing the reaction in the presence of oxidizing agent (for example, 2,3-dichloro-5,6-dicyano-para-benzoquinone) (see Example 72).

[Step 2]

The compound (Ic) can be prepared by performing an amidation reaction or an esterification reaction on the compound (Ib) according to a conventional method. For example, this reaction can be achieved by converting the compound (Ib) into reactive derivatives thereof (for example, active esters, anhydrides or acid halides) in appropriate solvents or under solvent-free condition followed by reacting the resultant compounds with various amines or various alcohols. Specific examples of active ester include p-nitrophenyl ester, 2,4,5-trichlorophenyl ester, N-hydroxysuccinimide ester, N-hydroxyphthalimide ester, 1-hydroxybenzotriazole ester, N-hydroxypiperidine ester, 2-pyridylthiol ester, N-methylimidazole ester and the others. The anhydrides may be used as symmetrical anhydrides or mixed anhydrides. Specific examples of mixed anhydrides include mixed anhydrides of ethyl chlorocarbonate and isovaleric acid, and the others.

Also, the compound (Ic) can be prepared by reacting the compound (Ib) with various amines and various alcohols in the presence of a condensing agent according to a conventional method. Specific examples of the condensing agent include N,N'-dicyclohexylcarbodiimide, 1-ethyl-3-(3-dimethylaminopropyl)carbodiimide.monohydrochloride, N,N'-carbonyldiimidazole, dimethylaminosulfonic acid chloride, 1-ethoxycarbonyl-2-ethoxy-1,2-dihydroquinoline, benzotriazol-1-yl-oxytris(pyrrolidino)phosphonium hexafluorophosphate and the others. These condensing agents may be used alone or in combination with peptide synthesis reagents (for example, N-hydroxysuccinimide or N-hydroxybenzotriazole) (see Examples 75-82).

The hydrolysis reaction of ester group, or the amidation reaction or esterification reaction shown in the above-mentioned processes may be applied to the case where the ester group on $Ar^1$, L, $Ar^2$ and the others is converted into a carboxyl group, an amide group or an ester group (see Examples 103-106, Examples 142-145).

Specific examples of solvents to be used for each step in Process D should be selected depending on the kind of starting materials and the kind of reagents used, and include, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid, and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Process E]

The compound (I) wherein $R^1$ represents a $C_{1-10}$ alkyl group substituted with NHR$^a$, a $C_{2-6}$ alkene group or a three to six-membered saturated- or four to six-membered unsaturated-aliphatic ring group each optionally containing one to two heteroatoms independently selected from the group consisting of N, O and S [the below-mentioned compound of formula (Ie)], the compound (I) wherein $R^1$ represents a $C_{1-10}$ alkyl group substituted with NR$^a$C(=O)R$^b$, NR$^a$C(=O)NR$^c$R$^d$ or NR$^a$S(=O)$_m$R$^b$, a $C_{2-6}$ alkene group, or a three to six-membered saturated- or four to six-membered unsaturated-aliphatic ring group each optionally containing one to two heteroatoms independently selected from the group consisting of N, O and S [the below-mentioned compound of formula (If)] can be prepared according to the below-mentioned processes.

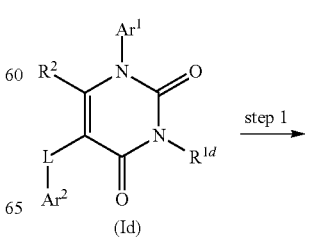

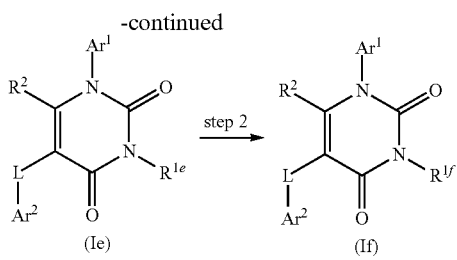

(wherein, $Ar^1$, L, $Ar^2$ and $R^2$ are the same as defined above, $R^{1d}$ represents a $C_{1-10}$ alkyl group substituted with $NR^aC(=O)OR^b$, a $C_{2-6}$ alkene group or a three to six-membered saturated- or four to six-membered unsaturated-aliphatic ring group optionally containing one to two heteroatoms independently selected from the group consisting of N, O and S, $R^{1e}$ represents a $C_{1-10}$ alkyl group substituted with $NHR^a$, a $C_{2-6}$ alkene group or a three to six-membered saturated- or four to six-membered unsaturated-aliphatic ring group optionally containing one to two heteroatoms independently selected from the group consisting of N, O and S, $R^{1f}$ represents a $C_{1-10}$ alkyl group substituted with $NR^aC(=O)R^b$, $NR^aC(=O)NR^cR^d$ or $NR^aS(=O)_mR^b$, a $C_{2-6}$ alkene group or a three to six-membered saturated- or four to six-membered unsaturated-aliphatic ring group optionally containing one to two heteroatoms independently selected from the group consisting of N, O and S, and $R^a$, $R^b$, $R^c$ and $R^d$ are the same as defined above)

[Step 1]

The compound (Ie) can be prepared by performing a deprotection of a carbamate group in the compound (Id) via a hydrolysis reaction or a reduction reaction. For example, this reaction can be achieved according to the similar method to those of [Step 1] in Process D (see Example 85).

[Step 2]

The compound (If) can be prepared by performing an amidation reaction on the compound (Ie) according to a conventional method. For example, this reaction can be achieved by reacting the compound (Ie) with active ester, anhydrides or acid halides each being derivatized from carboxylic acid derivatives and sulfonic acid derivatives in appropriate solvents or under solvent-free condition. Specific examples of the active ester include p-nitrophenyl ester, 2,4,5-trichlorophenyl ester, N-hydroxysuccinimide ester, N-hydroxyphthalimide ester, 1-hydroxybenzotriazole ester, N-hydroxypiperidine ester, 2-pyridylthiol ester, N-methylimidazole ester and the others. The anhydrides may be used as symmetrical anhydrides or mixed anhydrides. Specific examples of mixed anhydrides include a mixed anhydride of ethyl chlorocarbonate and isovaleric acid, and the others (see Example 86, Example 113).

Also, the compound (If) can be prepared by reacting the compound (Ie) with various carboxylic acids and various sulfonic acids in the presence of a condensing agent according to a conventional method. Specific examples of the condensing agent include N,N'-dicyclohexylcarbodiimide, 1-ethyl-3-(3-dimethylaminopropyl)carbodiimide monohydrochloride, N,N'-carbonyldiimidazole, dimethylaminosulfonic acid chloride, 1-ethoxycarbonyl-2-ethoxy-1,2-dihydroquinoline, benzotriazol-1-yl-oxytris(pyrrolidino)phosphonium hexafluorophosphate, and the others. These condensing agents may be used alone or in combination with peptide synthesis reagents (for example, N-hydroxysuccinimide or N-hydroxybenzotriazole).

Also, the compound (If) can be prepared by performing an urea formation on the compound (Ie) according to a conventional method. For example, this reaction can be achieved by reacting the compound (Ie) with various substituted isocyanate compounds and the others in appropriate solvents or under solvent-free condition. Also, the compound (If) can be prepared by converting the compound (Ie) into reactive derivatives thereof (for example, active carbamates) followed by reacting the resultant compounds with various amines according to a conventional method. For example, this reaction can be achieved by reacting the compound (Ie) with phenyl chloroformate, carbodiimidazole or the others followed by reacting the resultant compounds with various amines in appropriate solvents or under solvent-free condition. Such urea formation reactions may be optionally carried out in metal hydride reagents (for example, sodium hydride or potassium hydride), inorganic bases (for example, potassium carbonate or sodium hydrogen carbonate) or organic bases (for example, triethylamine, ethyldiisopropylamine, N-methylmorpholine, pyridine or 4-dimethylaminopyridine).

The deprotection reaction of carbamate, an amidation reaction or an urea formation reaction as shown in the above-mentioned processes can be applied to the case of a deprotection reaction of a carbamate group, an amidation reaction or an urea formation reaction on $Ar^1$, L, $Ar^2$ or $R^1$ other than the above-mentioned ones (see Example 112).

Specific examples of solvents to be used for Process E should be selected depending on the kind of starting materials or the kind of reagents used, and include, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid, or alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Step F]

The compound of formula (I) wherein $R^1$ represents a $C_{1-10}$ alkyl group substituted with hydroxy, a $C_{2-6}$ alkene group or a three to six-membered saturated- or four to six-membered unsaturated-aliphatic ring group optionally containing one to two heteroatoms independently selected from the group consisting of N, O and S [the below-mentioned compound of formula (Ih)] can be prepared according to the below-mentioned processes.

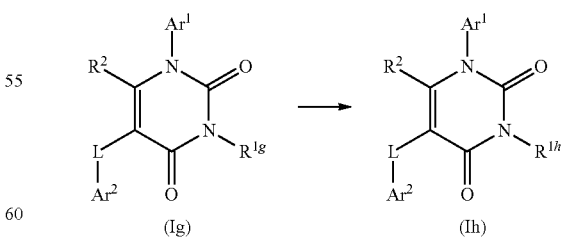

(wherein, $Ar^1$, L, $Ar^2$ and $R^2$ are the same as defined above, $R^{1g}$ represents a $C_{1-10}$ alkyl group substituted with $CO_2R^b$, $C_{2-6}$ alkene group, or a three to six-membered saturated- or four to six-membered unsaturated-aliphatic ring group optionally containing one to two heteroatoms independently selected from the group consisting of N, O and S, $R^{1h}$ represents a $C_{1-10}$ alkyl group substituted with hydroxy, a $C_{2-6}$ alkene group, or a three to six-membered saturated- or four to six-membered unsaturated aliphatic ring group each optionally containing one to two heteroatoms independently selected from the group consisting of N, O and S, and $R^b$ is the same as defined above)

The compound (Ih) can be prepared by performing a reduction reaction on the compound (Ig) according to a conventional method. For example, this reaction can be achieved by reacting the compound (Ig) with reducing agents (for example, borane tetrahydrofuran complex or lithium aluminium hydride) in appropriate solvents, or alternatively when $R^b$ represents a hydrogen atom, can be achieved by reacting the compound (Ig) with anhydrides or acid halides so as to be derivatized to a mixed anhydrides, followed by treating the resultant mixed anhydrides with reducing agents (for example, sodium borohydride) (see Examples 83, 84 and 122).

The reduction reaction on ester group or carboxyl group as shown in the above-mentioned processes may be applied to the case of a reduction on the ester group or the carboxyl group on $Ar^1$, L or $Ar^2$ (see Example 138).

Specific examples of solvents to be used in Process F should be selected depending on the kind of starting materials or the kind of reagents used, and include, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid, and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Step G]

The compound of formula (I) wherein $R^1$ represents a $C_{1-10}$ alkyl group substituted with hydroxy, a $C_{2-6}$ alkene group or a three to six-membered saturated- or four to six-membered unsaturated-aliphatic ring group optionally containing one to two heteroatoms independently selected from the group consisting of N, O and S [the below-mentioned compound of formula (Ih)] can be prepared according to the below-mentioned processes.

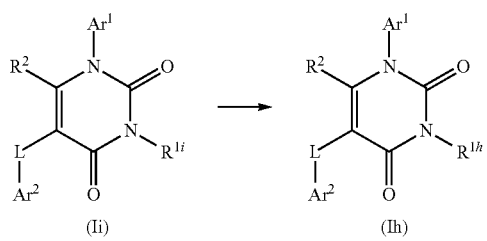

(wherein, $Ar^1$, L, $Ar^2$ and $R^2$ are the same as defined above, $R^{1i}$ represents a $C_{1-10}$ alkyl group substituted with $OCOR^a$, a $C_{2-6}$ alkene group, or a three to six-membered saturated- or four to six-membered unsaturated-aliphatic ring group each optionally containing one to two heteroatoms independently selected from the group consisting of N, O and S, $R^{1h}$ represents a $C_{1-10}$ alkyl group substituted with hydroxy, a $C_{2-6}$ alkene group, or a three to six-membered saturated- or four to six-membered unsaturated-aliphatic ring group optionally containing one to two heteroatoms independently selected from the group consisting of N, O and S, and $R^a$ is the same as defined above)

The compound (Ih) can be prepared by performing a reduction reaction on the compound (Ii) according to a conventional method. For example, this reaction can be achieved by reacting the compound (Ii) with reducing agents (for example, diisobutylaluminium hydride or lithium aluminium hydride) in appropriate solvents.

Also, the compound (Ih) can be prepared by performing a hydrolysis reaction on the compound (Ii) according to a conventional method. For example, this reaction can be achieved by performing a hydrolysis reaction on the compound (Ii) under basic condition with bases (for example, potassium carbonate or sodium hydroxide) or under acidic condition with acids (for example, hydrochloric acid) (see Examples 109-110).

Specific examples of solvents to be used in Process G should be selected depending on the kind of starting materials or the kind of reagents used and include, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Process H]

The compound of formula (I) wherein $R^1$ represents a hydrogen atom [the below-mentioned compound of formula (Ik)] and the compound of formula (I) can be prepared according to the below-mentioned processes.

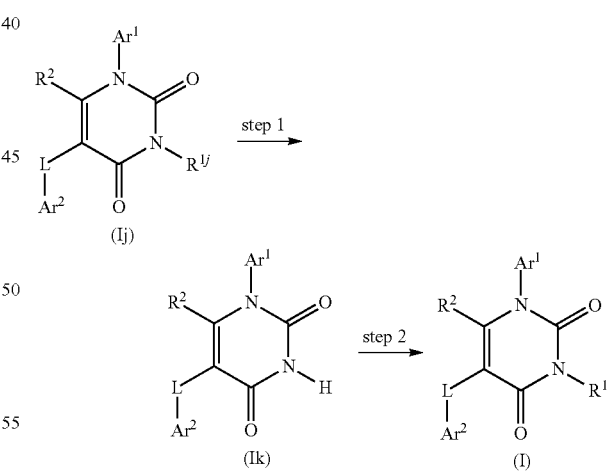

(wherein, $Ar^1$, L, $Ar^2$, $R^1$ and $R^2$ are the same as defined above, and $R^{1j}$ represents a benzyl group optionally substituted with nitro or methoxy)

[Step 1]

The compound (Ik) can be prepared by performing a reduction reaction on the compound (Ij) according to a conventional method. For example, this reaction can be achieved by reacting the compound (Ij) with catalytic reduction reagents (for example, palladium on carbon or palladium hydroxide)

in charged states of hydrogen gas or in the presence of ammonium formate, by performing a reaction in the presence of acids (for example, trifluoroacetic acid), or by performing a reaction in the presence of oxidizing agents (for example, 2,3-dichloro-5,6-dicyanopara-benzoquinone).

[Step 2]

The compound (I) can be prepared by performing an alkylation reaction on the compound (Ik) according to a conventional method. For example, this reaction can be achieved by reacting the compound (Ik) with various alkylhalides reagents in the presence of hydrogenated metal reagents (for example, sodium hydride), alkali metal carbonates reagents (for example, potassium carbonate), alkali metal phosphates reagents (for example, potassium phosphate), organic bases reagents (for example, triethylamine), alkali metal halides reagents (for example, lithium chloride), alkali metal hydroxides (for example, sodium hydroxide), metal alkoxides (for example, potassium t-butoxide) or the others in appropriate solvents or under solvent-free condition.

Also, the compound (I) can be prepared by performing Mitsunobu reaction on the compound (Ik) and the corresponding alcohols according to a conventional method. For example, this reaction can be achieved by reacting the compound (Ik) with the corresponding alcohols in the presence of a condensing agent (for example, a combination of triphenyl phosphine and diethyl azodicarboxylate) in appropriate solvents or under solvent-free condition.

Specific examples of solvents to be used in Process H should be selected depending on the kind of starting materials or the kind of reagents used and include, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid, and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Process I]

The compound of formula (I) wherein $B^b$ as a part of a substituent of L represents —$NR^aC(=O)R^b$ [the below-mentioned compound of formula (Im)] can be prepared according to the below-mentioned processes.

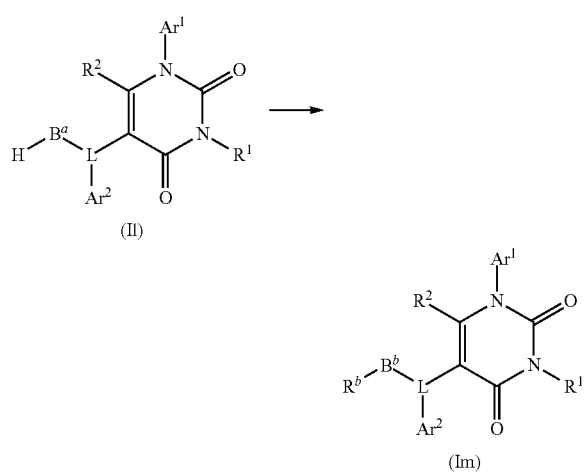

(wherein, $R^1$, $Ar^1$, L, $Ar^2$ and $R^2$ are the same as defined above, $B^a$ represents —$NR^a$—, $B^b$ represents —$NR^aC(=O)$—, and $R^a$ and $R^b$ are the same as defined above)

The compound (Im) can be prepared by performing an amidation reaction on the compound (Ii) according to the similar method to those of [Step 2] in Process E.

Specific examples of solvents to be used in Process I should be selected depending on the kind of starting materials or the kind of reagents used and include, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid, and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Process J]

The compound of formula (I) wherein BC as a part of a substituent of L represents —O— or —$NR^c$— [the below-mentioned compound of formula (Io)] can be prepared according to the below-mentioned processes.

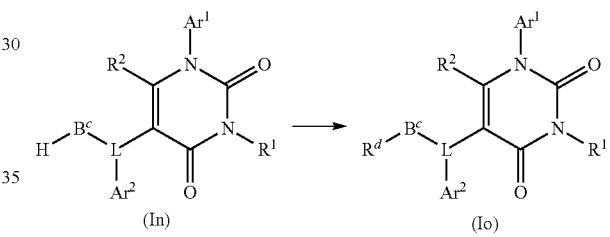

(wherein, $R^1$, $Ar^1$, L, $Ar^2$ and $R^2$ are the same as defined above, $B^c$ represents —O— or —$NR^c$—, and $R^d$ is the same as defined above)

The compound (Io) can be prepared by using the compound (In) according to the similar method to those of [Step 2] in Process H, or can be prepared by performing an alkylation reaction via a reductive amination on the compound (In) (see Example 141).

Specific examples of solvents to be used in Process J should be selected depending on the kind of starting materials or the kind of reagents used and include, for example, dichloromethane, chloroform, dichloroethane, toluene, tetrahydrofuran, 1,4-dioxane, dimethoxyethane, N,N-dimethylformamide and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Process K]

The compound of formula (I) wherein $B^e$ as a part of a substituent of L represents a halogen atom [the below-mentioned compound of formula (Iq)], the compound of formula (I) wherein $B^f$ as a part of a substituent of L represents —C(=O)— [the below-mentioned compounds of formula (Ir) and formula (Is)], the compound of formula (I) wherein $B^g$ as a part of a substituent of L represents —C(=O)$NR^c$—

[the below-mentioned compound of formula (It)] can be prepared according to the below-mentioned processes.

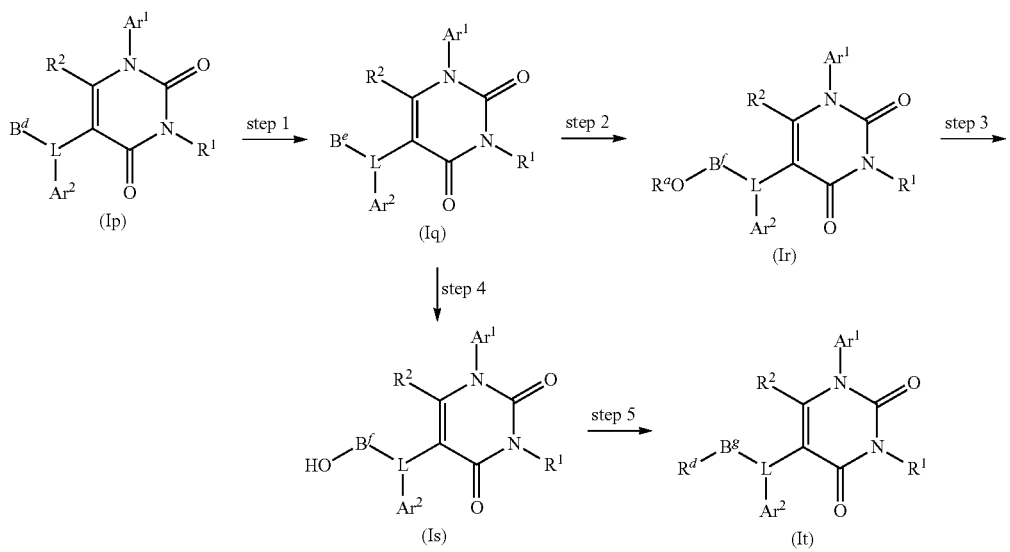

(wherein, $R^1$, $Ar^1$, L, $Ar^2$ and $R^2$ are the same as defined above, $B^d$ represents a hydrogen atom, $B^e$ represents a halogen atom, $B^f$ represents —C(=O)—, $B^g$ represents —C(=O)$NR^c$—, and $R^a$ and $R^d$ are the same as defined above)

[Step 1]

The compound (Ig) can be prepared by performing a halogenation reaction on the compound (Ip) according to the similar method to those of [Step 2] in the Process B (see Examples 93 to 101). Also, the compound (Iq) wherein Be represents a fluorine atom can be prepared by performing a fluorination reaction on the compound (Ip) according to a conventional method. For example, this reaction can be achieved by reacting the compound (1) with fluorination agents (for example, Selectfluor (trade mark)) in appropriate solvents or under solvent-free condition (see Example 358).

[Step 2]

The compound (Ir) can be prepared by performing a carbon monoxide insertion reaction on the compound (Iq) in the presence of alcohols (see Example 134).

[Step 3]

The compound (Is) can be prepared by performing a hydrolysis reaction or a reduction reaction on the compound (Ir) according to the similar method to those of [Step 1] of Process D.

[Step 4]

The compound (Is) can be prepared by performing a carbon monoxide insertion reaction on the compound (Iq) in the presence of water according to the similar method to those of [Step 2] of Process K (see Examples 132 to 133).

[Step 5]

The compound (It) can be prepared by performing an amidation reaction on the compound (Is) according to the similar method to those of [Step 2] in Process D (see Examples 142 to 145).

Specific examples of solvents to be used for each step in the Process K should be selected depending on the kind of starting materials or the kind of reagents used and include, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid, and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Step L]

The compound of formula (I) wherein $B^h$ as a part of a substituent of L represents an optionally substituted alkyl group, an optionally substituted alkene group or a cyano group [the below-mentioned compound of formula (Iu)] can be prepared according to the below-mentioned processes.

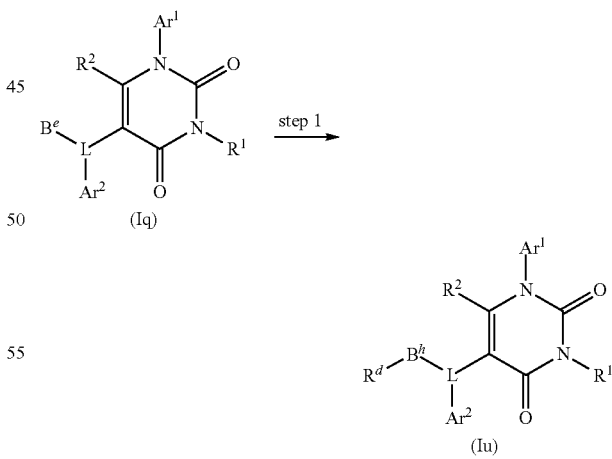

(wherein, $R^1$, $Ar^1$, L, $Ar^2$ and $R^2$ are the same as defined above, $B^e$ represents a halogen atom, $B^h$ represents an optionally substituted alkyl group, an optionally substituted alkene group or a cyano group)

[Step 1]

The compound (Iu) can be prepared by performing a coupling reaction on the compound (Iq). This reaction can be achieved according to the similar method to those of Process A-1. Also, a cyanation reaction can be achieved by using cyano coupling agents (for example, zinc cyanide or copper cyanide) (see Examples 126 to 131 and 363).

Specific examples of solvents to be used for each step in Process L should be selected depending on the kind of starting materials or the kind of reagents used and include, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid and alcohols (for example, methanol, ethanol or isopropanol) and the others, which can be used alone or as a mixed solvent thereof. The reaction temperature may be varied depending on the kind of starting materials used and the kind of reagents and the others, and includes usually within a range of –40° C. to 150° C., preferably within a range of 0° C. to 120° C., and the reaction may be optionally carried out under pressurized condition.

[Process M]

The compound of formula (I) wherein $R^1$ represents a $C_{1-10}$ alkyl group substituted with alkoxy, alkylthio, alkylamino or dialkylamino, an $C_{2-6}$ alkene group or a three to six-membered saturated- or four to six-membered unsaturated-aliphatic ring group each optionally containing one to two heteroatoms independently selected from the group consisting of N, O and S [the below-mentioned compound of formula (Iw)] can be prepared according to the below-mentioned processes.

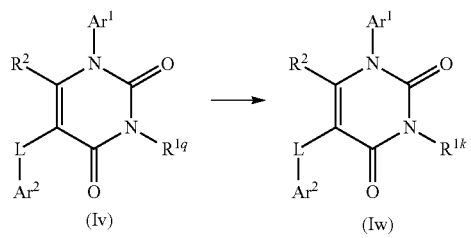

(wherein, $Ar^1$, L, $Ar^2$ and $R^2$ are the same as defined above, $R^{1g}$ represents a $C_{1-10}$ alkyl group substituted with hydroxy, thio, amino, monoalkylamino, a $C_{2-6}$ alkene group or a three to six-membered saturated- or four to six-membered unsaturated-aliphatic ring group each optionally containing one to two heteroatoms independently selected from the group consisting of N, O and S, $R^{1k}$ represents a $C_{1-10}$ alkyl group substituted with alkoxy, alkylthio, alkylamino or dialkylamino, a $C_{2-6}$ alkene group, or a three to six-membered saturated- or four to six-membered unsaturated-aliphatic ring group each optionally containing one to two heteroatoms independently selected from the group consisting of N, O and S)

The compound (Iw) can be prepared by performing an alkylation reaction on the compound (Iv) according to the similar method to those of [Step 2] in Process H.

The method for an alkylation reaction shown in the above-mentioned processes can be also applied to the case where OH, SH, $NH_2$ or $NHR^a$ on $Ar^1$, L or $Ar^2$ is alkylated.

Specific examples of solvents to be used in the Process M should be selected depending on the kind of starting materials or the kind of reagents used and include, for example, dichloromethane, chloroform, dichloroethane, toluene, tetrahydrofuran, 1,4-dioxane, dimethoxyethane, N,N-dimethylformamide and the others, which can be used alone or as a mixed solvent thereof. The reaction temperature may be varied depending on the kind of starting materials used and the kind of reagents used and the others, and includes usually within a range of –40° C. to 150° C., preferably within a range of 0° C. to 120° C., and the reaction may be optionally carried out under pressurized condition.

[Process N]

The compound of formula (I) wherein $R^1$ represents a $C_{1-10}$ alkyl group substituted with aldehyde, a $C_{2-6}$ alkene group, or a three to six-membered saturated- or four to six-membered unsaturated-aliphatic ring group each optionally containing one to two heteroatoms independently selected from the group consisting of N, O and S [the below-mentioned compound of formula (Iy)] and the compound of formula (I) wherein $R^1$ represents a $C_{1-10}$ alkyl group substituted with monoalkylamino group or dialkylamino group, a $C_{2-6}$ alkene group or a three to six-membered saturated- or four to six-membered unsaturated-aliphatic ring group each optionally containing one to two heteroatoms independently selected from the group consisting of N, O and S [the below-mentioned compound of formula (Iz)] can be prepared according to the below-mentioned processes.

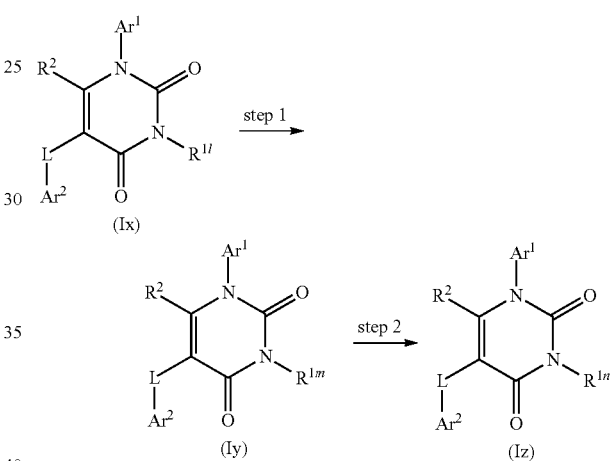

(wherein, $Ar^1$, L, $Ar^2$ and $R^2$ are the same as defined above, $R^{1l}$ represents a $C_{1-10}$ alkyl group substituted with acetal $(CH(OR^j)_2)$, a $C_{2-6}$ alkene group or a three to six-membered saturated- or four to six-membered unsaturated-aliphatic ring group each optionally containing one to two heteroatoms independently selected from the group consisting of N, O and S, $R^{1m}$ represents a $C_{1-10}$ alkyl group substituted with aldehyde, a $C_{2-6}$ alkene group or a three to six-membered saturated- or four to six-membered unsaturated-aliphatic ring group each optionally containing one to two heteroatoms independently selected from the group consisting of N, O and S, $R^{1n}$ represents a $C_{1-10}$ alkyl group substituted with monoalkylamino or dialkylamino, a $C_{2-6}$ alkene group or a three to six-membered saturated- or four to six-membered unsaturated-aliphatic ring group each optionally containing one to two heteroatoms independently selected from the group consisting of N, O and S, and $R^j$ is the same as defined above)

[Step 1]

The compound (Iy) can be prepared by performing a deprotection reaction on acetal group in the compound (Ix) according to a conventional method. For example, this reaction can be achieved by reacting the compound (Ix) with acids (for example, p-toluenesulfonic acid, trifluoroacetic acid or hydrochloric acid) in appropriate solvents or under solvent-free condition (see Example 68).

[Step 2]

The compound (Iz) can be prepared by performing a reductive amination reaction on the compound (Iy) according to a conventional method. For example, this reaction can be achieved by reacting the compound (Iy) with monoalkylamine or dialkylamine in the co-presence of hydride reagents (for example, sodium borohydride, triacetoxysodium borohydride or sodium cyanoborohydride) and acids (for example, acetic acid or hydrochloric acid) in appropriate solvents or under solvent-free condition (see Examples 69 to 70).

The deprotection of acetal group as shown in the Step 1 of the above-mentioned processes may be applied to the case of a conversion reaction of acetal group on $Ar^1$, L and $Ar^2$ into aldehyde group.

Specific examples of solvents to be used in Process N should be selected depending on the kind of starting materials or the kind of reagents used and include, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid, and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Step O]

The compound of formula (I) wherein $R^1$ represents a $C_{1-10}$ alkyl group substituted with aldehyde, oxo, carboxyl, sulfonyl or sulfoxide, a $C_{2-6}$ alkene group or a three to six-membered saturated- or four to six-membered unsaturated-aliphatic ring group each optionally containing one to two heteroatoms independently selected from the group consisting of N, O and S [the below-mentioned compound of formula (Ib')] can be prepared according to the below-mentioned processes.

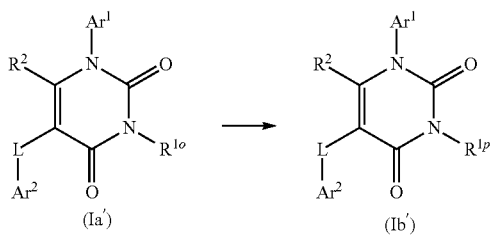

(wherein, $Ar^1$, L, $Ar^2$ and $R^2$ are the same as defined above, $R^{1o}$ represents a $C_{1-10}$ alkyl group substituted with hydroxy, aldehyde, thiol, alkylthio or sulfoxide, a $C_{2-6}$ alkene group or a three to six-membered saturated- or four to six-membered unsaturated-aliphatic ring group each optionally containing one to two heteroatoms independently selected from the group consisting of N, O and S, and $R^{1p}$ represents a $C_{1-10}$ alkyl group substituted with aldehyde, oxo, carboxyl, sulfoxide or sulfonyl, a $C_{2-6}$ alkene group or a three to six-membered saturated- or four to six-membered unsaturated-aliphatic ring group each optionally containing one to two heteroatoms independently selected from the group consisting of N, O and S)

When $R^{1o}$ in the compound (Ia') represents a $C_{1-10}$ alkyl group substituted with hydroxy or aldehyde, a $C_{2-6}$ alkene group or a three- to six-membered saturated- or four to six-membered unsaturated-aliphatic ring group each optionally containing one to two heteroatoms independently selected from the group consisting of N, O and S, the compound (Ia') is oxidized according to a conventional method to produce the compound (Ib') wherein $R^{1p}$ represents a $C_{1-10}$ alkyl group substituted with oxo or carboxyl, a $C_{2-6}$ alkene group or a three to six-membered saturated- or four to six-membered unsaturated-aliphatic ring group each optionally containing one to two heteroatoms independently selected from the group consisting of N, O and S. For example, this reaction can be achieved by reacting the compound (Ia') with oxidizing agents (for example, Dess-Martin reagent, potassium dichromate, sodium hypochlorite, Jones reagent or pyridinium dichromate).

Also, when $R^{1o}$ in the compound (Ia') represents a $C_{1-10}$ alkyl group substituted with thiol or sulfoxide, a $C_{2-6}$ alkene group or a three to six-membered saturated- or four to six-membered unsaturated-aliphatic ring group each optionally containing one to two heteroatoms independently selected from the group consisting of N, O and S, the compound (Ia') can be oxidized according to a conventional method to produce the compound of the formula (Ib') wherein $R^{1p}$ represents a $C_{1-10}$ alkyl group substituted with sulfoxide or sulfonyl, a $C_{2-6}$ alkene group or a three to six-membered saturated- or four to six-membered unsaturated-aliphatic ring group each optionally containing one to two heteroatoms independently selected from the group consisting of N, O and S. For example, this reaction can be achieved by reacting the compound (Ia') with peroxidizing reagents (for example, metachloroperbenzoic acid or hydrogen peroxide) in appropriate solvents.

The oxidation reaction as shown in the above-mentioned processes may be applied to the case of an oxidation reaction of methyl alcohol, methylthiol, aldehyde or sulfoxide as a substituent of $Ar^1$, L and $Ar^2$ so as to convert it into aldehyde, carboxylic acid, sulfoxide or sulfonyl respectively.

Specific examples of solvents to be used for each reaction in Process O should be selected depending on the kind of starting materials or the kind of reagents used and include, for example, dichloromethane, chloroform, dichloroethane, toluene, tetrahydrofuran, 1,4-dioxane, dimethoxyethane, N,N-dimethylformamide and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Process P]

The compound (I) can be prepared according to the below-mentioned processes.

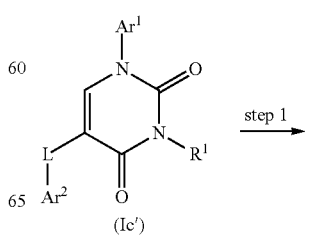

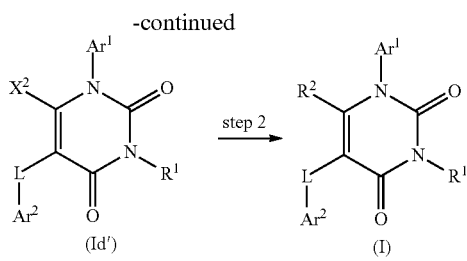

(wherein, $Ar^1$, L, $Ar^2$, $R^1$ and $R^2$ are the same as defined above, and $X^2$ represents a halogen atom (for example, iodine atom or bromine atom).)

[Step 1]

The compound (Id') can be prepared by performing a halogenation reaction on the compound (Ic') according to a conventional method. For example, this reaction can be achieved by reacting the compound (Ic') with halogenating agents (for example, N-iodosuccinimide, N-bromosuccinimide, a combination of potassium iodide and cerium ammonium nitrate, iodine or bromine) in appropriate solvents or under solvent-free condition.

[Step 2]

When $R^2$ in compound (I) represents an alkyl group, the compound (I) can be prepared by performing a coupling reaction on the compound (Id') and $Z^1$—$R^2$ (wherein $Z^1$ is the same as defined above) according to a conventional method. This reaction can be achieved according to the similar method to those of Process A-1.

Also, when $R^2$ in the compound (I) represents an amino group, the compound (I) can be prepared by performing an amination reaction on the compound (Id') according to a conventional method. For example, this reaction can be achieved by reacting the compound (Id') with aminating agents (for example, ammonia, ammonium salt, alkylamine reagents or dialkylamine reagents) in appropriate solvents or under solvent-free condition. Also, this reaction can be achieved by performing an amination reaction on the compound (Id') and various amine reagents in the presence of palladium catalysts (for example, tetrakis(triphenylphosphin)palladium), copper reagents (for example, copper iodide), zinc reagents or iron chelating reagents, optionally with an addition of phosphorus catalyst (typically, 2,2'-bis(diphenylphosphino)-1,1-binaphthalene or 2-(di-t-butyl)phosphinobiphenyl).

Also, when $R^2$ in the compound (I) represents a cyano group, the compound (I) can be prepared by performing a cyanation reaction on the compound (Id) according to a conventional method. For example, this reaction can be achieved by reacting the compound (Id') with cyanating agents (for example, potassium cyanide, sodium cyanide or copper cyanide). Also, this reaction can be also achieved in the presence of palladium catalysts (typically, tetrakis(triphenylphosphin) palladium), copper catalysts (typically, copper iodide), zinc reagents or iron chelating reagents, optionally with an addition of phosphorus catalyst (for example, 2,2'-bis(diphenylphosphino)-1,1-binaphthalene or 2-(di-t-butyl)phosphinobiphenyl).

Specific examples of solvents to be used in Process P should be selected depending on the kind of starting materials or the kind of reagents used and include, for example, dichloromethane, chloroform, dichloroethane, toluene, tetrahydrofuran, 1,4-dioxane, dimethoxyethane, N,N-dimethylformamide, acetonitrile, dimethyl sulfoxide, acetic acid and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 150° C., preferably within a range of 0° C. to 120° C., and the reaction may be optionally carried out under pressurized condition.

[Process Q]

Next, the starting materials (IIa) and (IIb) to be used in the above-mentioned Processes A to C are known compounds or are prepared, for example, according to the method shown in the below-mentioned reaction scheme. Herein, the compound (IIa) represents the below-mentioned compound (VII) wherein $X^3$ represents a halogen atom or the below-mentioned compound (VIII) wherein $X^3$ represents an amino group, and the compound (IIb) represents the below-mentioned compound (VII) wherein $X^3$ represents a halogen atom.

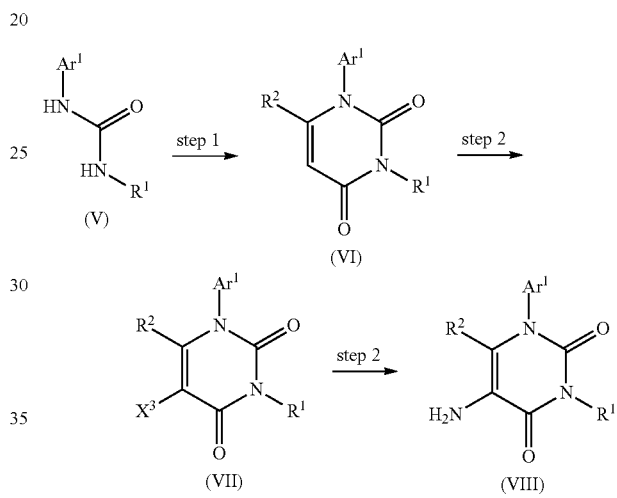

(wherein, $Ar^1$, $R^1$ and $R^2$ are the same as defined above, and $X^3$ represents a chlorine atom, a bromine atom, an iodine atom or a nitro group)

The compound (V) is a well-known compound or can be prepared according to equivalent processes to those for known compounds. For example, said compound can be prepared according to the method described in Journal of Medicinal Chemistry, 2004, 47(7), 1617-1630 and the others, or equivalent methods thereto.

[Step 1]

The compound (VI) wherein $R^2$ represents a methyl group is a known compound or can be prepared by using the compound (V) according to equivalents processes to known processes. For example, said compound can be prepared according to the methods described in Heterocycles, 1993, 36(2), 307-314, J. Med. Chem. 2008, 51, 7478 and the others, or equivalent methods thereto.

Also, the compound (VI) wherein $R^2$ represents an amino group is a known compound or can be prepared by using the compound (V) according to equivalent processes to known processes. For example, said compound can be prepared according to the method described in Chemical & Pharmaceutical Bulletin 1989, 37(8), 2008-2011 and the others or equivalent methods thereto.

Also, the compound (VI) wherein $R^2$ represents a hydrogen atom is a known compound or can be prepared by using the compound (V) according to equivalent processes to known processes. For example, said compound can be prepared according to the methods described in Synthesis 1986, (12), 1041-1044 or equivalent processes thereto.

The compound (VI) and the compound (VII) wherein in both formulae, $R^2$ represents —N=CHN(CH$_3$)$_2$ can be prepared by reacting the compounds with N,N-dimethylformamide dimethyl acetal in appropriate solvents or under solvent-free condition according to a conventional method.

Also, the compound (VI) and the compound (VII) wherein in both formulae, $R^2$ represents —N=CHN(CH$_3$)$_2$ can be performed a deprotection reaction under acidic condition (for example, hydrochloric acid or trifluoroacetic acid) or under alkali condition (for example, aqueous sodium hydroxide solution) so as to convert into the compound (VI) and the compound (VII) wherein in both formulae, $R^2$ represents NH$_2$ (see Reference Example 52, and Examples 57 and 58).

[Step 2]

The compound (VII) can be prepared by performing a halogenation reaction or a nitration reaction on the compound (VI) according to a conventional method. For example, the halogenation reaction can be achieved by reacting the compound (VI) with halogenating agents (for example, N-iodosuccinimide, N-bromosuccinimide, a combination of potassium iodide and ammonium cerium nitrate, iodine and bromine) in appropriate solvents or under solvent-free condition. The nitration reaction can be achieved by reacting the compound (VI) with nitrating agents (for example, fuming nitric acid) in appropriate solvents or under solvent-free condition (see Reference Examples 60, 62-94 and 192).

[Step 3]

When $X^3$ in the compound (VII) represents a nitro group, the compound (VIII) can be prepared by performing a reduction reaction on the compound (VII) according to a conventional method. For example, this reaction can be achieved by reacting the compound (VII) with metal reagents (for example, palladium on carbon, platinum oxide, Raney nickel or reduced iron) in charged states of hydrogen gas or in the co-presence of ammonium chloride in appropriate solvents or under solvent-free condition (see Reference Examples 193 and 197).

Also, when $X^3$ in the compound (VII) represents a halogen atom, the compound (VIII) can be prepared by performing an amination reaction on the compound (VII) according to a conventional method. For example, this reaction can be achieved by reacting the compound (VII) with amine reagents (for example, ammonia or ammonium salt) in appropriate solvents or under solvent-free condition.

Specific examples of solvents to be used for each reaction in Process P should be selected depending on the kind of starting materials and include, for example, dichloromethane, chloroform, dichloroethane, tetrahydrofuran, 1,4-dioxane, dimethoxyethane, N,N-dimethylformamide, acetonitrile, dimethyl sulfoxide, acetic acid and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 200° C., preferably within a range of 0° C. to 150° C., and the reaction may be optionally carried out under pressurized condition.

[Process R]

Also, in the above-mentioned Process Q, the compound (VI) wherein $R^2$ represents a hydrogen atom can be also prepared according to the below-mentioned reaction scheme. Herein, the above-mentioned compound (VI) represents the compound (XIII) and the compound (XIV).

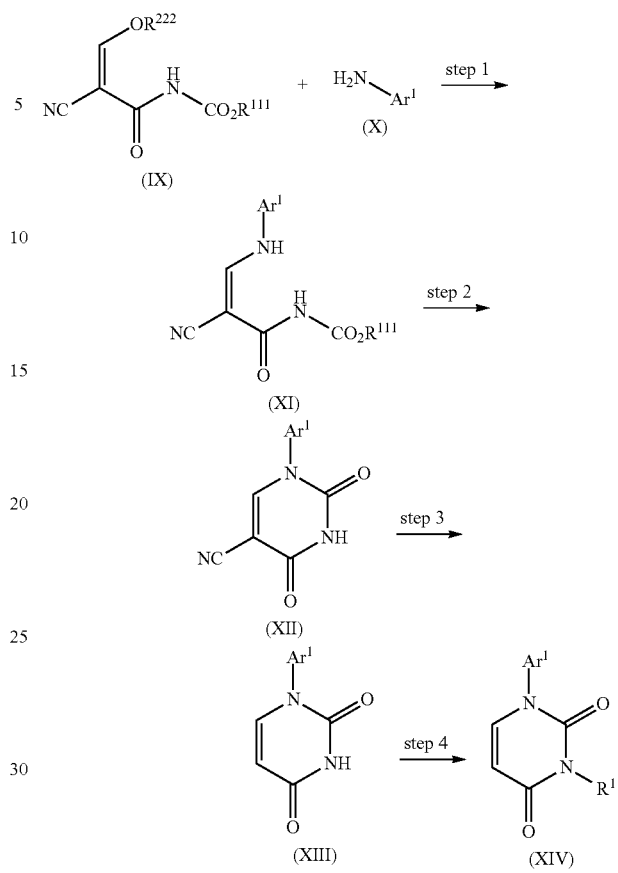

(wherein, $Ar^1$ and $R^1$ are the same as defined above, and $R^{111}$ and $R^{222}$ represent independently of each other an alkyl group having one to six carbon atoms)

The compound (IX) is a known compound or can be prepared according to equivalent processes to a process for known compound. For example, said compound can be prepared, for example, according to the method described in Chemical & Pharmaceutical Bulletin, 1972, 20(7), 1380-1388 or equivalent methods thereto.

[Step 1]

The compound (XI) is a known compound or can be prepared by using the compound (IX) and the compound (X) according to equivalent processes to a known process. For example, said compound can be prepared, for example, according to the method described in Chemical & Pharmaceutical Bulletin, 1972, 20(7), 1380-1388 or equivalent method thereto (see Reference Examples 111 and 115).

[Step 2]

The compound (XII) is a known compound or can be prepared by performing a cyclization reaction on the compound (XI) according to equivalent processes to a known process. For example, said compound can be prepared, for example, according to the method described in Bioorganic & Medicinal Chemistry, 2006, 14(7), 3399-3404 and the others or equivalent methods thereto (see Reference Examples 112 and 116).

[Step 3]

The compound (XIII) is a known compound or can be prepared by converting a cyano group in the compound (XII) into a hydrogen atom according to equivalent processes to known process. For example, said compound can be prepared, for example, according to a method described in Chemical & Pharmaceutical Bulletin, 1972, 20(7), 1389-1396 or equivalent methods thereto (see Reference Examples 113 and 117).

[Step 4]

The compound (XIV) can be prepared, for example, in the presence of bases, by performing a reaction of the compound (XIII) with electrophilic reagents (for example, halogenated alkyl or carbamates), or by performing Mitsunobu reaction on the compound (XIII) and alcohols. Examples of the bases include metal hydrides (for example, sodium hydride), alkali or alkaline-earth carbonates (for example, potassium carbonate) or tertiary amine (for example, triethylamine) (see Reference Examples 100 and 101).

Specific examples of solvents to be used for each reaction in Process R should be selected depending on the kind of starting materials and include, for example, dichloromethane, chloroform, dichloroethane, tetrahydrofuran, 1,4-dioxane, dimethoxyethane, N,N-dimethylformamide, acetonitrile, dimethyl sulfoxide, acetic acid and alcohols (for example, methanol, ethanol or isopropanol) and the others, which may be used alone or as a mixed solvent thereof. The reaction temperature may be varied depending on the kind of starting materials used and the kind of reagents and the others, and includes usually within a range of −40° C. to 200° C., preferably within a range of 0° C. to 150° C., and the reaction may be optionally carried out under pressurized condition.

[Process S]

Also, in the above-mentioned Process R, the compound (XIII) can be prepared according to the below-mentioned reaction scheme.

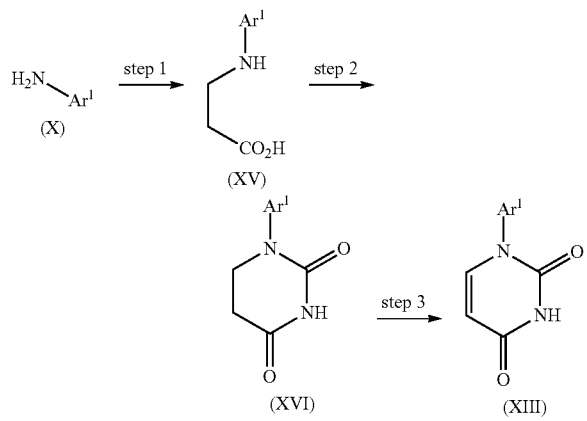

(wherein, $Ar^1$ is the same as defined above)

[Step 1]

The compound (XV) is a known compound or can be prepared by reacting the compound (X) with acrylic acid according to equivalent processes to the known process. For example, said compound can be prepared, for example, according to the method described in WO 2009/39127 A1 and the others or equivalent methods thereto (see Reference Example 95).

[Step 2]

The compound (XVI) is a known compound or can be prepared by reacting the compound (XV) with urea according to equivalent processes to known process. For example, said compound can be prepared, for example, according to the method described in WO 2009/39127 A1 and the others or equivalent methods thereto (see Reference Example 96).

[Step 3]

The compound (XIII) can be prepared by reacting the compound (XVI) with bromine followed by the resultant compound with Lewis acids (for example, lithium chloride) or bases according to a conventional process. For example, said compound can be prepared, for example, according to the method described in Journal of Organic Chemistry, 2002, 67(5), 1480-1489, Journal of the American Chemical Society, 1956, 78, 1612-1614 or the others or equivalent methods thereto (see Reference Example 98).

Specific examples of solvents to be used in Process S should be selected depending on the kind of starting materials and the others and include, for example, water, dichloromethane, chloroform, dichloroethane, tetrahydrofuran, 1,4-dioxane, dimethoxyethane, N,N-dimethylformamide, acetonitrile, dimethyl sulfoxide, acetic acid and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 200° C., preferably within a range of 0° C. to 100° C., and the reaction may be optionally carried out under pressurized condition.

[Process T]

Also, in the above-mentioned Process S, the compound (XIII) can be also prepared according to the below-mentioned reaction scheme.

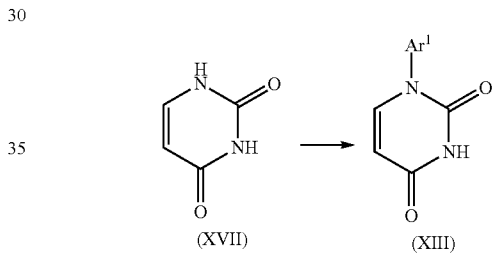

(wherein, $Ar^1$ is the same as defined above)

The compound (XIII) can be prepared by performing an arylation reaction on the compound (XVII) according to a conventional method. For example, said compound can be prepared, for example, according to the method described in Helvetica Chimica Acta, 2008, 91(6), 1008-1014 or equivalent thereto (see Reference Examples 99).

Specific examples of solvents to be used in Process T should be selected depending on the kind of starting materials and include, for example, water, dichloromethane, chloroform, dichloroethane, tetrahydrofuran, 1,4-dioxane, dimethoxyethane, N,N-dimethylformamide, acetonitrile, dimethyl sulfoxide, acetic acid, and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 200° C., preferably within a range of 0° C. to 100° C.

[Process U]

Also, in the compounds (I), (IIa), (IIb), (III), (IV), (II), (Im), (In), (Io), (Ip), (Iq), (Ir), (Is), (It), (Iu), (Ib'), (Ic'), (Id'), (VI), (VII) or (VIII) in the above-mentioned processes, when $R^1$ represents a hydrogen atom, that is, a formula (XVIII), $R^1$ other than a hydrogen atom can be introduced according to the below-mentioned reaction scheme so as to convert it into the compound (XIX).

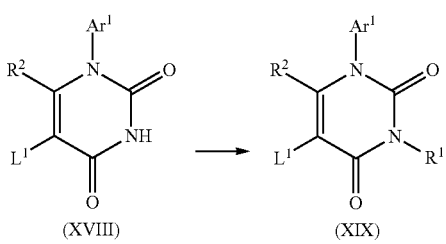

(wherein, $Ar^1$, $R^1$ and $R^2$ are the same as defined above, $L^1$ represents a hydrogen atom, $X^1$, $X^2$, $X^3$, $Ar^2$-L-, $Z^5$-L- or a substituent represented by the following formulae:

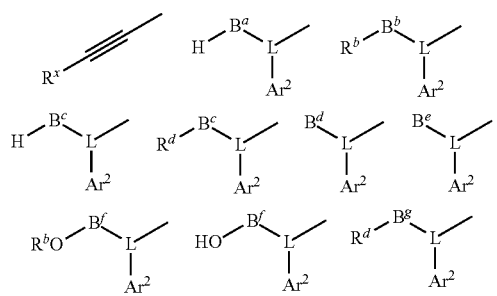

-continued $B^h\diagdown L\diagup$
$|$
$Ar^2$ , $X^1$, $X^2$, $X^3$, L, $Ar^2$, $Z^5$, $R^x$, $R^b$, $R^d$, $B^a$, $B^b$, $B^c$, $B^d$, $B^e$, $B^f$ and $B^g$ are the same as defined above)

The compound (XIX) can be prepared by performing a reaction of the compound (XVIII) with alkyl compounds having a leaving group (for example, halogenated alkyls) in the presence of bases according to a conventional method, or by performing a Mitsunobu reaction on the compound (XVIII) and alcohols. The bases may use as metal hydrides (for example, sodium hydride), metal alkoxides (for example, potassium tert-butoxide), alkali or alkaline-earth carbonates (for example, potassium carbonate) or tertiary amines (for example, triethylamine). Also, as for the condition for Mitsunobu reaction, azodicarboxylic acid diisopropyl ester and the like as well as triphenyl phosphine and the like can be used in combination (see Reference Examples 100, 101, 104, 105, 119, Examples 88-92).

Specific examples of solvents to be used in Process U should be selected depending on the kind of starting materials and include, for example, dichloromethane, chloroform, dichloroethane, tetrahydrofuran, 1,4-dioxane, dimethoxyethane, N,N-dimethylformamide, acetonitrile, dimethyl sulfoxide, acetic acid, and alcohols (for example, methanol, ethanol or isopropanol) and the others, which can be used alone or as a mixed solvent thereof. The reaction temperature may be varied depending on the kind of starting materials used and the kind of reagents used and the others, and includes usually within a range of −40° C. to 200° C., preferably within a range of 0° C. to 100° C.

[Process V]

The compounds of formula (2), formula (3), formula (4), formula (6), formula (7) and formula (8) can be prepared according to the below-mentioned processes.

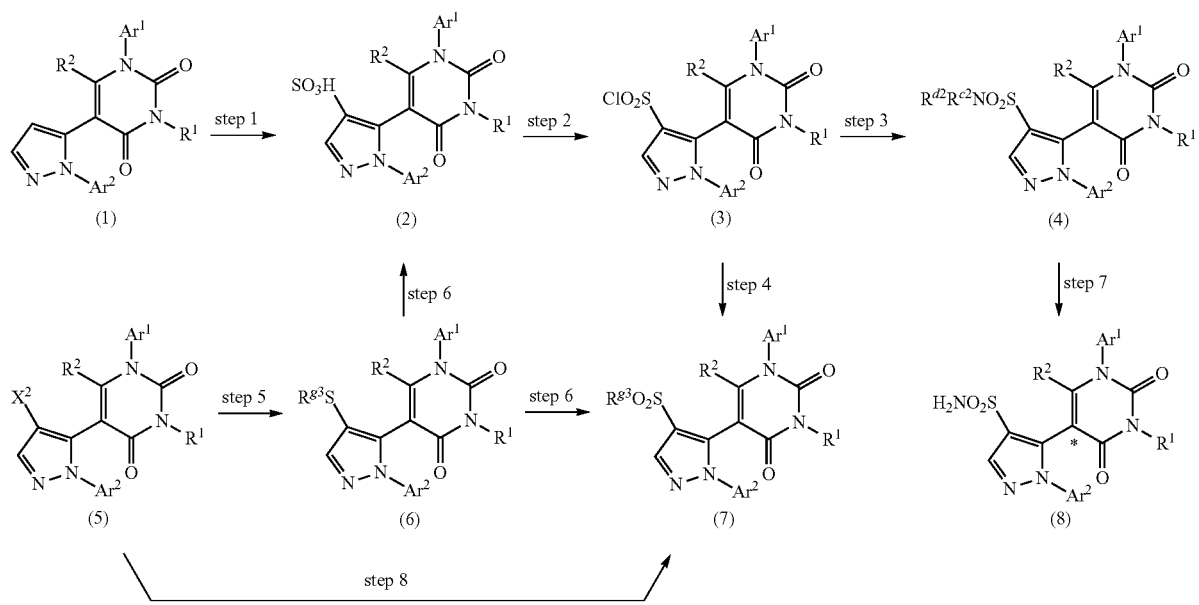

* represents atropisomer.

(wherein, $Ar^1$, $R^1$, $R^2$, $Ar^2$, $R^{c2}$, $R^{d2}$ and $R^{g3}$ are the same as defined above, and $X^2$ represents a halogen atom (for example, iodine atom or bromine atom))

[Step 1]

The compound (2) can be prepared by performing a sulfonation reaction on the compound (1) according to a conventional method. For example, this reaction can be achieved by reacting the compound (1) with sulfuric acid or chlorosulfonic acid in appropriate solvents or under solvent-free condition (see Example 191).

[Step 2]

The compound (3) can be prepared by performing an acid chlorination reaction on the compound (2) according to a conventional method. For example, this reaction can be achieved by reacting the compound (2) with phosphorus oxychloride, oxalyl chloride, phosphorus pentachloride or the others in appropriate solvents or under solvent-free condition. Such acid chlorination reaction may be optionally carried out in the presence of organic bases (for example, triethylamine, ethyldiisopropylamine, N-methylmorpholine, pyridine or 4-dimethylaminopyridine) (see Example 204).

[Step 3]

The compound (4) can be prepared by performing a sulfonamidation reaction on the compound (3) according to a conventional method. For example, this reaction can be achieved by reacting the compound (3) with amine reagents in appropriate solvents or under solvent-free condition. Such solfonamidation reaction may be optionally carried out in the presence of hydrogenated metal reagents (for example, sodium hydride or potassium hydride), inorganic bases (for example, potassium carbonate or sodium hydrogen carbonate) or organic bases (for example, triethylamine, ethyldiisopropylamine, N-methylmorpholine, pyridine or 4-dimethylaminopyridine).

Also, when either of $R^{c2}$ or $R^{d2}$ in the compound (4) represents an alkyl group containing asymmetric carbon (for example, (R) or (S)-1-phenethyl group or (R) or (S)-2-phenylethanol group), the compound (4) may form diastereoisomer compounds, and the resultant atropisomers can be thus resolved (see Examples 205, 212, 217-259).

[Step 4]

The compound (7) can be prepared by converting a chloro group in the compound (3) into a methyl group according to a conventional method. For example, this reaction can be achieved by reacting the compound (3) with methyl iodide, sodium sulfite or sodium hydrogen carbonate in appropriate solvents or under solvent-free condition. For example, said compound can be prepared, for example according to the method described in J. Med. Chem. 2003, 46(23), 4955 and the others, or equivalent methods thereto (see Example 265).

[Step 5]

The compound (6) can be prepared by performing a coupling reaction on the compound (5) according to a conventional method. For example, this reaction can be achieved by reacting the compound (5) with sulfur reagents in appropriate solvents or under solvent-free condition. Also, the reaction can be achieved by performing an amination reaction on the compound (5) and various sulfur reagents in the presence of palladium catalysts (typically, tetrakis(triphenylphosphin) palladium) or copper catalysts (for example, copper iodide), zinc reagents or iron chelating reagents optionally with an addition of phosphorus catalysts (for example, 2,2'-bis(diphenylphosphino)-1,1-binaphthalene or 2-(di-t-butyl)phosphinobiphenyl) (see Example 269).

[Step 6]

The compound (2) and the compound (7) can be prepared by performing an oxidation reaction on the corresponding compound (6) according to a conventional method. For example, this reaction can be achieved by reacting the compound (6) with peroxidizing agents (for example, meta-chloroperbenzoic acid or hydrogen peroxide) in appropriate solvents or under solvent-free condition (see Example 270).

[Step 7]

In order to obtain sulfonamide derivative as atropisomer, the compound (4) wherein either of $R^{c2}$ or $R^{d2}$ represents a benzyl derivative group (for example, (R) or (S)-1-phenethyl group or (R) or (S)-2-phenylethanol group) is performed a diastereomer resolution followed by performing a deprotection reaction of the benzyl group according to a conventional method so as to produce compound (8) as one of the atropisomer. For example, the deprotection reaction can be achieved according to the similar method to those of Step 1 in Process H (see Examples 262 and 263).

[Step 8]

The compound (7) can be prepared by performing a coupling reaction on the compound (5) according to a conventional method. For example, this reaction can be achieved by using alkyl sulphinates (for example, sodium methane sulphinate) in appropriate solvents or under solvent-free condition according to the similar method to those of [Step 5] (see Example 275).

[Process W]

The compound (II) can be prepared according to the below-mentioned processes.

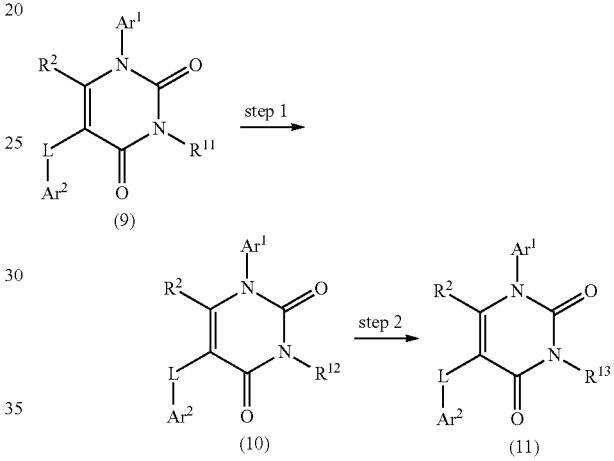

(wherein, $Ar^1$, $R^2$, L and $Ar^2$ are the same as defined above, $R^{11}$ represents a $C_{1-6}$ alkyl group substituted with hydroxy or a three to six-membered aliphatic ring group, $R^{12}$ represents a $C_{1-6}$ alkyl group substituted with iodine or tosylate, or a three to six-membered aliphatic ring group, and $R^{13}$ represents a $C_{1-6}$ alkyl group substituted with thiol, alkylthio or amino or a three to six-membered aliphatic ring group)

[Step 1]

The compound (10) can be prepared by performing a halogenation reaction or a tosylation reaction on the compound (9) according to a conventional method. For example, such halogenation reaction can be achieved by reacting the compound (9) with halogenating agents (for example, iodine or bromine) in appropriate solvents or under solvent-free condition. Such halogenation reaction may be optionally carried out in the presence of imidazole, triphenyl phosphine or the others. Also, such tosylation reaction can be achieved by reacting the compound (9) with tosyl chloride in appropriate solvents or under solvent-free condition. The tosylation reaction may be carried out in the presence of organic bases (for example, triethylamine, ethyldiisopropylamine, N-methylmorpholine, pyridine or 4-dimethylaminopyridine) (see Example 374).

[Step 2]

The compound (11) can be prepared by performing a nucleophilic reaction on the compound (10) according to a conventional method. For example, among the nucleophilic reactions, the thiolation reaction can be achieved by reacting the compound (10) with sodium hydrosulfide in appropriate solvents or under solvent-free condition. Alternatively, the reaction can be also achieved by reacting the compound with thiorea followed by reacting with sodium disulfite. Also, such thioalkylation reaction or amination reaction can be achieved by reacting the compound (10) with alkylthio reagents or amino reagents in appropriate solvents or under solvent-free condition. Such nucleophilic reaction may be optionally carried out in the presence of hydrogenated metal reagents (for example, sodium hydride or potassium hydride), inorganic bases (for example, potassium carbonate or sodium hydrogen carbonate) or organic bases (for example, triethylamine, ethyldiisopropylamine, N-methylmorpholine, pyridine or 4-dimethylaminopyridine) (see Example 374).

The Process W can be also applied to the case of $Z^a$ in the below-mentioned compound of formula (12) (wherein, $Ar^1$, $R^2$, L or $Ar^2$ are the same as defined above, and $Z^a$ represents a $C_{1-6}$ alkyl group substituted with hydroxy or a three to six-membered aliphatic ring group).

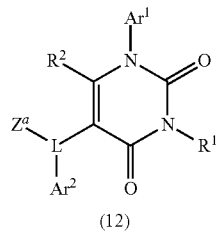

(12)

[Process X]

The compound (16) can be prepared according to the below-mentioned processes.

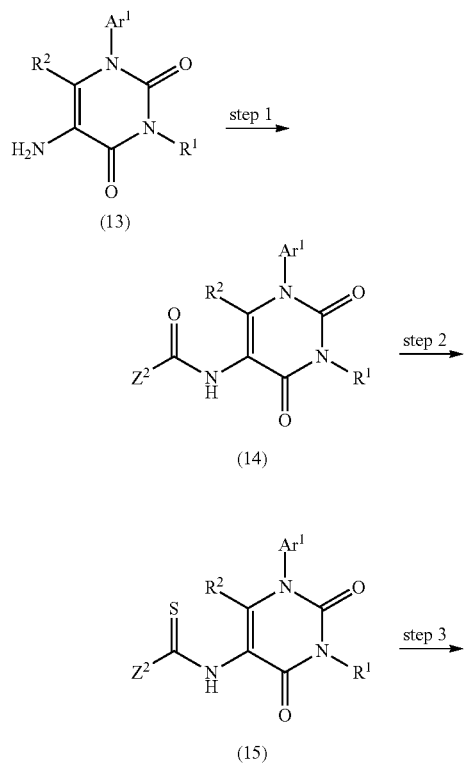

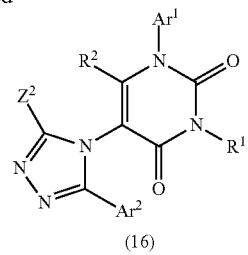

(16)

(wherein, $Ar^1$, $R^1$, $R^2$ and $Ar^2$ are the same as defined above, and $Z^2$ represents an optionally substituted $C_{1-6}$ alkyl group, a three to six-membered aliphatic ring group, —C(=O)NR$^c$R$^d$ or —C(=O)OR$^{b2}$)

[Step 1]

The compound (14) can be prepared by performing an amidation reaction on the compound (13) according to a conventional method. The reaction can be achieved according to the similar method to those of Step 2 in Process D (See Reference Examples 240 and 243).

[Step 2]

The compound (15) can be prepared by performing a thioamidation reaction on the compound (14) according to a conventional method. For example, the reaction can be achieved by reacting the compound (14) with sulfurizing agents (for example, Lawesson's reagent) in appropriate solvents or under solvent-free condition (see Reference Example 244).

[Step 3]

The compound (16) can be prepared by performing a cyclization reaction on the compound (15) according to a conventional reaction. For example, the reaction can be achieved by reacting the compound (15) with $Ar^2$—C(=O)NHNH$_2$, Lewis acids (for example, trimethylsilyl triflate) or metal acid compounds (for example, silver trifluoroacetate) in appropriate solvents or under solvent-free condition. However, if $Z^2$ in the compound (15) represents —C(=O)OR$^{b2}$, the $Z^2$ is preferably converted into —C(=O)NR$^c$R$^d$ via an amination reaction before cyclization reaction (see Reference Example 409).

With respect to the case where the Present compound represented by formula (I), or intermediate compounds or starting materials therefor contain a functional group, some examples of optional conversion reaction are illustrated as aforementioned. However, without limiting to such illustrated examples, a substituent introduction reaction or a functional group transformation reaction or the others can be carried out according to a conventional method for a person skilled in the art. As examples of such reaction, the methods described in "Experimental Chemistry (Edited by Chemical Society in Japan, published by Maruzen)" or "Comprehensive Organic Transformations, edited by Larock R. C. (VCH publishers, Inc., 1989)" or the others can be used. Examples of the functional group transformation reaction include a carbon-carbon binding reaction (for example, Friedel-Crafts reaction or wittig reaction), a reductive amination reaction or a carbon-nitrogen binding reaction (for example, an alkylation of amine), an oxidation reaction or a reduction reaction and the others.

Also, when the present compound represented by formula (I) or intermediate compound therefor contains a functional group (for example, amino, carboxyl, hydroxy or oxo), if necessary, a protection reaction or a deprotection reaction may be carried out. Examples of preferred protective group, a protection method and a deprotection method are described in detail in "Protective Groups in Organic Synthesis 4th Edition (John Wiley & Sons, Inc.; 2007)" and the others.

The compound (I) that prepared in each of the above-mentioned processes can be isolated or purified according to a conventional method (for example, chromatography, recrystallization or reprecipitation). Also, the compound of formula (1) or pharmacologically acceptable salts thereof may form an axial chirality (i.e., atropisomer) or may contain a substituent having an asymmetric carbon, and an optical isomer may be existed in such compounds. The Present compound encompasses a mixture or an isolates of each isomer. Examples of the method for preparing such optical isomer in pure form include optical resolutions (for example, chromatography with optically active column, preferential crystallization or diastereomeric resolution).

As for optical resolution, when the Present compound or intermediate compound therefor contains a basic functional group, they may form salts with optical active acids (for example, monocarboxylic acids such as mandelic acid, N-benzyloxy alanine and lactic acid; dicarboxylic acids such as tartalic acid, o-diisopropylidene tartalic acid and malic acid; and sulfonic acids such as camphorsulfonic acid and bromocamphorsulfonic acid) in an inert solvent (for example, alcohols such as methanol, ethanol and 2-propanol; ethers such as diethyl ether; esters such as ethyl acetate; aromatic hydrocarbons such as toluene; acetonitrile; and mixed solvents thereof.

Also, when the Present compound or intermediate compound therefor contains an acidic substituents such as carboxyl group or sulfonic acid group, they may form salts with optical active bases (for example, α-phenethylamine, kinin, quinidine, cinchonidine, cinchonine, strychnine, cis-2-benzylaminocyclohexanemethanol or organic amines (for example, amino acids)). The temperature at forming the salt includes, for example, a range of room temperature to a boiling point of the solvent used (including water). In order to increase an optical purity, it is desirous to raise the reaction temperature once to near the boiling point of the solvent. If necessary, the precipitated salts are cooled before a collection with filtering so as to improve a yield. The amount of optical active acid or amine is appropriately within a range of about 0.5 to about 2.0 equivalents, preferably around 1 (one) equivalent as opposed to that of substrate used. If necessary, the crystals are recrystallized in an inert solvent (for example, alcohols such as methanol, ethanol and 2-propanol; ethers such as diethyl ether; esters such as ethyl acetate; aromatic hydrocarbons such as toluene; acetonitrile; and mixed solvents thereof) so as to obtain optical active salts with high purity. If necessary, the obtained salts may be treated with acids or bases according to a conventional method so as to obtain free products.

The compound (I) may be obtained in the form of free base or acid addition salts depending on the kind of functional group present in the structure, a selection of starting materials or a condition for reaction treatment and the resultant compounds can be converted into the compound of formula (I) according to a conventional method. Also, the compound of formula (I) can be treated with various acids according to a conventional method to be derivatized to acid addition salts.

The uracil derivative of the present invention has strong neutrophilelastase inhibitory activity as below-mentioned, and thus is expected to being useful medicinal drug for diseases that are desirous for and/or required for elastase inhibitory activity. The administration route of the Present compound may be either oral administration, parenteral administration or intrarectal administration, and the daily dose may vary depending on the kind of the compound, the administration method, and the condition or ages of the patients. For example, for oral administration, the dose is usually within a range of about 0.01 to 3,000 mg, preferably about 0.1 to 500 mg per 1 kg human or mammal, and can be administered once daily or in divided doses. For example, for parenteral administration such as intravenous injection, the dose is usually within a range of about 0.01 to 500 mg, preferably about 1 to 100 mg per 1 kg human or mammal, and can be administered once daily or in divided doses.

When the Present compound is used as the above-mentioned medicinal use, said compound is administered in the form of pharmaceutical formulations that are prepared by mixing with carriers for pharmaceutical formulation. The carriers for formulation may be used as non-toxic substances that are commonly used in the pharmaceutical formulation arts and also are not reactive with the Present compound. Specific examples of carriers for pharmaceutical formulation include citric acid, glutamic acid, glycine, lactose, inositol, glucose, mannitol, dextran, sorbitol, cyclodextrin, starch, partly pregelatinized starch, sucrose, methyl parahydroxybenzoate, propyl parahydroxybenzoate, magnesium aluminometa silicate, synthetic aluminum silicate, crystalline cellulose, carboxymethyl cellulose sodium, hydroxypropylstarch, carboxymethyl cellulose potassium, ion exchange resin, methyl cellulose, gelatin, gum arabic, pullulan, hydroxypropyl cellulose, low substituted hydroxypropyl cellulose, hydroxypropylmethyl cellulose, polyvinylpyrrolidone, polyvinyl alcohol, alginic acid, sodium alginate, light anhydrous silicic acid, magnesium stearate, talc, tragacanth, bentonite, Veegum (trade mark), carboxyvinyl polymer, titanium oxide, sorbitan fatty acid ester, sodium lauryl sulfate, glycerine, glycerin-fatty acid ester, purified lanolin, glycerogelatin, polysorbate, macrogol, vegetable oil, wax, propylene glycol, ethanol, benzyl alcohol, sodium chloride, sodium hydroxide, hydrochloric acid, water and the others.

Examples of the pharmaceutical formulations include tablets, capsules, granules, powders, syrups, suspensions, injectable solutions, suppositories, eye-drops, ointments, liniments, patches, inhalations and the others. Such formulations can be prepared according to a conventional method. As for liquid formulations, the formulations may be in a form that the compounds are solved or suspended in water or other appropriate media at time of use. Also, the tablets and granules may be coated according to a well-known method. Moreover, such formulations may further contain other ingredients with therapeutic values.

The present compound or physiologically acceptable salts thereof have an elastase inhibitory activity, and can be thus used as elastase inhibitors, or a therapeutic agent or a prophylactic agent for diseases associated with elastase. Examples of the diseases in which elastase is suggested to associate with pathological conditions include inflammatory disease, specifically chronic obstructive pulmonary disease (COPD), pulmonarycystic fibrosis, emphysema, adult respiratory distress syndrome (ARDS), acute lung injury (ALI), idiopathic interstitial pneumonia (IIP) including idiopathic pulmonary fibrosis (IPF), chronic interstitial pneumonia, chronic bronchitis, chronic airway infection, diffuse panbronchiolitis, bronchiectasis, asthma, pancreatitis, nephritis, hepatic failure, chronic rheumatoid arthritis, arthrosclerosis, osteoarthritis, psoriasis, periodontitis, atherosclerosis, rejection of organ transplantation, premature rupture of membrane, bullosa, shock, sepsis, systemic lupus erythematodes (SLE), Crohn disease, disseminated intravascular coagulation (DIC), ischemia-reperfusion induced-tissue injury, corneal scar tissue formation, myelitis, lung squamous cell carcinoma, pulmonary adenocarcinoma, lung cancers such as non-small cell lung cancer, breast cancer, liver cancer, bladder cancer, colorectal cancer, skin cancer, pancreas cancer, glioma and the others.

For treatment for the above-mentioned diseases that required for elastase inhibitory activities, the Present compound or physiologically acceptable salts thereof (or pharmaceutically acceptable salts), or a pharmaceutical composition or pharmaceutical preparations comprising the Present compound may be administered in combination with the below-mentioned therapeutic agent or prophylactic agent.

Specific examples of therapeutic agent or prophylactic agent that may be used in combination include the followings: a short-lasting or long-lasting muscarinic receptor (subtypes M1, M2 and M3) antagonists (for example, ipratropium bromide and tiotropium bromide); a short-lasting or long-lasting β receptor (subtypes β1, β2, β3 and β4) agonist (for example, fenoterol hydrobromide, salbutamol sulfate, salmeterol xinafoate or formoterol fumarate); inhaled or oral steroids (for example, fluticasone propionate, beclometasone propionate or budesonide); combination drugs of β receptor agonists and inhaled steroids (for example, combination drug of salmeterol xinafoate and fluticasone propionate); phosphodiesterase (PDE) inhibitors (for example, PDE4 inhibitors such as methylxanthine (including theophylline, aminophylline and the others); expectorans (for example, carbocysteine); and antibiotics (for example, erythromycin or clarithromycin) and the others.

The present compound or physiologically acceptable salts thereof may be administered prior to, simultaneously with or after the above-mentioned therapeutic agent or prophylactic agent that may be used in combination to human or mammal.

EXAMPLES

Hereinafter, the present invention is explained in more detail with some Reference Examples, Examples and Test Examples, but the present invention should not be construed to be limited thereto. The compounds were identified by elemental analysis value, mass spectrum, high performance liquid chromatography-mass spectrometer; LC-MS, IR spectrum, NMR spectrum, high performance liquid chromatography (HPLC) and the others.

Hereinafter, the following abbreviations are sometimes used in Reference Example, Example and the tables described in the Example to simplify the description of the specification.

The abbreviations to be used as substituent include the followings: Me: methyl, Et: ethyl, Ph: phenyl, CN: cyano, Bn: benzyl, $NO_2$: nitro, n-Pr: normal propyl, i-Pr: isopropyl, c-Pr: cyclopropyl, t-Bu: tert-butyl, Ac: acetyl, Cbz: benzyloxycarbonyl, Boc: tert-butyloxycarbonyl, TBDPS: tert-butyldiphenylsilyl, Ms: methanesulfonyl, IPA: isopropyl alcohol. Also, eutomer (abbreviation "e") means an optical isomer having high physiological activity, and distomer (abbreviation "d") means an optical isomer having low physiological activity. Also, the symbol representing enantiomeric excess is expressed as "ee", and the symbol representing diastereomeric excess is expressed as "de". With respect to the symbols to be used in NMR include the followings: s: singlet, d: doublet, dd: double doublet, t: triplet, td: triple doublet, q: quartet, quint: quintet, sept: septet, m: multiplet, br: broad, brs: broad singlet, brd: broad doublet, brt: broad triplet, and J: coupling constant.

The measurement conditions in NMR are as follows:
Measurement condition 1: 300 MHz, $CDCl_3$
Measurement condition 2: 300 MHz, DMSO-$d_6$
Measurement condition 3: 300 MHz, $CD_3OD$
Measurement condition 4: 400 MHz, $CDCl_3$
Measurement condition 5: 400 MHz, DMSO-$d_6$
Measurement condition 6: 400 MHz, $CD_3OD$ high performance liquid chromatography-mass spectrometer; a measurement condition for LC-MS is shown below (measurement conditions 7, 8 and 9) and the observed values by mass analysis [MS (m/z)] is expressed as MH+ and the retention time is expressed as Rt (min.).
Measurement condition 7:
Detector: LC/MS-2010EV (manufactured by SHIMAZU CO.)
HPLC: LC/MS-2010C HT (manufactured by SHIMAZU CO.)
Column: CAPCELL PAK, C18 MGII (manufactured by SHISEIDO CO.) (S-3 μm, 4.6×35 mm)
Solvent: A solution; acetonitrile, B solution; 0.05% trifluoroacetic acid/water,
Elution Condition:
0.0-5.0 (min.); A/B=10:90→99:1
5.0-7.0 (min.); A/B=99:1
7.01-10.0 (min.); A/B=10:90
Flow rate: 0.35 ml/min.
UV: 220 nm
Column temperature: 40° C.
Measurement condition 8:
MS detector: Waters micromass ZQ
HPLC: Waters 2790 separations module
Column: Impact Cadenza CD-C18 2.0 mm×20 mm
Flow rate: 1.0 ml/min.
detection wavelength: 254 nm
Mobile phase:
A solution; water
B solution; acetonitrile
C solution; 2% formic acid acetonitrile solution
Elution Condition:
0.0-0.1 (min.); A solution:B solution:C solution=95:2:3
0.1-3.1 (min.); A solution:B solution:C solution=95:2:3→1:96:3
3.1-3.5 (min.); A solution:B solution:C solution=1:96:3
Measurement condition 9:
MS DETECTOR: ACQUITY (trade mark) SQ Detector (Waters)
HPLC: ACQUITY UPLC (trade mark)
Column: ACQUITY UPLC (trade mark) BEH C18 1.7 μm 2.1×30 mm Column
Flow rate: 0.8 ml/min.
Detection wavelength: 254 nm
Mobile phase:
A; 0.06% formic acid water
B; 0.06% formic acid acetonitrile
Elution Condition:
0-1.3 min.; A:B=98:2→A:B=4:96
1.3-1.5 min.; A:B=4:96→A:B=98:2

Reference Examples 1-18

The compounds 1a indicated in the below-mentioned table (Reference Examples 1-18) were prepared according to the process described in Journal of Medicinal Chemistry, 2004, 47(7), 1617-1630 and the others.

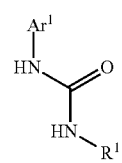

1a

TABLE 1

| Ref Ex. | Ar¹ | R¹ | Measurement cond. | ¹H-NMR (δ PPM) |
|---|---|---|---|---|
| 1 |  |  | 1 | 1.24 (t, 3H. J = 6.9 Hz), 2.58 (t, 2H, J = 5.7 Hz), 3.54 (dt, 2H, J = 6.0, 5.7 Hz), 4.15 (q, 2H, J = 7.5 Hz), 5.54 (brs, 1H), 6.99 (brs, 1H), 7.27 (d, 1H, J = 7.8 Hz), 7.36 (dd, 1H, J = 8.1, 7.8 Hz), 7.52 (d, 1H, J = 2.4 Hz), 7.61 (s, 1H) |
| 2 |  | 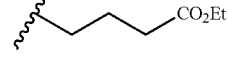 | 1 | 1.24 (t, 3H, J = 7.2 Hz), 1.87 (quin, 2H, J = 6.6 Hz), 2.39 (t, 2H, J = 6.6 Hz), 3.31 (dd, 2H, J = 6.9, 6.3 Hz), 4.14 (q, 2H, J = 7.2 Hz), 7.37 (t, 1H, J = 8.1 Hz), 7.56-7.66 (m, 3H) |
| 3 |  | 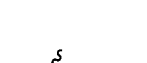 | 1 | 4.10 (d, 2H, J = 5.5 Hz), 5.19 (s, 2H), 5.42 (brs, 1H), 6.88 (brs, 1H), 7.24-7.34 (m, 7H), 7.42 (d, 1H, J = 8.4 Hz), 7.61 (s, 1H) |
| 4 |  |  | 1 | 3.40-3.47 (m, 8H), 4.40 (t, 1H, J = 4.6 Hz), 5.44 (brs, 1H), 7.21 (d, 1H, J = 7.7 Hz), 7.31 (t, 1H, J = 8.1 Hz), 7.45 (d, 1H, J = 8.3 Hz), 7.57 (s, 1H) |
| 5 |  | 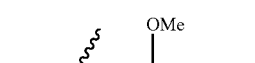 | 1 | 1.31-1.55 (m, 15H), 2.67 (t, 1H, J = 6.6 Hz), 3.06-3.14 (m, 2H), 3.21-3.27 (m, 2H), 4.75 (brs, 1H), 5.63 (brs, 1H), 7.19 (d, 1H, J = 7.5 Hz), 7.34 (t, 1H, J = 7.8 Hz), 7.60 (s, 1H), 7.64 (d, 1H, J = 8.8 Hz) |
| 6 |  |  | 1 | 3.77 (s, 3H), 4.37 (d, 2H, J = 5.1 Hz), 4.94 (brs, 1H), 6.54 (brs, 1H), 6.86 (dd, 2H, J = 6.6, 1.8 Hz), 7.21-7.27 (m, 3H), 7.36 (t, 1H, J = 7.8 Hz), 7.50 (d, 1H, J = 7.2 Hz), 7.58 (s, 1H) |
| 7 |  |  | 4 | 2.91 (s, 3H), 7.35 (dt, 1H, J = 1.3, 8.0 Hz), 7.41 (t, 1H, J = 8.0 Hz), 7.61 (ddd, 1H, J = 1.3, 1.8, J = 8.0 Hz), 7.73 (t, 1H, J = 1.8 Hz) |
| 8 |  |  | 4 | 2.85 (s, 3H), 3.90 (s, 3H), 5.18 (brs, 1H), 7.10 (s, 1H), 7.37 (t, 1H, J = 7.9 Hz), 7.68-7.73 (m, 2H), 7.89 (t, 1H, J = 1.9 Hz) |
| 9 |  |  | 1 | 1.28 (s, 9H), 2.81 (d, 3H, J = 3.9 Hz), 4.77 (brs, 1H), 6.37 (brs, 1H), 7.08-7.4 (m, 2H), 7.22-7.27 (m, 2H) |

TABLE 2

| Ref. Ex. | Ar¹ | R¹ | Measurement cond. | ¹H-NMR (δ PPM) |
|---|---|---|---|---|
| 10 | 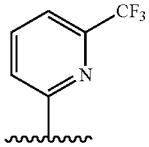 [SMILES: *c1cccc(C(F)(F)F)n1] |  | 1 | 2.96 (d, 3H, J = 4.8 Hz), 6.97 (d, 1H, J = 8.1 Hz), 7.21 (brs, 1H), 7.73 (t, 1H, J = 7.8 Hz), 8.53 (brs, 1H), 8.86 (brs, 1H) |
| 11 | 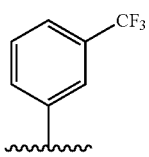 [SMILES: *c1cccc(C(F)(F)F)c1] | $^i$Pr | 1 | 1.18 (d, 6H, J = 6.3 Hz), 1.40 (d, 1H, J = 6.6 Hz), 7.27 (s, 1H), 7.37 (t, 1H, J = 7.5 Hz), 7.50 (d, 1H, J = 8.4 Hz), 7.60 (s, 1H) |
| 12 | 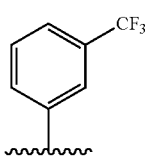 [SMILES: *c1cccc(C(F)(F)F)c1] | 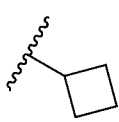 | 1 | 1.66-1.75 (m, 2H), 1.78-1.88 (m, 2H), 2.32-2.41 (m, 2H), 4.24 (sept, 1H, J = 7.8 Hz), 4.83 (brs, 1H), 6.42 (brs, 1H), 7.26 (s, 1H), 7.37 (t, 1H, J = 7.8 Hz), 7.52 (d, 1H, J = 8.4 Hz), 7.59 (s, 1H) |
| 13 | 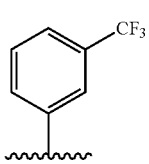 [SMILES: *c1cccc(C(F)(F)F)c1] | 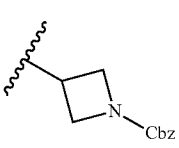 [SMILES: *C1CN(C(=O)OCc2ccccc2)C1] | 1 | 3.77 (dd, 2H, J = 9.6, 4.8 Hz), 4.34 (dd, 2H, J = 9.3, 7.5 Hz), 4.57 (d, 1H, J = 7.2 Hz), 5.09 (s, 2H), 5.31 (d, 1H, J = 7.8 Hz), 6.82 (s, 1H), 7.26-7.32 (m, 6H), 7.37 (t, 1H, J = 7.5 Hz), 7.50 (d, 1H, J = 8.7 Hz), 7.61 (s, 1H) |
| 14 | 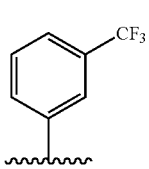 [SMILES: *c1cccc(C(F)(F)F)c1] | 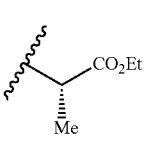 | 1 | 1.30 (t, 3H, J = 6.3 Hz), 1.43 (d, 3H, J = 7.5 Hz), 4.23 (q, 2H, J = 6.9 Hz), 4.50-4.57 (m, 1H), 5.69 (brs, 1H), 7.07 (brs, 1H), 7.18 (d, 1H, J = 7.5 Hz), 7.24-7.30 (m, 1H), 7.38 (d, 1H, J = 7.5 Hz), 7.59 (s, 1H) |
| 15 | 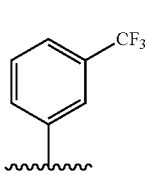 [SMILES: *c1cccc(C(F)(F)F)c1] | 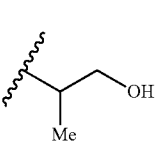 [SMILES: *C(C)CO] | 1 | 1.16 (d, 3H, J = 6.9 Hz), 3.45-3.54 (m, 1H), 3.71 (dd, 1H, J = 10.8, 3.3 Hz), 3.95-3.99 (m, 1H), 7.25 (s, 1H), 7.35 (t, 1H, J = 7.8 Hz), 7.48 (d, 1H, J = 8.7 Hz), 7.59 (s, 1H) |
| 16 | 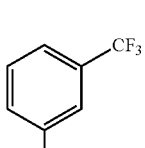 | 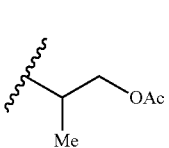 [SMILES: *C(C)COC(C)=O] | 1 | 1.19 (d, 3H, J = 6.6 Hz), 2.07 (s, 3H), 3.97 (dd, 1H, J = 10.5, 4.2 Hz), 4.07-4.21 (m, 2H), 4.96 (d, 1H, J = 7.2 Hz), 6.94 (brs, 1H). 7.24-7.26 (m, 1H), 7.33 (t, 1H, J = 7.8 Hz), 7.53 (d, 1H, J = 7.8 Hz), 7.62 (s, 1H) |
| 17 | 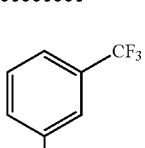 | 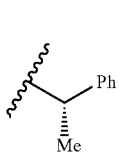 | 4 | 1.42 (d, 3H, J = 6.9 Hz), 4.89 (dq, 1H, J = 6.9, 6.9 Hz), 5.55 (d, 1H, J = 6.9 Hz), 7.12 (s, 1H), 7.19-7.33 (m, 7H), 7.37 (d, 1H, J = 8.2 Hz), 7.49 (s, 1H) |
| 18 | 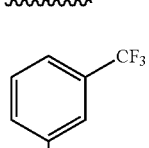 | 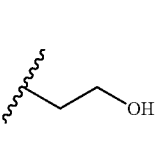 [SMILES: *CCO] | 3 | 3.30-3.34 (m, 2H), 3.63 (t, 2H, J = 5.4 Hz), 7.22 (d, 1H, J = 7.5 Hz), 7.41 (t, 1H, J = 8.1 Hz), 7.51 (d, 1H, J = 8.7 Hz), 7.83 (s, 1H) |

Reference Example 19

Acetic acid 2-(3-(3-(trifluoromethyl)phenyl)ureido)ethyl ester was obtained by using the compound of Reference Example 18 according to a known method.

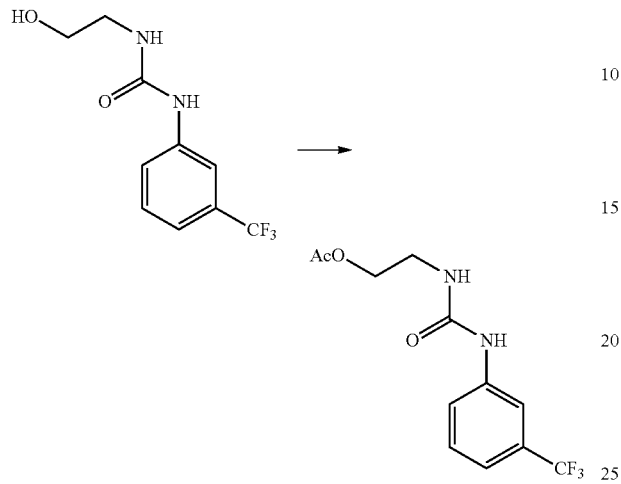

$^1$H-NMR (CDCl$_3$: 300 MHz) (δ PPM):
2.07 (d, 3H, J=3.3 Hz), 3.51-3.54 (m, 2H), 4.20 (dt, 2H, J=5.1, 3.0 Hz), 7.27 (d, 1H, J=9.9 Hz), 7.38 (dt, 1H, J=7.5, 3.6 Hz), 7.51 (d, 1H, J=2.5 Hz), 5.60 (s, 1H)

Reference Examples 20-51

The compounds (1b) indicated in the below-mentioned table (Reference Examples 20-51) were prepared by using the compounds of Reference Examples 1-19 and well-known compounds according to the process described in Heterocycles 1993, 36(2), 307-314.

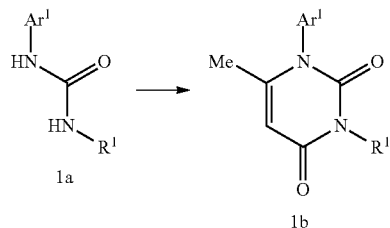

TABLE 3

| Ref. Ex. | Ar$^1$ | R$^1$ | Measurement cond. | $^1$H-NMR (δ PPM) |
|---|---|---|---|---|
| 20 | 3-CF$_3$-C$_6$H$_4$ | —Me | 1 | 1.80 (d, 3H, J = 0.6 Hz), 3.30 (s, 3H), 5.77 (d, 1H, J = 0.9 Hz), 7.40 (d. 1H, J = 7.5 Hz), 7.46 (s, 1H), 7.61 (t, 1H, J = 7.8 Hz), 7.71 (d, 1H, J = 7.8 Hz) |
| 21 | 3-CF$_3$-C$_6$H$_4$ | —CH$_2$CH$_2$Me | 2 | 0.85 (t, 3H, J = 7.4 Hz), 1.51-1.57 (m, 2H), 1.77 (s, 3H), 3.73 (t, 2H, J = 7.4 Hz), 5.81 (s, 1H), 7.74-7.75 (m, 2H), 7.84-7.85 (m, 1H), 7.93 (s, 1H) |
| 22 | 3-CF$_3$-C$_6$H$_4$ | —CH$_2$CO$_2$Et | 1 | 1.26 (t, 3H, J = 6.9 Hz), 1.87 (d, 3H, J = 0.9 Hz), 4.21 (q, 2H, J = 7.2 Hz), 4.68 (d, 2H, J = 1.8 Hz), 5.79 (d, 1H, J = 0.9 Hz), 7.47 (d, 1H, J = 8.1 Hz), 7.53 (s, 1H), 7.64 (t, 1H, J = 8.1 Hz), 7.75 (d, 1H, J = 8.1 Hz) |
| 23 | 3-CF$_3$-C$_6$H$_4$ | —CH$_2$CH$_2$CO$_2$Et | 1 | 1.22 (t, 3H, J = 7.2 Hz), 1.84 (d, 3H, J = 0.9 Hz), 2.66 (t, 2H, J = 7.5 Hz), 4.11 (q, 2H, J = 7.2 Hz), 4.24 (t, 2H, J = 7.2 Hz), 5.73 (d, 1H, J = 0.9 Hz), 7.44 (d, 1H, J = 7.8 Hz), 7.51 (s, 1H), 7.65 (t, 1H, J = 8.1 Hz), 7.75 (d, 1H, J = 7.8 Hz) |
| 24 | 3-CF$_3$-C$_6$H$_4$ | —CH$_2$CH$_2$CH$_2$CO$_2$Et | 1 | 1.21 (t, 3H, J = 7.2 Hz), 1.83 (d, 3H, J = 0.6 Hz), 1.97 (quin, 2H, J = 6.3 Hz), 2.36 (t, 2H, J = 7.5 Hz), 3.99 (t, 2H, J = 6.9 Hz), 4.10 (q, 2H, J = 6.9 Hz), 5.72 (d, 1H, J = 0.9 Hz), 7.31-7.56 (m, 2H), 7.64 (t, 1H. J = 8.1 Hz), 7.74 (d, 1H, J = 7.8 Hz) |

TABLE 3-continued

| Ref. Ex. | Ar¹ | R¹ | Measurement cond. | ¹H-NMR (δ PPM) |
|---|---|---|---|---|
| 25 | 3-CF₃-phenyl | ~CH₂CO₂Bn | 1 | 1.88 (s, 3H), 4.76 (s, 2H), 5.19 (s, 2H), 5.81 (s, 1H), 7.31-7.37 (m, 5H), 7.45 (d, 1H, J = 7.8 Hz), 7.53 (s, 1H), 7.66 (t, 1H, J = 7.8 Hz), 7.76 (d, 1H, J = 7.8 Hz) |
| 26 | 3-CF₃-phenyl | ~CH₂CH(OMe)₂ | 1 | 1.86 (s, 3H), 3.37 (s, 6H), 4.12 (d, 2H, J = 5.7 Hz), 4.84 (t, 1H, J = 5.7 Hz), 5.76 (s, 1H), 7.47 (d, 1H, J = 7.9 Hz), 7.54 (s, 1H), 7.67 (t, 1H, J = 7.9 Hz), 7.76 (d, 1H, J = 7.9 Hz) |

TABLE 4

| Ref. Ex. | Ar¹ | R¹ | Measurement cond. | ¹H-NMR (δ PPM) |
|---|---|---|---|---|
| 27 | 3-CF₃-phenyl | ~(CH₂)₅NHC(O)OC(Me)₃ | 1 | 1.30-1.38 (m, 2H), 1.41 (s, 9H), 1.46-1.52 (m, 2H), 1.60-1.68 (m, 2H), 1.83 (s, 3H), 3.03-3.11 (m, 2H), 3.91 (t, 2H, J = 7.6 Hz), 4.51 (brs, 1H), 5.72 (s, 1H), 7.44 (d, 1H, J = 7.9 Hz), 7.52 (s, 1H), 7.65 (t, 1H, J = 7.9 Hz), 7.74 (d, 1H, J = 7.9 Hz) |
| 28 | 3-CF₃-phenyl | ~CH₂-(4-OMe-phenyl) | 1 | 1.81 (d, 3H, J = 0.9 Hz), 3.76 (s, 3H), 5.04 (s, 2H), 5.74 (d, 1H, J = 0.9 Hz), 6.78-6.83 (m, 2H), 7.39-7.49 (m, 4H), 7.36 (t, 1H, J = 1.8 Hz), 7.73 (d, 1H, J = 7.8 Hz) |
| 29 | 3-CN-phenyl | ~Me | 4 | 1.89 (d, 3H, J = 0.8 Hz), 3.38 (s, 3H), 5.80 (d, 1H, J = 0.8 Hz), 7.53 (ddd, 1H, J = 1.3, 1.7, 7.9 Hz), 7.60 (t, 1H, J = 1.7 Hz), 7.69 (t, 1H, J = 7.9 Hz), 7.82 (dt, 1H, J = 1.3, 7.9 Hz) |
| 30 | 3-CO₂Me-phenyl | ~Me | 4 | 1.80 (d, 3H, J = 0.8 Hz), 3.30 (s, 3H), 3.87 (s, 3H), 5.69 (d, 1H, J = 0.8 Hz), 7.38 (ddd, 1H, J = 1.3, 1.8, 7.9 Hz), 7.55 (t, 1H, J = 7.9 Hz), 7.86 (t, 1H, J = 1.8 Hz), 8.10 (dt, 1H, J = 1.3, 7.9 Hz) |
| 31 | 3-F-phenyl | ~Me | 4 | 1.91 (d, 3H, J = 0.8 Hz), 3.38 (s, 3H), 5.77 (d, 1H, J = 0.8 Hz), 7.01 (dt, 1H, J = 2.2, 8.6 Hz), 7.05-7.08 (m, 1H), 7.23 (ddt, 1H, J = 0.8, 1.6, 8.4 Hz), 7.51 (dt, 1H, J = 6.2, 8.2 Hz) |
| 32 | 3-OMe-phenyl | ~Me | 4 | 1.92 (d, 3H, J = 0.8 Hz), 3.38 (s, 3H), 3.85 (s, 3H), 5.75 (d, 1H, J = 0.8 Hz), 6.77 (t, 1H, J = 2.2 Hz), 6.83 (ddd, 1H, J = 0.8, 1.9, 7.8 Hz), 7.03 (ddd, 1H, J = 0.8, 2.2, 8.5 Hz), 7.43 (t, 1H, J = 8.1 Hz) |

TABLE 4-continued

| Ref. Ex. | Ar$^1$ | R$^1$ | Measurement cond. | $^1$H-NMR (δ PPM) |
|---|---|---|---|---|
| 33 | 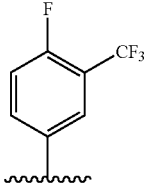 [SMILES: *c1ccc(F)c(C(F)(F)F)c1] |  | 4 | 1.81 (d, 3H, J = 0.8 Hz), 3.29 (s, 3H), 5.71 (d, 1H, J = 0.8 Hz), 7.31 (t, 1H, J = 9.1 Hz), 7.36-7.41 (m, 1H), 7.44-7.47 (m, 1H) |

TABLE 5

| Ref. Ex. | Ar$^1$ | R$^1$ | Measurement cond. | $^1$H-NMR (δ PPM) |
|---|---|---|---|---|
| 34 | 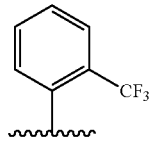 [SMILES: *c1ccccc1C(F)(F)F] | 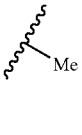 | 1 | 1.81 (d, 3H, J = 0.9 Hz), 3.34 (s, 3H), 5.75 (d, 1H, J = 0.9 Hz), 7.35 (d, 1H, J = 7.5 Hz), 7.63 (t, 1H, J = 7.5 Hz), 7.72 (t, 1H, J = 6.3 Hz), 7.84 (d, 1H, J = 6.6 Hz) |
| 35 | 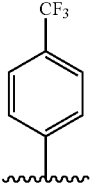 |  | 1 | 1.85 (d, 3H, J = 0.9 Hz), 3.34 (s, 3H), 5.75 (s, 1H), 7.38 (d, 2H, J = 8.4 Hz), 7.79 (d, 2H, J = 8.7 Hz) |
| 36 | 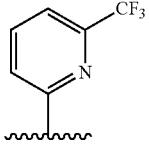 [SMILES: *c1cccc(C(F)(F)F)n1] |  | 1 | 1.86 (d, 3H, J = 0.9 Hz), 3.29 (s, 3H), 5.72 (d, 1H, J = 0.6 Hz), 7.57 (d, 1H, J = 1.8 Hz), 7.77 (d, 1H, J = 7.8 Hz), 8.05 (t, 1H, J = 8.1 Hz) |
| 37 | 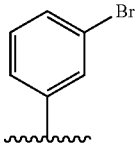 |  | 1 | 1.32 (d, 3H, J = 0.9 Hz), 3.29 (s, 3H), 5.68 (d, 1H, J = 0.9 Hz), 7.11-7.14 (m, 1H), 7.31-7.36 (m, 2H), 7.55-7.58 (m, 1H) |
| 38 | 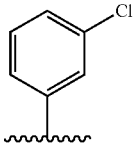 [SMILES: *c1cccc(Cl)c1] |  | 1 | 1.86 (d, 3H, J = 0.9 Hz), 3.33 (s, 3H), 5.72 (d, 1H, J = 0.6 Hz), 7.11-7.14 (m, 1H), 7.24-7.25 (m, 1H), 7.43-7.45 (m, 2H) |
| 39 | 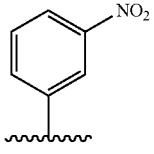 [SMILES: *c1cccc([N+](=O)[O-])c1] |  | 1 | 1.87 (d, 3H, J = 0.9 Hz), 3.34 (s, 3H), 5.78 (s, 1H), 7.57-7.61 (m, 1H), 7.72 (t, 1H, J = 8.1 Hz), 8.14 (t, 1H, J = 2.1 Hz), 8.34-8.37 (m, 1H) |
| 40 | 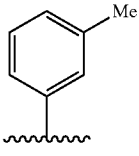 [SMILES: *c1cccc(C)c1] |  | 1 | 1.85 (d, 3H, J = 0.9 Hz), 2.38 (s, 3H), 3.34 (s, 3H), 5.70 (d, 1H, J = 0.9 Hz), 6.99-7.01 (m, 2H), 7.27 (s, 1H), 7.37 (t, 1H, J = 7.2 Hz) |

TABLE 5-continued

| Ref. Ex. | Ar¹ | R¹ | Measurement cond. | ¹H-NMR (δ PPM) |
|---|---|---|---|---|
| 41 | 3-(C(Me)₃)-phenyl (tBu-like, C(Me)₃ shown as CMe₃ on phenyl) | Me (attached via wavy bond) | 1 | 1.31 (s, 9H), 1.82 (s, 3H), 3.35 (s, 3H), 5.71 (s, 1H), 7.00-7.02 (m, 1H), 7.17 (t, 1H, J = 1.5 Hz), 7.38-7.49 (m, 2H) |
| 42 | 3-(SO₂Me)-phenyl | Me | 1 | 1.85 (d, 3H, J = 0.9 Hz), 3.10 (s, 3H), 3.34 (s, 3H), 5.77 (d, 1H, J = 0.9 Hz), 7.53 (ddd, 1H, J = 7.8, 2.1, 0.9 Hz), 7.74 (t, 1H, J = 7.8 Hz), 7.84 (t, 1H, J = 2.1 Hz), 8.03-8.06 (m, 1H) |

TABLE 6

| Ref. Ex. | Ar¹ | R¹ | Measurement cond. | ¹H-NMR (δ PPM) |
|---|---|---|---|---|
| 43 | 3-CF₃-phenyl | Et | 1 | 1.23 (t, 3H, J = 7.2 Hz), 1.83 (d, 3H, J = 0.9 Hz), 3.99 (q, 2H, J = 6.9 Hz), 5.73 (s, 1H), 7.44 (d, 1H, J = 7.5 Hz), 7.52 (s, 1H), 7.65 (t, 1H, J = 7.5 Hz), 7.73 (d, 1H, J = 8.1 Hz) |
| 44 | 3-CF₃-phenyl | $^i$Pr | 1 | 1.45 (d, 6H, J = 6.9 Hz), 1.80 (d, 3H, J = 0.3 Hz), 5.18 (quintet, 1H, J = 6.9 Hz), 5.68 (s, 1H), 7.44 (d, 1H, J = 7.8 Hz), 7.51 (s, 1H), 7.64 (t, 1H, J = 7.8 Hz), 7.73 (d, 1H, J = 7.8 Hz) |
| 45 | 3-CF₃-phenyl | $^c$Pr | 1 | 0.74-0.85 (m, 2H), 1.07-1.14 (m, 2H), 1.81 (s, 3H), 2.65-2.73 (m, 1H), 5.96 (d, 1H, J = 0.9 Hz), 7.42 (d, 1H, J = 8.1 Hz), 7.50 (s, 1H), 7.64 (t, 1H, J = 8.1 Hz), 7.73 (d, 1H, J = 7.8 Hz) |
| 46 | 3-CF₃-phenyl | cyclobutyl | 1 | 1.65-1.90 (m, 5H), 2.16-2.25 (m, 2H), 2.91 (dseptet, 2H, J = 9.6, 1.8 Hz), 5.28 (septet, 1H, J = 8.7 Hz), 5.68 (s, 1H), 7.44 (d, 1H, J = 8.1 Hz), 7.51 (s, 1H), 7.65 (t, 1H, J = 7.8 Hz), 7.73 (d, 1H, J = 7.8 Hz) |
| 47 | 3-CF₃-phenyl | N-Cbz-azetidin-3-yl | 1 | 1.83 (d, 3H, J = 0.9 Hz), 4.25 (t, 2H, J = 9.0 Hz), 4.50 (dd, 2H, J = 9.0, 6.3 Hz), 5.06 (s, 2H), 5.36-5.46 (m, 1H), 5.71 (d, 1H, J = 9.0 Hz), 7.25-7.33 (m, 5H), 7.43 (d, 1H, J = 8.1 Hz), 7.50 (s, 1H), 7.66 (t, 1H, J = 7.8 Hz), 7.75 (d, 1H, J = 7.8 Hz) |
| 48 | 3-CF₃-phenyl | CH(Me)CO₂Et | 1 | 1.16 (dt, 3H, J = 7.2, 0.9 Hz), 1.52 (d, 3H, J = 6.9 Hz), 1.80 (s, 3H), 4.04-4.17 (m, 2H), 5.41 (dq, 1H, J = 6.9, 2.4 Hz), 5.69 (d, 1H, J = 0.9 Hz), 7.36-7.49 (m, 2H), 7.59 (t, 1H, J = 8.1 Hz), 7.68 (d, 1H, J = 8.1 Hz) |

TABLE 6-continued

| Ref. Ex. | Ar¹ | R¹ | Measurement cond. | ¹H-NMR (δ PPM) |
|---|---|---|---|---|
| 49 | 3-CF₃-phenyl | CH(Me)CH₂OAc | 1 | 1.47 (d, 3H, J = 7.2 Hz), 1.83 (d, 3H, J = 0.6 Hz), 2.01 (d, 3H, J = 0.3 Hz), 4.26-4.35 (m, 1H), 4.65 (dq, 1H, J = 10.8, 8.4 Hz), 5.25 (brs, 1H), 5.70 (s, 1H), 7.40-7.55 (m, 2H), 7.65 (t, 1H, J = 7.8 Hz), 7.74 (d, 1H, J = 8.1 Hz) |
| 50 | 3-CF₃-phenyl | CH(Me)Ph | 4 | 1.82 (s, 3H), 1.87 (d, 3H, J = 7.1 Hz), 5.74 (s, 1H), 6.31 (q, 1H, J = 6.8 Hz), 7.22-7.34 (m, 3.5H), 7.45-7.48 (m, 3H), 7.53 (s, 0.5H), 7.60-7.68 (m, 1H), 7.70-7.73 (m, 1H) |
| 51 | 3-CF₃-phenyl | (CH₂)₃OAc | 1 | 1.85 (d, 3H, J = 0.9 Hz), 1.99 (s, 3H), 4.20-4.24 (m, 2H), 4.31-4.36 (m, 2H), 5.74 (s, 1H), 7.44 (d, 1H, J = 7.5 Hz), 7.52 (s, 1H), 7.65 (t, 1H, J = 7.8 Hz), 7.44 (d, 1H, J = 8.1 Hz) |

Reference Examples 52-53

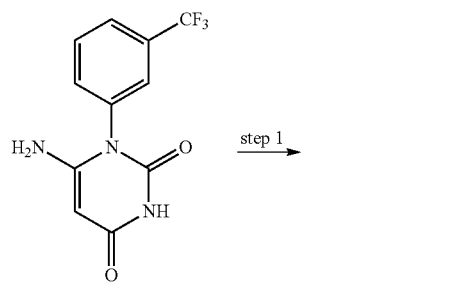

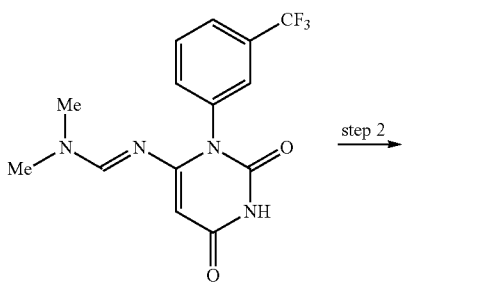

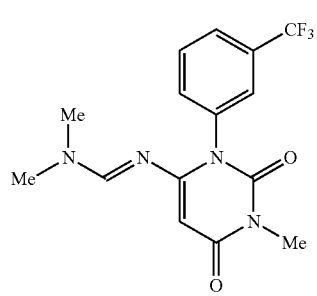

Step 1

Reference Example 52

To a solution of 6-amino-1-(3-trifluoromethylphenyl)-pyrimidin-2,4-(1H,3H)-dione (3.0 g) (prepared according to the method described in Bioorganic & Medicinal Chemistry 2003, 11(23), 4933-4940) in methanol (75.0 ml) was added N,N-dimethylformamide dimethylacetal (3.9 g) and the resulting mixture was stirred with heating under reflux for two hours. The precipitated solids were collected by filtration with methanol to afford N'-[2,6-dioxo-3-(3-trifluorophenyl)-1,2,3,6-tetrahydropyrimidin-4-yl]-N,N-dimethylformimidamide (1.8 g).

¹H-NMR (CDCl₃: 300 MHz) (δ PPM):
2.62 (s, 3H), 3.04 (s, 3H), 5.09 (d, 1H, J=2.2 Hz), 7.41 (d, 1H, J=7.8 Hz), 7.49 (s, 1H), 7.53 (t, 1H, J=7.8 Hz), 7.58-7.62 (m, 2H), 7.85 (s, 1H)

Step 2

Reference Example 53

To a solution of N'-[2,6-dioxo-3-(3-trifluorophenyl)-1,2,3,6-tetrahydropyrimidin-4-yl]-N,N-dimethylformimidamide (600 mg), potassium carbonate (508.0 mg) in N,N-dimethyformamide (5.0 ml) was added methyl iodide (340 μl) and the resulting mixture was stirred at 80° C. for six hours. The reaction mixture was poured into ice water and the precipitated solids were collected by filtration with water to afford N,N-dimethyl-N'-[1-methyl-2,6-dioxo-3-(3-trifluorophenyl)-1,2,3,6-tetrahydropyrimidin-4-yl]formimidamide (550.0 mg).

¹H-NMR (CDCl₃: 300 MHz) (δ PPM):
2.61 (s, 3H), 3.02 (s, 3H), 3.35 (s, 3H), 5.18 (s, 1H), 7.39 (d, 1H, J=7.7 Hz), 7.47 (s, 1H), 7.52 (t, 1H, J=7.7 Hz), 7.58-7.61 (m, 2H)

Reference Example 54

The below-mentioned compound was obtained by using the corresponding starting materials according to the similar reaction and treatment method to those described in Reference Example 53.

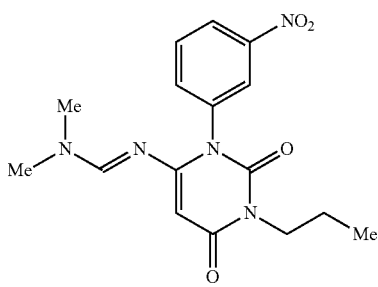 [SMILES: CCCn1c(=O)cc(/N=C/N(C)C)n(-c2cccc([N+](=O)[O-])c2)c1=O]

¹H-NMR (CDCl₃: 300 MHz) (δ PPM):
0.85 (t, 3H, J=7.4 Hz), 1.50-1.59 (m, 2H), 2.51 (s, 3H), 3.00 (s, 3H), 3.73 (t, 2H, J=7.4 Hz), 5.32 (s, 1H), 7.67-7.74 (m, 2H), 8.04 (s, 1H), 8.17 (s, 1H), 8.23 (d, 1H, J=7.6 Hz)

Reference Examples 55-57

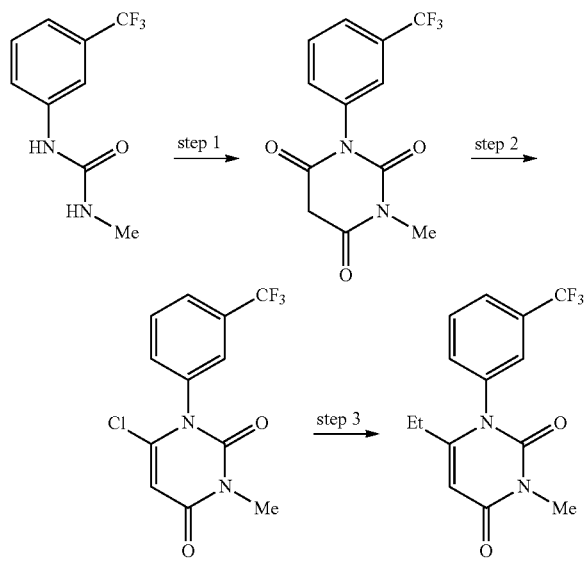

Step 1

Reference Example 55

1-Methyl-3-(3-(trifluoromethyl)phenyl)urea (available from Crescent Chemical Co., Inc.) (4.03 g) and malonic acid (2.11 g) were suspended into acetic anhydride (12 ml) and the resulting mixture was stirred at 80° C. for one hour. After the reaction solutions were concentrated under reduced pressure, to the residue was added saturated aqueous sodium hydrogen carbonate solution and the resulting mixture was washed with ethyl acetate. The aqueous layer was acidified with concentrated hydrochloric acid and the resulting mixture was extracted with ethyl acetate (50 ml×2). The organic layer was washed with saturated saline (50 ml), dried over anhydrous magnesium sulfate and then concentrated under reduced pressure. The residue was purified by silica gel column chromatography (eluent: chloroform/methanol) to afford 1-methyl-3-(3-(trifluoromethyl)phenyl)pyrimidin-2,4,6-(1H, 3H, 5H)-trione (2.75 g).

¹H-NMR (400 MHz, DMSO-d₆) (δ PPM):
3.15 (s, 3H), 3.88 (s, 2H), 7.57 (d, 1H, J=7.9 Hz), 7.66 (s, 1H), 7.74 (t, 1H, J=7.9 Hz), 7.82 (d, 1H, J=7.9 Hz)

Step 2

Reference Example 56

To a solution of 1-methyl-3-(3-(trifluoromethyl)phenyl)pyrimidin-2,4,6(1H, 3H, 5H)-trione (2.74 g) (prepared in Reference Example 55) in phosphorus oxychloride (22 ml) was added water (0.55 ml) slowly and the resulting mixture was stirred with heating under reflux for one hour. After concentration under reduced pressure, the reaction solutions were cooled to 0° C. and to the residue was added water (50 ml) slowly with stirring. The resulting mixture was extracted with ethyl acetate (50 ml×3), and the resulting extracts were dried and then concentrated under reduced pressure. The residue was purified by silica gel column chromatography (eluent: hexane/ethyl acetate) to afford 6-chloro-3-methyl-1-(3-(trifluoromethyl)phenyl)pyrimidin-2,4(1H,3H)-dione (1.54 g).

¹H-NMR (400 MHz, DMSO-d₆) (δ PPM):
3.18 (s, 3H), 6.29 (s, 1H), 7.76-7.83 (m, 2H), 7.89 (d, 1H, J=7.2 Hz), 7.99 (s, 1H)

Step 3

Reference Example 57

To a solution of 6-chloro-3-methyl-1-(3-(trifluoromethyl)phenyl)pyrimidin-2,4(1H,3H)-dione (prepared in Reference Example 56) (1.12 g) in THF (tetrahydrofuran) (30 ml) were added under nitrogen atmosphere bis(tri-tert-butyl phosphine)palladium (188 mg) and zinc diethyl (1.1 M hexane solution, 10 ml) and the resulting mixture was stirred at room temperature for twenty minutes. The reaction solutions were added into 1 N (normality) of hydrochloric acid and the resulting mixture was extracted with ethyl acetate (50 ml×2). The organic layer was washed with saturated saline (50 ml), dried over anhydrous magnesium sulfate, and then concentrated under reduced pressure. The residue was purified by silica gel column chromatography (eluent: hexane/ethyl acetate) to afford 6-ethyl-3-methyl-1-(3-(trifluoromethyl)phenyl)pyrimidin-2,4(1H,3H)-dione (0.94 g).

¹H-NMR (400 MHz, CDCl₃) (δ PPM):
1.08 (t, 3H, J=7.3 Hz), 2.06 (q, 2H, J=7.3 Hz), 3.37 (s, 3H), 5.79 (s, 1H), 7.45 (d, 1H, J=8.1 Hz), 7.53 (s, 1H), 7.67 (t, 1H, J=7.9 Hz), 7.82 (d, 1H, J=7.9 Hz)

Reference Example 58

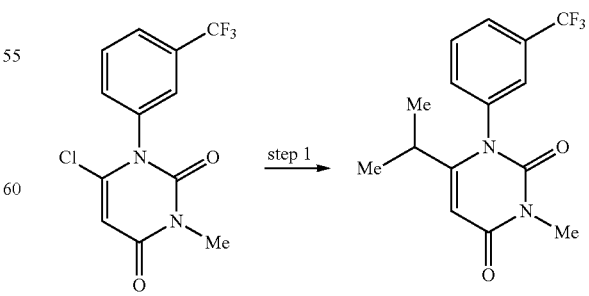

To a mixed solution of 6-chloro-3-methyl-1-(3-(trifluoromethyl)phenyl)pyrimidin-2,4(1H,3H)-dione (prepared in Reference Example 56) (149 mg) in THF (5 ml) and N-methylpyrrolidone (0.5 ml) were added under nitrogen atmosphere iron(III) acetylacetonate (26 mg) and isopropylmagnesium chloride (2M THF solution, 1 ml), and the resulting mixture was stirred at room temperature for two and a half hours. The reaction solutions were added to 1N hydrochloric acid, and the resulting mixture was extracted with ethyl acetate (20 ml×2). The organic layer washed with saturated saline (20 ml), dried over anhydrous magnesium sulfate and then concentrated under reduced pressure. The residue was purified by silica gel column chromatography (eluent: hexane/ethyl acetate) to afford 6-isopropyl-3-methyl-1-(3-(trifluoromethyl)phenyl)pyrimidin-2,4(1H,3H)-dione (53 mg).

$^1$H-NMR (400 MHz, CDCl$_3$) (δ PPM):

1.07 (d, 3H, J=6.7 Hz), 1.09 (d, 3H, J=6.7 Hz), 2.30 (sept, 1H, J=6.7 Hz), 3.36 (s, 3H), 5.81 (s, 1H), 7.46 (d, 1H, J=7.9 Hz), 7.53 (s, 1H), 7.68 (t, 1H, J=7.9 Hz), 7.77 (d, 1H, J=7.9 Hz)

Reference Example 59

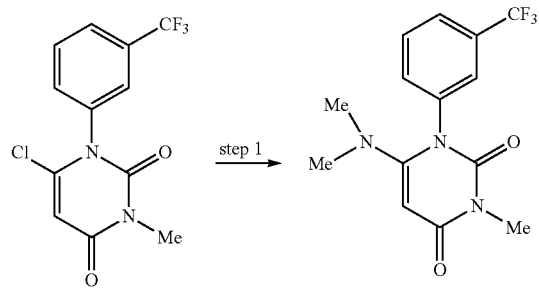 [SMILES: Cn1c(=O)cc(Cl)n(-c2cccc(C(F)(F)F)c2)c1=O ; CN(C)c1cc(=O)n(C)c(=O)n1-c1cccc(C(F)(F)F)c1]

To a suspension of 6-chloro-3-methyl-1-(3-(trifluoromethyl)phenyl)pyrimidin-2,4(1H,3H)-dione (prepared in Reference Example 56) (301 mg) in isopropyl alcohol (10 ml) was added 50% aqueous dimethyl amine solution (0.5 ml) and the resulting mixture was stirred at 80° C. for two and a half hours. The reaction solutions were concentrated under reduced pressure, and to the residue were added water and methanol, and the resulting mixture was stirred. The precipitated solids were collected by filtration, and washed with water and diethylther to afford 6-(dimethylamino)-3-methyl-1-(3-(trifluoromethyl)phenyl)pyrimidin-2,4(1H,3H)-dione (220 mg).

$^1$H-NMR (400 MHz, DMSO-d$_6$) (δ PPM):

2.41 (s, 6H), 3.13 (s, 3H), 5.22 (s, 1H), 7.68-7.71 (m, 2H), 7.76-7.79 (m, 1H), 7.85 (s, 1H)

Reference Examples 60-61

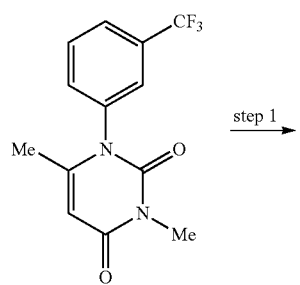

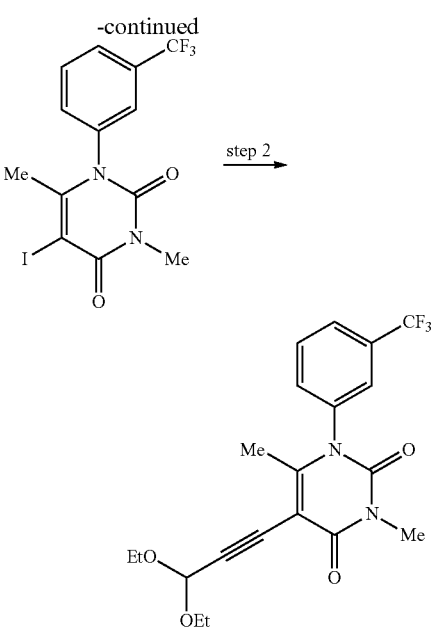

Step 1

Reference Example 60

To a solution of 3,6-dimethyl-1-(3-trifluoromethylphenyl)-pyrimidin-2,4(1H,3H)-dione (prepared in Reference Example 20) (800.0 mg) in acetic acid (13.0 ml) was added in water bath N-iodosuccinimide (784.5 mg) and the resulting mixture was stirred at room temperature for five hours. To the reaction mixture was added water (20 ml) and the resulting mixture was stirred for thirty minutes, and thereto was added sodium thiosulfate solution (20 ml) and the resulting mixture was stirred for thirty minutes. The precipitated solids were collected by filtration and washed with water to afford 5-iodo-3,6-dimethyl-1-(3-trifluoromethylphenyl)pyrimidin-2,4(1H,3H)-dione (819.3 mg).

$^1$H-NMR (CDCl$_3$: 300 MHz) (δ PPM):

2.22 (s, 3H), 3.43 (s, 3H), 7.43 (d, 1H, J=7.8 Hz), 7.49 (s, 1H), 7.67 (t, 1H, J=7.8 Hz), 7.77 (d, 1H, J=8.1 Hz)

Step 2

Reference Example 61

A solution of 5-iodo-3,6-dimethyl-1-(3-trifluoromethylphenyl)pyrimidin-2,4(1H,3H)-dione (prepared in Reference Example 60) (20.0 mg), propargylaldehyde diethyl acetal (62.5 mg), tetrakis(triphenylphosphine)palladium (5.6 mg), copper iodide (1.0 mg) and triethylamine (68 μL) in tetrahydrofuran (1.0 ml) was stirred at room temperature under nitrogen atmosphere for twelve hours. To the reaction mixture was added water (10 ml) and the resulting mixture was extracted with ethyl acetate (10 ml×2). The organic layer was washed with saturated saline (20 ml), dried over anhydrous sodium sulfate and then concentrated under reduced pressure. The residue was purified silica gel column chromatography (eluent: hexane/ethyl acetate) to afford 5-(3,3-diethoxyprop-1-ynyl)-3,6-dimethyl-1-(3-trifluoromethylphenyl)-pyrimidin-2,4(1H,3H)-dione (216.0 mg).

$^1$H-NMR (CDCl$_3$: 300 MHz) (δ PPM):
1.23 (t, 6H, J=7.2 Hz), 2.09 (s, 3H), 3.37 (s, 3H), 3.60-3.66 (m, 2H), 3.75-3.81 (m, 2H), 5.48 (s, 1H), 7.42 (d, 1H, J=7.2 Hz), 7.49 (s, 1H), 7.67 (t, 1H, J=8.1 Hz), 7.78 (d, 1H, J=7.8 Hz)

Reference Examples 62-92

The below-mentioned compounds Ic (Reference Examples 62-92) were obtained by using the compounds of Reference Examples 21-51 according to the similar reaction and treatment method to those described in Reference Example 60.

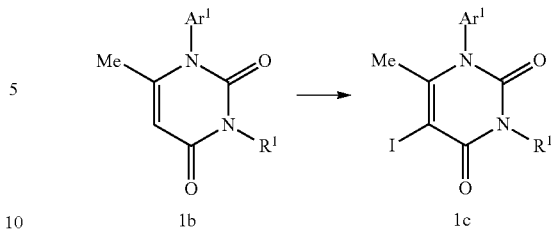

TABLE 7

| Ref. Ex. | Ar$^1$ | R$^1$ | Measurement cond. | $^1$H-NMR (δ PPM) |
|---|---|---|---|---|
| 62 | 3-CF$_3$-phenyl | -CH$_2$CH$_2$CH$_2$Me | 1 | 0.86 (t, 3H, J = 7.4 Hz), 1.52-1.60 (m, 2H), 2.11 (d, 3H, J = 1.2 Hz), 3.81 (t, 2H, J = 7.4 Hz), 7.76-7.80 (m, 2H), 7.84-7.90 (m, 1H), 7.96 (s, 1H) |
| 63 | 3-CF$_3$-phenyl | -CH$_2$CO$_2$Et | 1 | 1.24 (3H, t, J = 6.9 Hz), 2.24 (3H, s), 4.22 (2H, t, J = 7.2 Hz), 4.74 (2H, s), 7.45 (d, 1H, J = 7.8 Hz), 7.52 (s, 1H), 7.66 (t, 1H, J = 8.1 Hz), 7.76 (t, 1H, J = 7.8 Hz) |
| 64 | 3-CF$_3$-phenyl | -CH$_2$CH$_2$CO$_2$Et | 1 | 1.21 (t, 3H, J = 7.2 Hz), 2.22 (s, 3H), 2.66 (t, 2H, J = 7.5H), 4.11 (q, 2H, J = 7.8 Hz), 4.31 (t, 2H, J = 7.2 Hz), 7.43 (d, 1H, J = 8.1 Hz), 7.49 (s, 1H), 7.66 (t, 1H, J = 8.1 Hz), 7.76 (d, 1H, J = 8.1 Hz) |
| 65 | 3-CF$_3$-phenyl | -CH$_2$CH$_2$CH$_2$CO$_2$Et | 1 | 1.21 (t, 3H, J = 7.2 Hz), 1.99 (quin, 2H, J = 7.2 Hz), 2.21 (s, 3H), 2.35 (t, 2H, J = 7.8 Hz), 4.08 (q, 4H, J = 7.2 Hz), 7.44 (d, 1H, J = 7.2 Hz), 7.50 (s, 1H), 7.66 (t, 1H, J = 7.8 Hz), 7.75 (d, 1H, J = 8.1 Hz) |
| 66 | 3-CF$_3$-phenyl | -CH$_2$CO$_2$Bn | 1 | 2.26 (s, 3H), 4.82 (s, 2H), 5.19 (s, 2H), 7.31-7.37 (m, 5H), 7.43 (d, 1H, J = 7.8 Hz), 7.52 (s, 1H), 7.68 (t, 1H, J = 7.8 Hz), 7.77 (d, 1H, J = 7.8 Hz) |
| 67 | 3-CF$_3$-phenyl | -CH$_2$CH(OMe)$_2$ | 1 | 2.22 (s, 3H), 3.34 (s, 6H), 4.16 (d, 2H, J = 5.8 Hz), 4.83 (t, 1H, J = 5.8 Hz), 7.43 (d, 1H, J = 7.9 Hz), 7.50 (s, 1H), 7.66 (t, 1H, J = 7.9 Hz), 7.75 (d, 1H, J = 7.9 Hz) |

TABLE 8

| Ref. Ex. | Ar$^1$ | R$^1$ | Measurement cond. | $^1$H-NMR (δ PPM) |
|---|---|---|---|---|
| 68 | 3-CF$_3$-phenyl | -(CH$_2$)$_5$NHC(O)OC(Me)$_3$ | 1 | 1.30-1.36 (m, 2H), 1.41 (s, 9H), 1.44-1.50 (m, 2H), 1.62-1.68 (m, 2H), 2.21 (s, 3H), 3.02-3.12 (m, 2H), 3.98 (t, 2H, J = 7.7 Hz), 4.50 (brs, 1H), 7.42 (d, 1H, J = 8.4 Hz), 7.50 (s, 1H), 7.66 (t, 1H, J = 8.4 Hz), 7.75 (d, 1H, J = 8.4 Hz) |

TABLE 8-continued

| Ref. Ex. | Ar¹ | R¹ | Measurement cond. | ¹H-NMR (δ PPM) |
|---|---|---|---|---|
| 69 | 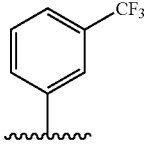 [SMILES: *c1cccc(C(F)(F)F)c1] | 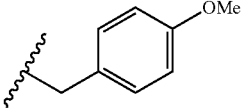 [SMILES: *Cc1ccc(OC)cc1] | 1 | 2.18 (s, 2H), 2.19 (s, 1H), 3.75 (s, 2H), 3.82 (s, 1H), 5.05 (s, 0.5H), 5.10 (s, 1.5H), 6.72 (d, 0.5H, J = 8.4 Hz), 6.81 (d, 1.5H, J = 8.7 Hz), 7.38 -7.51 (m, 4H), 7.62-7.74 (m, 2H) |
| 70 | 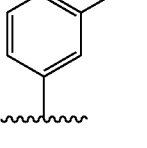 |  | 4 | 2.26 (s, 3H), 3.46 (s, 3H), 7.52 (ddd, 1H, J = 1.3, 1.6, 7.9 Hz), 7.58 (t, 1H. J = 1.6 Hz), 7.70 (t, 1H, J = 7.9 Hz), 7.83 (dt, 1H, J = 1.3, 7.9 Hz) |
| 71 | 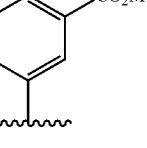 |  | 4 | 2.18 (s, 3H), 3.38 (s, 3H), 3.87 (s, 3H), 7.35 (ddd, 1H, J = 1.3, 1.8, 7.9 Hz), 7, 56 (t, 1H, J = 7.9 Hz), 7.83 (t, 1H, J = 1.8 Hz), 8.10 (dt, 1H, J = 1.3, 7.9 Hz) |
| 72 | 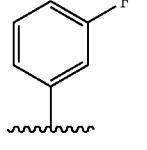 |  | 4 | 2.20 (s, 3H), 3.38 (s, 3H), 6.91 (dt, 1 H, J = 2.2, 8.6 Hz), 6.96 (dd, 1H, J = 1.2, 7.9 Hz), 7.13-7.20 (m, 1H), 7.45 (dt, 1H, J = 6.1, 8.2 Hz) |
| 73 | 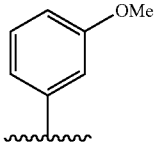 [SMILES: *c1cccc(OC)c1] |  | 4 | 2.21 (s, 3H), 3.38 (s, 3H), 3.76 (s, 3H), 6.66 (dd, 1H, J = 1.9, 2.2 Hz), 6.72 (ddd, 1H, J = 0.8, 1.9, 8.0 Hz), 6.95 (ddd, 1 H, J = 0.8, 2.2, 8.0 Hz), 7.36 (t, 1H. J = 8. 1 Hz) |
| 74 | 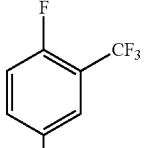 |  | 4 | 2.19 (s, 3H), 3.38 (s, 3H), 7.32 (t, 1H, J = 8.9 Hz), 7.34-7.39 (m, 1H), 7.42-7.45 (m, 1H) |
| 75 | 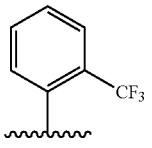 [SMILES: *c1ccccc1C(F)(F)F] |  | 1 | 2.17 (s, 3H), 3.42 (s, 3H), 7.33 (d, 1H, J = 7.5 Hz), 7.64 (t, 1H, J = 7.8 Hz), 7.74 (t, 1H, J = 7.8 Hz), 7.85 (d, 1H, J = 7.8 Hz) |

TABLE 9

| Ref. Ex. | Ar¹ | R¹ | Measurement cond. | ¹H-NMR (δ PPM) |
|---|---|---|---|---|
| 76 | 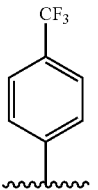 |  | 1 | 2.21 (s, 1H), 2.22 (s, 2H), 3.42 (s, 1H), 3.43 (s, 2H), 7.37 (d, 2H, J = 8.1 Hz), 7.81 (d, 2H, J = 7.8 Hz) |

TABLE 9-continued

| Ref. Ex. | Ar¹ | R¹ | Measurement cond. | ¹H-NMR (δ PPM) |
|---|---|---|---|---|
| 77 | pyridine with CF₃ | Me | 1 | 2.18 (s, 3H), 3.37 (s, 3H), 7.56 (d, 1H, J = 7.8 Hz), 7.79 (d, 1H, J = 7.8 Hz), 8.08 (t, 1H, J = 7.8 Hz) |
| 78 | 3-Br-phenyl | Me | 1 | 2.24 (s, 3H), 3.42 (s, 3H), 7.14-7.17 (m, 1H), 7.37-7.42 (m, 2H), 7.60-7.63 (m, 1H) |
| 79 | 3-Cl-phenyl | Me | 1 | 2.24 (s, 3H), 3.42 (s, 3H), 7.09-7.13 (m, 1H), 7.22-7.23 (m, 1H), 7.45-7.47 (m, 2H) |
| 80 | 3-NO₂-phenyl | Me | 1 | 2.25 (s, 3H), 3.43 (s, 3H), 7.55-7.59 (m, 1H), 7.74 (t, 1H, J = 8.2 Hz), 8.12 (t, 1H, J = 2.1 Hz), 8.35-8.38 (m, 1H) |
| 81 | 3-Me-phenyl | Me | 1 | 2.23 (s, 3H), 2.39 (s, 3H), 3.43 (s, 3H), 6.97-6.99 (m, 2H), 7.27 (d, 1H, J = 7.2 Hz), 7.39 (t, 1H, J = 6.6 Hz) |
| 82 | 3-tBu-phenyl | Me | 1 | 1.31 (s, 9H), 2.21 (s, 3H) 3.43 (s, 3H), 6.97-7.00 (m, 1H), 7.14-7.16 (m, 1H), 7.40-7.50 (m, 2H) |
| 83 | 3-(SO₂Me)-phenyl | Me | 1 | 2.22 (s, 3H), 3.10 (s, 3H), 3.43 (s, 3H), 7.05-7.36 (m, 1H), 7.76 (t, 1H, J = 7.8 Hz), 7.82 (t, 1H, J = 1.5 Hz), 8.04-8.08 (m, 1H) |
| 84 | 3-CF₃-phenyl | Et | 1 | 1.24 (t, 3H, J = 7.2 Hz), 2.21 (s, 3H), 4.06 (q, 2H, J = 7.2 Hz), 7.42 (d. 1H, J = 8.1 Hz), 7.50 (s, 1H), 7.66 (t, 1H, J = 7.8 Hz), 7.75 (d, 1H, J = 8.1 Hz) |
| 85 | 3-CF₃-phenyl | ⁱPr | 1 | 1.45 (d, 6H, J = 6.9 Hz), 2.18 (s, 3H), 5.19 (quintet, 1H. J = 7.8 Hz). 7.42 (d, 1H, J = 7.8 Hz), 7.50 (s, 1H), 7.66 (t, 1H, J = 7.8 Hz), 7.74 (d, 1H, J = 8.4 Hz) |

TABLE 10

| Ref. Ex. | Ar¹ | R¹ | Measurement cond. | ¹H-NMR (δ PPM) |
|---|---|---|---|---|
| 86 | 3-CF₃-C₆H₄- | $^c$Pr | 1 | 0.79-0.85 (in, 2H), 1.12 (q, 2H, J = 6.9 Hz), 2.19 (s, 3H), 2.72-2.82 (m, 1H), 7.40 (d, 1H, J = 7.8 Hz), 7.48 (s, 1H), 7.65 (t, 1H, J = 7.8 Hz), 7.73 (d, 1H, J = 7.8 Hz) |
| 87 | 3-CF₃-C₆H₄- | cyclobutyl-CH₂- | 1 | 1.63-1.91 (m, 2H), 2.16-2.28 (m, 5H), 2.86 (dseptet, 2H, J = 9.6, 2.4 Hz), 5.24 (septet, 1H, J = 8.7 Hz), 7.42 (d, 1H, J = 7.8 Hz), 7.49 (s, 1H), 7.66 (t, 1H, J = 7.8 Hz), 7.74 (d, 1H, J = 7.8 Hz) |
| 88 | 3-CF₃-C₆H₄- | N-Cbz-azetidin-3-yl | 1 | 2.22 (s, 3H), 4.25 (t, 2H, J = 9.0 Hz), 4.47 (dd, 2H, J = 9.0, 7.2 Hz), 5.07 (s, 2H), 5.37-5.42 (m, 1H), 7.27-7.33 (n, 5H), 7.41 (d, 1H, J = 7.8 Hz), 7.48 (s, 1H), 7.68 (t, 1H, J = 7.8 Hz), 7.77 (d, 1H, J = 8.1 Hz) |
| 89 | 3-CF₃-C₆H₄- | -CH(Me)-CO₂Et | 1 | 1.22 (dt, 3H, J = 6.9, 0.9 Hz), 1.58 (d, 3H, J = 6.9 Hz), 2.23 (s, 3H), 4.10-4.25 (m, 2H), 5.50 (dq, 1H, J = 6.9, 1.8 Hz), 7.40-7.53 (m, 2H), 7.66 (t, 1H, J = 7.5 Hz), 7.75 (d, 1H, J = 7.8 Hz) |
| 90 | 3-CF₃-C₆H₄- | -CH(Me)-CH(Me)-OAc | 1 | 1.46 (d, 3H, J = 6.9 Hz), 2.00 (s, 3H), 2.21 (s, 3H), 4.29-4.38 On, 1H), 4.57-4.68 (m, 1H), 5.25 (brs, 1H), 7.42 (t, 1H, J = 9.3 Hz), 7.51 (d, 1H, J = 15.6 Hz), 7.67 (t, 1H, J = 6.9 Hz), 7.75 (d, 1H, J = 7.8 Hz) |
| 91 | 3-CF₃-C₆H₄- | -CH(Me)-Ph | 4 | 1.75 (d, 1.5H, J = 7.1 Hz), 1.76 (d, 1.5H, J = 7.0 Hz), 2.11 (s, 3H), 6.10 (q, 1H, J = 6.9 Hz), 7.20-7.24 (n. 1H), 7.28-7.34 (m, 4H), 7.72-7.79 (m, 1.5H), 7.82-7.87 (m, 1.5 Hz), 7.94 (s, 0.5H), 8.03 (s, 0.5H) |
| 92 | 3-CF₃-C₆H₄- | -CH₂-CH₂-OAc | 1 | 1.98 (s, 3H), 2.22 (s, 3H), 4.30-4.35 (m, 4H), 7.43 (d, 1H, J = 7.8 Hz), 7.50 (s, 1H), 7.67 (t, 1H, J = 8.1 Hz), 7.75 (d, 1H, J = 7.8 Hz) |

Reference Examples 93-94

The compounds Id (Reference Examples 93-94) indicated in the below-mentioned Table were obtained by using the compounds of Reference Examples 53-54 according to the similar reaction and treatment method to those described in Reference Example 60.

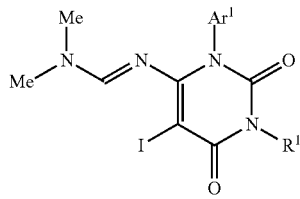

Id

TABLE 11

| Ref. Ex. | Ar¹ | R¹ | Measurement cond. | ¹H-NMR (δ PPM) |
|---|---|---|---|---|
| 93 | 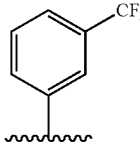 |  | 1 | 2.60 (s, 3H), 2.98 (s, 3H), 3.42 (s, 3H), 7.35 (d, 1H, J = 7.8 Hz), 7.42 (s, 1H), 7.52 (t, 1H, J = 7.8 Hz), 7.60 (d, 1H, J = 8.8 Hz), 7.64 (s, 1H) |
| 94 | 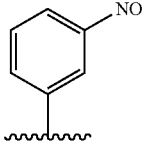 | 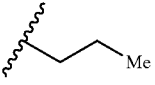 [SMILES: *CCC] | 1 | 0.87 (t, 3H, J = 7.4 Hz), 1.51-1.61 (m, 2H), 2.51 (s, 3H), 2.94 (s, 3H), 3.81 (t, 2H, J = 7.4 Hz), 7.68-7.74 (m, 2H), 7.82 (s, 1H), 8.21-8.23 (m, 2H) |

Reference Examples 95-98

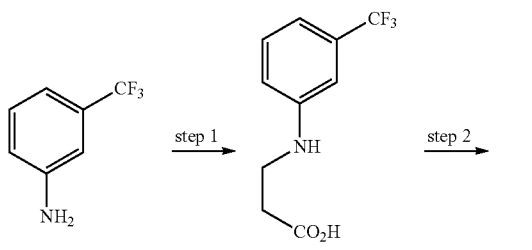

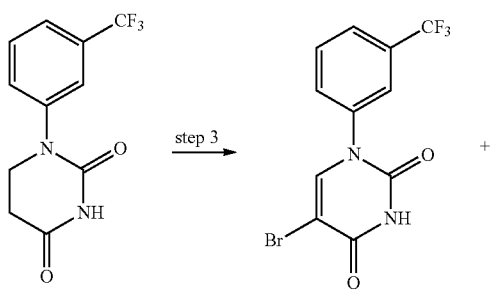
Ref. Exam. 97

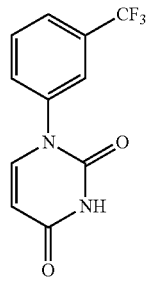
Ref. Exam. 98

Step 1

Reference Example 95

To an aqueous solution of 3-trifluoromethylphenyl aniline (5.0 g) in water (15.0 ml) was added acrylic acid (3.2 ml) and the resulting mixture was stirred at 100° C. for one hour. The reaction mixture was basified with 5N aqueous sodium hydroxide solution and extracted with ethyl acetate (100 ml×2). The resulting organic layer was washed with saturated saline (50 ml), dried over anhydrous sodium sulfate and then concentrated under reduced pressure. The residue was purified by silica gel column chromatography (eluent: chloroform/methanol) to afford 3-(3-trifluoromethylphenylamino) propionic acid (8.4 g).

¹H-NMR (CDCl₃: 300 MHz) (δ PPM):
2.68 (t, 2H, J=6.0 Hz), 3.48 (t, 2H, J=6.2 Hz), 6.74 (d, 1H, J=8.0 Hz), 6.80 (s, 1H), 6.94 (d, 1H, J=7.5 Hz), 7.22-7.27 (m, 1H)

Step 2

Reference Example 96

A solution of 3-(3-trifluoromethylphenylamino)propanoic acid (2.0 g) (prepared in Reference Example 95) and urea (1.0 g) in acetic acid (20.0 ml) was stirred with heating under reflux for seven hours. To the reaction mixture was water (50 ml) and the resulting mixture was extracted with ethyl acetate (30 ml×3). The organic layer was washed with water (20 ml×2) and saturated saline (20 ml), dried over anhydrous sodium sulfate and then concentrated under reduced pressure. The residue was purified by silica gel column chromatography (eluent: chloroform/methanol) to afford 1-(3-trifluoromethylphenyl)dihydropyrimidin-2,4(1H,3H)-dione (1.5 g).

¹H-NMR (CDCl₃: 300 MHz) (δ PPM):
2.86 (t, 2H, J=6.6 Hz), 3.91 (t, 2H, J=6.7 Hz), 7.50-7.54 (m, 4H), 7.80 (brs, 1H)

Step 3

Reference Examples 97 and 98

To a solution of 1-(3-trifluoromethylphenyl)dihydropyrimidin-2,4(1H,3H)-dione (prepared in Reference Example 96) (770.0 mg) in acetic acid (10.0 ml) was added bromine (0.18 ml) and the resulting mixture was stirred with heating under reflux for two hours. To the reaction mixture were added water (30 ml) and 10% aqueous sodium thiosulfate solution (5 ml) and the precipitated solids were collected by filtration with water to afford a mixture containing 5-bromo-1-(3-trifluoromethylphenyl)pyrimidin-2,4(1H,3H)-dione, 5,5-dibromo-1-(3-trifluoromethylphenyl)dihydropyrimidin-2,4(1H,3H)-dione and 5-bromo-1-(3-trifluoromethylphenyl)

dihydropyrimidin-2,4(1H,3H)-dione (800.0 mg). A solution of the resulting mixture (800.0 mg) and lithium chloride (122.3 mg) in N,N-dimethyl formamide (5.0 ml) was stirred at 120° C. for one and a half hours. To the reaction mixture was added water (20 ml) and the resulting mixture was extracted with ethyl acetate (20 ml×2), and the organic layer was washed with water (20 ml×2) and saturated saline (20 ml), dried over anhydrous sodium sulfate and then concentrated under reduced pressure. The residue was purified by silica gel column chromatography (eluent: hexane/ethyl acetate) to afford 5-bromo-1-(3-trifluoromethylphenyl)pyrimidin-2,4(1H,3H)-dione (473.1 mg) and 1-(3-trifluoromethylphenyl)pyrimidin-2,4(1H,3H)-dione (135.8 mg).

5-Bromo-1-(3-trifluoromethylphenyl)pyrimidin-2,4(1H,3H)-dione (Reference Example 97)

¹H-NMR (CDCl₃: 300 MHz) (δ PPM):
7.52 (d, 1H, J=8.3 Hz), 7.58 (s, 1H), 7.60-7.63 (m, 2H), 7.68 (d, 1H, J=7.9 Hz), 8.50 (brs, 1H)

1-(3-Trifluoromethylphenyl)pyrimidin-2,4(1H,3H)-dione (Reference Example 98)

¹H-NMR (CDCl₃: 300 MHz) (δ PPM):
5.83 (d, 1H, J=7.9 Hz), 7.29 (d, 1H, J=6.8 Hz), 7.50-7.66 (m, 4H), 9.27 (brs, 1H)

Reference Example 99

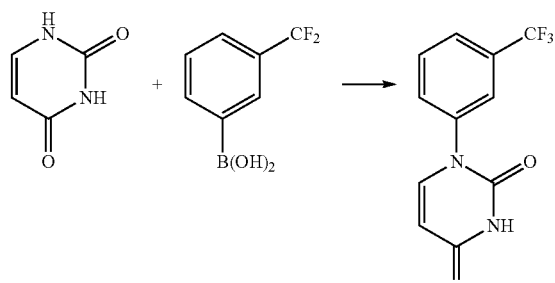

To a solution of uracil (8.9 g), copper(II) acetate (9.6 g), N,N,N,N-tetramethylethylenediamine (10.2 ml) in methanol/dimethy formamide/water (500/100/100 ml) was added 3-trifluoromethylphenyl boronic acid (10.0 g) and the resulting mixture was stirred at room temperature for twelve hours. The reaction mixture was concentrated under reduced pressure so as to remove methanol and thereto was added water (100 ml). The resulting mixture was extracted with ethyl acetate (100 ml×3) and the organic layer was washed with water (100 ml×2) and saturated saline (50 ml), dried over anhydrous sodium sulfate and then concentrated under reduced pressure. The residue was purified by silica gel column chromatography (eluent: hexane/ethyl acetate) to afford 1-(3-trifluoromethylphenyl)pyrimidin-2,4(1H,3H)-dione (650.0 mg).

Reference Example 100

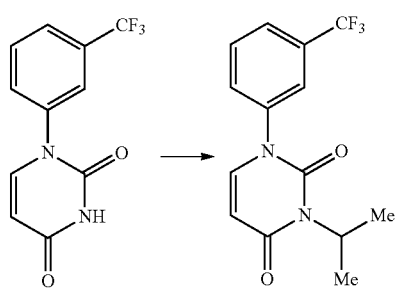 [SMILES: O=c1ccn(-c2cccc(C(F)(F)F)c2)c(=O)[nH]1 ; CC(C)n1c(=O)ccn(-c2cccc(C(F)(F)F)c2)c1=O]

To a solution of 1-(3-trifluoromethylphenyl)pyrimidin-2,4(1H,3H)-dione (prepared in Reference Example 98 or 99) (135.0 mg) in N,N-dimethy formamide (5.0 ml) were added at room temperature sodium hydride (25.3 mg) and isopropyl iodide (265 μl) and the resulting mixture was stirred at 110° C. for two hours. To the reaction mixture was added saturated aqueous ammonium chloride solution (30.0 ml), and the resulting mixture was extracted with ethyl acetate (20 ml×2) and the organic layer was washed with water (20 ml×2) and saturated saline (20 ml), dried over anhydrous sodium sulfate and then concentrated under reduced pressure. The residue was purified by silica gel column chromatography (eluent: hexane/ethyl acetate) to afford 3-isopropyl-1-(3-trifluoromethylphenyl)pyrimidin-2,4(1H,3H)-dione (122.5 mg).

¹H-NMR (CDCl₃: 300 MHz) (δ PPM):
1.43 (d, 6H, J=7.00 Hz), 5.12-5.22 (m, 1H), 7.79 (d, 1H, J=7.9 Hz), 7.17 (d, 1H, J=7.9 Hz), 7.48-7.64 (m, 4H)

Reference Example 101-103

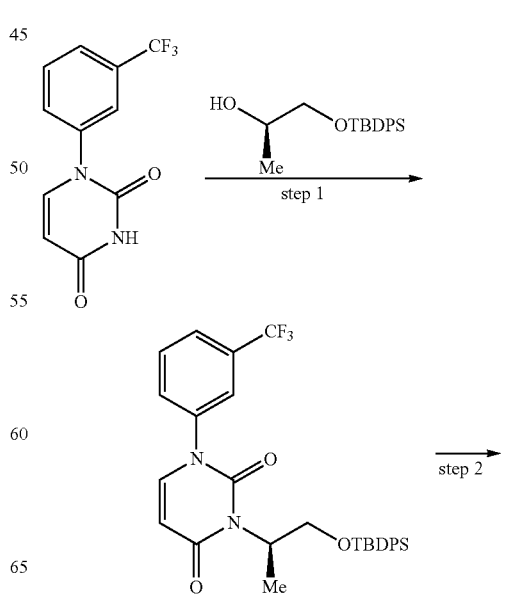

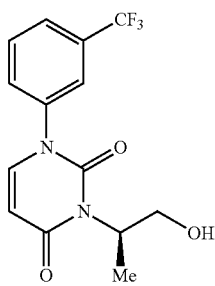 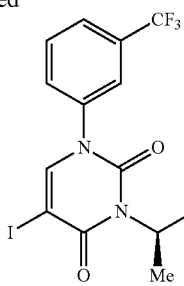

Step 1

Reference Example 101

To a solution of 1-(3-trifluoromethylphenyl)pyrimidin-2,4 (1H,3H)-dione (prepared in Reference Example 98 or 99) (740.0 mg) in tetrahydrofuran (10.0 ml) was added (R)-1-(tert-butyldiphenylsilyloxy)propane-2-ol (1.82 g), triphenylphosphine (1.5 g) and diethyl azodicarboxylate (2.7 ml:2.2 M toluene solution) and the resulting mixture was stirred at room temperature for twelve hours. To the reaction mixture was added water (50 ml), and the resulting mixture was extracted with ethyl acetate (30 ml×2) and the organic layer was washed with water (20 ml) and saturated saline (20 ml), dried over anhydrous sodium sulfate and then concentrated under reduced pressure. The residue was purified by silica gel column chromatography (eluent: hexane/ethyl acetate) to afford (R)-3-[1-(tert-butyldiphenylsilyloxy)propane-2-yl]-1-(3-trifluoromethylphenyl)pyrimidin-2,4(1H, 3H)-dione (969.8 mg).

$^1$H-NMR (CDCl$_3$: 300 MHz) (δ PPM):
0.98 (s, 9H), 1.36 (d, 3H, J=7.1 Hz), 3.77 (dd, 1H, J=9.9, 5.9 Hz), 4.30 (t, 1H, J=9.5 Hz), 5.26-5.40 (m, 1H), 5.86 (d, 1H, J=7.9 Hz), 7.23 (d, 1H, J=7.9 Hz), 7.33-7.70 (m, 14H)

Step 2

Reference Example 102

To a solution of (R)-3-[1-(tert-butyldiphenylsilyloxy)propane-2-yl]-1-(3-trifluoromethylphenyl)pyrimidin-2,4(1H, 3H)-dione (prepared in Reference Example 101) (7.1 g) in ethanol (50.0 ml) was added 1N hydrochloric acid (64.0 ml) and the resulting mixture was stirred at 90° C. for two hours. The reaction mixture was concentrated under reduced pressure and the residue was purified by silica gel column chromatography (eluent: ethyl acetate/methanol) to afford (R)-3-(1-hydroxypropan-2-yl)-1-(3-trifluoromethylphenyl) pyrimidin-2,4(1H,3H)-dione (2.6 g).

$^1$H-NMR (CDCl$_3$: 300 MHz) (δ PPM):
1.45 (d, 3H, J=7.0 Hz), 3.01 (brd, 1H, J=10.8 Hz), 3.83-3.88 (m, 1H), 3.99-4.09 (m, 1H), 5.21-5.27 (m, 1H), 5.90 (d, 1H, J=7.9 Hz), 7.27 (d, 1H, J=7.9 Hz), 7.56 (d, 1H, J=8.1 Hz), 7.60-7.63 (m, 2H), 7.69 (t, 1H, J=8.4 Hz)

Step 3

Reference Example 103

To a solution of (R)-3-(1-hydroxypropan-2-yl)-1-(3-trifluoromethylphenyl)pyrimidin-2,4(1H,3H)-dione (prepared in Reference Example 102) (1.3 g) in chloroform (20.0 ml) was added iodine chloride (12.4 ml, 1M dichloromethane solution) and the resulting mixture was stirred for two hours at room temperature. The reaction mixture was concentrated under reduced pressure and the residue was purified by silica gel column chromatography (eluent: hexane/ethyl acetate) to afford (R)-3-(1-hydroxypropan-2-yl)-5-iodo-1-(3-trifluoromethylphenyl)pyrimidin-2,4(1H,3H)-dione (1.4 g).

$^1$H-NMR (CDCl$_3$: 300 MHz) (δ PPM):
1.44 (d, 3H, J=7.3 Hz), 3.75-3.80 (m, 1H), 3.88-3.93 (m, 1H), 4.76-4.82 (m, 1H), 7.40 (d, 1H, J=7.2 Hz), 7.49 (s, 1H), 7.60 (t, 1H, J=7.9 Hz), 7.68 (d, 1H, J=7.5 Hz), 7.90 (s, 1H)

Reference Example 104

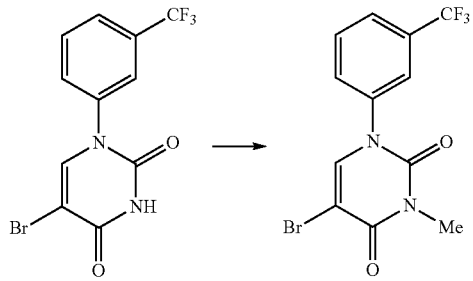 [SMILES: O=c1[nH]c(=O)n(-c2cccc(C(F)(F)F)c2)cc1Br ; Cn1c(=O)c(Br)cn(-c2cccc(C(F)(F)F)c2)c1=O]

To a solution of 5-bromo-1-(3-trifluoromethylphenyl)pyrimidin-2,4(1H,3H)-dione (prepared in Reference Example 97) (150.0 mg) and potassium carbonate (181.6 mg) in N,N-dimethyl formamide (4.0 ml) was added at room temperature, methyl iodide (0.042 ml) and the resulting mixture was stirred at 70° C. for two and a half hours. To the reaction mixture was added saturated aqueous ammonium chloride solution (20.0 ml), and the resulting mixture was extracted with ethyl acetate (20 ml×2) and the organic layer was washed with water (20 ml×2) and saturated saline (20 ml), dried over anhydrous sodium sulfate and then concentrated under reduced pressure. The residue was purified by silica gel column chromatography (eluent: hexane/ethyl acetate) to afford 5-bromo-3-methyl-1-(3-trifluoromethylphenyl)pyrimidin-2, 4(1H,3H)-dione (153.6 mg).

$^1$H-NMR (CDCl$_3$: 300 MHz) (δ PPM):
3.41 (s, 3H), 7.50 (d, 1H, J=7.9 Hz), 7.57-7.62 (m, 3H), 7.67 (d, 1H, J=7.7 Hz)

Reference Example 105

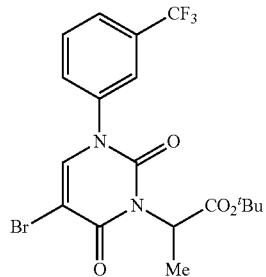 [SMILES: CC(C(=O)OC(C)(C)C)n1c(=O)c(Br)cn(-c2cccc(C(F)(F)F)c2)c1=O]

The compound was prepared according to the similar process to those of Reference Example 104.

$^1$H-NMR (CDCl$_3$: 300 MHz) (δ PPM):
1.38 (s, 9H), 1.52 (d, 3H, J=7.2 Hz), 5.41 (q, 1H, J=7.0 Hz), 5.17-5.26 (m, 1H), 7.50 (d, 1H, J=7.9 Hz), 7.56-7.67 (m, 4H)

Reference Examples 106-110

The compound 1e indicated in the below-mentioned table (Reference Examples 106-110) was obtained by using the compounds of Reference Examples 57-59 and 99-100 according to the similar reaction and treatment method to those described in Reference Example 60.

1e

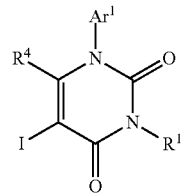

TABLE 12

| Ref. Ex. | Ar¹ | R¹ | R⁴ | Measurement cond. | ¹H-NMR (δ PPM) |
|---|---|---|---|---|---|
| 106 | 3-CF₃-C₆H₄- | Me | Et | 4 | 1.03 (t, 3H, J = 7.5 Hz), 2.55 (q, 2H, J = 7.5 Hz), 3.45 (s, 3H), 7.47 (d, 1H, J = 7.9 Hz), 7.55 (s, 1H), 7.70 (t, 1H, J = 7.9 Hz), 7.79 (d, 1H, J = 7.9 Hz) |
| 107 | 3-CF₃-C₆H₄- | Me | ⁱPr | 4 | 1.24 (brs, 6H), 2.80 (brs, 1H), 3.44 (s, 3H), 7.44 (d, 1H, J = 7.9 Hz), 7.52 (s, 1H), 7.68 (t, 1H, J = 7.9 Hz), 7.78 (d, 1H, J = 7.9 Hz) |
| 108 | 3-CF₃-C₆H₄- | Me | NMe₂ | 4 | 2.38 (s, 6H), 3.22 (s, 3H), 7.71-7.73 (m, 2H), 7.78-7.80 (m, 1H), 7.86 (s, 1H) |
| 109 | 3-CF₃-C₆H₄- | H | H | 3 | 7.58 (d, 1H, J = 8.3 Hz), 7.64 (s, 1H), 7.67 (t, 1H, J = 7.9 Hz), 7.74 (d, 1H, J = 7.8 Hz), 7.80 (s, 1H), 8.31 (s, 1H) |
| 110 | 3-CF₃-C₆H₄- | ⁱPr | H | 1 | 1.43 (d, 6H, J = 6.9 Hz), 5.19 (quin, 1H, J = 6.9 Hz), 7.50 (d, 1H, J = 8.1 Hz), 7.57 (d, 1H, J = 7.8 Hz), 7.62 (d, 1H, J = 9.9 Hz), 7.67 (s, 1H) |

Reference Examples 111-114

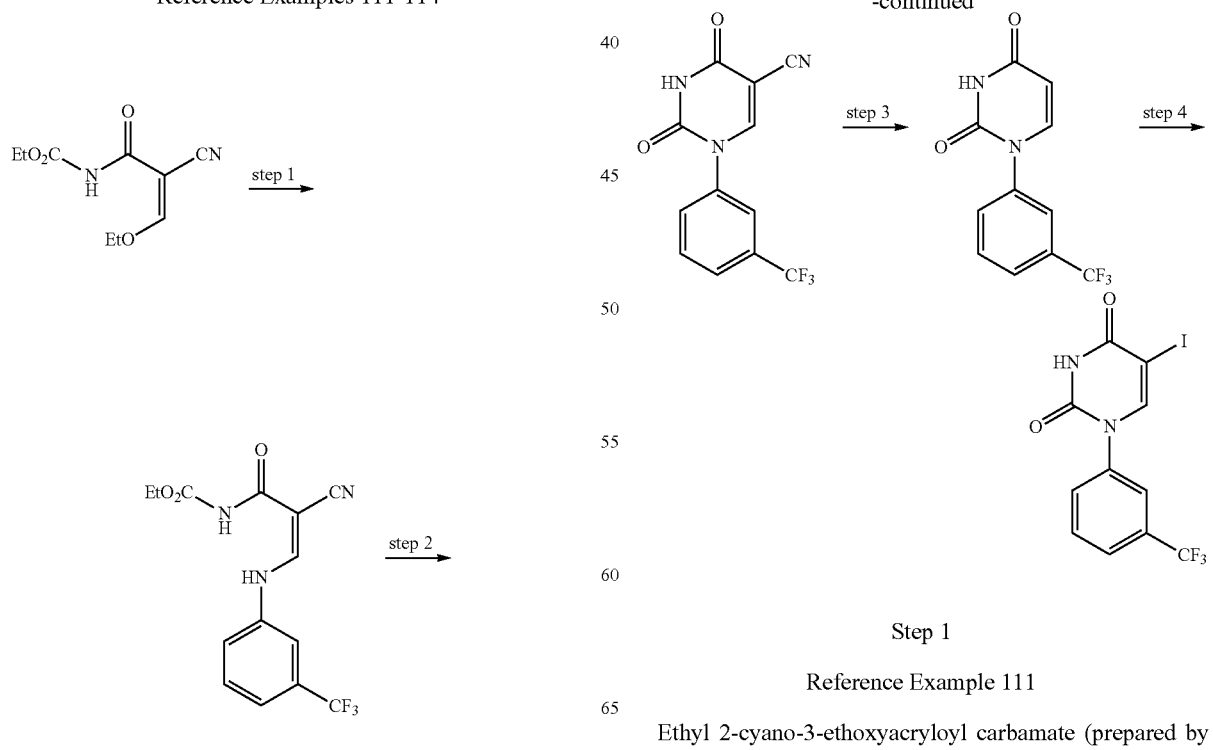

Step 1

Reference Example 111

Ethyl 2-cyano-3-ethoxyacryloyl carbamate (prepared by the method described in Chem. Pharm. Bull. 1972, 20, 1380-

1388) (20.0 g) was suspended in ethanol (200 ml) and thereto was added 3-(trifluoromethyl)aniline (12.36 ml), and the resulting mixture was stirred at room temperature for nineteen hours. The precipitated solids were collected by filtration and washed with ethanol to afford ethyl 2-cyano-3-(3-(trifluoromethyl)phenylamino)acryloyl carbamate. Further, the filtrates were concentrated and thereto was added ethanol, and the solids were collected by filtration, and washed with ethanol three times repeatedly to afford the intended products (26.2 g).

$^1$H-NMR (400 MHz, CDCl$_3$) (δ PPM):
1.34 (t, 3H, J=6.8 Hz), 4.28 (q, 2H, J=6.9 Hz), 7.38 (d, 1H, J=5.7 Hz), 7.44 (s, 1H), 7.49-7.53 (m, 1H), 7.56-7.58 (m, 1H), 7.78 (s, 1H), 8.26-8.30 (m, 1H), 8.57-8.63 (m, 1H)

Step 2

Reference Example 112

To a suspension of 2-cyano-3-(3-(trifluoromethyl)phenylamino)acryloylcarbamate (prepared in Reference Example 111) (26.2 g) in acetonitrile (300 ml) was added triethylamine (111 ml) and the resulting mixture was stirred for six hours with heating under reflux. The reaction solutions were concentrated under reduced pressure, and to the residue was added 1M hydrochloric acid and the resulting mixture was extracted with ethyl acetate twice. The organic layer was washed with 1M hydrochloric acid and saturated saline. The resulting mixture was dried over anhydrous magnesium and then concentrated under reduced pressure to afford 2,4-dioxo-1-(3-(trifluoromethyl)phenyl)-1,2,3,4-tetrahydropyrimidin-5-carbonitrile (22.7 g).

$^1$H-NMR (400 MHz, DMSO-d$_6$) (δ PPM):
7.75-7.83 (m, 2H), 7.87 (d, 1H, J=7.5 Hz), 7.96 (s, 1H), 8.89 (s, 1H), 12.25 (s, 1H)

Step 3

Reference Example 113

2,4-Dioxo-1-(3-(trifluoromethyl)phenyl)-1,2,3,4-tetrahydropyrimidin-5-carbonitrile (prepared in Reference Example 112) (22.7 g) was suspended in hydrobromic acid (48%, 220 ml) and the resulting mixture was stirred with heating under reflux for ten hours. The resulting mixture was cooled to 0° C. and to the reaction solutions was then added 28% ammonia water (145 ml) dropwise, and the precipitated solids were collected by filtration and washed with water to afford 1-(3-(trifluoromethyl)phenyl)pyrimidin-2,4(1H,3H)-dione (17.8 g).

Step 4

Reference Example 114

To a suspension of 1-(3-(trifluoromethyl)phenyl)pyrimidin-2,4(1H,3H)-dione (prepared in Reference Example 113) (5.09 g) in acetonitrile (75 ml) were added iodine (3.03 g) and cerium ammonium nitrate (6.54 g) and the resulting mixture was stirred at 80° C. for thirty minutes. The resulting mixture was cooled to 0° C. and thereto were then added ethyl acetate (150 ml), saturated saline (50 ml) and 5% sodium hydrogen sulfite solution (100 ml) so as to separate the layer. Furthermore, the aqueous layer was extracted with ethyl acetate, and the organic layer was washed with 5% aqueous sodium hydrogen sulfite solution and saturated saline. The resulting mixture was dried over anhydrous magnesium sulfate and then concentrated under reduced pressure. To the residue were added ethyl acetate (50 ml) and hexane (100 ml) and the resulting mixture was stirred for fifteen minutes, and the precipitated solids were then collected by filtration and washed with hexane to afford 5-iodo-1-(3-(trifluoromethyl)phenyl)pyrimidin-2,4(1H,3H)-dione (7.34 g).

Reference Examples 115-119

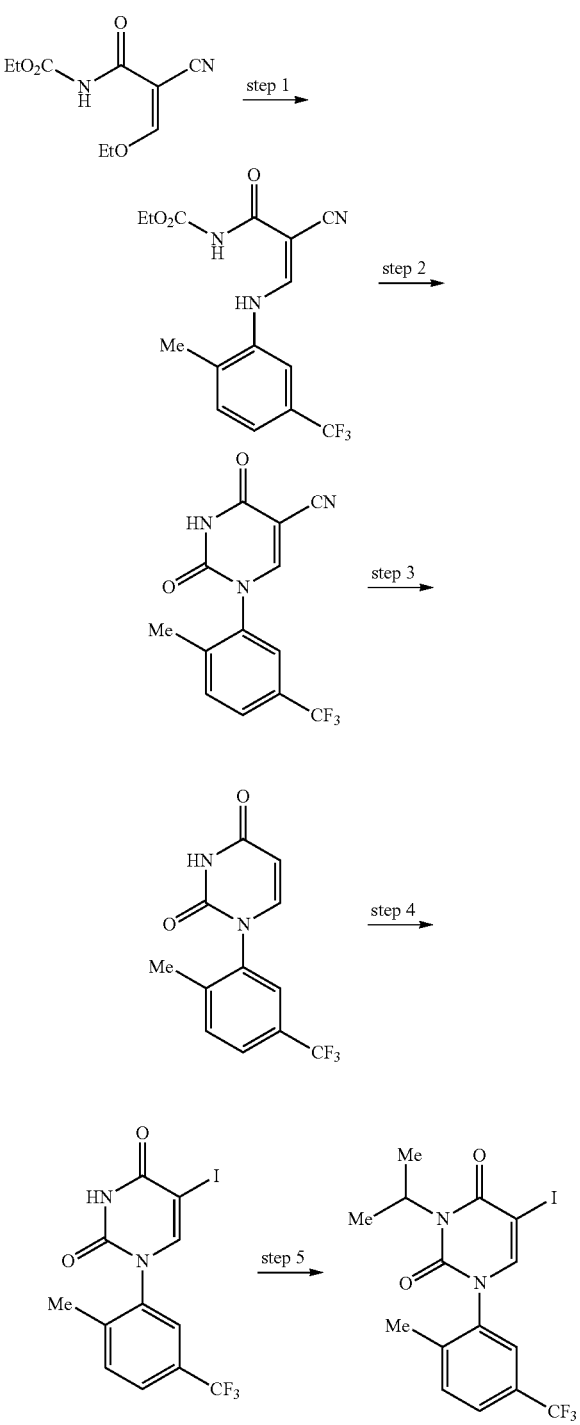

Step 1

Reference Example 115

The intended product, (Z)-ethyl 2-cyano-3-(2-methyl-5-(trifluoromethyl)phenylamino)acryloylcarbamate was obtained according to the similar process to those of Reference Example 111.

$^1$H-NMR (400 MHz, CDCl$_3$) (δ PPM):
1.35 (t, 3H, J=7.1 Hz), 2.46 (s, 3H), 4.29 (q, 2H, J=7.1 Hz), 7.36-7.43 (m, 3H), 7.91 (s, 1H), 7.93 (d, 1H, J=13.0 Hz), 11.76 (d, 1H, J=12.6 Hz)

Step 2

Reference Example 116

The intended product, 1-(2-methyl-5-(trifluoromethyl)phenyl)-2,4-dioxo-1,2,3,4-tetrahydropyrimidin-5-carbonitrile was obtained according to the similar process to those of Reference Example 112.

1H-NMR (400 MHz, DMSO-d$_6$) (δ PPM):
2.25 (s, 3H), 7.64 (d, 1H, J=8.1 Hz), 7.80 (d, 1H, J=8.0 Hz), 7.92 (s, 1H), 8.78 (s, 1H), 12.27 (s, 1H)

Step 3

Reference Example 117

The intended product, 1-(2-methyl-5-(trifluoromethyl)phenyl)pyrimidin-2,4(1H,3H)-dione was obtained according to the similar process to those of Reference Example 113.

$^1$H-NMR (400 MHz, CDCl$_3$) (δ PPM):
2.32 (s, 3H), 5.87 (dd, 1H, J=1.2, 7.9 Hz), 7.18 (d, 1H, J=7.9 Hz), 7.48-7.52 (m, 2H), 7.65 (dd, 1H, J=1.1, 8.1 Hz), 8.57 (s, 1H)

Step 4

Reference Example 118

The intended product, 5-iodo-1-(2-methyl-5-(trifluoromethyl)phenyl)pyrimidin-2,4(1H,3H)-dione was obtained according to the similar process to those of Reference Example 114.

$^1$H-NMR (400 MHz, CDCl$_3$) (δ PPM):
2.33 (s, 3H), 7.48-7.52 (m, 2H), 7.65 (s, 1H), 7.67 (d, 1H, J=8.1 Hz), 8.46 (s, 1H)

Step 5

Reference Example 119

To a solution of 5-iodo-1-(2-methyl-5-(trifluoromethyl)phenyl)pyrimidin-2,4(1H,3H)-dione (prepared in Reference Example 118) (645 mg) in THF (20 ml) were added isopropyl alcohol (0.25 ml), triphenylphosphine (855 mg), diethyl azodicarboxylate (2.2 M toluene solution, 1.48 ml), and the resulting mixture was stirred at room temperature for twenty-five minutes. The reaction solutions were concentrated under reduced pressure and the residue was then purified by silica gel column chromatography (eluent: hexane/ethyl acetate) to afford 5-iodo-3-isopropyl-1-(2-methyl-5-(trifluoromethyl)phenyl)pyrimidin-2,4(1H,3H)-dione (548 mg).

$^1$H-NMR (400 MHz, CDCl$_3$) (δ PPM):
1.49-1.56 (m, 6H), 2.28 (s, 3H), 5.24-5.29 (m, 1H), 7.48-7.50 (m, 2H), 7.60 (s, 1H), 7.64 (d, 1H, J=7.8 Hz)

Reference Examples 120-151

The compounds If indicated in the below-mentioned Table (Reference Examples 120-151) were obtained by using the compounds of Reference Examples 62-92 or known compounds according to the similar reaction and treatment method to those described in Reference Example 61.

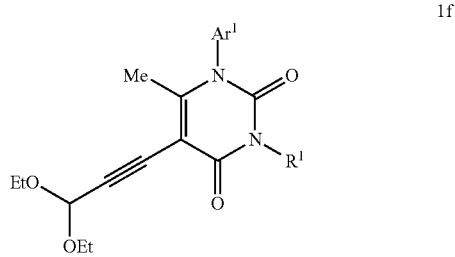

1f

TABLE 13

| Ref. Ex. | Ar$^1$ | R$^1$ | Measurement cond. | $^1$H-NMR (δ PPM) (or LC-MS: [M + H]+/Rt) |
|---|---|---|---|---|
| 120 | 3-CF$_3$-phenyl | -(CH$_2$)$_2$-Me | 1 | 0.87 (t, 3H, J = 7.4 Hz), 1.16 (t, 6H, J = 7.5 Hz), 1.57-1.65 (m, 2H), 2.04 (s, 3H), 3.56 (q, 1H, J = 7.5 Hz), 3.60 (q, 1H, J = 7.5 Hz), 3.68-3.78 (m, 2H), 3.85 (t, 2H, J = 7.4 Hz), 5.43 (s, 1H), 7.35 (d, 1H, J = 7.9 Hz), 7.44 (s, 1H), 7.62 (t, 1H, J = 7.9 Hz), 7.71 (d, 1H, J = 7.9 Hz) |
| 121 | 3-CF$_3$-phenyl | -CH$_2$-CO$_2$Et | 1 | 437 (M—OEt)/2.43 (min) |

TABLE 13-continued

| Ref. Ex. | Ar¹ | R¹ | Measurement cond. | ¹H-NMR (δ PPM) (or LC-MS: [M + H]+/Rt) |
|---|---|---|---|---|
| 122 | 3-CF₃-C₆H₄- | -CH₂CH₂CH₂CO₂Et | 1 | 1.19-1.25 (m 9H), 2.09 (s, 3H), 2.65 (t, 2H, J = 7.5 Hz), 3.58-3.68 (m, 2H), 3.73-3.82 (m, 2H), 4.10 (q, 2H, J = 7.2 Hz), 4.25 (t, 2H, J = 7.2 Hz), 5.47 (s, 1H), 7.42 (d, 1H, J = 6.9 Hz), 7.49 (s, 1H), 7.66 (t, 1H, J = 7.8 Hz), 7.77 (d, 1H, J = 7.8 Hz) |
| 123 | 3-CF₃-C₆H₄- | -CH₂CH₂CH₂CH₂CO₂Et | 1 | 1.15-1.29 (m, 9H), 2.04 (s, 3H), 2.31 (t, 2H, J = 7.2 Hz), 3.49-3.63 (m, 2H), 3.68-3.78 (m, 2H), 4.10 (q, 2H, J = 7.2 Hz), 4.25 (t, 2H, J = 7.2 Hz), 5.47 (s, 1H), 7.40 (t, 1H, J = 7.5 Hz), 7.49 (s, 1H), 7.66 (t, 1H, J = 7.8 Hz), 7.77 (d, 1H, J = 7.8 Hz) |
| 124 | 3-CF₃-C₆H₄- | -CH₂CH₂CO₂Bn | 1 | 1.25 (t, 6H, J = 7.2 Hz), 2.13 (s, 3H), 3.63 (q, 1H, J = 7.2 Hz), 3.66 (q, 1H, J = 7.2 Hz), 3.75-3.84 (m, 2H), 4.77 (s, 2H), 5.19 (s, 2H), 5.49 (s, 1H), 7.32-7.38 (m, 5H), 7.42 (d, 1H, J = 7.9 Hz), 7.51 (s, 1H), 7.68 (t, 1H, J = 7.9 Hz), 7.78 (d, 1H, J = 7.9 Hz) |
| 125 | 3-CF₃-C₆H₄- | -CH₂CH(OMe)₂ type | 1 | 1.22 (t, 6H, J = 7.1 Hz), 2.09 (s, 3H), 3.33 (s, 6H), 3.60 (q, 1H, J = 7.1 Hz), 3.63 (q, 1H, J = 7.1 Hz), 3.71-3.82 (m, 2H), 4.10 (d, 2H, J = 5.7 Hz), 4.81 (t, 1H, J = 5.7 Hz), 5.47 (s, 1H), 7.42 (d, 1H, J = 7.9 Hz), 7.49 (s, 1H), 7.66 (t, 1H, J = 7.9 Hz), 7.75 (d, 1H, J = 7.9 Hz) |

TABLE 14

| Ref. Ex. | Ar¹ | R¹ | Measurement cond. | ¹H-NMR (δ PPM) |
|---|---|---|---|---|
| 126 | 3-CF₃-C₆H₄- | -(CH₂)₅NHC(O)OC(Me)₃ | 1 | 1.22 (t, 6H, J = 7.1 Hz), 1.32-1.36 (m, 2H), 1.40 (s, 9H), 1.42-1.50 (m, 2H), 1.62-1.68 (m, 2H), 2.08 (s, 3H), 3.02-3.10 (m, 2H), 3.60 (q, 1H, J = 7.1 Hz), 3.64 (q, 1H, J = 7.1 Hz), 3.76 (q, 2H, J = 7.1 Hz), 3.93 (t, 2H, J = 7.5 Hz), 5.47 (s, 1H), 7.42 (d, 1H, J = 7.9 Hz), 7.49 (s, 1H), 7.66 (t, 1H, J = 7.9 Hz), 7.75 (d, 1H, J = 7.9 Hz) |
| 127 | 3-CF₃-C₆H₄- | -CH₂-(4-OMe-C₆H₄) | 1 | 1.15-1.22 (m, 6H), 2.01 (s, 1.5H), 2.15 (s, 1.5H), 3.52-3.64 (m, 2H), 3.66-3.81 (m, 2H), 3.71 (s, 2H), 3.77 (s, 1H), 5.42 (s, 0.5H), 5.45 (s, 0.5H), 6.72 (d, 0.5H, J = 8.7 Hz), 6.76 (d, 1.5H, J = 8.4 Hz), 7.32-7.44 (m, 4H), 7.57-7.62 (m, 1H), 7.68 (s, 0.5H), 7.71 (s, 0.5H) |
| 128 | 3-CN-C₆H₄- | -Me | 4 | 1.18 (t, 6H, J = 7.1 Hz), 2.05 (s, 3H), 3.32 (s, 3H), 3.55-3.62 (m, 2H), 3.68-3.76 (m, 2H), 5.43 (s, 1H), 7.41 (ddd, 1H, J = 1.3, 1.7, 7.9 Hz), 7.49 (t, 1H, J = 1.7 Hz), 7.62 (t, 1H, J = 7.9 Hz), 7.75 (dt, 1H, J = 1.3, 7.9 Hz) |
| 129 | 3-CO₂Me-C₆H₄- | -Me | 1 | 1.30 (t, 6H, J = 6.9 Hz), 2.09 (s, 3H), 3.37 (s, 3H), 3.58-3.68 (m, 2H), 3.73-3.81 (m, 2H), 3.92 (s, 3H), 5.48 (s, 1H), 7.37 (m, 1H), 7.61 (t, 1H, J = 8.1 Hz), 7.88 (t, 1H, J = 2.1 Hz), 8.17 (dt, 1H, J = 7.8, 1.2 Hz) |

TABLE 14-continued
| Ref. Ex. | Ar¹ | R¹ | Measurement cond. | ¹H-NMR (δ PPM) |
|---|---|---|---|---|
| 130 | 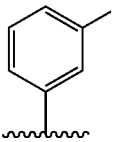 |  | 1 | 1.23 (t, 6H, J = 6.9 Hz), 2.12 (s, 3H), 3.36 (s, 3H), 3.60-3.66 (m, 2H), 3.76-3.81 (m, 2H), 5.48 (s, 1H), 6.93-7.01 (m, 2H), 7.19-7.22 (m, 1H), 7.46-7.53 (m, 1H) |
TABLE 15
| Ref. Ex. | Ar¹ | R¹ | Measurement cond. | ¹H-NMR (δ PPM) (or LC-MS: [M + H]+/Rt) |
|---|---|---|---|---|
| 131 | 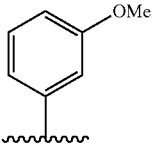 |  | 4 | 1.18 (t, 6H, J = 7.1 Hz), 2.08 (s, 3H), 3.31 (s, 3H), 3.55-3.62 (m, 2H), 3.70-3.78 (m, 2H), 3.76 (s, 3H), 5.43 (s, 1H), 6.65 (t, 1H, J = 2.2 Hz), 6.70-6.73 (m, 1H), 6.95-6.97 (m, 1H), 7.36 (t, 1H, J = 8.1 Hz) |
| 132 | 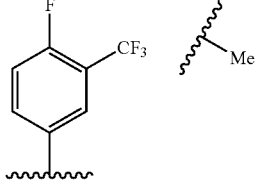 |  | 4 | 1.18 (t, 6H, J = 7.1 Hz), 2.06 (s, 3H), 3.31 (s, 3H), 3.55-3.62 (m, 2H), 3.69-3.77 (m, 2H), 5.43 (s, 1H), 7.28-7.47 (m, 3H) |
| 133 | 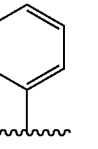 |  | 4 | 1.27 (t, 6H, J = 7.1 Hz), 2.13 (s, 3H), 3.41 (s, 3H), 3.63-3.71 (m, 2H), 3.77-3.87 (m, 2H), 5.52 (s, 1H), 7.18-7.29 (m, 2H), 7.47-7.58 (m, 3H) |
| 134 | 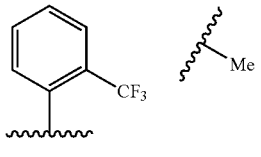 |  | 8 | 365 (M—OEt)/2.29 (min) |
| 135 | 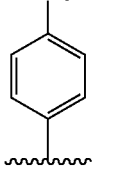 |  | 1 | 1.23 (t, 6H, J = 6.9 Hz), 2.10 (s, 3H), 3.67 (s, 3H), 3.58-3.68 (m, 2H), 3.74-3.84 (m, 2H), 5, 48 (s, 1H), 7.36 (d, 2H, J = 8.4 Hz), 7.81 (d, 2H, J = 8.4 Hz) |
| 136 | 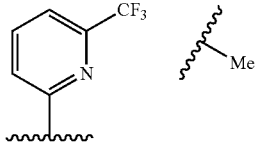 |  | 8 | 366 (M—OEt)/2.25 (min) |
| 137 | 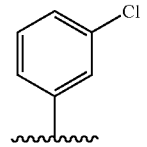 |  | 1 | 1.23 (t, 6H, J = 6.9 Hz), 2.11 (s, 3H), 3.36 (s, 3H), 3.58-3.68 (m, 2H), 3.73-3.81 (m, 2H), 5.48 (s, 1H), 7.08-7.11 (m, 1H), 7.21-7.24 (m, 1H), 7.45-7.48 (m, 2H) |

TABLE 15-continued

| Ref. Ex. | Ar¹ | R¹ | Measurement cond. | ¹H-NMR (δ PPM) (or LC-MS: [M + H]+/Rt) |
|---|---|---|---|---|
| 138 | 3-Br-phenyl | -CH(Me)- | 1 | 1.28 (t, 6H, J = 7.2 Hz), 2.11 (s, 3H), 3.36 (s, 3H), 3.58-3.68 (m, 2H), 3.73-3.83 (m, 2H), 5.47 (s, 1H), 7.13-7.16 (m, 1H), 7.37-7.46 (m, 2H), 7.61-7.64 (m, 1H) |

TABLE 16

| Ref. Ex. | Ar¹ | R¹ | Measurement cond. | ¹H-NMR (δ PPM) (or LC-MS: [M + H]+/Rt) |
|---|---|---|---|---|
| 139 | 3-NO₂-phenyl | -CH(Me)- | 1 | 1.23 (t, 6H, J = 7.1 Hz), 2.12 (s, 3H), 3.37 (s, 3H), 3.60 (q, 1H, J = 7.1 Hz), 3.64 (q, 1H, J = 7.1 Hz), 3.73-3.82 (m, 2H), 7.54-7.58 (m, 1H), 7.74 (t, 1H, J = 8.1 Hz), 8.12 (t, 1H, J = 2.0 Hz), 8.35-8.39 (m, 1H) |
| 140 | 3-Me-phenyl | -CH(Me)- | 8 | 311 (M—OEt), 2.23 (min) |
| 141 | 3-(CMe₃)-phenyl | -CH(Me)- | 1 | 1.23 (t, 6H, J = 7.2 Hz), 1.31 (s, 9H), 2.08 (s, 3H), 3.37 (s, 3H), 3.60-3.81 (m, 4H), 5.48 (s, 1H), 6.97-7.00 (m, 1H), 7.14 (t, 1H, J = 1.8 Hz), 7.42 (t, 1H, J = 7.5 Hz), 7.49 (dt, 1H, J = 8.4, 1.2 Hz) |
| 142 | 3-(SO₂Me)-phenyl | -CH(Me)- | 8 | 375 (M—OEt)/1.99 (min) |
| 143 | 3-CF₃-phenyl | Et | 1 | 1.09-1.15 (m, 3H), 1.23 (t, 6H, J = 6.9 Hz), 2.02 (s, 3H), 3.68-3.85 (m, 4H), 3.98-4.06 (m, 2H), 5.48 (s, 1H), 7.44 (d, 1H, J = 6.9 Hz), 7.49 (s, 1H), 1 7.67 (t, 1H, J = 7.8 Hz), 7.76 (d, 1H, J = 7.5 Hz) |
| 144 | 3-CF₃-phenyl | ⁱPr | 1 | 1.22 (t, 6H, J = 7.2 Hz), 1.45 (d, 6H, J = 6.9 Hz), 2.06 (s, 3H), 3.58-3.68 (m, 2H), 3.72-3.83 (m, 2H), 5.18 (s, 1H), 5.48 (s, 1H), 7.41 (d, 1H, J = 7.8 Hz), 7.49 (s, 1H), 7.66 (t, 1H, J = 7.8 Hz), 7.75 (d, 1H, J = 7.8 Hz) |
| 145 | 3-CF₃-phenyl | ᶜPr | 1 | 0.80-0.86 (m, 2H), 1.11 (q, 2H, J = 7.2 Hz), 1.23 (t, 6H, J = 7.2 Hz), 2.06 (s, 3H), 2.69-2.74 (m 1H), 3.58-3.68 (m, 2H), 3.73-3.81 (m, 2H), 5.47 (s, 1H), 7.39 (d, 1H, J = 7.5 Hz), 7.47 (s, 1H), 7.66 (t, 1H, J = 7.8 Hz), 7.75 (d, 1H, J = 7.8 Hz) |

TABLE 17

| Ref. Ex. | Ar¹ | R¹ | Measurement cond. | ¹H-NMR (δ PPM) |
|---|---|---|---|---|
| 146 | 3-CF₃-phenyl | cyclobutyl | 1 | 1.22 (t, 6H, J = 7.2 Hz), 1.66-1.87 (m, 2H), 2.06 (s, 3H), 2.18-2.28 (m, 2H), 2.81-2.91 (m, 2H), 3.58-3.68 (m, 2H), 3.72-3.82 (m, 2H), 5.23 (quintet, 1H, J = 9.0 Hz), 5.47 (s, 1H), 7.41 (d, 1H, J = 8.1 Hz), 7.49 (s, 1H), 7.66 (t, 1H, J = 7.5 Hz), 7.75 (d, 1H, J = 7.8 Hz) |
| 147 | 3-CF₃-phenyl | 1-Cbz-azetidin-3-yl | 1 | 1.18 (t, 6H, J = 6.9 Hz), 2.04 (s, 3H), 3.52-3.62 (m, 2H), 3.67-3.77 (m, 2H), 4.21 (t, 2H, J = 9.0 Hz), 4.40-4.46 (m, 2H), 5.02 (s, 2H), 5.28-5.36 (m, 1H), 5.42 (s, 1H), 7.23-7.26 (m, 5H), 7.36 (d, 1H, J = 7.2 Hz), 7.43 (s, 1H), 7.63 (t, 1H, J = 7. Hz), 7.73 (d, 1H, J = 9.0 Hz) |
| 148 | 3-CF₃-phenyl | CH(Me)CO₂Et | 1 | 1.17-1.23 (m, 9H), 1.56 (d, 3H, J = 6.9 Hz), 2.09 (s, 3H), 3.56-3.66 (m, 2H), 3.71-3.81 (m, 2H), 4.07-4.23 (m, 2H), 5.43-5.51 (m, 2H), 7.36-7.51 (m, 2H), 7.65 (t, 1H, J = 7.2 Hz), 7.74 (d, 1H, J = 7.8 Hz) |
| 149 | 3-CF₃-phenyl | CH(Me)CH₂OAc | 1 | 1.22 (t, 6H, J = 8.1 Hz), 1.45 (d, 3H, J = 7.5 Hz), 1.99 (s, 3H), 2.08 (s, 3H), 3.57-3.80 (m, 4H), 4.20-4.34 (m, 1H), 4.58-4.70 (m, 1H), 5.25 (brs, 1H), 5.74 (s, 1H), 7.39-7.52 (m, 2H), 7.62-7.81 (m, 2H) |
| 150 | 3-CF₃-phenyl | CH(Me)Ph | 4 | 1.25 (t, 6H, J = 7.1 Hz), 1.87 (d, 3H, J = 7.2 Hz), 2.08 (s, 3H), 3.62-3.67 (m, 2H), 3.75-3.82 (m, 2H), 5.49 (s, 1H), 6.29-6.35 (m, 1H), 7.24-7.33 (m, 3.5H), 7.42-7.50 (m, 3H), 7.60-7.72 (m, 1.5H), 7.72-7.75 (m, 1H) |
| 151 | 3-CF₃-phenyl | CH₂CH₂CH₂OAc | 1 | 1.23 (t, 6H, J = 7.2 Hz), 1.97 (s, 3H), 2.10 (s, 3H), 3.58-3.69 (m, 2H), 3.72-3.83 (m, 2H), 4.22-4.27 (m, 2H), 4.31-4.36 (m, 2H), 5.48 (s, 1H), 7.38 (d, 1H, J = 9.0 Hz), 7.50 (s, 1H), 7.67 (t, 1H, J = 7.8 Hz), 7.76 (d, 1H, J = 7.5 Hz) |

Reference Examples 152-153

The compounds 1g indicated in the below-mentioned table (Reference Examples 152-153) were obtained by using the compounds of Reference Examples 93-94 or known compounds according to the similar reaction or treatment method to those described in Reference Example 61.

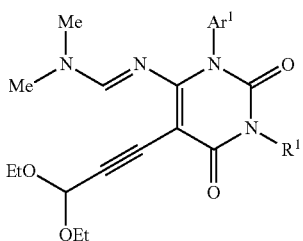

1g

TABLE 18

| Ref. Ex. | Ar¹ | R¹ | Measurement cond. | ¹H-NMR (δ PPM) |
|---|---|---|---|---|
| 152 | 3-CF₃-phenyl | -CH(Me)- | 1 | 1.15 (t, 6H, J = 7.1 Hz), 2.55 (s, 3H), 2.98 (s, 3H), 3.31 (s, 3H), 2.08 (s, 3H), 3.50 (q, 1H, J = 7.1 Hz), 3.53 (q, 1H, J = 7.1 Hz), 3.66 (q, 1H, J = 7.1 Hz), 3.69 (q, 1H, J = 7.1 Hz), 5.34 (s, 1H), 7.31 (d, 1H, J = 7.9 Hz), 7.40 (s, 1H), 7.48 (t, 1H, J = 7.9 Hz), 7.56 (d, 1H, J = 7.9 Hz), 8.33 (s, 1H) |
| 153 | 3-NO₂-phenyl | -CH(CH₂CH₂Me)- | 1 | 0.94 (t, 3H, J = 7.5 Hz), 1.22 (t, 6H, J = 7.1 Hz), 1.65-1.75 (m, 2H), 2.63 (s, 3H), 3.06 (s, 3H), 3.58 (q, 1H, J = 7.1 Hz), 3.60 (q, 1H, J = 7.1 Hz), 3.73 (q, 1H, J = 7.1 Hz), 3.76 (q, 1H, J = 7.1 Hz), 3.92 (t, 3H, J = 7.5 Hz), 5.41 (s, 1H), 7.64-7.70 (m, 2H), 8.08 (t, 1H, J = 1.8 Hz), 8.22-8.26 (m, 1H), 8.42 (s, 1H) |

Reference Examples 154-162

The compounds 1h indicated in the below-mentioned Table (Reference Examples 154-162) were obtained by using the compounds of Reference Examples 103-110 and 119 or known compounds according to the similar reaction or treatment method to those described in Reference Example 61.

1h

TABLE 19

| Ref. Ex. | Ar¹ | R¹ | R⁴ | Measurement cond. | ¹H-NMR (δ PPM) (or LC-MS: [M + H]+/Rt) |
|---|---|---|---|---|---|
| 154 | 3-CF₃-phenyl | Me | Et | 9 | 379 [M—OEt]+/Rt = 1/12 |
| 155 | 3-CF₃-phenyl | Me | ⁱPr | 4 | 1.23-1.28 (m, 6H), 1.34 (d, 6H, J = 7.1 Hz), 2.49-2.57 (m, 1H), 3.38 (s, 3H), 3.66-3.72 (m, 2H), 3.79-3.85 (m, 2H), 5.52 (s, 1H), 7.42 (d, 1H, J = 8.0 Hz), 7.49 (s, 1H), 7.69 (t, 1H, J = 7.9 Hz), 7.79 (d, 1H, J = 7.9 Hz) |
| 156 | 3-CF₃-phenyl | Me | NMe₂ | 9 | 394 [M—OEt]+/Rt = 1/10 |

TABLE 19-continued

| Ref. Ex. | Ar¹ | R¹ | R⁴ | Measurement cond. | ¹H-NMR (δ PPM) (or LC-MS: [M + H]+/Rt) |
|---|---|---|---|---|---|
| 157 | 3-CF₃-phenyl | H | H | 3 | 1.25 (t, 6H, J = 7.1 Hz), 3.59-3.68 (m, 2H), 3.74-3.83 (m, 2H), 5.46 (s, 1H), 7.57 (d, 1H, J = 8.1 Hz), 7.63 (s, 1H), 7.67 (s, 1H), 7.67 (t, 1H, J = 7.9 Hz), 7.74 (d, 1H, J = 7.8 Hz ), 8.63 (s, 1H) |
| 158 | 3-CF₃-phenyl | ⁱPr | H | 1 | 1.18 (t, 6H, J = 6.9 Hz), 1.43 (d, 6H, J = 9.9 Hz), 3.52-3.62 (m, 2H), 3.67-3.77 (m, 2H), 5.17 (quip, 1H, J = 6.9 Hz), 5.39 (s, 1H), 7.49 (d, 1H, J = 7.8 Hz), 7.53 (s, 1H), 7.55 (s, 1H), 7.59 (d, 1H, J = 7.8 Hz), 7.65 (d, 1H, J = 7.8 Hz) |
| 159 | 4-Me-5-CF₃-phenyl | CH(Me)₂ | H | 4 | 1.25 (t, 6H, J = 7.1 Hz), 1.49 (d, 3H, J = 6.9 Hz), 1.50 (d, 3H, J = 6.9 Hz), 2.26 (s, 3H), 3.59-3.66 (m, 2H), 3.76-3.81 (m, 2H), 5.24 (sept, 1H, J = 6.9 Hz), 5.46 (s, 1H), 7.45 (s, 1H), 7.47-7.50 (m, 2H), 7.64 (d, 1H, J = 7.9 Hz) |

TABLE 20

| Ref. Ex. | Ar¹ | R¹ | R⁴ | Measurement cond. | ¹H-NMR (δ PPM) |
|---|---|---|---|---|---|
| 160 | 3-CF₃-phenyl | Me | H | 1 | 1.22 (t, 6H, J = 7.1 Hz), 3.40 (s, 3H), 3.59 (q, 1H, J = 7.0 Hz), 3.63 (q, 1H, J = 7.0 Hz), 3.75 (q, 1H, J = 7.1 Hz), 3.79 (q, 1H, J = 7.1 Hz), 5.44 (s, 1H), 7.53 (d, 1H, J = 7.9 Hz), 7.60-7.66 (m, 3H), 7.71 (d, 1H, J = 7.9 Hz) |
| 161 | 3-CF₃-phenyl | CH(Me)CO₂ⁱBu | H | 1 | 1.18 (t, 6H, J = 7.1 Hz), 1.37 (s, 9H), 1.50 (d, 3H, J = 7.1 Hz), 3.54 (q, 1H, J = 7.1 Hz), 3.57 (q, 1H, J = 7.1 Hz), 3.70 (q, 1H, J = 7.1 Hz), 3.73 (q, 1H, J = 7.1 Hz), 5.36-5.42 (m, 2H ), 7.48 (d, 1H, J = 7.9 Hz), 7.51-7.63 (m, 3H), 7.66 (d, 1H, J = 8.0 Hz) |
| 162 | 3-CF₃-phenyl | CH(Me)CH₂OH | H | 1 | 1.18 (t, 6H, J = 7.1 Hz), 1.39 (d, 3H, J = 7.1 Hz), 3.55 (q, 1H, J = 7.1 Hz), 3.58 (q, 1H, J = 7.1 Hz), 3.70 (q, 1H, J = 7.1 Hz), 3.73 (q, 1H, J = 7.1 Hz), 3.79 (dd, 1H J = 1/1.8, 3.4 Hz), 3.98-4.05 (m, 1H), 5.12-5.22 (m, 1H), 5.39 (s, 1H), 7.39-7.63 (m, 4H), 7.64 (d, 1H, J = 7.9 Hz) |

Reference Example 163

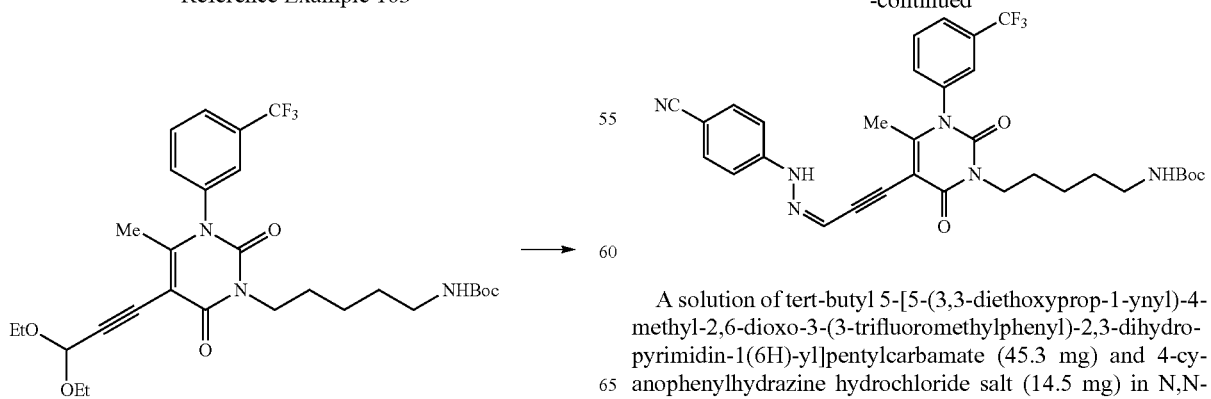

A solution of tert-butyl 5-[5-(3,3-diethoxyprop-1-ynyl)-4-methyl-2,6-dioxo-3-(3-trifluoromethylphenyl)-2,3-dihydropyrimidin-1(6H)-yl]pentylcarbamate (45.3 mg) and 4-cyanophenylhydrazine hydrochloride salt (14.5 mg) in N,N-dimethy formamide (1.0 ml) solution was stirred at 40° C. for two and a half hours. To the reaction mixture was added water (10 ml) and the resulting mixture was extracted with ethyl acetate (10 ml×2). The organic layer was washed with water (10 ml×2) and saturated saline (10 ml), dried over anhydrous sodium sulfate and then concentrated under reduced pressure. The residue was purified by silica gel column chromatography (eluent: hexane/ethyl acetate) to afford (Z)-tert-butyl 5-[5-[3-[2-(4-cyanophenyl)hydrazono]prop-1-ynyl]-4-methyl-2,6-dihydro-3-(3-trifluorophenyl)-2,3-dihydropyrimidin-1(6H)-yl]pentylcarbamate (23.7 mg).

$^1$H-NMR (CDCl$_3$: 300 MHz) (δ PPM):

1.38-1.42 (m, 11H), 1.50-1.56 (m, 2H), 1.65-1.77 (m, 2H), 2.13 (s, 3H), 3.06-3.14 (m, 2H), 4.05 (t, 3H, J=7.4 Hz), 4.52 (brs, 1H), 6.59 (s, 1H), 7.33 (d, 2H, J=8.8 Hz), 7.47 (d, 1H, J=7.9 Hz), 7.53-7.56 (m, 3H), 7.70 (t, 1H, J=7.9 Hz), 7.79 (d, 1H, J=7.9 Hz), 10.35 (s, 1H)

Reference Examples 164-173

The compounds 1i indicated in the below-mentioned table (Reference Examples 164-173) were obtained by using the corresponding starting materials according to the similar reaction and treatment method to those described in Reference examples 163.

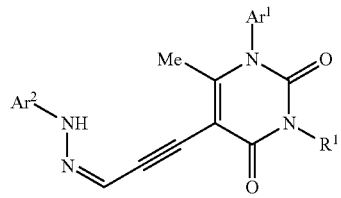

1i

TABLE 21

| Ref. Ex. | Ar$^1$ | Ar$^2$ | R$^1$ | Measurement cond. | $^1$H-NMR (δ PPM) (or LC-MS: [M + H]+/Rt) |
|---|---|---|---|---|---|
| 164 | 3-CF$_3$-phenyl | 4-NC-phenyl | Me | 1 | 2.15 (s, 3H), 3.50 (s, 3H), 6.60 (s, 1H), 7.38 (d, 1H, J = 8.7 Hz), 7.47 (d, 1H, 8.7 Hz), 7.54-7.57 (m, 3H), 7.74 (d, 1H, J = 7.8 Hz), 7.79 (s, 1H), 10.38 (brs, 1H) |
| 165 | 3-CO$_2$Me-phenyl | 4-NC-phenyl | Me | 1 | 2.10 (s, 3H), 3.44 (s, 3H), 3.88 (s, 3H), 6.55 (s, 1H), 7.33 (d, 2H, J = 9.0 Hz), 7.38-7.41 (m, 1H), 7.51 (d, 2H, J = 7.2 Hz), 7.50 (t, 1H, J = 7.5 Hz), 7.88 (t, 1H, J = 2.1 Hz), 8.16 (dt, 1H, J = 8.1, J = 1.5 Hz), 10.35 (brs, 1H) |
| 166 | 6-CF$_3$-pyridin-2-yl | 4-NC-phenyl | Me | 1 | 2.10 (s, 3H), 3.44 (s, 3H), 3.88 (s, 3H), 6.55 (s, 1H), 7.33 (d, 2H, J = 9.0 Hz), 7.38-7.41 (m, 1H), 7.51 (d, 2H, J = 7.2 Hz), 7.50 (t, 1H, J = 7.5 Hz), 7.88 (t, 1H, J = 2.1 Hz), 8.16 (dt, 1H, J = 8.1, J = 1.5 Hz), 10.35 (brs, 1H) |
| 167 | 3-Br-phenyl | 4-NC-phenyl | Me | 1 | 2.12 (s, 3H), 3.44 (s, 3H), 6.55 (s, 1H), 7.14-7.16 (m, 1H), 7.29-7.41 (m, 4H), 7.51 (d, 2H, J = 8.7 Hz), 7.64 (d, 1H, J = 8.4 Hz), 10.34 (brs, 1H) |
| 168 | 3-Cl-phenyl | 4-NC-phenyl | Me | 8 | 418 (MH+)/2.46 (min) |
| 169 | 3-CF$_3$-phenyl | 3-NC-phenyl | Me | 1 | 2.10 (s, 3H), 3.50 (s, 3H), 6.50 (s, 1H), 7.04-7.15 (m, 1H), 7.30 (t, 1H, J = 7.8 Hz), 7.41-7.76 (m, 6H), 10.21 (brs, 1H) |

TABLE 21-continued

| Ref. Ex. | Ar¹ | Ar² | R¹ | Measurement cond. | ¹H-NMR (δ PPM) (or LC-MS: [M + H]+/Rt) |
|---|---|---|---|---|---|
| 170 | 3-CF₃-phenyl | 4-SMe-2-CN-phenyl (NC, SMe substituted) | Me | 1 | 2.11 (s, 3H), 2.35 (s, 3H), 3.36 (s, 3H), 6.77 (s, 1H), 7.43 (d, 1H, J = 8.4 Hz), 7.45 (d, 2H, J = 0.9 Hz), 7.49 (s, 1H), 7.63 (t, 1H, J = 1.2 Hz), 7.67 (d, 1H, J = 7.8 Hz), 7.77 (d, 1H, J = 7.8 Hz), 9.79 (brs, 1H) |
| 171 | 3-Me-phenyl | 4-CN-phenyl | Me | 1 | 2.09 (s, 3H), 2.36 (s, 3H), 3.42 (s, 3H), 6.53 (s, 1H), 6.98 (d, 2H, J = 1.5 Hz), 7.25-7.39 (m, 4H), 7.48 (d, 2H, J = 8.4 Hz), 10.37 (brs, 1H) |
| 172 | 3-tBu-phenyl | 4-CN-phenyl | Me | 1 | 1.27 (s, 9H), 2.06 (s, 3H), 3.41 (s, 3H), 6.53 (s, 1H), 6.97-7.01 (m, 1H), 7.15-7.19 (m, 1H), 7.29 (d, 2H, J = 8.7 Hz), 7.40 (t, 1H, J = 7.8 Hz), 7.45-7.48 (m, 3H), 10.37 (brs, 1H) |
| 173 | 3-(MeSO₂)-phenyl | 4-CN-phenyl | Me | 8 | 462 (MH+)/2.21 (min) |

Reference Example 174

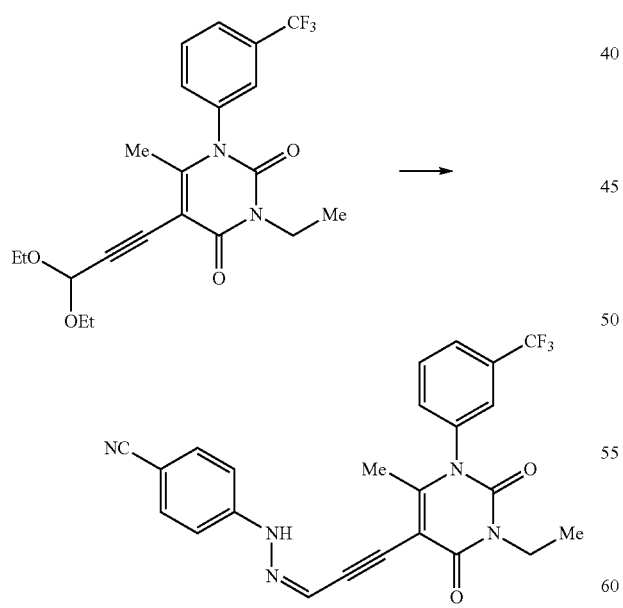

To a solution of 5-(3,3-diethoxyprop-1-ynyl)-3-ethyl-6-methyl-1-(3-(trifluoromethyl)phenyl)pyrimidin-2,4(1H,3H)-dione (2.40 g) in acetonitrile (72 ml) were added 4-cyanophenylhydrazine (1.11 g) and concentrated sulfuric acid (0.30 ml) and the resulting mixture was stirred at room temperature for thirty minutes. The resulting mixture was cooled to 0° C. and thereto was added water (140 ml) dropwise, and the solids were collected by filtration and washed with water to afford (Z)-4-(2-(3-(3-ethyl-6-methyl-2,4-dioxo-1-(3-(trifluoromethyl)phenyl)-1,2,3,4-tetrahydropyrimidin-5-yl)prop-2-yneylidene)hydrazinyl)benzonitrile (2.50 g) as brown solid.

¹H-NMR (CDCl₃: 300 MHz) (δ PPM):

1.27 (t, 3H, J=7.2 Hz), 2.08 (s, 3H), 4.08 (q, 2H, J=7.2 Hz), 6.54 (s, 1H), 7.30 (d, 2H, J=9.0 Hz), 7.42 (d, 1H, J=8.4 Hz), 7.48-7.51 (m, 3H), 7.65 (t, 1H, J=7.8 Hz), 7.75 (d, 1H, J=7.8 Hz), 10.33 (s, 1H)

Reference Examples 175-182

The compounds 1j indicated in the below-mentioned table (Reference Examples 175-182) was obtained by using the corresponding starting materials according to the similar method and treatment methods to those described in the Reference Example 174.

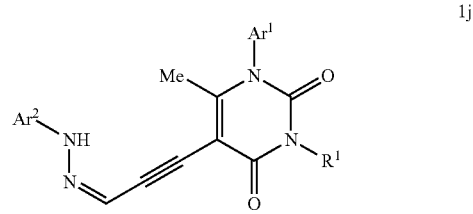

1j

TABLE 22

| Ref. Ex. | Ar¹ | Ar² | R¹ | Measurement cond. | ¹H-NMR (δ PPM) |
|---|---|---|---|---|---|
| 175 | 3-CF₃-phenyl | 4-CN-phenyl | $^i$Pr | 1 | 1.53 (d, 6H, J = 6.9 Hz), 2.10 (s, 3H), 5.29 (septet, 1H, J = 7.2 Hz), 6.57 (s, 1H), 7.33 (d, 2H, J = 8.7 Hz), 7.46-7.55 (m, 4H), 7.69 (t, 1H, J = 7.8 Hz), 7.78 (d, 1H, J = 7.8 Hz), 10.40 (s, 1H) |
| 176 | 3-CF₃-phenyl | 4-CN-phenyl | $^c$Pr | 1 | 0.88-0.94 (m, 2H), 1.20 (q, 2H, J = 6.6 Hz), 2.12 (s, 3H), 2.80-2.88 (m, 1H), 6.59 (s, 1H), 7.37 (d, 2H, J = 8.7 Hz), 7.44 (d, 1H, J = 8.4 Hz), 7.52-7.57 (m, 3H), 7.70 (t, 1H, J = 7.5 Hz), 7.79 (d, 1H, J = 8.71 Hz), 10.40 (s, 1H) |
| 177 | 3-CF₃-phenyl | 4-CN-phenyl | cyclobutyl | 1 | 1.77-1.95 (m, 2H), 2.11 (s, 3H), 2.29-2.38 (m, 2H), 2.89-2.97 (m, 2H), 5.27-5.39 (m, 1H), 6.59 (s, 1H), 7.37 (d, 2H, J = 8.7 Hz), 7.46 (d, 1H, J = 8.1 Hz), 7.54-7.57 (m, 3H), 7.70 (t, 1H, J = 7.5 Hz), 7.79 (d, 1H, J = 7.5 Hz), 10.46 (s, 1H). |
| 178 | 3-CF₃-phenyl | 4-CN-phenyl | N-Cbz-azetidin-3-yl | 1 | 2.08 (s, 3H), 4.27 (t, 2H, J = 9.0 Hz), 4.53 (t, 2H, J = 8.7 Hz), 5.00 (s, 0.5H), 5.04 (s, 1.5 Hz), 5.45-5.55 (m, 1H), 6.52 (s, 1H), 7.19-7.30 (m, 7H), 7.40-7.42 (m, 3H), 7.50 (s, 1H), 7.62-7.76 (m, 2H), 10.22 (s, 1H) |
| 179 | 3-CF₃-phenyl | 4-Br-phenyl | CH(Me)CO₂Me | 1 | 1.23 (t, 3H, J = 6.9 Hz), 1.65 (d, 3H, J = 6.9 Hz), 2.12 (s, 3H), 4.15-4.30 (m, 2H), 5.56 (ddd, 1H, J = 14.1, 6.9, 2.4 Hz), 7.15 (d, 2H, J = 8.7 Hz), 7.36 (d, 2H, J = 9.0 Hz), 7.43-7.61 (m, 2H), 7.69 (t, 1H, J = 7.8 Hz), 7.78 (d, 1H, J = 7.8 Hz), 10.03 (s, 1H) |
| 180 | 3-CF₃-phenyl | 4-CN-phenyl | CH(Me)CH₂OAc | 1 | 1.49 (d, 3H, J = 7.2 Hz), 1.99 (s, 3H), 2.14 (s, 3H), 4.29 (dt, 1H, J = 1/1.7, 2.1 Hz), 4.62-4.74 (m, 1H), 5.29 (brs, 1H), 7.04 (d, 2H, J = 8.7 Hz), 7.26 (s, 1H), 7.39-7.61 (m, 4H), 7.69 (t, 1H, J = 7.5 Hz), 7.77 (d, 1H, J = 7.8 Hz), 9.36 (s, 1H) |
| 181 | 3-CF₃-phenyl | 4-CN-phenyl | CH(Me)Ph | 4 | 1.95 (d, 1.5H, J = 7.2 Hz), 1.96 (d, 1.5H, J = 7.2 Hz), 2.13 (s, 3H), 6.37-6.42 (m, 1H), 6.60 (s, 1H), 7.29-7.37 (m, 5.5H), 7.49-7.52 (m, 3H), 7.55-7.58 (m, 2.5H), 7.63-7.75 (m, 1H), 7.78-7.80 (m, 1H), 10.44 (s, 1H) |
| 182 | 3-CF₃-phenyl | 4-CN-phenyl | CH₂CH₂OAc | 1 | 1.94 (s, 3H), 2.15 (s, 3H), 4.36-4.44 (m, 4H), 6.60 (d, 1H, J = 4.5 Hz), 7.34 (d, 2H, J = 8.4 Hz), 7.48 (d, 1H, J = 7.5 Hz), 7.54-7.57 (m 3H), 7.71 (t, 1H, J = 7.8 Hz), 7.80 (d, 1H, J = 7.5 Hz), 10.38 (s, 1H) |

Reference Examples 183-188

The compounds 1k indicated in the below-mentioned table (Reference Examples 183-188) were obtained by using the corresponding starting materials according to the similar reaction and method treatment to those described in Reference Example 174.

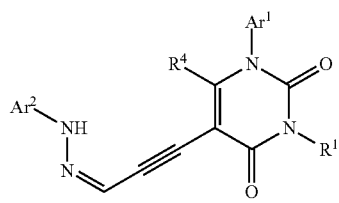

1k

TABLE 23

| Ref. Ex. | Ar¹ | Ar² | R¹ | R⁴ | Measurement cond. | ¹H-NMR (δ PPM) |
|---|---|---|---|---|---|---|
| 183 | 3-CF₃-phenyl | 4-CN-phenyl | Me | Et | 4 | 1.10 (t, 3H, J = 7.6 Hz), 2.50 (q, 2H, J = 7.6 Hz), 3.51 (s, 3H), 6.63 (s, 1H), 7.37-7.41 (m, 2H), 7.51 (d, 1H, J = 7.9 Hz), 7.55-7.59 (m, 3H), 7.74 (t, 1H, J = 7.9 Hz), 7.83 (d, 1H, J = 7.81 Hz), 10.44 (s, 1H) |
| 184 | 3-CF₃-phenyl | 4-CN-phenyl | Me | ⁱPr | 4 | 1.38 (d, 3H, J = 7.0 Hz), 1.39 (d, 3H, J = 7.0 Hz), 2.51 (sept, 1H, J = 7.0 Hz), 3.52 (s, 3H), 6.66 (s, 1H), 7.40 (dd, 2H, J = 7.0, 1.8 Hz), 7.46 (d, 1H, J = 7.8 Hz), 7.53 (s, 1H), 7.57 (dd, 2H, J = 7.0, 1.8 Hz), 7.73 (t, 1H, J = 7.9 Hz), 7.83 (d, 1H, J = 7.9 Hz), 10.76 (s, 1H) |
| 185 | 3-CF₃-phenyl | 4-CN-phenyl | H | H | 5 | 6.93 (s, 0.75H), 7.06 (d, 0.5H, J = 8.8 Hz), 7.29 (d, 1.5H, J = 8.8 Hz), 7.38 (s, 0.25H), 7.63 (d, 0.5H, J = 8.8 Hz), 7.70 (d, 1.5H, J = 8.8 Hz), 7.72-7.89 (m, 3H), 7.95 (s, 0.25H), 8.01 (s, 0.75H), 8.36 (s, 0.25H), 8.52 (s, 0.75H), 10.36 (s, 0.75H), 11.37 (s, 0.25H), 11.94 (s, 0.25H), 12.20 (s, 0.75H) (Z/E = 3/1) |
| 186 | 3-CF₃-phenyl | 4-CN-phenyl | ⁱPr | H | 1 | 1.57 (d, 6H, J = 5.1 Hz), 4.37 (quin, 1H, J = 6.6 Hz), 6.58 (s, 1H), 7.33 (d, 2H, J = 8.4 Hz), 7.51-7.69 (m, 6H), 7.74 (d, 1H, J = 6.61 Hz), 10.24 (s, 1H) |
| 187 | 3-CF₃-phenyl | 4-CN-phenyl | CH(Me)CH₂OH | H | 1 | 1.52 (d, 3H, J = 7.2 Hz), 3.92 (dd, 1H, J = 1/1.7, 4.2 Hz), 4.20 (dd, 1H, J = 1/1.7, 8.4 Hz), 5.35 (brs, 1H), 6.58 (s, 1H), 7.29 (d, 2H, J = 6.9 Hz), 7, 54-7.60 (m, 3H), 7.65 (brs, 2H), 7.69 (d, 1H, J = 7.8 Hz), 7.76 (d, 1H, J = 8.1 Hz), 10.08 (s, 1H) |
| 188 | 4-CF₃-2-Me-phenyl | 4-CN-phenyl | CH(Me)₂ | H | 4 | 1.58 (d, 3H, J = 6.9 Hz), 1.59 (d, 3H, J = 6.9 Hz), 2.30 (s, 3H), 5.36 (sept, 1H, J = 6.9 Hz), 6.60 (s, 1H), 7.35 (dd, 2H, J = 1.8, 7.0 Hz), 7.51 (s, 1H), 7.51-7.53 (m, 2H), 7.58 (dd, 2H, J = 1.8, 7.0 Hz), 7.68 (d, 1H, J = 8.8 Hz), 10.27 (s, 1H) |

Reference Example 189

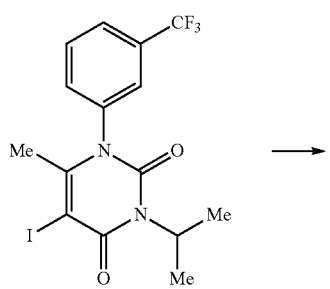

→

-continued

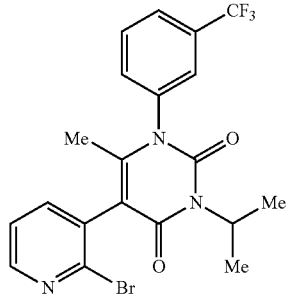

5-Iodo-3-isopropyl-6-methyl-1-(3-trifluoromethylphenyl)pyrimidin-2,4(1H,3H)-dione (prepared in Reference Example 85) (600 mg) and 2-bromo-3-pyridine boronic acid pinacol ester (878 mg) were dissolved in 1,2-dimethoxyethane (30 ml). Thereto were added under nitrogen atmosphere water (6 ml), sodium carbonate (290 mg), 2-(dicyclohexylphosphino)biphenyl (57.6 mg) and tetrakis(triphenylphosphine)palladium (316 mg) and the resulting mixture was stirred with heating under reflux for four and a half hours. The reaction solution was concentrated under reduced pressure and to the residue was added water, and the resulting mixture was extracted with ethyl acetate (50 ml). The organic layer was washed with saturated saline (50 ml), dried over anhydrous magnesium sulfate and then concentrated under reduced pressure. The residue was purified by silica gel column chromatography (eluent: hexane/ethyl acetate) to afford 5-(2-bromopyridin-3-yl)-3-isopropyl-6-methyl-1-(3-(trifluoromethyl)phenyl)pyrimidin-2,4(1H,3H)-dione (134 mg).

$^1$H-NMR (400 MHz, CDCl$_3$) (δ PPM):

1.52 (d, 6H, J=6.9 Hz), 1.68 (s, 3H), 5.23 (sept, 1H, J=6.9 Hz), 7.35-7.39 (m, 1H), 7.50-7.59 (m, 1H), 7.60-7.66 (m, 2H), 7.67-7.73 (m, 1H), 7.77 (d, 1H, J=7.9 Hz), 8.40 (dd, 1H, J=2.2, 4.7 Hz)

Reference Example 190

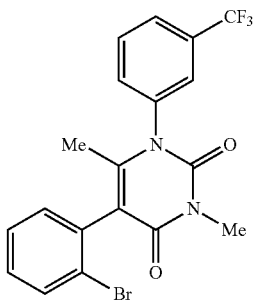 [SMILES: Cc1c(-c2ccccc2Br)c(=O)n(C)c(=O)n1-c1cccc(C(F)(F)F)c1]

The compound was prepared by using the corresponding starting materials according to the similar reaction and treatment method to those described in the Reference Example 189.

$^1$H-NMR (CDCl$_3$: 300 MHz) (δ PPM):

1.84 (s, 3H), 3.42 (s, 3H), 7.08 (dd, 1H, J=5.0, 1.3 Hz), 7.25 (dd, 1H, J=3.0, 1.3 Hz), 7.38 (dd, 1H, J=5.0, 3.0 Hz), 7.51 (d, 1H, J=7.8 Hz), 7.59 (s, 1H), 7.69 (t, 1H, J=7.8 Hz), 7.77 (d, 1H, J=7.8 Hz)

Reference Example 191

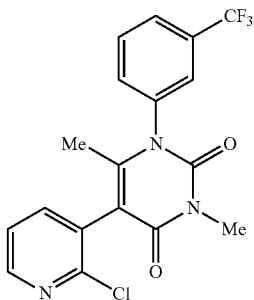 [SMILES: Cc1c(-c2cccnc2Cl)c(=O)n(C)c(=O)n1-c1cccc(C(F)(F)F)c1]

The compound was obtained by using the corresponding starting materials according to the similar reaction and treatment method to those described in Reference Example 189.

LC-Mass: 396 (MH+)/7.60 (min) (measurement condition 7)

Reference Examples 192-193

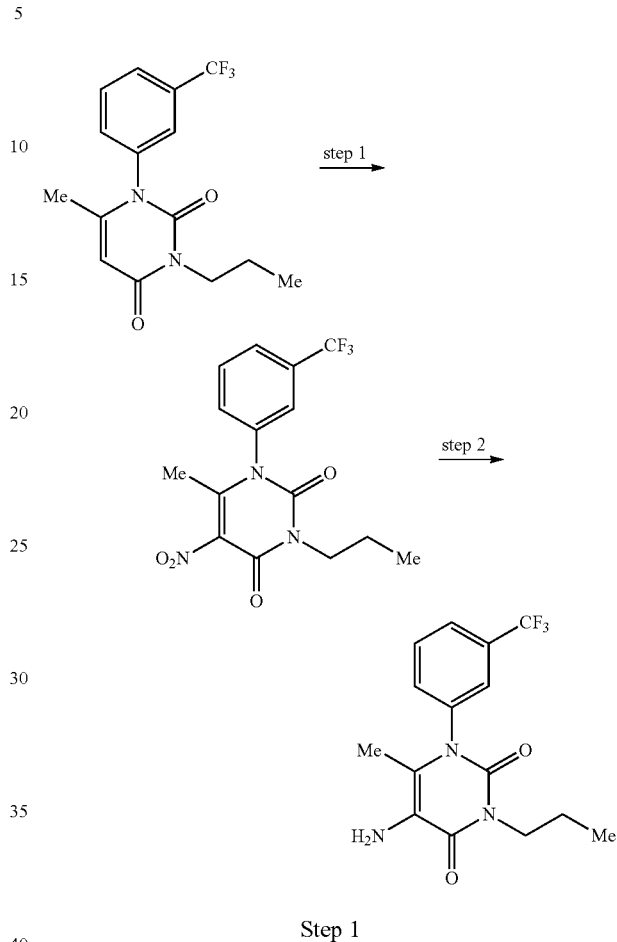

Step 1

Reference Example 192

To concentrated sulfuric acid (2.0 ml) were added in ice bath fuming nitric acid (0.2 ml), 6-methyl-3-propyl-1-(3-trifluoromethylphenyl)pyrimidin-2,4(1H,3H)-dione (prepared in Reference Example 21) (200.0 mg) and the resulting mixture was stirred for three hours in ice bath. The reaction mixture was poured into ice water, and the precipitated solids were collected by filtration to afford 6-methyl-5-nitro-3-propyl-1-(3-trifluoromethylphenyl)pyrimidin-2,4(1H,3H)-dione (219.0 mg).

$^1$H-NMR (CDCl$_3$: 400 MHz) (δ PPM):

0.97 (t, 3H, J=7.4 Hz), 1.66-1.76 (m, 2H), 2.04 (s, 3H), 3.95 (t, 2H, J=7.4 Hz), 7.49 (d, 1H, J=7.9 Hz), 7.57 (s, 1H), 7.74 (t, 1H, J=7.9 Hz), 7.49 (d, 1H, J=7.9 Hz)

Step 2

Reference Example 193

To a solution of 6-methyl-5-nitro-3-propyl-1-(3-trifluoromethylphenyl)pyrimidin-2,4(1H,3H)-dione (200.0 mg) in methanol (10.0 ml) was added palladium hydrate (20.0 mg) and the resulting mixture was stirred at room temperature under catalytic hydrogenation condition for twelve hours. The reaction mixture was degassed and then filtered through Celite (trade mark), and then concentrated under reduced pressure to afford 5-amino-6-methyl-3-propyl-1-(3-trifluoromethylphenyl)pyrimidin-2,4(1H,3H)-dione (190.0 mg).

$^1$H-NMR (CDCl$_3$: 400 MHz) (δ PPM):
0.96 (t, 3H, J=7.4 Hz), 1.66-1.75 (m, 2H), 1.82 (s, 3H), 3.32 (brs, 2H), 3.97 (t, 2H, J=7.4 Hz), 7.45 (d, 1H, J=7.8 Hz), 7.51 (s, 1H), 7.65 (t, 1H, J=7.8 Hz), 7.73 (d, 1H, J=7.8 Hz)

Reference Examples 194-196

The compounds 1l indicated in the below-mentioned Table (Reference Examples 194-196) were obtained by using the corresponding starting materials according to the similar reaction and treatment method described in Reference Example 192.

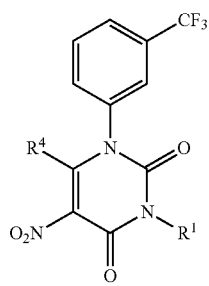

TABLE 24

| Ref. Ex. | R$^1$ | R$^4$ | Measurement cond. | $^1$H-NMR (δ PPM) (or LC-MS: [M + H]+ /Rt) |
|---|---|---|---|---|
| 194 | $^i$Pr | H | 1 | 1.46 (d, 6H, J = 6.8 Hz), 5.17-5.26 (m, 1H), 7.55 (d, 1H, J = 8.4 Hz), 7.63-7.68 (m, 2H), 7.75 (d, 1H, J = 7.9 Hz), 8.66 (s, 1H) |
| 195 | $^i$Pr | Me | 7 | 358 (M + H)/3.48 (min) |
| 196 | Me | Me | 7 | 330 (M + H)/3.04 (min) |

Reference Example 197

The compounds 1m indicated in the below-mentioned table (Reference Example 197) was obtained by using the corresponding starting materials according to the similar reaction and treatment method to those described in Reference Example 193.

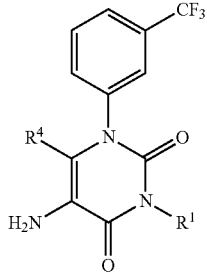

1m

TABLE 25

| Ref. Ex. | R$^1$ | R$^4$ | Measurement cond. | $^1$H-NMR (δ PPM) |
|---|---|---|---|---|
| 197 | $^i$Pr | H | 4 | 1.52 (d, 6H, J = 6.9 Hz), 5.28 (sept, 1H, J = 6.9 Hz), 6.79 (s, 1H), 7.57-7.61 (m, 2H), 7.63-7.66 (m, 2H) |

Reference Example 198

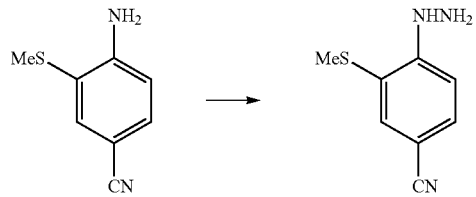 [SMILES: CSc1cc(C#N)ccc1N ; CSc1cc(C#N)ccc1NN]

To a solution of 4-amino-3-(methylthio)benzonitrile (71.1 mg) and 5N aqueous hydrochloric acid (2.0 ml)/ethanol (0.5 ml) was added under ice cooling sodium nitrite (32.5 mg) and the resulting mixture was stirred for one and a half hours. To the reaction mixture was added tin(II) chloride (101.4 mg) and the resulting mixture was stirred at 0° C. for two and a half hours. The reaction mixture was filtered, and the mother liquor was basified (pH=about 10) with potassium carbonate and extracted with chloroform (30 ml) three times, and the organic layer was dried over sodium sulfate and then concentrated under reduced pressure to afford 4-hydrazinyl-3-(methylthio)benzonitrile (57.7 mg).

$^1$H-NMR (CDCl$_3$: 300 MHz) (δ PPM):
2.28 (s, 3H), 3.69 (brs, 2H), 6.59 (brs, 1H), 7.12 (d, 1H, J=8.4 Hz), 7.50 (d, 1H, J=1.8 Hz), 7.41 (ddd, 1H, J=8.7, 2.7, 0.6 Hz), J=1.8 Hz)

Reference Example 199

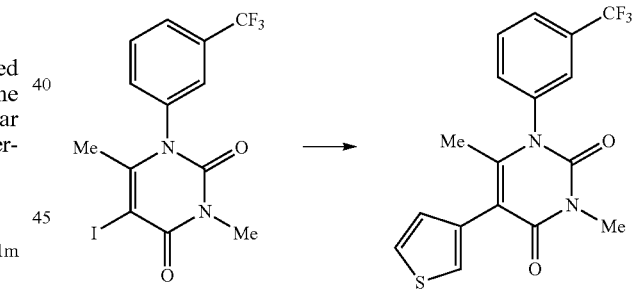

To a solution of 5-iodo-3,6-dimethyl-1-(3-trifluoromethylphenyl)pyrimidin-2,4(1H,3H)-dione (prepared in Reference Example 60) (60.0 mg), 2-thiophen boronic acid (84.6 mg), sodium carbonate (84.6 mg) in tetrahydrofuran (2.0 ml)/water (0.3 ml) was added tetrakis(triphenylphosphine) palladium (25.2 mg) and the resulting mixture was stirred with heating under reflux for five hours. The reaction mixture was filtered through Celite (trade mark) and thereto was added water (10 ml), and the resulting mixture was extracted with ethyl acetate (10 ml×2). The organic layer was washed with saturated saline (20 ml), dried over anhydrous sodium sulfate and then concentrated under reduced pressure. The residue was purified by silica gel column chromatography (eluent: hexane/ethyl acetate) and further purified by silica gel column chromatography (eluent: chloroform/methanol) to afford 3,6-dimethyl-5-(thiophen-3-yl)-1-(3-trifluoromethylphenyl)pyrimidin-2,4(1H,3H)-dione (27.3 mg).

¹H-NMR (CDCl₃: 300 MHz) (δ PPM):
1.84 (s, 3H), 3.42 (s, 3H), 7.08 (dd, 1H, J=5.0, 1.3 Hz), 7.25 (dd, 1H, J=3.0, 1.3 Hz), 7.38 (dd, 1H, J=5.0, 3.0 Hz), 7.51 (d, 1H, J=7.8 Hz), 7.59 (s, 1H), 7.69 (t, 1H, J=7.8 Hz), 7.77 (d, 1H, J=7.8 Hz)

Reference Example 200 corresponding starting materials and according to the similar reaction and treatment method to those described in Reference Example 199.

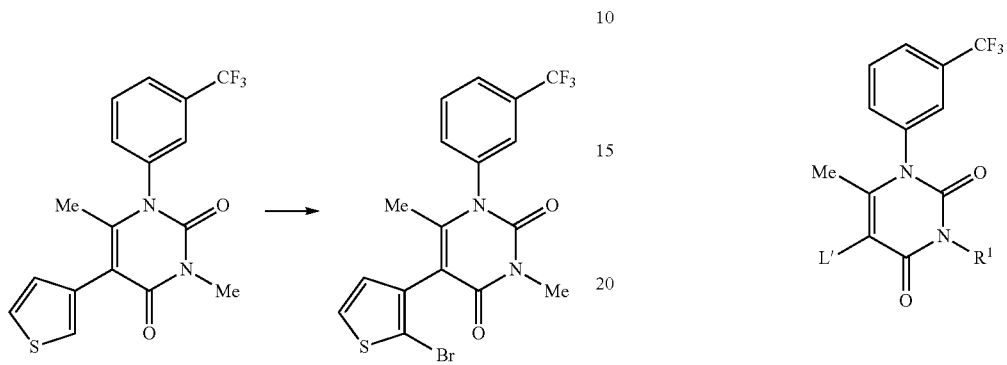

TABLE 26

| Ref. Ex. | L' | R¹ | Measurement cond. | ¹H-NMR (δ PPM) |
|---|---|---|---|---|
| 201 | pyrrole (NH) | Me | 1 | 2.13 (s, 3H), 3.45 (s, 3H), 6.18-6.21 (m, 1H), 6.26-6.29 (m, 1H), 6.89-6.92 (m, 1H), 7.40 (brd, 1H, J = 7.8 Hz), 7.49 (d, 1H, J = 7.8 Hz), 7.57 (s, 1H), 7.69 (t, 1H, J = 7.8 Hz), 7.77 (d, 1H, J = 7.8 Hz) |
| 202 | bromocyclopentenyl | propyl (Me) | 4 | 0.95 (t, 3H, J = 7.4 Hz), 1.66-1.75 (m, 2H), 1.84 (s, 3H), 2.00-2.07 (m, 1H), 2.11-2.22 (m, 1H), 2.24-2.35 (m, 1H), 2.70-2.85 (m, 2H), 2.90-3.00 (m, 1H), 3.92 (t, 3H, J = 7.4 Hz), 7.48 (d, 1H, J = 7.8 Hz), 7.53 (s, 0.5H), 7.57 (s, 0.5H), 7.64-7.69 (m, 1H), 7.75 (d, 1H, J = 7.8 Hz) |

To a solution of 3,6-dimethyl-5-(thiophen-3-yl)-1-(3-trifluoromethylphenyl)pyrimidin-2,4(1H,3H)-dione (prepared in Reference example 199) (30.7 mg) in acetic acid (1.5 ml) was added N-bromosuccinimide (20.2 mg) and the resulting mixture was stirred at room temperature for three hours. To the reaction mixture were added an aqueous saturated sodium hydrogen carbonate solution (10 ml) and an aqueous saturated sodium thiosulfate solution (10 ml), and the resulting mixture was extracted with ethyl acetate (10 ml×2). The organic layer was washed with saturated saline (20 ml), dried over anhydrous sodium sulfate and then concentrated under reduced pressure. The residue was purified by silica gel column chromatography (eluent: hexane/ethyl acetate) to afford 5-(2-bromothiophen-3-yl)-3,6-dimethyl-1-(3-trifluoromethylphenyl)pyrimidin-2,4(1H,3H)-dione (17.4 mg).

¹H-NMR (CDCl₃: 300 MHz) (δ PPM):
1.77 (s, 3H), 3.42 (s, 3H), 6.92 (dd, 1H, J=5.7, 3.3 Hz), 7.34 (dd, 1H, J=5.7, 1.5 Hz), 7.51 (d, 1H, J=7.8 Hz), 7.59 (brd, 1H, J=10.0 Hz), 7.66-7.72 (m, 1H), 7.78 (d, 1H, J=7.8 Hz)

Reference Examples 201-202

The compounds 1n indicated in the below-mentioned table (Reference Examples 201-202) were obtained by using the Reference Example 203

4-[3-[3,6-Dimethyl-2,4-dioxo-1-(3-trifluoromethylphenyl)-1,2,3,4-tetrahydropyrimidin-5-yl]thiophen-2-yl]benzonitrile

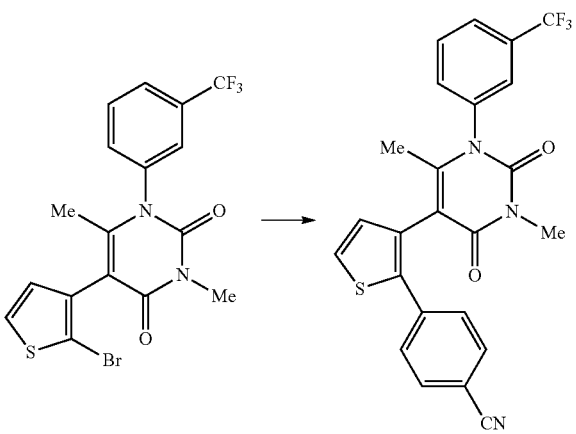 [SMILES: Cc1c(-c2ccsc2Br)c(=O)n(C)c(=O)n1-c1cccc(C(F)(F)F)c1 ; Cc1c(-c2ccsc2-c2ccc(C#N)cc2)c(=O)n(C)c(=O)n1-c1cccc(C(F)(F)F)c1]

To a solution of 5-(2-bromothiophen-3-yl)-3,6-dimethyl-1-(3-trifluoromethylphenyl)pyrimidin-2,4(1H,3H)-dione (prepared in Reference Example 200) (17.0 mg), 4-cyanophenylboronic acid (11.2 mg) and sodium carbonate (20.2 mg) in tetrahydrofuran (1.0 ml)/water (0.2 ml) was added tetrakis(triphenylphosphine)palladium (4.4 mg) and the resulting mixture was stirred with heating under reflux for twelve hours. To the reaction mixture was added water (10 ml) and the resulting mixture was extracted with ethyl acetate (10 ml×2). The organic layer was washed with saturated saline (10 ml), dried over anhydrous sodium sulfate and then concentrated under reduced pressure. The residue was purified by silica gel column chromatography (eluent: hexane/ethyl acetate) to afford 4-[3-[3,6-dimethyl-2,4-dioxo-1-(3-trifluoromethylphenyl)-1,2,3,4-tetrahydropyrimidin-5-yl]thiophen-2-yl]benzonitrile (16.4 mg).

$^1$H-NMR (CDCl$_3$: 300 MHz) (δ PPM):

1.43 (s, 1.5H), 1.45 (s, 1.5H), 3.43 (s, 1.5H), 3.44 (s, 1.5H), 7.05 (d, 0.5H, J=3.4 Hz), 7.07 (d, 0.5H, J=3.4 Hz), 7.16 (d, 0.5H, J=8.5 Hz), 7.21 (s, 0.5H), 7.46-7.55 (m, 4H), 7.61-7.74 (m, 4H)

Reference Example 204

4-[2-[6-Methyl-2,4-dioxo-3-propyl-1-(3-trifluoromethylphenyl)-1,2,3,4-tetrahydropyrimidin-5-yl]cyclopent-1-enyl]benzonitrile

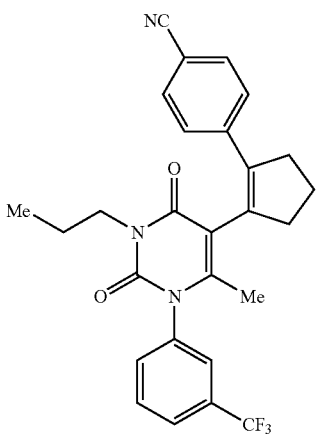 [SMILES: CCCn1c(=O)c(C2=C(c3ccc(C#N)cc3)CCC2)c(C)n(-c2cccc(C(F)(F)F)c2)c1=O]

The intended compound was obtained by using the corresponding starting materials according to the similar reaction and treatment method to those described in Reference Example 203.

$^1$H-NMR (CDCl$_3$: 300 MHz) (δ PPM):

0.96 (t, 3H, J=7.4 Hz), 1.44 (s, 1.5H), 1.46 (s, 1.5H), 1.66-1.76 (m, 2H), 2.04-2.20 (m, 2H), 2.40-2.52 (m, 1H), 2.75-2.85 (m, 1H), 2.95-3.10 (m, 2H), 3.96 (brt, 2H, J=6.6 Hz), 7.12-7.18 (m, 1H), 7.31-7.46 (m, 3H), 7.52-7.65 (m, 3H), 7.71 (d, 1H, J=8.1 Hz)

Reference Example 205

4-[2-[3,6-Dimethyl-2,4-dioxo-1-(3-trifluoromethylphenyl)-1,2,3,4-tetrahydropyrimidin-5-yl]-1H-pyrrol-1-yl]benzonitrile

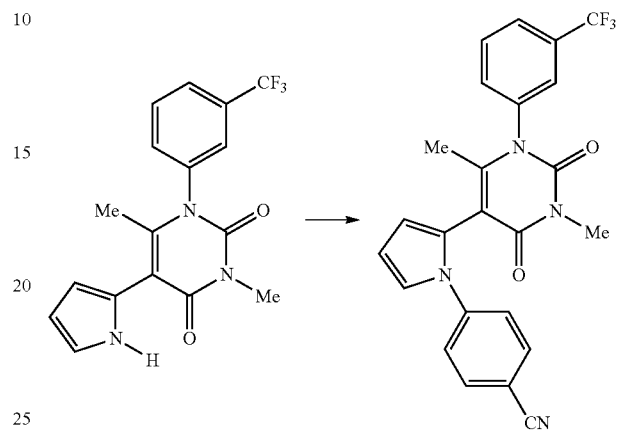

A solution of 3,6-dimethyl-5(1H-pyrrol-2-yl)-1-(3-trifluoromethylphenyl)pyrimidin-2,4(1H,3H)-dione (prepared in Reference Example 201) (20.0 mg), 4-cyanoiodobenzene (39.4 mg), copper(I) iodide (1.0 mg), cyclohexyldiamine (0.6 mg) and potassium phosphate (36.4 mg) in 1,4-dioxane (2.0 ml) was stirred with heating under reflux for fifteen hours. Thereto were added 4-cyanoiodobenzene (39.4 mg), copper (I) iodide (1.0 mg), cyclohexyldiamine (0.6 mg) and potassium phosphate (36.4 mg) and the resulting mixture was stirred with heating under reflux for four hours. To the reaction mixture was added water (10 ml) and the resulting mixture was extracted with ethyl acetate (10 ml×2). The organic layer was washed with saturated saline (20 ml), dried over anhydrous sodium sulfate and then concentrated under reduced pressure. The residue was purified by silica gel column chromatography (eluent: hexane/ethyl acetate) and further purified by silica gel column chromatography (eluent: hexane/acetone/methanol) to afford 4-[2-[3,6-dimethyl-2,4-dioxo-1-(3-trifluoromethylphenyl)-1,2,3,4-tetrahydropyrimidin-5-yl]-1H-pyrrol-1-yl]benzonitrile (8.2 mg).

$^1$H-NMR (CDCl$_3$: 300 MHz) (δ PPM):

1.68 (s, 1.5H), 1.72 (s, 1.5H), 3.30 (s, 1.5H), 3.32 (s, 1.5H), 6.31-6.34 (m, 1H), 6.41-6.44 (m, 1H), 6.98-7.00 (m, 1H), 7.26-7.38 (m, 3H), 7.46 (d, 0.5H, J=8.1 Hz), 7.56 (s, 0.5H), 7.63-7.77 (m, 4H)

Reference Examples 207-210

The compounds indicated in the below-mentioned table (Reference Examples 207-210) were obtained by using the corresponding starting materials according to the similar reaction and treatment method to those described in Reference Example 1-18.

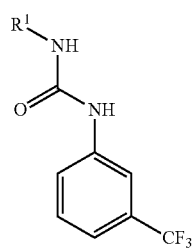

TABLE 27

| Ref. Ex. | R¹ | Measurement cond. | (LC-MS: [M + H]+/Rt |
|---|---|---|---|
| 207 | CbzN-pyrrolidine | 9 | 408 (M + H)/1.06 (min) |
| 208 | CbzN-pyrrolidine | 9 | 408 (M + H)/1.06 (min) |
| 209 | CbzN-piperidine | 9 | 422 (M + H)/1.06 (min) |
| 210 | CbzN-piperidine | 9 | 422 (M + H)/1.06 (min) |

Reference Examples 211-216

The compounds indicated in the below-mentioned table (Reference Examples 211-216) were obtained by using the corresponding 616 starting materials according to the similar reaction and treatment method to those described in Reference Examples 20-51 or J. Med. Chem. 2008, 51, 7478.

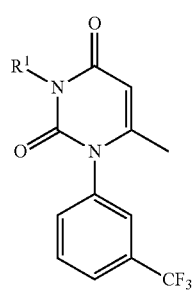

TABLE 28

| Ref. Ex. | R¹ | Measurement cond. | (LC-MS: [M + H]+/Rt) |
|---|---|---|---|
| 211 | CbzN-pyrrolidine | 9 | 474 (M + H)/1.08 (min) |
| 212 | CbzN-pyrrolidine | 9 | 474 (M + H)/1.08 (min) |
| 213 | CbzN-piperidine | 9 | 488 (M + H)/1.07 (min) |
| 214 | CbzN-piperidine | 9 | 488 (M + H)/1.09 (min) |
| 215 | CbzN-piperidine | 9 | 488 (M + H)/1.09 (min) |
| 216 | H | 9 | 271 (M + H)/0.70 (min) |

Reference Examples 217-223

The compounds indicated in the below-mentioned table (Reference Examples 217-223) were obtained by using the corresponding starting materials according to the similar reaction and treatment method to those described in Reference Example 60.

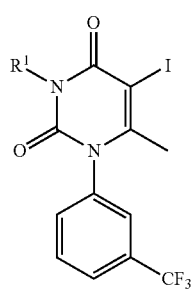

TABLE 29

| Ref. Ex. | R¹ | Measurement cond. | (LC-MS: [M + H]+/Rt) |
|---|---|---|---|
| 217 | CbzN-pyrrolidin-3-yl | 9 | 600 (M + H)/1.20 (min) |
| 218 | CbzN-pyrrolidin-3-yl (stereo) | 9 | 600 (M + H)/1.20 (min) |
| 219 | CbzN-piperidin-4-yl | 9 | 614 (M + H)/1.19 (min) |
| 220 | CbzN-piperidin-3-yl | 9 | 614 (M + H)/1.20 (min) |
| 221 | CbzN-piperidin-3-yl (stereo) | 9 | 614 (M + H)/1.20 (min) |
| 222 | H₂NO₂S-CH(CH₃)CH₂- | 9 | 518 (M + H)/0.896 (min) |
| 223 | H | 9 | 397 (M + H)/0.84 (min) |

Reference Examples 224-230

The compounds indicated in the below-mentioned table (Reference Examples 224-230) were obtained by using the corresponding starting materials according to the similar reaction and treatment method to those described in Reference Example 61.

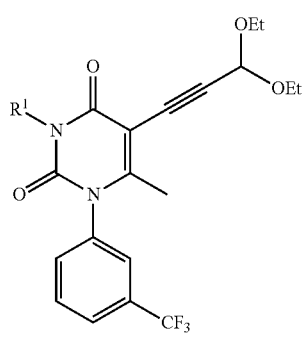

TABLE 30

| Ref. Ex. | R¹ | Measurement cond. | (LC-MS: [M + H]+/Rt) |
|---|---|---|---|
| 224 | CbzN-pyrrolidin-3-yl | 9 | 554 (M − OEt)/1.27 (min) |
| 225 | CbzN-pyrrolidin-3-yl (stereo) | 9 | 554 (M − OEt)/1.27 (min) |
| 226 | CbzN-piperidin-4-yl | 9 | 568 (M − OEt)/0.89 (min) |
| 227 | CbzN-piperidin-3-yl | 9 | 568 (M − OEt)/1.25 (min) |
| 228 | CbzN-piperidin-3-yl (stereo) | 9 | 554 (M − OEt)/1.27 (min) |
| 229 | H₂NO₂S-CH(CH₃)CH₂- | 9 | 472 (M − OEt)/1.005 (min) |
| 230 | H | 9 | 397/0.836 (min) |

Reference Examples 231-237

The compounds indicated in the below-mentioned table (Reference Examples 231-237) were obtained by using the corresponding starting materials according to the similar reaction and treatment method to those described in Reference Example 174.

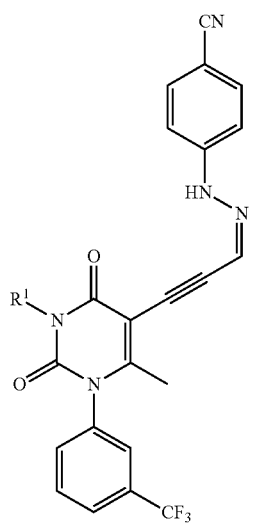

TABLE 31

| Ref. Ex. | R[1] | Measurement cond. | (LC-MS: [M + H]+/Rt) |
|---|---|---|---|
| 231 | CbzN-pyrrolidine | 9 | 641 (M + H)/1.17 (min) |
| 232 | CbzN-pyrrolidine (stereo) | 9 | 641 (M + H)/1.17 (min) |
| 233 | CbzN-piperidine (4-yl) | 9 | 655 (M + H)/1.16 (min) |
| 234 | CbzN-piperidine (3-yl) | 9 | 655 (M + H)/1.17 (min) |
| 235 | CbzN-piperidine (stereo) | 9 | 655 (M + H)/1.17 (min) |
| 236 | H₂NO₂S-CH₂CH(CH₃)- | 9 | 559 (M + H)/1.121 (min) |
| 237 | H | 9 | 438 (M + H)/1.066 (min) |

Reference Examples 238-239

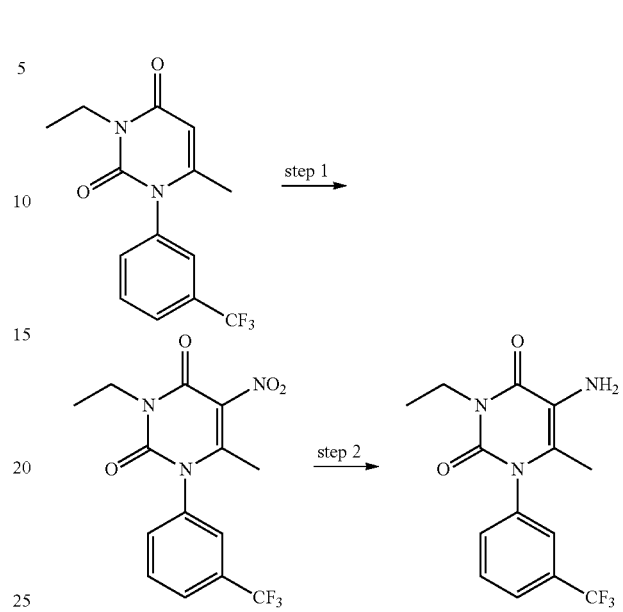

Step 1

Reference Example 238

The above-mentioned nitro compound was obtained by using the corresponding starting materials according to the similar reaction and treatment method to those described in Reference Example 192. UPLC/MS 344 (M+H)/0.987 min. (measurement condition 9)

Step 2

Reference Example 239

The above-mentioned amino compounds was obtained by using the corresponding starting materials according to the similar reaction and treatment method to those described in Reference Example 193. UPLC/MS 314 (M+H)/0.759 min. (measurement condition 9)

Reference Example 240

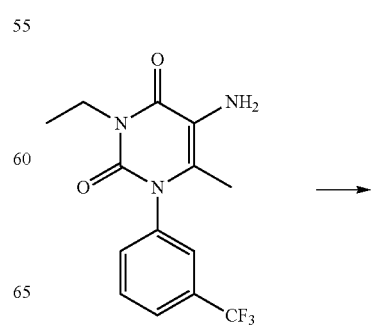

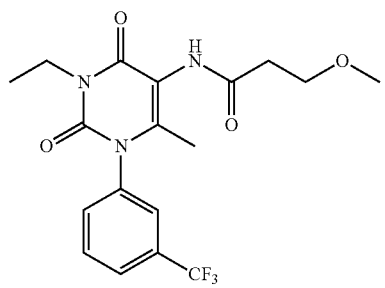

A solution of 5-amino-3-ethyl-6-methyl-1-(3-trifluoromethylphenyl)pyrimidin-2,4(1H,3H)-dione (prepared in Reference Example 239) (200 mg), 3-methoxypropionic acid (0.15 ml), HATU (487 mg), HOAT (174 mg) and diisopropylethyl amine (0.21 ml) in DMF (5.0 ml) was stirred at room temperature for two hours. To the reaction mixture was added water (10 ml) and the resulting mixture was extracted with ethyl acetate (10 ml×2). The organic layer was washed with water (10 ml) and saturated saline (10 ml), dried over anhydrous sodium sulfate and then concentrated under reduced pressure. The residue was purified by silica gel column chromatography (eluent: hexane/ethyl acetate) to afford the above-mentioned N-(3-ethyl-6-methyl-2,4-dioxo-1-(3-trifluoromethylphenyl)-1,2,3,4-tetrahydropyrimidin-5-yl)-3-methoxypropaneamide (222 mg). UPLC/MS 400 (M+H)/0.754 min. (measurement condition 9)

The compounds indicated in the below-mentioned table (Reference Examples 241-242) were obtained by using the corresponding starting materials according to the similar reaction and treatment method to those described in Reference Example 240.

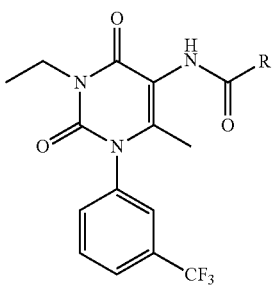

TABLE 32

| Ref. Ex. | R | Measurement cond. | (LC-MS: [M + H]+/Rt) |
|---|---|---|---|
| 241 | ~~~CO₂ᵗBu | 9 | 456 (M + H)/0.990 (min) |
| 242 | ⟨N-Me piperidinyl⟩ | 9 | 440 (M + H)/0.574 (min) |

Reference Examples 243-249

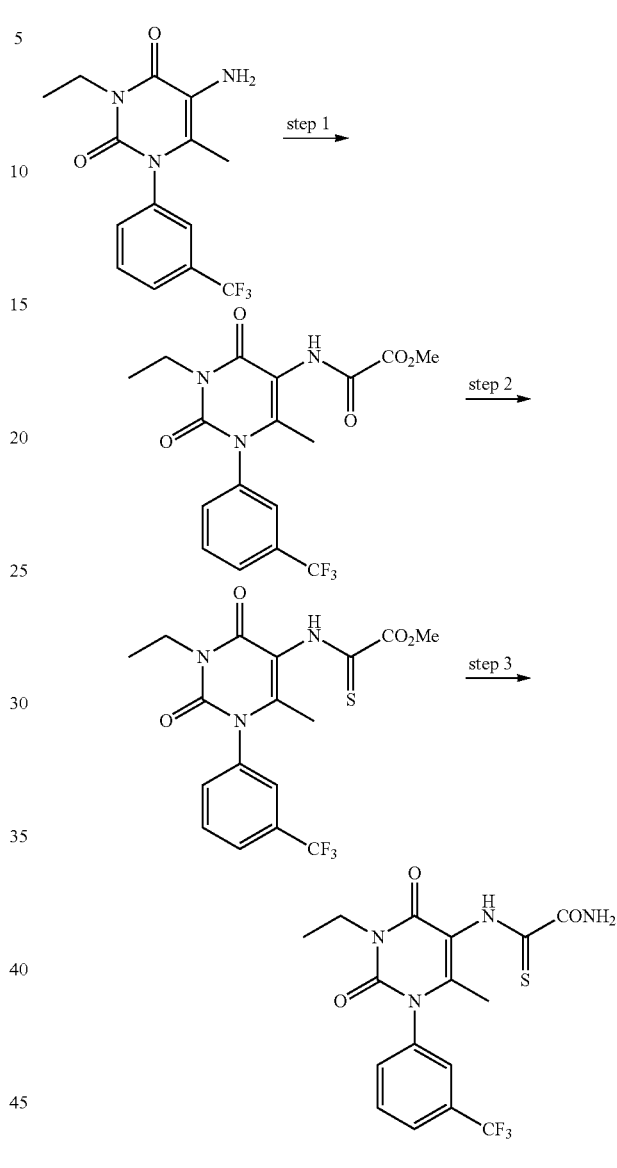

Step 1

Reference Example 243

The compound obtained in Reference Example 239 (316 mg) was dissolved in methylene chloride (10 ml) and thereto was added at 0° C. methyl chloroglyoxylate (0.31 ml) and the resulting mixture was stirred for twenty minutes. To the reaction solutions were added water (30 ml) and chloroform (30 ml×2) such that the intended products were extracted into an organic layer. The organic layer was washed with saturated saline (30 ml), dried over magnesium sulfate and then concentrated under reduced pressure. The residue was purified by silica gel column chromatography (eluent: chloroform/methanol) to afford the above-mentioned methyl 2-(3-ethyl-6-methyl-2,4-dioxo-1-(3-trifluoromethylphenyl)-1,2,3,4-tetrahydropyrimidin-5-yl)-2-oxoacetate (410 mg). UPLC/MS 400 (M+H)/0.77 min. (measurement condition 9)

Step 2

Reference Example 244

The compound obtained in Reference Example 243 (410 mg) was dissolved in toluene (10 ml) and thereto was added Lawesson's reagent (624 mg), and the resulting mixture was stirred at 80° C. for one hour. The precipitates were filtered and the filtrates were concentrated under reduced pressure, and thereto were then added water (30 ml) and ethyl acetate/hexane=2/1 (30 ml×2) such that the intended products were extracted into an organic layer. The organic layer was washed with saturated saline (30 ml), dried over magnesium sulfate and then concentrated under reduced pressure. The residue was purified silica gel column chromatography (eluent: hexane/ethyl acetate) to afford the above-mentioned methyl 2-(3-ethyl-6-methyl-2,4-dioxo-1-(3-trifluoromethylphenyl)-1,2,3,4-tetrahydropyrimidin-5-yl)-2-thioxo acetate (413 mg). UPLC/MS 416 (M+H)/0.89 min. (measurement condition 9)

The compounds indicated in the below-mentioned table (Reference Examples 245-247) were obtained by using the corresponding starting materials according to the similar reaction and treatment method to those described in Reference Example 244.

Reference Example 245

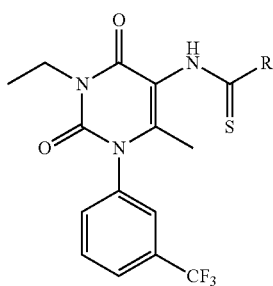

TABLE 33

| Ref. Ex. | R | Measurement cond. | (LC-MS: [M + H]+/Rt) |
|---|---|---|---|
| 245 | —CH₂—CO₂ᵗBu | 9 | 472 (M + H)/1.092 (min) |
| 246 | N-methylpiperidin-4-yl | 9 | 455 (M + H)/0.669 (min) |
| 247 | —CH₂CH₂—OMe | 9 | 416 (M + H)/0.880 (min) |

Step 3

Reference Example 248

The compound obtained in Reference Example 244 (549 mg) was dissolved in DMF (5 ml) and thereto was added 28% ammonia water (4.79 ml) and the resulting mixture was stirred for forty minutes. To the reaction solution were added ethyl acetate (15 ml) and 20% aqueous citric acid solution (15 ml) followed by an addition of further ethyl acetate (30 ml×2) such that the intended products were extracted into an organic layer. The organic layer was washed with saturated saline (30 ml), dried over magnesium sulfate and then concentrated under reduced pressure. The residue was purified by silica gel column chromatography (eluent: hexane/ethyl acetate) to afford the above-mentioned 2-(3-ethyl-6-methyl-2,4-dioxo-1-(3-trifluoromethylphenyl)-1,2,3,4-tetrahydropyrimidin-5-ylamino)-2-oxoacetamide (318 mg). UPLC/MS 401 (M+H)/0.82 min. (measurement condition 9)

Reference Example 249

The below-mentioned compound was obtained by using the corresponding starting materials according to the similar reaction and treatment method to those described in Reference Example 248.

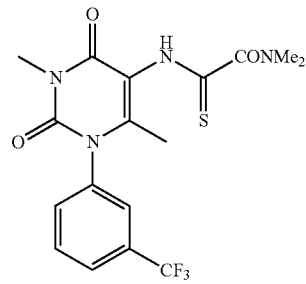

UPLC/MS 429 (M+H)/0.810 min. (measurement condition 9)

Reference Examples 250-254

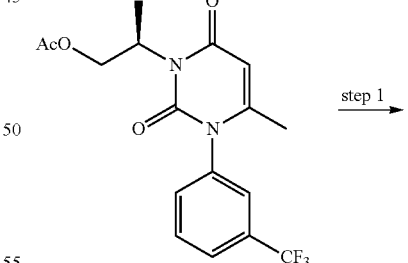

step 1

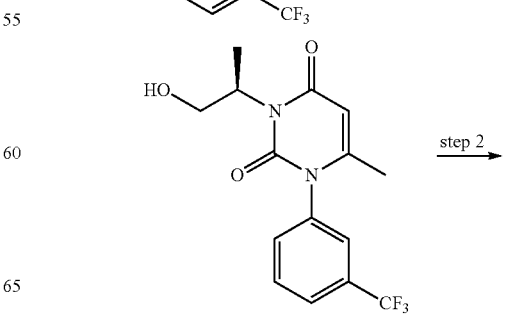

step 2

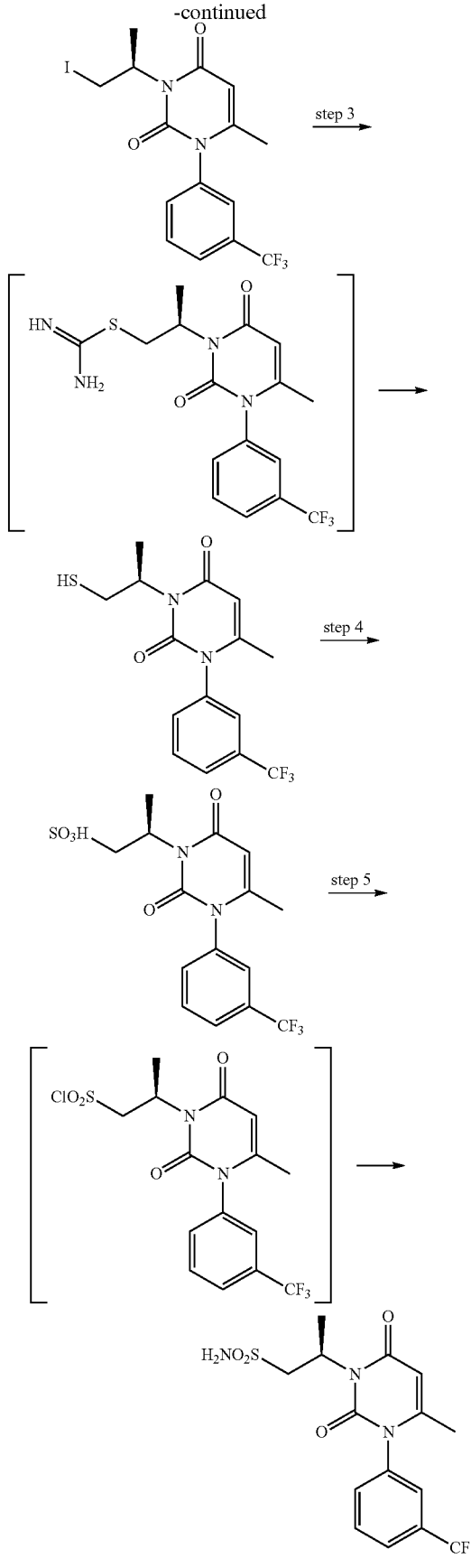

Step 1

Reference Example 250

To a solution of the compound obtained in Reference Example 49 (1.0 g) in ethanol (10 ml) was added 1N aqueous sodium hydroxide solution (5.4 ml) and the resulting mixture was stirred at room temperature for two hours. To the reaction mixture was added water (10 ml) and thereto was then added ethyl acetate (20 ml×2) such that the intended products were extracted into an organic layer. The organic layer was washed with water (10 ml) and saturated saline (10 ml), dried over anhydrous sodium sulfate and then concentrated under reduced pressure. The residue was purified by silica gel column chromatography (eluent: hexane/ethyl acetate) to afford the above-mentioned (R)-3-(1-hydroxypropan-2-yl)-6-methyl-1-(3-trifluoromethylphenyl)pyrimidin-2,4(1H,3H)-dione (880 mg). UPLC/MS 329 (M+H)/0.759 min (measurement condition 9)

Step 2

Reference Example 251

To a solution of the compound obtained in Reference Example 250 (2.0 g), imidazole (456 mg) and triphenylphosphine (1.7 g) in THF (30 ml) was added iodine (1.7 g) and the resulting mixture was stirred at room temperature for fifteen hours. To the reaction mixture was added 10% hypo water (30 ml) and thereto was then added ethyl acetate (20 ml×2) such that the intended products were extracted into an organic layer. The organic layer was washed with water (20 ml) and saturated saline (20 ml), dried over anhydrous sodium sulfate and then concentrated under reduced pressure. The residue was purified by silica gel column chromatography (eluent: hexane/ethyl acetate) to afford the above-mentioned (R)-3-(1-iodopropane-2-yl)-6-methyl-1-(3-trifluoromethylphenyl)pyrimidin-2,4(1H,3H)-dione (2.0 g). UPLC/MS 439 (M+H)/1.038 min. (measurement condition 9)

Step 3

Reference Example 252

To a solution of the compound obtained in Reference Example 251 (4.0 g) in acetone (50 ml) was added thiourea (929 mg) and the resulting mixture was stirred at 70° C. for two hours (note: it was confirmed a formation of (R)-2-(4-methyl-2,6-dioxo-3-(3-(trifluoromethyl)phenyl)-2,3-dihydropyrimidin-1(6H)-yl)propyl carbamidothioate of the above-mentioned intermediate: UPLC/MS 387 (M+H)/0.665 min). The reaction mixture was concentrated under reduced pressure and thereto were added sodium disulfite (1.7 g) and dichloromethane/water (50 ml/10 ml), and the resulting mixture was stirred with heating under reflux for one and a half hours. To the reaction mixture was added water (20 ml) and followed by an addition of ethyl acetate (30 ml×2) such that the intended products were extracted into an organic layer. The organic layer was washed with water (20 ml) and saturated saline (20 ml), dried over anhydrous sodium sulfate and then concentrated under reduced pressure to afford the above-mentioned (R)-3-(1-mercaptopropan-2-yl)-6-methyl-1-(3-trifluoromethylphenyl)pyrimidin-2,4(1H,3H)-dione (1.5 g). UPLC/MS 345 (M+H)/0.907 min. (measurement condition 9)

Step 4

Reference Example 253

To a solution of the compound obtained Reference Example 252 (3.0 g) in formic acid (20 ml) was added at 0° C. 30% aqueous hydrogen peroxide solution (0.98 ml) and the resulting mixture was stirred at room temperature for three hours. To the reaction mixture were added 10% hypo water (50 ml) and ethyl acetate (20 ml), and insoluble materials were then removed by filtration and the aqueous layer was washed with ethyl acetate (20 ml×2). To the aqueous layer was added chloroform/ethanol (10 ml/1.0 ml×10) such that the intended products were extracted into an organic layer, and the organic layer was dried over anhydrous sodium sulfate and then concentrated under reduced pressure to afford the above-mentioned (R)-2-(4-methyl-2,6-dioxo-3-(3-trifluoromethylphenyl)-2,3-dihydropyrimidin-1(6H)-yl)propane-1-sulfonic acid (1.2 g).

UPLC/MS 393 (M+H)/0.602 min. (measurement condition 9)

Step 5

Reference Example 254

To a solution of the compound prepared in Reference Example 253 (1.0 g) in acetonitrile (20 ml) was added phosphorus oxychloride (1.3 ml) and the resulting mixture was stirred at 60° C. for three hours (note: it was confirmed a formation of the above-mentioned intermediate, (R)-2-(4-methyl-2,6-dioxo-3-(3-(trifluoromethyl)phenyl)-2,3-dihydropyrimidin-1(6H)-yl)propane-1-sulfonylchloride; UPLC/MS 41.3 (M+H)/0.980 min). The reaction solution was cooled to 0° C. and thereto was added ammonia water (5.0 ml) dropwise and the resulting mixture was stirred for one hour. To the reaction mixture was added water (30 ml) and thereto was added ethyl acetate (20 ml×3) such that the intended products were extracted into an organic layer. The organic layer was washed with water (10 ml) and saturated saline (10 ml), dried on anhydrous sodium sulfate and then concentrated under reduced pressure. The residue was purified by silica gel column chromatography (eluent: hexane/ethyl acetate) to afford the above-mentioned (R)-2-(4-methyl-2,6-dioxo-3-(3-trifluoromethylphenyl)-2,3-dihydropyrimidin-1(6H)-yl)propane-1-sulfonamide (560 mg). UPLC/MS 392 (M+H)/0.753 min. (measurement condition 9)

Example 1

4-[5-[3,6-dimethyl-2,4-dioxo-1-(3-trifluoromethylphenyl)-1,2,3,4-tetrahydropyrimidin-5-yl]-1H-pyrazol-1-yl]benzonitrile

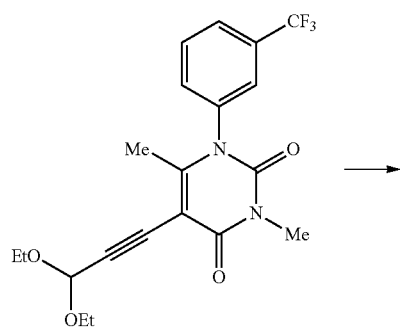

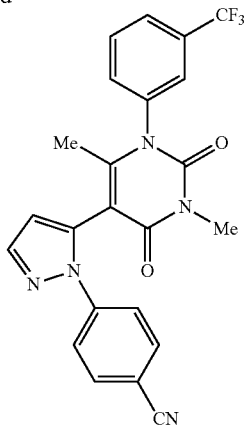

A solution of 5-(3,3-diethoxyprop-1-ynyl)-3,6-dimethyl-1-(3-trifluoromethylphenyl)-pyrimidin-2,4(1H,3H)-dione (prepared in Reference Example 61) and 4-cyanophenylhydrazine hydrochloride (27.9 mg) in N,N-dimethy formamide (2.0 ml) was stirred at 130° C. for seven hours. To the reaction mixture was added water (10 ml) and the resulting mixture was extracted with ethyl acetate (10 ml×2). The organic layer was washed with water (10 ml×2) and saturated saline (10 ml), dried over anhydrous sodium sulfate and then concentrated under reduced pressure. The residue was purified by silica gel column chromatography (eluent: hexane/ethyl acetate) to afford 4-[5-[3,6-dimethyl-2,4-dioxo-1-(3-trifluoromethylphenyl)-1,2,3,4-tetrahydropyrimidin-5-yl]-1H-pyrazol-1-yl]benzonitrile (17.9 mg).

$^1$H-NMR (CDCl$_3$: 300 MHz) (δ PPM):
1.63 (s, 1.5H), 1.68 (s, 1.5H), 3.30 (s, 1.5H), 3.35 (s, 1.5H), 6.46 (dd, 1H, J=7.5, 1.8 Hz), 7.30 (d, 0.5H, J=7.8 Hz), 7.38 (s, 0.5H), 7.48 (d, 0.5H, J=7.8 Hz), 7.55-7.59 (m, 2.5H), 7.63-7.79 (m, 4H), 7.80 (t, 1H, J=1.8 Hz)

Examples 2-18

The compounds indicated in the below-mentioned table (Examples 2-18) were prepared by using the corresponding starting materials according to the similar reaction and treatment method to those described in Example 1.

Example 2

4-[5-[6-methyl-2,4-dioxo-3-propyl-1-(3-trifluoromethylphenyl)-1,2,3,4-tetrahydropyrimidin-5-yl]-1H-pyrazol-1-yl]benzonitrile;

Example 3

2-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]ethyl acetate ester;

Example 4

3-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]propanoic acid ethyl ester;

Example 5

4-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]butanoic acid ethyl ester;

Example 6

2-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]acetic acid benzyl ester;

Example 7

4-[5-[3-(2,2-dimethoxyethyl)-6-methyl-2,4-dioxo-1-(3-trifluoromethylphenyl)-1,2,3,4-tetrahydropyrimidin-5-yl]-1H-pyrazol-1-yl]benzonitrile;

Example 8 tert-butyl 5-[5-[1-(4-cyanophenyl)-1H-pyrazol-5-yl]-4-methyl-2,6-dioxo-3-(3-trifluoromethyl)-2,3-dihydropyrimidine-1(6H)-yl]pentylcarbamate;

Example 9

4-[5-[3-(4-methoxybenzyl)-6-methyl-2,4-dioxo-1-(3-trifluoromethylphenyl)-1,2,3,4-tetrahydropyrimidin-5-yl]-1H-pyrazol-1-yl]benzonitrile;

Example 10

3-[5-[1-(4-cyanophenyl)-1H-pyrazol-5-yl]-3,6-dimethyl-2,4-dioxo-3,4-dihydropyrimidin-1(2H)-yl]benzonitrile;

Example 11

4-[5-[1-(3-fluorophenyl)-3,6-dimethyl-2,4-dioxo-1,2,3,4-tetrahydropyrimidin-5-yl]-1H-pyrazol-1-yl]benzonitrile;

Example 12

4-[5-[1-(3-methoxyphenyl)-3,6-dimethyl-2,4-dioxo-1,2,3,4-tetrahydropyrimidin-5-yl]-1H-pyrazol-1-yl]benzonitrile;

Example 13

4-[5-[1-(4-fluoro-3-trifluorophenyl)-3,6-dimethyl-2,4-dioxo-1,2,3,4-tetrahydropyrimidin-5-yl]-1H-pyrazol-1-yl]benzonitrile;

Example 14

4-[5-(1-phenyl-3,6-dimethyl-2,4-dioxo-1,2,3,4-tetrahydropyrimidin-5-yl)-1H-pyrazol-1-yl]benzonitrile;

Example 15

4-[5-[3,6-dimethyl-2,4-dioxo-1-(2-trifluoromethylphenyl)-1,2,3,4-tetrahydropyrimidin-5-yl]-1H-pyrazol-1-yl]benzonitrile;

Example 16

4-[5-[3,6-dimethyl-2,4-dioxo-1-(4-trifluoromethylphenyl)-1,2,3,4-tetrahydropyrimidin-5-yl]-1H-pyrazol-1-yl]benzonitrile;

Example 17

4-[5-[1-(3-chlorophenyl)-3,6-dimethyl-2,4-dioxo-1,2,3,4-tetrahydropyrimidin-5-yl]-1H-pyrazol-1-yl]benzonitrile;

Example 18

4-[5-[1-(3-nitrophenyl)-3,6-dimethyl-2,4-dioxo-1,2,3,4-tetrahydropyrimidin-5-yl]-1H-pyrazol-1-yl]benzonitrile

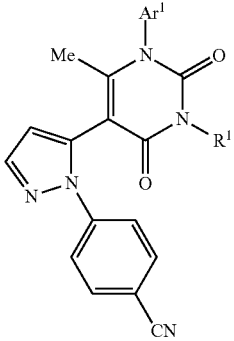

TABLE 34

| Ex. | Ar¹ | R¹ | Measurement cond. | ¹H-NMR (δ PPM) |
|---|---|---|---|---|
| 2 | 3-CF₃-phenyl | -(CH₂)₂-Me | 1 | 0.81 (t, 1.5H, J = 7.4 Hz), 0.82 (t, 1.5H, J = 7.4 Hz), 1.50-1.58 (m, 2H), 1.63 (s, 1.5H), 1.67 (s, 1.5H), 3.76-3.85 (m, 2H), 6.40 (d, 0.5H, J = 7.7 Hz), 6.41 (d, 0.5H, J = 7.7 Hz), 7.28 (d, 0.5H, J = 7.5 Hz), 7.36 (s, 0.5H), 7.41 (d, 0.5H, J = 7.5 Hz), 7.50-7.54 (m, 3.5H), 7.58-7.75 (m, 4H) |
| 3 | 3-CF₃-phenyl | -CH₂-CO₂Et | 1 | 1.23 (t, 3H, J = 6.0 Hz), 1.61 (s, 1.5H), 1.66 (s, 1.5H), 4.18 (dq, 2H, J = 6.9, 1.8 Hz), 4.65 (t, 2H, J = 3.0 Hz), 6.47 (dd, 1H, J = 7.5, 2.1 Hz), 7.31-7.38 (m, 0.5H), 7.41-7.47 (m, 1.5H), 7.52-7.66 (m, 4H), 7.70-7.77 (m, 3H) |

TABLE 34-continued

| Ex. | Ar¹ | R¹ | Measurement cond. | ¹H-NMR (δ PPM) |
|---|---|---|---|---|
| 4 | 3-CF₃-phenyl | ~CH₂CH₂CH₂CO₂Et | 1 | 1.18 (t, 3H, J = 3.0 Hz), 1.55 (s, 1.5H), 1.60 (s, 1.5H), 2.48-2.56 (m, 2H), 3.99-4.07 (m, 2H), 4.13-4.27 (m, 2H), 6.42 (dd, 2H, J = 6.0, 3.0 Hz), 7.21-7.75 (m, 9H) |
| 5 | 3-CF₃-phenyl | ~CH₂CH₂CH₂CH₂CO₂Et | 1 | 1.17 (t, 3H, J = 3.0 Hz), 1.59 (s, 1.5H) 1.63 (s, 1.5H), 1.83-1.92 (m, 2H), 2.26 (t, 2H, J = 6.0 Hz), 3.86-4.00 (m, 4H), 6.42 (dd, 1H, J = 6.0, 3.0 Hz), 7.25-7.75 (m, 9H) |
| 6 | 3-CF₃-phenyl | ~CH₂CO₂Bn | 1 | 1.60 (s, 1.5H), 1.65 (s, 1.5H), 4.67-4.82 (m, 2H), 5.12-5.22 (m, 2H), 6.47 (d, 0.5H, J = 7.0 Hz), 6.48 (d, 0.5H, J = 7.0 Hz), 7.30-7.38 (m, 6.5H), 7.45 (d, 0.5H, J = 8.1 Hz), 7.52-7.58 (m, 2H), 7.62-7.69 (m, 3H), 7.76 (d, 1H, J = 8.1 Hz), 7.79 (t, 1H, J = 1.8 Hz) |

TABLE 35

| Ex. | Ar¹ | R¹ | Measurement cond. | ¹H-NMR (δ PPM) |
|---|---|---|---|---|
| 7 | 3-CF₃-phenyl | ~CH₂CH(OMe)₂ | 1 | 1.60 (s, 1.5H), 1.65 (s, 1.5H), 3.20 (s, 1.5H), 3.21 (s, 1.5H), 3.26 (s, 1.5H), 3.28 (s, 1.5H), 3.94-4.12 (m, 2H), 4.64 (dd, 1H, J = 10.5, 4.8 Hz), 6.41 (d, 0.5H, J = 8.3 Hz), 6.42 (d, 0.5H, J = 8.3 Hz), 7.28 (d, 0.5H, J = 7.9 Hz), 7.36 (s, 0.5H), 7.41 (d, 0.5H, J = 7.9 Hz), 7.49 (s, 0.5H), 7.51-7.56 (m, 3H), 7.58-7.75 (m, 4H) |
| 8 | 3-CF₃-phenyl | ~(CH₂)₅NHC(O)OC(Me)₃ | 1 | 1.23-1.52 (m, 13H), 1.64-1.70 (m, 2H), 2.16 (s, 3H), 3.04-3.11 (m, 2H), 3.96 (t, 2H, J = 7.7 Hz), 4.51 (brs, 1H), 7.06 (d, 1H, J = 8.8 Hz), 7.21 (s, 1H), 7.44-7.58 (m, 4H), 7.65-7.79 (m, 3H), 8.53 (s, 1H) |
| 9 | 3-CF₃-phenyl | ~CH₂-(4-OMe-phenyl) | 1 | 1.69 (s, 1.5H), 1.73 (s, 1.5H), 3.80 (s, 3H), 4.93 (dd, 1H, J = 13.5, 4.2 Hz) 5.02 (dd 1H, J = 13.5, 7.8 Hz), 6.44 (dd, 1H, J = 9.0, 3.0 Hz), 6.79 (d, 2H, 9.0), 7.26-7.29 (m, 2H), 7.51-7.55 (m, 3H), 7.62-7.68 (m, 4H), 7.74-7.76 (m, 1H), 7.78 (t, 1H, J = 1.5 Hz) |
| 10 | 3-CN-phenyl | ~CH(Me) | 4 | 1.58 (s, 1.5H), 1.66 (s, 1.5H), 3.28 (s, 1.5H), 3.30 (s, 1.5H), 6.38 (d, 0.5H, J = 1.8 Hz), 6.42 (d, 0.5H, J = 1.8 Hz), 7.27-7.32 (s, 0.5H), 7.43-7.55 (m, 3.5H), 7.57-7.72 (m, 3H), 7.73-7.77 (m, 2H) |
| 11 | 3-F-phenyl | ~CH(Me) | 1 | 1.64 (s, 1.5H), 1.68 (s, 1.5H), 3.33 (s, 1.5H), 3.35 (s, 1.5H), 6.45 (dd, 1H, J = 4.2, 1.8 Hz), 6.83-6.89 (m, 1H), 6.99-7.07 (m, 1H), 7.21 (d, 1H, J = 8.1 Hz), 7.49 (t, 1H, J = 6.0 Hz), 7.57 (d, 2H, J = 8.4 Hz), 7.71 (d, 1H, J = 1.8 Hz), 7.74 (d, 1H, J = 2.1 Hz), 7.79 (t, 1H, J = 1.5 Hz) |

TABLE 36

| Ex. | Ar¹ | R¹ | Measurement cond. | ¹H-NMR (δ PPM) |
|---|---|---|---|---|
| 12 | 3-OMe-phenyl | Me | 4 | 1.60 (s, 1.5H), 1.61 (s, 1.5H), 3.30 (s, 3H), 3.75 (s, 1.5 H), 3.77 (s, 1.5 H), 6.39-6.41 (m, 1H), 6.51 (t, 0.5H, J = 2.2 Hz), 6.56-6.58 (m, 0.5H), 6.71 (t, 0.5H, J = 2.3 Hz), 6.75-6.78 (m, 0.5H), 6.92-6.97 (m, 1H), 7.32-7.38 (m, 1H), 7.50-7.54 (m, 2H), 7.65-7.68 (m, 2H), 7.74 (d, 1H, J = 1.8 Hz) |
| 13 | 4-F-3-CF₃-phenyl | Me | 4 | 1.60 (s, 1.5H), 1.65 (s, 1.5H), 3.28 (s, 1.5H), 3.30 (s, 1.5H), 6.39-6.42 (m, 1H), 7.23-7.36 (m, 2H), 7.39-7.45 (m, 0.5H), 7.47-7.54 (m, 2.5H), 7.65-7.71 (m, 2H), 7.74-7.76 (m, 1H) |
| 14 | phenyl | Me | 4 | 1.57 (s, 3H), 3.30 (s, 3H), 6.41 (d, 1H, J = 1.8 Hz), 6.97-7.03 (m, 1H), 7.16-7.22 (m, 1H), 7.38-7.55 (m, 5H), 7.64-7.68 (m, 2H), 7.74 (d, 1H, J = 1.8 Hz) |
| 15 | 2-CF₃-phenyl | Me | 1 | 1.60 (s, 3H), 3.28 (s, 2H), 3.29 (s, 1H), 6.40 (d, 0.75H, J = 1.8 Hz), 6.41 (d, 0.25H, J = 1.8 Hz), 7.36 (d, 1H, J = 8.4 Hz), 7.48-7.53 (m, 2H), 7.58-7.79 (m, 6H) |
| 16 | 4-CF₃-phenyl | Me | 1 | 1.63 (s, 3H), 3.35 (s, 3H), 6.46 (d, 1H, J = 1.8 Hz), 7.39 (t, 1H, J = 1.8 Hz), 7.58 (d, 2H, J = 6.0 Hz), 7.71-7.80 (m, 6H) |
| 17 | 3-Cl-phenyl | Me | 1 | 1.65 (s, 1.5H), 1.68 (s, 1.5H), 3.33 (s, 1.5H), 3.34 (s, 1.5H), 6.45 (dd, 1H, J = 7.8, 1.8 Hz), 7.04 (d, 0.5H, J = 8.4 Hz), 7.19-7.22 (m, 0.5H), 7.27-7.35 (m, 1H) 7.38-7.43 (m, 1H), 7.54-7.64 (m, 3H), 7.70-7.73 (m, 2H), 7.79 (t, 1H, J = 1.5 Hz) |
| 18 | 3-NO₂-phenyl | Me | 1 | 1.62 (s, 1.5H), 1.68 (s, 1.5H), 3.28 (s, 1.5H), 3.30 (s, 1.5H), 6.39 (d, 0.5H, J = 1.7 Hz), 6.43 (d, 0.5H, J = 1.7 Hz), 7.40-7.43 (m, 0.5H), 7.50-7.60 (m, 2.5H), 7.65-7.76 (m, 4H), 8.01 (t, 0.5H, J = 2.1 Hz), 8.13 (t, 0.5H, J = 2.1 Hz), 8.30-8.34 (m, 1H) |

Reference Example 206

In the preparation of Example 18, a purification by silica gel column chromatography (eluent: hexane/ethyl acetate) gave a regioisomer of the compound of Example 18, 4-[4-[3,6-dimethyl-1-(3-nitrophenyl)-2,4-dioxo-1,2,3,4-tetrahydropyrimidin-5-yl]-1H-pyrazol-1-yl]benzonitrile.

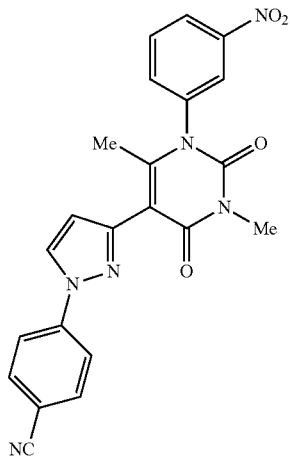 [SMILES: Cc1c(-c2ccn(-c3ccc(C#N)cc3)n2)c(=O)n(C)c(=O)n1-c1cccc([N+](=O)[O-])c1]

$^1$H-NMR (CDCl$_3$: 300 MHz) (δ PPM):
1.96 (s, 1.5H), 1.98 (s, 1.5H), 3.40 (s, 3H), 6.85 (d, 0.5H, J=3.0 Hz), 6.89 (d, 0.5H, J=3.0 Hz), 6.97-7.03 (m, 2H), 7.17-7.21 (m, 1H), 7.49-7.52 (m, 2H), 7.56-7.60 (m, 0.5H), 7.64-7.67 (m, 0.5H), 7.74 (d, 0.5H, J=8.8 Hz), 7.79 (d, 0.5H, J=8.8 Hz), 8.14 (t, 0.5H, J=2.1 Hz), 8.19 (t, 0.5H, J=2.1 Hz), 8.38-8.41 (m, 1H)

Examples 20-23

The compounds indicated in the below-mentioned table (Examples 20-33) were obtained by using the corresponding starting materials according to the similar reaction and treatment method to those described in Example 1.

Example 20

3,6-dimethyl-5-(1-phenyl-1H-pyrazol-5-yl)-1-(3-trifluoromethylphenyl)pyrimidin-2,4(1H,3H)-dione;

Example 21

5-[1-(-chlorophenyl)-1H-pyrazol-5-yl]-3,6-dimethyl-1-(3-trifluoromethylphenyl)pyrimidin-2,4(1H,3H)-dione;

Example 22

5-[1-(4-fluorophenyl)-1H-pyrazol-5-yl]-3,6-dimethyl-1-(3-trifluoromethylphenyl)pyrimidin-2,4(1H,3H)-dione;

Example 23

5-[5-[3,6-dimethyl-2,4-dioxo-1-(3-trifluoromethylphenyl)-1,2,3,4-tetrahydropyrimidin-5-yl]-1H-pyrazol-1-yl]picolinonitrile

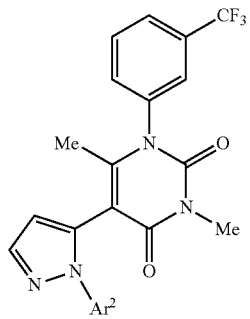

TABLE 37

| Ex. | Ar² | Measurement cond. | $^1$H-NMR (δ PPM) (or LC-MS: [M + H]+/Rt) |
|---|---|---|---|
| 20 | phenyl | 1 | 1.40 (s, 1.5H), 1.44 (s, 1.5H), 3.32 (s, 3H), 6.40 (dd, 1H, J = 1.8, 0.9 Hz), 7.08 (d, 1H, J = 7.8 Hz), 7.27-7.41 (m, 5H), 7.48-7.60 (m, 2H), 7.67 (d, 1H, J = 8.1 Hz), 7.71 (d, 1H, J = 1.8 Hz) |
| 21 | 4-chlorophenyl | 1 | 1.51 (s, 1.5H), 1.52 (s, 1.5H), 3.30 (s, 1.5H), 3.31 (s, 1.5H), 6.39 (dd, 1H, J = 3.6, 2.1 Hz), 7.24-7.28 (m, 1H), 7.30-7.37 (m, 4H), 7.48 (s, 1H), 7.61 (d, 1H, J = 8.4 Hz), 7.68-7.71 (m, 2H) |
| 22 | 4-fluorophenyl | 1 | 1.50 (s, 1.5H), 1.51 (s, 1.5H), 3.29 (s, 1.5H), 3.30 (s, 1.5H), 6.37 (dd, 1H, J = 3.3, 1.8 Hz), 6.77-7.09 (m, 4H), 7.28-7.33 (m, 1H), 7.37-7.48 (m, 1H), 7.54-7.69 (m, 3H) |

TABLE 37-continued

| Ex. | Ar² | Measurement cond. | ¹H-NMR (δ PPM) (or LC-MS: [M + H]+/Rt) |
|---|---|---|---|
| 23 | (5-(2-cyanopyridyl)) | 8 | 453 (MH+)/2.21 (min) |

Examples 24-27

The compounds indicated in the below-mentioned table (Examples 24-27) were obtained by using the starting materials according to the similar reaction and treatment method to those described in Example 1.

Example 24

5-(1-(5-bromopyridin-2-yl)-1H-pyrazol-5-yl)-3-isopropyl-6-methyl-1-(3-(trifluoromethyl)phenyl)pyrimidin-2,4(1H,3H)-dione;

Example 25

5-(5-(3-isopropyl-6-methyl-2,4-dioxo-1-(3-(trifluoromethyl)phenyl)-1,2,3,4-tetrahydropyrimidin-5-yl)-1H-pyrazol-1-yl)nicotinonitrile;

Example 26

4-(5-(3-methyl-2,4-dioxo-1-(3-(trifluoromethyl)phenyl)-1,2,3,4-tetrahydropyrimidin-5-yl)-1H-pyrazol-1-yl)benzonitrile;

Example 27 tert-butyl 2-(5-(1-(4-cyanophenyl)-1H-pyrazol-5-yl)-2,6-dioxo-3-(3-(trifluoromethyl)phenyl)-2,3-dihydropyrimidin-1(6H)-yl)propionate

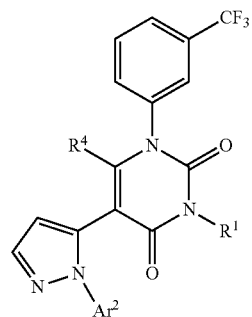

TABLE 38

| Ex. | R¹ | R⁴ | Ar² | Measurement cond. | ¹H-NMR (δ PPM) |
|---|---|---|---|---|---|
| 24 | CH(Me)Me (isopropyl) | Me | 5-bromopyridin-2-yl | 1 | 1.33 (d, 3H, J = 6.9 Hz), 1.37 (d, 3H, J = 6.9 Hz), 1.71 (s, 1.5H), 1.72 (s, 1.5H), 4.99-5.09 (m, 1H), 6.34 (d, 0.5H, J = 3.7 Hz), 6.35 (d, 0.5H, J = 1.7 Hz), 7.45 (t, 1H, J = 8.3 Hz), 7.52 (s, 1H), 7.62 (t, 1H, J = 7.8 Hz), 7.68-7.71 (m, 2H), 7.83-7.85 (m, 2H), 8.23-8.24 (m, 0.5H), 8.27-8.28 (m, 0.5H) |
| 25 | CH(Me)Me (isopropyl) | Me | 5-(2-cyanopyridyl) | 1 | 1.30 (dd, 3H, J = 7.0, 2.0 Hz), 1.37 (d, 3H, J = 6.8 Hz), 1.80 (s, 1.5H), 1.82 (s, 1.5H), 4.96-5.06 (m, 1H), 6.46 (d, 0.5H, J = 1.7 Hz), 6.48 (d, 0.5H, J = 1.7 Hz), 7.45-7.70 (m, 4H), 7.76-7.83 (m, 2H), 8.08-8.14 (m, 1H), 8.74 (d, 0.5H, J = 2.4 Hz), 8.78 (d, 0.5H, J = 2.4 Hz) |
| 26 | CH(Me)CO₂ᵗBu | H | 4-cyanophenyl | 1 | 1.35 (s, 9H), 1.45 (d, 3, J = 7.0 Hz), 5.29 (q, 1H, J = 7.0 Hz), 6.48 (d, 1H, J = 1.8 Hz), 7.44 (s, 1H), 7.48-7.54 (m, 2H), 7.56-7.62 (m, 3H), 7.65-7.70 (m, 4H) |

TABLE 38-continued

| Ex. | R[1] | R[4] | Ar[2] | Measurement cond. | $^1$H-NMR (δ PPM) |
|---|---|---|---|---|---|
| 27 | ⟋Me | H | ⟋–C₆H₄–CN | 1 | 3.30 (s, 3H), 6.49 (d, 1H, J = 1.8 Hz), 7.39 (s, 1H), 7.46-7.48 (m, 2H), 7.55-7.62 (m, 3H), 7.66-7.70 (m, 4H) |

Examples 28-29

The compounds indicated in the below-mentioned table (Examples 28-29) were obtained by using the corresponding starting materials according to the similar reaction and treatment method to those described in Example 1.

Example 28

N'-[5-[1-(4-cyanophenyl)-1H-pyrazol-5-yl]-1-methyl-2,6-dioxo-3-(3-trifluoromethylphenyl)-1,2,3,6-tetrahydropyrimidin-4-yl]-N,N-dimethylformimidamide;

Example 29

N'-[5-[1-(4-cyanophenyl)-1H-pyrazol-5-yl]-3-(3-nitrophenyl)-2,6-dioxo-1-propyl-1,2,3,6-tetrahydropyrimidin-4-yl]-N,N-dimethylformimidamide

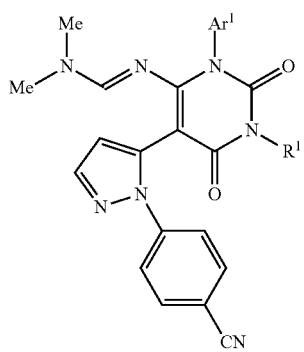

Example 30

Tert-butyl 5-[5-[1-(4-cyanophenyl)-1H-pyrazol-5-yl]-4-methyl-2,6-dioxo-3-(3-trifluoromethyl)-2,3-dihydropyrimidine-1(6H)-yl]pentylcarbamate

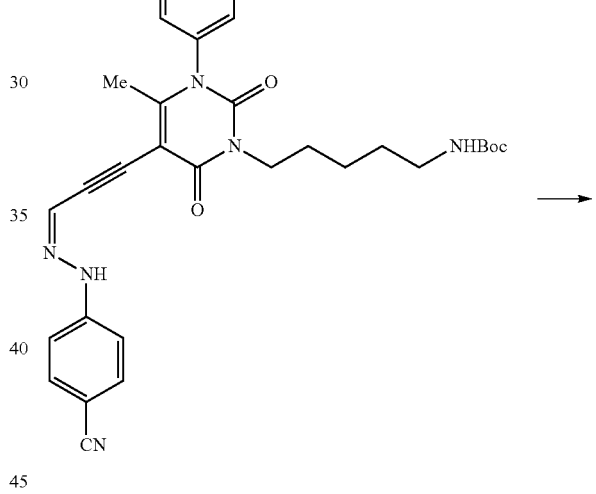

TABLE 39

| Ex. | Ar[1] | R[1] | Measurement cond. | $^1$H-NMR (δ PPM) |
|---|---|---|---|---|
| 28 | 3-CF₃-C₆H₄– | ⟋Me | 1 | 2.20 (s, 3H), 2.63 (s, 3H), 3.35 (s, 3H), 6.47 (s, 1H), 6.75 (s, 1H), 7.13-7.17 (m, 1H), 7.25-7.35 (m, 1H), 7.45 (t, 1H, J = 7.8 Hz), 7.52-7.56 (m, 3H), 7.65-7.69 (m, 3H) |
| 29 | 3-NO₂-C₆H₄– | ⟋⟋Me | 1 | 0.85 (t, 3H, J = 7.4 Hz), 1.58-1.68 (m, 2H), 2.24 (brs, 3H), 2.65 (s, 3H), 3.88 (t, 2H, J = 7.4 Hz), 6.82 (s, 1H), 7.39-7.69 (m, 9H), 8.15 (dd, 1H, J = 9.2, 2.2 Hz) |

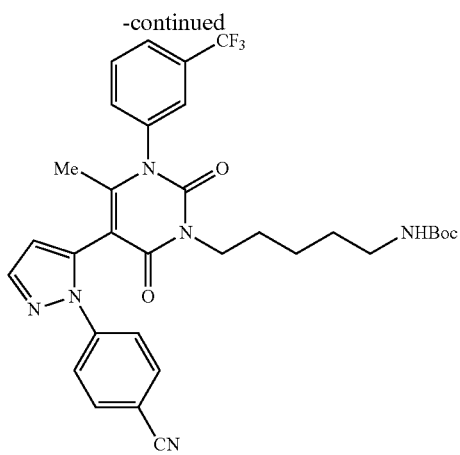

A solution of tert-butyl 5-[5-[3-[2-(4-cyanophenyl)hydrazono]prop-1-ynyl]-4-methyl-2,6-dihydro-3-(3-trifluorophenyl)-2,3-dihydropyrimidin-1(6H)-yl]pentylcarbamate (prepared in Reference Example 163) (23.7 mg) in N,N-dimethyformamide (1.0 ml) was stirred at 120° C. for two hours and then at 150° C. for two hours. To the reaction mixture was added water (10 ml) and the resulting mixture was extracted with ethyl acetate (10 ml×2). The organic layer was washed with water (10 ml) and saturated saline (10 ml), dried over anhydrous sodium sulfate and then concentrated under reduced pressure. The residue was purified by silica gel column chromatography (eluent: hexane/ethyl acetate) to afford tert-butyl 5-[5-[1-(4-cyanophenyl)-1H-pyrazole-5-yl]-4-methyl-2,6-dioxo-3-(3-trifluoromethyl)-2,3-dihydropyrimidine-1(6H)-yl]pentylcarbamate (14.1 mg).

$^1$H-NMR: the same as those of Example 8

Examples 31-40

The compounds indicated in the below-mentioned table (Examples 31-40) were obtained by using the corresponding starting materials according to the similar reaction and treatment method to those described in Example 30.

Example 31

4-[5-[3,6-dimethyl-2,4-dioxo-1-(3-trifluoromethylphenyl)-1,2,3,4-tetrahydropyrimidin-5-yl]-1H-pyrazol-1-yl]benzonitrile;

Example 32

3-[5-[1-(4-cyanophenyl)-1H-pyrazol-5-yl]-3,6-dimethyl-2,4-dioxo-3,4-dihydropyrimidin-1(2H)-yl]benzoic acid methyl ester;

Example 33

4-[5-[3,6-dimethyl-2,4-dioxo-1-(6-trifluoromethylpyridine-2-yl)-1,2,3,4-tetrahydropyrimidin-5-yl]-1H-pyrazol-1-yl]benzonitrile;

Example 34

4-[5-[1-(3-bromophenyl)-3,6-dimethyl-2,4-dioxo-1,2,3,4-tetrahydropyrimidin-5-yl]-1H-pyrazol-1-yl]benzonitrile;

Example 35

3-[5-[3,6-dimethyl-2,4-dioxo-1-(3-trifluoromethylphenyl)-1,2,3,4-tetrahydropyrimidin-5-yl]-1H-pyrazol-1-yl]benzonitrile;

Example 36

4-[5-[3,6-dimethyl-2,4-dioxo-1-(3-trifluoromethylphenyl)-1,2,3,4-tetrahydropyrimidin-5-yl]-1H-pyrazol-1-yl]-3-(methylthio)benzonitrile;

Example 37

4-(5-(3,6-dimethyl-2,4-dioxo-1-m-tolyl-1,2,3,4-tetrahydropyrimidin-5-yl)-1H-pyrazol-1-yl)benzonitrile;

Example 38

4-(5-(1-(3-tert-butylphenyl)-3,6-dimethyl-2,4-dioxo-1,2,3,4-tetrahydropyrimidin-5-yl)-1H-pyrazol-1-yl)benzonitrile;

Example 39

4-(5-(3,6-dimethyl-1-(3-(methylsulfonyl)phenyl)-2,4-dioxo-1,2,3,4-tetrahydropyrimidin-5-yl)-1H-pyrazol-1-yl)benzonitrile;

Example 40

5-(1-(4-methoxyphenyl)-1H-pyrazol-5-yl)-3,6-dimethyl-1-(3-(trifluoromethyl)phenyl)pyrimidin-2,4(1H,3H)-dione;

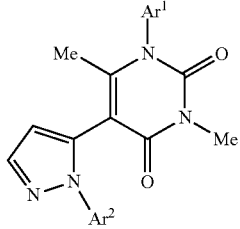

TABLE 40

| Ex. | Ar$^1$ | Ar$^2$ | Measurement cond. | $^1$H-NMR (δ PPM) |
|---|---|---|---|---|
| 31 | ![3-CF3-phenyl] | ![4-CN-phenyl] | 1 | those as the same as Ex. 1 |

TABLE 40-continued

| Ex. | Ar¹ | Ar² | Measurement cond. | ¹H-NMR (δ PPM) |
|---|---|---|---|---|
| 32 | 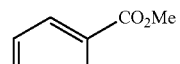 |  | 1 | 1.63 (s, 1.5H), 1.65 (s, 1.5H), 3.34 (s, 1.5H), 3.35 (s, 1.5H), 3.92 (s, 1.5H), 3.94 (s, 1.5H), 6.64 (dd, 1H, J = 5.1, 1.8 Hz), 7.27-7.30 (m, 0.5H), 7.44-7.47 (m, 0.5H), 7.55-7.64 (m, 3H), 7.70-7.76 (m, 2.5H), 7.79 (t, 1H, J = 2.1 Hz), 7.93 (t, 0.5H, J = 1.8 Hz), 8.17 (d, 1H, J = 7.8 Hz) |
| 33 | 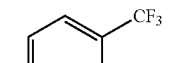 |  | 1 | 1.66 (s, 3H), 3.28 (s, 3H), 6.43 (d, 1H, J = 1.5 Hz), 7.52-7.57 (m, 3H), 7.70 (d, 2H, J = 8.1 Hz), 7.75 (d, 1H, J = 1.5 Hz), 7.79 (d, 1H, J = 7.8 Hz), 8.07 (t, 1H, J = 8.1 Hz) |
| 34 | 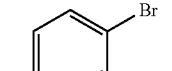 |  | 1 | 1.64 (s, 1.5H), 1.68 (s, 1.5H), 3.32 (s, 1.5H), 3.34 (s, 1.5H), 6.45 (dd, 1H, J = 4.8, 1.8 Hz), 6.98 (dt, 0.5H, J = 7.2, 1.8 Hz), 7.12-7.17 (m, 1H), 7.27 (t, 0.5H, J = 1.5 Hz), 7.45-7.47 (m, 2H), 7.57-7.61 (d, 2H, J = 8.7, 1.5 Hz), 7.69-7.72 (m, 2H), 7.79 (t, 1H, J = 1.5 Hz) |
| 35 | 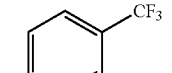 | 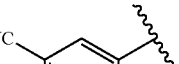 | 1 | 1.61 (s, 1.5H), 1.63 (s, 1.5H), 3.29 (s, 3H), 6.40 (dd, 1H, J = 4.2, 1.8 Hz), 7.31 (d, 1H, J = 9.6 Hz), 7.50-7.54 (m, 1H), 7.59-7.74 (m, 7H) |
| 36 | 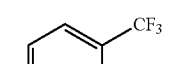 |  | 1 | 1.76 (d, 3H, J = 3.0 Hz), 2.36 (d, 3H, J = 4.2 Hz), 3.22 (s, 3H), 6.39 (d, 1H, J = 4.2 Hz), 7.25-7.33 (m, 1H), 7.39-7.46 (m, 4H), 7.59-7.62 (m, 1H), 7.71 (d, 1H, J = 7.8 Hz), 7.78 (d, 1H, J = 1.8 Hz) |

TABLE 41

| Ex. | Ar¹ | Ar² | Measurement cond. | ¹H-NMR (δ PPM) |
|---|---|---|---|---|
| 37 | 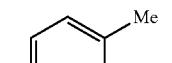 |  | 1 | 1.59 (d, 3H, J = 6.3 Hz), 2.33 (d, 3H, J = 2.7 Hz), 3.29 (d, 3H, J = 2.7 Hz), 6.40 (d, 1H, J = 2.2 Hz), 6.80 (d, 1H, J = 9.9 Hz), 6.98 (d, 1H, J = 9.9 Hz), 7.22 (d, 1H, J = 7.8 Hz), 7.33 (q, 1H, J = 7.5 Hz), 7.50-7.54 (m, 2H), 7.64-7.68 (m, 2H), 7.74 (d, 1H, J = 1.8 Hz) |

TABLE 41-continued

| Ex. | Ar¹ | Ar² | Measurement cond. | ¹H-NMR (δ PPM) |
|---|---|---|---|---|
| 38 | (3-(2-methyl-2-propyl)phenyl) | (4-cyanophenyl) | 1 | 1.23 (s, 4.5H), 1.26 (s, 4.5H), 1.50 (s, 1.5H), 1.56 (s, 1.5H), 3.30 (d, 3H, J = 3.9 Hz), 6.42 (d, 1H, J = 1.8 Hz), 6.81 (ddd, 0.5H, J = 7.8, 2.1, 1.2 Hz), 6.86 (t, 0.5H, J = 2.1 Hz), 6.99 (ddd, 0.5H, J = 7.5, 2.1, 1.2 Hz), 7.16 (t, 0.5H, J = 2.1 Hz), 7.33-7.35 (m, 2H), 7.52 (t, 2H, J = 6.6 Hz), 7.67 (t, 2H, J = 7.8 Hz), 7.74 (dd, 1H, J = 1.8, 0.9 Hz) |
| 39 | (3-(methylsulfonyl)phenyl) | (4-cyanophenyl) | 1 | 1.59 (s, 1H), 1.67 (s, 1H), 1.80 (d, 1H, J = 0.9 Hz), 3.10 (d, 3H, J = 2.1 Hz), 3.30 (d, 3H, J = 1.2 Hz), 6.38 (d, 0.5H, J = 1.8 Hz), 6.42 (d, 0.5H, J = 1.5 Hz), 7.34-7.42 (m, 1H), 7.46-7.83 (m, 6H), 7.79 (t, 0.5H, J = 1.8 Hz), 7.83 (t, 0.5H, J = 1.8 Hz), 8.00-8.03 (m, 1H) |
| 40 | (3-(trifluoromethyl)phenyl) | (4-methoxyphenyl) | 1 | 1.44 (s, 1.5H), 1.47 (s, 1.5H), 3.31 (s, 3H), 3.78 (s, 3H), 6.36 (dd, 1H, J = 1.8 Hz), 6.60-7.01(m, 5H), 7.29 (d, 1H, J = 9.0 Hz), 7.38-7.66 (m, 2H), 7.70 (d, 1H, J = 2.1 Hz) |

Examples 41-49

The compounds indicated in the below-mentioned table (Examples 41-49) were obtained by using the corresponding starting materials according to the similar reaction and treatment method to those described in Example 30.

Example 41

4-(5-(3-ethyl-6-methyl-2,4-dioxo-1-(3-(trifluoromethyl)phenyl)-1,2,3,4-tetrahydropyrimidin-5-yl)-1H-pyrazol-1-yl)benzonitrile;

Example 42

4-(5-(3-isopropyl-6-methyl-2,4-dioxo-1-(3-(trifluoromethyl)phenyl)-1,2,3,4-tetrahydropyrimidin-5-yl)-1H-pyrazol-1-yl)benzonitrile;

Example 43

4-(5-(3-cyclopropyl-6-methyl-2,4-dioxo-1-(3-(trifluoromethyl)phenyl)-1,2,3,4-tetrahydropyrimidin-5-yl)-1H-pyrazol-1-yl)benzonitrile;

Example 44

4-(5-(3-cyclobutyl-6-methyl-2,4-dioxo-1-(3-(trifluoromethyl)phenyl)-1,2,3,4-tetrahydropyrimidin-5-yl)-1H-pyrazol-1-yl)benzonitrile;

Example 45 benzyl 3-(5-(1-(4-cyanophenyl)-1H-pyrazol-5-yl)-4-methyl-2,6-dioxo-3-(3-(trifluoromethyl)phenyl)-2,3-dihydropyrimidin-1(6H)-yl)azetidine-1-carboxylate;

Example 46

(S)-ethyl 2-(5-(1-(4-bromophenyl)-1H-pyrazol-5-yl)-4-methyl-2,6-dioxo-3-(3-(trifluoromethyl)phenyl)-2,3-dihydropyrimidin-1(6H)-yl)propanoate;

Example 47 acetic acid (R)-2-(5-(1-(4-cyanophenyl)-1H-pyrazol-5-yl)-4-methyl-2,6-dioxo-3-(3-(trifluoromethyl)phenyl)-2,3-dihydropyrimidin-1(6H)-yl)propyl ester;

Example 48

(S)-4-(5-(6-methyl-2,4-dioxo-3-(1-phenylethyl)-1-(3-(trifluoromethyl)phenyl)-1,2,3,4-tetrahydropyrimidin-5-yl)-1H-pyrazol-1-yl)benzonitrile;

Example 49 acetic acid 2-(5-(1-(4-cyanophenyl)-1H-pyrazol-5-yl)-4-methyl-2,6-dioxo-3-(3-(trifluoromethyl)phenyl)-2,3-dihydropyrimidin-1(6H)-yl)ethyl ester

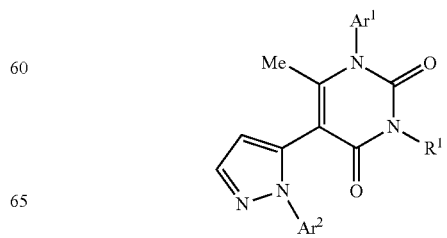

TABLE 42

| Ex. | Ar¹ | Ar² | R¹ | Measurement cond. | ¹H-NMR (δ PPM) |
|---|---|---|---|---|---|
| 41 | 3-CF₃-phenyl | 4-CN-phenyl | Et | 1 | 1.17 (t, 3H, J = 6.9 Hz), 1.66 (s, 1.5H), 1.71 (s, 1.5H), 3.91-4.00 (m, 2H), 6.45 (d, 0.5H, J = 1.8 Hz), 6.76 (d, 0.5H, J = 2.1 Hz), 7.33 (d, 1H, J = 8.1H), 7.41 (s, 0.5H), 7.47 (d, 0.5H, J = 8.1 Hz), 7.55-7.59 (m, 2H), 7.63-7.67 (m, 1H), 7.70-7.75 (m, 3H), 7.79 (t, 1H, J = 1.5 Hz) |
| 42 | 3-CF₃-phenyl | 4-CN-phenyl | $^i$Pr | 1 | 1.28-1.37 (m, 6H), 1.61 (brs, 2H), 1.65 (brs, 1H), 5.02 (sept, 1H, J = 6.9 Hz), 6.40 (dd, 1H, J = 8.1, 1.8 Hz), 7.33 (d, 1H, J = 8.1 Hz), 7.41 (d, 1H, J = 1/1.7 Hz), 7.50-7.57 (m, 2H), 7.60-7.71 (m, 4H), 7.73 (t, 1H, J = 1.5 Hz) |
| 43 | 3-CF₃-phenyl | 4-CN-phenyl | $^c$Pr | 1 | 0.45-0.60 (m, 1H), 0.74-0.76 (m, 1H), 0.99-1.07 (m, 2H), 1.61 (s, 1.5H), 1.66 (s, 1.5H), 2.58-2.67 (m, 1H), 6.39 (dd, 1H, J = 6.3, 1.8 Hz), 7.27 (d, 0.5H, J = 7.8 Hz), 7.36 (s, 0.5H), 7.40 (d, 0.5H, J = 7.8 Hz), 7.50-7.54 (m, 2.5H), 7.58-7.74 (m, 5H) |
| 44 | 3-CF₃-phenyl | 4-CN-phenyl | cyclobutyl | 1 | 1.62 (s, 1.5H), 1.67 (s, 1.5H), 1.70-1.85 (m, 2H), 2.14-2.26 (m, 2H), 2.65-2.82 (m, 2H), 5.09-5.17 (m, 1H), 6.44 (dd, 1H, J = 7.2, 1.8 Hz), 7.32 (d, 0.5H, J = 7.2 Hz), 7.40 (s, 0.5H), 7.46 (d, 0.5H, J = 8.1 Hz), 7.54-7.60 (m, 2.5H), 7.63-7.76 (m, 4H), 7.79 (t, 1H, J = 1.8 Hz) |

TABLE 43

| Ex. | Ar¹ | Ar² | R¹ | Measurement cond. | ¹H-NMR (δ PPM) |
|---|---|---|---|---|---|
| 45 | 3-CF₃-phenyl | 4-CN-phenyl | 1-Cbz-azetidin-3-yl | 1 | 1.60 (s, 1.5H), 1.64 (s, 1.5H), 4.14-4.19 (m, 2H), 4.23-4.35 (m, 2H), 5.00 (d, 2H, J = 2.1 Hz), 5.19-5.27 (m, 1H), 6.40 (dd, 1H, J = 6.0, 1.8 Hz), 7.22-7.27 (m, 6H), 7.33 (s, 0.5H), 7.41 (d, 0.5H, J = 7.5 Hz), 7.48-7.51 (m, 2H), 7.59-7.75 (m, 5H) |
| 46 | 3-CF₃-phenyl | 4-Br-phenyl | CH(Me)CO₂Et | 1 | 1.15-1.20 (m, 3H), 1.47-1.55 (m, 6H), 4.05-4.18 (m, 2H), 5.35-5.46 (m, 1H), 6.39-6.42 (m, 1H), 7.21-7.27 (m, 3H), 7.38-7.61 (m, 4H), 7.67-7.69 (m, 2H) |
| 47 | 3-CF₃-phenyl | 4-CN-phenyl | CH(Me)CH₂OAc | 1 | 1.36-1.48 (m, 3H), 1.63 (dd, 3H, J = 13.5, 3.0 Hz), 1.95-2.02 (m, 3H), 4.06-4.27 (m, 1H), 4.54-4.71 (m, 1H), 5.15 (brs, 1H), 6.43 (d, 0.25H, J = 1.8 Hz), 6.46 (t, 0.5H, J = 1.8 Hz), 6.49 (d, 0.25H, J = 1.8 Hz), 7.27-7.36 (m, 1H), 7.41-7.50 (m, 1H), 7.57-7.79 (m, 7H) |
| 48 | 3-CF₃-phenyl | 4-CN-phenyl | CH(Me)Ph | 4 | 1.56-1.59 (m, 1.5H), 1.65-1.69 (m, 1.5H), 1.83 (d, 1.5H, J = 3.6 Hz), 1.89 (d, 1.5H, J = 4.5 Hz), 5.90 (q, 1H, J = 6.9 Hz), 6.57 (d, 0.5H, J = 2.7 Hz), 6.57 (d, 0.5H, J = 3.2 Hz), 7.05-7.09 (m, 1H), 7.12-7.17 (m, 1H), 7.19-7.29 (m, 3H), 7.62-7.69 (m, 1H), 7.73-8.10 (m, 8H) |

TABLE 43-continued

| Ex. | Ar¹ | Ar² | R¹ | Measurement cond. | ¹H-NMR (δ PPM) |
|---|---|---|---|---|---|
| 49 | 3-CF₃-phenyl | 4-CN-phenyl | -CH(CH₃)CH₂OAc | 3 | 1.57 (s, 1.5H), 1.59 (s, 1.5H), 1.94 (s, 1.5H), 1.95 (s, 1.5H), 4.09-4.14 (m, 1H), 4.18-4.24 (m, 2H), 4.37-4.46 (m, 1H), 6.45 (d, 0.5H, J = 1.5Hz), 6.48 (d, 0.5H, J = 9.6 Hz), 7.28 (d, 0.5H, J = 9.6 Hz), 7.37 (s, 0.5H), 7.47 (d, 0.5H, J = 7.5 Hz), 7.54 (s, 0.5H), 7.63-7.68 (m, 3H), 7.72-7.76 (m, 3H), 7.80 (t, 1H, J = 1.8 Hz) |

Examples 50-56

The compounds indicated in the below-mentioned table (Examples 50-56) were obtained by using the corresponding starting materials according to the similar reaction and treatment method to those described in Example 30.

Example 50

4-(5-(6-ethyl-3-methyl-2,4-dioxo-1-(3-(trifluoromethyl)phenyl)-1,2,3,4-tetrahydropyrimidin-5-yl)-1H-pyrazol-1-yl)benzonitrile;

Example 51

4-(5-(6-isopropyl-3-methyl-2,4-dioxo-1-(3-(trifluoromethyl)phenyl)-1,2,3,4-tetrahydropyrimidin-5-yl)-1H-pyrazol-1-yl)benzonitrile;

Example 52

4-(5-(6-(dimethylamino)-3-methyl-2,4-dioxo-1-(3-(trifluoromethyl)phenyl)-1,2,3,4-tetrahydropyrimidin-5-yl)-1H-pyrazol-1-yl)benzonitrile;

Example 53

4-(5-(2,4-dioxo-1-(3-(trifluoromethyl)phenyl)-1,2,3,4-tetrahydropyrimidin-5-yl)-1H-pyrazol-1-yl)benzonitrile;

Example 54

4-(5-(3-isopropyl-2,4-dioxo-1-(3-(trifluoromethyl)phenyl)-1,2,3,4-tetrahydropyrimidin-5-yl)-1H-pyrazol-1-yl)benzonitrile;

Example 55

(R)-4-(5-(3-(1-hydroxypropan-2-yl)-6-methyl-2,4-dioxo-1-(3-(trifluoromethyl)phenyl)-1,2,3,4-tetrahydropyrimidin-5-yl)-1H-pyrazol-1-yl)benzonitrile;

Example 56

4-(5-(3-isopropyl-1-(2-methyl-5-(trifluoromethyl)phenyl)-2,4-dioxo-1,2,3,4-tetrahydropyrimidin-5-yl)-1H-pyrazol-1-yl)benzonitrile

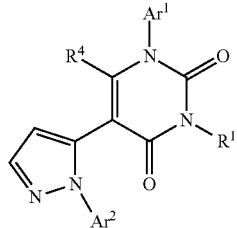

TABLE 44

| Ex. | Ar¹ | Ar² | R¹ | R⁴ | Measurement cond. | ¹H-NMR (δ PPM) |
|---|---|---|---|---|---|---|
| 50 | 3-CF₃-phenyl | 4-CN-phenyl | Me | Et | 4 | 0.68 (t, 1.5H, J = 7.6 Hz), 0.70 (t, 1.5H, J = 7.5 Hz), 1.98-2.07 (m, 1H), 2.09-2.19 (m, 1H), 3.37 (s, 1.5H), 3.38 (s, 1.5H), 6.49 (d, 0.5H, J = 7.2 Hz), 6.50 (d, 0.5H, J = 7.2 Hz), 7.33-7.36 (m, 0.5H), 7.39 (s, 0.5H), 7.55-7.58 (m, 0.5H), 7.63-7.70 (m, 3H), 7.70-7.80 (m, 3.5H), 7.82-7.84 (m, 1H) |
| 51 | 3-CF₃-phenyl | 4-CN-phenyl | Me | ⁱPr | 4 | 0.57 (t, 3H, J = 7.8 Hz), 0.88 (t, 3H, J = 7.0 Hz), 2.50-2.58 (m, 1H), 3.39 (s, 1.5H), 3.40 (s, 1.5H), 6.47 (d, 0.5H, 4.3 Hz), 6.48 (d, 0.5H, J = 4.3 Hz), 7.35-7.40 (m, 0.5H), 7.44 (s, 0.5H), 7.52-7.60 (m, 0.5H), 7.64 (s, 0.5H), 7.66-7.68 (m, 3H), 7.70-7.82 (m, 3H), 7.82-7.83 (m, 1H) |

TABLE 44-continued

| Ex. | Ar¹ | Ar² | R¹ | R⁴ | Measurement cond. | ¹H-NMR (δ PPM) |
|---|---|---|---|---|---|---|
| 52 | 3-CF₃-phenyl | 4-CN-phenyl | Me | NMe₂ | 4 | 1.88 (s, 6H), 3.41 (s, 3H), 6.51 (s, 1H), 7.44-7.66 (m, 2H), 7.61 (t, 1H, J = 8.0 Hz), 7.66 (d, 1H, J = 8.1 Hz), 7.70-7.77 (m, 4H), 7.81-7.84 (m, 1H) |

TABLE 45

| Ex. | Ar¹ | Ar² | R¹ | R⁴ | Measurement cond. | ¹H-NMR (δ PPM) |
|---|---|---|---|---|---|---|
| 53 | 3-CF₃-phenyl | 4-CN-phenyl | H | H | 4 | 6.59 (d, 1H, J = 1.8 Hz), 7.49 (s, 1H), 7.56 (s, 1H), 7.56 (d, 1H, J = 8.0 Hz), 7.62-7.70 (m, 3H), 7.74-7.79 (m, 4H), 8.31 (s, 1H) |
| 54 | 3-CF₃-phenyl | 4-CN-phenyl | ⁱPr | H | 1 | 1.37 (d, 6H, J = 6.9 Hz), 5.08 (quin, 1H, J = 6.9 Hz), 6.51 (d, 1H, J = 1.5 Hz), 7.46 (s, 1H), 7.55-7.67 (m, 5H), 7.71-7.74 (m, 4H) |
| 55 | 3-CF₃-phenyl | 4-CN-phenyl | CH(Me)CH₂OH | Me | 1 | 1.30-1.37 (m, 3H), 1.66 (d, 1.5H, J = 1.8 Hz), 1.70 (d, 1.5H, J = 1.8 Hz), 3.71-3.81 (m, 1H), 3.92-4.00 (m, 1H), 5.10 (brs, 1H). 6.43-6.45 (m, 1H), 7.26-7.30 (m, 1H), 7.49-7.59 (m, 3H), 7.64-7.80 (m, 5H) |
| 56 | 2-Me-5-CF₃-phenyl | 4-CN-phenyl | ⁱPr | H | 4 | 1.41 (d, 6H, J = 6.9 Hz), 2.26 (s, 3H), 5.12 (sept, 1H, J = 6.9 Hz), 6.53 (d, 1H, J = 1.8 Hz), 7.29 (s, 1H), 7.47 (s, 1H), 7.50 (d, 1H, J = 8.1 Hz), 7.61-7.67 (m, 3H), 7.72-7.77 (m, 3H) |

Example 57

4-[5-[6-Amino-1-(3-nitrophenyl)-2,4-dioxo-3-propyl-1,2,3,4-tetrahydropyrimidin-5-yl]-1H-pyrazol-1-yl]benzonitrile

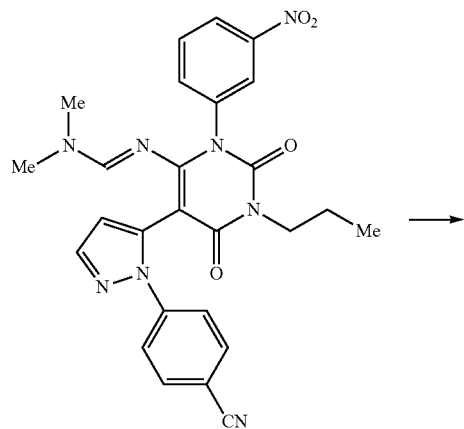

→

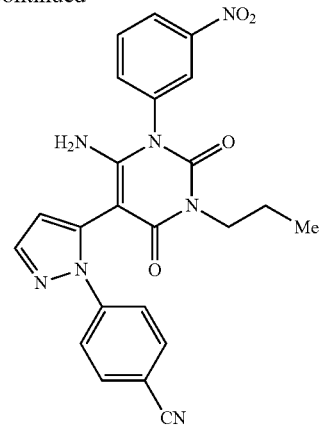

To a solution of N'-[5-[1-(4-cyanophenyl)-1H-pyrazol-5-yl]-3-(3-nitrophenyl)-2,6-dioxo-1-propyl-1,2,3,6-tetrahydropyrimidin-4-yl]-N,N-dimethylformimidamide (prepared in Example 29) (11.0 mg) in ethanol (1.0 ml) was added 1N hydrochloric acid (2.0 ml) and the resulting mixture was stirred with heating under reflux for six hours. The reaction mixture was concentrated under reduced pressure, and weakly basified with aqueous sodium hydroxide solution, and thereto was added water and the resulting mixture was extracted with ethyl acetate (10 ml×2). The organic layer was washed with saturated saline (10 ml), dried over anhydrous sodium sulfate and then concentrated under reduced pressure. The residue was purified by silica gel column chromatography (eluent: chloroform/methanol) to afford 4-[5-[6-amino-1-(3-nitrophenyl)-2,4-dioxo-3-propyl-1,2,3,4-tetrahydropyrimidin-5-yl]-1H-pyrazol-1-yl]benzonitrile (7.0 mg).

¹H-NMR (CDCl₃: 300 MHz) (δ PPM):

0.77 (t, 1.5H, J=7.4 Hz), 0.79 (t, 1.5H, J=7.4 Hz), 1.48-1.52 (m, 2H), 3.64-3.82 (m, 2H), 4.37 (s, 1H), 4.41 (s, 1H), 6.47 (d, 1H, J=9.4 Hz), 7.38-7.76 (m, 7H), 8.18 (brs, 0.5H), 8.25 (brs, 0.5H), 8.37 (brd, 1H, J=7.9 Hz)

Example 58

4-[5-[6-Amino-3-methyl-2,4-dioxo-1-(3-trifluoromethylphenyl)-1,2,3,4-tetrahydropyrimidin-5-yl]-1H-pyrazol-1-yl]benzonitrile

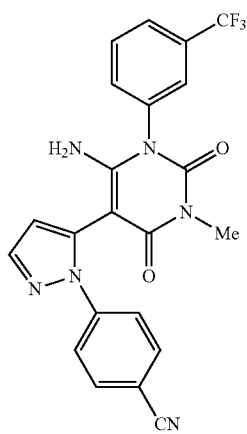 [SMILES: Cn1c(=O)c(-c2ccnn2-c2ccc(C#N)cc2)c(N)n(-c2cccc(C(F)(F)F)c2)c1=O]

The above-mentioned compound was obtained by using the corresponding starting materials according to the similar reaction and treatment method to those described in Example 57.

¹H-NMR (CDCl₃: 300 MHz) (δ PPM):

3.21 (s, 1.5H), 3.22 (s, 1.5H), 4.27 (s, 1H), 4.32 (s, 1H), 6.47 (d, 1H, J=5.3 Hz), 7.43-7.81 (m, 9H)

Example 59

4-(3-(3-Isopropyl-6-methyl-2,4-dioxo-1-(3-(trifluoromethyl)phenyl)-1,2,3,4-tetrahydropyrimidin-5-yl)pyridin-2-yl)benzonitrile

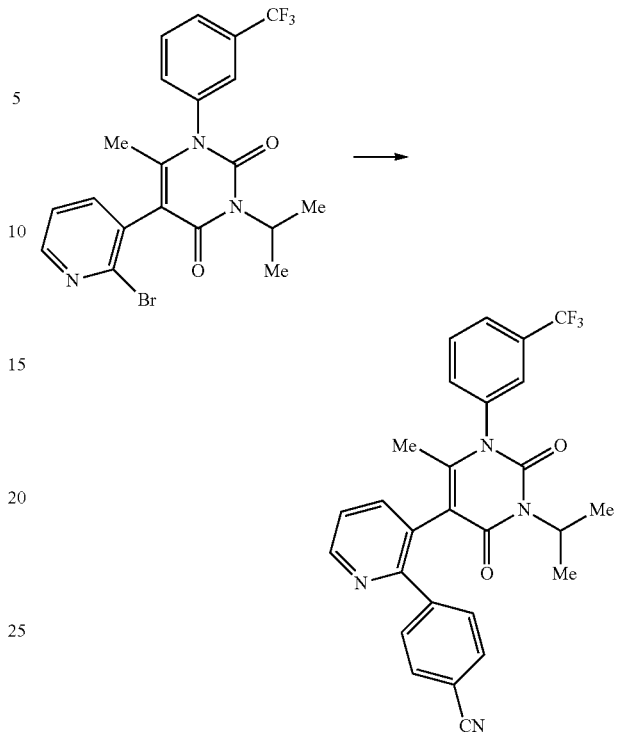

5-(2-Bromopyridin-3-yl)-3-isopropyl-6-methyl-1-(3-(trifluoromethyl)phenyl)pyrimidin-2,4(1H,3H)-dione (prepared in Reference Example 189) (132 mg) and 4-cyanophenylboronic acid (166 mg) were dissolved in 1,4-dioxane (10 ml). Thereto were added under nitrogen atmosphere water (1 ml), sodium carbonate (239 mg) and tetrakis(triphenylphosphine)palladium (33 mg) and the resulting mixture was stirred with heating under reflux for one and a half hours. The reaction mixture was cooled to room temperature, and thereto was then water and the resulting mixture was extracted with ethyl acetate (50 ml). The organic layer was washed with saturated saline (50 ml), dried over anhydrous magnesium sulfate and then concentrated under reduced pressure. The residue was purified by silica gel column chromatography (eluent: firstly hexane/ethyl acetate, secondly chloroform/methanol) to afford 4-(3-(3-isopropyl-6-methyl-2,4-dioxo-1-(3-(trifluoromethyl)phenyl)-1,2,3,4-tetrahydropyrimidin-5-yl)pyridin-2-yl)benzonitrile (118 mg).

¹H-NMR (400 MHz, DMSO-d₆) (δ PPM):

1.13 (d, 3H, J=6.9 Hz), 1.24 (dd, 3H, J=4.8, 6.8 Hz), 1.56 (s, 1.5H), 1.60 (s, 1.5H), 4.78-4.88 (m, 1H), 7.50-7.56 (m, 1H), 7.60-7.67 (m, 2.5H), 7.75 (s, 0.5H), 7.78-7.83 (m, 2.5H), 7.87-7.91 (m, 3H), 7.94 (s, 0.5H), 8.71 (dd, 1H, J=0.6, 4.7 Hz)

Examples 60-61

The compounds indicated in the below-mentioned table (Examples 60-61) were obtained by using the corresponding starting materials according to the similar reaction and treatment method to those described in Example 59.

Example 60

2-[3,6-dimethyl-2,4-dioxo-1-(3-trifluoromethylphenyl)-1,2,3,4-tetrahydropyrimidin-5-yl]biphenyl-4-carbonitrile;

Example 61

4-[3-[3,6-dimethyl-2,4-dioxo-1-(3-trifluoromethylphenyl)-1,2,3,4-tetrahydropyrimidin-5-yl]-pyridin-2-yl]benzonitrile

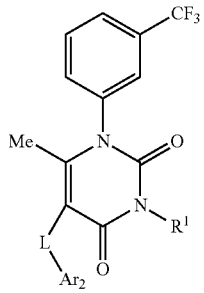

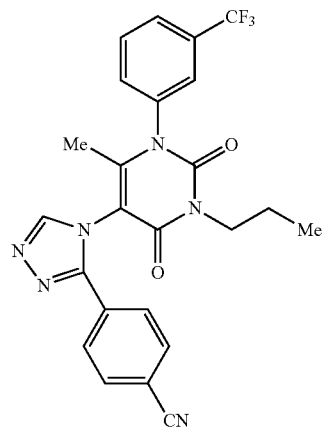

TABLE 46

| Ex. | L—Ar² | R¹ | Measurement cond. | ¹H-NMR (δ PPM) |
|---|---|---|---|---|
| 60 | biphenyl-CN | Me | 4 | 1.39 (s, 1.5H), 1.40 (s, 1.5H), 3.38 (s, 1.5H), 3.39 (s, 1.5H), 6.98 (s, 1H), 7.34-7.41 (m, 4H), 7.45-7.53 (m, 3H), 7.58-7.70 (m, 4H) |
| 61 | pyridyl-phenyl-CN | Me | 1 | 1.29 (s, 1.5H), 1.31 (s, 1.5H), 3.35 (s, 1.5H), 3.36 (s, 1.5H), 6.95 (brs, 1H), 7.35-7.39 (m, 2H), 7.46 (brs, 0.5H), 7.52-7.61 (m, 3H), 7.64-7.69 (m, 4H), 8.69 (d, 1H, J = 5.0 Hz) |

Example 62

4-[4-[6-Methyl-2,4-dioxo-3-propyl-1-(3-trifluoromethylphenyl)-1,2,3,4-tetrahydropyrimidin-5-yl]-4H-1,2,4-triazol-3-yl]benzonitrile

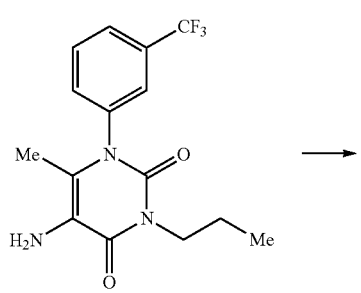 →

A solution of 4-cyanobenzohydrazide (46.0 mg) and dimethylformamide dimethylacetal (110 μl) in N,N-dimethyl formamide (2.0 ml) was stirred at 50° C. for thirty minutes and then cooled to room temperature, and thereto were added 5-amino-6-methyl-3-propyl-1-(3-trifluoromethylphenyl)pyrimidin-2,4(1H,3H)-dione (prepared in Reference Example 193) (20.0 mg) and acetic acid (0.5 ml) and the resulting mixture was stirred at 130° C. for eight hours. To the reaction mixture was added water (10 ml) and the resulting mixture was extracted with ethyl acetate (10 ml×2). The organic layer was washed with water (10 ml×2) and saturated saline (20 ml), dried over anhydrous sodium sulfate and then concentrated under reduced pressure. The residue was purified by silica gel column chromatography (eluent: chloroform/methanol) to afford 4-[4-[6-methyl-2,4-dioxo-3-propyl-1-(3-trifluoromethylphenyl)-1,2,3,4-tetrahydropyrimidin-5-yl]-4H-1,2,4-triazol-3-yl]benzonitrile (7.8 mg).

¹H-NMR (CDCl₃: 300 MHz) (δ PPM):
0.95 (t, 3H, J=8.5 Hz), 1.59 (s, 1.5H), 1.62 (s, 1.5H), 1.66-1.74 (m, 2H), 3.93-4.00 (m, 2H), 7.30 (d, 0.5H, J=6.0

Hz), 7.38 (s, 0.5H), 7.49 (d, 0.5H, J=6.0 Hz), 7.59 (s, 0.5H), 7.66-7.82 (m, 5H), 8.26 (d, 1H, J=5.5 Hz)

Examples 63-64

The compound indicated in the below-mentioned table (Examples 63-64) were prepared by using the starting materials according to the similar reaction and treatment method to those described in Example 62.

Example 63

4-(4-(3-isopropyl-2,4-dioxo-1-(3-(trifluoromethyl)phenyl)-1,2,3,4-tetrahydropyrimidin-5-yl)-5-methyl-4H-1,2,4-triazol-3-yl)benzonitrile;

Example 64

4-(4-(3-isopropyl-2,4-dioxo-1-(3-(trifluoromethyl)phenyl)-1,2,3,4-tetrahydropyrimidin-5-yl)-4H-1,2,4-triazol-3-yl)benzonitrile;

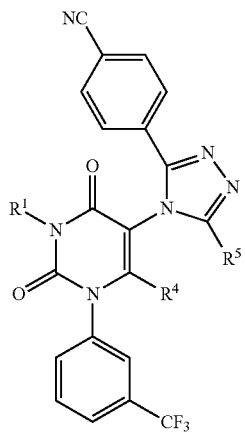

TABLE 47

| Ex. | R¹ | R⁴ | R⁵ | Measurement cond. | ¹H-NMR (δ PPM) |
|---|---|---|---|---|---|
| 63 | $^i$Pr | H | ⸺Me | 4 | 1.51 (d, 3H, J = 6.8 Hz), 1.52 (d, 3H, J = 6.8 Hz), 2.45 (s, 3H), 5.22 (sept, 1H, J = 6.9 Hz), 7.49 (d, 1H, J = 7.9 Hz), 7.54 (s, 1H), 7.64-7.70 (m, 4H), 7.73-7.77 (m, 3H) |
| 64 | $^i$Pr | H | H | 1 | 1.47 (d, 6H, J = 7.0 Hz), 5.13-5.23 (m, 1H), 7.48-7.55 (m, 3H), 7.65 (t, 1H, J = 7.5 Hz), 7.72 (s, 1H), 7.75-7.78 (m, 4H), 8.30 (s, 1H) |

Example 65

4-(4-(3-Isopropyl-6-methyl-2,4-dioxo-1-(3-(trifluoromethyl)phenyl)-1,2,3,4-tetrahydropyrimidin-5-yl)-4H-1,2,4-triazol-3-yl)benzonitrile

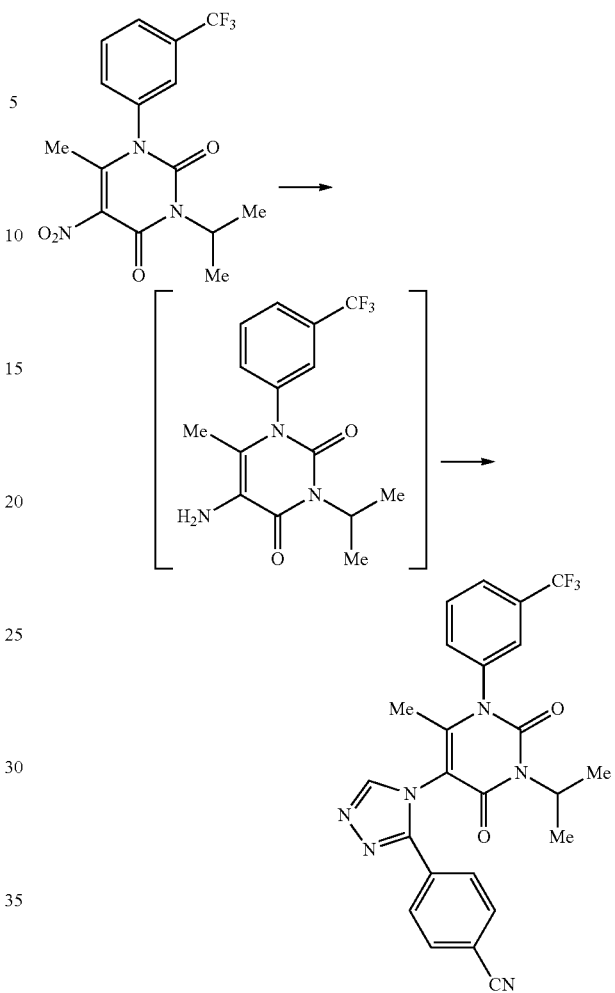

To a solution of 3-isopropyl-6-methyl-5-nitro-1-(3-trifluoromethylphenyl)pyrimidin-2,4(1H,3H)-dione (prepared in Reference Example 195) (1.68 g) in ethyl acetate/methanol (20.0 ml/20.0 ml) was added palladium hydroxide (500.0 mg) and the resulting mixture was performed catalytic hydrogenation at room temperature for four and a half hours. The reaction mixture was degassed and then filtered through Celite (trade mark) and then concentrated under reduced pressure to afford the residue (897.0 mg) containing 5-amino-3-isopropyl-6-methyl-1-(3-trifluoromethylphenyl)pyrimidin-2,4(1H,3H)-dione. A solution of the resulting residue (150.0 mg), dimethylformamide dimethylacetal (340 μl) and acetic acid (7 μl) in N,N-dimethy formamide (4.0 ml) was stirred at 110° C. for forty-five minutes and then cooled to room temperature, and thereto were added 4-cyanobenzohydrazide (221.4 mg) and acetic acid (690 μl) and the resulting mixture was stirred at 130° C. for two hours. To the reaction mixture was added water (30 ml) and the resulting mixture was extracted with ethyl acetate (30 ml×2). The organic layer was washed with water (30 ml×2) and saturated saline (30 ml), dried over anhydrous sodium sulfate and then concentrated under reduced pressure. The residue was purified by silica gel column chromatography (eluent: chloroform/methanol) and aminosilica gel column chromatography (eluent: ethyl acetate/methanol) to afford 4-(4-(3-isopropyl-6-methyl-2,4-dioxo-1-(3-(trifluoromethyl)phenyl)-1,2,3,4-tetrahydropyrimidin-5-yl)-4H-1,2,4-triazol-3-yl)benzonitrile (64.1 mg).

221

¹H-NMR (CDCl₃: 300 MHz) (δ PPM):
1.39-1.43 (m, 6H), 1.50 (s, 1.5H), 1.52 (s, 1.5H), 5.40-5.16 (m, 1H), 7.25 (d, 0.5H, J=7.7 Hz), 7.32 (s, 0.5H), 7.43 (d, 0.5H, J=7.7 Hz), 7.52 (s, 0.5H), 7.59-7.72 (m, 6H), 8.25 (brs, 1H)

Example 66

4-(4-(3,6-Dimethyl-2,4-dioxo-1-(3-(trifluoromethyl)phenyl)-1,2,3,4-tetrahydropyrimidin-5-yl)-4H-1,2,4-triazol-3-yl)benzonitrile

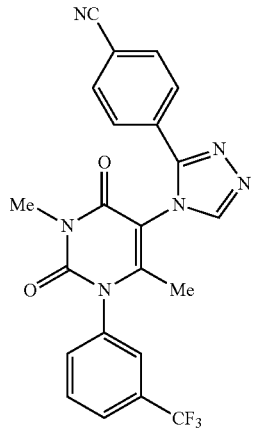 [SMILES: Cc1c(-n2cnnc2-c2ccc(C#N)cc2)c(=O)n(C)c(=O)n1-c1cccc(C(F)(F)F)c1]

The intended product was obtained by using the corresponding starting materials according to the similar reaction and treatment method described in Example 62.

¹H-NMR (300 MHz, CDCl₃) (δ PPM):
1.52 (s, 1.5H), 1.55 (s, 1.5H), 3.37 (s, 1.5H), 3.39 (s, 1.5H), 7.23 (s, 0.5H), 7.30 (s, 0.5H), 7.42-7.65 (m, 0.5H), 7.52 (brs, 0.5H), 7.60-7.65 (m, 1H), 7.72-7.76 (m, 5H), 8.23 (brs, 1H)

Example 67

5-(3-(5-Bromopyridin-2-yl)-4H-1,2,4-triazol-4-yl)-3-isopropyl-6-methyl-1-(3-(trifluoromethyl)phenyl)pyrimidin-2,4(1H,3H)-dione

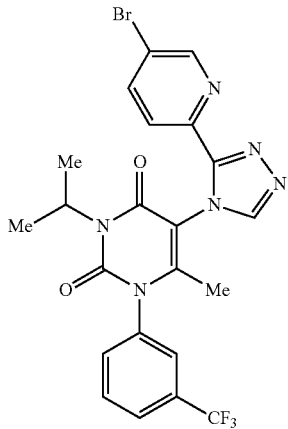 [SMILES: Cc1c(-n2cnnc2-c2ccc(Br)cn2)c(=O)n(C(C)C)c(=O)n1-c1cccc(C(F)(F)F)c1]

The intended product was obtained by using the corresponding starting materials according to the similar reaction and treatment method described in Example 65.

¹H-NMR (300 MHz, CDCl₃) (δ PPM):
1.43-1.47 (m, 6H), 1.68 (s, 3H), 5.09-5.18 (m, 1H), 7.47-7.53 (m, 1.5H), 7.61 (s, 0.5H), 7.70 (t, 1H, J=8.0 Hz), 7.78 (d, 1H, J=7.7 Hz), 7.94-7.97 (m, 1H), 8.20 (d, 1H, J=3.5 Hz), 8.30 (d, 1H, J=8.6 Hz), 8.56 (dd, 1H, J=8.8, 2.2 Hz)

Example 68

4-[5-[6-Methyl-4-oxo-3-(2-oxoethyl)-1-(3-trifluoromethylphenyl)-1,2,3,4-tetrahydropyrimidin-5-yl]-1H-pyrazol-1-yl]benzonitrile

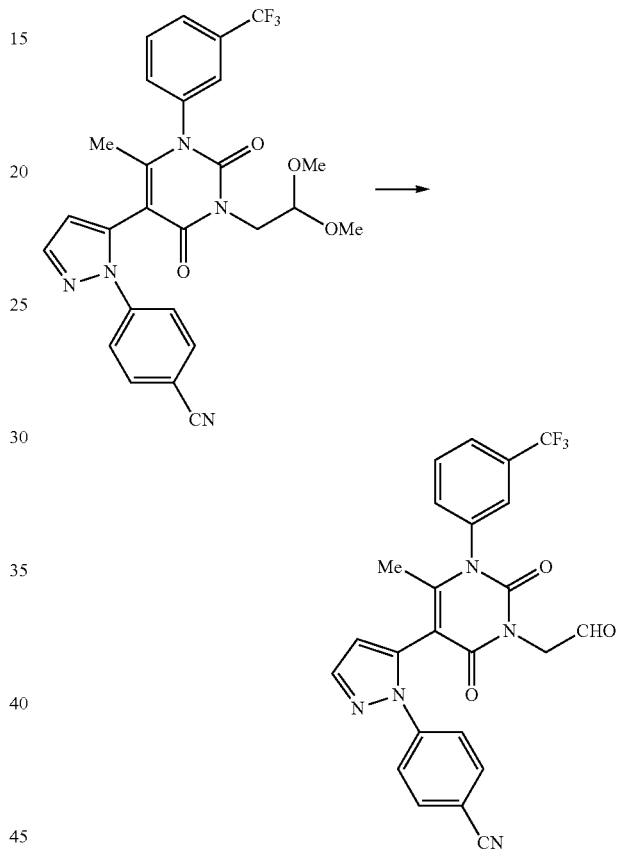

To a solution of 4-[5-[3-(2,2-dimethoxyethyl)-6-methyl-2,4-dioxo-1-(3-trifluoromethylphenyl)-1,2,3,4-tetrahydropyrimidin-5-yl]-1H-pyrazol-1-yl]benzonitrile (prepared in Example 7) (10.0 mg) in tetrahydrofuran (0.5 ml)/water (0.1 mL) was added trifluoroacetic acid (40 μl) and the resulting mixture was stirred at 100° C. for three hours. The reaction mixture was neutralized with aqueous sodium hydroxide solution, and thereto was added water and the resulting mixture was extracted with ethyl acetate (10 ml×2). The organic layer was washed with saturated saline (10 ml), dried over anhydrous sodium sulfate and then concentrated under reduced pressure to afford 4-[5-[6-methyl-4-oxo-3-(2-oxoethyl)-1-(3-trifluoromethylphenyl)-1,2,3,4-tetrahydropyrimidin-5-yl]-1H-pyrazol-1-yl]benzonitrile (9.1 mg).

¹H-NMR (CDCl₃: 300 MHz) (δ PPM):
1.60 (s, 1.5H), 1.65 (s, 1.5H), 4.76-4.88 (m, 2H), 6.42 (d, 0.5H, J=6.2 Hz), 6.43 (d, 0.5H, J=6.2 Hz), 7.28 (d, 0.5H, J=9.6 Hz), 7.38 (s, 0.5H), 7.43 (d, 0.5H, J=9.6 Hz), 7.50 (s, 0.5H), 7.52-7.56 (m, 3H), 7.69-7.75 (m, 4H), 9.53 (s, 0.5H), 9.55 (s, 0.5H)

Example 69

4-[5-[3-(2-Dimethylaminoethyl)-6-methyl-2,4-dioxo-1-(3-trifluoromethylphenyl)-1,2,3,4-tetrahydropyrimidin-5-yl]-1H-pyrazol-1-yl]benzonitrile

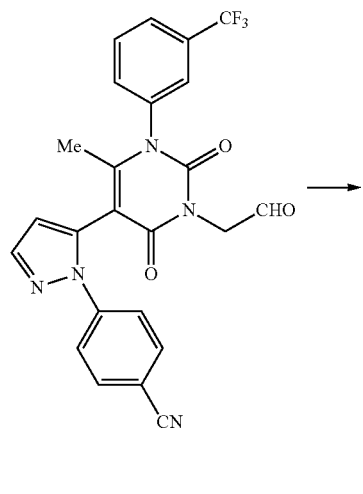

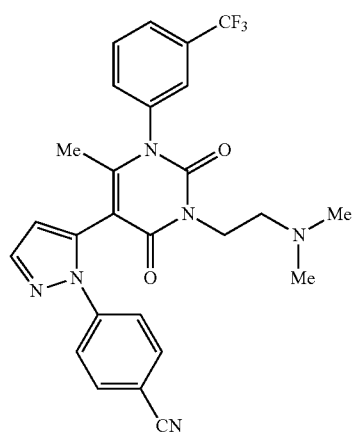 [SMILES: CNCCn1c(=O)c(-c2ccnn2-c2ccc(C#N)cc2)c(C)n(-c2cccc(C(F)(F)F)c2)c1=O]

To a solution of 4-[5-[6-methyl-4-oxo-3-(2-oxoethyl)-1-(3-trifluoromethylphenyl)-1,2,3,4-tetrahydropyrimidin-5-yl]-1H-pyrazol-1-yl]benzonitrile (prepared in Example 68) (12.8 mg), dimethyl amine (133 μl) and acetic acid (10 μl) in tetrahydrofuran (1.0 ml) was added sodium triacetoxyborohydride (8.5 mg) and the resulting mixture was stirred at room temperature for four hours. To the reaction mixture was added water (10 ml) and the resulting mixture was extracted with ethyl acetate (10 ml×2). The organic layer was washed with water (10 ml) and saturated saline (10 ml), dried over anhydrous sodium sulfate and then concentrated under reduced pressure. The residue was purified by silica gel column chromatography (eluent: chloroform/methanol) to afford 4-[5-[3-(2-dimethylaminoethyl)-6-methyl-2,4-dioxo-1-(3-trifluoromethylphenyl)-1,2,3,4-tetrahydropyrimidin-5-yl]-1H-pyrazol-1-yl]benzonitrile (7.4 mg).

$^1$H-NMR (CDCl$_3$: 300 MHz) (δ PPM):

1.64 (s, 1.5H), 1.68 (s, 1.5H), 2.23 (s, 6H), 2.42-2.48 (m, 2H), 4.03-4.07 (m, 2H), 6.46 (d, 1H, J=5.1 Hz), 7.30-7.79 (m, 9H)

Example 70

4-[5-[6-Methyl-3-(2-methylaminoethyl)-2,4-dioxo-1-(3-trifluoromethylphenyl)-1,2,3,4-tetrahydropyrimidin-5-yl]-1H-pyrazol-1-yl]benzonitrile

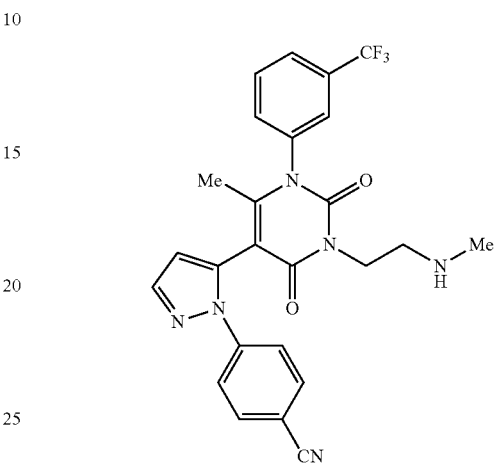

The above-mentioned compound was prepared by using the corresponding starting materials according to the similar reaction and treatment method to those described in Example 69.

$^1$H-NMR (CD$_3$OD: 300 MHz) (δ PPM):

1.63 (brs, 3H), 1.69-1.75 (m, 3H), 2.18-2.24 (m, 1H), 2.40-2.54 (m, 1H), 3.96-4.00 (m, 1H), 4.02-4.08 (m, 1H), 6.42-6.46 (m, 1H), 7.47-7.79 (m, 9H)

Example 71

N-[2-[5-[1-(4-Cyanophenyl)-1H-pyrazol-5-yl]-4-methyl-2,6-dioxo-3-(3-trifluoromethylphenyl)-2,3-dihydropyrimidin-1(6H)-yl]ethyl]acetamide

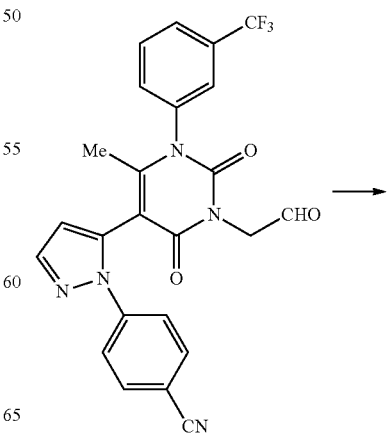

-continued

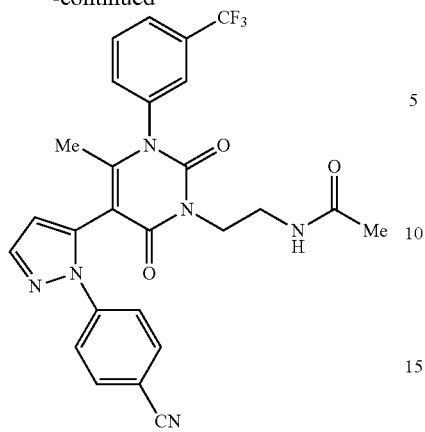

To a solution of 4-[5-[6-methyl-4-oxo-3-(2-oxoethyl)-1-(3-trifluoromethylphenyl)-1,2,3,4-tetrahydropyrimidin-5-yl]-1H-pyrazol-1-yl]benzonitrile (prepared in Example 68) (18.0 mg), ammonia (0.4 ml: 0.5 N tetrahydrofuran solution) and acetic acid (4 μl) in tetrahydrofuran (1.0 ml) was added sodium triacetoxyborohydride (11.9 mg) and the resulting mixture was stirred at room temperature for two hours. To the reaction mixture were added diisopropylethyl amine (48 μl) and acetic anhydride (78 μl) and the resulting mixture was stirred at 55° C. for two hours. To the reaction mixture was added water (20 ml) and the resulting mixture was extracted with ethyl acetate (20 ml×2). The organic layer was washed with water (10 ml) and saturated saline (10 ml), dried over anhydrous sodium sulfate and then concentrated under reduced pressure. The residue was purified by silica gel column chromatography (eluent: chloroform/methanol) to afford N-[2-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]ethyl]acetamide (7.6 mg).

$^1$H-NMR (CDCl$_3$: 300 MHz) (δ PPM):
1.54 (s, 1.5H), 1.59 (s, 1.5H), 1.89 (s, 1.5H), 1.90 (s, 1.5H), 4.10-4.20 (m, 4H), 4.34-4.40 (m, 1H), 6.41 (d, 0.5H, J=7.5 Hz), 6.42 (d, 0.5H, J=7.5 Hz), 7.23 (d, 0.5H, J=6.1 Hz), 7.32 (s, 0.5H), 7.42 (d, 0.5H, J=6.1 Hz), 7.50 (s, 0.5H), 7.57-7.75 (m, 7H)

Example 72

2-[5-[1-(4-Cyanophenyl)-1H-pyrazole-5-yl]-4-methyl-2,6-dioxo-3-(3-trifluoromethylphenyl)-2,3-dihydropyrimidin-1(6H)-yl]acetic acid

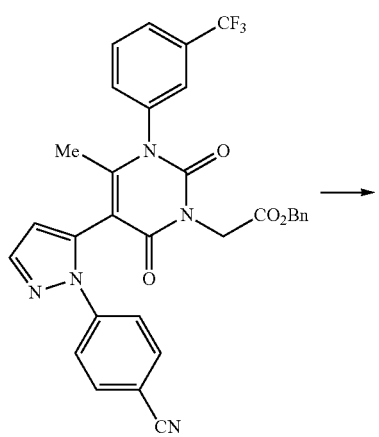

-continued

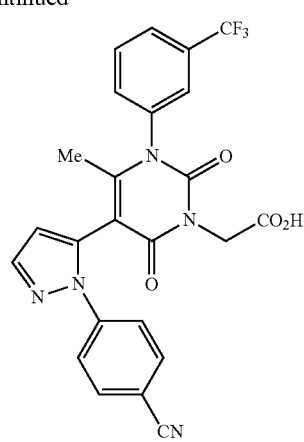

To a solution of 2-[5-[1-(4-cyanophenyl)-1H-pyrazole-5-yl]-4-methyl-2,6-dioxo-3-(3-trifluoromethylphenyl)-2,3-dihydropyrimidin-1(6H)-yl]acetic acid benzyl ester (prepared in Example 6) (50.0 mg) in ethyl acetate (3.0 ml)/methanol (3.0 ml) was added 5% palladium/carbon (9.0 mg) and the resulting mixture was stirred at room temperature under hydrogen atmosphere for six hours. The reaction mixture was degassed and then filtered through Celite (trade mark) and then concentrated under reduced pressure to afford 2-[5-[1-(4-cyanophenyl)-1H-pyrazole-5-yl]-4-methyl-2,6-dioxo-3-(3-trifluoromethylphenyl)-2,3-dihydropyrimidin-1(6H)-yl]acetic acid (47.0 mg).

$^1$H-NMR (CDCl$_3$: 300 MHz) (δ PPM):
1.74 (s, 1.5H), 1.77 (s, 1.5H), 4.53 (d, 2H, J=4.2 Hz), 6.59 (d, 0.5H, J=4.0 Hz), 6.60 (d, 0.5H, J=4.00 Hz), 7.76-7.85 (m, 9H).

Example 73

3-[5-[1-(4-Cyanophenyl)-1H-pyrazol-5-yl]-4-methyl-2,6-dioxo-3-(3-trifluoromethylphenyl)-2,3-dihydropyrimidin-1(6H)-yl]propanoic acid

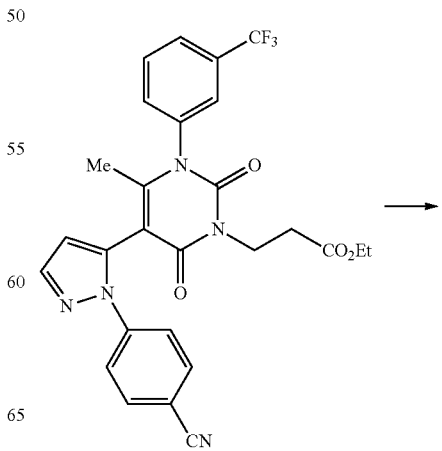

-continued

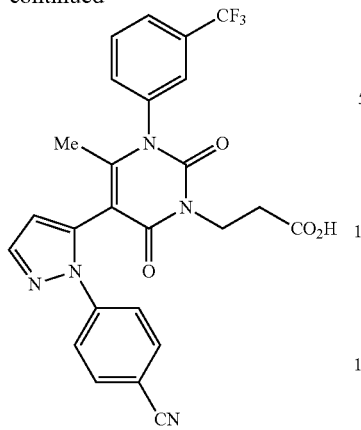

A solution of 3-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]propanoic acid ethyl ester (prepared in Example 4) (351.0 mg) in methanol (1.0 ml) was cooled under ice-cooling and thereto was added 2N aqueous sodium hydroxide solution (340 μl) and the resulting mixture was stirred at room temperature for twelve hours. The reaction mixture was diluted with diethylether (30 ml) and thereto was added water (30 ml). The organic layer and the aqueous layer were separated and the aqueous layer was then acidified with sodium hydrogen sulfate (500 mg) and extracted with ethyl acetate (50 ml×3). The organic layer was dried over anhydrous sodium sulfate and then concentrated under reduced pressure. The obtained amorphous was washed with hexane (30 ml) to afford 3-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]propanoic acid (239.5 mg).

$^1$H-NMR (CDCl$_3$: 300 MHz) (δ PPM):
1.60 (s, 1.5H), 1.64 (s, 1.5H), 2.64 (q, 2H, J=6.0 Hz), 4.25 (t, 2H, J=6.0 Hz), 6.46 (dd, 1H, J=6.0, 3.0 Hz), 7.26-7.31 (m, 1.5H), 7.38 (s, 0.5H), 7.44-7.53 (m, 1H), 7.55-7.66 (m, 2H), 7.68-7.75 (m, 3H), 7.79 (t, 1H, J=1.8 Hz)

Example 74

4-[5-[1-(4-Cyanophenyl)-1H-pyrazol-5-yl]-4-methyl-2,6-dioxo-3-(3-trifluoromethylphenyl)-2,3-dihydropyrimidin-1(6H)-yl]butanoic acid

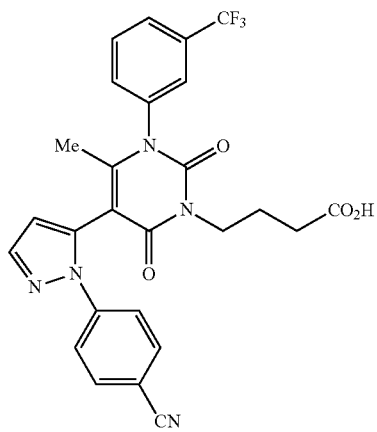 [SMILES: Cc1c(-c2ccnn2-c2ccc(C#N)cc2)c(=O)n(CCCC(=O)O)c(=O)n1-c1cccc(C(F)(F)F)c1]

The above-mentioned compound was prepared by using 4-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]butanoic acid ethyl ester (prepared in Example 5) according to the similar reaction and treatment method to those described in the Example 73.

$^1$H-NMR (CDCl$_3$: 300 MHz) (δ PPM):
1.55 (s, 0.75H), 1.57 (s, 0.75H), 1.66 (s, 0.75H), 1.70 (s, 0.75H), 1.89-1.97 (m, 2H), 2.31 (brs, 2H), 3.96-4.04 (m, 2H), 6.44 (d, 0.25H, J=11.8 Hz), 6.46 (d, 0.75H, J=1.5 Hz), 7.30-7.86 (m, 8H), 8.11 (dd, 1H, J=6.9, 5.7 Hz)

Example 75

3-[5-[1-(4-Cyanophenyl)-1H-pyrazol-5-yl]-4-methyl-2,6-dioxo-3-(3-trifluoromethylphenyl)-2,3-dihydropyrimidin-1(6H)-yl]-N,N-dimethylpropaneamide

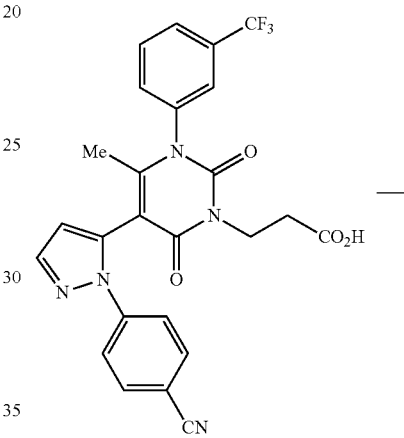

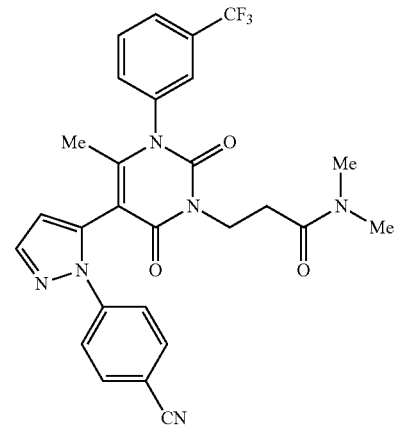

A solution of 3-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]propanoic acid (prepared in Example 73) (26.4 mg), 1-ethyl-3-(3-dimethylaminopropyl)carbodiimide (13.8 mg), 1-hydroxy-7-azabenzotriazole (15.9 mg) and N,N-diisopropylethylamine (0.1 ml) in tetrahydrofuran (0.5 ml) was cooled under ice-cooling and thereto was added dimethylamine (0.05 ml: 2M tetrahydrofuran solution) and the resulting mixture was stirred at room temperature for five hours. To the reaction mixture was 1M aqueous potassium hydrogen sulfate solution (20 ml) and the resulting mixture was then extracted with ethyl acetate (20 ml×2). The organic layer was washed with water (10 ml) and saturated saline (20 ml), dried over anhydrous sodium sulfate and then concentrated under reduced pressure. The residue was purified by silica gel column chromatography (eluent: chloroform/methanol) to afford 3-[5-[1-(4-cyanophenyl)-1H-pyrazole-5-yl]-4-methyl-2,6-dioxo-3-(3-trifluoromethylphenyl)-2,3-dihydropyrimidin-1(6H)-yl]-N,N-dimethylpropaneamide (3.1 mg).

$^1$H-NMR (CDCl$_3$: 300 MHz) (δ PPM):
1.64 (s, 3H), 2.62 (m, 2H), 2.86 (s, 3H), 2.99 (s, 1.5H), 3.01 (s, 1.5H), 4.21-4.26 (m, 2H), 6.47 (dd, 1H, J=6.0, 3.0 Hz), 7.38-7.55 (m, 4H), 7.64 (d, 1H, J=2.4 Hz), 7.67 (d, 1H, J=2.7 Hz), 7.73-7.79 (m, 3H)

Examples 76-82

The compounds indicated in the below-mentioned table (Examples 76-82) were obtained by using the corresponding starting materials according to the similar reaction and treatment method to those described in Example 75.

Example 76

2-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]-acetamide;

Example 77

2-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]-N-methylacetamide;

Example 78

2-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]-N,N-dimethylacetamide;

Example 79

3-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]-N-methylpropaneamide;

Example 80

4-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]-N-methylbutaneamide;

Example 81

4-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]-N,N-dimethylbutaneamide;

Example 82

(S)-2-(5-(1-(4-cyanophenyl)-1H-pyrazole-5-yl)-4-methyl-2,6-dioxo-3-(3-(trifluoromethyl)phenyl)-2,3-dihydropyrimidin-1(6H)-yl)-N-(1-phenylethyl)acetamide

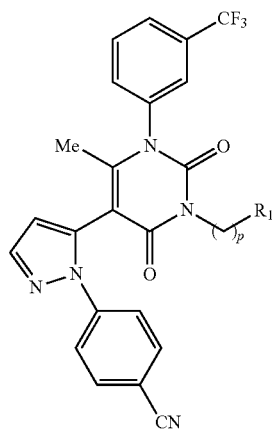

TABLE 48

| Ex. | p | R$^1$ | Measurement cond. | $^1$H-NMR (δ PPM) |
|---|---|---|---|---|
| 76 | 1 | ⟋⟍C(O)NH$_2$ | 1 | 1.56 (s, 1.5H), 1.61 (s, 1.5H), 4.53-4.65 (m, 2H), 5.51 (brs, 2H), 6.43 (d, 0.5H, J = 6.3 Hz), 6.44 (d, 0.5H, J = 6.3 Hz), 7.30 (d, 0.5H, J = 7.9 Hz), 7.38 (d, 0.5H, J = 7.9 Hz), 7.43 (d, 0.5H, J = 7.9 Hz), 7.50 (s, 0.5H), 7.53-7.63 (m, 3H), 7.67-7.75 (m, 4H) |
| 77 | 1 | ⟋⟍C(O)NHMe | 1 | 1.61 (s, 1.5H), 1.66 (s, 1.5H), 2.82 (brs, 3H), 4.54 (d, 1H, J = 1/12 Hz), 4.57 (d, 1H, J = 1/12 Hz), 5.55 (brs, 1H), 6.47 (d, 0.5H, J = 6.5 Hz), 6.48 (d, 0.5H, J = 6.5 Hz), 7.30 (d, 0.5H, J = 6.8 Hz), 7.42 (s, 0.5H), 7.46 (d, 0.5H, J = 6.8 Hz), 7.54 (s, 0.5H), 7.58-7.63 (m, 3H), 7.72-7.79 (m, 4H) |
| 78 | 1 | ⟋⟍C(O)NMe$_2$ | 1 | 1.55 (s, 1.5H), 1.61 (s, 1.5H), 2.90 (s, 1.5H), 2.91 (s, 1.5H), 2.97 (s, 1.5H), 2.98 (s, 1.5H), 4.65 (d, 1H, J = 15.1 Hz). 4.75 (d, 1H, J = 15.1 Hz), 6.43 (d, 0.5H, J = 6.3 Hz), 6.44 (d, 0.5H, J = 6.3 Hz), 7.30 (d, 0.5H, J = 8.2 Hz), 7.39 (s, 0.5H), 7.42 (d, 0.5H, J = 8.2 Hz), 7.50 (s, 0.5H), 7.57-7.60 (m, 3H), 7.66-7.74 (m, 4H) |
| 79 | 2 | ⟋⟍CH$_2$C(O)NHMe | 1 | 1.65 (s, 3H), 2.45-2.53 (m, 2H), 2.73 (d, 3H, J = 3.0 Hz), 4.23 (m, 2H), 6.47 (dd, 1H, J = 6.0, 3.0 Hz), 7.45-7.54 (m, 2H), 7.59-7.68 (m, 3H), 7.71-7.80 (m, 4H) |

TABLE 48-continued

| Ex. | p | R¹ | Measurement cond. | ¹H-NMR (δ PPM) |
|---|---|---|---|---|
| 80 | 3 | ![structure: -C(=O)-N(H)-Me] | 1 | 1.61 (s, 0.75H), 1.63 (s, 0.75H), 1.66 (s, 0.75H), 1.69 (s, 0.75H), 1.92-1.97 (m, 2H), 2.13-2.16 (m, 2H), 2.74-2.77 (m, 3H), 3.95-3.97 (m, 2H), 6.44-6.47 (m, 1H), 7.43-7.79 (m, 8H), 8.11 (t, 1H, J = 9.0 Hz) |
| 81 | 3 | ![structure: -C(=O)-N(Me)-Me] | 1 | 1.46 (s, 0.75H), 1.48 (s, 0.75H), 1.57 (s, 0.75H), 1.61 (s, 0.75H), 1.83-2.02 (m, 2H), 2.25-2.28 (m, 2H), 2.86-2.88 (m, 6H), 3.95 (t, 2H, J = 7.2 Hz), 6.39-6.42 (m, 1H), 7.46-7.51 (m, 2H), 7.58-7.71 (m, 5H), 7.73-7.75 (m, 1H), 8.06 (t, 1 H, J = 7.8 Hz) |
| 82 | 1 | ![structure: -C(=O)-NH-CH(Me)-Ph] | 1 | 1.38-1.41 (m, 3H), 1.50 (s, 0.5H), 1.55 (s, 0.5H), 1.56 (s, 0.5H), 1.60 (s, 0.5H), 4.52-4.55 (m, 2H), 4.97-5.04 (m, 1H), 5.86-5.95 (m, 1H), 6.40-6.43 (m, 1H), 7.16-7.31 (m, 6H), 7.39 (s, 1H), 7.47-7.50 (m, 2H), 7.55-7.58 (m, 2H), 7.66-7.74 (m, 3H) |

Example 83

4-[5-[3-(3-Hydroxypropyl)-6-methyl-2,4-dioxo-1-(3-trifluoromethylphenyl)-1,2,3,4-tetrahydropyrimidin-5-yl]-1H-pyrazol-1-yl]benzonitrile

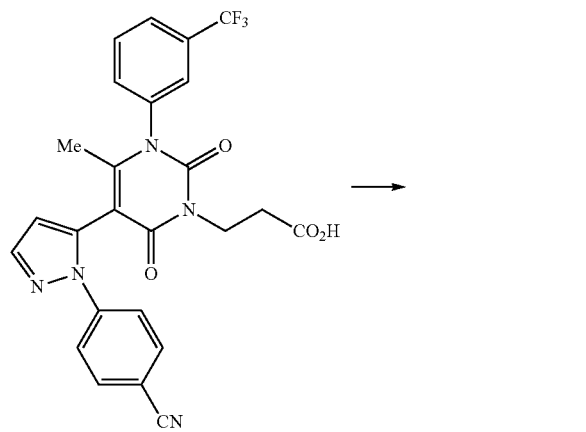

To a solution of 3-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]propanoic acid (prepared in Example 73) (36.2 mg) in tetrahydrofuran (0.5 ml) was added under ice-cooling borane tetrahydrofuran complex (0.1 ml:1.09 M tetrahydrofuran solution), and the resulting mixture was stirred at room temperature for eighteen hours. The reaction mixture was cooled again under ice-cooling and thereto was added borane tetrahydrofuran complex (0.2 ml:1.09 M tetrahydrofuran solution) and the resulting mixture was stirred at room temperature for five hours. To the reaction mixture was added saturated aqueous ammonium chloride solution (2 ml) and the resulting mixture was extracted with ethyl acetate (20 ml×2). The organic layer was washed with water (20 ml) and saturated saline (20 ml), dried over anhydrous sodium sulfate and then concentrated under reduced pressure. The residue was purified by silica gel column chromatography (eluent: chloroform/methanol) to afford 4-[5-[3-(3-hydroxypropyl)-6-methyl-2,4-dioxo-1-(3-trifluoromethylphenyl)-1,2,3,4-tetrahydropyrimidin-5-yl]-1H-pyrazol-1-yl]benzonitrile (26.2 mg).

¹H-NMR (CDCl₃: 300 MHz) (δ PPM):
1.66 (s, 2H), 1.70 (s, 1H), 1.73-1.81 (m, 2H), 3.23-3.33 (m, 1H), 3.41-3.53 (m, 1H), 3.95-4.06 (m, 2H), 6.40-6.43 (m, 1H), 7.25-7.38 (m, 0.5H), 7.37-7.44 (m, 1.5H), 7.49-7.53 (m, 2H), 7.59-7.71 (m, 3.5H), 7.75 (q, 1H, J=1.8 Hz), 8.03-8.08 (m, 0.5H)

Example 84

4-[5-[3-(4-hydroxybutyl)-6-methyl-2,4-dioxo-1-(3-trifluoromethylphenyl)-1,2,3,4-tetrahydropyrimidin-5-yl]-1H-pyrazol-1-yl]benzonitrile

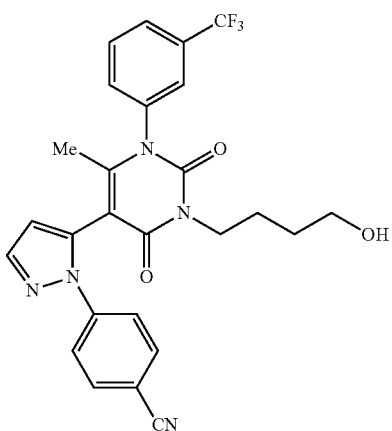 [SMILES: Cc1c(-c2ccnn2-c2ccc(C#N)cc2)c(=O)n(CCCCO)c(=O)n1-c1cccc(C(F)(F)F)c1]

The above-mentioned compound was obtained by using the corresponding starting materials according to the similar reaction and treatment method to those described in Example 83.

$^1$H-NMR (CDCl$_3$: 300 MHz) (δ PPM):
1.50-1.62 (m, 4H), 1.68 (s, 1.5H), 1.73 (s, 1.5H), 3.62 (t, 2H, J=6.00 Hz), 3.94-3.98 (m, 2H), 6.44-6.46 (m, 1H), 7.42-7.79 (m, 8H), 8.10 (t, 1H, J=9.0 Hz).

Example 85

4-[5-[3-(5-Aminopentyl)-6-methyl-2,4-dioxo-1-(3-trifluoromethylphenyl)-1,2,3,4-tetrahydropyrimidin-5-yl]-1H-pyrazol-1-yl]benzonitrile hydrochloride

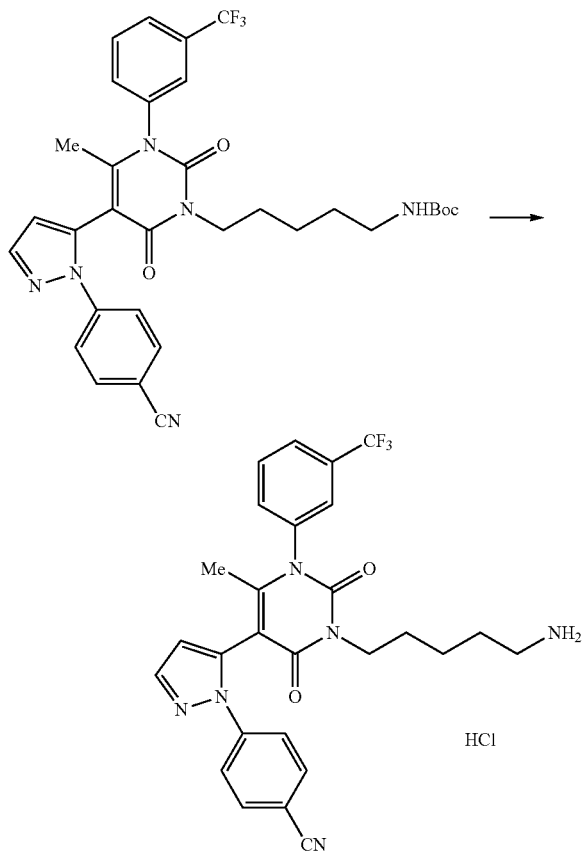

To a solution of tert-butyl 5-[5-[1-(4-cyanophenyl)-1H-pyrazol-5-yl]-4-methyl-2,6-dioxo-3-(3-trifluoromethyl)-2,3-dihydropyrimidine-1(6H)-yl]pentylcarbamate (prepared in Example 8) (12.0 mg) in ethanol (1.0 ml) was added 2N hydrochloric acid/ethanol (40 μl) and the resulting mixture was stirred at 80° C. for one hour. The reaction mixture was concentrated under reduced pressure to afford 4-[5-[3-(5-aminopentyl)-6-methyl-2,4-dioxo-1-(3-trifluoromethylphenyl)-1,2,3,4-tetrahydropyrimidin-5-yl]-1H-pyrazol-1-yl]benzonitrile hydrochloride (10.4 mg).

$^1$H-NMR (CDCl$_3$: 300 MHz) (δ PPM):
1.26-1.34 (m, 2H), 1.44-1.68 (m, 4H), 1.88 (s, 1.5H), 1.91-(s, 1.5H), 2.86 (t, 2H, J=7.2 Hz), 3.80-3.87 (m, 2H), 6.58-(t, 1H, J=1.7 Hz), 7.68-7.91 (m, 9H)

Example 86

N-[5-[5-[1-(4-Cyanophenyl)-1H-pyrazol-5-yl]-4-methyl-2,6-dioxo-3-(3-trifluoromethylphenyl)-2,3-dihydropyrimidin-1(6H)-yl]pentyl]acetamide

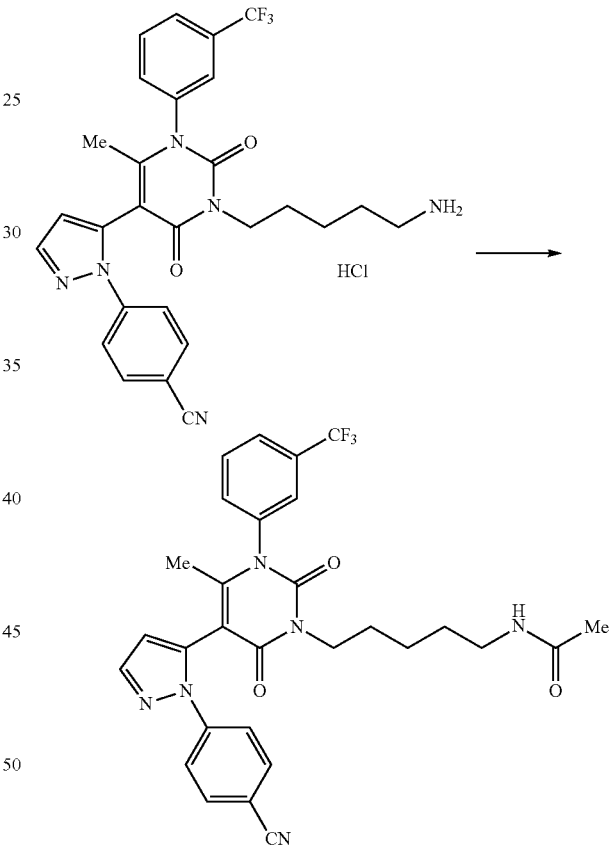

To a solution of 4-[5-[3-(5-aminopentyl)-6-methyl-2,4-dioxo-1-(3-trifluoromethylphenyl)-1,2,3,4-tetrahydropyrimidin-5-yl]-1H-pyrazol-1-yl]benzonitrile hydrochloride (prepared in Example 85) (6.4 mg) and triethylamine (10 μl) in dichloromethane (1.0 ml) was added acetyl chloride (0.7 mg) in ice-cooling and the resulting mixture was stirred for five minutes and stirred at room temperature for thirty minutes. To the reaction mixture was added aqueous saturated sodium hydrogen carbonate solution (10 ml) and the resulting mixture was extracted with chloroform (10 ml×2). The organic layer was dried over anhydrous sodium sulfate and then concentrated under reduced pressure. The residue was purified by silica gel column chromatography (eluent: chloroform/ methanol) to afford N-[5-[5-[1-(4-cyanophenyl)-1H-pyrazol-5-yl]-4-methyl-2,6-dioxo-3-(3-trifluoromethylphenyl)-2,3-dihydropyrimidin-1(6H)-yl]pentyl]acetamide (3.0 mg).

$^1$H-NMR (CDCl$_3$: 300 MHz) (δ PPM):
1.18-1.24 (m, 2H), 1.42-1.52 (m, 4H), 1.66 (s, 1.5H), 1.71-(s, 1.5H), 1.84 (s, 3H), 3.10-3.18 (m, 2H), 3.80-3.87 (m, 2H), 5.51 (brs, 1H), 6.40 (d, 0.5H, J=7.0 Hz), 6.41 (d, 0.5H, J=7.0 Hz), 7.31-7.62 (m, 4H), 7.63-7.74 (m, 5H)

Example 87

N-[2-[5-[1-(4-Cyanophenyl)-1H-pyrazol-5-yl]-4-methyl-2,6-dioxo-3-(3-trifluoromethylphenyl)-2,3-dihydropyrimidin-1(6H)-yl]pentyl]menthanesulfonamide

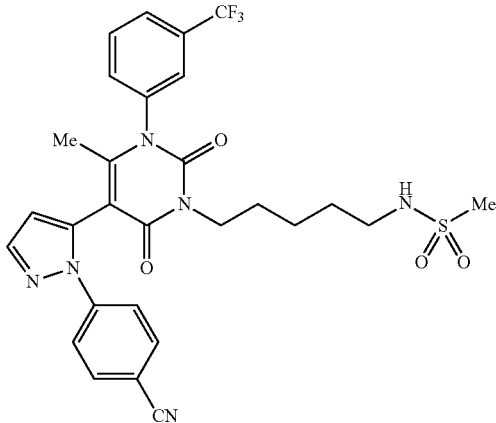 [SMILES: Cc1c(-c2ccnn2-c2ccc(C#N)cc2)c(=O)n(CCCCCNS(C)(=O)=O)c(=O)n1-c1cccc(C(F)(F)F)c1]

The above-mentioned compound was prepared by using the corresponding starting materials according to the similar reaction and treatment method to those described in Example 86.

$^1$H-NMR (CDCl$_3$: 300 MHz) (δ PPM):
1.21-1.29 (m, 2H), 1.50-1.59 (m, 4H), 1.67 (s, 1.5H), 1.72-(s, 1.5H), 2.87 (s, 3H), 3.01-3.07 (m, 2H), 3.82-3.88 (m, 2H), 4.16 (brs, 1H), 6.42 (d, 0.5H, J=8.3 Hz), 6.43 (d, 0.5H, J=8.3 Hz), 7.36 (d, 0.5H, J=7.2 Hz), 7.45-7.54 (m, 3.5H), 7.62-7.75 (m, 5H)

Example 88

4-(5-(2,4-Dioxo-3-(tetrahydro-2H-pyran-4-yl)-1-(3-(trifluoromethyl)phenyl)-1,2,3,4-tetrahydropyrimidin-5-yl)-1H-pyrazol-1-yl)benzonitrile

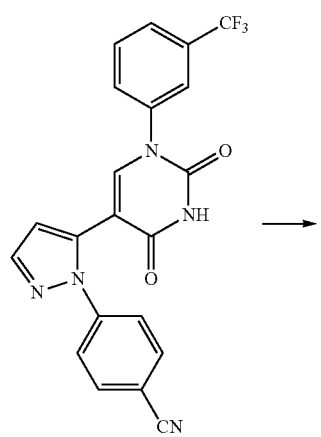

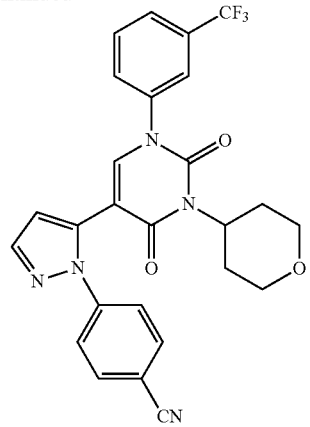

To a solution of 4-(5-(2,4-dioxo-1-(3-(trifluoromethyl)phenyl)-1,2,3,4-tetrahydropyrimidin-5-yl)-1H-pyrazol-1-yl)benzonitrile (prepared in Example 53) (30 mg) in THF (2 ml) were added tetrahydro-2H-pyran-4-ol (0.014 ml), triphenylphosphine (37 mg) and diethyl azodicarboxylate (2.2 M toluene solution, 0.065 ml) and the resulting mixture was stirred at room temperature for fifteen minutes. The reaction solution was concentrated under reduced pressure and the residue was then purified by silica gel column chromatography (eluent: hexane/ethyl acetate) and reversed phase liquid chromatography (eluent: TFA water/acetonitrile) to afford-4-(5-(2,4-dioxo-3-(tetrahydro-2H-pyran-4-yl)-1-(3-(trifluoromethyl)phenyl)-1,2,3,4-tetrahydropyrimidin-5-yl)-1H-pyrazol-1-yl)benzonitrile (7 mg).

$^1$H-NMR (400 MHz, CDCl$_3$) (δ PPM):
1.46 (dd, 2H, J=2.2, 11.8 Hz), 2.61 (dd, 1H, J=4.7, 12.4 Hz), 2.67 (dd, 1H, J=4.7, 12.4 Hz), 3.42 (t, 2H, J=11.7 Hz), 4.03 (dd, 2H, J=4.4, 11.4 Hz), 4.96 (tt, 1H, J=4.0, 12.2 Hz), 6.53 (d, 1H, J=1.8 Hz), 7.51 (s, 1H), 7.57-7.60 (m, 2H), 7.62-7.66 (m, 2H), 7.68 (d, 1H, J=7.8 Hz), 7.74 (d, 1H, J=1.9 Hz), 7.76-7.78 (m, 3H)

Examples 89-92

The compounds indicated in the below-mentioned table (Examples 89-92) were obtained by using the corresponding starting materials according to the similar reaction and treatment method to those described in Example 88.

Example 89

4-(5-(3-(1-methylpiperidin-4-yl)-2,4-dioxo-1-(3-(trifluoromethyl)phenyl)-1,2,3,4-tetrahydropyrimidin-5-yl)-1H-pyrazol-1-yl)benzonitrile

Example 90

(S)-4-(5-2,4-dioxo-3-(5-oxopyrrolidin-3-yl)-1-(3-(trifluoromethyl)phenyl)-1,2,3,4-tetrahydropyrimidin-5-yl)-1H-pyrazol-1-yl)benzonitrile

Example 91

4-(5-(3-(1-(dimethylamino)propan-2-yl)-2,4-dioxo-1-(3-(trifluoromethyl)phenyl)-1,2,3,4-tetrahydropyrimidin-5-yl)-1H-pyrazol-1-yl)benzonitrile

Example 92

4-(5-(3-(oxetan-3-yl)-2,4-dioxo-1-(3-(trifluoromethyl)phenyl)-1,2,3,4-tetrahydropyrimidin-5-yl)-1H-pyrazol-1-yl)benzonitrile

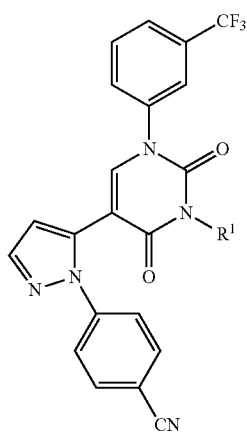

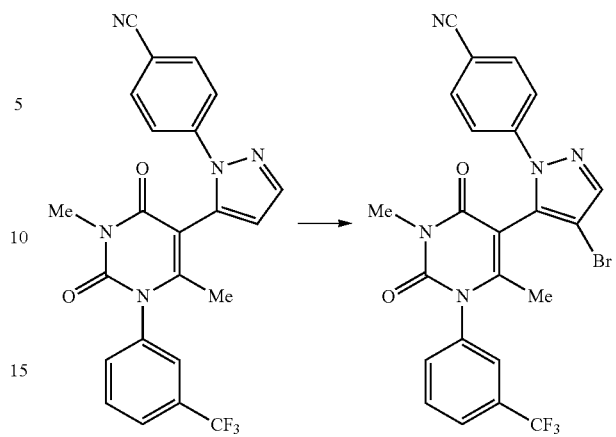

To a solution of 4-(5-(3,6-dimethyl-2,4-dioxo-1-(3-(trifluoromethyl)phenyl)-1,2,3,4-tetrahydropyrimidin-5-yl)-1H-pyrazol-1-yl)benzonitrile (prepared in Example 1) (665 mg) in acetic acid (15 ml) was added at room temperature bromine (0.75 ml) dropwise and the resulting mixture was stirred at room temperature for fifteen minutes. To the reaction mixture

TABLE 49

| Ex. | R$^1$ | Measurement cond. | $^1$H-NMR (δ PPM) |
|---|---|---|---|
| 89 | N-methylpiperidin-4-yl | 4 | 1.49 (d, 2H, J = 9.9 Hz), 2.03 (t, 2H, J = ¹/₁.₅ Hz), 2.27 (s, 3H), 2.55-2.67 (m, 2H), 2.91 (d, 2H, J = ¹/₁.₅ Hz), 4.69 (tt, 1H, J = 4.1, 12.2 Hz), 6.52 (d, 1H, J = 1.8 Hz), 7.50 (s, 1H), 7.59-7.67 (m, 5H), 7.73 (d, 1H, J = 1.8 Hz), 7.74-7.77 (m, 3H) |
| 90 | 5-oxopyrrolidin-3-yl | 4 | 2.60 (dd, 1H, J = 10.6, 17.1 Hz), 2.73 (dd, 1H, J = 6.6, 17.1 Hz), 3.52 (dd, 1H, J = 5.6, 8.7 Hz), 3.67 (dd, 1H, J = 9.4, 10.8 Hz), 5.60 (brs, 1H), 5.75-5.85 (m, 1H), 6.57 (d, 1H, J = 1.8 Hz), 7.49 (s, 1H), 7.55-7.58 (m, 2H), 7.61-7.65 (m, 2H), 7.68 (t, 1H, J = 7.7 Hz), 7.75-7.79 (m, 4H) |
| 91 | 3-(dimethylamino)-2-methylpropyl | 4 | 1.34 (d, 3H, J = 6.8 Hz), 2.08-2.20 (m, 1H), 2.15 (s, 6H), 3.16-3.24 (m, 1H), 5.05-5.15 (m, 1H), 6.52 (d, 1H, J = 1.8 Hz), 7.47 (s, 1H), 7.50-7.54 (m, 2H), 7.55-7.62 (m, 3H), 7.64-7.69 (m, 3H), 7.3-7.77 (m, 1H) |
| 92 | oxetan-3-yl | 1 | 3.80 (dd, 2H, J = ¹/₁.₄, 6.0 Hz), 4.04 (t, 2H, J = 10.2 Hz), 5.37-5.42 (m, 1H), 6.53 (s, 1H), 7.57-7.76 (m, 10H) |

Example 93

4-(4-Bromo-5-(3,6-dimethyl-2,4-dioxo-1-(3-(trifluoromethyl)phenyl)-1,2,3,4-tetrahydropyrimidin-5-yl)-1H-pyrazol-1-yl)benzonitrile was added 10% aqueous sodium thiosulfate solution (30 ml) and the solids formed were filtered and then washed with hexane (50 ml) and dried under reduced pressure to afford 4-(4-bromo-5-(3,6-dimethyl-2,4-dioxo-1-(3-(trifluoromethyl)phenyl)-1,2,3,4-tetrahydropyrimidin-5-yl)-1H-pyrazol-1-yl)benzonitrile (692.8 mg) as brown solid.

¹H-NMR (300 MHz, CDCl₃) (δ PPM):
1.73 (s, 1.5H), 1.78 (s, 1.5H), 3.33 (d, 3H, J=6.0 Hz), 7.48 (s, 1H), 7.54-7.58 (m, 3H), 7.71-7.77 (m, 4H), 7.81 (d, 1H, J=1.2 Hz)

Examples 94-100

The compounds indicated in the below-mentioned table (Examples 94-100) were obtained by using the corresponding starting materials according to the similar reaction and treatment method to those described in Example 93.

Example 94

4-(4-bromo-5-(3-isopropyl-2,4-dioxo-1-(3-(trifluoromethyl)phenyl)-1,2,3,4-tetrahydropyrimidin-5-yl)-1H-pyrazol-1-yl)benzonitrile;

Example 95

(R)-2-(5-(4-bromo-1-(4-cyanophenyl)-1H-pyrazol-5-yl)-4-methyl-2,6-dioxo-3-(3-(trifluoromethyl)phenyl)-2,3-dihydropyrimidin-1(6H)-yl)propylacetate;

Example 96

(R)-4-(4-bromo-5-(3-(1-hydroxypropan-2-yl)-2,4-dioxo-1-(3-(trifluoromethyl)phenyl)-1,2,3,4-tetrahydropyrimidin-5-yl)-1H-pyrazol-1-yl)benzonitrile;

Example 97

4-(4-bromo-5-(3-methyl-2,4-dioxo-1-(3-(trifluoromethyl)phenyl)-1,2,3,4-tetrahydropyrimidin-5-yl)-1H-pyrazol-1-yl)benzonitrile;

Example 98

2-(5-(4-bromo-1-(4-cyanophenyl)-1H-pyrazol-5-yl)-4-methyl-2,6-dioxo-3-(3-(trifluoromethyl)phenyl)-2,3-dihydropyrimidin-1(6H)-yl)ethylacetate;

Example 99

4-(4-bromo-5-(6-ethyl-1,3-methyl-2,4-dioxo-1-(3-(trifluoromethyl)phenyl)-1,2,3,4-tetrahydropyrimidin-5-yl)-1H-pyrazol-1-yl)benzonitrile;

Example 100

4-(4-bromo-5-(3-isopropyl-6-methyl-2,4-dioxo-1-(3-(trifluoromethyl)phenyl)-1,2,3,4-tetrahydropyrimidin-5-yl)-1H-pyrazol-1-yl)benzonitrile

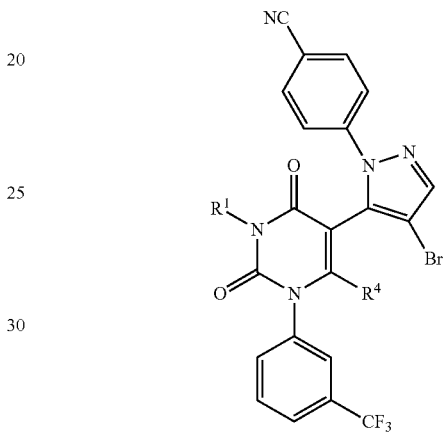

TABLE 50

| Ex. | R¹ | R⁴ | Measurement cond. | ¹H-NMR (δ PPM) |
|---|---|---|---|---|
| 94 | ⁱPr | H | 1 | 1.33 (d, 6H, J = 6.9 Hz), 5.01 (septet, 1H, J = 6.6 Hz), 7.58-7.74 (m, 9H), 7.76 (s, 1H) |
| 95 | ⸺CH(Me)CH₂OAc | Me | 1 | 1.37-1.46 (m, 3H), 1.68 (s, 1.5H), 1.73 (d, 1.5H, J = 3.3 Hz), 1.93 (s, 1H), 1.99-2.03 (m, 2H), 4.00-4.13 (m, 1H), 4.50-4.78 (m, 1H), 5.17 (brs, 1H), 7.34 (d, 0.25H, J = 7.5 Hz), 7.40 (d, 0.25H, J = 8.4 Hz), 7.48 (d, 0.5H, J = 13.2 Hz), 7.55-7.80 (m, 8H) |
| 96 | ⸺CH(Me)CH₂OH | H | 1 | 1.25 (d, 3H, J = 7.2 Hz), 2.11 (brs, 1H), 3.65 (brd, 1H, J = 10.1 Hz), 3.84-3.94 (m, 1H), 4.96-5.04 (m, 1H), 5.03-5.09 (m, 1H), 7.55-7.64 (m, 4H), 7.66-7.72 (m, 5H), 7.74 (s, 1H) |
| 97 | Me | H | 1 | 3.26 (s, 3H), 7.53-7.57 (m, 3H), 7.61-7.71 (m, 6H), 7.74 (s, 1H) |
| 98 | ⸺CH₂CH₂OAc | Me | 3 | 1.78 (s, 1.5H), 1.82 (s, 1.5H), 1.89 (s, 1.5H), 1.90 (s, 1.5H), 4.06-4.25 (m, 3H), 4.33-4.39 (m, 1H), 7.62-7.88 (m, 8H), 7.91 (s, 1H) |
| 99 | Me | Et | 1 | 0.62 (t, 3H, J = 7.5 Hz), 1.85-2.15 (m, 2H), 3.39 (s, 1.5H), 3.40 (s, 1.5H), 7.33 (d, 0.5H, J = 7.2 Hz), 7.44 (s, 0.5H), 7.50 (d, 0.5H, J = 8.4 Hz), 7.57-7.68 (m, 3.5H), 7.71-7.78 (m, 3H), 7.82 (d, 1H, J = 1.5 Hz) |

TABLE 50-continued

| Ex. | R$^1$ | R$^4$ | Measurement cond. | $^1$H-NMR (δ PPM) |
|---|---|---|---|---|
| 100 | $^i$Pr | Me | 1 | 1.29 (t, 3H, J = 6.6 Hz), 1.34 (dd, 3H, J = 7.2, 2.7 Hz), 3.68 (s, 1.5H), 1.72 (s, 1.5H), 4.94-5.05 (m, 1H), 7.36 (d, 0.5H, J = 7.8 Hz), 7.42-7.46 (m, 1H), 7.50-7.55 (m, 2.5H), 7.60-7.75 (m, 5H) |

Example 101

4-(4-Iodo-5-(3-isopropyl-6-methyl-2,4-dioxo-1-(3-(trifluoromethyl)phenyl)-1,2,3,4-tetrahydropyrimidin-5-yl)-1H-pyrazol-1-yl)benzonitrile

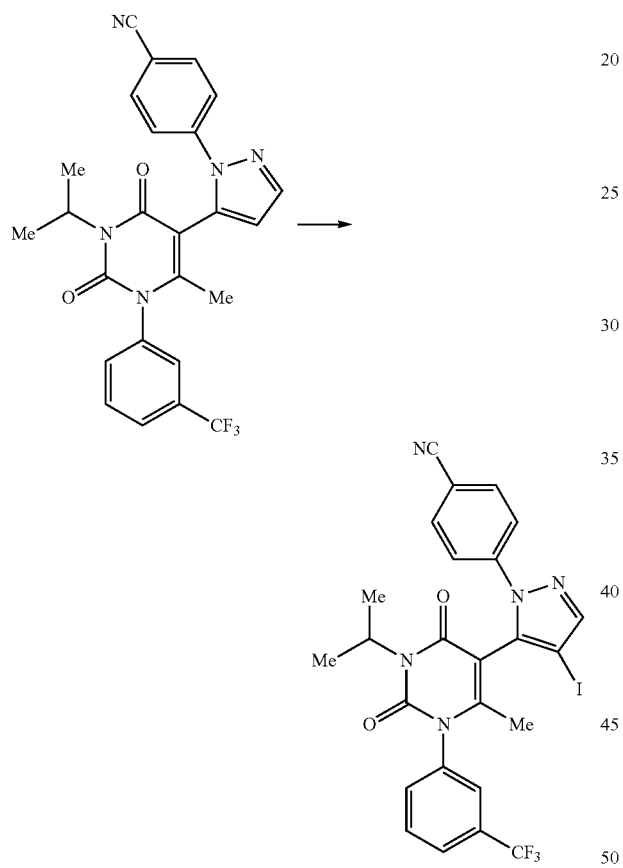

To a suspension of 4-(5-(3-isopropyl-6-methyl-2,4-dioxo-1-(3-(trifluoromethyl)phenyl)-1,2,3,4-tetrahydropyrimidin-5-yl)-1H-pyrazol-1-yl)benzonitrile (prepared in Example 42) (0.82 g) in acetonitrile (15 ml) were added iodine (0.26 g) and cerium ammonium nitrate (0.56 g) and the resulting mixture was stirred at 50° C. for one hour. The reaction mixture was cooled to room temperature, and thereto were added ethyl acetate (50 ml) and 5% aqueous sodium hydrogen sulfite solution (25 ml), and the mixture was partitioned. The aqueous layer was extracted with ethyl acetate, and the organic layer was washed with saturated saline and dried over anhydrous magnesium sulfate and then concentrated under reduced pressure. The residue was purified by silica gel column chromatography (eluent: hexane/ethyl acetate) to afford 4-(4-iodo-5-(3-isopropyl- 6-methyl-2,4-dioxo-1-(3-(trifluoromethyl)phenyl)-1,2,3,4-tetrahydropyrimidin-5-yl)-1H-pyrazol-1-yl)benzonitrile (0.95 g) as white solid.

$^1$H-NMR (300 MHz, CDCl$_3$) (δ PPM):
1.36-1.38 (m, 6H), 1.61 (s, 1.5H), 1.66 (s, 1.5H), 4.97-5.08 (m, 1H), 7.33 (d, 0.5H, J=7.8 Hz), 7.43-7.55 (m, 3.5H), 7.59-7.73 (m, 4H), 7.78 (d, 1H, J=1.5H)

Example 102

4-[5-[3,6-Dimethyl-2,4-dioxo-1-(3-trifluoromethylphenyl)-1,2,3,4-tetrahydropyrimidin-5-yl]-1H-pyrazol-1-yl]-3-(methylsulfonyl)benzonitrile

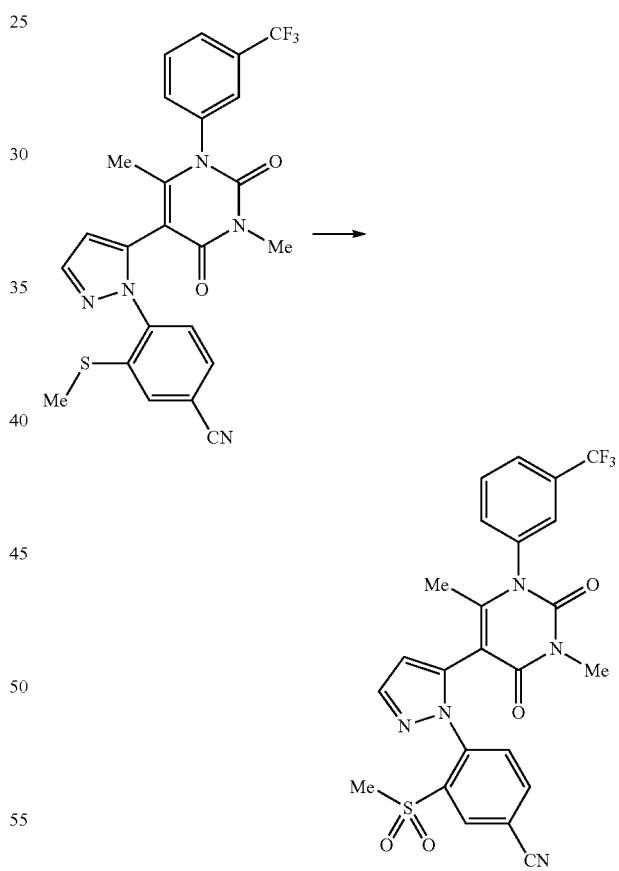

To a solution of 4-[5-[3,6-dimethyl-2,4-dioxo-1-(3-trifluoromethylphenyl)-1,2,3,4-tetrahydropyrimidin-5-yl]-1H-pyrazol-1-yl]-3-methylthiobenzonitrile (prepared in Example 36) (6.5 mg) in dichloromethane (1.0 ml) were added under ice-cooling meta-chloro benzoyl peroxide (7.6 mg) and the resulting mixture was stirred at room temperature. After four hours, thereto was added under ice-cooling meta-chloro benzoyl peroxide (1.5 mg) and the resulting mixture was stirred at room temperature for three hours. To the resulting mixture was added chloroform (20 ml) and washed with saturated aqueous sodium hydrogen carbonate solution (10 ml), and the organic layer was dried over sodium sulfate and then concentrated under reduced pressure. The residue was purified by preparative thin-layer chromatography to afford 4-[5-[3,6-dimethyl-2,4-dioxo-1-(3-trifluoromethylphenyl)-1,2,3,4-tetrahydropyrimidin-5-yl]-1H-pyrazol-1-yl]-3-(methylsulfonyl)benzonitrile.

$^1$H-NMR (CDCl$_3$: 300 MHz) (δ PPM):
1.68 (s, 3H), 3.32 (s, 3H), 3.41 (s, 3H), 6.41 (d, 1H, J=1.8 Hz), 7.69 (d, 1H, J=8.1 Hz), 7.15-7.45 (m, 2H), 7.57 (t, 1H, J=7.2 Hz), 7.77 (d, 1H, J=1.8 Hz), 7.91 (d, 2H, J=1.5 Hz), 8.44 (s, 1H)

Example 103

3-[5-[1-(4-Cyanophenyl)-1H-pyrazol-5-yl]-3,6-dimethyl-2,4-dioxo-3,4-dihydropyrimidin-1(2H)yl]benzoic acid

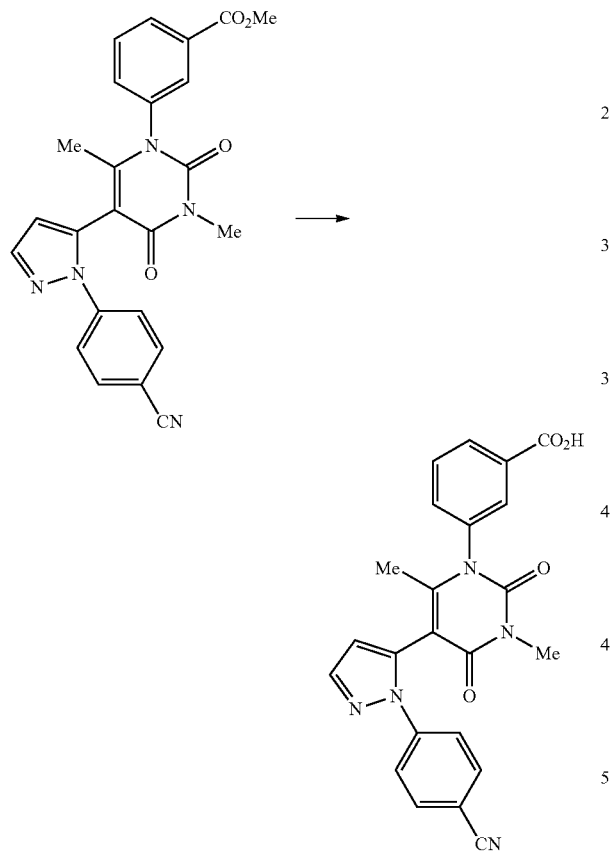

To a solution of 3-[5-[1-(4-cyanophenyl)-1H-pyrazol-5-yl]-3,6-dimethyl-2,4-dioxo-3,4-dihydropyrimidin-1(2H)-yl]phenylacetic acid methyl ester (prepared in Example 32) (239.6 mg) in tetrahydrofuran (2.0 ml) was added under ice-cooling sodium hydroxide (5M aqueous solution, 108 μl) and the resulting mixture was stirred at room temperature for twenty hours. The reaction mixture was washed with diethylether (15 ml), and the aqueous layer was acidified (pH=3) with potassium hydrogen sulfate and then extracted with ethyl acetate (50 ml), dried over anhydrous sodium sulfate and then concentrated under reduced pressure. The residue was purified by silica gel column chromatography (eluent: chloroform/methanol) to afford 3-(5-(1-(4-cyanophenyl)- 1H-pyrazol-5-yl)-3,6-dimethyl-2,4-dioxo-3,4-dihydropyrimidin-1(2H)-yl)benzoic acid (67.2 mg).

$^1$H-NMR (CDCl$_3$: 300 MHz) (δ PPM):
1.52 (s, 1.5H), 1.59 (s, 1.5H), 3.31 (d, 3H, J=2.4 Hz), 6.44 (d, 1H, J=1.8 Hz), 7.22-7.26 (m, 1H), 7.44 (s, 1H), 7.51-7.57 (m, 3H), 7.66-7.76 (m, 3H), 8.13 (s, 1H)

Example 104

3-[5-[1-(4-Cyanophenyl)1H-pyrazol-5-yl]-3,6-dimethyl-2,4-dioxo-3,4-dihydropyrimidin-1(2H)yl]benzamide

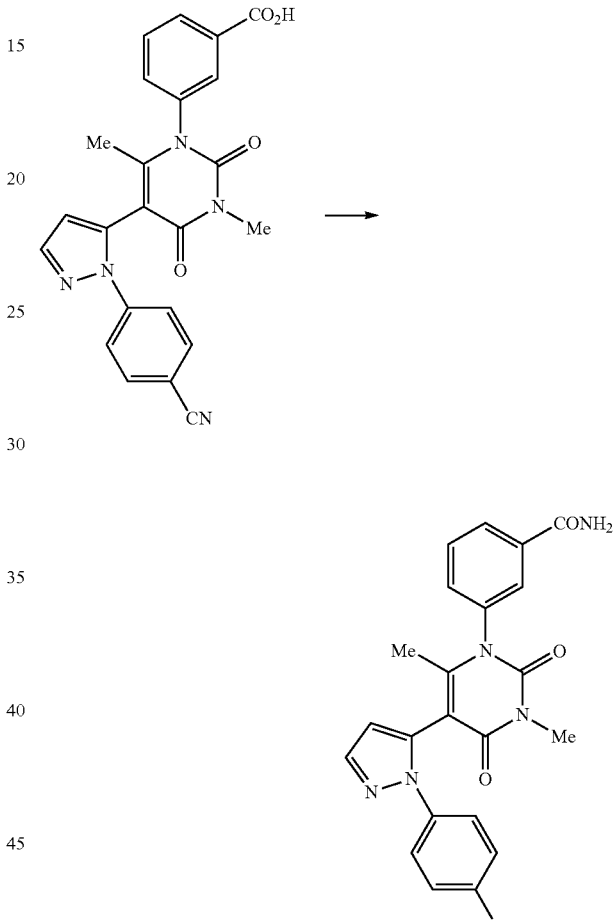

A solution of 3-[5-[1-(4-cyanophenyl)1H-pyrazol-5-yl]-3,6-dimethyl-2,4-dioxo-3,4-dihydropyrimidin-1(2H)yl]phenylacetic acid (prepared in Example 103), benzotriazol-1-yl-oxytripyrrolidine phosphonium hexafluorophosphate (30.8 mg), 1-hydroxy-7-azabenzotriazole (8.6 mg) and N,N-diethylisopropylamine (76 μl) in N,N-dimethy formamide (0.7 ml) was stirred at room temperature for thirty minutes. Thereto was added ammonium chloride (15.7 mg) and the resulting mixture was stirred at room temperature for twenty-two hours, and to the reaction mixture was added ethyl acetate (30 ml) and the resulting mixture was washed with 1M hydrochloric acid (10 ml) and saturated saline (10 ml), dried over anhydrous sodium sulfate and then concentrated under reduced pressure. The residue was purified by silica gel column chromatography (eluent: chloroform/methanol) to afford 3-(5-(1-(4-cyanophenyl)-1H-pyrazol-5-yl)-3,6-dimethyl-2,4-dioxo-3,4-dihydropyrimidin-1(2H)-yl)benzamide (18.0 mg).
¹H-NMR (CDCl₃: 300 MHz) (δ PPM):
1.59 (s, 1.5H), 1.65 (s, 1.5H), 3.28 (s, 1.5H), 3.30 (s, 1.5H), 6.41 (dd, 1H, J=7.5, 1.8 Hz), 7.20-7.22 (m, 0.5H), 7.37-7.40 (m, 0.5H), 7.50-7.57 (m, 3H), 7.62-7.71 (m, 3H), 7.73-7.75 (m, 2H)

Examples 105-106

The compounds indicated in the below-mentioned table (Examples 105-106) were obtained by using the corresponding starting materials according to the similar reaction and treatment method to those described in Example 104.

Example 105

3-[5-[1-(4-cyanophenyl)1H-pyrazol-5-yl]-3,6-dimethyl-2,4-dioxo-3,4-dihydropyrimidin-1(2H)yl]-N-methylbenzamide;

Example 106

3-[5-[1-(4-cyanophenyl)1H-pyrazol-5-yl]-3,6-dimethyl-2,4-dioxo-3,4-dihydropyrimidin-1(2H)yl]-N,N-dimethylbenzamide;

Example 107

4-(5-(1-(Biphenyl-3-yl)-3,6-dimethyl-2,4-dioxo-1,2,3,4-tetrahydropyrimidin-5-yl)-1H-pyrazol-1-yl)benzonitrile

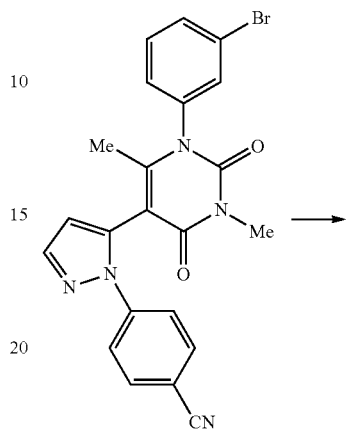

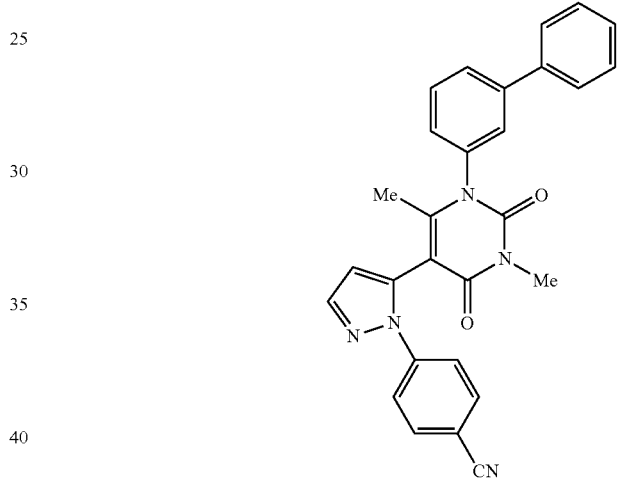

TABLE 51

| Ex. | Ar¹ | Measurement cond. | ¹H-NMR (δ PPM) |
|---|---|---|---|
| 105 | 3-CONHMe-phenyl | 1 | 1.58 (s, 1.5H), 1.66 (s, 1.5H), 2.95 (dd, 3H, J = 4.8, 1.5 Hz), 3.30 (d, 3H, J = 8.1 Hz), 6.21 (brs, 1H), 6.40 (dd, 1H, J = 9.0, 1.8 Hz), 7.14-7.18 (m, 1H), 7.31-7.34 (m, 1H), 7.50-7.57 (m, 3H), 7.65-7.75 (m, 4H) |
| 106 | 3-CONMe₂-phenyl | 1 | 1.59 (s, 1.5H), 1.66 (s, 1.5H), 2.94 (s. 1.5H), 2.95 (s, 1.5H), 3.05 (s, 3H), 3.30 (d, 3H, J = 6.0 Hz), 6.39 (dd, 1H, J = 2.4, 1.8 Hz), 7.06-7.08 (m, 0.5H), 7.14-7.15 (m, 0.5H), 7.23-7.28 (m, 1H), 7.48-7.53 (m, 4H), 7.65-7.68 (m, 2H), 7.74 (t, 1H, J = 1.8 Hz) |

A solution of 4-[5-[1-(3-bromophenyl)-3,6-dimethyl-2,4-dioxo-1,2,3,4-tetrahydropyrimidin-5-yl]-H-pyrazol-1-yl]benzonitrile (prepared in Example 34) (2.2 mg), phenylboronic acid (2.3 mg), tetrakis(triphenylphosphine)palladium (2.4 mg) and sodium carbonate (2.2 mg) in N,N-dimethy formamide/water=1/1 (1.0 ml) was stirred at 100° C. for one hour. To the reaction mixture was added ethyl acetate (30 ml) and the resulting mixture was washed with water (10 ml) and saturated saline (10 ml), dried over anhydrous sodium sulfate and then concentrated under reduced pressure. The residue was purified by preparative thin-layer chromatography to afford 4-(5-(1-(biphenyl-3-yl)-3,6-dimethyl-2,4-dioxo-1,2,3,4-tetrahydropyrimidin-5-yl)-1H-pyrazol-1-yl)benzonitrile (2.3 mg).

$^1$H-NMR (CDCl$_3$: 300 MHz) (δ PPM):

1.63 (d, 3H, J=1.8 Hz), 3.32 (s, 3H), 6.42 (dd, 1H, J=4.2, 1.8 Hz), 6.97-7.00 (m, 0.5H), 7.15-7.18 (m, 0.5H), 7.37-7.55 (m, 9H), 7.63-7.69 (m, 3H), 7.75 (t, 1H, J=1.5 Hz)

Example 108

4-[5-[3,6-Dimethyl-2,4-dioxo-1-(3-ethylphenyl)-1,2,3,4-tetrahydropyrimidin-5-yl]-1H-pyrazol-1-yl]benzonitrile

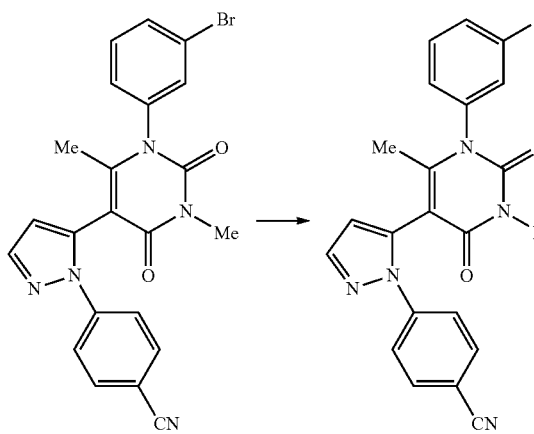

To a solution of 4-[5-[1-(3-bromophenyl)-3,6-dimethyl-2,4-dioxo-1,2,3,4-tetrahydropyrimidin-5-yl]-1H-pyrazol-1-yl]benzonitrile (prepared in Example 34) (15.5 mg) and bis(tri-t-butylphosphine)palladium (1.0 mg) in tetrahydrofuran (1.0 ml) was added zinc diethyl (1.0 M normal hexane solution, 0.06 ml) and the resulting mixture was stirred at 60° C. for thirty minutes. To the reaction mixture was added ethyl acetate (30 ml) and the mixture was washed with water (10 ml) and saturated saline (10 ml), dried over anhydrous sodium sulfate and then concentrated under reduced pressure. The residue was purified by preparative thin-layer chromatography to afford 4-[5-[3,6-dimethyl-2,4-dioxo-1-(3-ethylphenyl)-1,2,3,4-tetrahydropyrimidin-5-yl]-1H-pyrazol-1-yl]benzonitrile (3.6 mg).

$^1$H-NMR (CDCl$_3$: 300 MHz) (δ PPM):

1.16-1.22 (m, 3H), 1.58 (s, 3H), 2.61-2.68 (m, 2H), 3.30 (s, 3H), 6.41 (d, 1H, J=1.8 Hz), 6.81 (d, 1H, J=6.6 Hz), 6.99 (d, 1H, J=9.0 Hz), 7.25 (d, 1H, J=7.8 Hz), 7.23-7.39 (m, 1H), 7.52 (dd, 2H, J=8.4, 3.9 Hz), 7.67 (dd, 2H, J=8.4, 3.3 Hz), 7.74 (d, 1H, J=1.8 Hz)

Example 109

(R)-4-(5-(3-(1-Hydroxypropan-2-yl)-6-methyl-2,4-dioxo-1-(3-(trifluoromethyl)phenyl)-1,2,3,4-tetrahydropyrimidin-5-yl)-1H-pyrazol-1-yl)benzonitrile

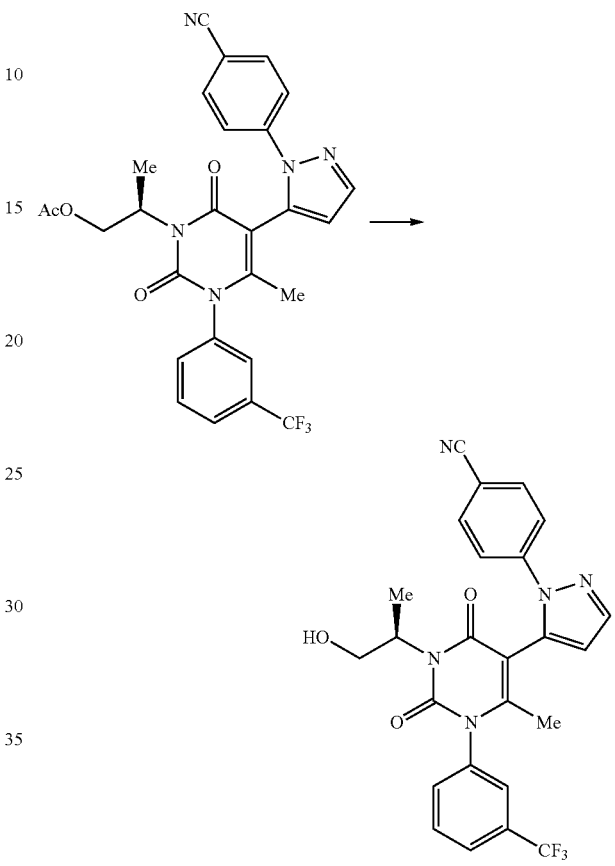

To a solution of (R)-2-(5-(1-(4-cyanophenyl)-1H-pyrazol-5-yl)-4-methyl-2,6-dioxo-3-(3-(trifluoromethyl)phenyl)-2,3-dihydropyrimidin-1(6H)-yl)propyl acetate (prepared in example 47) (31.9 mg) in ethanol (1.0 ml) was added under ice-cooling 1M aqueous sodium hydroxide solution (65.2 μl) and the resulting mixture was stirred for one hour under ice-cooling. To the reaction mixture was added ethyl acetate (100 ml) and the mixture was washed with 1M hydrochloric acid (30 ml) and saturated saline (30 ml), dried over anhydrous sodium sulfate and then concentrated under reduced pressure. The residue was purified by silica gel column chromatography (eluent: hexane/ethyl acetate) to afford (R)-4-(5-(3-(1-hydroxypropan-2-yl)-6-methyl-2,4-dioxo-1-(3-(trifluoromethyl)phenyl)-1,2,3,4-tetrahydropyrimidin-5-yl)-1H-pyrazol-1-yl)benzonitrile (24.6 mg) as brown solid.

$^1$H-NMR (300 MHz, CDCl$_3$) (δ PPM):

1.25-1.39 (m, 3H), 1.65 (s, 1.5H), 1.70 (s, 1.5H), 2.57-(brs, 1H), 3.64-3.73 (m, 1H), 3.88-4.01 (m, 1H), 5.08 (brs, 1H), 6.46 (d, 1H, J=7.2 Hz), 7.35-7.78 (m, 9H)

Example 110

(R)-4-(5-(3-(1-Hydroxypropan-2-yl)-6-methyl-2,4-dioxo-1-(3-(trifluoromethyl)phenyl)-1,2,3,4-tetrahydropyrimidin-5-yl)-4-methyl-1H-pyrazol-1-yl)benzonitrile

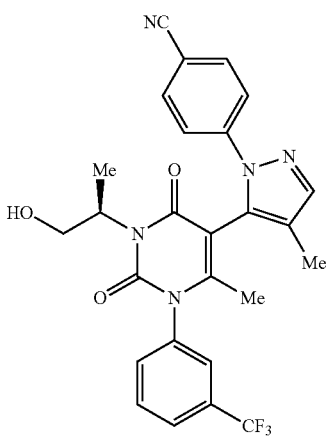 [SMILES: Cc1cnn(-c2ccc(C#N)cc2)c1-c1c(C)n(-c2cccc(C(F)(F)F)c2)c(=O)n([C@H](C)CO)c1=O]

The intended compound was obtained by using the corresponding starting materials according to the similar reaction and treatment method to those described in Example 109.

¹H-NMR (300 MHz, CDCl₃) (δ PPM):
1.21-1.40 (m, 3H), 1.56 (d, 1.5H, J=1.5 Hz), 1.61 (d, 1.5H, J=1.5 Hz), 2.02-2.04 (m, 3H), 3.75 (brs, 1H), 3.98 (brs, 1H), 5.13 (brs, 1H), 7.31-7.55 (m, 4H), 7.66-7.78 (m, 5H)

Example 111

(R)-4-(5-(3-(1-Hydroxypropan-2-yl)-2,4-dioxo-1-(3-(trifluoromethyl)phenyl)-1,2,3,4-tetrahydropyrimidin-5-yl)-1H-pyrazol-1-yl)benzonitrile

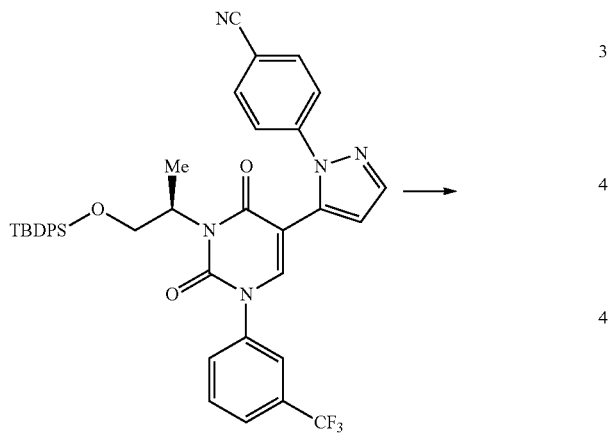

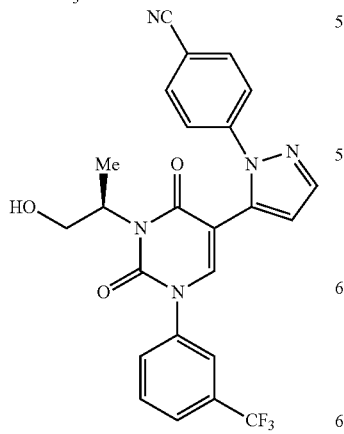

The intended compound was obtained by using the corresponding starting materials according to the similar reaction and treatment method to those described in Reference Example 102.

¹H-NMR (300 MHz, CDCl₃) (δ PPM):
1.33 (d, 3H, J=7.0 Hz), 2.30 (brs, 1H), 3.73 (dd, 1H, J=11.8, 3.8 Hz), 3.98 (t, 1H, J=9.0 Hz), 5.07-5.14 (m, 1H), 6.51 (d, 1H, J=1.7 Hz), 7.50 (s, 1H), 7.55-7.68 (m, 5H), 7.71-7.75 (m, 4H)

Examples 112-113

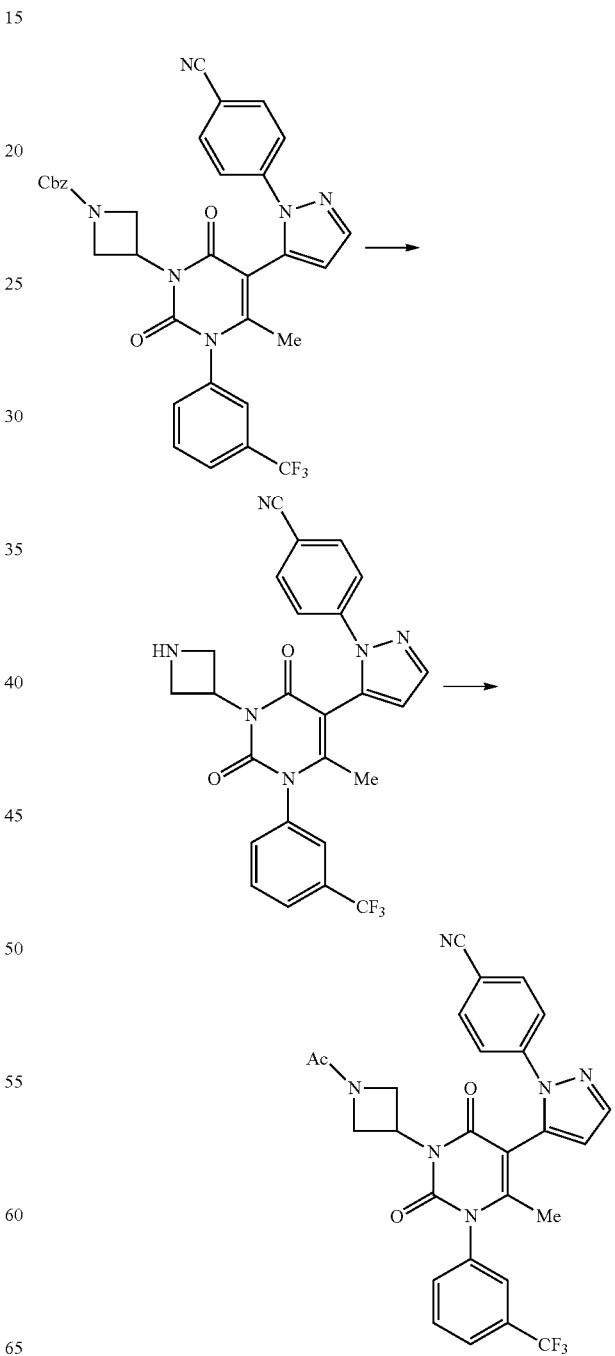

Example 112

4-(5-(3-(Azetidin-3-yl)-6-methyl-2,4-dioxo-1-(3-(trifluoromethyl)phenyl)-1,2,3,4-tetrahydropyrimidin-5-yl)-1H-pyrazol-1-yl)benzonitrile The intended compound was obtained by using the starting materials prepared in Example 45 according to the similar reaction and treatment method to those described in Example 72.

$^1$H-NMR (CDCl$_3$: 300 MHz) (δ PPM):
1.85 (d, 3H, J=5.7 Hz), 4.06-4.47 (m, 4H), 5.33-5.53 (m, 1H), 6.58-6.64 (m, 1H), 7.48-7.88 (m, 9H)

Example 113

4-(5-(3-(1-Acetylazetidin-3-yl)-6-methyl-2,4-dioxo)-1H-pyrazol-1-yl)benzonitrile-1-(3-(trifluoromethyl)phenyl)-1,2,3,4-tetrahydropyrimidin-5-yl The intended compound was obtained by using 4-(5-(3-(azetidin-3-yl)-6-methyl-2,4-dioxo-1-(3-(trifluoromethyl)phenyl)-1,2,3,4-tetrahydropyrimidin-5-yl)-1H-pyrazol-1-yl)benzonitrile (prepared in Example 112) according to the similar reaction and treatment method to those described in Example 86.

$^1$H-NMR (CDCl$_3$: 300 MHz) (δ PPM):
1.66-1.70 (m, 3H), 1.80-1.84 (m, 3H), 4.17-4.53 (m, 4H), 5.31-5.42 (m, 1H), 6.45 (dd, 1H, J=5.7, 1.5 Hz), 7.32 (d, 1H, J=9.3 Hz), 7.39 (s, 0.5H), 7.47 (d, 0.5H, J=8.1 Hz), 7.56 (dd, 2H, J=9.0, 2.4 Hz), 7.65-7.80 (m, 5H)

Example 114

4-(5-(6-Methyl-3-(1-methylazetidin-3-yl)-2,4-dioxo-1-(3-(trifluoromethyl)phenyl)-1,2,3,4-tetrahydropyrimidin-5-yl)-1H-pyrazol-1-yl)benzonitrile The intended compound was obtained by using 4-(5-(3-(azetidin-3-yl)-6-methyl-2,4-dioxo-1-(3-(trifluoromethyl)phenyl)-1,2,3,4-tetrahydropyrimidin-5-yl)-1H-pyrazol-1-yl)benzonitrile (prepared in Example 112) and formaldehyde according to the similar reaction and treatment method to those described in Example 69.

$^1$H-NMR (CDCl$_3$: 300 MHz) (δ PPM):
1.61 (s, 1.5H), 1.65 (s, 1.5H), 2.25 (d, 3H, J=1.5 Hz), 2.66-2.78 (m, 1H), 2.95 (t, 1H, J=6.9 Hz), 3.82-3.88 (m, 2H), 4.37-4.49 (m, 1H), 6.40 (dd, 1H, J=6.9, 1.5 Hz), 7.27 (d, 1H, J=8.4 Hz), 7.35 (s, 0.5H), 7.40 (d, 0.5H, J=8.4 Hz), 7.49-7.54 (m, 2H), 7.58-7.61 (m, 1H), 7.68-7.74 (m, 4H)

Examples 115-117

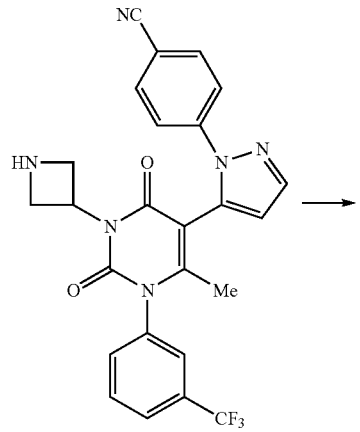

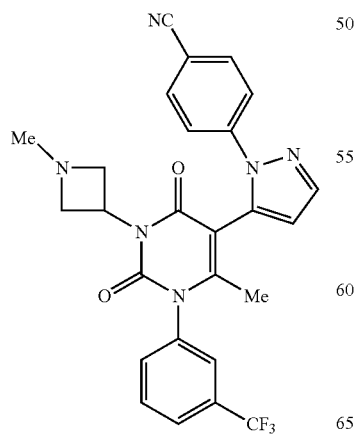

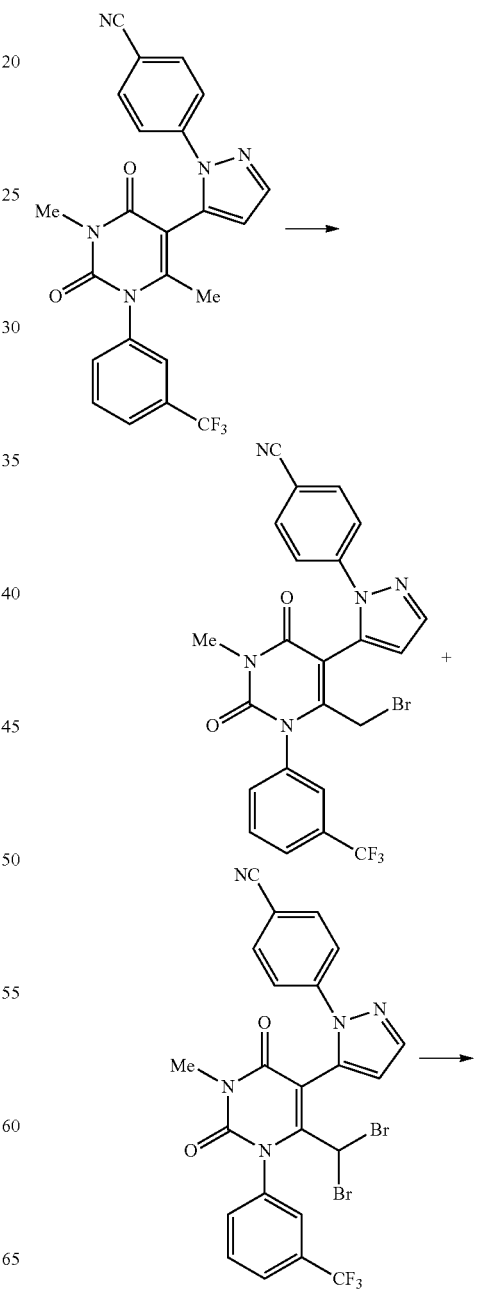

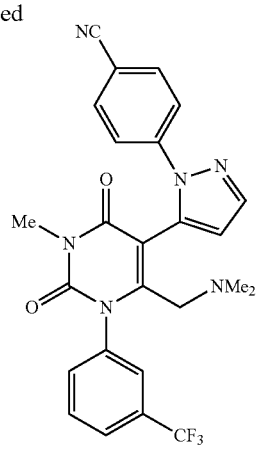

Example 115

4-(5-(6-(bromomethyl)-3-methyl-2,4-dioxo-1-(3-(trifluoromethyl)phenyl)-1,2,3,4-tetrahydropyrimidin-5-yl)-1H-pyrazol-1-yl)benzonitrile;

Example 116

4-(5-(6-(dibromomethyl)-3-methyl-2,4-dioxo-1-(3-(trifluoromethyl)phenyl)-1,2,3,4-tetrahydropyrimidin-5-yl)-1H-pyrazol-1-yl)benzonitrile To a solution of 4-[5-[3,6-dimethyl-2,4-dioxo-1-(3-trifluoromethylphenyl)-1,2,3,4-tetrahydropyrimidin-5-yl]-1H-pyrazol-1-yl]benzonitrile (prepared in Example 1) (30.0 mg) in tetrahydrofuran (1.0 ml) was added at 0° C. lithium hexamethyldisilazide (0.1 ml: 1M tetrahydrofuran solution) followed by an addition of N-bromosuccinimide (14.4 mg), and the resulting mixture was stirred at 0° C. for a half hour. To the reaction mixture was added saturated aqueous ammonium chloride solution (5 ml) and the mixture was extracted with ethyl acetate (10 ml×2). The organic layer was washed with saturated saline (10 ml), dried over anhydrous sodium sulfate and then concentrated under reduced pressure. The residue was purified by silica gel column chromatography (eluent: hexane/ethyl acetate) to afford 4-[5-(6,6-dibromomethyl)-3-methyl-2,4-dioxo-1-(3-trifluoromethylphenyl)-1,2,3,4-tetrahydropyrimidin-5-yl]-1H-pyrazol-1-yl]benzonitrile (5.4 mg) and 4-[5-(6-bromomethyl)-3-methyl-2,4-dioxo-1-(3-trifluoromethylphenyl)-1,2,3,4-tetrahydropyrimidin-5-yl]-1H-pyrazol-1-yl]benzonitrile (6.9 mg). 4-(5-(6-(Bromomethyl)-3-methyl-2,4-dioxo-1-(3-(trifluoromethyl)phenyl)-1,2,3,4-tetrahydropyrimidin-5-yl)-1H-pyrazol-1-yl)benzonitrile:

$^1$H-NMR (CDCl$_3$: 300 MHz) (δ PPM):
3.29 (s, 1.5H), 3.30 (s, 1.5H), 3.65 (d, 0.5H, J=11.0 Hz), 3.68 (d, 0.5H, J=11.0 Hz), 3.99 (d, 0.5H, J=11.0 Hz), 4.01 (d, 0.5H, J=11.0 Hz), 6.60 (d, 0.5H, J=1.8 Hz), 6.10 (d, 0.5H, J=1.8 Hz), 7.58-7.74 (m, 7H), 7.80-7.84 (m, 2H)

4-(5-(6-(Dibromomethyl)-3-methyl-2,4-dioxo-1-(3-(trifluoromethyl)phenyl)-1,2,3,4-tetrahydropyrimidin-5-yl)-1H-pyrazol-1-yl)benzonitrile $^1$H-NMR (CDCl$_3$: 300 MHz) (δ PPM):
3.27 (s, 1.5H), 3.28 (s, 1.5H), 3.44 (s, 0.5H), 3.47 (s, 0.5H), 6.68 (d, 1H, J=1.5 Hz), 7.61 (d, 2H, J=6.8 Hz), 7.68-7.77 (m, 4H), 7.82 (s, 1H), 7.84-7.87 (m, 2H)

Example 117

4-(5-(6-((Dimethylamino)methyl)-3-methyl-2,4-dioxo-1-(3-(trifluoromethyl)phenyl)-1,2,3,4-tetrahydropyrimidin-5-yl)-1H-pyrazol-1-yl)benzonitrile To a solution of 4-[5-(6-bromomethyl)-3-methyl-2,4-dioxo-1-(3-trifluoromethylphenyl)-1,2,3,4-tetrahydropyrimidin-5-yl]-1H-pyrazol-1-yl]benzonitrile (prepared in Example 115) (20.0 mg) in acetonitrile (1.0 ml) was added at room temperature dimethyl amine (40 μl: 1M tetrahydrofuran solution) and the resulting mixture was stirred at room temperature for one hour. The reaction mixture was concentrated under reduced pressure and the residue was purified by silica gel column chromatography (eluent: hexane/ethyl acetate) to afford 4-[5-(6-(dimethylamino)methyl)-3-methyl-2,4-dioxo-1-(3-trifluoromethylphenyl)-1,2,3,4-tetrahydropyrimidin-5-yl]-1H-pyrazol-1-yl]benzonitrile (5.1 mg).

$^1$H-NMR (CDCl$_3$: 300 MHz) (δ PPM):
11.55 (s, 3H), 1.58 (s, 3H), 2.52-2.61 (m, 2H), 3.34 (s, 1.5H), 3.36 (s, 1.5H), 6.38 (d, 0.5H, J=1.8 Hz), 6.42 (d, 0.5H, J=1.8 Hz), 7.50-7.58 (m, 4H), 7.60-7.69 (m, 4H), 7.75 (d, 0.5H, J=1.8 Hz), 7.76 (d, 0.5H, J=1.8 Hz)

Example 118

4-(5-(6-(Hydroxymethyl)-3-methyl-2,4-dioxo-1-(3-(trifluoromethyl)phenyl)-1,2,3,4-tetrahydropyrimidin-5-yl)-1H-pyrazol-1-yl)benzonitrile

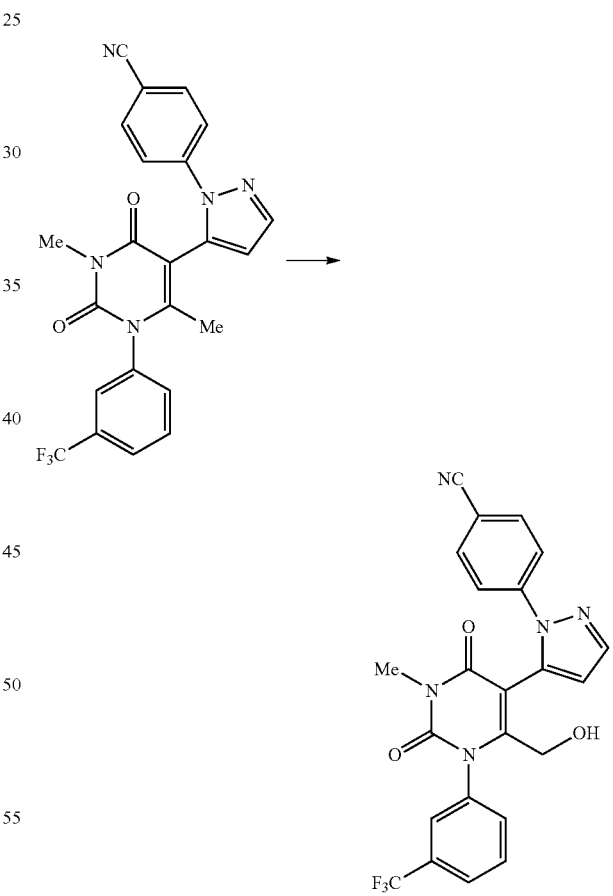

To a solution of 4-[5-[3,6-dimethyl-2,4-dioxo-1-(3-trifluoromethylphenyl)-1,2,3,4-tetrahydropyrimidin-5-yl]-1H-pyrazol-1-yl]benzonitrile (prepared in Example 1) (50.0 mg) in dioxane (1.0 ml) were added acetic acid (0.5 ml) and selenium dioxide (74.0 mg) and the resulting mixture was stirred with heating under reflux for six hours. The reaction mixture was concentrated under reduced pressure and the residue was purified by silica gel column chromatography (eluent: hexane/ethyl acetate) to afford 4-[5-(6-hydroxymethyl)-3-methyl-2,4-dioxo-1-(3-trifluoromethylphenyl)-1,2,3,4-tetrahydropyrimidin-5-yl]-1H-pyrazol-1-yl]benzonitrile (3.7 mg).

$^1$H-NMR (CDCl$_3$: 300 MHz) (δ PPM):
3.23 (s, 1.5H), 3.25 (s, 1.5H), 3.93 (dd, 1H, J=11.8, 5.6 Hz), 4.15 (d, 1H, J=11.8 Hz), 6.46 (t, 1H, J=2.1 Hz), 7.46-7.74 (m, 9H)

Example 119

(R)-4-(5-(3-(1-Methoxypropan-2-yl)-2,4-dioxo-1-(3-(trifluoromethyl)phenyl)-1,2,3,4-tetrahydropyrimidin-5-yl)-1H-pyrazol-1-yl)benzonitrile

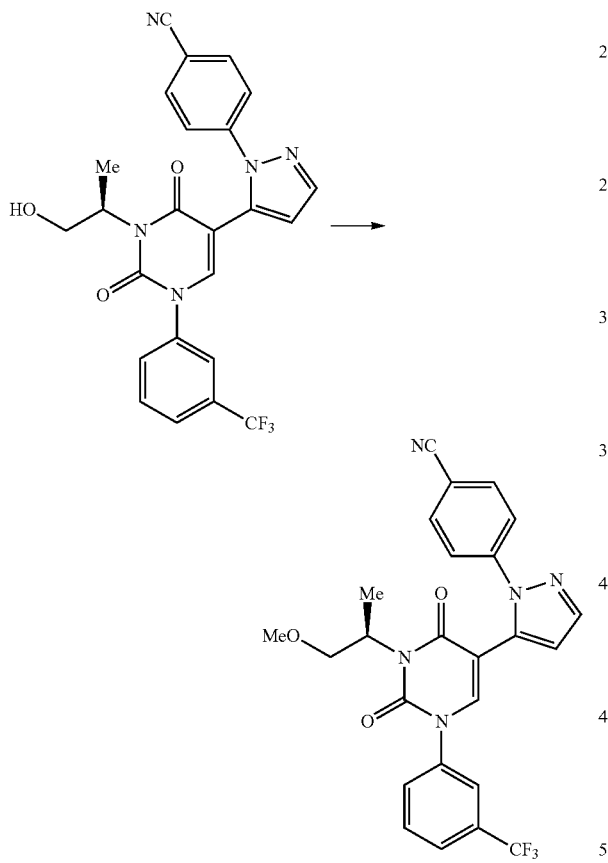

To a solution of (R)-4-(5-(3-(1-hydroxypropan-2-yl)-2,4-dioxo-1-(3-(trifluoromethyl)phenyl)-1,2,3,4-tetrahydropyrimidin-5-yl)-1H-pyrazol-1-yl)benzonitrile (prepared in Example 111) (95.1 mg) in dichloromethane (1.0 ml) were added under ice-cooling trifluoromethanesulfonic anhydride (50.2 μl) and N,N-diisopropylethylamine (70.2 μl) and the resulting mixture was stirred under ice-cooling for one hour. To the reaction mixture was added methanol (5 ml) and the mixture was stirred at room temperature for one hour. The reaction mixture was concentrated under reduced pressure and the residue was purified by silica gel column chromatography (eluent: hexane/ethyl acetate) to afford (R)-4-(5-(3-(1-methoxypropan-2-yl)-2,4-dioxo-1-(3-(trifluoromethyl)phenyl)-1,2,3,4-tetrahydropyrimidin-5-yl)-1H-pyrazol-1-yl)benzonitrile (51.0 mg) as pale yellow solid.

$^1$H-NMR (CDCl$_3$: 300 MHz) (δ PPM):
1.31 (d, 3H, J=7.2 Hz), 3.25 (s, 3H), 3.33 (dd, 1H, J=7.2, 2.5 Hz), 3.99 (t, 1H, J=9.9 Hz), 5.14-5.25 (m, 1H), 6.51 (s, 1H), 7.49 (s, 1H), 7.56-7.66 (m, 5H), 7.70-7.74 (m, 4H)

Example 120

(R)-2-(5-(1-(4-Cyanophenyl)-1H-pyrazol-5-yl)-2,6-dioxo-3-(3-(trifluoromethyl)phenyl)-2,3-dihydropyrimidin-1(6H)-yl)propylmethane sulfonate

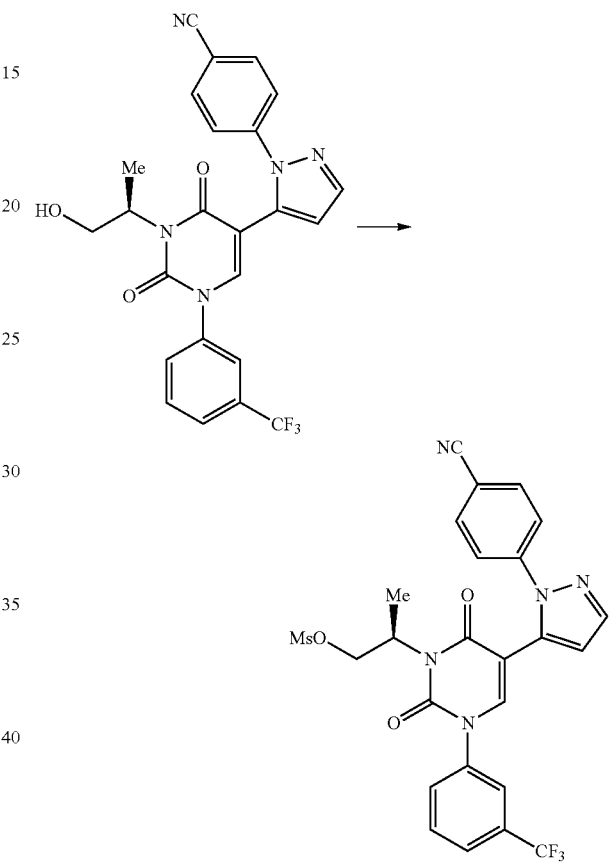

To a solution of (R)-4-(5-(3-(1-hydroxypropan-2-yl)-2,4-dioxo-1-(3-(trifluoromethyl)phenyl)-1,2,3,4-tetrahydropyrimidin-5-yl)-1H-pyrazol-1-yl)benzonitrile (prepared in Example 111) (17.3 mg) in dichloromethane (1.0 ml) was added under ice-cooling methanesulfonyl chloride (5.6 μl) and triethylamine (10.0 μl) and the resulting mixture was stirred under ice-cooling for fifteen minutes. To the reaction mixture was added saturated aqueous sodium hydrogen carbonate solution (1 ml) followed by an addition of ethyl acetate (50 ml), and the resulting mixture was washed with water (10 ml) and saturated saline (10 ml), dried over anhydrous sodium sulfate and then concentrated under reduced pressure. The residue was purified by silica gel column chromatography (eluent: hexane/ethyl acetate) to afford (R)-2-(5-(1-(4-cyanophenyl)-1H-pyrazole-5-yl)-2,6-dioxo-3-(3-(trifluoromethyl)phenyl)-2,3-dihydropyrimidin-1(6H)-yl)propyl-methanesulfonate (2.6 mg) as brown solid.

$^1$H-NMR (CDCl$_3$: 300 MHz) (δ PPM):
1.39 (d, 3H, J=7.2H), 2.94 (s, 3H), 4.04-4.11 (m, 2H), 5.28-5.32 (m, 1H), 6.51 (d, 1H, J=1.8 Hz), 7.33 (s, 1H), 7.51-7.73 (m, 9H)

Example 121

2-(5-(1-(4-Cyanophenyl)-1H-pyrazol-5-yl)-2,6-dioxo-3-(3-(trifluoromethyl)phenyl)-2,3-dihydropyrimidin-1(6H)-yl)propionic acid

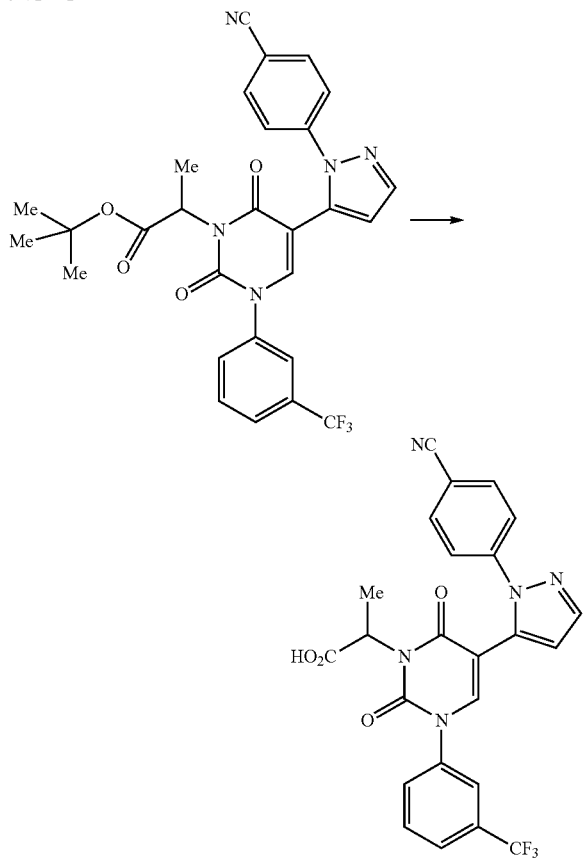

The intended compound was prepared by using the compound prepared in Example 26 according to the similar reaction and treatment method to those described in Example 85.

$^1$H-NMR (CDCl$_3$: 300 MHz) (δ PPM):
1.45 (d, 3H, J=7.0 Hz), 5.38 (q, 1H, J=7.0 Hz), 6.66 (d, 1H, J=1.8 Hz), 7.73-7.83 (m, 8H), 7.89 (s, 1H), 8.08 (s, 1H)

Example 122

(S)-5-(1-(4-Bromophenyl)-1H-pyrazol-5-yl)-3-(1-hydroxypropan-2-yl)-6-methyl-1-(3-(trifluoromethyl)phenyl)pyrimidin-2,4(1H,3H)-dione

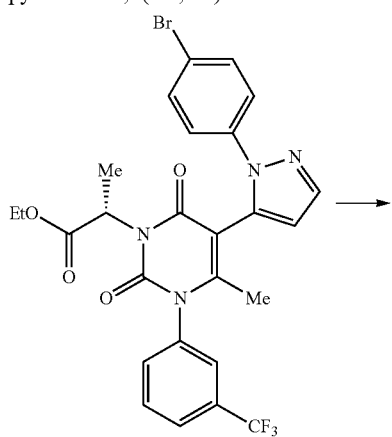

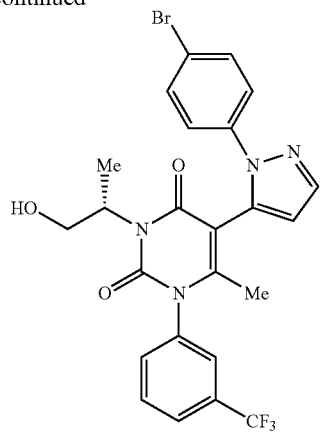

To a solution of (S)-ethyl 2-(5-(1-(4-bromophenyl)-1H-pyrazol-5-yl)-4-methyl-2,6-dioxo-3-(3-(trifluoromethyl)phenyl)-2,3-dihydropyrimidin-1(6H)-yl)propanoate (prepared in Example 46) (51.6 mg) in dichloromethane (0.9 ml) was added a solution of diisobutylaluminium hydride in hexane (1.0 M, 0.21 ml) at −78° C. and the resulting mixture was stirred at −78° C. for seven hours. To the reaction mixture were added 2M aqueous potassium sodium tartrate solution (1 ml) and diethylether (20 ml) and the resulting mixture was stirred at room temperature for thirty minutes. To the reaction mixture was then added ethyl acetate (50 ml) and the resulting mixture was washed with water (10 ml) and saturated saline (10 ml), dried over anhydrous sodium sulfate and then concentrated under reduced pressure. The residue was dissolved in methanol (1.0 ml) and thereto was added at 0° C. sodium borohydride (4.9 mg) and the resulting mixture was stirred at room temperature for two hours. To the reaction mixture was added 1M hydrochloric acid and the resulting mixture was stirred at room temperature for thirty minutes. To the reaction mixture was then added ethyl acetate (50 ml) and the mixture was washed with water (10 ml), saturated aqueous sodium hydrogen carbonate solution (10 ml) and saturated saline (10 ml), dried over anhydrous sodium sulfate and then concentrated under reduced pressure. The residue was purified by silica gel column chromatography (eluent: hexane/ethyl acetate) to afford (S)-5-(1-(4-bromophenyl)-1H-pyrazol-5-yl)-3-(1-hydroxypropan-2-yl)-6-methyl-1-(3-(trifluoromethyl)phenyl)pyrimidin-2,4(1H,3H)-dione (15.0 mg) as colorless liquid.

$^1$H-NMR (CDCl$_3$: 300 MHz) (δ PPM):
1.27-1.35 (m, 3H), 1.54 (d, 3H, J=5.1 Hz), 3.65-3.76 (m, 1H), 3.87-3.97 (m, 1H), 5.08 (brs, 1H), 6.40 (dt, 1H, J=4.5, 1.8 Hz), 7.23 (dt, 1.5H, J=8.7, 1.5 Hz), 7.30 (d, 0.5H, J=5.4 Hz), 7.37-7.42 (m, 1H), 7.47-7.63 (m, 5H), 7.68-7.71 (m, 1H)

Example 123

(S)-4-(5-(3-(1-Hydroxypropan-2-yl)-6-methyl-2,4-dioxo-1-(3-(trifluoromethyl)phenyl)-1,2,3,4-tetrahydropyrimidin-5-yl)-1H-pyrazol-1-yl)benzonitrile

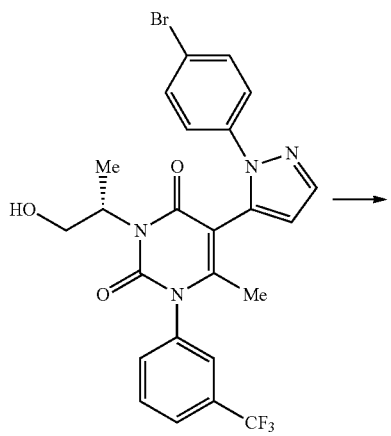

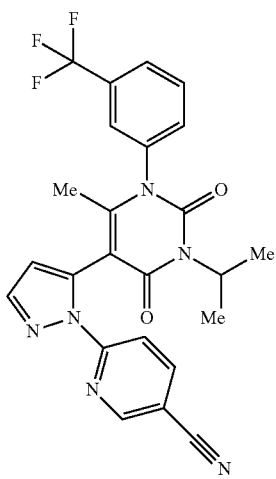 [SMILES: Cc1c(-c2ccnn2-c2ccc(C#N)cn2)c(=O)n(C(C)C)c(=O)n1-c1cccc(C(F)(F)F)c1]

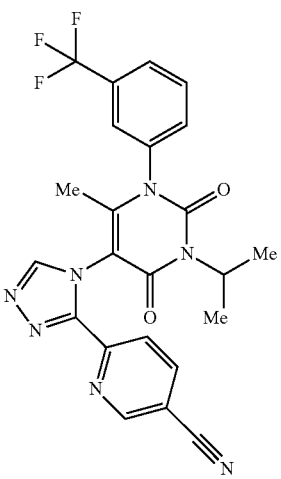 [SMILES: Cc1c(-n2cnnc2-c2ccc(C#N)cn2)c(=O)n(C(C)C)c(=O)n1-c1cccc(C(F)(F)F)c1]

To a solution of (S)-5-(1-(4-bromophenyl)-1H-pyrazol-5-yl)-3-(1-hydroxypropan-2-yl)-6-methyl-1-(3-(trifluoromethyl)phenyl)pyrimidin-2,4(1H,3H)-dione (prepared in Example 122) (5.0 mg) in N,N-dimethy formamide (1.0 ml) were added zinc cyanide (10.3 mg), zinc dust (1.2 mg) and tetrakis(triphenylphosphine)palladium (5.3 mg) and the resulting mixture was stirred at 120° C. for four hours. The reaction mixture was filtered and thereto was added ethyl acetate (50 ml) and the mixture was washed with water (10 ml) and saturated saline (10 ml), dried over anhydrous sodium sulfate and then concentrated under reduced pressure. The residue was purified by silica gel column chromatography (eluent: hexane/ethyl acetate) to afford (S)-4-(5-(3-(1-hydroxypropan-2-yl)-6-methyl-2,4-dioxo-1-(3-(trifluoromethyl)phenyl)-1,2,3,4-tetrahydropyrimidin-5-yl)-1H-pyrazol-1-yl)benzonitrile (1.9 mg) as white solid.

¹H-NMR (CDCl₃: 300 MHz) (δ PPM):

1.30-1.37 (m, 3H), 1.66 (d, 1.5H, J=1.8 Hz), 1.70 (d, 1.5H, J=1.8 Hz), 3.71-3.81 (m, 1H), 3.92-4.00 (m, 1H), 5.10 (brs, 1H), 6.43-6.45 (m, 1H), 7.26-7.30 (m, 1H), 7.49-7.59 (m, 3H), 7.64-7.80 (m, 5H)

Example 124

6-(5-(3-Isopropyl-6-methyl-2,4-dioxo-1-(3-(trifluoromethyl)phenyl)-1,2,3,4-tetrahydropyrimidin-5-yl)-1H-pyrazol-1-yl)nicotinonitrile The intended compound was obtained by using the compound prepared in Example 24 according to the similar reaction and treatment method to those described in Example 123.

¹H-NMR (CDCl₃: 300 MHz) (δ PPM):

1.38 (d, 3H, J=7.0 Hz), 1.45 (d, 3H, J=7.0 Hz), 1.79 (s, 1.5H), 1.80 (s, 1.5H), 5.04-5.13 (m, 1H), 6.42 (d, 0.5H, J=1.7 Hz), 6.45 (d, 0.5H, J=1.7 Hz), 7.50 (t, 1H, J=7.7 Hz), 7.55-7.58 (m, 2H), 7.68 (t, 1H, J=7.8 Hz), 7.75 (t, 1H, J=8.1 Hz), 7.80 (t, 1H, J=1.5 Hz), 8.02 (d, 0.5H, J=2.2 Hz), 8.04 (d, 0.5H, J=2.2 Hz), 8.01 (d, 0.5H, J=2.2 Hz), 8.03 (d, 0.5H, J=2.2 Hz), 8.14 (d, 0.5H, J=0.8 Hz), 8.17 (d, 0.5H, J=0.8 Hz), 8.51 (d, 0.5H, J=2.2 Hz), 8.55 (d, 0.5H, J=2.2 Hz)

Example 125

4-(4-(3-Isopropyl-6-methyl-2,4-dioxo-1-(3-(trifluoromethyl)phenyl)-1,2,3,4-tetrahydropyrimidin-5-yl)-4H-1,2,4-triazol-3-yl)nicotinonitrile The intended compound was obtained by using the compound prepared in Example 67 according to the similar reaction and treatment method to those described in Example 123.

¹H-NMR (CDCl₃: 300 MHz) (δ PPM):

1.45 (t, 6H, J=6.7 Hz), 1.71 (s, 3H), 5.08-5.17 (m, 1H), 7.49-7.61 (m, 2H), 7.72 (t, 1H, J=7.5 Hz), 7.80 (d, 1H, J=7.7 Hz), 8.10 (dd, 1H, J=8.2, 1.9 Hz), 8.24 (d, 1H, J=5.0 Hz), 8.57 (d, 1H, J=8.4 Hz), 8.74-8.78 (m, 1H)

Example 126

4-(5-(3,6-Dimethyl-2,4-dioxo-1-(3-(trifluoromethyl)phenyl)-1,2,3,4-tetrahydropyrimidin-5-yl)-4-methyl-1H-pyrazol-1-yl)benzonitrile

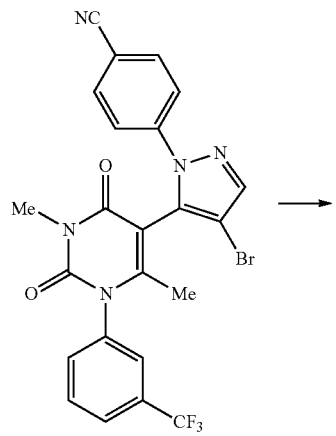

The intended compound was obtained by using the compound prepared in Example 93 according to the similar reaction and treatment method to those described in Example 108.

$^1$H-NMR (300 MHz, CDCl$_3$) (δ PPM):
1.49 (s, 1.5H), 1.55 (s, 1.5H), 1.98 (s, 3H), 3.31 (d, 3H, J=7.2 Hz), 7.22-7.42 (m, 1.5H), 7.46-7.50 (m, 2.5H), 7.58-7.73 (m, 5H)

Examples 127-131

The compounds indicated in the below-mentioned table (Examples 127-131) were obtained by using the corresponding starting materials according to the similar reaction and treatment method to those described in Example 108.

Example 127 acetic acid (R)-2-(5-(1-(4-cyanophenyl)-4-methyl-1H-pyrazol-5-yl)-4-methyl-2,6-dioxo-3-(3-(trifluoromethyl)phenyl)-2,3-dihydropyrimidin-1(6H)-yl)propylester;

Example 128

4-(5-(3,6-dimethyl-2,4-dioxo-1-(3-(trifluoromethyl)phenyl)-1,2,3,4-tetrahydropyrimidin-5-yl)-4-propyl-1H-pyrazol-1-yl)benzonitrile;

Example 129

(R)-4-(5-(3-(1-hydroxypropan-2-yl)-2,4-dioxo-1-(3-(trifluoromethyl)phenyl)-1,2,3,4-tetrahydropyrimidin-5-yl)-4-(propa-1-en-2-yl)-1H-pyrazol-1-yl)benzonitrile;

Example 130

4-(5-(3,6-dimethyl-2,4-dioxo-1-(3-(trifluoromethyl)phenyl)-1,2,3,4-tetrahydropyrimidin-5-yl)-4-(propa-1-en-2-yl)-1H-pyrazol-1-yl)benzonitrile;

Example 131

4-(5-(6-ethyl-3-methyl-2,4-dioxo-1-(3-(trifluoromethyl)phenyl)-1,2,3,4-tetrahydropyrimidin-5-yl)-4-methyl-1H-pyrazol-1-yl)benzonitrile

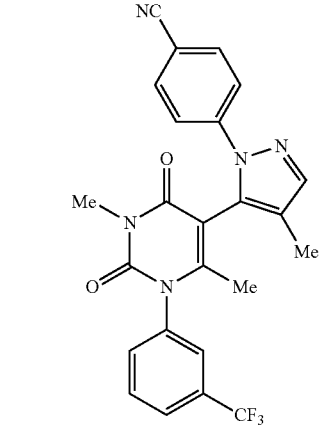

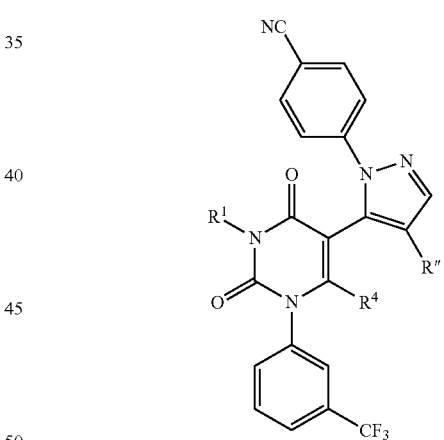

TABLE 52

| Ex. | R$^1$ | R$^4$ | R" | Measurement cond. | $^1$H-NMR (δ PPM) (or LC-MS: [M + H]+/Rt) |
|---|---|---|---|---|---|
| 127 | ⸺CH(Me)CH$_2$OAc | Me | Me | 4 | 1.41-1.55 (m, 6H), 1.96-2.04 (m, 6H), 4.03-4.27 (m, 1H), 4.60-4.83 (m, 1H), 5.19 (brs, 1H), 7.21-7.47 (m, 1H), 7.53-7.76 (m, 8H) |

TABLE 52-continued

| Ex. | R¹ | R⁴ | R" | Measurement cond. | ¹H-NMR (δ PPM) (or LC-MS: [M + H]+/Rt) |
|---|---|---|---|---|---|
| 128 | Me | Me | ⁿPr | 1 | 0.94 (dt, 3H, J = 7.2, 3.0 Hz), 1.48 (s, 1.5H), 1.54 (s, 1.5H), 1.56-1.66 (m, 2H), 2.28-2.35 (m, 2H), 3.37 (s, 1.5H), 3.39 (s, 1.5H), 7.21 (d, 0.5H, J = 9.6 Hz), 7.32 (s, 0.5H), 7.44 (d, 0.5H, J = 8.4 Hz), 7.49-7.54 (m, 2.5H), 7.61-7.76 (m, 5H) |
| 129 | 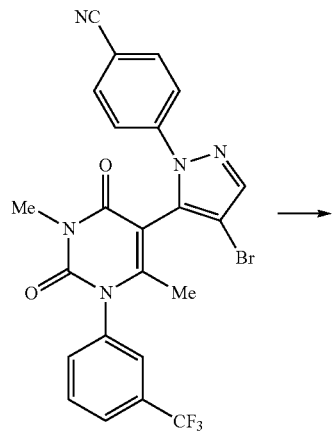 | H | 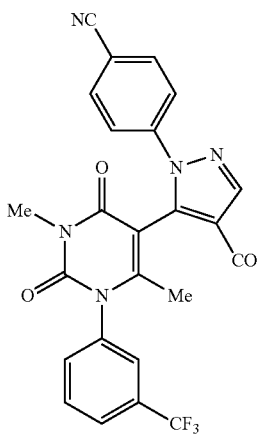 | 1 | 1.33 (d, 3H, J = 7.2 Hz), 1.99 (s, 3H), 2.22-2.28 (m, 1H), 3.72 (dd, 1H, J = 12.1, 1.5 Hz), 3.92-4.00 (m, 1H), 5.00 (s, 1H), 5.05 (s, 1H), 5.08-5.14 (m, 1H), 7.31 (s, 1H), 7.41-7.46 (m, 2H), 7.54 (d, 2H, J = 8.4 Hz), 7.59 (d, 1H, J = 8.3 Hz), 7.64-7.68 (m, 3H), 7.72 (s, 1H) |
| 130 | Me | Me |  | 9 | 492.1 (M + H)/1.124 (min) |
| 131 | Me | Et | Me | 1 | 0.53 (dt, 3H, J = 7.2, 3.6 Hz), 1.76-1.97 (m, 2H), 2.02-2.03 (m, 4H), 3.41 (s, 1.5H), 3.42 (s, 1.5H), 7.28 (d, 0.5H, J = 9.0 Hz), 7.37 (s, 0.5H), 7.47 (d, 0.5H, J = 7.5 Hz), 7.54-7.60 (m, 2.5H), 7.63-7.76 (m, 4H) |

Example 132

1-(4-Cyanophenyl)-5-(3,6-dimethyl-2,4-dioxo-1-(3-(trifluoromethyl)phenyl)-1,2,3,4-tetrahydropyrimidin-5-yl)-1H-pyrazole-4-carboxylic acid To a solution of 4-(4-bromo-5-(3,6-dimethyl-2,4-dioxo-1-(3-(trifluoromethyl)phenyl)-1,2,3,4-tetrahydropyrimidin-5-yl)-1H-pyrazol-1-yl)benzonitrile (prepared in Example 93) (139.8 mg) in 1,4-dioxane (2.0 ml) were added tetrakis(triphenylphosphine)palladium (30.7 mg), N,N-diisopropylethylamine (46.8 μl) and water (0.5 ml) and the resulting mixture was stirred at 100° C. under carbon monoxide atmosphere for four hours. To the reaction mixture was added ethyl acetate (100 ml) and the mixture was washed with 1M hydrochloric acid (30 ml) and saturated saline (30 ml), dried over anhydrous sodium sulfate and then concentrated under reduced pressure. The residue was purified by silica gel column chromatography (eluent: chloroform/methanol) to afford 1-(4-cyanophenyl)-5-(3,6-dimethyl-2,4-dioxo-1-(3-(trifluoromethyl)phenyl)-1,2,3,4-tetrahydropyrimidin-5-yl)-1H-pyrazole-4-carboxylic acid (24.5 mg) as brown solid.

¹H-NMR (300 MHz, CDCl₃) (δ PPM):
1.66 (s, 1.5H), 1.69 (s, 1.5H), 3.33 (d, 3H, J=7.5 Hz), 7.30 (d. 0.5H, J=8.1 Hz), 7.42-7.49 (m, 1.5H), 7.56-7.71 (m, 3H), 7.75-7.79 (m, 2H), 8.08 (dd, 1H, J=8.4, 1.2 Hz), 8.27 (d, 1H, J=1.2 Hz)

Example 133

1-(4-Cyanophenyl)-5-(3-isopropyl-2,4-dioxo-1-(3-(trifluoromethyl)phenyl)-1,2,3,4-tetrahydropyrimidin-5-yl)-1H-pyrazole-4-carboxylic acid

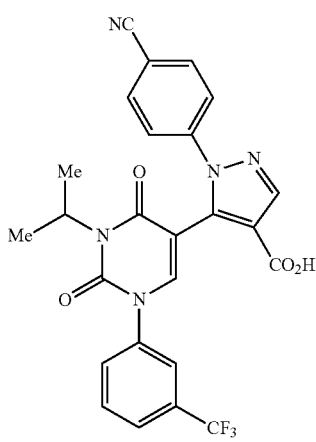 [SMILES: CC(C)n1c(=O)c(-c2c(C(=O)O)cnn2-c2ccc(C#N)cc2)cn(-c2cccc(C(F)(F)F)c2)c1=O]

The intended compound was obtained by using the corresponding starting materials according to the similar reaction and treatment method to those described in Example 132.

¹H-NMR (300 MHz, CDCl₃) (δ PPM):
1.33-1.41 (m, 6H), 1.63 (s, 1.5H), 1.66 (s, 1.5H), 5.00-5.09 (m, 1H), 7.37 (d, 0.5H, J=9.1 Hz), 7.46 (d, 1H, J=6.6 Hz), 7.55 (s, 0.5H), 7.60-7.68 (m, 3H), 7.73-7.79 (m, 3H), 8.25 (d, 1H, J=2.1 Hz)

Example 134

1-(4-Cyanophenyl)-5-(3,6-dimethyl-2,4-dioxo-1-(3-(trifluoromethyl)phenyl)-1,2,3,4-tetrahydropyrimidin-5-yl)-1H-pyrazole-4-carboxylic acid methyl ester

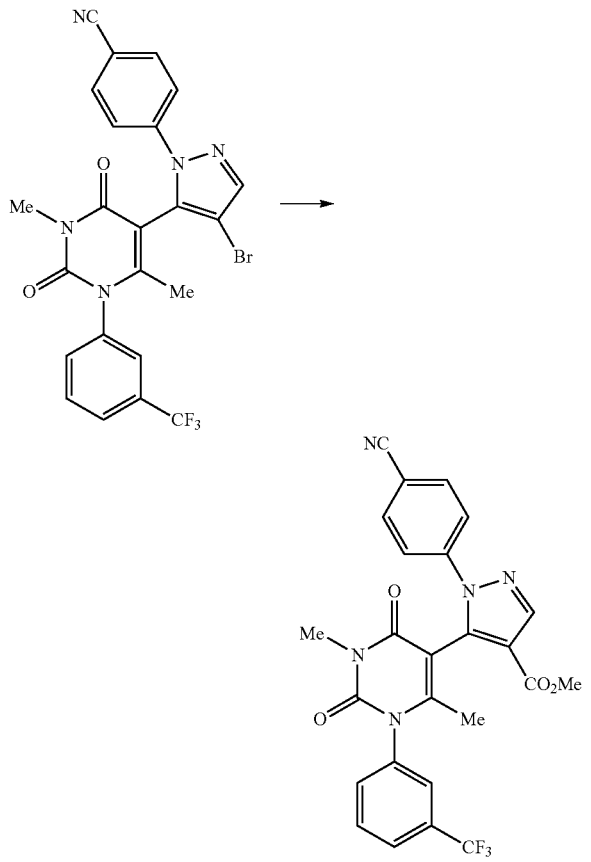

To a solution of 4-(4-bromo-5-(3,6-dimethyl-2,4-dioxo-1-(3-(trifluoromethyl)phenyl)-1,2,3,4-tetrahydropyrimidin-5-yl)-1H-pyrazol-1-yl)benzonitrile (prepared in Example 93) (50.4 mg) in 1,4-dioxane (1.0 ml) were added bis(tri-tert-butylphosphine)palladium (4.9 mg), N,N-diisopropylethylamine (32.0 L) and methanol (1.0 mL), and the resulting mixture was stirred at 10° C. under carbon monoxide atmosphere for four hours. To the reaction mixture was added ethyl acetate (100 ml) and the resulting mixture was washed with water (30 ml) and saturated saline (30 ml), dried over anhydrous sodium sulfate and then concentrated under reduced pressure. The residue was purified by silica gel column chromatography (eluent: hexane/ethyl acetate) to afford methyl-1-(4-cyanophenyl)-5-(3,6-dimethyl-2,4-dioxo-1-(3-(trifluoromethyl)phenyl)-1,2,3,4-tetrahydropyrimidin-5-yl)-1H-pyrazole-4-carboxylate (9.4 mg) as white solid.

¹H-NMR (300 MHz, CDCl₃) (δ PPM):
1.63 (s, 1.5H), 1.70 (s, 1.5H), 3.31 (d, 3H, J=9.0 Hz), 3.83 (d, 3H, J=3.0 Hz), 7.30 (d, 0.5H, J=8.1 Hz), 7.43 (s, 0.5H), 7.52-7.78 (m, 7H), 8.18 (d, 1H, J=1.2 Hz)

Example 135

4-(4-Acetyl-5-(3,6-dimethyl-2,4-dioxo-1-(3-trifluoromethylphenyl)-1,2,3,4-tetrahydropyrimidin-5-yl)-1H-pyrazol-1-yl)benzonitrile

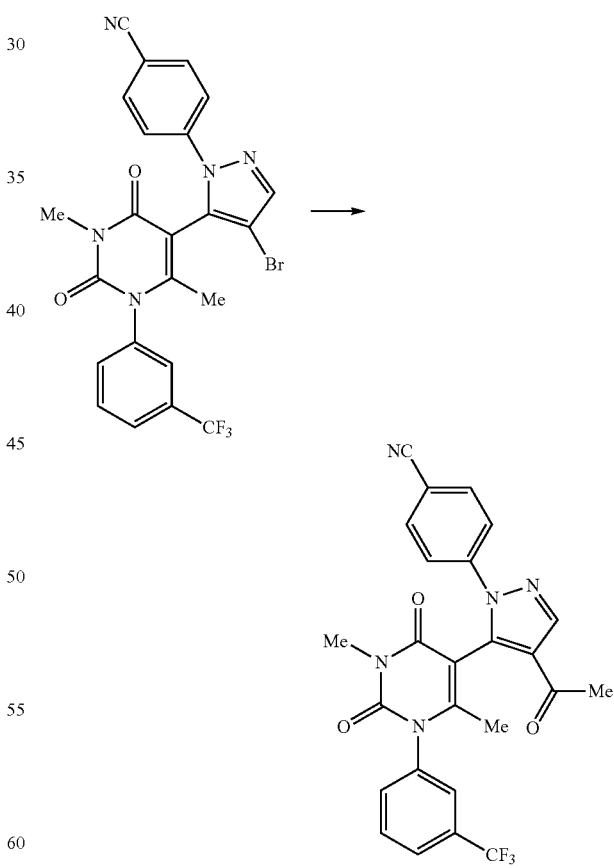

To a solution of 4-(4-bromo-5-(3,6-dimethyl-2,4-dioxo-1-(3-(trifluoromethyl)phenyl)-1,2,3,4-tetrahydropyrimidin-5-yl)-1H-pyrazol-1-yl)benzonitrile (prepared in Example 93) (54.6 mg) in 1,4-dioxane (1.0 ml) were added tetrakis(triphenylphosphine)palladium (23.8 mg) and tributyl(1-ethoxyvinyl)tin (103.4 µl) and the resulting mixture was stirred for one hour with heating in microwave instrument (120° C.). To the reaction mixture were then added 1M hydrochloric acid (1 mL) and ethyl acetate (2 ml) and the resulting mixture was stirred at room temperature for one hour. To the reaction mixture was ethyl acetate (50 ml) and the mixture was washed with 10% aqueous potassium carbonate solution (30 ml) and saturated saline (30 ml), dried over anhydrous sodium sulfate and then concentrated under reduced pressure. The residue was purified by silica gel column chromatography (eluent: hexane/ethyl acetate) to afford 4-(4-acetyl-5-(3,6-dimethyl-2,4-dioxo-1-(3-(trifluoromethyl)phenyl)-1,2,3,4-tetrahydropyrimidin-5-yl)-1H-pyrazol-1-yl)benzonitrile (19.0 mg) as white solid.

¹H-NMR (300 MHz, CDCl₃) (δ PPM):

1.61 (s, 1.5H), 1.68 (s, 1.5H), 2.50 (s, 3H), 3.26 (s, 1.5H), 3.30 (s, 1.5H), 7.30 (d, 0.5H, J=8.4 Hz), 7.44 (s, 0.5H), 7.60-7.63 (m, 4H), 7.73-7.77 (m, 3H), 8.19 (d, 1H, J=0.9 Hz)

Example 136

4-(4-Acetyl-5-(2,4-dioxo-3-isopropyl-1-(3-trifluoromethylphenyl)-1,2,3,4-tetrahydropyrimidin-5-yl)-1H-pyrazol-1-yl)benzonitrile

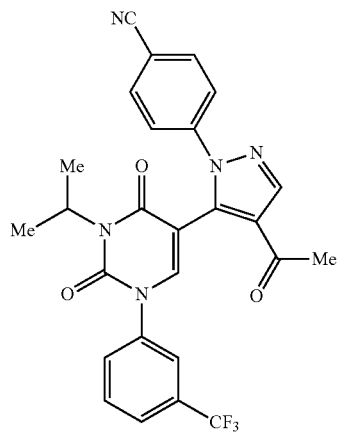 [SMILES: CC(=O)c1cnn(-c2ccc(C#N)cc2)c1-c1cn(-c2cccc(C(F)(F)F)c2)c(=O)n(C(C)C)c1=O]

The intended compound was obtained by using the corresponding starting materials according to the similar reaction and treatment method to those described in Example 135.

¹H-NMR 300 MHz, CDCl₃) (δ PPM):

1.24 (d, 6H, J=3.3 Hz), 2.48 (s, 3H), 4.93 (quin, 1H, J=6.9 Hz), 7.57-7.77 (m, 8H), 7.94 (s, 1H), 8.11 (s, 1H)

Example 137

4-(4-(2-Hydroxypropan-2-yl)-5-(3-isopropyl-2,4-dioxo-1-(3-(trifluoromethyl)phenyl)-1,2,3,4-tetrahydropyrimidin-5-yl)-1H-pyrazol-1-yl)benzonitrile

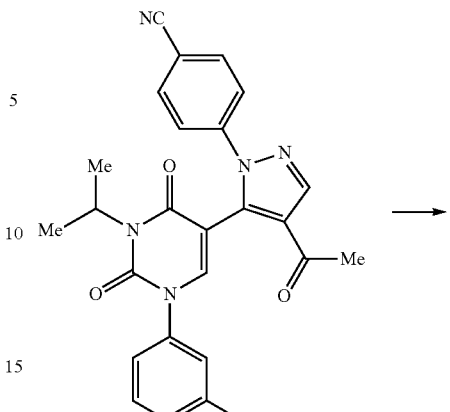

To a solution of 4-(4-acetyl-5-(3-isopropyl-2,4-dioxo-1-(3-(trifluoromethyl)phenyl)-1,2,3,4-tetrahydropyrimidin-5-yl)-1H-pyrazol-1-yl)benzonitrile (prepared in Example 136) (28.2 mg) in tetrahydrofuran (1.0 ml) was added under ice-cooling methyl magnesium chloride (3.0 M tetrahydrofuran solution, 27.8 µl) dropwise and the resulting mixture was stirred under ice-cooling for one hour. To the resulting mixture was water (1 mL) followed by an addition of ethyl acetate (50 ml), and the mixture was washed with water (10 ml) and saturated saline (10 ml), dried over anhydrous sodium sulfate and then concentrated under reduced pressure. The residue was purified by silica gel column chromatography (eluent: hexane/ethyl acetate) to afford 4-(4-(2-hydroxypropan-2-yl)-5-(3-isopropyl-2,4-dioxo-1-(3-(trifluoromethyl)phenyl)-1,2,3,4-tetrahydropyrimidin-5-yl)-1H-pyrazol-1-yl)benzonitrile (4.3 mg) as white solid.

¹H-NMR (300 MHz, CDCl₃) (δ PPM):

1.29 (s, 3H), 1.39 (dd, 3H, J=12.0, 6.0 Hz), 1.55 (s, 6H), 2.98 (s, 1H), 4.93 (quin, 0.33H, J=6.9 Hz), 5.11 (quin, 0.67H, J=6.6 Hz), 7.38-7.72 (m, 8H), 7.79 (s, 0.33H), 7.92 (s, 0.33H), 8.11 (s, 0.33H)

Example 138

4-(5-(3,6-Dimethyl-2,4-dioxo-1-(3-(trifluoromethyl)phenyl)-1,2,3,4-tetrahydropyrimidin-5-yl)-4-(hydroxymethyl)-1H-pyrazol-1-yl)benzonitrile

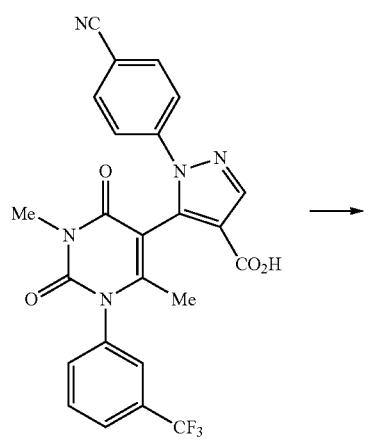

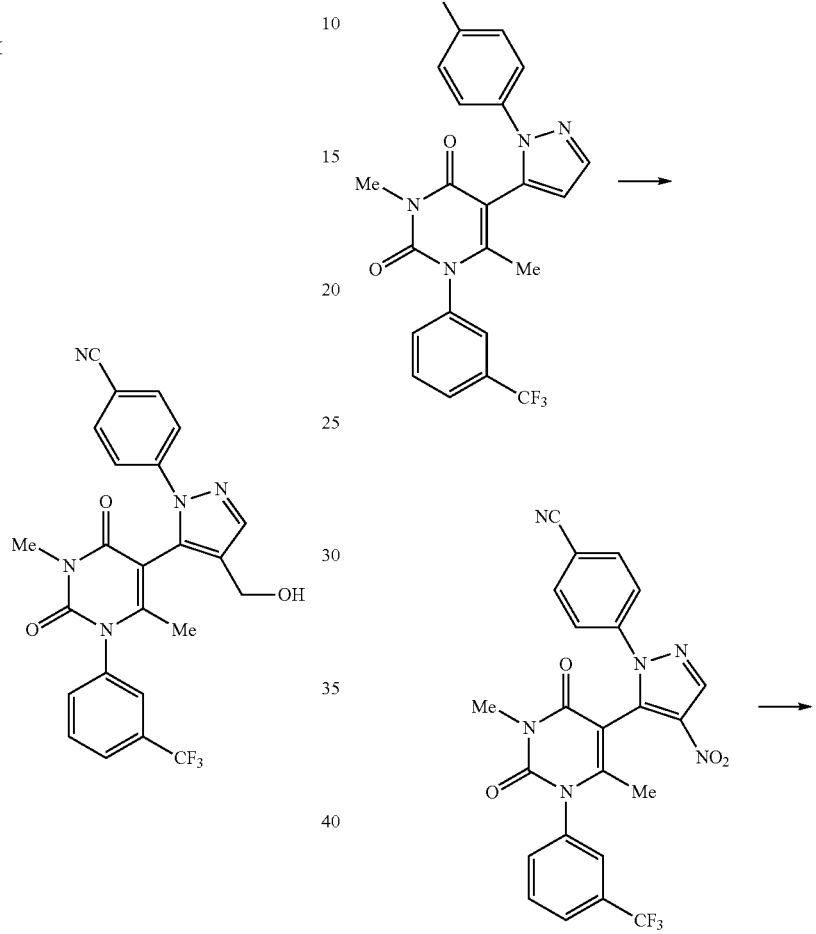

To a solution of 1-(4-cyanophenyl)-5-(3,6-dimethyl-2,4-dioxo-1-(3-(trifluoromethyl)phenyl)-1,2,3,4-tetrahydropyrimidin-5-yl)-1H-pyrazole-4-carboxylic acid (prepared in Example 132) (100 mg) and N-methylmorpholine (66 μL) in tetrahydrofuran (2 ml) was added at 0° C. isobutyl chloroformate (79 μl). After thirty minutes, to the reaction mixture was added sodium borohydride (26.4 mg) and the resulting mixture was stirred for three and a half hours. Thereto was added sodium borohydride (55.6 mg) and the mixture was stirred for another thirty minutes and thereto were added water and saturated aqueous ammonium chloride solution, and the mixture was extracted with ethyl acetate. The organic layer was washed with saturated saline and then dried over sodium sulfate, and then concentrated on evaporator instrument. The residue was purified by silica gel column chromatography to afford the intended 4-(5-(3,6-dimethyl-2,4-dioxo-1-(3-(trifluoromethyl)phenyl)-1,2,3,4-tetrahydropyrimidin-5-yl)-4-(hydroxymethyl)-1H-pyrazol-1-yl)benzonitrile.

$^1$H-NMR (300 MHz, CDCl$_3$) (δ PPM):

1.36 (s, 1.5H), 1.39 (s, 1.5H), 3.43 (s, 1.5H), 3.44 (s, 1.5H), 4.46 (s, 2H), 7.07 (d, 0.5H, J=8.1H), 7.13 (s, 0.5H), 7.45 (d, 0.5H, J=8.4 Hz), 7.52 (dd, 2H, J=8.7, 1.5 Hz), 7.57 7.68 (m, 1H), 7.72-7.77 (m, 3.5H), 7.86 (d, 1H, J=2.7 Hz)

Examples 139-141

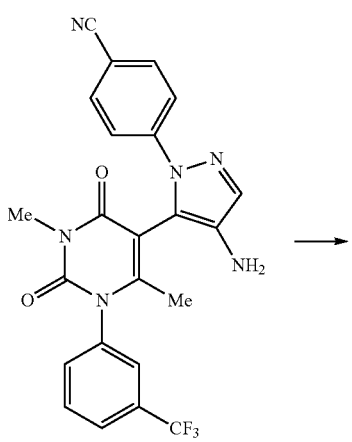

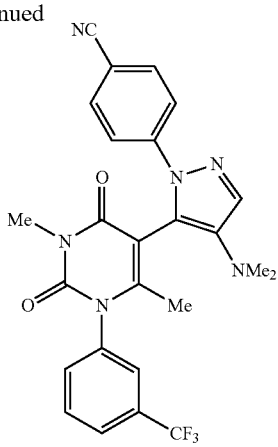

Example 139

4-[5-[3,6-Dimethyl-2,4-dioxo-1-(3-trifluoromethylphenyl)-1,2,3,4-tetrahydropyrimidin-5-yl]-4-nitro-1H-pyrazol-1-yl]benzonitrile The intended compound was obtained according to the corresponding starting materials according to the similar reaction and treatment method to those described in Reference Example 192.

$^1$H-NMR (300 MHz, CDCl$_3$) ($\delta$ PPM):
1.62 (s, 1.5H), 1.68 (s, 1.5H), 3.27 (s, 1.5H), 3.29 (s, 1.5H), 7.25 (d, 0.5H, J=6.6 Hz), 7.37 (s, 0.5H), 7.47 (d, 0.5H, J=7.8 Hz), 7.53-7.69 (m, 3.5H), 7.73-7.78 (m, 3H), 8.39 (s, 1H)

Example 140

4-(4-amino-5-(3,6-dimethyl-2,4-dioxo-1-(3-trifluoromethylphenyl)-1,2,3,4-tetrahydropyrimidin-5-yl)-1H-pyrazol-1-yl)benzonitrile The intended compound was obtained according to the corresponding starting materials according to the similar reaction and treatment method to those described in Reference Example 193.

$^1$H-NMR (CDCl$_3$: 300 MHz) ($\delta$ PPM):
1.49 (s, 1.5H), 1.51 (s, 1.5H), 3.40 (s, 1.5H), 3.41 (s, 1.5H), 7.17 (d, 0.5H, J=8.1 Hz), 7.23 (d, 0.5H, J=8.7 Hz), 7.43-7.52 (m, 4H), 7.61-7.91 (m, 4H)

Example 141

4-(5-(3,6-Dimethyl-2,4-dioxo-1-(3-trifluoromethylphenyl)-1,2,3,4-tetrahydropyrimidin-5-yl)-4-(dimethylamino)-1H-pyrazol-1-yl)benzonitrile The intended compound was obtained according to the corresponding starting materials according to the similar reaction and treatment method to those described in Example 69.

1H-NMR (CDCl$_3$: 300 MHz) ($\delta$ PPM):
1.56 (s, 1.5H), 1.62 (s, 1.5H), 2.63 (s, 3H), 2.64 (s, 3H), 3.30 (s, 1.5H), 3.32 (s, 1.5H), 7.23 (s, 0.5H), 7.33 (s, 0.5H), 7.39 (d, 1H, J=7.5 Hz), 7.45-7.49 (m, 2.5H), 7.53 (d, 1H, J=1.2 Hz), 7.60-7.66 (m, 2.5H), 7.71 (d, 1H, J=7.5 Hz)

Example 142

1-(4-Cyanophenyl)-5-(3,6-dimethyl-2,4-dioxo-1-(3-(trifluoromethyl)phenyl)-1,2,3,4-tetrahydropyrimidin-5-yl)-N-methyl-1H-pyrazole-4-carboxamide

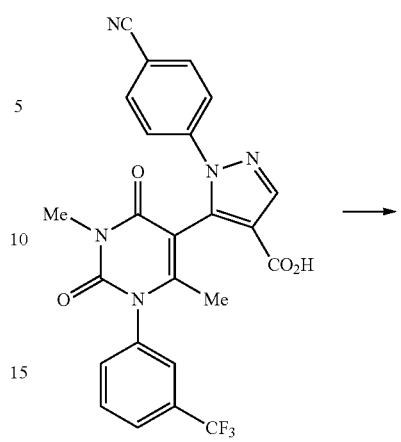

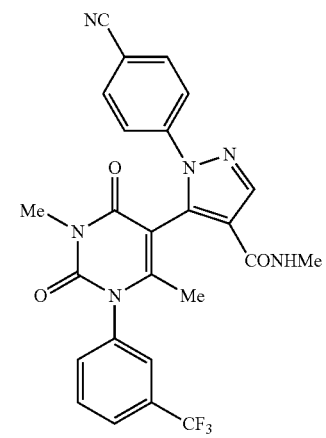

The intended compound was obtained according to the corresponding starting materials according to the similar reaction and treatment method to those described in Example 75.

$^1$H-NMR (300 MHz, CDCl$_3$) ($\delta$ PPM):
1.55 (s, 1.5H), 1.64 (s, 1.5H), 2.86 (s, 0.75H), 2.88 (s, 0.75H), 2.90 (s, 0.75H), 2.93 (s, 0.75H), 3.32 (s, 1.5H), 3.36 (s, 1.5H), 6.24-6.30 (m, 1H), 7.18 (d, 0.5H, J=8.4 Hz), 7.32 (s, 0.5H), 7.53-7.69 (m, 4H), 7.72-7.77 (m, 3H), 7.98-(d, 1H, J=6.9 Hz)

Examples 143-145

The compounds indicated in the below-mentioned table (Examples 143-145) were obtained according to the corresponding starting materials according to the similar reaction and treatment method to those described in Example 75.

Example 143

1-(4-cyanophenyl)-5-(3-isopropyl-6-methyl-2,4-dioxo-1-(3-(trifluoromethyl)phenyl)-1,2,3,4-tetrahydropyrimidin-5-yl)-1H-pyrazole-4-carboxamide;

Example 144

1-(4-cyanophenyl)-5-(3-isopropyl-6-methyl-2,4-dioxo-1-(3-(trifluoromethyl)phenyl)-1,2,3,4-tetrahydropyrimidin-5-yl)-N-methyl-1H-pyrazole-4-carboxamide;

Example 145

1-(4-cyanophenyl)-5-(3-isopropyl-6-methyl-2,4-dioxo-1-(3-(trifluoromethyl)phenyl)-1,2,3,4-tetrahydropyrimidin-5-yl)-N,N-dimethyl-1H-pyrazole-4-carboxamide

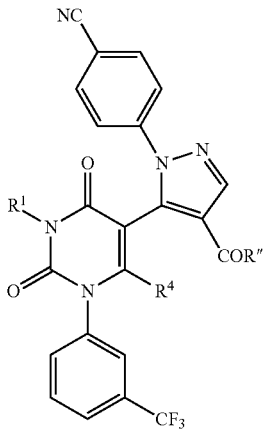

-continued

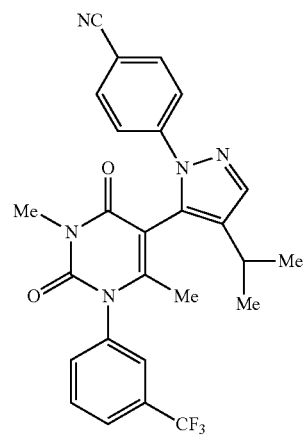

TABLE 53

| Ex. | R¹ | R⁴ | R" | Measurement cond | ¹H-NMR (δ PPM) |
|---|---|---|---|---|---|
| 143 | $^i$Pr | Me | NH₂ | 4 | 1.38 (d, 1.5H, J = 6.9 Hz), 1.42 (d, 1.5H, J = 6.9 Hz), 1.43 (d, 1.5H, J = 7.0 Hz), 1.45 (d, 1.5H, J = 7.0 Hz), 1.56 (s, 1.5H), 1.64 (s, 1.5H), 5.00-5.15 (m, 1H), 5.50 (brs, 1H), 6.02 (brs, 1H), 7.20-7.25 (m, 0.5H), 7.32 (s, 0.5H), 7.53-7.67 (m, 4H), 7.78-7.81 (m, 3H), 8.06 (s, 0.5H), 8.07 (s, 0.5H) |
| 144 | $^i$Pr | Me | NHMe | 1 | 1.32-1.50 (m, 6H), 1.52 (s, 1H), 1.61 (s, 1H), 1.65 (d, 1H, J = 9.9 Hz), 2.92 (s, 1.5H), 2.93 (s, 1.5H), 5.03-5.14 (m, 1H), 7.53-7.79 (m, 9H), 7.99 (d, 1H, J = 5.4 Hz) |
| 145 | Me | Me | NMe₂ | 1 | 1.54 (s, 1.5H), 1.59 (s, 1.5H), 2.87 (s, 1H), 2.95 (s. 1H), 3.00 (brs, 2H), 3.13 (brs, 2H), 3.29 (s, 1.5H), 3.30 (s, 1.5H), 7.14 (d, 1H, J = 1.8 Hz), 7.26 (s, 0.5H), 7.45-7.63 (m, 4H), 7.67-7.73 (m, 2.5H), 7.80 (d, 1H, J = 1.8 Hz) |

Example 146

4-(5-(3,6-Dimethyl-2,4-dioxo-1-(3-(trifluoromethyl)phenyl)-1,2,3,4-tetrahydropyrimidin-5-yl)-4-isopropyl-1H-pyrazol-1-yl)benzonitrile

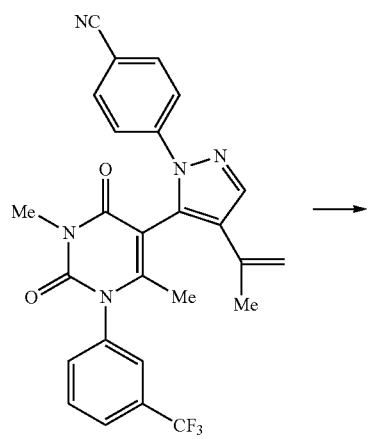

→

The intended 4-(5-(3,6-dimethyl-2,4-dioxo-1-(3-(trifluoromethyl)phenyl)-1,2,3,4-tetrahydropyrimidin-5-yl)-4-isopropyl-1H-pyrazol-1-yl)benzonitrile was obtained by using 4-(5-(3,6-dimethyl-2,4-dioxo-1-(3-(trifluoromethyl)phenyl)-1,2,3,4-tetrahydropyrimidin-5-yl)-4-(propa-1-en-2-yl)-1H-pyrazol-1-yl)benzonitrile (prepared in Example 130) according to the similar reaction and treatment method to those described in Example 72.

¹H-NMR (300 MHz, CDCl₃) (δ PPM):
1.15-1.21 (m, 6H), 1.41 (s, 1.5H), 1.46 (s, 1.5H), 1.71 (s, 0.5H), 1.76 (s, 0.5H), 2.61 (q, 1H, J=7.8 Hz), 3.81-3.85 (m, 2H), 4.19-4.23 (m, 2H), 7.13-7.17 (m, 1H), 7.45-7.55 (m, 3H), 7.59-7.72 (m, 5H)

Example 147

4-(5-(3-(2-Hydroxyethyl)-6-methyl-2,4-dioxo-1-(3-(trifluoromethyl)phenyl)-1,2,3,4-tetrahydropyrimidin-5-yl)-4-isopropyl-1H-pyrazol-1-yl)benzonitrile

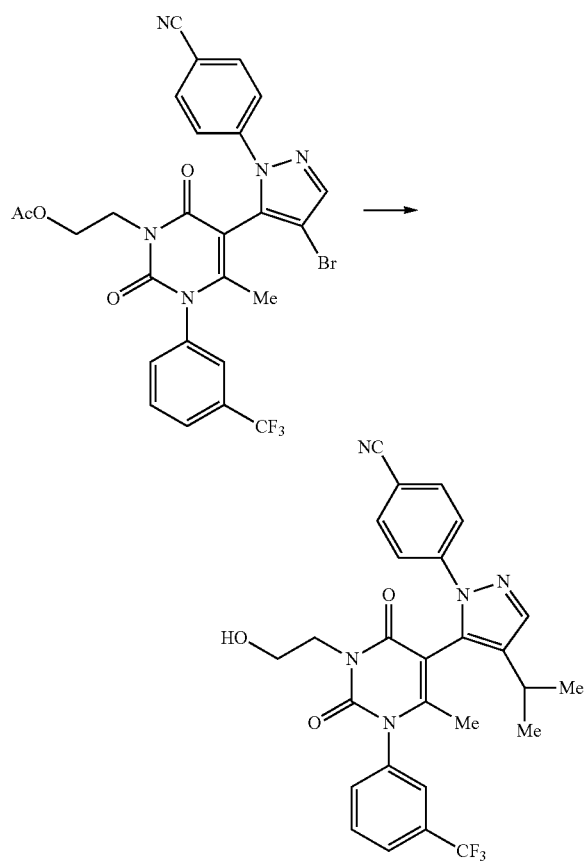

To a solution of 2-(5-(4-bromo-1-(4-cyanophenyl)-1H-pyrazol-5-yl)-4-methyl-2,6-dioxo-3-(3-(trifluoromethyl)phenyl)-2,3-dihydropyrimidin-1(6H)-yl)ethyl acetate (prepared in Example 98) (220.3 mg) in dimethoxyethane (4.0 ml) were added isopropenyl boronic acid pinacol ester (69.0 µl), tetrakis(triphenylphosphine)palladium (85.2 mg), sodium carbonate (194.3 mg) and water (0.4 ml) and the resulting mixture was stirred at 100° C. for seven hours. To the reaction mixture was added ethyl acetate (100 ml) and the mixture was washed with water (30 ml) and saturated saline (30 ml), dried over anhydrous sodium sulfate and then concentrated under reduced pressure. To a solution of the residue in methanol (4 ml) was added palladium carbon (28.7 mg) and the resulting mixture was stirred at room temperature under hydrogen atmosphere for six hours. The reaction mixture was filtered through Celite (trade mark) and then concentrated under reduced pressure. To a solution of the residue in methanol (5 ml) was added under ice-cooling 1M aqueous potassium carbonate solution (392 µl) and the resulting mixture was stirred under ice-cooling for one hour. To the reaction mixture was added 1M hydrochloric acid (329 µl) and the mixture was concentrated under reduced pressure. The residue was purified by silica gel column chromatography (eluent: toluene/ethyl acetate) to afford 4-(5-(3-(2-hydroxyethyl)-6-methyl-2,4-dioxo-1-(3-(trifluoromethyl)phenyl)-1,2,3,4-tetrahydropyrimidin-5-yl)-4-isopropyl-1H-pyrazol-1-yl)benzonitrile (62.6 mg) as white solid.

$^1$H-NMR (300 MHz, CDCl$_3$) (δ PPM):
1.15-1.21 (m, 6H), 1.41 (s, 1.5H), 1.46 (s, 1.5H), 1.71 (s, 0.5H), 1.76 (s, 0.5H), 2.61 (q, 1H, J=7.8 Hz), 3.81-3.85 (m, 2H), 4.19-4.23 (m, 2H), 7.13-7.17 (m, 1H), 7.45-7.55 (m, 3H), 7.59-7.72 (m, 5H)

Examples 148-179

The compounds indicated in the below-mentioned table (Examples 148-179) were obtained by using the corresponding starting materials according to the similar reaction and treatment method to those described in Example 142.

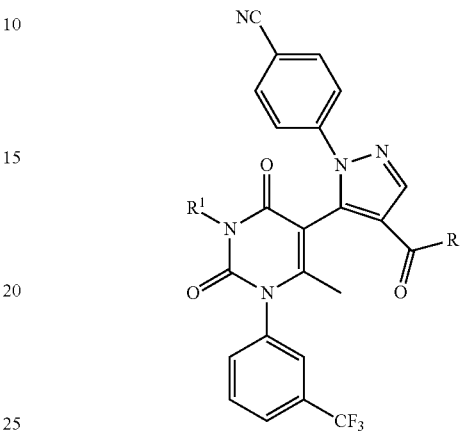

TABLE 54

| Ex. | R | R$^1$ | m.p. | Measurement cond. | (LC-MS: Rt/ [M + H]+) | |
|---|---|---|---|---|---|---|
| 148 | NH$_2$ | Me | 263 | 9 | 0.86 | 495 |
| 149 | NH$_2$ | Et | | 9 | 0.85 | 509 |
| 150 | NHEt | Me | | 9 | 0.89 | 523 |
| 151 | NHEt | i-Pr | 258 | 9 | 0.99 | 551 |
| 152 | NHEt | Et | 242 | 9 | 0.93 | 537 |
| 153 | NMe$_2$ | i-Pr | | 9 | 0.96 | 551 |
| 154 | NMe$_2$ | Et | 193 | 9 | 0.90 | 537 |
| 155 | ⟨azetidinyl⟩ | Me | | 9 | 0.91 | 535 |
| 156 | ⟨3-OH-azetidinyl⟩ | Et | | 9 | 0.83 | 565 |
| 157 | ⟨3-OH-azetidinyl⟩ | Me | 235 | 9 | 0.79 | 551 |
| 158 | ⟨3-OMe-azetidinyl⟩ | Et | 167 | 9 | 0.94 | 579 |
| 159 | ⟨3-OMe-azetidinyl⟩ | Me | 244 | 9 | 0.91 | 565 |

TABLE 54-continued

| Ex. | R | R¹ | m.p. | Measurement cond. | (LC-MS: Rt/ [M + H]+) | |
|---|---|---|---|---|---|---|
| 160 | azetidine-OH, Me | Me | | 9 | 0.84 | 565 |
| 161 | azetidine-F,F | Et | | 9 | 0.99 | 585 |
| 162 | pyrrolidine | Me | 227 | 9 | 0.91 | 549 |
| 163 | pyrrolidine-F,F | Et | | 9 | 0.99 | 599 |

TABLE 55

| Ex. | R | R¹ | m.p. | Measurement cond. | (LC-MS: Rt/ [M + H]+) | |
|---|---|---|---|---|---|---|
| 164 | azetidine-NHBoc | Me | | 9 | 2.93 | 650 |
| 165 | azetidine-NHAc | Me | | 9 | 0.72 | 592 |
| 166 | azetidine-NMe₂ | Me | | 9 | 0.70 | 578 |
| 167 | azetidine-CH₂NHBoc | Me | | 9 | 2.97 | 664 |
| 168 | azetidine-CH₂NHAc | Me | | 9 | 0.81 | 606 |

TABLE 55-continued

| Ex. | R | R¹ | m.p. | Measurement cond. | (LC-MS: Rt/ [M + H]+) | |
|---|---|---|---|---|---|---|
| 169 | azetidine-CH₂NMe₂ | Me | | 9 | 0.68 | 592 |
| 170 | NH-C(=NH)-N=N | Me | | 9 | 0.91 | 563 |
| 171 | piperazine-Boc | Me | | 9 | 1.06 | 678 |
| 172 | piperazine-NH | Me | | 9 | 0.70 | 578 |
| 173 | morpholine | Et | | 9 | 0.90 | 579 |
| 174 | piperidine-OH | Et | | 9 | 0.84 | 593 |
| 175 | NH-CH₂CN | Me | | 9 | 0.87 | 534 |
| 176 | N(Me)CH₂CH₂OH | Et | | 9 | 0.84 | 567 |
| 177 | N(CH₂CH₂OH)₂ | Et | | 9 | 0.8 | 597 |
| 178 | NH-CH₂CH₂OMe | Me | 226 | 9 | 0.87 | 553 |
| 179 | NH-cyclopropyl | Me | | 9 | 0.9 | 535 |

Example 180

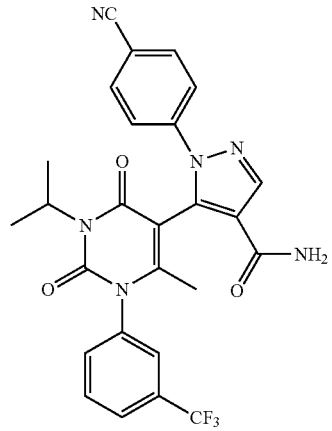

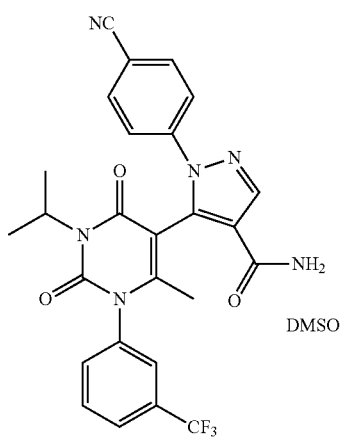

To 1-(4-cyanophenyl)-5-(3-isopropyl-6-methyl-2,4-dioxo-1-(3-(trifluoromethyl)phenyl)-1,2,3,4-tetrahydropyrimidin-5-yl)-1H-pyrazole-4-carboxamide (prepared in example 143) (500 mg) was added DMSO (1.2 ml) and the resulting mixture was stirred at 90° C. for one hour and at room temperature for six hours. The formed crystals were collected by filtering with DMSO to afford 1-(4-cyanophenyl)-5-(3-isopropyl-6-methyl-2,4-dioxo-1-(3-(trifluoromethyl)phenyl)-1,2,3,4-tetrahydropyrimidin-5-yl)-1H-pyrazole-4-carboxamide DMSO solvate (240 mg).

$^1$H-NMR (CD$_3$OD: 300 MHz) δ: 1.27-1.37 (m, 6H), 1.68 (s, 1.5H), 1.73 (s, 1.5H), 2.65 (s, 6H), 4.90-5.03 (m, 1H), 7.61-7.91 (m, 8H), 8.28 (d, 1H, J=0.6 Hz).

Examples 181-186

The atropisomers of the compounds prepared in Examples 143, 148 and 360 (20 mg respectively) were resolved on chiral column to afford the compounds indicated in the below-mentioned table (Examples 181-186).

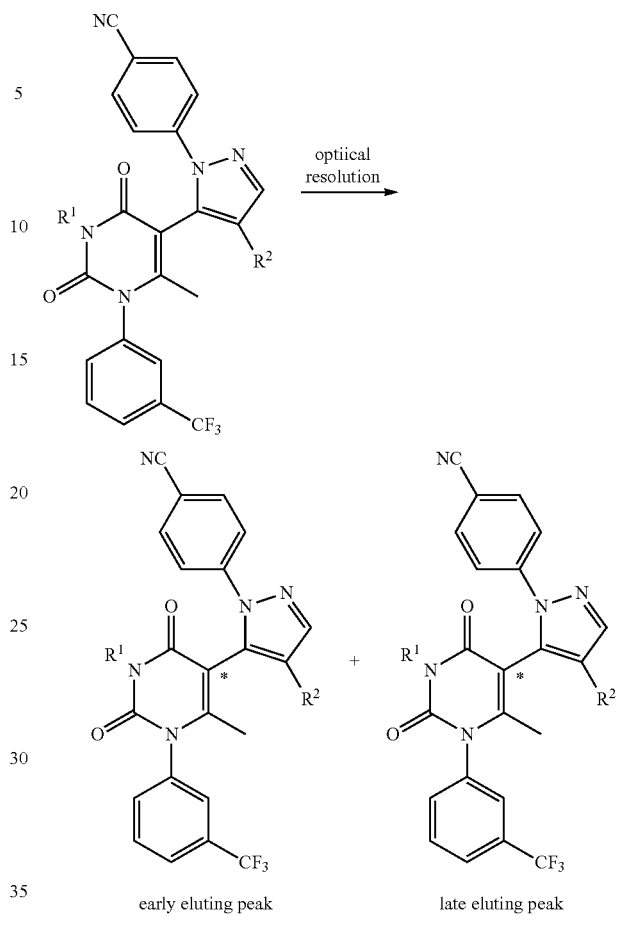

[Resolution Condition]
Detector: SPD-6A (manufactured by SHIMAZU CO.)
HPLC: LC-6A (manufactured by SHIMAZU CO.)
Column: CHIRALCEL OD-H (manufactured by DAICEL CO.) (S-5 μm, 20×250 mm)
Elution Condition:
0.0-60.0 (minute); A/B=1:1
Flow rate: 5.0 ml/minute
UV: 254 nm
Column temperature: 25° C.
(with the proviso that the compounds of Examples 185-186 were separated on CHIRAL FLASH IC)

TABLE 56

| Ex. | R$^1$ | R$^2$ | Solvent | Retention time (min.)/ Yield (mg) | |
|---|---|---|---|---|---|
| 181 | Me | CONH$_2$ | n-hexane/ | 16.2/2.2 | 57.3/2.7 |
| 182 | | | isopropanol = 1/1 | | |
| 183 | i-Pr | CONH$_2$ | n-hexane/ | 16.4/4.3 | 29.2/1.6 |
| 184 | | | isopropanol = 1/1 | | |
| 185 | Me | Cl | n-hexane/ethyl | 12.9/3.8 | 25.3/4.0 |
| 186 | | | acetate = 2/1 | | |

Example 187

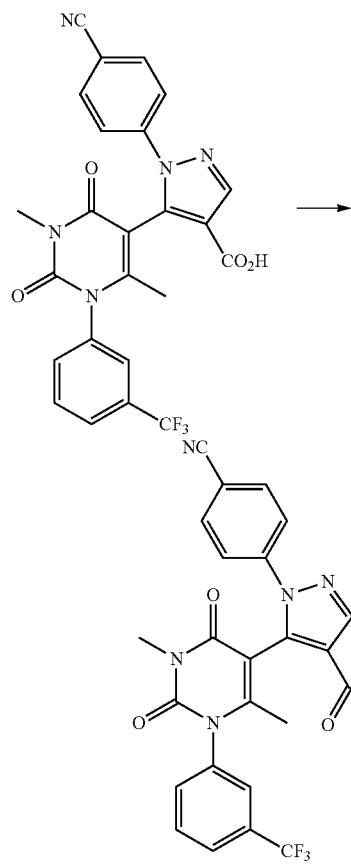

To a solution of 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-carboxylic acid (prepared in Example 132) (153 mg) in acetonitrile (5 ml) was added 4-dimethylaminobutanol (0.21 ml), 1-hydroxy-7-azabenzotriazole (126 mg) and 1-ethyl-3-(3-dimethylaminopropyl)carbodiimide hydrochloride (177 mg) and the resulting mixture was stirred at room temperature for sixteen hours. To the reaction solution were added saturated aqueous sodium hydrogen carbonate solution (10 ml) and ethyl acetate (20 ml×2) such that the intended products were extracted into an organic layer. The organic layer was washed with saturated saline (20 ml), dried over anhydrous magnesium sulfate and then concentrated under reduced pressure. The residue was purified by silica gel column chromatography (eluent: chloroform/methanol) to afford 4-(dimethylamino)butyl 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-carboxylate (137 mg). UPLC/MS 595 (M+H)/0.73 min (measurement condition 9)

Examples 188-190

The compounds indicated in the below-mentioned table (Examples 188-190) were obtained by using the corresponding starting materials according to the similar reaction and treatment method to those described in Example 187.

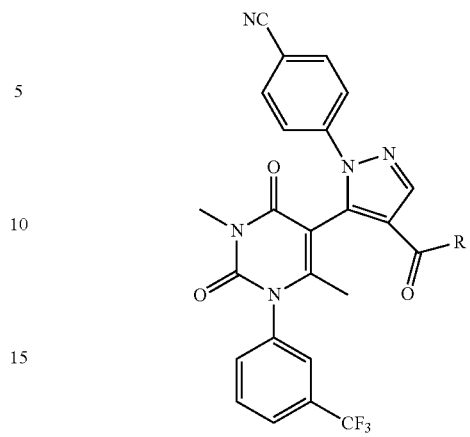

TABLE 57

| Ex. | R | Measurement cond. | (LC-MS: Rt/[M + H]+) | |
|---|---|---|---|---|
| 188 | ~~O~~ | 9 | 0.98 | 510 |
| 189 | ~~O~~\~ | 9 | 1.03 | 524 |
| 190 | ~~O~~\~\~OH | 9 | 0.876 | 540 |

Example 191

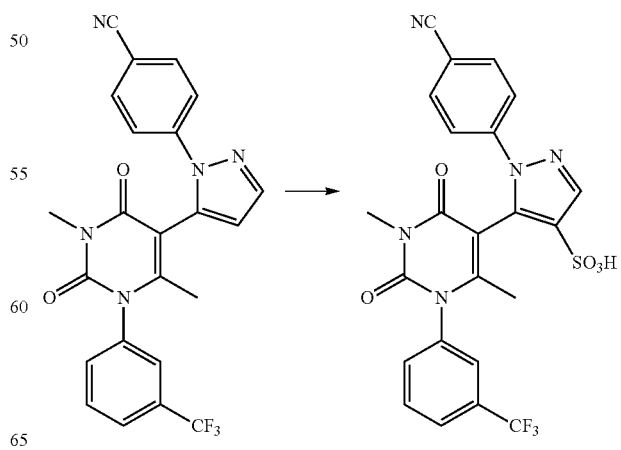

To a suspension of the compound prepared in Example 1 (2.0 g) in acetonitrile (20 ml) was added concentrated sulfuric acid (1.08 ml) and the resulting mixture was stirred with heating under reflux for three hours. The reaction mixture was cooled to room temperature and thereto were added water (40 ml) and ethyl acetate (40 ml×1, 20 ml×1) such that the intended products were extracted into an organic layer. The organic layer was washed with saturated saline (20 ml), dried over anhydrous magnesium sulfate and then concentrated under reduced pressure. To the residue was added chloroform (10 ml) and the resulting mixture was stirred at 60° C. for thirty minutes. The mixture was stirred at room temperature overnight and the precipitated crystals were collected by filtration and washed with chloroform to afford 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (2.06 g).

$^1$H-NMR (DMSO-$d_6$: 400 MHz) δ: 1.78 (s, 1.5H), 1.79 (s, 1.5H), 3.10 (s, 1.5H), 3.10 (s, 1.5H), 7.52-7.60 m, 1H), 7.69-7.74 (m, 2H), 7.81-7.86 (m, 2.5H), 7.89-7.92 (m, 3H), 8.02 (s, 0.5H).

UPLC/MS 532 (M+H)/0.73 min. (measurement condition 9)

Examples 192-194

The compounds indicated in the below-mentioned table (Examples 192-194) were obtained by using the corresponding starting materials according to the similar reaction and treatment method to those described in the Example 191.

TABLE 58

| Ex. | R$^1$ | R$^2$ | Measurement cond | (LC-MS: Rt/ [M + H]+) | |
|---|---|---|---|---|---|
| 192 | i-Pr | Me | 9 | 560 | 0.77 |
| 193 | Et | Me | 9 | 546 | 0.70 |
| 194 | Me | Et | 9 | 546 | 0.75 |

Examples 195-196

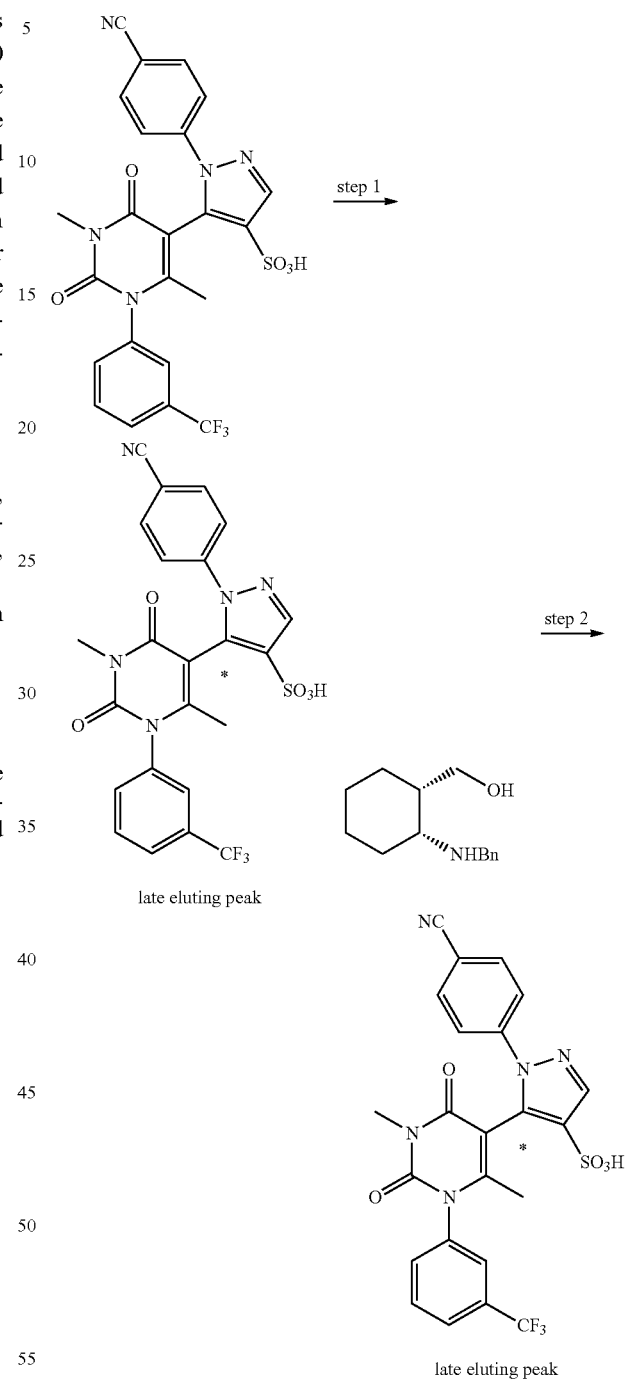

Step 1

Example 195

The 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (prepared in Example 191) (20.0 g) was dissolved in methanol (300 ml) and the mixture was concentrated under reduced pressure. Thereto were added (−)-cis-2-benzylaminocyclohexane methanol (8.3 g) and ethyl acetate (200 ml), and the resulting mixture was stirred with heating under reflux for two hours and then stirred at room temperature for fifteen hours. The precipitated solids were collected by filtration and washed with ethyl acetate to afford crude crystals (11.5 g, optical purity 35.3% de). The obtained crude crystals were dissolved in methanol (100 ml) and then concentrated under reduced pressure, and thereto was added ethyl acetate (100 ml) and the resulting mixture was stirred with heating under reflux for one hour and stirred at room temperature for fifteen hours. The precipitated crystals were collected by filtration and washed with ethyl acetate to afford (−)-cis-2-benzylaminocyclohexane methanol salt of 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (4.2 g, optical purity 99.4% de. late eluting peak).

$^1$H-NMR (CD$_3$OD: 300 MHz) δ: 1.40-1.60 (m, 4H), 1.78-1.87 (m, 7H), 2.38-2.44 (m, 1H), 3.24 (s, 1.5H), 3.25 (s, 1.5H), 3.32-3.39 (m, 1H), 3.74 (dd, 1H, J=10.8, 4.4 Hz), 4.05-(dd, 1H, J=10.8, 9.2 Hz), 4.15 (d, 1H, J=13.0 Hz), 4.38 (d, 1H, J=13.0 Hz), 7.40-7.47 (m, 5H), 7.49-7.96 (m, 6H), 8.02 (s, 1H).

Step 2

Example 196

To the crystals obtained in Example 195 were added ethyl acetate (50 ml) and 5 N hydrochloric acid (10 ml) followed by an addition of ethyl acetate (50 ml×2) such that the intended products were extracted into an organic layer. The organic layer was washed with saturated saline (50 ml), dried over anhydrous sodium sulfate and then concentrated under reduced pressure to afford (+)-1-(4-cyanophenyl)-5-(3,6-dimethyl-2,4-dioxo-1-(3-trifluoromethylphenyl)-1,2,3,4-tetrahydropyridin-5-yl)-1H-pyrazole-4-sulfonic acid (2.7 g, optical purity 99.3% ee, late eluting peak).

[α]$_D^{25}$=70.36, c 0.122, MeOH

UPLC/MS 532 (M+H)/0.73 min. (measurement condition 9)

[Analysis Condition of Examples 195 and 196 and the Others]

UPLC: ACQUITY UPLC (trade mark, manufactured by Waters Corp.)

Detector: PDA detector, manufactured by Waters Corp.

Column: CHIRALPAK IC (manufactured by Daicel Corp.) (S-5 µm, 4.6×250 mm)

Flow rate: 1.0 ml/min

Detection wavelength: 254 nm

Mobile phase: 0.1% TFA/MeOH

Elution Condition: 15 min.

Early eluting peak: 7.198 (min.)

Late eluting peak: 8.299 (min.)

Example 197

The compound of Example 195 was also prepared according to the below-mentioned processes.

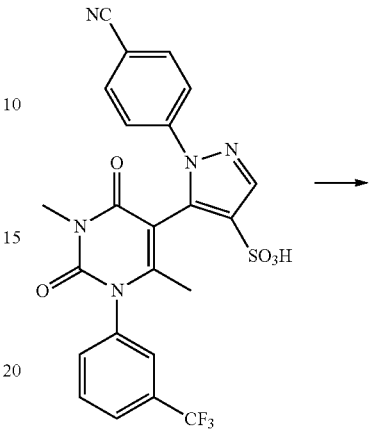

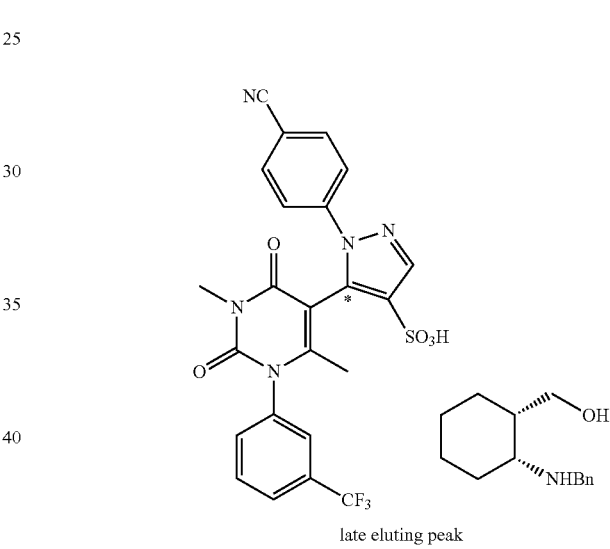

late eluting peak

A solution of 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (prepared in Example 191) (36.0 g) and (−)-cis-2-benzylaminocyclohexanemethanol (14.9 g) in methanol (360 ml) was stirred for one hour with heating under reflux. The reaction mixture was concentrated under reduced pressure and thereto was added methanol (15.0 ml). The mixture was stirred at 80° C. and thereto was added ethyl acetate (360 ml) and the mixture was stirred for one and a half hours and then stirred at room temperature for fifteen hours. The precipitated solids were collected by filtration and washed with ethyl acetate to afford the same product as that of Example 197, (−)-cis-2-benzylaminocyclohexanemethanol salt of (+)-1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (16.6 g, optical purity 99.4% de, late eluting peak).

Examples 198-199

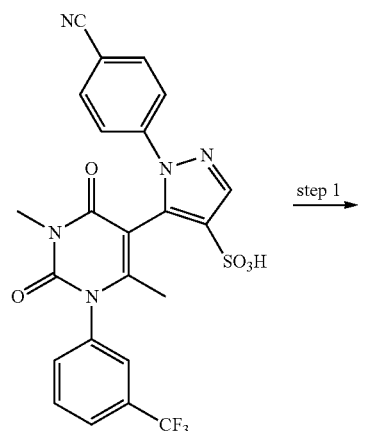

step 1

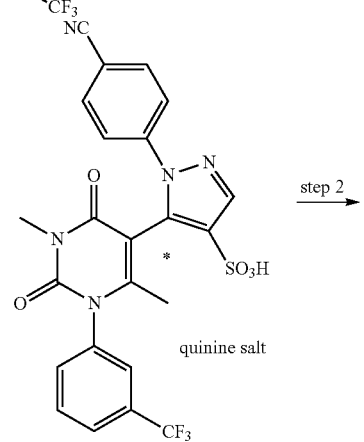

quinine salt late eluting peak

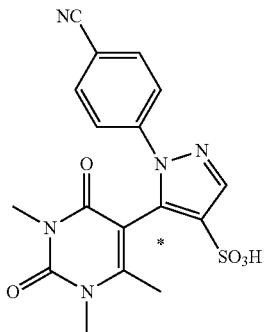

early eluting peak

Step 1

Example 198

1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (prepared in Example 191 (7.2 g) and quinine (4.4 g) were dissolved in methanol (12 ml) and the resulting mixture was stirred with heating under reflux for fifteen minutes, at room temperature for one hour and at 0° C. for four hours. The precipitated solids were collected by filtration and washed with isopropanol to afford quinine salt of 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (3.6 g, optical purity>99.8% de, early eluting peak).

$^1$H-NMR (CD$_3$OD: 300 MHz) δ: 1.57-1.65 (m, 1H), 1.77 (s, 1.5H), 1.81 (s, 1.5H), 1.90-1.95 (m, 1H), 2.09-2.26 (m, 3H), 2.77-(brs, 1H), 3.22-3.32 (m, 6H), 3.54-3.62 (m, 2H), 4.01 (s, 3H), 4.17 (brs, 1H), 5.02-5.15 (m, 2H), 5.74-5.87 (m, 2H), 7.38 (d, 1H, J=2.6 Hz), 7.49 (dd, 1H, J=9.3, 2.7 Hz), 7.57-7.88 (m, 9H), 7.94-8.03 (m, 2H), 8.72 (d, 1H, J=4.6 Hz).

Step 2

Example 199

To a crystal prepared in Example 200 (2.0 g) were added ethyl acetate (30 ml) and 5 N hydrochloric acid (5 ml) followed by an addition of ethyl acetate (30 ml×3) such that the intended products were extracted into an organic layer. The organic layer was washed with saturated saline (30 ml), dried over anhydrous sodium sulfate and then concentrated under reduced pressure to afford (-)-1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (1.2 g, optical purity>99.8% ee, early eluting peak). UPLC/MS 532 (M+H)/0.73 min. (measurement condition 9)

The optical resolution for the compound of Example 198 can be also carried out by using chiral amine indicated in the below-mentioned table other than quinine (Examples 200-203).

TABLE 59

| Ex. | Chiral amine | Solvent |
| --- | --- | --- |
| 200 | cinchonine | MeOH |
| 201 | cinchonidine | MeOH/IPA |
| 202 | (+)-cis-2-benzylaminocyclohexane methanol | IPA |
| 203 | (1S,2S)-(-)-2-amino-1-phenyl-1,3-propanediol | AcOEt |

Examples 204-205

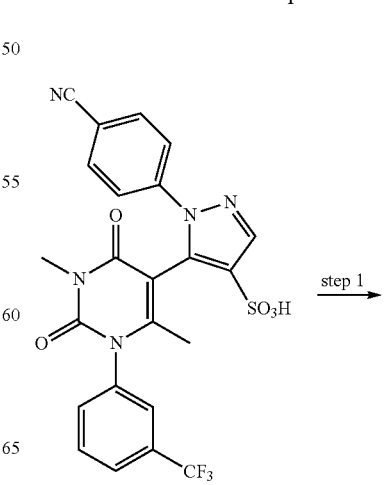

step 1

289

-continued

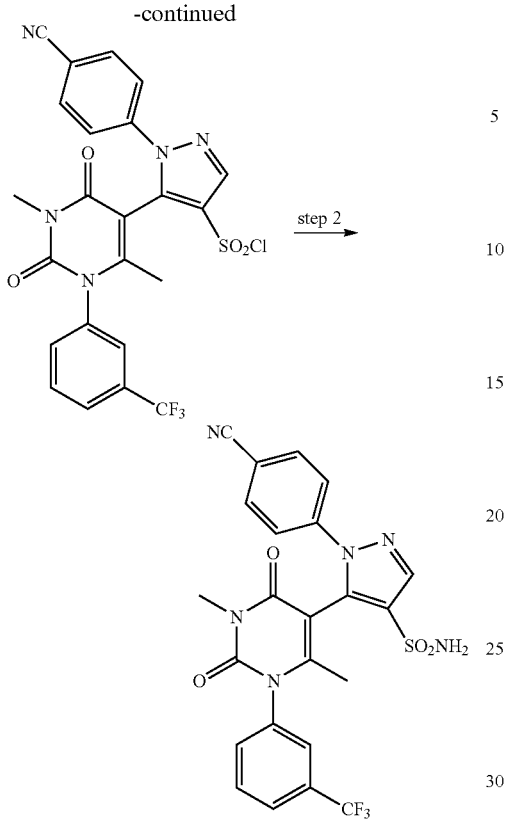

Step 11

Example 204

To a suspension of the compound prepared in Example 191 (10.0 g) in acetonitrile (70 ml) was added phosphorus oxychloride (7.04 ml) and the resulting mixture was stirred at 90° C. for two hours. The mixture was concentrated on evaporator instrument under reduced pressure and to the residue were then added ethyl acetate (50 ml) and hexane (50 ml) and the mixture was stirred for thirty minutes. The precipitated solids were collected by filtration and washed with ethyl acetate/hexane=1/1 to afford 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonylchloride (10.3 g). UPLC/MS 550 (M+H)/1.08 min. (measurement condition 9).

Step 2

Example 205

A suspension of the compound prepared in Example 204 (50.0 mg) in acetonitrile (20 ml) was cooled to 0° C. and thereto was added ammonia water (28%, 5.0 ml) dropwise and the mixture was stirred for another ten minutes. The reaction solution was concentrated under reduced pressure and the residue was purified by silica gel column chromatography (eluent: hexane/ethyl acetate) to afford 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide (42.0 mg). UPLC/MS 531 (M+H)/0.87 min. (measurement condition 9)

290

Examples 206-208

The compound indicated in the below-mentioned table (Examples 206-208) were obtained by using the corresponding starting materials according to the similar reaction and treatment method to those described in Examples 204 and 305.

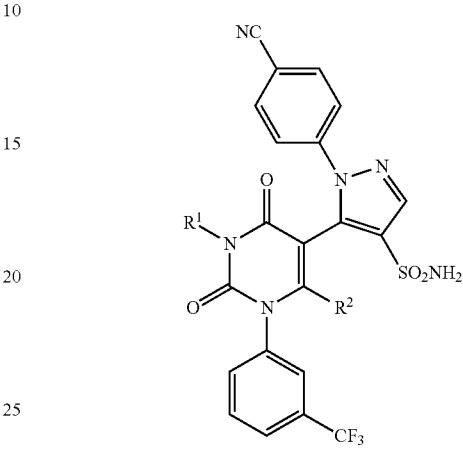

TABLE 60

| Ex. | $R^1$ | $R^2$ | melting point (m.p.) | Measurement cond. | (LC-MS: Rt/[M + H]+) | |
|---|---|---|---|---|---|---|
| 206 | i-Pr | Me |  | 9 | 559 | 0.97 |
| 207 | Et | Me | 195 | 9 | 545 | 0.91 |
| 208 | Me | Et |  | 9 | 545 | 0.94 |

Example 209

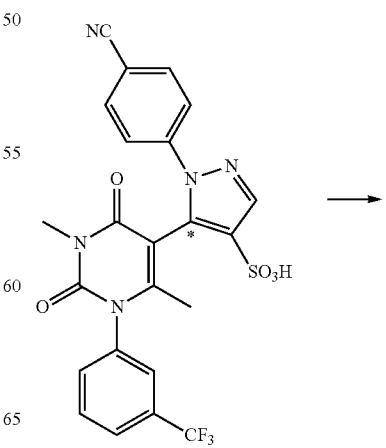

-continued

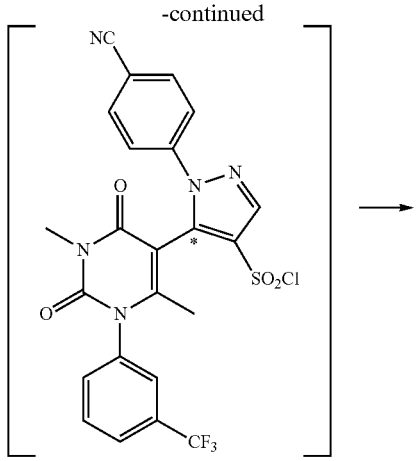

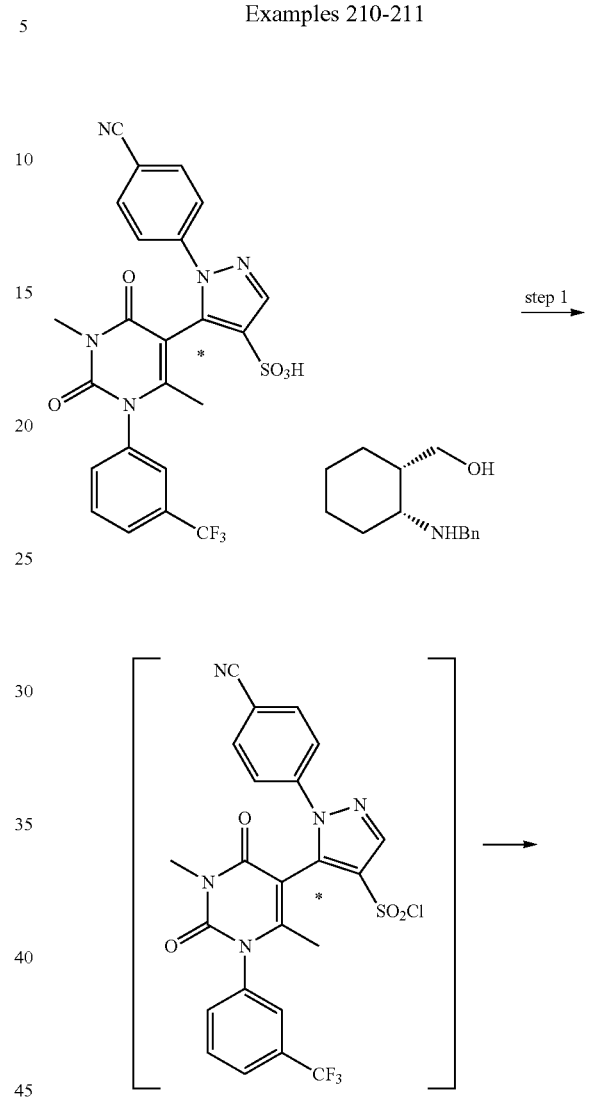

pyrazole-4-sulfonamide (2.33 g). UPLC/MS 531 (M+H)/ 0.87 min. (measurement condition 9)

Examples 210-211

To a suspension of (+)-1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (prepared in Example 196) (2.67 g) in acetonitrile (20 ml) were added pyridine (0.81 ml) and phosphorus oxychloride (1.87 ml) and the resulting mixture was stirred at room temperature for forty five minutes. Without an isolation of the formed 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonyl chloride, the reaction solution was added dropwise to ammonia water (28%, 20 ml) that cooled to 0° C. and the resulting mixture was stirred for ten minutes. To the reaction solution were added water (40 ml) and ethyl acetate (40 ml×2) such that the intended products were extracted into an organic layer. The organic layer washed with 4% ammonia water (20 ml), saturated saline (8 ml), 1N hydrochloric acid (20 ml×2) and saturated saline (20 ml), dried over anhydrous magnesium sulfate and then concentrated under reduced pressure. The residue was purified by silica gel column chromatography (eluent: hexane/ethyl acetate) to afford (+)-1-(4-cyanophenyl)-5-(3,6-dimethyl-2,4-dioxo-1-(3-trifluoromethylphenyl)-1,2,3,4- tetrahydropyrimidin-5-yl)-1H-

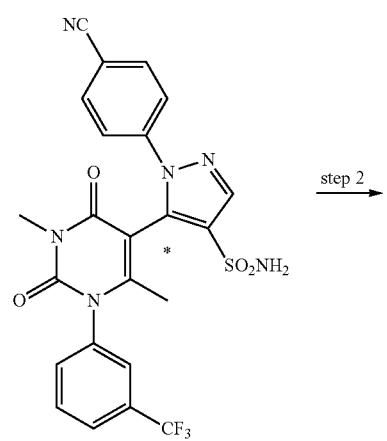

-continued

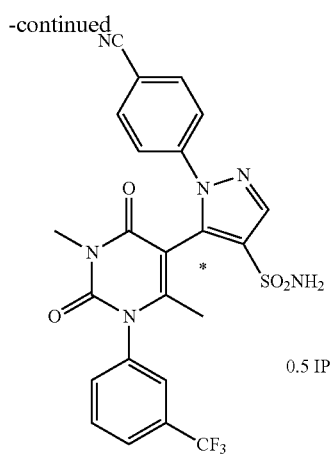

0.5 IPA

Step 1

Examples 210

To a suspension of (−)-cis-2-benzylaminocyclohexanemethanol salt of 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (prepared in Example 195) (6.83 g) in acetonitrile (48 ml) were added pyridine (1.47 ml) and phosphorus oxychloride (3.39 ml) and the resulting mixture was stirred at room temperature for two hours. The reaction solution was added dropwise to ammonia water (28%, 48 ml) that cooled to 0° C. and the mixture was stirred for another ten minutes. To the reaction solution were added water (50 ml) and ethyl acetate (100 ml×2) such that the intended products were extracted into an organic layer. The organic layer was washed with 4% ammonia water (50 ml), saturated saline (20 ml), 1N hydrochloric acid (50 ml×2) and saturated saline (50 ml), dried over anhydrous magnesium sulfate and then concentrated under reduced pressure. The residue was purified by silica gel column chromatography (eluent: hexane/ethyl acetate) to afford the same product as Example 209, (+)-1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide (4.84 g). UPLC/MS 531 (M+H)/0.87 min. (measurement condition 9)

Step 2

Example 211

(+)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide (prepared in Example 210) (331 mg) was recrystallized from isopropanol (IPA) to afford (+)-1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide 0.5 IPA solvates (299 mg) ($[\alpha]_D^{25}$=276.4, c 0.109, CHCl$_3$)

$^1$H-NMR (DMSO-d$_6$: 300 MHz) δ: 1.02 (d, 3H, J=6.0 Hz), 1.64-(s, 1.5H), 1.68 (s, 1.5H), 3.12 (s, 1.5H), 3.14 (s, 1.5H), 3.73-3.79 (0.5H, m), 4.43 (d, 0.5H, J=4.2 Hz), 7.49 (brs, 2H), 7.66-7.72 (m, 3H), 7.78-7.84 (m, 2H), 7.91-8.00 (m, 4H), 8.14 (s, 1H)

Example 212

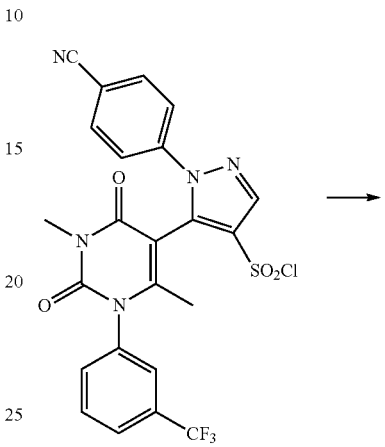

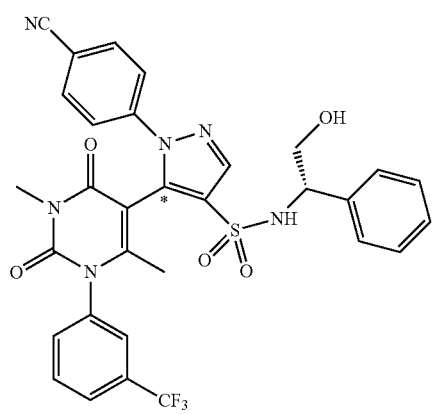

To a suspension of 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid chloride (prepared in Example 204) (2.05 g) in chloroform (60 ml) were added (S)-2-phenylglycinol (767 mg) and diisopropylethylamine (0.99 ml) and the resulting mixture was stirred at room temperature for one hour. The reaction solution was concentrated under reduced pressure and thereto were added 1N hydrochloric acid (30 ml) and ethyl acetate (60 ml) such that the intended products were extracted into an organic layer. The organic layer was washed with 1N hydrochloric acid (30 ml) and saturated saline (30 ml), dried over anhydrous magnesium sulfate and then concentrated under reduced pressure. The residue was purified by silica gel column chromatography (eluent: chloroform/methanol) to afford (S)-1-(4-cyanophenyl)-5-(3,6-dimethyl-2,4-dioxo-1-(3-trifluoromethylphenyl)-1,2,3,4-tetrahydropyrimidin-5-yl)-N-(2-hydroxy-1-phenylethyl)-1H-pyrazole-4-sulfonamide (813 mg).

UPLC/MS 651 (M+H)/0.98 min. (measurement condition 9)

Example 213

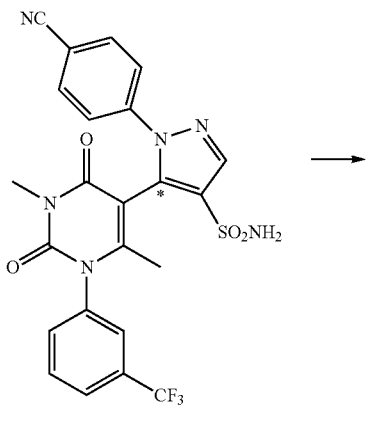

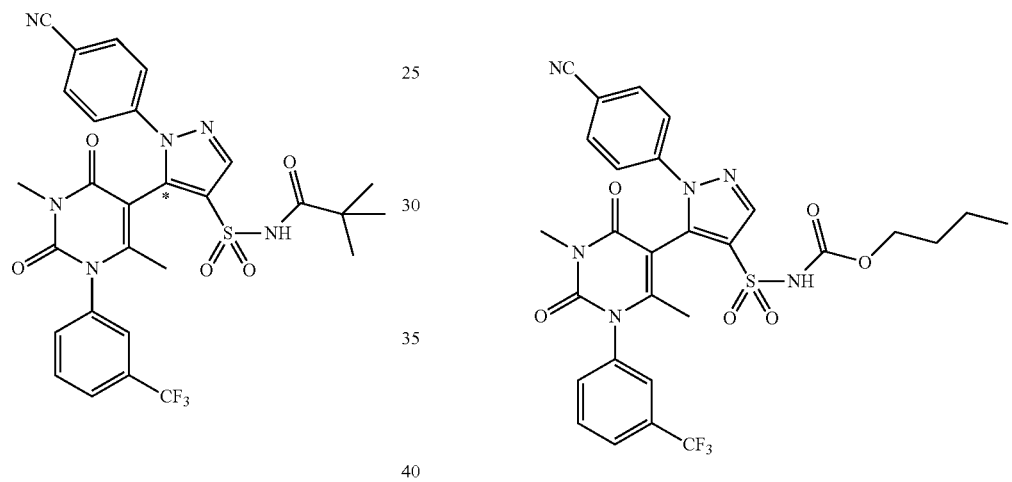

(+)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide (prepared in Example 209) (49 mg) was dissolved in acetonitrile (1 ml) and thereto were added trimethylacetic anhydride (0.086 ml) and concentrated sulfuric acid (0.01 ml) and the resulting mixture was stirred at 60° C. for ten minutes. The mixture was cooled to room temperature, and thereto were water (30 ml) and ethyl acetate (30 ml) such that the intended products were extracted into an organic layer. The organic layer was washed with saturated saline (30 ml), dried over anhydrous magnesium sulfate and then concentrated under reduced pressure. The residue was purified by silica gel column chromatography (eluent: hexane/ethyl acetate). The mixture was concentrated, and thereto were added chloroform (0.5 ml) and hexane (2 ml) and the mixture was stirred for one hour. The precipitated solids were collected by filtration and washed with chloroform/hexane=1/4 to afford N-(1-(4-cyanophenyl)-5-(3,6-dimethyl-2,4-dioxo-1-(3-trifluoromethylphenyl)-1,2,3,4-tetrahydropyrimidin-5-yl)-1H-pyrazol-4-ylsulfonyl)pivalamine (48 mg).

$^1$H-NMR (DMSO-$d_6$: 400 MHz) δ: 1.04 (s, 9H), 1.51 (s, 1.5H), 1.64 (s, 1.5H), 3.13 (s, 1.5H), 3.18 (s, 1.5H), 7.64-7.66 (m, 0.5H), 7.70-7.74 (m, 2H), 7.78-7.86 (m, 2H), 7.91-8.00 (m, 4H), 8.28-8.30 (m, 0.5H), 11.54 (s, 1H).

UPLC/MS 615 (M+H)/1.16 min. (measurement condition 9)

Example 214

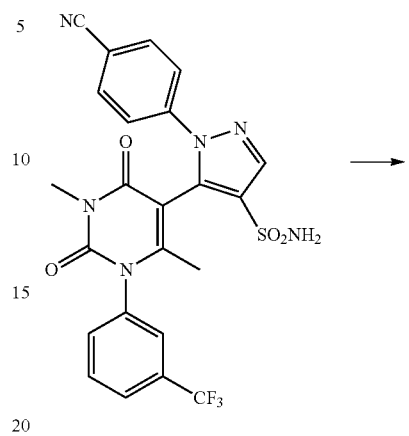

1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide (prepared in Example 205) (99 mg) was dissolved in acetone (8 ml) and thereto were added butyl chloroformate (0.036 ml) and potassium carbonate (52 mg) and the mixture was stirred at 60° C. for fifteen hours. The mixture was cooled to room temperature, and to the reaction solution were added 1N hydrochloric acid (20 ml) and ethyl acetate (30 ml×2) such that the intended products were extracted into an organic layer. The organic layer was washed with saturated saline (30 ml), dried over magnesium sulfate and then concentrated under reduced pressure. The residue was purified by silica gel column chromatography (eluent: chloroform/methanol) to afford butyl 1-(4-cyanophenyl)-5-(3,6-dimethyl-2,4-dioxo-1-(3-trifluoromethylphenyl)-1,2,3,4-tetrahydropyrimidin-5-yl)-1H-pyrazol-4-ylsulfonyl)carbamate (100 mg).

$^1$H-NMR (DMSO-$d_6$: 400 MHz) δ: 0.80 (t, 1.5H, J=7.4 Hz), 0.82 (t, 1.5H, J=7.3 Hz), 1.17-1.27 (m, 2H), 1.41-1.49 (m, 2H), 1.60 (s, 1.5H), 1.66 (s, 1.5H), 3.14 (s, 1.5H), 3.16 (s, 1.5H), 3.90-3.98 (m, 2H), 7.70-7.74 (m, 2.5H), 7.81-7.95 (m,

3H), 7.99-8.01 (m, 2.5H), 8.29-8.31 (m, 1H), 11.88 (s, 0.5H), 11.92 (s, 0.5H). UPLC/MS 631 (M+H)/1.07 min. (measurement condition 9)

Example 215

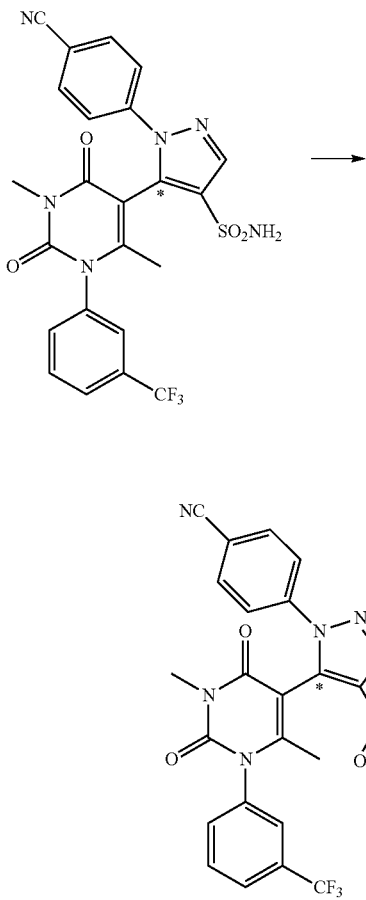

(+)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide (prepared in Example 209) (46 mg) was dissolved in acetonitrile (1 ml) and thereto were added benzoic acid (13 mg), 4-dimethylaminopyridine (21 mg) and 1-ethyl-3-(3-dimethylaminopropyl)carbodiimide hydrochloride (25 mg) and the resulting mixture was stirred for three hours at room temperature. To the reaction solution were added 1N hydrochloric acid (20 ml) and ethyl acetate (30 ml×2) such that the intended products were extracted into an organic layer. The organic layer was washed with 1N hydrochloric acid (20 ml) and saturated saline (30 ml) successively, dried over magnesium sulfate and then concentrated under reduced pressure. The residue was purified by silica gel column chromatography (eluent: chloroform/methanol) to afford N-(1-(4-cyanophenyl)-5-(3,6-dimethyl-2,4-dioxo-1-(3-trifluoromethylphenyl)-1,2,3,4-tetrahydropyrimidin-5-yl)-1H-pyrazol-4-ylsulfonyl)benzamide (51 mg).

$^1$H-NMR (DMSO-$d_6$: 400 MHz) δ: 1.55 (s, 3H), 3.02 (s, 1.5H), 3.04 (s, 1.5H), 7.25-7.50 (m, 4H), 7.68-7.78 (m, 4H), 7.82-7.95 (m, 6H), 8.15-8.17 (m, 1H), 12.46 (s, 1H). UPLC/MS 635 (M+H)/1.02 min. (measurement condition 9)

Example 216

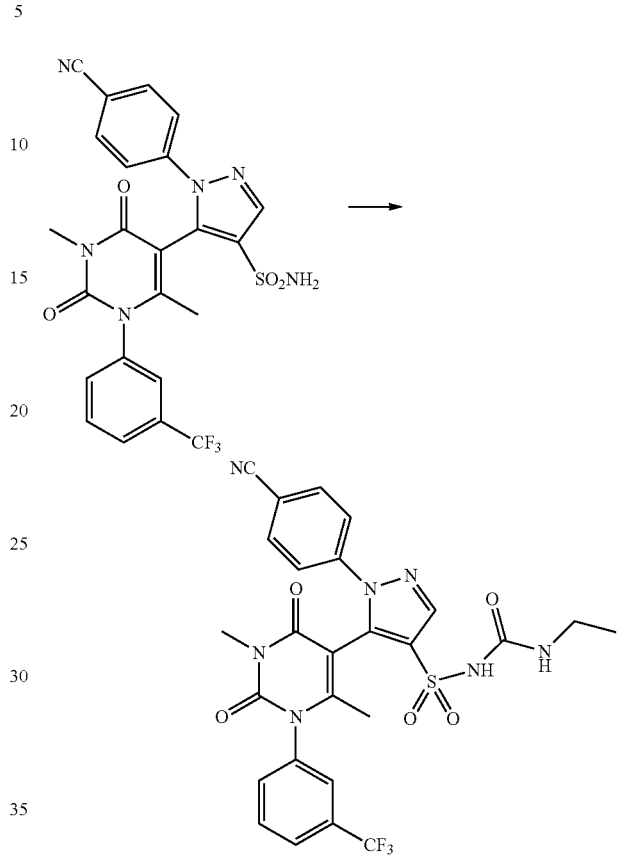

1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide (prepared in Example 205) (97 mg) was dissolved in acetonitrile (2 ml) and thereto were added ethyl isocyanate (0.043 ml) and diisopropylethylamine (0.065 ml) and the resulting mixture was stirred at 50° C. for four hours. The mixture was cooled to room temperature, and thereto were then added 1N hydrochloric acid (20 ml) and ethyl acetate (30 ml) such that the intended products were extracted into an organic layer. The organic layer was washed with 1N hydrochloric acid (20 ml) and saturated saline (30 ml) successively, dried over magnesium sulfate and then concentrated under reduced pressure. The residue was purified by silica gel column chromatography (eluent: chloroform/methanol) to afford 1-(4-cyanophenyl)-5-(3,6-dimethyl-2,4-dioxo-1-(3-trifluoromethylphenyl)-1,2,3,4-tetrahydropyrimidin-5-yl)-N-(ethylcarbonyl)-1H-pyrazole-4-sulfonamide (88 mg).

$^1$H-NMR (DMSO-$d_6$: 400 MHz) δ: 0.86 (t, 1.5H, J=7.1 Hz), 0.91 (t, 1.5H, J=7.2 Hz), 1.49 (s, 1.5H), 1.58 (s, 1.5H), 2.87-3.00 (m, 2H), 3.16 (s, 1.5H), 3.19 (s, 1.5H), 6.30-6.33 (m, 1H), 7.68-7.83 (m, 4H), 7.89-7.92 (m, 2H), 7.98-8.02 (m, 2H), 8.25-8.27 (m, 2H), 10.79 (s, 1H).
UPLC/MS 602 (M+H)/0.93 min. (measurement condition 9)

Examples 217-259

The compounds indicated in the below-mentioned table (Examples 217-259) were obtained by using the corresponding starting materials (racemates, optical isomers) according to the similar reaction and methods to those described in Examples 204-205 and 212-216.

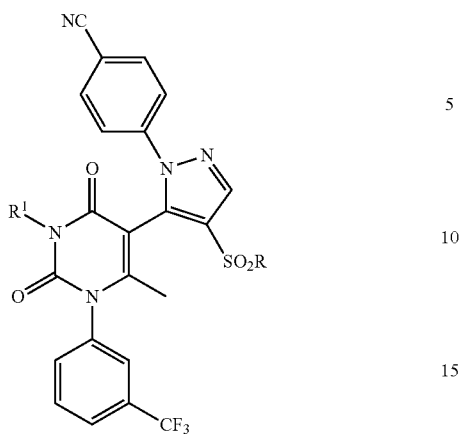
TABLE 61
| Ex. | R | R¹ | Optical activity of product r: racemate, e: eutomer d: distomer | Measurement cond. | (LC-MS: Rt/[M + H]+) | |
|---|---|---|---|---|---|---|
| 217 | NHMe | Me | r | 9 | 0.93 | 545 |
| 218 | NHMe | Me | e | 9 | 0.93 | 545 |
| 219 | NMe₂ | Me | r | 9 | 1.03 | 559 |
| 220 | pyrrolidinyl | Me | r | 9 | 1.08 | 585 |
| 221 | morpholinyl | Me | r | 9 | 1.04 | 601 |
| 222 | 4-hydroxypiperidinyl | Me | r | 9 | 0.913 | 616 |
| 223 | 4-(dimethylamino)piperidinyl | Me | r | 9 | 0.758 | 643 |
| 224 | 4-(NHBoc)piperidinyl | Me | r | 9 | 1.093 | 715 |

TABLE 61-continued
| Ex. | R | R¹ | Optical activity of product r: racemate, e: eutomer d: distomer | Measurement cond. | (LC-MS: Rt/[M + H]+) | |
|---|---|---|---|---|---|---|
| 225 | 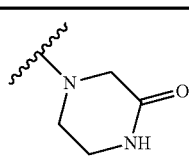 | Me | r | 9 | 0.876 | 615 |
| 226 | 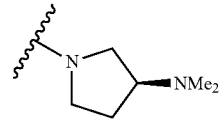 [SMILES: *N1CC[C@H](N(C)C)C1] | Me | r | 9 | 0.893 | 643 |
| 227 | 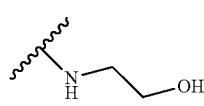 | Me | e | 9 | 0.86 | 575 |
| 228 | 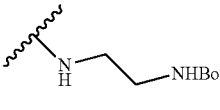 | Me | e | 9 | 1.04 | 674 |
| 229 | 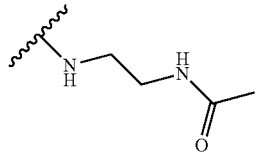 [SMILES: *NCCNC(C)=O] | Me | r | 9 | 0.855 | 617 |
| 230 | 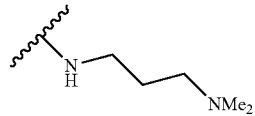 [SMILES: *NCCCN(C)C] | Me | r | 9 | 0.723 | 616 |
| 231 | 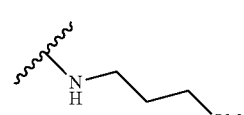 | Me | r | 9 | 0.967 | 604 |
| 232 | 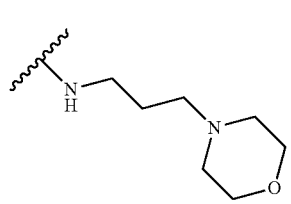 [SMILES: *NCCCN1CCOCC1] | Me | r | 9 | 0.738 | 659 |
TABLE 62
| 233 | 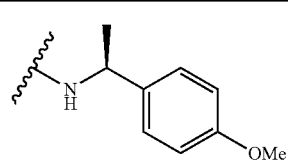 | Me | e | 9 | 1.09 | 665 |
| 234 | 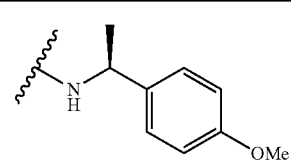 | Me | d | 9 | 1.08 | 665 |

TABLE 62-continued

| # | Structure | R | x | n | a | b |
|---|---|---|---|---|---|---|
| 235 | ~NH-CH(CH3)-C6H4-OMe | Et | e | 9 | 1.130 | 679 |
| 236 | ~NH-CH(CH3)-C6H4-OMe | Et | d | 9 | 1.129 | 679 |
| 237 | ~HN-C(O)-O-menthyl | Me | r | 9 | 1.28 | 713 |
| 238 | ~NH-CH(Ph)-CH2OH | Me | e | 9 | 0.98 | 651 |
| 239 | ~N-oxazolidin-2-one | Me | e | 9 | 0.97 | 601 |
| 240 | ~N-imidazolidin-2-one-N'Boc | Me | e | 9 | 1.09 | 644 |
| 241 | ~N-imidazolidin-2-one-NH | Me | e | 9 | 0.90 | 601 |
| 242 | ~NH-C(O)-CH3 | Me | r | 9 | 0.92 | 573 |
| 243 | ~NH-C(O)-C4H9 | Me | e | 9 | 1.05 | 615 |
| 244 | ~NH-C(O)-C4H9 | Me | r | 9 | 1.05 | 615 |
| 245 | ~NH-C(O)-C4H9 | Et | r | 9 | 1.07 | 629 |
| 246 | ~NH-C(O)-iPr | Me | r | 9 | 0.99 | 601 |
| 247 | ~NH-C(O)-cyclohexyl | Me | r | 9 | 1.08 | 641 |
| 248 | ~NH-C(O)-cyclohexyl | Me | e | 9 | 1.08 | 641 |
| 249 | ~NH-C(O)-Ph | Me | e | 9 | 1.02 | 635 |
| 250 | ~NH-C(O)-C6H4-F | Me | e | 9 | 1.02 | 653 |

TABLE 63

| # | Structure | R | x | n | a | b |
|---|---|---|---|---|---|---|
| 251 | ~NH-C(O)-C6H4-Cl | Me | e | 9 | 1.06 | 669 |
| 252 | ~NH-C(O)-O-Me | Me | r | 9 | 0.95 | 589 |

TABLE 63-continued
| | | | | | | |
|---|---|---|---|---|---|---|
| 253 | ~~NH-C(O)-O-butyl~~ | Me | r | 9 | 1.07 | 631 |
| 254 | ~~NH-C(O)-O-t-Bu~~ | Me | r | 9 | 1.05 | 575 (- t-Bu) |
| 255 | ~~NH-C(O)-O-t-Bu~~ | Me | e | 9 | 1.16 | 615 |
| 256 | ~~NH-C(O)-NH-Et~~ | Me | r | 9 | 0.93 | 602 |
| 257 | ~~NH-C(O)-NH-Et~~ | Me | e | 9 | 0.91 | 602 |
| 258 | ~~NH-C(O)-N(Me)₂~~ | Me | r | 9 | 0.90 | 602 |
| 259 | ~~NH-C(O)-O-cyclohexyl~~ | Me | e | 9 | 1.10 | 657 |
The NMR data of Examples 243 and 248 are shown below.
Example 243
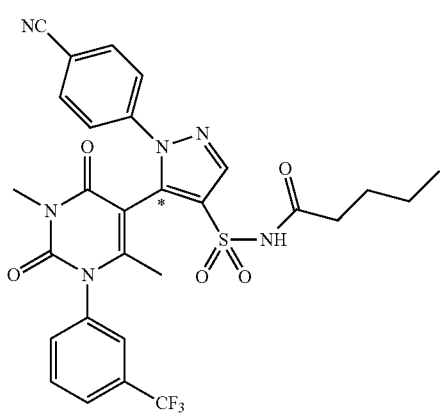
¹H-NMR (DMSO-d₆: 400 MHz) δ: 0.79 (t, 1.5H, J=7.4 Hz), 0.82 (t, 1.5H, J=7.3 Hz), 1.16-1.24 (m, 2H), 1.35-1.42 (m, 2H), 1.54 (s, 1.5H), 1.63 (s, 1.5H), 2.08-2.17 (m, 2H), 3.16 (s, 1.5H), 3.18 (s, 1.5H), 7.60-7.66 (m, 0.5H), 7.70-7.75 (m, 2H), 7.78-7.86 (m, 2H), 7.92-7.95 (m, 1.5H), 7.98-8.02 (m, 2H), 8.29-8.31 (m, 1H), 11.87 (s, 1H).
Example 248
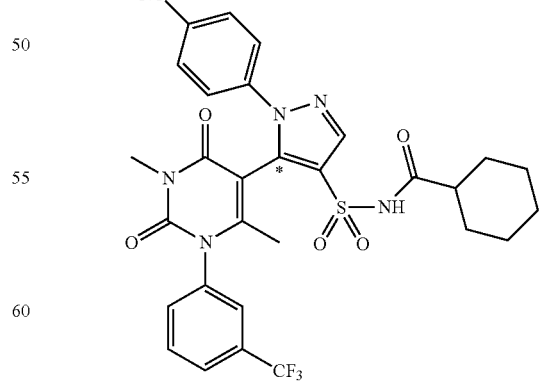
¹H-NMR (DMSO-d₆: 400 MHz) δ: 1.07-1.24 (m, 5H), 1.51 (s, 1.5H), 1.55-1.74 (m, 5H), 1.63 (s, 1.5H), 1.98-2.06 (m, 1H), 3.15 (s, 1.5H), 3.19 (s, 1.5H), 7.62-7.66 (m, 0.5H), 7.70-7.73 (m, 2H), 7.74-7.86 (m, 2H), 7.95-7.98 (m, 1.5H), 7.98-8.02 (m, 2H), 8.29-8.31 (m, 1H), 11.76 (s, 0.5H), 11.82 (s, 0.5H).

Example 260

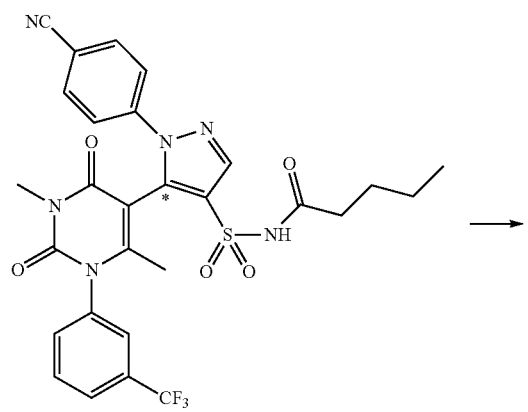

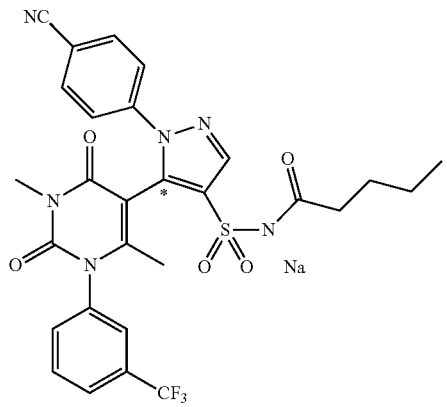 [SMILES: CCCCC(=O)NS(=O)(=O)c1cnn(-c2ccc(C#N)cc2)c1-c1c(C)n(-c2cccc(C(F)(F)F)c2)c(=O)n(C)c1=O]

The compound prepared in Example 243 (131 mg) was dissolved in THF (2.6 ml) and thereto was added 5N aqueous sodium hydroxide solution (0.045 ml) and the mixture was stirred at room temperature for fifteen minutes. The solvent was distilled under reduced pressure on evaporator instrument to afford sodium salt compound (135 mg).

$^1$H-NMR (DMSO-$d_6$: 400 MHz) δ: 0.77 (t, 1.5H, J=7.2 Hz), 0.79 (t, 1.5H, J=7.2 Hz), 1.14-1.19 (m, 2H), 1.30-1.35 (m, 2H), 1.66 (s, 1.5H), 1.73 (s, 1.5H), 1.85-1.92 (m, 2H), 3.11 (s, 1.5H), 3.13 (s, 1.5H), 7.58-7.61 (m, 0.5H), 7.68-7.73 (m, 2.5H), 7.81-7.87 (m, 1.5H), 7.91-7.98 (m, 4.5H).

UPLC/MS 615 (M+H)/1.04 min. (measurement condition 9)

Example 261

The below-mentioned compound was obtained according to the similar process to those of Example 260.

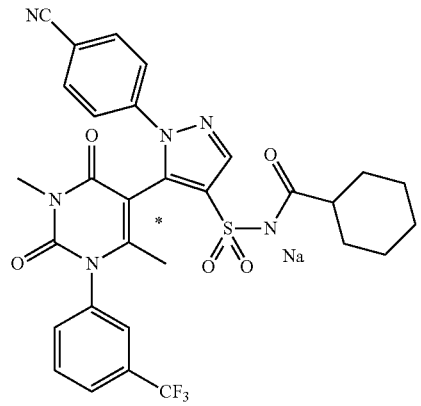

$^{1H}$-NMR (DMSO-$d_6$: 400 MHz) δ: 1.05-1.21 (m, 5H), 1.23 (s, 1.5H), 1.50-1.85 (m, 6H), 1.73 (s, 1.5H), 3.11 (s, 1.5H), 3.13 (s, 1.5H), 7.57-7.61 (m, 0.5H), 7.67-7.74 (m, 2.5H), 7.80-7.87 (m, 1.5H), 7.92-8.02 (m, 4.5H).

UPLC/MS 641 (M+H)/1.08 min (measurement condition 9)

Example 262

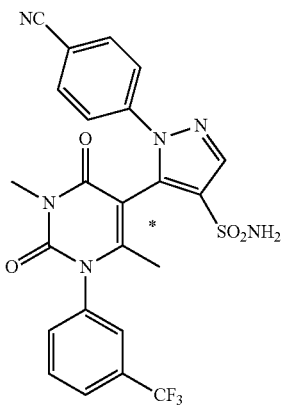

To (S)-1-(4-cyanophenyl)-5-(3,6-dimethyl-2,4-dioxo-1-(3-trifluoromethylphenyl)-1,2, 3,4-tetrahydropyrimidin-5- yl)-N-(2-hydroxy-1-phenylethyl)-1H-pyrazole-4-sulfonamide (prepared in Example 212) (813 mg) was added in water bath (at 20° C.) concentrated sulfuric acid (30 ml) and the resulting mixture was stirred for fifteen minutes. The mixture was cooled to 0° C. and to the reaction solution was then added water (60 ml) dropwise followed by an addition of chloroform (50 ml×2) such that the intended products were extracted into an organic layer. The organic layer was washed with saturated saline (50 ml), dried over anhydrous magnesium sulfate and then concentrated under reduced pressure. The residue was purified by silica gel column chromatography (eluent: chloroform/methanol) to afford the same product as Example 209, (+)-1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide (406 mg).

$^1$H-NMR (DMSO-$d_6$: 400 MHz) δ: 1.65 (s, 1.5H), 1.69 (s, 1.5H), 3.12 (s, 1.5H), 3.14 (s, 1.5H), 7.51 (brs, 2H), 7.66-7.72 (m, 2.5H), 7.78-7.84 (m, 2H), 7.91-8.00 (m, 3.5H), 8.15 (s, 1H).

UPLC/MS 531 (M+H)/0.87 min. (measurement condition 9)

Example 263

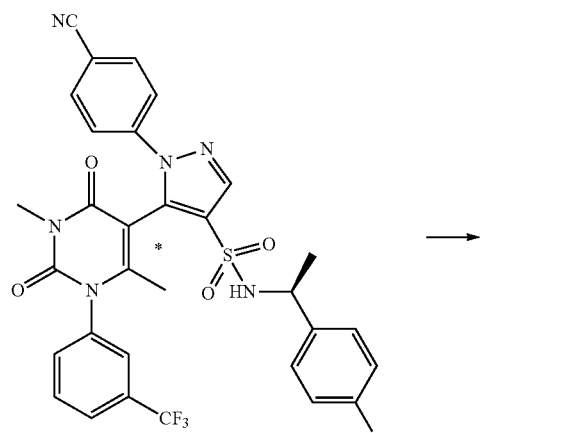
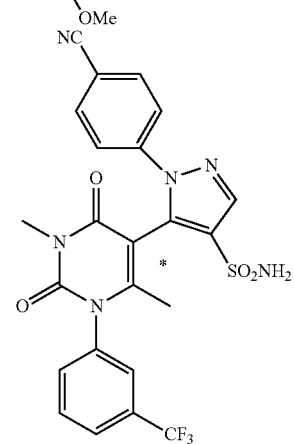

To the compound prepared in Example 233 (1.10 g) was added at room temperature trifluoroacetic acid (5 ml) and the resulting mixture was stirred at room temperature for fifteen minutes. The reaction mixture was concentrated under reduced pressure, and diluted with ethyl acetate (200 ml), washed with saturated aqueous sodium hydrogen carbonate solution (50 ml) and saturated saline (50 ml), dried over anhydrous sodium sulfate and then concentrated under reduced pressure. The residue was purified by silica gel column chromatography (eluent: hexane/ethyl acetate) to afford the same product as Example 209, (+)-1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide (896.1 mg).

Example 264

The below-mentioned compound was obtained by using the compound of Example 235 according to the similar reaction and treatment method to those described in Example 263.

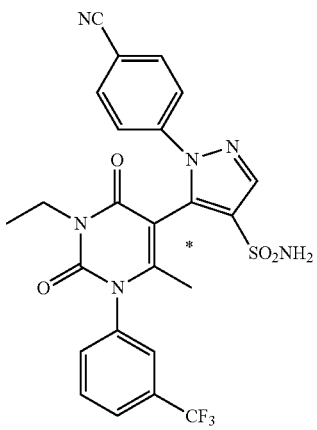 [SMILES: CCn1c(=O)c(-c2c(S(N)(=O)=O)cnn2-c2ccc(C#N)cc2)c(C)n(-c2cccc(C(F)(F)F)c2)c1=O]

(+)-1-(4-Cyanophenyl)-5-(3-ethyl-6-methyl-2,4-dioxo-1-(3-trifluoromethylphenyl)-1,2,3,4-tetrahydropyrimidin-5-yl)-1H-pyrazole-4-sulfonamide $^1$H-NMR (CDCl$_3$: 300 MHz) δ: 1.23-1.28 (m, 3H), 1.34 (d, 3H, J=6.6 Hz), 4.04 (d, 3H, J=7.2 Hz), 7.02 (d, 0.5H, J=8.1 Hz), 7.09 (s, 0.5H), 7.48-7.66 (m, 4H), 7.71 (d, 1H, J=7.8 Hz), 7.78-7.82 (m, 2H), 8.14 (s, 1H).

UPLC/MS 545 (M+H)/0.93 min (measurement condition 9), $[α]_D^{24}$=100.32, c 0.261, CHCl$_3$.

Example 265

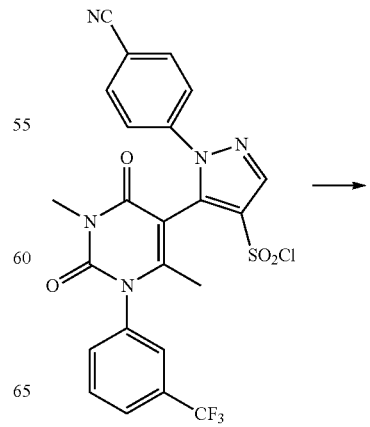

-continued

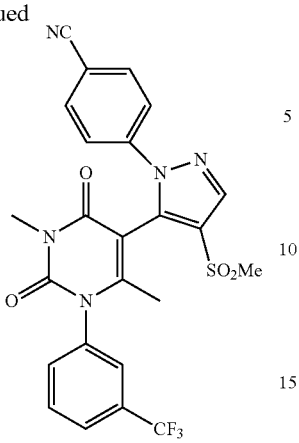

The solution of the compound prepared in Example 204 (55 mg) in tetrahydrofuran (20 ml) was added at 0° C. to an aqueous solution of sodium sulfite (25 mg) and sodium hydrogen carbonate (25 mg) in water (1.0 ml) and the resulting mixture was stirred at the same temperature for one hour. To the reaction solution was then added methyl iodide (142 mg) and the resulting mixture was stirred at 25° C. for fifty hours. The reaction solution was concentrated under reduced pressure and thereto were then added water (10 ml) and ethyl acetate (10 ml×2) such that the intended products were extracted into an organic layer. The organic layer was washed with saturated saline (10 ml), dried over anhydrous sodium sulfate and then concentrated under reduced pressure. The residue was purified by silica gel column chromatography (eluent: hexane/ethyl acetate) to afford 4-(5-(3,6-dimethyl-2, 4-dioxo-1-(3-trifluoromethylphenyl)-1,2,3,4-tetrahydropyrimidin-5-yl-4-(methylsulfonyl)-1H-pyrazol-1-yl)benzonitrile (58 mg). UPLC/MS 530 (M+H)/0.97 min. (measurement condition 9)

Examples 266-267

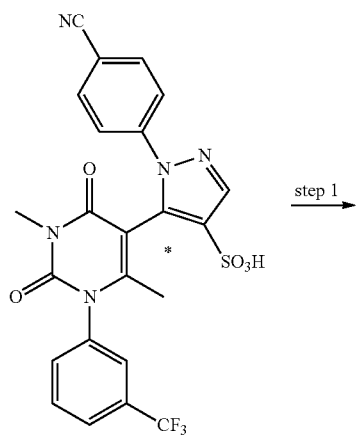

-continued

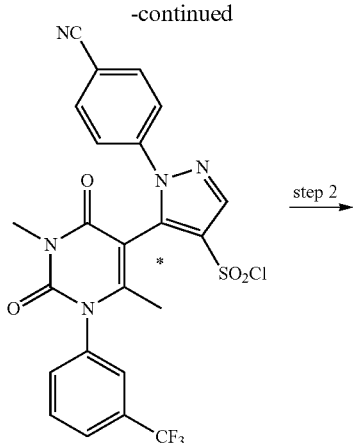

step 2

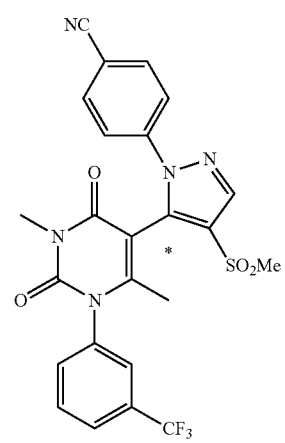

Step 1

Example 266

To a suspension of (+)-1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid (prepared in Example 196) (315 mg) in acetonitrile (2.2 ml) were added pyridine (94 mg) and phosphorus oxychloride (365 mg) and the resulting mixture was stirred at room temperature for thirty minutes. To the reaction mixture was added water (5 ml) followed by an addition of ethyl acetate (10 ml×2) such that the intended products were extracted into an organic layer. The organic layer was washed with saturated saline (10 ml), dried over anhydrous sodium sulfate and then concentrated under reduced pressure to afford 1-(4-cyanophenyl)-5-(3,6-dimethyl-2,4-dioxo-1-(3-trifluoromethylphenyl)-1,2,3, 4-tetrahydropyrimidin-5-yl)-1H-pyrazole-4-sulfonic acid chloride (330 mg).

UPLC/MS 550 (M+H)/1.08 min (measurement condition 9)

Step 2

Example 267

A solution of the compound prepared in Example 266 (1.78 g) in tetrahydrofuran (30 ml) was added at 0° C. to an aqueous solution of sodium sulfite (774 mg) and sodium hydrogen carbonate (774 mg) in water (15 ml) and the resulting mixture was stirred at the same temperature for one hour. To the reaction solution was then added methyl iodide (4.4 g) and the resulting mixture was stirred at 25° C. for twenty hours. The reaction solution was concentrated under reduced pressure, and thereto were then added water (10 ml) and ethyl acetate (50 ml×2) such that the intended products were extracted into an organic layer. The organic layer was washed with saturated saline (50 ml), dried over anhydrous sodium sulfate and then concentrated under reduced pressure. The residue was purified by silica gel column chromatography (eluent: hexane/ethyl acetate) to afford (+)-4-(5-(3,6-dimethyl-2,4-dioxo-1-(3-trifluoromethylphenyl)-1,2,3,4-tetrahydropyrimidin-5-yl-4-(methylsulfonyl)-1H-pyrazol-1-yl)benzonitrile (1.25 g, $[\alpha]_D^{24}$=243.76, c 0.119, $CHCl_3$).

UPLC/MS 530 (M+H)/0.97 min. (measurement condition 9)

Examples 268-269

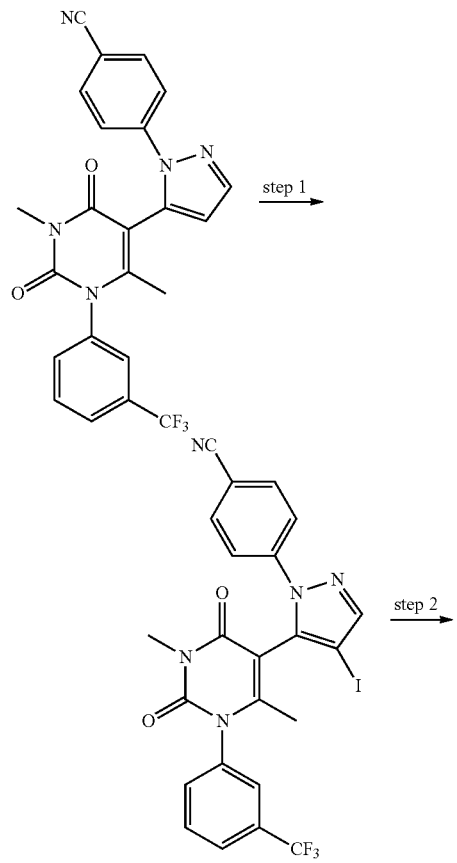

Step 1

Example 268

4-(5-(3-Ethyl-6-methyl-2,4-dioxo-1-(3-trifluoromethylphenyl)-1,2,3,4-tetrahydropyrimidin-5-yl)-4-iodo-1H-pyrazol-1-yl)benzonitrile was obtained by using the compound prepared in Example 1 according to the similar reaction and treatment method to those described in Example 101. UPLC/MS 578 (M+H)/1.07 min. (measurement condition 9)

Step 2

Example 269

To a solution of 4-(5-(3-ethyl-6-methyl-2,4-dioxo-1-(3-trifluoromethylphenyl)-1,2,3,4-tetrahydropyrimidin-5-yl)-4-iodo-1H-pyrazol-1-yl)benzonitrile (prepared in Example 268) (98.1 mg) in N,N-dimethy formamide (1.0 ml) were added palladium dibenzylidene acetone complex (15.9 mg), 1,1'-bis(diphenylphosphino)ferrocene) (18.9 mg), N,N-diisopropylethylamine (33.8 μl) and sodium methanethiolate (13.4 mg) and the resulting mixture was stirred at 110° C. for four hours. The reaction mixture was diluted with ethyl acetate (50 ml) and washed with saturated saline (20 ml), dried over anhydrous sodium sulfate and then concentrated under reduced pressure. The residue was purified by silica gel column chromatography (eluent: hexane/ethyl acetate) to afford 4-(5-(3,6-dimethyl-2,4-dioxo-1-(3-trifluoromethylphenyl)-1,2,3,4-tetrahydropyrimidin-5-yl-4-(methylthio)-1H-pyrazol-1-yl)benzonitrile (57.4 mg).

UPLC/MS 498 (M+H)/1.04 min. (measurement condition 9)

Example 270

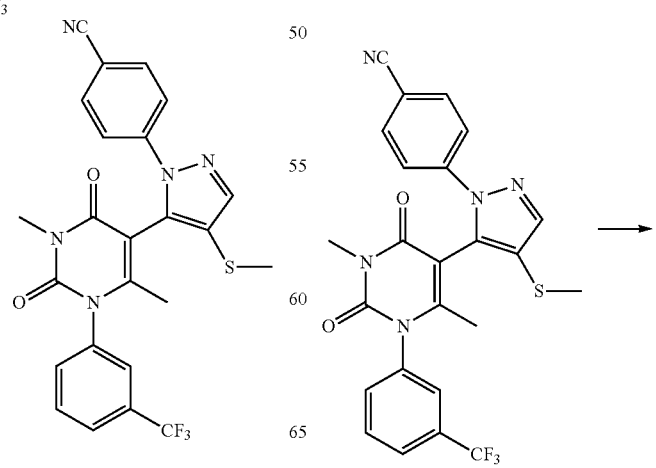

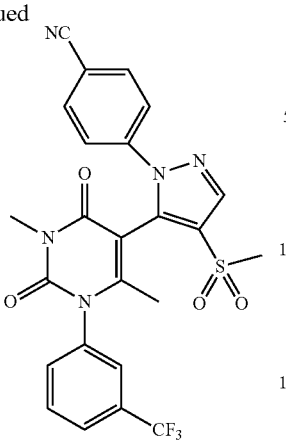

To a solution of 4-(5-(3,6-dimethyl-2,4-dioxo-1-(3-trifluoromethylphenyl)-1,2,3,4-tetrahydropyrimidin-5-yl-4-(methylthio)-1H-pyrazol-1-yl)benzonitrile (prepared in Example 269) (57.4 mg) in acetic acid (1.0 ml) were added aqueous hydrogen peroxide solution (63.4 µl) and sodium tungstate (3.8 mg) and the resulting mixture was stirred at room temperature for four hours. To the reaction mixture was added 10% aqueous sodium thiosulfate solution (1 ml) and the resulting mixture was stirred at room temperature for one hour. The reaction mixture was diluted with ethyl acetate (50 ml) and then washed with saturated saline (20 ml) and the organic layer was dried over anhydrous sodium sulfate. The organic layer was concentrated under reduced pressure and the residue was purified by silica gel column chromatography (eluent: hexane/ethyl acetate) to afford 4-(5-(3,6-dimethyl-2,4-dioxo-1-(3-trifluoromethylphenyl)-1,2,3,4-tetrahydropyrimidin-5-yl-4-(methylsulfonyl)-1H-pyrazol-1-yl)benzonitrile (29.4 mg).

UPLC/MS 530 (M+H)/0.97 min. (measurement condition 9)

Examples 271-274

The compounds indicated in the below-mentioned table (Examples 271-274) were obtained by using the corresponding starting materials according to the similar reaction and treatment method to those described in Examples 269 and 270.

TABLE 64

| Ex. | $R^2$ | Measurement cond. | (LC-MS: Rt/ [M + H]+) | |
|---|---|---|---|---|
| 271 | 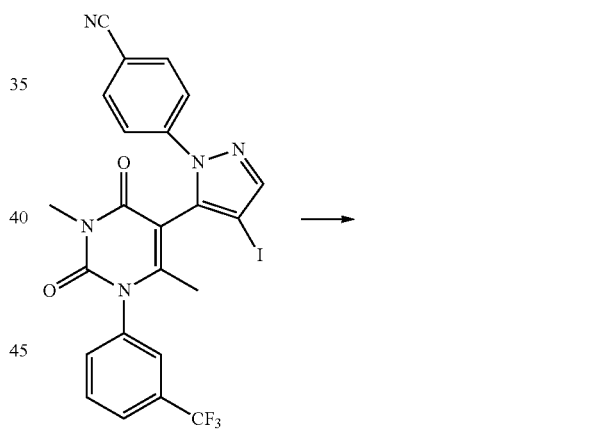 | 9 | 0.94 | 542 |
| 272 | | 9 | 0.72 | 582 |
| 273 | | 9 | 0.88 | 574 |
| 274 | | 9 | 0.72 | 614 |

Example 275

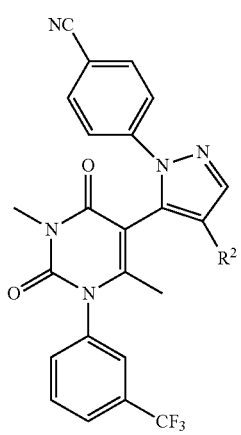

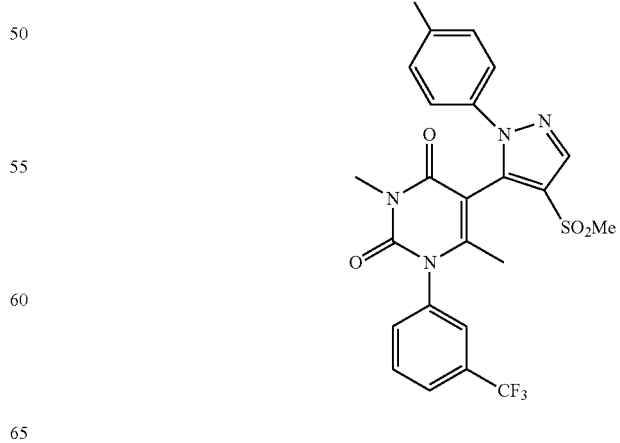

To a solution of the compound prepared in Example 269 (2.84 g) in dimethyl sulfoxide (9.8 ml) were added methanesulfinic acid sodium (2.00 g), copper trifluoromethane-sulfonate benzene complex (1.24 g), N,N-dimethylethylene-diamine (529 mg) and the resulting mixture was stirred at 110° C. for seven hours. The reaction mixture was diluted with ethyl acetate (300 ml), and the organic layer was washed with 10% ammonia water (50 ml) and saturated saline (50 ml), dried over anhydrous sodium sulfate and then concentrated under reduced pressure. The residue was purified by silica gel column chromatography (eluent: hexane/ethyl acetate) to afford 4-(5-(3,6-dimethyl-2,4-dioxo-1-(3-trifluoromethylphenyl)-1,2,3,4-tetrahydropyrimidin-5-yl-4-(methylsulfonyl)-1H-pyrazol-1-yl)benzonitrile (1.25 g).

$^1$H-NMR (CDCl$_3$: 300 MHz) δ: 1.51 (d, 3H, J=11.7 Hz), 3.12 (d, 3H, J=6.0 Hz), 3.40 (d, 3H, J=2.7 Hz), 7.18 (d, 0.5H, J=8.4 Hz), 7.31 (s, 0.5H), 7.46 (d, 0.5H, J=7.5 Hz), 7.53-7.61 (m, 3H), 7.65 (t, 0.5H, J=3.6 Hz), 7.73 (d, 1H, J=7.8 Hz), 7.80 (dd, 2H, J=3.6, 6.0 Hz), 8.18 (d, 1H, J=0.3 Hz).

Example 276

The below-mentioned compound was obtained by using the corresponding starting materials according to the similar reaction and treatment method to those described in Example 275.

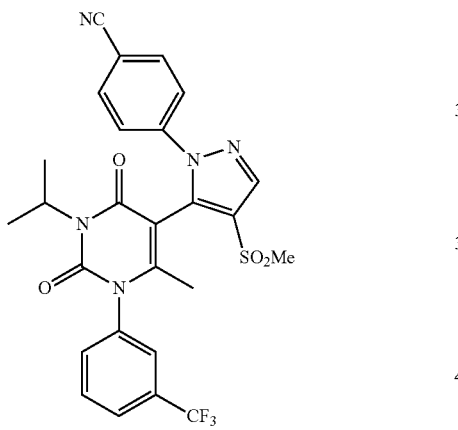

(±)-4-(5-(3-Isopropyl-6-methyl-2,4-dioxo-1-(3-trifluoromethylphenyl)-1,2,3,4-tetrahydropyrimidin-5-yl-4-(methylsulfonyl)-1H-pyrazol-1-yl)benzonitrile UPLC/MS 558 (M+H)/1.03 (measurement condition 9)

Examples 277-286

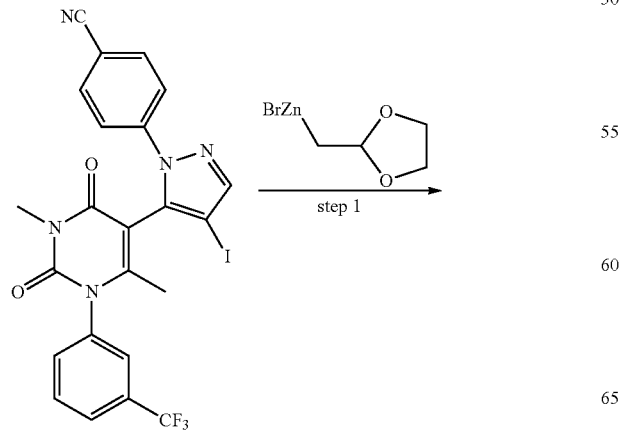

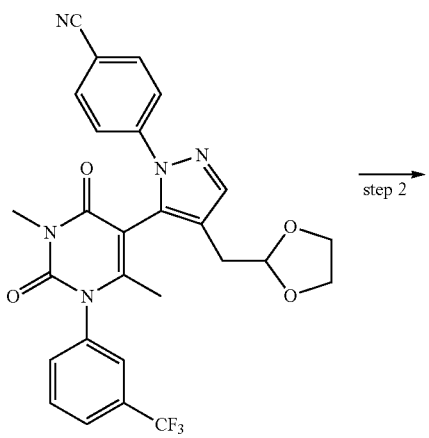

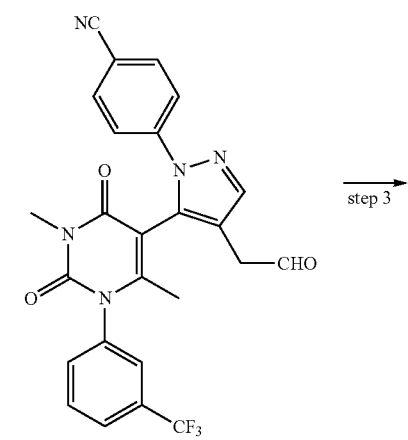

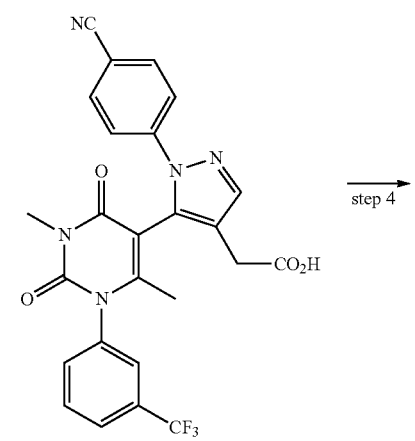

-continued

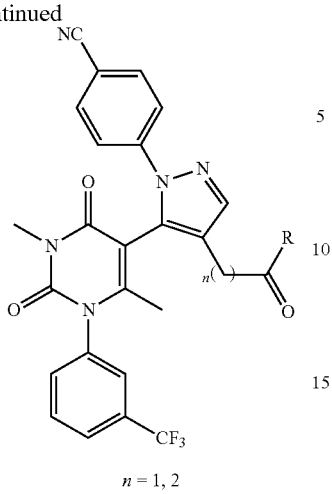

n = 1, 2

Step 1

Example 277

The iodide product prepared in Example 269 (1.0 g) was performed the similar reaction and treatment method to those described in Example 269 using the corresponding zinc bromide reagent to afford the acetal product (467 mg). UPLC/MS 538 (M+H)/0.968 min. (measurement condition 9)

Example 278

The below-mentioned compound was prepared by using the corresponding zinc bromide reagent according to the similar process to those of Example 277.

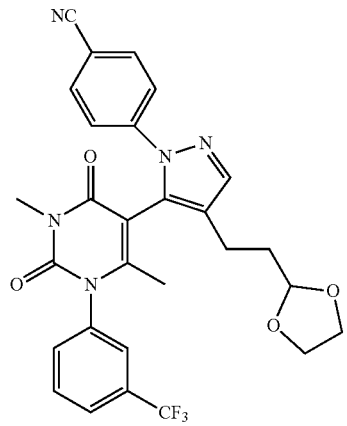 [SMILES: Cc1c(-c2c(CCC3OCCO3)cnn2-c2ccc(C#N)cc2)c(=O)n(C)c(=O)n1-c1cccc(C(F)(F)F)c1]

UPLC/MS 552 (M+H)/1.001 min.

Step 2

Example 279

A solution of the compound prepared in Example 277 (467 mg) and 10% hydrochloric acid (9.0 ml) in THF (9.0 ml) was stirred at room temperature for one and a half hours. To the reaction mixture was added water (10 ml) followed by an addition of ethyl acetate (20 ml×2) such that the intended products were extracted into an organic layer. The organic layer was washed with water (10 ml) and saturated saline (10 ml), dried over anhydrous sodium sulfate and then concentrated under reduced pressure. The residue was purified by silica gel column chromatography (eluent: hexane/ethyl acetate) to afford the aldehyde product (429 mg).

UPLC/MS 494 (M+H)/0.995 min. (measurement condition 9)

Example 280

The below-mentioned compound was prepared according to the similar process to those of Example 279.

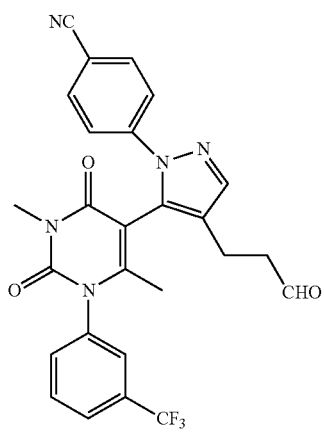 [SMILES: Cc1c(-c2c(CCC=O)cnn2-c2ccc(C#N)cc2)c(=O)n(C)c(=O)n1-c1cccc(C(F)(F)F)c1]

UPLC/MS 508 (M+H)/1.007 min. (measurement condition 9)

Step 3

Example 281

To a solution of the compound prepared in Example 279 (429 mg) and sodium hydrogenphosphate (474 mg) in acetonitrile/water (5.0 ml/5.0 ml) was added at 0° C. sodium chlorite (315 mg) and the resulting mixture was stirred for twenty minutes. To the reaction mixture were added 10% aqueous sodium thiosulfate solution (10 ml) and 10% hydrochloric acid (10 ml) followed by an addition of ethyl acetate (10 ml×2) such that the intended products were extracted into an organic layer. The organic layer was washed with water (10 ml) and saturated saline (10 ml). dried over anhydrous sodium sulfate and then concentrated under reduced pressure. The residue was purified by silica gel column chromatography (eluent: ethyl acetate/methanol) to afford the carboxylic acid product (207 mg).

UPLC/MS 510 (M+H)/0.913 min. (measurement condition 9)

Example 282

The below-mentioned compound was prepared according to the similar process to those of Example 279.

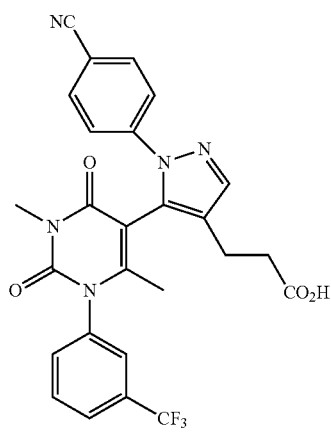 [SMILES: Cc1c(-c2c(CCC(=O)O)cnn2-c2ccc(C#N)cc2)c(=O)n(C)c(=O)n1-c1cccc(C(F)(F)F)c1]

UPLC/MS 524 (M+H)/0.937 min. (measurement condition 9)

Step 4

The compounds indicated in the below-mentioned table (Examples 283-286) were obtained by using the carboxylic acid products prepared in Examples 281 and 282 according to the similar reaction and treatment method to those of Example 75.

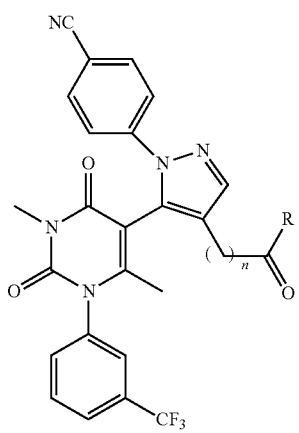

TABLE 65

| Ex. | R | n | m.p. | Measurement cond. | (LC-MS: Rt/[M + H]+) | |
|-----|------|---|------|------|------|-----|
| 283 | NH$_2$ | 1 | 251 | 9 | 0.86 | 509 |
| 284 | NMe$_2$ | 1 |   | 9 | 0.93 | 537 |
| 285 | NH$_2$ | 2 | 242 | 9 | 0.87 | 523 |
| 286 | NMe$_2$ | 2 |   | 9 | 0.96 | 551 |

Examples 287-288

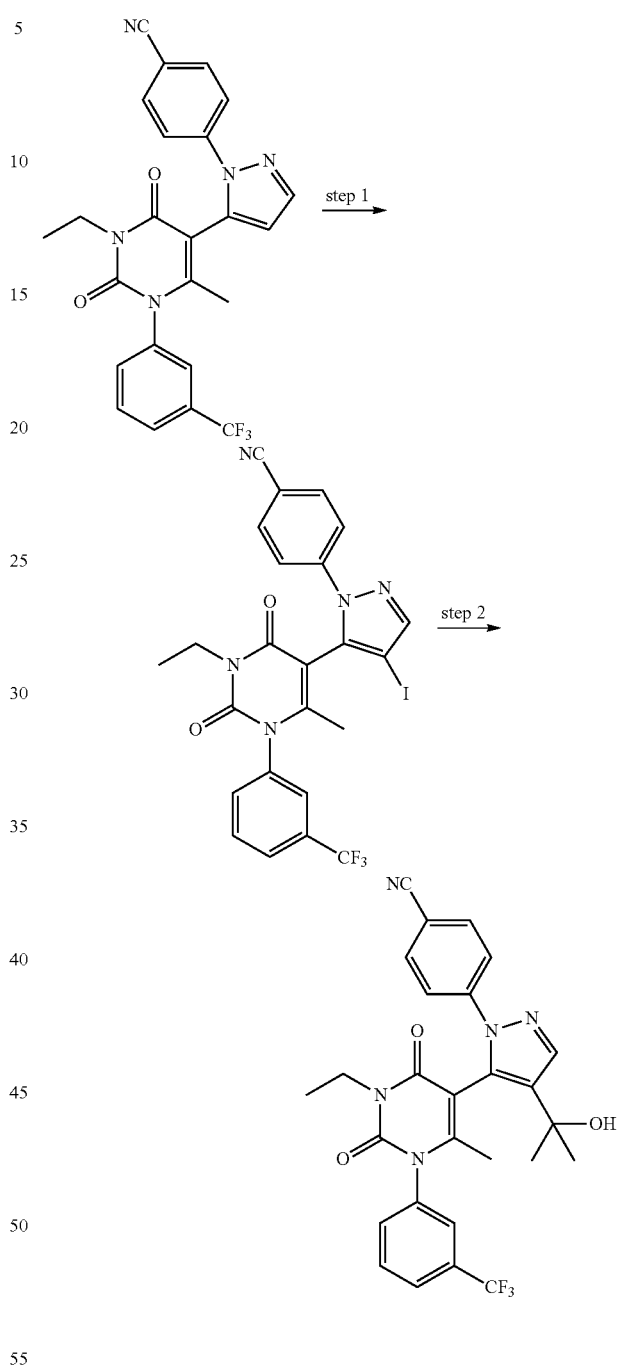

Step 1

Example 287

The above-mentioned compound was obtained by using the corresponding starting materials according to the similar reaction and treatment method to those described in Example 101. UPLC/MS 592 (M+H)/1.11 min. (measurement condition 9)

Step 2

Example 288

To a solution of the compound prepared in Example 287 (401.2 mg) in tetrahydrofuran (1.0 ml) was added at −78° C. a solution of isopropyl magnesium chloride-lithium chloride complex (1.3 M tetrahydrofuran solution, 0.78 ml) followed by an addition of acetone (150 μl) and the resulting mixture was stirred at −78° C. for five hours. To the reaction mixture was added saturated aqueous ammonium chloride solution (5 ml) followed by an addition of ethyl acetate (30 ml) such that the intended products were extracted into an organic layer. The organic layer was washed with water (10 ml) and saturated saline (10 ml), dried over anhydrous sodium sulfate and then concentrated under reduced pressure. The residue was purified by silica gel column chromatography (eluent: hexane/ethyl acetate) to afford 4-(5-(3-ethyl-6-methyl-2,4-dioxo-1-(3-trifluoromethylphenyl)-1,2,3,4-tetrahydropyrimidin-5-yl)-4-(2-hydroxypropan-2-yl)-1H-pyrazol-1-yl)benzonitrile (114.7 mg).

UPLC/MS 52 4 (M+H)/0.95 min. (measurement condition 9)

The compounds indicated in the below-mentioned table (Examples 289-293) were obtained by using the corresponding starting materials and treatment method to those described in Example 288. On the other hand, the compound of Example 293 was prepared by using the compound of Example 290 according to the similar process to those of Example 271.

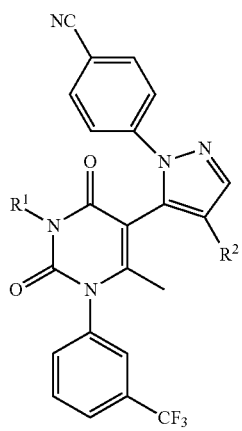

TABLE 66

| Ex. | R² | R¹ | Measurement cond. | (LC-MS: Rt/ [M + H]+) | |
|---|---|---|---|---|---|
| 289 | (cyclobutyl-OH) | Et | 9 | 1.00 | 536 |
| 290 | (thianyl-OH) | Me | 9 | 0.96 | 568 |

TABLE 66-continued

| Ex. | R² | R¹ | Measurement cond. | (LC-MS: Rt/ [M + H]+) | |
|---|---|---|---|---|---|
| 291 | (N-Boc azetidinyl-OH) | Me | 9 | 1.014 | 623 |
| 292 | (C(CH₃)₂-OH) | Me | 9 | 0.90 | 510 |
| 293 | (sulfonyl cyclohexyl-OH) | Me | 9 | 0.84 | 600 |

The compounds in below-mentioned table (Examples 294-296) were obtained by using the compound of Example 291 according to the similar reaction and treatment method to those described in Examples 85, 86 and 70.

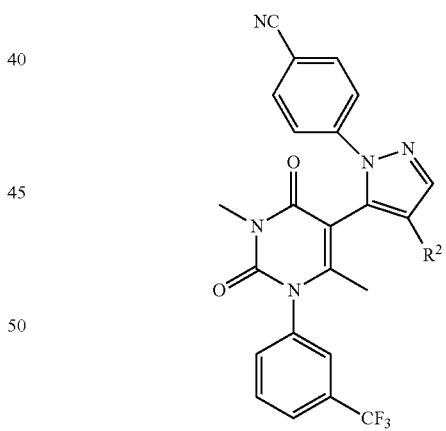

TABLE 67

| Ex. | R² | Measurement cond. | (LC-MS: Rt/ [M + H]+) | |
|---|---|---|---|---|
| 294 | (azetidinyl-OH, HN) | 9 | 0.653 | 294 |

TABLE 67-continued

| Ex. | R² | Measurement cond. | (LC-MS: Rt/ [M + H]+) |
|---|---|---|---|
| 295 | 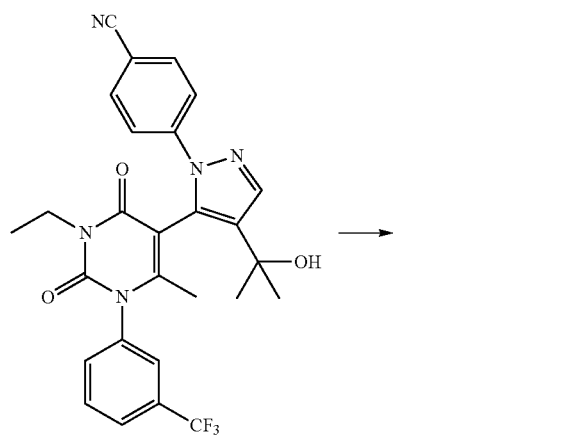 (shown in cell) | 9 | 0.804  295 |
| 296 | (shown in cell) | 9 | 0.664  296 |

Example 297

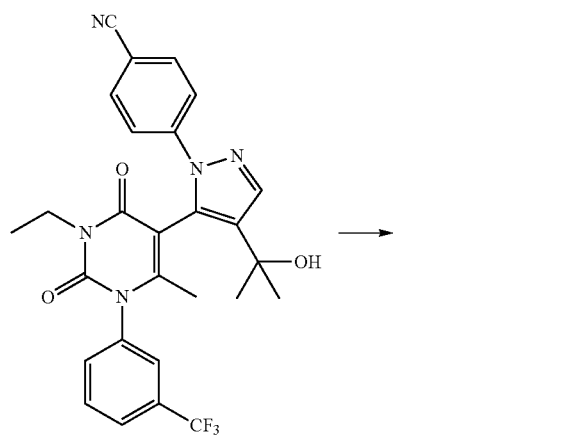

To a solution of 4-(5-(3-ethyl-6-methyl-2,4-dioxo-1-(3-trifluoromethylphenyl)-1,2,3,4-tetrahydropyrimidin-5-yl)-4-(2-hydroxypropan-2-yl)-1H-pyrazol-1-yl)benzonitrile (prepared in Example 288) (114.7 mg) in chloroform (1.0 ml) was added at room temperature sodium azide (28.4 mg) and trifluoroacetic acid (200 µl) and the resulting mixture was stirred at room temperature for sixteen hours. The reaction mixture was diluted with ethyl acetate (30 ml) and the organic layer was dried over anhydrous sodium sulfate and then concentrated under reduced pressure to afford the residue. To a solution of the obtained residue in acetic acid (1.0 ml) were added at room temperature zinc dust (143.2 mg) and water (200 µl) and the resulting mixture was stirred at room temperature for eight hours. The reaction mixture was diluted with ethyl acetate (30 ml) and the solids were then filtered, and the organic layer was washed with saturated aqueous sodium hydrogen carbonate solution (10 ml), dried over anhydrous sodium sulfate and then concentrated under reduced pressure. The residue was purified by silica gel column chromatography (eluent: hexane/ethyl acetate) to afford 4-(4-(2-aminopropane-2-yl)-5-(3-ethyl-6-methyl-2,4-dioxo-1-(3-trifluoromethylphenyl)-1,2,3,4-tetrahydropyrimidin-5-yl)-1H-pyrazol-1-yl)benzonitrile (51.8 mg). UPLC/MS 523 (M+H)/0.73 min. (measurement condition 9)

Example 298

The below-mentioned compound was obtained by using the corresponding starting materials according to the similar reaction and treatment method to those described in Example 297.

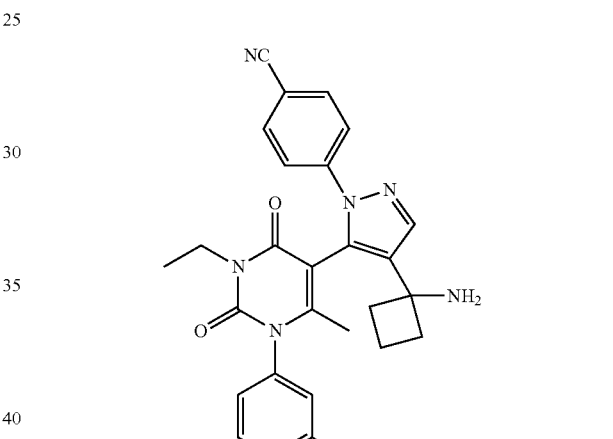

UPLC/MS 535 (M+H)/1.00 min (measurement condition 9)

Example 299

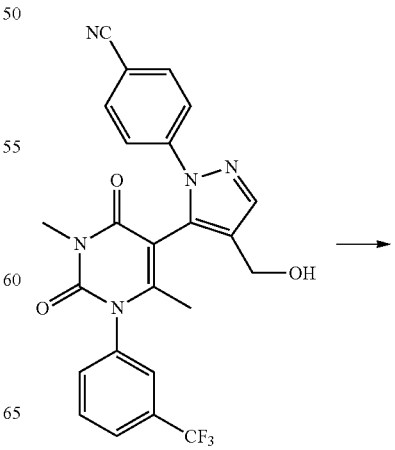

327
-continued

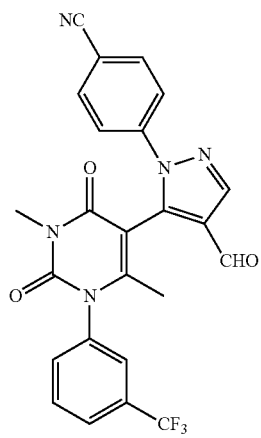

To a solution of 4-(5-(3,6-dimethyl-2,4-dioxo-1-(3-trifluoromethylphenyl)-1,2,3,4-tetrahydropyrimidin-5-yl-4-hydroxymethyl-1H-pyrazol-1-yl)benzonitrile (prepared in Example 138) (1.80 g) in chloroform (50 ml) was added manganese dioxide (9.00 g) and the resulting mixture was stirred at room temperature for thirteen hours. The reaction mixture was filtered through Celite (trade mark) and then concentrated under reduced pressure to afford 4-(5-(3,6-dimethyl-2,4-dioxo-1-(3-trifluoromethylphenyl)-1,2,3,4-tetrahydropyrimidin-5-yl-4-formyl-1H-pyrazol-1-yl)benzonitrile (1.70 g).

UPLC/MS 480 (M+H)/0.95 min. (measurement condition 9)

Examples 300-313

The compounds indicated in the below-mentioned table (Examples 300-313) were obtained by using the aldehyde product obtained in Example 299 and the corresponding starting materials according to the similar reaction and treatment method to those described in Example 69.

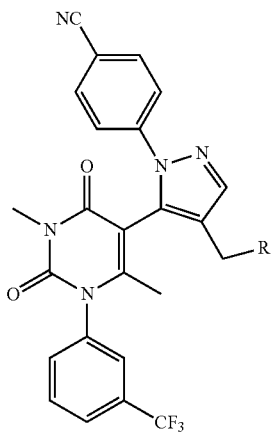

328
TABLE 68

| Ex. | R | Measurement cond. | (LC-MS: Rt/[M + H]+) | |
|---|---|---|---|---|
| 300 | morpholine (N-linked, with O) | 9 | 0.75 | 552 |
| 301 | NH-SO₂Me | 9 | 0.90 | 559 |
| 302 | azetidine-3-OH | 9 | 0.69 | 537 |
| 303 | azetidine-3-OH,3-Me | 9 | 0.72 | 551 |
| 304 | azetidine-3-OMe | 9 | 0.73 | 552 |
| 305 | azetidine-3,3-diF | 9 | 1.00 | 557 |
| 306 | pyrrolidine | 9 | 0.72 | 536 |
| 307 | pyrrolidine-3-OH | 9 | 0.70 | 552 |
| 308 | pyrrolidine-2-CH₂OMe,3-OH | 9 | 0.70 | 552 |

TABLE 68-continued

| Ex. | R | Measurement cond. | (LC-MS: Rt/ [M + H]+) | |
|---|---|---|---|---|
| 309 | ![piperidine-OH] | 9 | 0.70 | 566 |
| 310 | ![thiomorpholine SO2] | 9 | 0.89 | 600 |
| 311 | ![piperidine-SO2Me] | 9 | 0.75 | 628 |
| 312 | ![piperazine-SO2Me] | 9 | 0.76 | 629 |
| 313 | ![piperazine-acetyl] | 9 | 0.72 | 593 |

Example 314

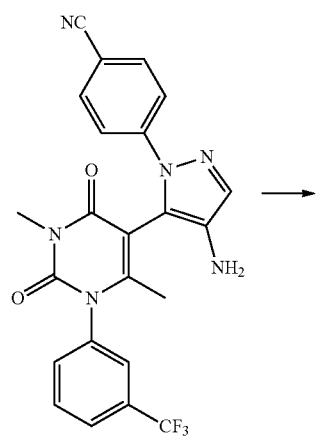

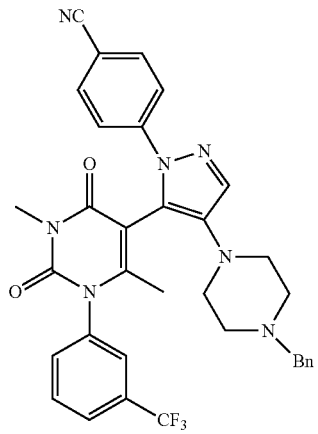

A solution of 4-(A4-amino(3,6-dimethyl-2,4-dioxo-1-(3-trifluoromethylphenyl)-1,2,3,4-tetrahydropyrimidin-5-yl)-1H-pyrazol-1-yl)benzonitrile (prepared in Example 140) (200 mg), N-benzyl-bis(2-chloroethyl)amine hydrochloride (576 mg), sodium iodide (322 mg), sodium hydrogen carbonate (181 mg) in NMP (2.0 ml) was stirred at 120° C. for three hours. To the reaction mixture was added water (10 ml) followed by an addition of ethyl acetate (20 ml×2) such that the intended products were extracted into an organic layer. The organic layer was washed with water (10 ml) and saturated saline (10 ml), dried over anhydrous sodium sulfate and then concentrated under reduced pressure. The residue was purified by silica gel column chromatography (eluent: hexane/ethyl acetate) to afford 4-(4-(4-benzylpiperidin-1-yl)-5-(3,6-dimethyl-2,4-dioxo-1-(3-trifluoromethylphenyl)-1,2,3,4-tetrahydropyrimidin-5-yl)-1H-pyrazol-1-yl)benzonitrile (97.1 mg). UPLC/MS 626 (M+H)/0.77 min. (measurement condition 9)

Example 315

The below-mentioned compound was obtained by using the corresponding starting materials according to the similar reaction and treatment method to those described in Example 314.

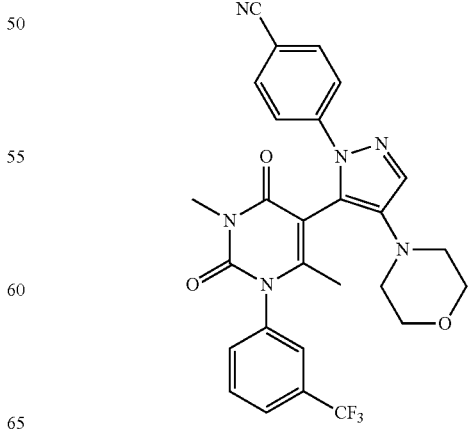

4-(5-(3,6-Dimethyl-2,4-dioxo-1-(3-trifluoromethylphenyl)-1,2,3,4-tetrahydropyrimidin-5-yl)-4-morpholino-1H-pyrazol-1-yl)benzonitrile UPLC/MS 537 (M+H)/0.97 min. (measurement condition 9)

Example 316

The below-mentioned compound was obtained by using 4-(4-(4-benzylpiperidine-1-yl)-5-(3,6-dimethyl-2,4-dioxo-1-(3-trifluoromethylphenyl)-1,2,3,4-tetrahydropyrimidin-5-yl)-1H-pyrazol-1-yl)benzonitrile (prepared in Example 314) according to the similar reaction and treatment method to those described in Example 72.

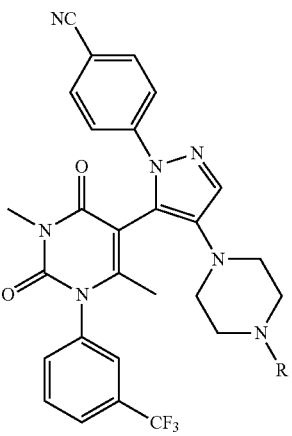

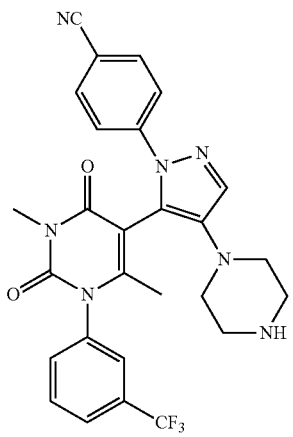 [SMILES: Cc1c(-c2c(N3CCOCC3)cnn2-c2ccc(C#N)cc2)c(=O)n(C)c(=O)n1-c1cccc(C(F)(F)F)c1]

4-(5-(3,6-Dimethyl-2,4-dioxo-1-(3-trifluoromethylphenyl)-1,2,3,4-tetrahydropyrimidin-5-yl)-4-piperazin-1-yl)-1H-pyrazol-1-yl)benzonitrile UPLC/MS 537 (M+H)/0.67 min. (measurement condition 9)

Examples 317-318

The compounds indicated in the below-mentioned table (Examples 317-318) were obtained by using the compound prepared in Example 316 according to the similar reaction and treatment method to those described in Example 69.

TABLE 69

| Ex. | R | Measurement cond. | (LC-MS: Rt/[M + H]+) |
|---|---|---|---|
| 317 | Me | 9 | 550 (M + H)/0.70 min |
| 318 | i-Pr | 9 | 578 (M + H)/0.72 min |

Examples 319-328

The compounds indicated in the below-mentioned table (Examples 319-328) were obtained by using the corresponding starting materials according to the similar reaction and treatment method to those described in Examples 1 and 30.

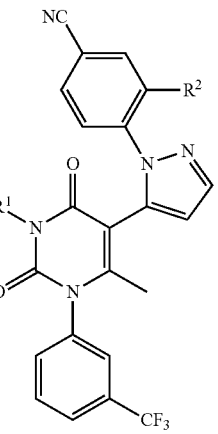

TABLE 70

| Ex. | R¹ | R² | Measurement cond. | m.p. | (LC-MS: Rt/[M + H]+) |
|---|---|---|---|---|---|
| 319 | 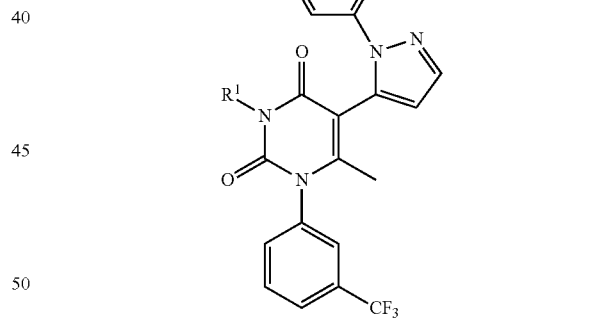 | H | 9 | | 1.19  641 |

TABLE 70-continued

| Ex. | R¹ | R² | Measurement cond. | m.p. | (LC-MS: Rt/ | [M + H]+) |
|---|---|---|---|---|---|---|
| 320 | CbzN-pyrrolidinyl | H | 9 | | 1.19 | 641 |
| 321 | CbzN-piperidin-4-yl | H | 9 | | 1.16 | 655 |
| 322 | CbzN-piperidin-3-yl | H | 9 | | 1.17 | 655 |
| 323 | CbzN-piperidin-3-yl | H | 9 | | 1.17 | 655 |
| 324 | H₂NO₂S-CH(Me)- | H | 9 | | 1.09 | 559 |
| 325 | H | H | 9 | 283 | 0.883 | 438 |
| 326 | Me | F | 9 | | 0.95 | 470 |
| 327 | Et | F | 9 | | 0.99 | 484 |
| 328 | Me | Me | 9 | | 0.98 | 466 |

The NMR data of Example 324 is shown below.

(R)-2-(5-(1-(4-Cyanophenyl)-1H-pyrazol-5-yl)-4-methyl-2,6-dioxo-3-(3-trifluoromethylphenyl)-2,3-dihydropyrimidin-1(6H)-yl)propane-1-sulfonamide ¹H-NMR (CDCl₃: 300 MHz) δ: 1.38 (brs, 3H), 1.55 (d, 3H, J=6.6 Hz), 3.01-3.10 (m, 1H), 4.15-4.25 (m, 1H), 4.83 (brs, 2H), 5.47-5.69 (m, 1H), 6.44-6.46 (m, 1H), 7.40-7.44 (m, 1H), 7.46-7.50 (m, 1H), 7.56-7.64 (m, 3H), 7.66-7.72 (m, 3H), 7.75-7.77 (m, 1H).

Example 329

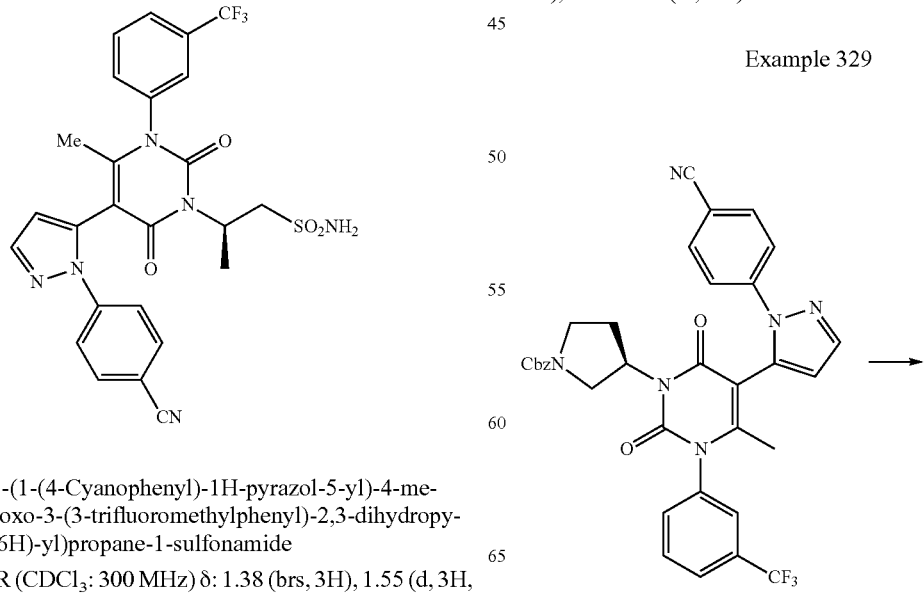

-continued

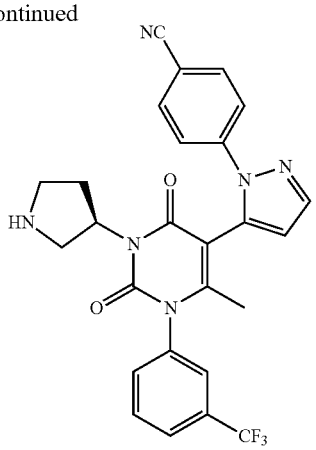

To a solution of the compound prepared in Example 319 (584.2 mg) in acetonitrile (5.0 ml) were added at room temperature sodium iodide (683.6 mg), trimethylsilyl chloride (582 μl) and the resulting mixture was stirred at room temperature for two hours. The reaction mixture was diluted with ethyl acetate (30 ml) and the organic layer was washed with saturated aqueous sodium hydrogen carbonate solution (10 ml) and saturated saline (10 ml), dried over anhydrous sodium sulfate and then concentrated under reduced pressure. The residue was purified by silica gel column chromatography (eluent: hexane/ethyl acetate) to afford (R)-4-(5-(6-methyl-2,4-dioxo-3-(pyrrolidin-3-yl)-1-(3-trifluoromethylphenyl)-1,2,3,4-tetrahydropyrimidin-5-yl)-1H-pyrazol-1-yl)benzonitrile (425.0 mg).

UPLC/MS 507 (M+H)/0.84 min. (measurement condition 9)

Examples 330-333

The compounds indicated in the below-mentioned table (Examples 330-333) were obtained by using the corresponding starting materials according to the similar reaction and treatment method to those described in Example 329.

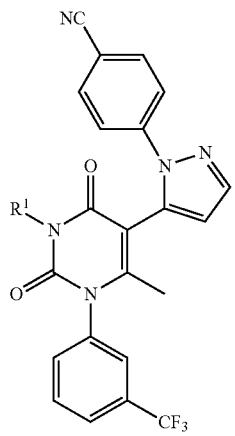

TABLE 71

| Ex. | R¹ | Measurement cond. | (LC-MS: Rt/ [M + H]+) | |
|---|---|---|---|---|
| 330 | (pyrrolidin-3-yl, HN) | 9 | 0.74 | 507 |
| 331 | (piperidin-4-yl, HN) | 9 | 0.76 | 521 |
| 332 | (piperidin-3-yl, HN) | 9 | 0.72 | 522 |
| 333 | (piperidin-3-yl, HN) | 9 | 0.72 | 522 |

Examples 334-357

The compounds indicated in the below-mentioned table (Examples 334-357) were obtained by using the corresponding starting materials according to the similar reaction and treatment method described in Examples 69, 75 and 85.

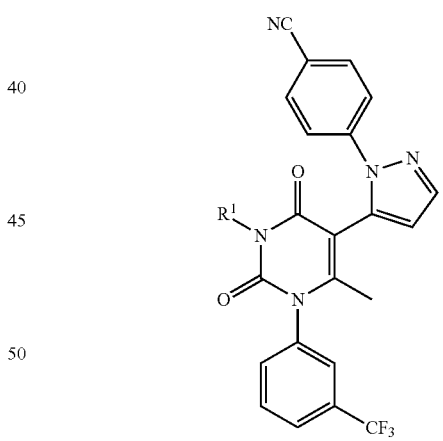

TABLE 72

| Ex. | R¹ | Measurement cond. | (LC-MS: Rt/ [M + H]+) | |
|---|---|---|---|---|
| 334 | (N-methylpiperidin-4-yl) | 9 | 0.76 | 535 |

TABLE 72-continued

| Ex. | R¹ | Measurement cond. | (LC-MS: Rt/[M + H]+) | |
|---|---|---|---|---|
| 335 | N-ethyl piperidine | 9 | 0.81 | 549 |
| 336 | N-isopropyl piperidine | 9 | 0.84 | 563 |
| 337 | N-acetyl piperidine | 9 | 0.94 | 563 |
| 338 | N-(2-hydroxyethyl) piperidine | 9 | 0.78 | 564 |
| 339 | N-(2,2,2-trifluoroethyl) piperidine | 9 | 1.08 | 604 |
| 340 | N-methyl pyrrolidine | 9 | 0.75 | 521 |
| 341 | N-methyl pyrrolidine | 9 | 0.75 | 521 |
| 342 | N-ethyl pyrrolidine | 9 | 0.73 | 535 |
| 343 | N-propyl pyrrolidine | 9 | 0.76 | 549 |
| 344 | N-butyl pyrrolidine | 9 | 0.76 | 564 |

TABLE 72-continued

| Ex. | R¹ | Measurement cond. | (LC-MS: Rt/[M + H]+) | |
|---|---|---|---|---|
| 345 | N-isopropyl pyrrolidine | 9 | 0.74 | 550 |
| 346 | N-(2,2,2-trifluoroethyl) pyrrolidine | 9 | 0.98 | 589 |
| 347 | N-(2-hydroxyethyl) pyrrolidine | 9 | 0.72 | 551 |
| 348 | N-(3-hydroxypropyl) pyrrolidine | 9 | 0.76 | 564 |
| 349 | N-acetyl pyrrolidine | 9 | 0.96 | 549 |
| 350 | N-acetyl pyrrolidine | 9 | 0.96 | 549 |

TABLE 73

| Ex. | R¹ | Measurement cond. | (LC-MS: Rt/[M + H]+) | |
|---|---|---|---|---|
| 351 | N-methyl piperidine | 9 | 0.72 | 536 |
| 352 | N-methyl piperidine | 9 | 0.71 | 536 |
| 353 | BocHN-C(CH₃)₂-C(O)-N-piperidine | 9 | 1.11 | 706 |

TABLE 73-continued

| | | | | |
|---|---|---|---|---|
| 354 | 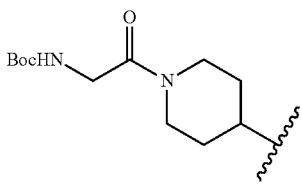 [SMILES: *C1CCN(C(=O)CNC(=O)OC(C)(C)C)CC1] | 9 | 1.10 | 678 |
| 355 | 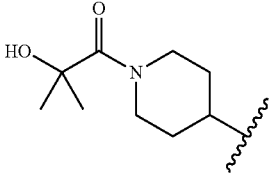 [SMILES: *C1CCN(C(=O)C(C)(C)O)CC1] | 9 | 0.95 | 607 |
| 356 | 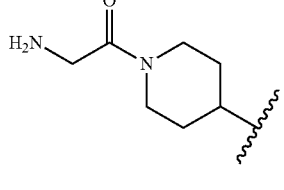 | 9 | 0.91 | 578 |
| 357 | 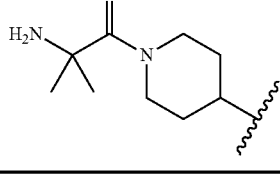 | 9 | 0.86 | 606 |

Example 358

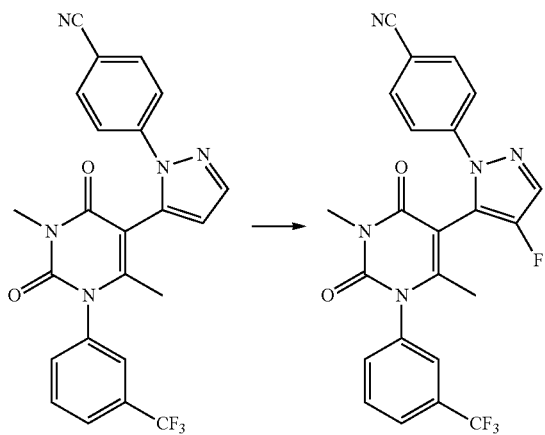 [SMILES: Cc1c(-c2ccnn2-c2ccc(C#N)cc2)c(=O)n(C)c(=O)n1-c1cccc(C(F)(F)F)c1 ; Cc1c(-c2c(F)cnn2-c2ccc(C#N)cc2)c(=O)n(C)c(=O)n1-c1cccc(C(F)(F)F)c1]

To a solution of 4-(5-(3,6-dimethyl-2,4-dioxo-1-(3-trifluoromethylphenyl)-1,2,3,4-tetrahydropyrimidin-5-yl)-1H-pyrazol-1-yl)benzonitrile (prepared in Example 1) (1.0 g) in acetonitrile (20 ml) was added Selectfluor (trade mark) (1.2 g) and the resulting mixture was stirred at 80° C. for four hours. To the reaction mixture was added 10% hydrochloric acid followed by an addition of ethyl acetate (20 ml×2) such the intended products were extracted into an organic layer. The organic layer was washed with saturated saline (20 ml), dried over anhydrous sodium sulfate and then concentrated under reduced pressure. The residue was purified by silica gel column chromatography (eluent: hexane/ethyl acetate) to afford 4-(5-(3,6-dimethyl-2,4-dioxo-1-(3-trifluoromethylphenyl)-1,2,3,4-tetrahydropyrimidin-5-yl)-4-fluoro-1H-pyrazol-1-yl)benzonitrile (238 mg). UPLC/MS 470 (M+H)/1.023 min. (measurement condition 9)

Example 359

The below-mentioned compound was obtained by using the corresponding starting materials according to the similar reaction and treatment method to those described in Example 358.

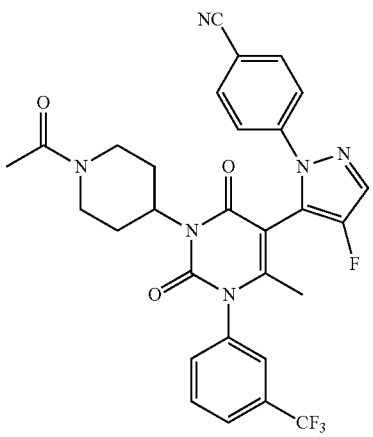 [SMILES: CC(=O)N1CCC(n2c(=O)c(-c3c(F)cnn3-c3ccc(C#N)cc3)c(C)n(-c3cccc(C(F)(F)F)c3)c2=O)CC1]

UPLC/MS 581 (M+H)/0.98 min.

Example 360

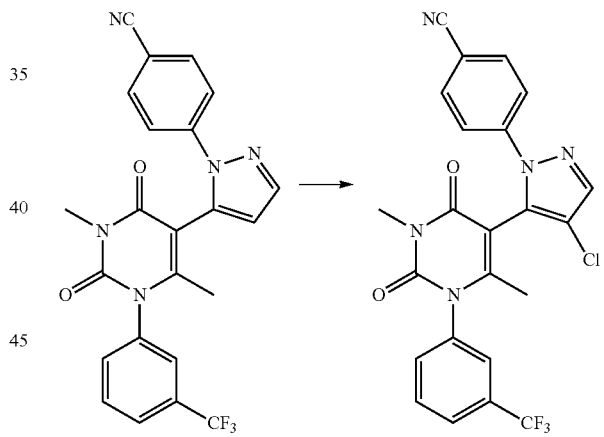

To a solution of 4-(5-(3,6-dimethyl-2,4-dioxo-1-(3-trifluoromethylphenyl)-1,2,3,4-tetrahydropyrimidin-5-yl)-1H-pyrazol-1-yl)benzonitrile (prepared in Example 1) (205 mg) in acetonitrile (10 ml) were added lithium chloride (23 mg), ammonium hexanitrato cerate(IV) (498 mg) and acetic acid (2.5 ml) and the resulting mixture was stirred with heating under reflux for five hours. To the reaction mixture was 10% aqueous sodium thiosulfate solution (10 ml) followed by an addition of ethyl acetate (20 ml×2) such that the intended products were extracted into an organic layer. The organic layer was washed with saturated saline (20 ml), dried over anhydrous sodium sulfate and then concentrated under reduced pressure. The residue was purified by silica gel column chromatography (eluent: hexane/ethyl acetate) to afford 4-(4-chloro-5-(3,6-dimethyl-2,4-dioxo-1-(3-trifluoromethylphenyl)-1,2,3,4-tetrahydropyrimidin-5-yl)-1H-pyrazol-1-yl)benzonitrile (238 mg). UPLC/MS 486 (M+H)/1.13 min (measurement condition 9)

The compounds indicated in the below-mentioned table (Example 361-362) was obtained by using the corresponding starting materials according to the similar reaction and treatment method to those described in Example 360.

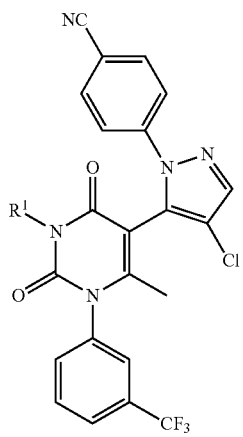

TABLE 74

| Ex. | R¹ | Measurement cond. | (LC-MS: Rt/[M + H]+) | |
|---|---|---|---|---|
| 361 | H₂N-C(=O)-CH(CH₃)- | 9 | 0.953 | 543 |
| 362 | N-methylpyrrolidin-3-yl | 9 | 0.791 | 557 |

Example 363

The below-mentioned compound was obtained by using the iodide product prepared in Example 101 according to the similar reaction and treatment method to those described in Example 123.

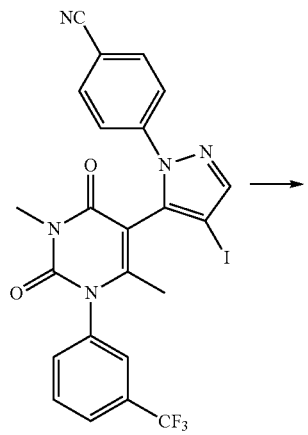 → 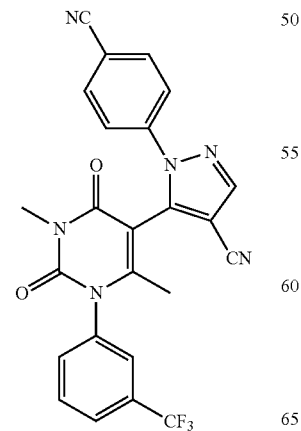

1-(4-Cyanophenyl)-5-(3,6-dimethyl-2,4-dioxo-1-(3-trifluoromethyl)-1,2,3,4-tetrahydropyrimidin-5-yl)-1H-pyrazole-4-carbonitrile UPLC/MS 477 (M+H)/0.990 min. (measurement condition 9)

Example 364-367

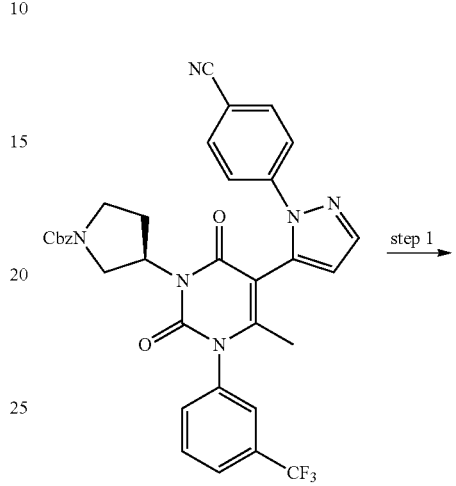 step 1

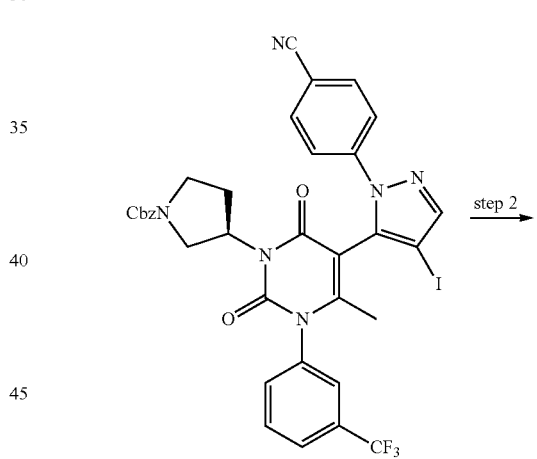 step 2

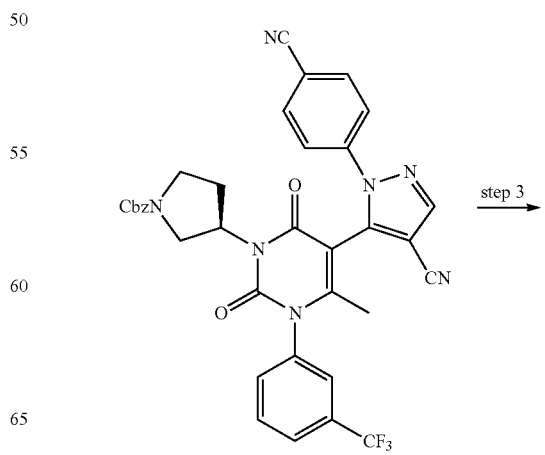 step 3

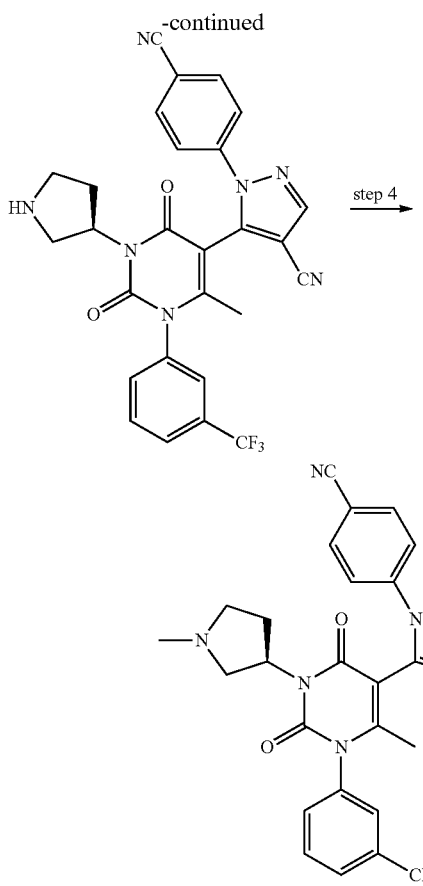

Step 1

Example 364

The iodide product was obtained by using the compound prepared in Example 319 according to the similar reaction and treatment method to those described in Example 101. UPLC/MS 767 (M+H)/1.20 min (measurement condition 9)

Step 2

Example 365

The cyano product was obtained by using the compound prepared in Example 364 according to the similar reaction and treatment method to those described in Example 363. UPLC/MS 666 (M+H)/1.128 min (measurement condition 9)

Step 3

Example 366

The de CBZ product was obtained by using the compound prepared in Example 365 according to the similar reaction and treatment method to those described in Example 329. UPLC/MS 533 (M+H)/0.71 min (measurement condition 9)

Step 4

Example 367

The methylated product was obtained by using the compound prepared in Example 366 according to the similar reaction and treatment method to those described in Example 69. UPLC/MS 546 (M+H)/1.09 min (measurement condition 9)

Examples 368-370

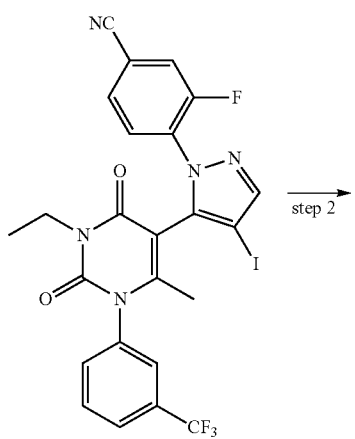

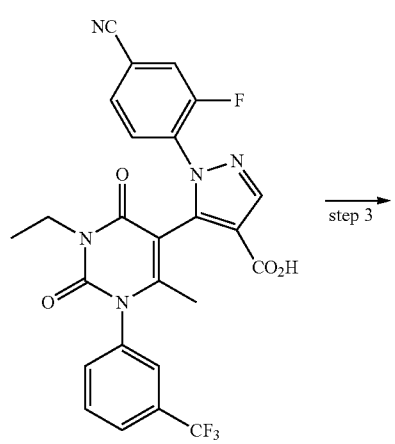

345

-continued

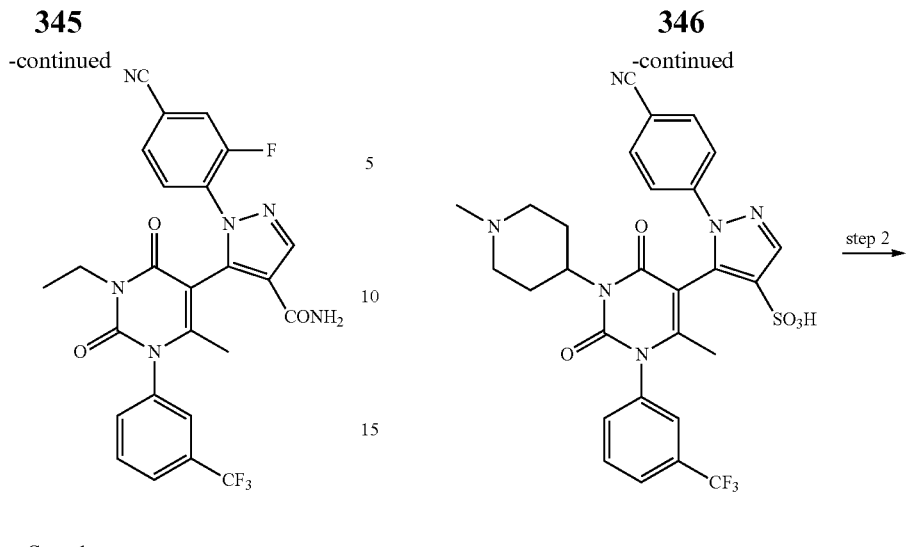

Step 1

Example 368

The iodide product was obtained by using the compound of Example 327 according to the similar reaction and treatment method to those described in Example 101. UPLC/MS 610 (M+H)/1.11 min (measurement condition 9)

Step 2

Example 369

The carboxylic product was obtained by using the compound prepared in Example 369 according to the similar reaction and treatment method to those described in Example 132. UPLC/MS 528 (M+H)/0.90 min (measurement condition 9)

Step 3

Example 370

The amide product was obtained by using the compound prepared in Example 369 according to the similar reaction and treatment method to those described in Example 142. UPLC/MS 527 (M+H)/0.86 min (measurement condition 9). Melting point: 261° C.

Examples 371-372

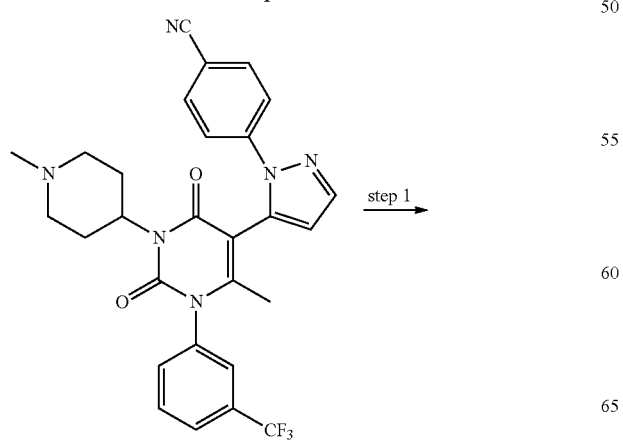

346

-continued

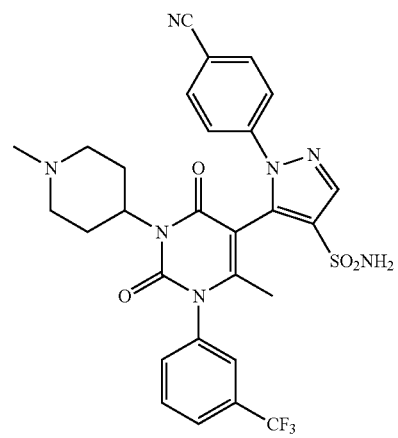

Step 1

Example 371

The sulfonic acid product was obtained by using the compound prepared in Example 334 according to the similar reaction and treatment method to those described in Example 191. UPLC/MS 614 (M+H)/0.708 min (measurement condition 9)

Step 2

Example 372

The sulfonamide product was obtained by using the compound prepared in Example 371 according to the similar reaction and treatment method to those described in Example 205. UPLC/MS 615 (M+H)/0.672 min (measurement condition 9)

Example 373

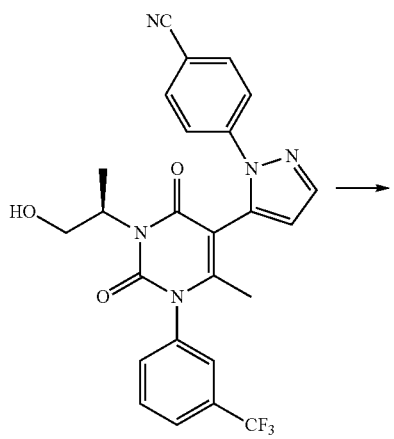

→

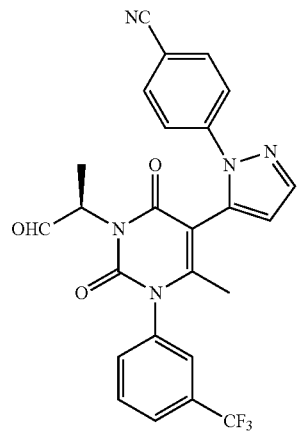

To a solution of the compound prepared in Example 111 (300 mg) in chloroform (4.0 ml) were added at room temperature 2,2,6,6-tetramethylpiperidine 1-oxyl (78 mg) and iodobenzene diacetate (322 mg), and the resulting mixture was stirred at room temperature for six hours. The reaction solution was concentrated under reduced pressure and the residue was purified by silica gel column chromatography (eluent: hexane/ethyl acetate) to afford (R)-4-(5-(6-methyl-2,4-dioxo-3-(1-oxopropane-2-yl)-1-(3-trifluoromethylphenyl)-1,2,3,4-tetrahydropyrimidin-5-yl)-1H-pyrazol-1-yl)benzonitrile (260 mg). UPLC/MS 494 (M+H)/1.016 min (measurement condition 9)

Example 374

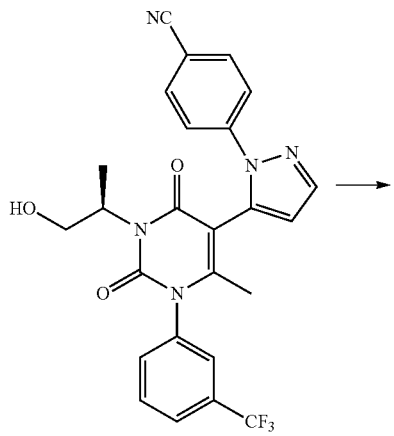

→

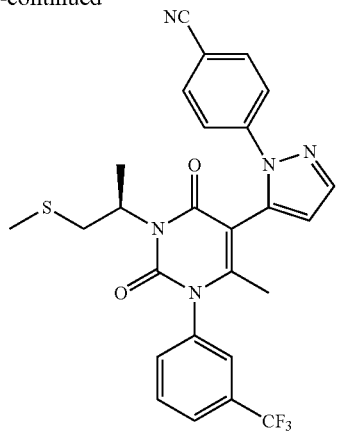

A solution of the compound prepared in Example 111 (200 mg), tosyl chloride (190 mg), N-methylimidazole (80 µl) and triethylamine (140 µl) in toluene (6.0 ml) was stirred at 25° C. for three hours. To the reaction solution was added water (20 ml) followed by an addition of ethyl acetate (20 ml×2) such that the intended products were extracted into an organic layer. The organic layer was washed with saturated saline (20 ml), dried over anhydrous sodium sulfate and then concentrated under reduced pressure. To the residue were then added sodium methanthiolate (2.0 g, 15% aqueous solution), N,N-dimethy formamide (3 ml) and the resulting mixture was stirred at 25° C. for three hours. To the reaction solution was added water (20 ml) followed by an addition of ethyl acetate (20 ml×2) such that the intended products were extracted into an organic layer. The organic layer was washed with saturated saline (20 ml), dried over anhydrous sodium sulfate and then concentrated under reduced pressure. The residue was purified by silica gel column chromatography (eluent: hexane/ethyl acetate) to afford (R)-4-(5-(6-methyl-3-(1-(methylthio)propane-2-yl)-2,4-dioxo-1-(3-trifluoromethylphenyl)-1,2,3,4-tetrahydropyrimidin-5-yl)-1H-pyrazol-1-yl)benzonitrile (115 mg).

UPLC/MS 526 (M+H)/1.094 min (measurement condition 9)

Example 375

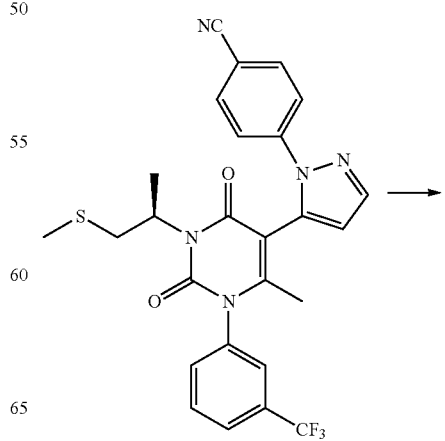

→

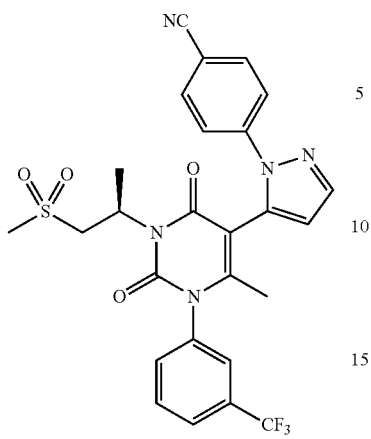

To a solution of the compound prepared in Example 374 (115 mg) in acetic acid (2.0 ml) was added at 25° C. sodium tungstate(VI) dihydrate (5.0 mg), aqueous hydrogen peroxide solution (110 mg, 31% aqueous solution) and the resulting mixture was stirred at the same temperature for four hours. To the reaction solution was added aqueous sodium hydrogen sulfite solution and the resulting mixture was stirred at 25° C. for one hour. To the reaction solution was added ethyl acetate (10 ml×2) such that the intended products were extracted into an organic layer. The organic layer was washed with saturated saline (10 ml), dried over anhydrous sodium sulfate and then concentrated under reduced pressure. The residue was purified by silica gel column chromatography (eluent: hexane/ethyl acetate) to afford (R)-4-(5-(6-methyl-3-(methanesulfonyl)propane-2-yl)-2,4-dioxo-3-(1-oxopropane-2-yl)-1-(3-trifluoromethylphenyl)-1,2,3,4-tetrahydropyrimidin-5-yl)-1H-pyrazol-1-yl)benzonitrile (108 mg). UPLC/MS 558 (M+H)/0.963 min Example 376

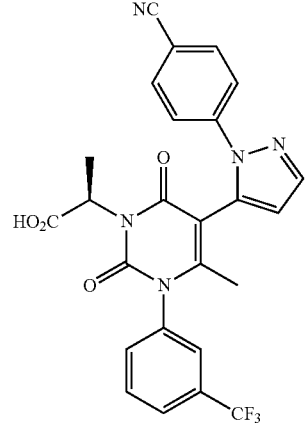

To a solution of the compound prepared in Example 111 (1.58 g) in chloroform (25 ml) were added 2,2,6,6-tetramethylpiperidine-1-oxyl (598 mg) and diacetoxy iodobenzene (2.47 g) and the resulting mixture was stirred for fourteen hours. To the reaction solution were water (25 ml) and chloroform (25 ml) such that the intended products were extracted into an organic layer, and the organic layer was washed with water (25 ml×3), dried over anhydrous magnesium sulfate and then concentrated under reduced pressure. The residue was diluted in hexane/ethyl acetate=1/1 (40 ml) and thereto was added 10% aqueous potassium carbonate solution (20 ml) such that the intended products were extracted into an aqueous layer. The aqueous layer was washed with hexane/ethyl acetate=1/1 (20 ml) and acidified with 20% aqueous citric solution and thereto added ethyl acetate (30 ml×2) such that the intended products were extracted into an organic layer. The organic layer was washed with saturated saline (20 ml), dried over anhydrous magnesium sulfate and then concentrated under reduced pressure. The residue was purified by silica gel column chromatography (eluent: chloroform/methanol) to afford (R)-2-(5-(1-(4-cyanophenyl)-1H-pyrazol-5-yl)-4-methyl-2,6-dioxo-3-(3-trifluoromethylphenyl)-2,3-dihydropyrimidin-1(6H)-yl)propionic acid (749 mg).

UPLC/MS 510 (M+H)/0.94 min (measurement condition 9)

Examples 377-384

The compounds indicated in the below-mentioned table (Examples 377-384) were obtained by using the carboxylic product prepared in Example 376 according to the similar reaction and treatment method to those described in Example 142.

TABLE 75

| Ex. | R¹ | m.p. | Measurement cond. | (LC-MS: Rt/ [M + H]+) | |
|---|---|---|---|---|---|
| 377 | NH₂ | 226 | 9 | 0.88 | 509 |
| 378 | NHMe | 188 | 9 | 0.91 | 523 |
| 379 | NMe₂ | | 9 | 0.93 | 537 |
| 380 | MeO∼∼NH– | | 9 | 0.93 | 567 |
| 381 | Me₂N-azetidinyl | | 9 | 0.73 | 592 |
| 382 | pyrrolidinyl | | 9 | 0.94 | 563 |
| 383 | HO-azetidinyl | | 9 | 0.86 | 565 |
| 384 | MeO-azetidinyl | | 9 | 0.94 | 579 |

Examples 385-393

The compounds indicated in the below-mentioned table (Examples 385-393) were obtained by using the corresponding starting materials according to the similar reaction and treatment method to those described in Example 69.

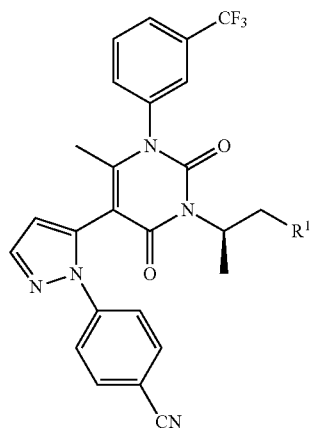

TABLE 76

| Ex. | R¹ | Measurement cond. | (LC-MS: Rt/ [M + H]+) | |
|---|---|---|---|---|
| 385 | NMe₂ | 9 | 0.74 | 524 |
| 386 | morpholinyl | 9 | 0.76 | 565 |
| 387 | MeO₂S-piperidinyl | 9 | 0.763 | 641 |
| 388 | MeO₂S-piperazinyl | 9 | 0.841 | 642 |
| 389 | O₂S-thiomorpholinyl | 9 | 0.992 | 613 |
| 390 | HO-azetidinyl | 9 | 0.716 | 551 |
| 391 | HO-methylazetidinyl | 9 | 0.746 | 566 |
| 392 | cyclopentyl-NH– | 9 | 0.795 | 564 |
| 393 | MeO₂S-NH– | 9 | 1.06 | 573 |

Examples 394-396

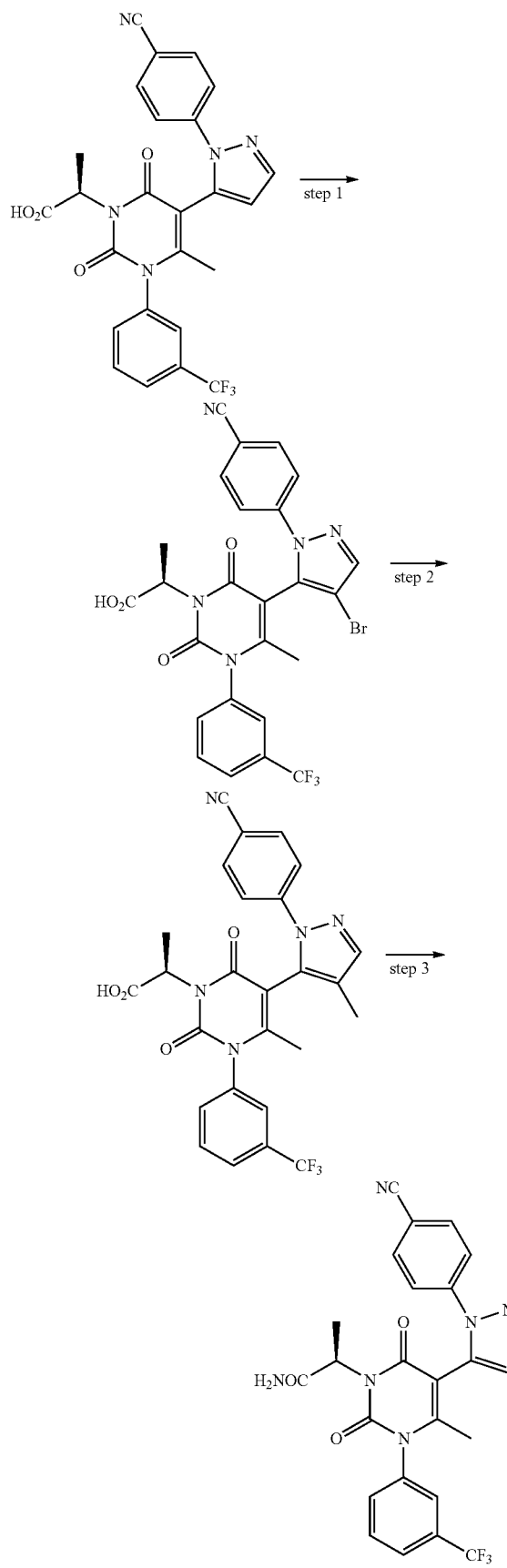

Step 1

Example 394

The bromo product was obtained by using the compound prepared in Example 376 according to the similar reaction and treatment method to those described in Example 93. UPLC/MS 590 (M+H)/1.023 min (measurement condition 9)

Step 2

Example 395

The methylated product was obtained by using the compound prepared in Example 394 according to the similar reaction and treatment method described in Example 108. UPLC/MS 524 (M+H)/0.804 min (measurement condition 9)

Step 31

Example 396

The amide product was obtained by using the compound prepared in Example 395 according to the similar reaction and treatment method to those described in Example 142. UPLC/MS 523 (M+H)/0.906 min (measurement condition 9)

Example 397

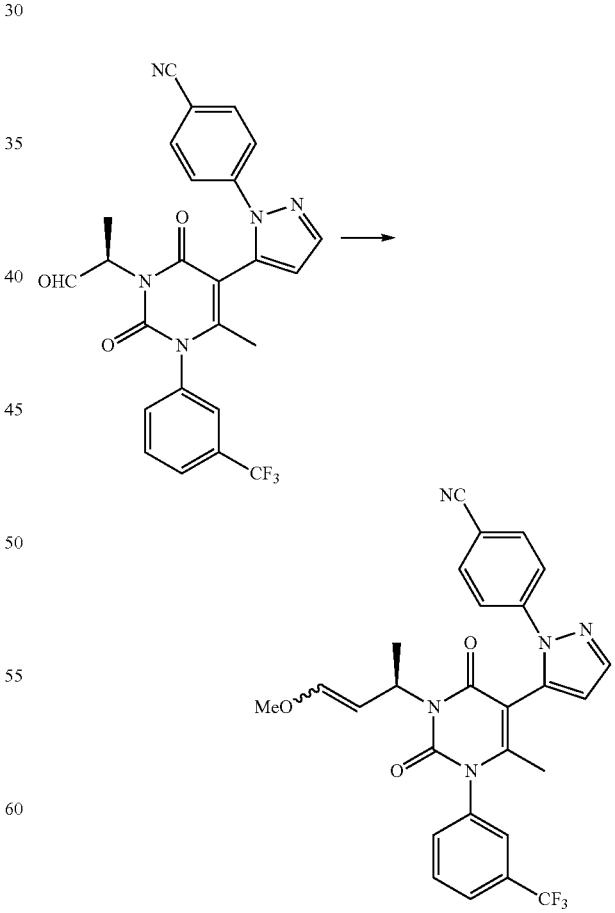

To (methoxymethyl)triphenylphoshonium chloride (1.74 g) and tertiary-butoxy potassium (853 mg) was added at 0° C.

glyme/toluene (10 ml/10 ml) and the resulting mixture was stirred for fifteen minutes. To the reaction mixture was added at 0° C. (R)-4-(5-(6-methyl-2,4-dioxo-3-(1-oxopropane-2-yl)-1-(3-trifluoromethylphenyl)-1,2,3,4-tetrahydropyrimidin-5-yl)-1H-pyrazol-1-yl)benzonitrile (prepared in Example 373) (500 mg) and the resulting mixture was stirred at room temperature for fifteen hours. To the reaction mixture was added water (20 ml) followed by an addition of ethyl acetate (30 ml×2) such that the intended products were extracted into an organic layer. The organic layer was washed with saturated saline (20 ml), dried over anhydrous sodium sulfate and then concentrated under reduced pressure. The residue was purified by silica gel column chromatography (eluent: hexane/ethyl acetate) to afford (R)-4-(5-(3-(4-methoxy-3-buten-2-yl)-6-methyl-2,4-dioxo-1-(3-trifluoromethylphenyl)-1,2,3,4-tetrahydropyrimidin-5-yl)-1H-pyrazol-1-yl)benzonitrile (350 mg). UPLC/MS 522 (M+H)/1.00 min. (measurement condition 9)

Example 398

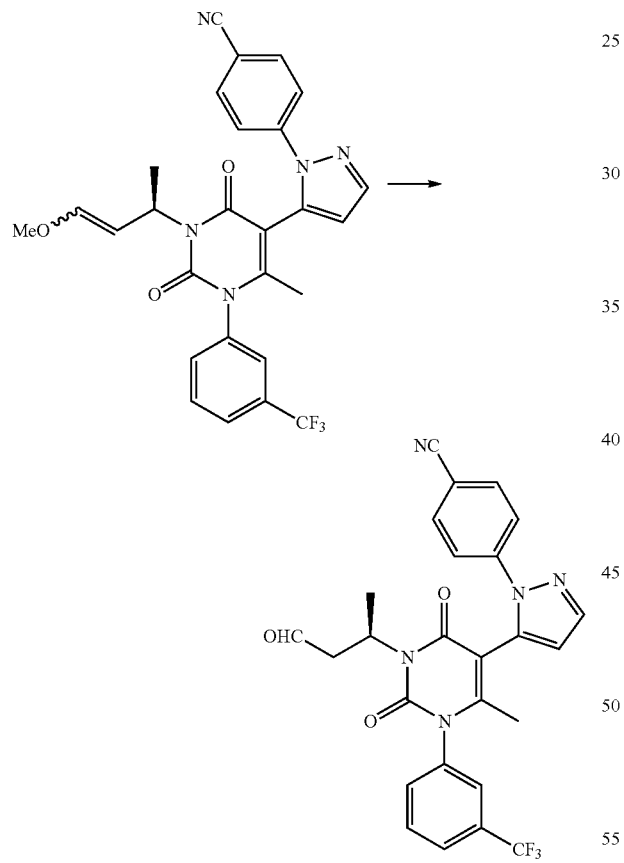

To a solution of (R)-4-(5-(3-(4-methoxy-3-buten-2-yl)-6-methyl-2,4-dioxo-1-(3-trifluoromethylphenyl)-1,2,3,4-tetrahydropyrimidin-5-yl)-1H-pyrazol-1-yl)benzonitrile (prepared in Example 397) (300 mg) in tetrahydrofuran (3.0 ml) was added 1N hydrochloric acid (10 ml) and the resulting mixture was stirred at 50° C. for two hours. To the reaction mixture was added water (10 ml) followed by an addition of ethyl acetate (20 ml×2) such that the intended products were extracted into an organic layer. The organic layer was washed with saturated saline (10 ml), dried over anhydrous sodium sulfate and then concentrated under reduced pressure. The residue was purified by silica gel column chromatography (eluent: hexane/ethyl acetate) to afford (R)-4-(5-(6-methyl-2,4-dioxo-3-(4-oxobutane-2-yl)-1-(3-trifluoromethylphenyl)-1,2,3,4-tetrahydropyrimidin-5-yl)-1H-pyrazol-1-yl)benzonitrile (309 mg). UPLC/MS 508 (M+H)/1.06 min (measurement condition 9)

Examples 399-408

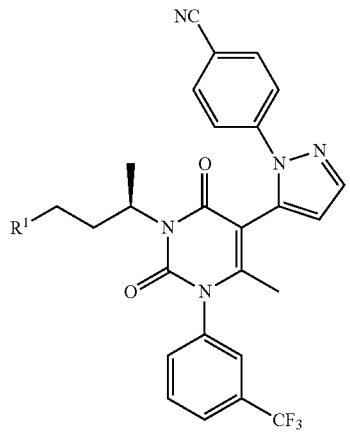

The compounds indicated in the below-mentioned table (Examples 399-408) were obtained by using the compound prepared in Example 398 according to the similar reaction and treatment method to those described in Example 69.

TABLE 77

| Ex. | $R^1$ | Measurement cond. | (LC-MS: Rt/ [M + H]+) | |
|---|---|---|---|---|
| 399 | (morpholine) | 9 | 0.807 | 579 |
| 400 | (ethylamino) | 9 | 0.807 | 537 |
| 401 | $NH_2$ | 9 | 0.894 | 523 |
| 402 | (dimethylamino) | 9 | 0.922 | 537 |
| 403 | (isopropylamino) | 9 | 0.897 | 551 |
| 404 | (cyclopentylamino) | 9 | 0.851 | 578 |
| 405 | (tetrahydropyran-4-ylamino) | 9 | 0.791 | 593 |

TABLE 77-continued

| Ex. | R¹ | Measurement cond. | (LC-MS: Rt/[M + H]+) | |
|---|---|---|---|---|
| 406 | 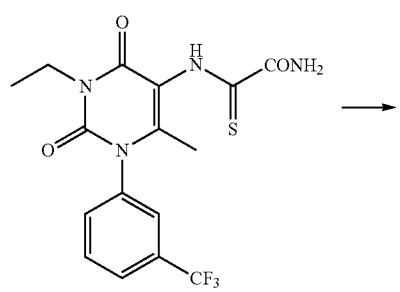 | 9 | 0.794 | 599 |
| 407 | F₃C─NH─ | 9 | 0.896 | 591 |
| 408 | (pyridin-4-yl)NH─ | 9 | 0.778 | 586 |

Example 409

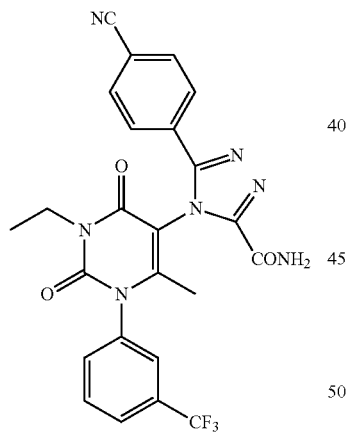

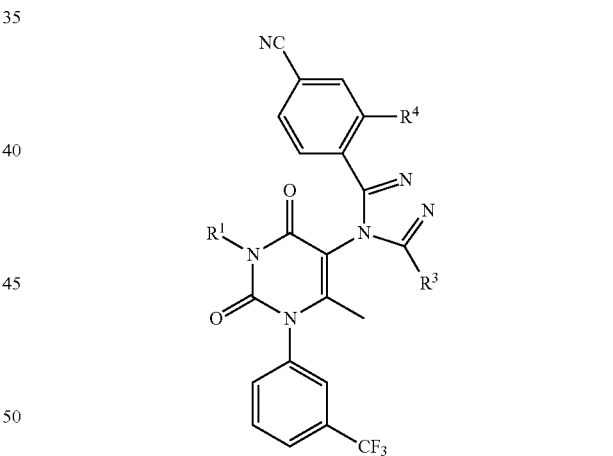

The compound prepared in Reference Example 248 was suspended in propanenitrile (30 ml) and thereto were added 4-cyanobenzohydrazide (383 mg), silver trifluoroacetate (263 mg) and trimethylsilyl triflate (0.23 ml) and the resulting mixture was stirred for two hours with heating under reflux. The mixture was cooled to 0° C. and thereto were then added ethyl acetate (50 ml), saturated aqueous sodium hydrogen carbonate solution (10 ml) and saturated saline (10 ml) and the precipitates were separated by filtration. The filtrates were concentrated under reduced pressure and thereto was then added ethyl acetate (30 ml×2) such that the intended products were extracted into an organic layer. The organic layer was washed with saturated saline (30 ml), dried over magnesium sulfate and then concentrated under reduced pressure. The residue was purified by silica gel column chromatography (eluent: ethyl acetate/methanol). The intended product obtained was recrystallized from ethyl acetate/hexane to afford 5-(4-cyanophenyl)-4-(3-ethyl-6-methyl-2,4-dioxo-1-(3-trifluoromethylphenyl)-1,2,3,4-tetrahydropyrimidin-5-yl)-4H-1,2,4-triazole-3-carboxamide (99 mg).

$^1$H-NMR (MeOH-$d_4$: 400 MHz) δ: 1.17 (t, 1.5H, J=7.1 Hz), 1.19 (t, 1.5H, J=7.0 Hz), 1.64 (s, 1.5H), 1.66 (s, 1.5H), 3.94-4.05-(m, 2H), 7.55-7.57 (m, 0.5H), 7.70-7.78 (m, 2H), 7.81-7.88 (m, 3H), 7.90-7.95 (m, 2.5H).

UPLC/MS 510 (M+H)/0.85 min (measurement condition 9), melting point: 256° C.

Examples 410-417

The compounds indicated in the below-mentioned table (Examples 410-417) were obtained by using the corresponding starting materials according to the similar reaction and treatment method to those described in Example 409.

TABLE 78

| Ex. | R³ | R¹ | R⁴ | Measurement cond. | (LC-MS: Rt/[M + H]+) | |
|---|---|---|---|---|---|---|
| 410 | ─CONMe₂ | Et | H | 9 | 538 | 0.897 |
| 411 | ─CO₂ᵗBu | Et | H | 9 | 581 | 1.039 |

TABLE 78-continued

| Ex. | R³ | R¹ | R⁴ | Measurement cond. | (LC-MS: Rt/[M + H]+) | |
|---|---|---|---|---|---|---|
| 412 | ![4-(N-methyl)piperidinyl] | Et | H | 9 | 564 | 0.738 |
| 413 | ![CH2CH2OCH3] | Et | H | 9 | 525 | 0.950 |
| 414 | ![CH2CH2OCH3] | Et | F | 9 | 544 | 0.913 |
| 415 | H | MeO₂S-CH₂-CH< | H | 9 | 559 | 0.831 |
| 416 | Me | MeO₂S-CH₂-CH< | H | 9 | 573 | 0.865 |
| 417 | Me | i-Pr | F | 9 | 513 | 0.954 |

Examples 418-422

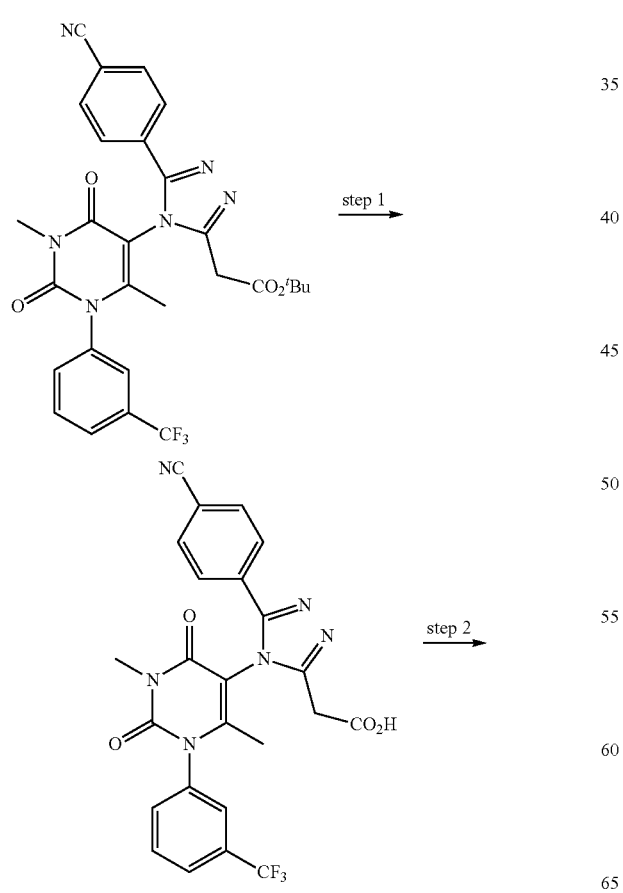

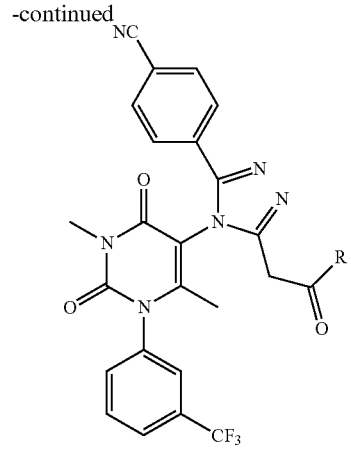

Step 1

Example 418

The carboxylic acid product was obtained by using the compound prepared in Example 411 according to the similar reaction and treatment method to those described in Example 85. UPLC/MS 525 (M+H)/0.831 min (measurement condition 9)

Step 2

The compounds indicated in the below-mentioned table (Examples 419-422) were obtained by using the carboxylic acid product prepared in Example 418 according to the similar reaction and treatment method to those described in Example 142.

TABLE 79

| Ex. | R | Measurement cond. | (LC-MS: Rt/[M + H]+) |
|---|---|---|---|
| 419 | NMe₂ | 9 | 552 (M + H)/0.890 (min) |
| 420 | NHMe | 9 | 538 (M + H)/0.860 (min) |
| 421 | NH₂ | 9 | 524 (M + H)/0.824 (min) |
| 422 | 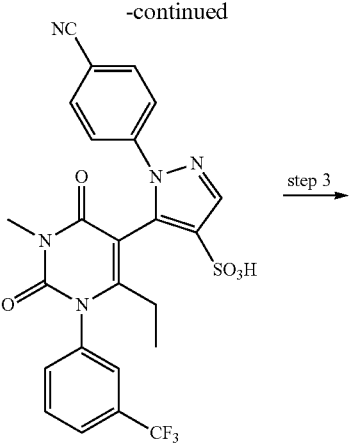 | 9 | 594 (M + H)/0.902 (min) |

Examples 423-425

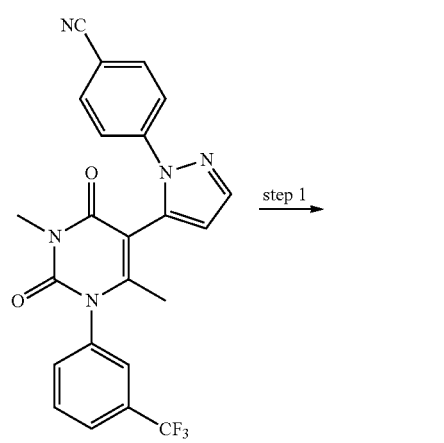

step 1 →

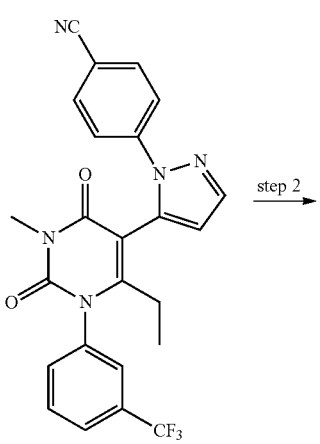

step 2 →

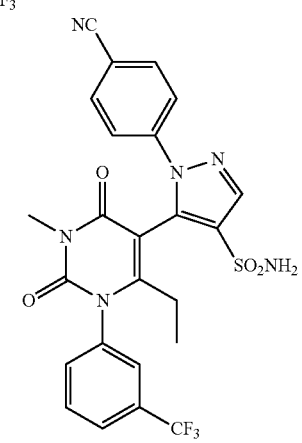

step 3 →

Step 1

Example 423

To a solution of the compound prepared in Example 1 (3.0 g) in DMF (30 ml) were added potassium hexamethyldisilazide (KHMDS) (2.65 g) and methyl iodide (0.8 ml) and the resulting mixture was stirred at room temperature for thirty minutes. To the reaction mixture was added 10% aqueous citric acid solution (30 ml) followed by an addition of ethyl acetate (30 ml×2) such that the intended products were extracted into an organic layer. The organic layer was washed with saturated saline (30 ml), dried over anhydrous sodium sulfate and then concentrated under reduced pressure. The residue was purified by silica gel column chromatography (eluent: hexane/ethyl acetate) to afford the ethyl product (2.1 g). UPLC/MS 466 (M+H)/1.010 min (measurement condition 9)

Step 2

Example 424

The sulfonic acid product (498 mg) was obtained by using the compound prepared in Example 423 (500 mg) according to the similar reaction and treatment method to those described in Example 191. UPLC/MS 546 (M+H)/0.748 min (measurement condition 9)

363

Step 3

Example 425

The sulfonamide product (235 mg) was obtained by using the compound prepared in Example 424 (358 mg) according to the similar reaction and treatment method to those described in Example 209. UPLC/MS 546 (M+H)/0.937 min (measurement condition 9)

Example 426

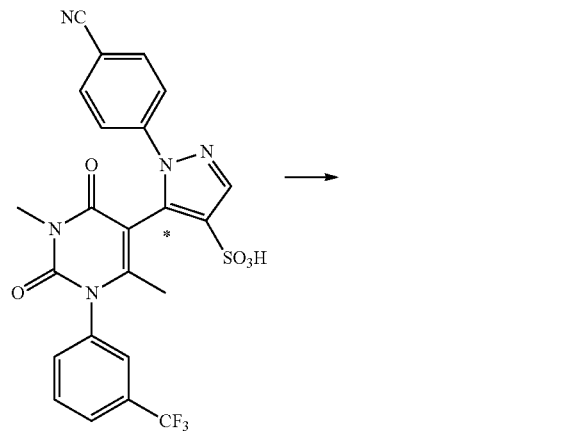

early eluting peak

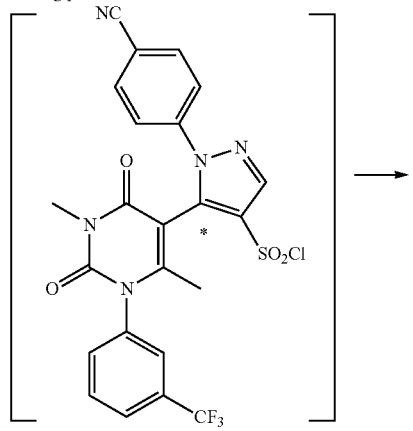

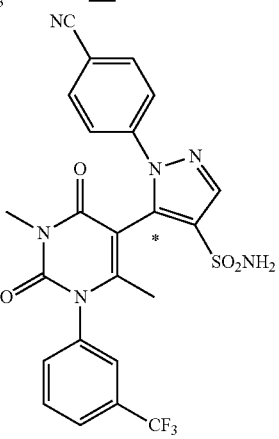

early eluting peak

364

(−)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide was obtained by using the compound prepared in Example 199 according to the similar reaction and treatment method to those described in Example 209.

UPLC/MS 531 (M+H)/0.87 min. (measurement condition 9)

Examples 427-429

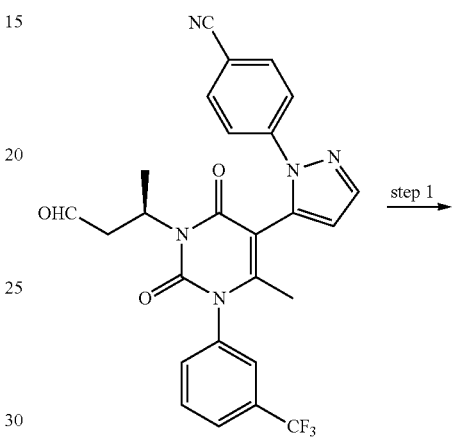

step 1

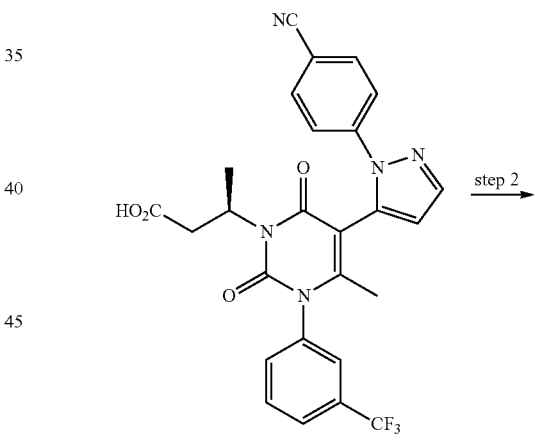

step 2

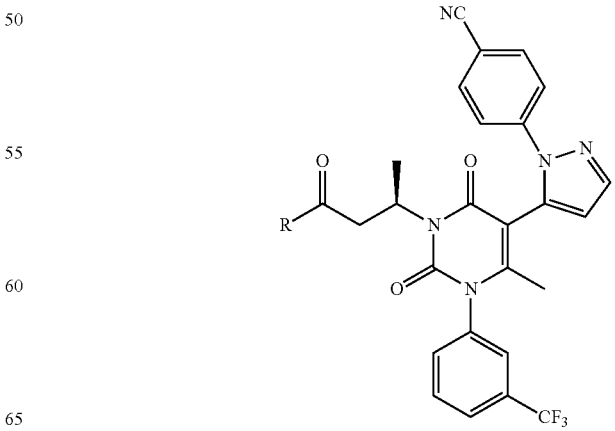

Step 1

Example 427

The carboxylic acid (128 mg) was obtained by using the compound prepared in Example 398 according to the similar reaction and treatment method to those described in Example 376. UPLC/MS 524 (M+H)/0.952 min (measurement condition 9)

Step 2

Examples 428-429

The compounds indicated in the below-mentioned table (Examples 428-429) were obtained by using the compounds prepared in Example 427 according to the similar reaction and treatment method to those described in Example 142.

TABLE 80

| Ex. | R | Measurement cond. | (LC-MS: Rt/[M + H]+) |
|---|---|---|---|
| 428 | $NH_2$ | 9 | 523 (M + H)/0.894 (min) |
| 429 | NHMe | 9 | 537 (M + H)/0.922 (min) |

Test Example 1

Inhibitory Action Against Human Neutrophil Elastase

Hereinafter, the pharmacological test result on the representative compound of the present invention was shown, but the present invention should not be limited to the results of these testing examples.

Assay buffer (0.4 unit/ml HNE (human neutrophil elastase, available from Elastin Products Company), 200 mM HEPES [N-(2-hydroxyethyl)piperazine-N'-(2-ethanesulfonic acid)], pH 7.5, 2M NaCl, 0.002% Brij-35) 100 μl, water for injection 40 μl and DMSO (dimethyl sulfoxide) solution of the present compound 20 μl were mixed in a 96 well plate and the mixed solutions were pre-incubated at 37° C. for five minutes. After pre-incubation, MeOSuc-AAPV-AMC (methoxysuccinyl-alanyl-alanyl-prolyl-valyl-aminomethyl cumaride (available from Sigma Aldrich Co.) solution as fluorogenic substrate (which was dissolved in 10% DMSO solution so as to adjust to 0.5 mM) 40 μl was added to the above-prepared mixed solution so as to initiate the reaction, and the mixture was incubated at 37° C. for five minutes. The fluorescence intensity of AMC was measured at an excitation wavelength of 380 nM and a fluorescence wavelength of 460 nm and the inhibition ratio was determined.

With respect to the compounds of Examples, $IC_{50}$ value (μM) (which means the compound concentration required for 50% inhibition of human neutrophil elastase) or inhibition ratio (%) at 100 μM is shown in the below-mentioned table.

TABLE 81

| Ex. | $IC_{50}$ value (μM) or Inhibition ratio (%) |
|---|---|
| 1 | 0.019 μM |
| 2 | 0.035 μM |
| 3 | 0.104 μM |
| 4 | 0.131 μM |
| 5 | 0.170 μM |
| 6 | 0.123 μM |
| 7 | 0.120 μM |
| 8 | 0.064 μM |
| 9 | 2.95 μM |
| 10 | 0.648 μM |
| 11 | 1.36 μM |
| 12 | 1.49 μM |
| 13 | 0.086 μM |
| 14 | 12.6 μM |
| 15 | 76% |
| 16 | 90% |
| 17 | 0.095 μM |
| 18 | 0.047 μM |
| 19 | 1.84 μM |
| 20 | 83% |
| 21 | 0.252 μM |
| 22 | 0.793 μM |
| 23 | 0.651 μM |
| 28 | 2.24 μM |
| 29 | 2.14 μM |
| 30 | 0.064 μM |
| 31 | 0.019 μM |
| 32 | 50% |
| 33 | 74.6 μM |
| 34 | 0.232 μM |
| 35 | 49% |
| 36 | 0.111 μM |
| 37 | 0.191 μM |
| 38 | 7.91 μM |
| 39 | 19.9 μM |
| 40 | 8.34 μM |
| 57 | 0.159 μM |
| 58 | 0.552 μM |
| 60 | 0.076 μM |
| 61 | 0.074 μM |
| 62 | 0.068 μM |
| 68 | 0.111 μM |
| 69 | 0.114 μM |
| 70 | 0.043 μM |
| 71 | 0.169 μM |
| 72 | 0.138 μM |
| 73 | 0.535 μM |
| 74 | 0.312 μM |
| 75 | 0.656 μM |
| 76 | 0.232 μM |
| 77 | 0.184 μM |
| 80 | 1.29 μM |
| 81 | 0.616 μM |
| 82 | 0.108 μM |
| 83 | 0.776 μM |
| 84 | 0.147 μM |
| 85 | 0.0043 μM |
| 86 | 0.0032 μM |
| 102 | 0.150 μM |
| 103 | 12.2 μM |
| 104 | 92.5 μM |
| 105 | 22.3 μM |
| 106 | 13.9 μM |
| 107 | 5.40 μM |
| 108 | 0.332 μM |

Test Example 2

Inhibitory Action 2 Against Human Neutrophil Elastase

Hereinafter, the pharmacological test result on the representative compound of the present invention was shown, but the present invention should not be limited to these testing examples.

Assay buffer (0.4 unit/ml HNE (human neutrophil elastase, available from Elastin Products Company), 200 mM HEPES [N-(2-hydroxyethyl)piperazine-N'-(2-ethanesulfonic acid)], pH 7.5, 400 mM NaCl, 0.2 mg/ml BSA (bovine serum albumin)) 100 μl, water for injection 20 μl and 1% DMSO (dimethyl sulfoxide) solution of the present compound 20 μl were mixed in a 96 well plate and the mixed solutions were pre-incubated at 37° C. for five minutes. After pre-incubation, MeOSuc-AAPV-AMC (methoxysuccinyl-alanyl-alanyl-prolyl-valyl-aminomethyl cumaride (available from Sigma Aldrich Corp.) solution as fluorogenic substrate (which was dissolved in 10% DMSO solution so as to adjust to 0.5 mM) 40 μl was added to the above-prepared mixed solution so as to initiate the reaction, and the mixture was incubated at 37° C. for five minutes. The fluorescence intensity of AMC was measured at an excitation wavelength of 380 nM and a fluorescence wavelength of 460 nm and the inhibition ratio was determined.

With respect to the compounds of Examples, $IC_{50}$ value (nM) (which means the compound concentration required for 50% inhibition of human neutrophil elastase) is shown in the below-mentioned table.

TABLE 82

| Ex. | $IC_{50}$ value (nM) |
|---|---|
| 1 | 16.9 |
| 2 | 18.6 |
| 17 | 23.4 |
| 37 | 64.2 |
| 41 | 12.6 |
| 42 | 3.5 |
| 50 | 13.7 |
| 55 | 4.9 |
| 65 | 5.5 |
| 90 | 353.1 |
| 143 | 6.9 |
| 148 | 14.5 |
| 151 | 6.0 |
| 153 | 5.4 |
| 156 | 10.0 |
| 162 | 12.6 |
| 173 | 7.9 |
| 176 | 11.4 |
| 178 | 13.5 |
| 179 | 8.7 |
| 183 | 363 |
| 184 | 5.3 |
| 187 | 19.4 |
| 188 | 18.6 |
| 191 | 23.1 |
| 196 | 8.4 |
| 205 | 15.0 |
| 206 | 9.3 |
| 207 | 13.5 |
| 209 | 9.3 |
| 211 | 8.8 |
| 218 | 14.7 |
| 220 | 21.7 |
| 221 | 19.8 |
| 227 | 7.8 |
| 239 | 7.7 |
| 242 | 14.3 |
| 243 | 5.4 |
| 249 | 11.9 |
| 252 | 20.6 |
| 255 | 9.2 |
| 257 | 7.7 |
| 261 | 7.2 |
| 265 | 23.7 |
| 267 | 11.6 |
| 274 | 14.0 |
| 276 | 12.0 |
| 283 | 26.0 |

TABLE 82-continued

| Ex. | $IC_{50}$ value (nM) |
|---|---|
| 285 | 24.3 |
| 288 | 26.2 |
| 293 | 25.1 |
| 295 | 14.6 |
| 297 | 29.7 |
| 298 | 42.7 |
| 300 | 14.3 |
| 305 | 22.0 |
| 306 | 41.0 |
| 313 | 27.2 |
| 315 | 24.2 |
| 318 | 14.9 |
| 324 | 9.6 |
| 326 | 24.3 |
| 328 | 24.8 |
| 337 | 4.5 |
| 339 | 7.3 |
| 343 | 7.3 |
| 351 | 7.4 |
| 355 | 8.1 |
| 357 | 10.2 |
| 358 | 29.5 |
| 359 | 15.3 |
| 360 | 16.7 |
| 361 | 6.3 |
| 363 | 19.1 |
| 367 | 14.0 |
| 371 | 17.4 |
| 375 | 12.3 |
| 377 | 11.0 |
| 379 | 18.7 |
| 383 | 12.8 |
| 386 | 10.1 |
| 387 | 8.9 |
| 390 | 10.4 |
| 392 | 5.1 |
| 393 | 26.3 |
| 399 | 12.9 |
| 404 | 14.2 |
| 406 | 12.9 |
| 408 | 14.7 |
| 412 | 21.0 |
| 413 | 22.3 |
| 416 | 16.3 |
| 417 | 39.8 |
| 420 | 28.6 |
| 422 | 14.5 |
| 428 | 9.0 |

INDUSTRIAL APPLICABILITY

The present compound is useful as a prophylactic agent and/or a therapeutic agent for various diseases associated with elastase such as inflammatory disease. The diseases in which elastase is suggested to associate with pathological conditions include, for example, chronic obstructive pulmonary disease (COPD), pulmonary cystic fibrosis, emphysema, adult respiratory distress syndrome (ARDS), acute lung injury (ALI), idiopathic pulmonary fibrosis (IPF), chronic interstitial pneumonia, chronic bronchitis, chronic airway infection, diffuse panbronchiolitis, bronchiectasis, asthma, pancreatitis, nephritis, hepatic failure, chronic rheumatoid arthritis, arthrosclerosis, osteoarthritis, psoriasis, periodontitis, atherosclerosis, rejection of organ transplantation, premature rupture of membrane, bullosa, shock, sepsis, systemic lupus erythematodes (SLE), Crohn disease, disseminated intravascular coagulation (DIC), ischemia-reperfusion induced-tissue injury, corneal scar tissue formation, myelitis, lung squamous cell carcinoma, pulmonary adenocarcinoma, lung cancers such as non-small cell lung cancer, breast cancer, liver cancer, bladder cancer, colorectal cancer, skin cancer, pancreas cancer, glioma and the others. Thus, an agent showing inhibitory activity for elastase is useful for treatment or prophylaxis of diseases associated with elastase.

The invention claimed is:

1. A compound represented by formula (I) or physiologically acceptable salts thereof:

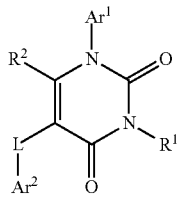

(I)

wherein
R$^1$ represents a hydrogen atom, a C$_{1-10}$alkyl group, a C$_{2-6}$ alkene group or a three to six-membered saturated- or four to six-membered unsaturated-aliphatic ring group optionally containing one to two heteroatoms independently selected from the group consisting of N, O and S,
said alkyl group and said alkene group for R$^1$ is optionally substituted at substitutable positions with one or multiple substituents selected from the group consisting of
Substituent List 1:
(1) hydroxy group,
(2) halogen atom,
(3) cyano group,
(4) C$_{1-6}$ alkoxy group wherein said alkoxy group is optionally substituted at substitutable positions with
hydroxy group,
halogen atom,
cyano group,
—C(═O)OR$^b$,
—C(═O)NR$^c$R$^d$,
five to six-membered aromatic ring group optionally containing one to four heteroatoms independently selected from the group consisting of N, O and S wherein said aromatic ring group is optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(═O)R$^b$ group, —NR$^a$C(═O)NR$^c$R$^d$ group, —NR$^a$S(═O)$_m$R$^b$ group, —C(═O)OR$^b$ group, —C(═O)NR$^c$R$^d$ group, —S(═O)$_m$NR$^c$R$^d$ group, —S(═O)$_m$R$^b$ group or —NR$^c$R$^d$ group or
three to six-membered saturated- or four to six-membered unsaturated-aliphatic ring group each optionally containing one to two heteroatoms independently selected from the group consisting of N, O and S wherein said aliphatic ring group is optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(═O)R$^b$ group, —NR$^a$C(═O)NR$^c$R$^d$ group, —NR$^a$S(═O)$_m$R$^b$ group, —C(═O)OR$^b$ group, —C(═O)NR$^c$R$^d$ group, —NR$^c$R$^d$ group or oxo group, (5) C$_{1-6}$ alkylthio group wherein said alkylthio group is optionally substituted at substitutable positions with
hydroxy group,
halogen atom,
cyano group,
—C(═O)OR$^b$,
—C(═O)NR$^c$R$^d$,
five to six-membered aromatic ring group optionally containing one to four heteroatoms independently selected from the group consisting of N, O and S wherein said aromatic ring group is optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(═O)R$^b$ group, —NR$^a$C(═O)NR$^c$R$^d$ group, —NR$^a$S(═O)$_m$R$^b$ group, —C(═O)OR$^b$ group, —C(═O)NR$^c$R$^d$ group, —S(═O)$_m$NR$^c$R$^d$ group, —S(═O)$_m$R$^b$ group or —NR$^c$R$^d$ group or
three to six-membered saturated- or four to six-membered unsaturated-aliphatic ring group each optionally containing one to two heteroatoms independently selected from the group consisting of N, O and S wherein said aliphatic ring group is optionally substituted at substitutable positions with C$_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(═O)R$^b$ group, —NR$^a$C(═O)NR$^c$R$^d$ group, —NR$^a$S(═O)$_m$R$^b$ group, —C(═O)OR$^b$ group, —C(═O)NR$^c$R$^d$ group, —NR$^c$R$^d$ group or oxo group, (6) five to six-membered aromatic ring group optionally containing one to four heteroatoms independently selected from the group consisting of N, O and S wherein said aromatic ring group is optionally substituted at substitutable positions with
C$_{1-3}$ alkyl group optionally substituted with hydroxy or halogen, $C_{1-3}$ alkoxy group optionally substituted with hydroxy or halogen,
hydroxy group,
halogen atom,
cyano group,
—NR$^a$C(=O)R$^b$,
—NR$^a$C(=O)NR$^c$R$^d$,
—NR$^a$S(=O)$_m$R$^b$,
—C(=O)OR$^b$,
—C(=O)NR$^c$R$^d$,
—S(=O)$_m$NR$^c$R$^d$,
—S(=O)$_m$R$^b$ or
—NR$^c$R$^d$, (7) three to six-membered saturated- or four to six-membered unsaturated-aliphatic ring group each optionally containing one to two heteroatoms independently selected from the group consisting of N, O and S wherein said aliphatic ring group is optionally substituted at substitutable positions with
$C_{1-3}$ alkyl group wherein said alkyl group is optionally substituted with hydroxy, halogen, cyano, —NR$^a$C(=O)R$^b$, —NR$^a$C(=O)NR$^c$R$^d$, —NR$^a$S(=O)$_m$R$^b$, —C(=O)OR$^b$, —C(=O)NR$^c$R$^d$ or —NR$^c$R$^d$,
$C_{1-3}$ alkoxy group optionally substituted with hydroxy or halogen,
hydroxy group,
halogen atom,
cyano group,
—NR$^a$C(=O)R$^b$,
—NR$^a$C(=O)NR$^c$R$^d$,
—NR$^a$S(=O)$_m$R$^b$,
—C(=O)OR$^b$,
—C(=O)NR$^c$R$^d$,
—C(O)R$^b$,
—S(=O)$_m$NR$^c$R$^d$,
—S(=O)$_m$R$^b$,
—NR$^c$R$^d$ or
oxo group, (8) —NR$^a$R$^c$ group,
(9) —OC(=O)NR$^c$R$^d$ group,
(10) —C(=O)R$^f$ group,
(11) —S(=O)$_m$R$^g$ group,
(12) thiol group,
(13) nitro group and
(14) —OR$^e$ group,
said three to six-membered saturated- or four to six-membered unsaturated-aliphatic ring group for R$^1$ is optionally substituted at substitutable positions with one or multiple substituents selected from the group consisting of
Substituent List 2:
(1) hydroxy group,
(2) halogen atom,
(3) cyano group,
(4) $C_{1-6}$ alkyl group wherein said alkyl group is optionally substituted at substitutable positions with
hydroxy group,
halogen atom,
cyano group,
five to six-membered aromatic ring group optionally containing one to four heteroatoms independently selected from the group consisting of N, O and S wherein said aromatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group,
—NR$^a$C(=O)R$^b$ group, —NR$^a$S(=O)$_m$R$^b$ group,
—C(=O)OR$^b$ group, —C(=O)NR$^c$R$^d$ group,
—S(=O)$_m$NR$^c$R$^d$ group, —S(=O)$_m$R$^b$ group or
—NR$^c$R$^d$ group or
three- to six-membered saturated aliphatic ring group optionally containing one to two heteroatoms independently selected from the group consisting of N, O and S wherein said aliphatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group, (5) $C_{1-6}$ alkoxy group wherein said alkoxy group is optionally substituted at substitutable positions with
hydroxy group,
halogen atom,
cyano group,
five to six-membered aromatic ring group optionally containing one to four heteroatoms independently selected from the group consisting of N, O and S wherein said aromatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group,
—NR$^a$C(=O)R$^b$ group, —NR$^a$S(=O)$_m$R$^b$ group,
—C(=O)OR$^b$ group, —C(=O)NR$^c$R$^d$ group,
—S(=O)$_m$NR$^c$R$^d$ group, —S(=O)$_m$R$^b$ group or a
—NR$^c$R$^d$ group or
three to six-membered saturated aliphatic ring group optionally containing one to two heteroatoms independently selected from the group consisting of N, O and S wherein said aliphatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group, (6) $C_{1-6}$ alkylthio group wherein said alkylthio group is optionally substituted at substitutable positions with
hydroxy group,
halogen atom,
cyano group,
five to six-membered aromatic ring group optionally containing one to four heteroatoms independently selected from the group consisting of N, O and S wherein said aromatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group,
—NR$^a$C(=O)R$^b$ group, —NR$^a$S(=O)$_m$R$^b$ group,
—C(=O)OR$^b$ group, —C(=O)NR$^c$R$^d$ group,
—S(=O)$_m$NR$^c$R$^d$ group, —S(=O)$_m$R$^b$ group or
—NR$^c$R$^d$ group or
three to six-membered saturated aliphatic ring group optionally containing one to two heteroatoms independently selected from the group consisting of N, O and S wherein said aliphatic ring group is optionally substituted at substitutable positions with $C_{1-3}$ alkyl group optionally substituted with hydroxy or halogen, C$_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group, (7) five to six-membered aromatic ring group optionally containing one to four heteroatoms independently selected from the group consisting of N, O and S wherein said aromatic ring group is optionally substituted at substitutable positions with
C$_{1-3}$ alkyl group optionally substituted with hydroxy or halogen,
C$_{1-3}$ alkoxy group optionally substituted with hydroxy or halogen,
hydroxy group,
halogen atom,
cyano group,
—NR$^a$C(=O)R$^b$,
—NR$^a$S(=O)$_m$R$^b$,
—C(=O)OR$^b$,
—C(=O)NR$^c$R$^d$,
—S(=O)$_m$NR$^c$R$^d$,
—S(=O)$_m$R$^b$ or
—NR$^c$R$^d$, (8) three to six-membered saturated aliphatic ring group optionally containing one to two heteroatoms independently selected from the group consisting of N, O and S wherein said aliphatic ring group is optionally substituted at substitutable positions with
C$_{1-3}$ alkyl group optionally substituted with hydroxy or halogen,
C$_{1-3}$ alkoxy group optionally substituted with hydroxy or halogen,
hydroxy group,
halogen atom,
cyano group,
—NR$^a$C(=O)R$^b$,
—NR$^a$S(=O)$_m$R$^b$,
—C(=O)OR$^b$,
—C(=O)NR$^c$R$^d$,
—NR$^c$R$^d$ or
oxo group, (9) —NR$^a$R$^e$ group,
(10) —OC(=O)NR$^c$R$^d$ group,
(11) —C(=O)R$^f$ group,
(12) —S(=O)$_m$R$^g$ group,
(13) thiol group,
(14) oxo group,
(15) nitro group,
(16) —NR$^a$C(=O)R$^b$ group,
(17) —NR$^a$C(=O)NR$^c$R$^d$ group,
(18) —NR$^a$S(=O)$_m$R$^b$ group,
(19) —C(=O)OR$^b$ group and
(20) —C(=O)NR$^c$R$^d$ group, R$^2$ represents a hydrogen atom, a halogen atom, a cyano group, a —NR$^c$R$^d$ group, a —N—CHN(CH$_3$)$_2$ group or a C$_{1-3}$ alkyl group wherein said alkyl group is optionally substituted with hydroxy, halogen, —NR$^c$R$^d$, —OR$^a$ or —OC(=O)R$^a$, Ar$^1$ represents a five to six-membered aromatic ring group optionally containing one to three heteroatoms independently selected from the group consisting of N, O and S wherein said aromatic ring group is substituted at substitutable positions with C$_{1-6}$ alkyl group optionally substituted with hydroxy or halogen, C$_{1-3}$ alkoxy group optionally substituted with hydroxy or halogen, hydroxy group, halogen atom, cyano group, nitro group, phenyl group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O)R$^a$ group, —S(=O)$_m$NR$^c$R$^d$ group, —S(=O)$_n$R$^h$ group or —NR$^c$R$^d$ group, L represents a six membered unsubstituted aromatic ring group optionally containing 1 to 2 nitrogen atoms, a Pyr-1 group of the following formula or a Tri-1 group of the following formula:

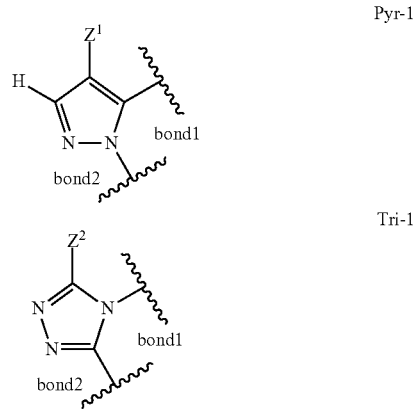

wherein the bond 1 represents a binding to uracil ring, the bond 2 represents a binding to Ar$^2$, and the Z$^1$ and Z$^2$ represent independently of each other a cyano group, a halogen atom, a —C(=O)NR$^c$R$^d$ group, a —C(=O)OR$^{b2}$ group, a —CHO group, a nitro group, a hydroxy group, a —NR$^c$R$^d$ group, a —NR$^a$C(=O)R$^h$ group, a hydrogen atom, a —S(=O)$_m$NR$^{c2}$R$^{d2}$ group, a —S(=O)$_m$NR$^a$C(=O)R$^{b3}$ group, a —S(=O)$_m$NR$^a$C(=O)OR$^{b4}$ group, a —S(=O)$_m$NR$^a$C(=O)NR$^a$R$^{b3}$ group, a —S(=O)$_m$R$^{g2}$ group, a —S—R$^{g3}$ group, a three to six-membered saturated aliphatic ring group optionally containing one to two heteroatoms independently selected from the group consisting of N, O and S wherein said saturated aliphatic ring group is optionally substituted with hydroxy, halogen, C$_{1-6}$ alkyl, C$_{1-3}$ alkoxy, —C(=O)OR$^a$, —C(=O)R$^a$ or —NR$^a$R$^b$, a C$_{1-6}$ alkyl group or an C$_{2-6}$ alkene group wherein said alkyl group and said alkene group are independently of each other optionally substituted with halogen, hydroxy, —NR$^c$R$^d$, —C(=O)NR$^c$R$^d$, —NR$^a$S(=O)$_m$R$^h$, —C(=O)NR$^c$R$^d$ or —C(=O)OR$^a$, Ar$^2$ represents a five to six-membered aromatic ring group optionally containing one to three heteroatoms independently selected from the group consisting of N, O and S wherein said aromatic ring group is substituted at one or more substitutable positions with C$_{1-6}$ alkyl group optionally substituted with hydroxy, cyano or halogen, C$_{1-3}$ alkoxy group optionally substituted with hydroxy or halogen, hydroxy group, halogen atom, cyano group, nitro group, —NR$^a$C(=O)R$^h$ group, —NR$^a$S(=O)$_m$R$^h$ group, —NR$^a$C(=O)NR$^c$R$^d$ group, —C(=O)NR$^c$R$^d$ group, —C(=O)OR$^a$ group, —C(=O)R$^a$ group, —S(=O)$_m$NR$^c$R$^d$ group, —S(=O)$_n$R$^h$ group or —NR$^c$R$^d$ group, $R^a$ represents a hydrogen atom or a $C_{1-6}$ alkyl group wherein said alkyl group is optionally substituted with hydroxy or halogen, $R^b$ represents a hydrogen atom, a $C_{1-6}$ alkyl group optionally substituted with hydroxy or halogen, a benzyl group optionally substituted with methoxy or nitro, or a $C_{3-6}$ cycloalkyl group optionally substituted with hydroxy or halogen, $R^{b2}$ represents a hydrogen atom, a $C_{1-6}$ alkyl group wherein said alkyl group is optionally substituted with hydroxy, —$NR^aR^b$ or halogen, a benzyl group wherein said benzyl group is optionally substituted with methoxy or nitro or a $C_{3-6}$ cycloalkyl group wherein said cycloalkyl group is optionally substituted with hydroxy or halogen, $R^{b3}$ represents a hydrogen atom, a phenyl group wherein said phenyl group is optionally substituted with halogen, a $C_{1-6}$ alkyl group wherein said alkyl group is optionally substituted with hydroxy or halogen or a $C_{3-6}$ cycloalkyl group wherein said cycloalkyl group is optionally substituted with hydroxy or halogen, $R^{b4}$ represents a hydrogen atom, a phenyl group wherein said phenyl group is optionally substituted with halogen, a $C_{1-6}$ alkyl group wherein said alkyl group is optionally substituted with hydroxy or halogen, a $C_{3-6}$ cycloalkyl group wherein said cycloalkyl group is optionally substituted with hydroxy or halogen or an 2-isopropyl-5-methylcyclohexyl, $R^c$ and $R^d$ represent independently of each other a hydrogen atom or a $C_{1-3}$ alkyl group optionally substituted with $C_{1-3}$ alkoxy, cyano, hydroxy or halogen, or alternatively may combine each other together with N to which they are attached and optionally together with further one to two heteroatoms independently selected from the group consisting of N, O and S to represent a four to six-membered saturated or unsaturated aliphatic ring group wherein said aliphatic ring group is optionally substituted at substitutable positions with $C_{1-6}$ alkyl group (said alkyl group is optionally substituted with hydroxy, —$NR^aR^b$, —$NR^aC(=O)OR^h$ or —$NR^aC(=O)R^h$), $C_{1-3}$ alkoxy group, —$NR^aR^b$ group, —$NR^aC(=O)OR^h$ group, —$NR^aC(=O)R^h$ group, —$C(=O)OR^a$ group, hydroxy group, halogen atom or oxo group, $R^{c2}$ and $R^{d2}$ represent independently of each other a hydrogen atom or a $C_{1-3}$ alkyl group wherein said alkyl group is optionally substituted with phenyl group optionally substituted with methoxy, —$NR^aR^b$ group, —$NR^a(C=O)OR^h$ group, —$NR^aC(=O)R^h$ group, $C_{1-3}$ alkoxy group, cyano group, hydroxy group or halogen atom, or alternatively may combine each other together with N to which they are attached and optionally together with further one to two heteroatoms independently selected from the group consisting of N, O and S to represent a four to six-membered saturated or unsaturated aliphatic ring group wherein said aliphatic ring group is optionally substituted at substitutable positions with $C_{1-6}$ alkyl group, $C_{1-3}$ alkoxy group, —$NR^aR^b$ group, —$NR^aC(=O)OR^h$ group, —$NR^aC(=O)R^h$ group, —$C(=O)OR^a$ group, hydroxy group, halogen atom or oxo group, $R^e$ represents a hydrogen atom, a $C_{1-6}$ alkyl group wherein said alkyl group is optionally substituted with hydroxy, cyano, halogen, $C_{1-3}$ alkoxy or —$NR^cR^d$, an -A group, a —$C(=O)$-A group, a $C_{1-6}$ alkylcarbonyl group wherein the alkyl moiety of said alkylcarbonyl is optionally substituted with hydroxy, halogen, cyano, $C_{1-3}$ alkoxy or —$NR^cR^d$, a $C_{1-6}$ alkoxycarbonyl group wherein the alkyl moiety of said alkoxycarbonyl group is optionally substituted with hydroxy or halogen, a —$C(=O)NR^cR^d$ group or a —$S(=O)_mR^b$ group, $R^f$ represents a hydrogen atom, a hydroxy group, a $C_{1-6}$ alkyl group wherein said alkyl group is optionally substituted with hydroxy, cyano, halogen, $C_{1-3}$ alkoxy or —$NR^cR^d$, a $C_{1-3}$ alkoxy group wherein said alkoxy group is optionally substituted with phenyl group optionally substituted with methoxy or nitro, hydroxy group, cyano group, halogen atom, $C_{1-3}$ alkoxy group or —$NR^cR^d$ group, an -A group or a —$NR^aR^i$ group, $R^g$ represents a hydroxy group, a chlorine atom, a $C_{1-6}$ alkyl group wherein said alkyl group is optionally substituted with hydroxy, cyano, halogen, $C_{1-3}$ alkoxy or —$NR^cR^d$, an -A group or a —$NR^aR^i$ group, $R^{g2}$ represents a hydroxy group, a chlorine atom, a $C_{1-6}$ alkyl group wherein said alkyl group is optionally substituted with hydroxy, cyano, halogen, $C_{1-3}$ alkoxy or —$NR^cR^d$ or an -A group, $R^{g3}$ represents a $C_{1-6}$ alkyl group wherein said alkyl group is optionally substituted with hydroxy, cyano, halogen, $C_{1-3}$ alkoxy or —$NR^cR^d$ or an -A group, $R^h$ represents a $C_{1-6}$ alkyl optionally substituted with hydroxy or halogen, $R^i$ represents a hydrogen atom, a $C_{1-6}$ alkyl group wherein said alkyl group is optionally substituted with hydroxy, cyano, halogen, $C_{1-3}$ alkoxy, $C_{3-6}$ cycloalkyl or —$NR^cR^d$, an -A group, a —$C(=O)R^h$ group, a —$C(=O)A$ group or a $C_{1-6}$ alkylcarbonyl group wherein the alkyl moiety of said alkylcarbonyl group is optionally substituted with hydroxy, halogen, cyano, $C_{1-3}$ alkoxy or —$NR^cR^d$, A represents a five to six-membered aromatic ring group optionally containing one to four heteroatoms independently selected from the group consisting of N, O and S wherein said aromatic group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —$C(=O)OH$ group or —$NR^cR^d$ group, a three to six-membered saturated- or four to six-membered unsaturated-aliphatic ring group each optionally containing one to two heteroatoms independently selected from the group consisting of N, O and S wherein said aliphatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —C(=O)OH group, —NR$^c$R$^d$ group or oxo group, m represents an integer of 1 or 2 and n represents an integer of 0 to 2.

2. The compound according to claim 1 or physiologically acceptable salts thereof, wherein $Z^1$ and $Z^2$ represent independently of each other a cyano group, a halogen atom, a —C(=O)NR$^c$R$^d$ group, a —C(=O)OR$^{b2}$ group, a —CHO group, a nitro group, a —NR$^a$C(=O)R$^b$ group, a hydrogen atom, a —S(=O)$_m$NR$^{c2}$R$^{d2}$ group, a —S(=O)$_m$NR$^a$C(O)R$^{b3}$ group, a —S(=O)$_m$NR$^a$C(=O)OR$^{b4}$ group, a —S(=O)$_m$NR$^a$C(=O)NR$^a$R$^{b3}$ group, a —S(=O)$_m$R$^{g2}$ group, a three to six-membered saturated aliphatic ring group optionally containing one to two heteroatoms independently selected from the group consisting of N, O and S wherein said saturated aliphatic ring group is optionally substituted with halogen, $C_{1-6}$ alkyl, —C(O)OR$^a$ or —C(=O)R$^a$ or a $C_{1-6}$ alkyl group wherein said alkyl group is optionally substituted with halogen, —C(=O)NR$^c$R$^d$, —NR$^a$S(=O)$_m$R$^h$, —C(=O)NR$^c$R$^d$ or —C(=O)OR$^a$.

3. The compound according to claim 1 or 2 or physiologically acceptable salts thereof wherein Ar$^1$ represents a benzene ring or a pyridine ring wherein said benzene ring and said pyridine ring are independently of each other substituted at one to three substitutable positions with $C_{1-6}$ alkyl group optionally substituted with hydroxy or halogen, $C_{1-3}$ alkoxy group optionally substituted with hydroxy or halogen, hydroxy group, halogen atom, cyano group, nitro group, phenyl group, —C(=O)NR$^c$R$^d$ group, —C(=O)OR$^a$ group, —C(=O)R$^a$ group, —S(=O)$_n$R$^h$ group or —NR$^c$R$^d$ group, and Ar$^2$ represent a benzene ring or a pyridine ring wherein said benzene ring and said pyridine ring are substituted independently of each other at one to three substitutable positions with $C_{1-6}$ alkyl group optionally substituted with hydroxy or halogen, $C_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group.

4. The compound according to claim 1 or physiologically acceptable salts thereof wherein Ar$^1$ represents the following formula of Ar$^1$-1:

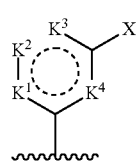

Ar$^1$-1 wherein $K^1$, $K^2$, $K^3$ and $K^4$ represent all carbon atoms for benzene ring, or only one nitrogen atom and the remaining carbon atoms for pyridine ring, and X represents a $C_{1-6}$ alkyl group optionally substituted with hydroxy or halogen, a $C_{1-3}$ alkoxy group optionally substituted with hydroxy or halogen, a hydroxy group, a halogen atom, a cyano group, a nitro group, a phenyl group, a —C(=O)NR$^c$R$^d$ group, a —C(=O)OR$^a$ group, a —C(=O)R$^a$ group, a —S(=O)$_n$R$^h$ group or a —NR$^c$R$^d$ group, said benzene ring and said pyridine ring are optionally substituted at one to two substitutable positions of $K^1$ to $K^4$ with further $C_{1-6}$ alkyl group optionally substituted with hydroxy or halogen, $C_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group, Ar$^2$ represents the following formula Ar$^2$-1:

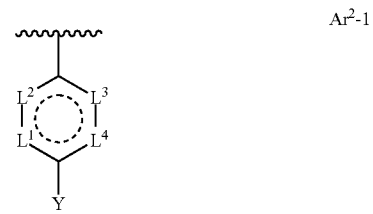

Ar$^2$-1 wherein $L^1$, $L^2$, $L^3$ and $L^4$ represent all carbon atoms for benzene ring, or only one nitrogen atom and the remaining carbon atoms for pyridine ring, and Y represents a $C_{1-6}$ alkyl group optionally substituted with hydroxy or halogen, a $C_{1-3}$ alkoxy group optionally substituted with hydroxy or halogen, a hydroxy group, a halogen atom, a cyano group, a nitro group, a —C(=O)NR$^c$R$^d$ group, a —C(=O)OR$^a$ group, a —C(=O)R$^a$ group, a —S(=O)$_n$R$^h$ group or a —NR$^c$R$^d$ group, said benzene ring and said pyridine ring are optionally substituted at one to two substitutable positions of $L^1$ to $L^4$ with further $C_{1-6}$ alkyl group optionally substituted with hydroxy or halogen, $C_{1-3}$ alkoxy group optionally substituted with hydroxy or halogen, hydroxy group, halogen atom, cyano group, nitro group, —C(=O)NR$^c$R$^d$ group, —C(=O)OR$^a$ group, —C(=O)R$^a$ group, —S(=O)$_n$R$^h$ group or —NR$^c$R$^d$ group.

5. The compound according to claim 1 or physiologically acceptable salts thereof wherein $R^2$ represents a —NR$^c$R$^d$ group, a —N=CHN(CH$_3$)$_2$ group or a $C_{1-3}$ alkyl group wherein said alkyl group is optionally substituted with hydroxy, halogen, —NR$^c$R$^d$, —OR$^a$ or —OC(=O)R$^a$.

6. The compound according to claim 1 or physiologically acceptable salts thereof, wherein $R^a$ represents a hydrogen atom or a $C_{1-6}$ alkyl group optionally substituted with hydroxy or halogen, $R^b$ represents a $C_{1-6}$ alkyl group optionally substituted with hydroxy or halogen, $R^{b2}$ represents a hydrogen atom, a $C_{1-6}$ alkyl group wherein said alkyl group is optionally substituted with hydroxy, —NR$^a$R$^b$ or fluorine or a $C_{3-6}$ cycloalkyl group wherein said cycloalkyl group is optionally substituted with hydroxy or fluorine, $R^{b3}$ represents a hydrogen atom, a phenyl group wherein said phenyl group is optionally substituted with fluorine or chlorine, a $C_{1-6}$ alkyl group wherein said alkyl group is optionally substituted with hydroxy or fluorine or a $C_{3-6}$ cycloalkyl group wherein said cycloalkyl group is optionally substituted with hydroxy or fluorine, $R^{b4}$ represents a hydrogen atom, a phenyl group wherein said phenyl group is optionally substituted with fluorine or chlorine, a $C_{1-6}$ alkyl group wherein said alkyl group is optionally substituted with hydroxy or fluorine, a $C_{3-6}$ cycloalkyl group wherein said cycloalkyl group is optionally substituted with hydroxy or fluorine or an 2-isopropyl-5-methylcyclohexyl, $R^c$ and $R^d$ represent independently of each other a hydrogen atom or a $C_{1-3}$ alkyl group wherein said alkyl group is optionally substituted with $C_{1-3}$ alkoxy, cyano, hydroxy or fluorine, or alternatively may combine each other together with N to which they are attached and optionally together with further one to two heteroatoms independently selected from the group consisting of N, O and S to represent a four to six-membered saturated aliphatic ring group wherein said aliphatic ring group is optionally substituted at substitutable positions with $C_{1-6}$ alkyl group wherein said alkyl group is optionally substituted with hydroxy, —$NR^aR^b$, —$NR^aC(=O)OR^h$ or —$NR^aC(=O)R^h$, $C_{1-3}$ alkoxy group, —$NR^aR^b$ group, —$NR^aC(=O)OR^a$ group, —$NR^aC(=O)R^a$ group, —$C(=O)OR^a$ group, hydroxy group, fluorine atom or oxo group, $R^{c2}$ an $R^{d2}$ represent independently of each other a hydrogen atom or a $C_{1-3}$ alkyl group wherein said alkyl group is optionally substituted with phenyl group optionally substituted with methoxy, —$NR^aR^b$ group, —$NR^a(C=O)OR^h$ group, —$NR^aC(=O)R^h$ group, $C_{1-3}$ alkoxy group, cyano group, hydroxy group or fluorine atom, or alternatively combine each other together with N to which they are attached and optionally together with further one to two heteroatoms independently selected from the group consisting of N, O and S to represent a four to six-membered saturated aliphatic ring group wherein said aliphatic ring group is optionally substituted at substitutable positions with $C_{1-6}$ alkyl, $C_{1-3}$ alkoxy, —$NR^aR^b$, —$NR^aC(=O)OR^h$, —$NR^aC(=O)R^h$, —$C(=O)OR^a$, hydroxy, fluorine or oxo, $R^e$ represents a $C_{1-6}$ alkyl group wherein said alkyl group is optionally substituted with hydroxy or fluorine, an -A group, an $C_{1-6}$ alkylcarbonyl group wherein the alkyl moiety of said alkylcarbonyl group is optionally substituted with hydroxy or fluorine or a —$S(=O)_2R^b$ group, $R^f$ represents a hydroxy group, an -A group or an —$NR^aR^i$ group, $R^g$ represents a hydroxy group, a $C_{1-3}$ alkyl group wherein said alkyl group is optionally substituted with hydroxy, fluorine or —$NR^cR^d$, a chlorine atom, an -A group or a —$NR^aR^i$ group, $R^{g2}$ represents a hydroxy group, a $C_{1-3}$ alkyl group wherein said alkyl group is optionally substituted with hydroxy or fluorine, a chlorine atom or an -A group, $R^{g3}$ represents a $C_{1-6}$ alkyl group wherein aid alkyl group is optionally substituted with hydroxy, fluorine or —$NR^cR^d$, $R^h$ represents a $C_{1-3}$ alkyl group optionally substituted with hydroxy or fluorine, $R^i$ represents a $C_{1-3}$ alkyl group wherein said alkyl group is optionally substituted with hydroxy, $C_{1-3}$ alkoxy or fluorine or an -A group, A represents an aromatic ring group selected from the group consisting of phenyl, pyridyl and tetrazolyl wherein said aromatic ring group is optionally substituted at substitutable positions with hydroxy or fluorine or an aliphatic ring group selected from the group consisting of cyclopropyl, cyclobutyl, cyclopentyl, cyclohexyl, pyranyl, azetidinyl, pyrrolidinyl, piperidinyl, piperazinyl and morpholinyl wherein said aliphatic ring group is optionally substituted at substitutable positions with $C_{1-3}$ alkyl, $C_{1-3}$ alkoxy, hydroxy, fluorine, —$NR^cR^d$ or oxo, and m represents an integer of 1 or 2.

7. The compound according to claim 1 or physiologically acceptable salts thereof wherein $R^1$ represents a $C_{1-10}$ alkyl group wherein said alkyl group is optionally substituted at substitutable positions with one to three substituents selected from the group consisting of Substituent List 8:
(1) hydroxy group,
(2) halogen atom,
(3) cyano group,
(7) three to six-membered saturated aliphatic ring group optionally containing one to two heteroatoms independently selected from the group consisting of N, O and S wherein said aliphatic ring group is optionally substituted at substitutable positions with
 $C_{1-3}$ alkyl group optionally substituted with hydroxy or halogen,
 $C_{1-3}$ alkoxy group optionally substituted with hydroxy or halogen,
 hydroxy group,
 halogen atom,
 cyano group,
 —$NR^aC(=O)R^b$,
 —$NR^aS(=O)_mR^b$,
 —$C(=O)OR^b$,
 —$C(=O)NR^cR^d$,
 —$C(=O)R^b$,
 —$NR^cR^d$ or
 oxo group;
(8) —$NR^aR^e$ group,
(10) —$C(=O)R^f$ group,
(11) —$S(=O)_mR^g$ group, and
(12) thiol group,
or
a three to six-membered saturated aliphatic ring group optionally containing one to two heteroatoms independently selected from the group consisting of N, O and S wherein said aliphatic ring group is optionally substituted at substitutable positions with one or multiple substituents selected from the group consisting of Substituent List 9:
(1) hydroxy group,
(2) halogen atom,
(3) cyano group,
(4) $C_{1-6}$ alkyl group wherein said alkyl group is optionally substituted at substitutable positions with
 hydroxy group,
 halogen atom,
 cyano group,
 five to six-membered aromatic ring group optionally containing one to four heteroatoms independently selected from the group consisting of N, O and S wherein said aromatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —$NR^aC(=O)R^b$ group, —$NR^aS(=O)_mR^b$ group, —$C(=O)OR^b$ group, —$C(=O)NR^cR^d$ group, —$S(=O)_mNR^cR^d$ group, —$S(O)_mR^b$ group or —$NR^cR^d$ group or
 three to six-membered saturated aliphatic ring group optionally containing one to two heteroatoms independently selected from the group consisting of N, O and S wherein said aliphatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group, (5) $C_{1-6}$ alkoxy group wherein said alkoxy group is optionally substituted at substitutable positions with
hydroxy group,
halogen atom,
cyano group,
five to six-membered aromatic ring group optionally containing one to four heteroatoms independently selected from the group consisting of N, O and S wherein said aromatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —S(=O)$_m$NR$^c$R$^d$ group, —S(=O)$_m$R$^b$ group or a —NR$^c$R$^d$ group or
three to six-membered saturated aliphatic ring group optionally containing one to two heteroatoms independently selected from the group consisting of N, O and S wherein said aliphatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy group, halogen atom, cyano group, —NR$^a$C(=O)R$^b$ group, —NR$^a$S(=O)$_m$R$^b$ group, —C(=O)OR$^b$ group, —C(=O)NR$^c$R$^d$ group, —NR$^c$R$^d$ group or oxo group,
(11) —C(=O)R$^f$ group,
(12) —S(=O)$_m$R$^g$ group, and
(14) oxo group.

8. The compound according to claim 1 or physiologically acceptable salts thereof wherein
R$^1$ represents
a $C_{1-10}$ alkyl group wherein said alkyl group is optionally substituted at substitutable positions with one to three substituents selected from the group consisting of
Substituent List 10:
(1) hydroxy group,
(2) halogen atom,
(7) three to six-membered saturated aliphatic ring group optionally containing one to two heteroatoms independently selected from the group consisting of N, O and S wherein said aliphatic ring group is optionally substituted at substitutable positions with $C_{1-3}$ alkyl group optionally substituted with hydroxy or halogen, $C_{1-3}$ alkoxy group optionally substituted with hydroxy or halogen, hydroxy, halogen, —C(=O)OR$^b$, —C(=O)NR$^c$R$^d$, —C(=O)R$^b$ or oxo group,
(8) —NR$^a$R$^e$ group, and
(11) —S(=O)$_2$R$^g$ group
or
a three to six-membered saturated aliphatic ring group optionally containing one to two heteroatoms independently selected from the group consisting of N and O wherein said aliphatic ring group is optionally substituted at substitutable positions with one or multiple substituents selected from the group consisting of Substituent List 11:
(1) hydroxy group,
(2) halogen atom,
(4) $C_{1-6}$ alkyl group wherein said alkyl group is optionally substituted at substitutable positions with hydroxy or halogen,
(9) —NR$^a$R$^e$ group,
(11) —C(=O)R$^f$ group and
(14) oxo group.

9. The compound according to claim 1 or physiologically acceptable salts thereof wherein L represents a Pyr-1 group.

10. The compound according to claim 1 or physiologically acceptable salts thereof wherein
the formula (I) represents the following formula (I'''):

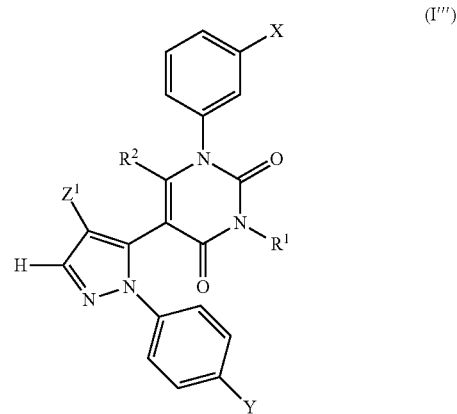

(I''')

wherein Z$^1$ represents a cyano group, a halogen atom, a —C(=O)NR$^c$R$^d$ group, a —C(=O)OR$^{b2}$ group, a hydrogen atom, a —S(=O)$_2$NR$^{c2}$R$^{d2}$ group, a —S(O)$_2$NR$^a$C(=O)R$^{b3}$ group, a —S(=O)$_2$NR$^a$C(=O)OR$^{b4}$ group, a —S(=O)$_2$NR$^a$C(=O)NR$^a$R$^{b3}$ group or a S(=O)$_2$R$^g$ group,
X represents a $C_{1-3}$ alkyl group optionally substituted one or multiple fluorine atoms or a nitro group, and
Y represents a cyano group, a chlorine atom or a nitro group.

11. The compound according to claim 10 or physiologically acceptable salts thereof wherein
Z$^1$ represents a —C(=O)NR$^c$R$^d$ group, a —C(=O)OR$^{b2}$ group, a —S(=O)$_2$NR$^{c2}$R$^{d2}$ group, a —S(=O)$_2$NR$^{a2}$C(=O)R$^{b3}$ group, a —S(=O)$_2$NR$^a$C(=O)OR$^{b4}$ group, a —S(=O)—NR$^a$C(=O)NR$^a$R$^{b3}$ group, a S(=O)$_2$R$^g$ group, an iodine atom, a bromine atom or a chlorine atom, and
R$^2$ represents a $C_{1-3}$ alkyl group optionally substituted with hydroxy.

12. The compound according to claim 1 selected from the following Group or physiologically acceptable salts thereof, Group:
4-[5-[3,6-Dimethyl-2,4-dioxo-1-(3-trifluoromethylphenyl)-1,2,3,4-tetrahydropyrimidin-5-yl]-1H-pyrazol-1-yl]benzonitrile,
4-[5-[6-Methyl-2,4-dioxo-3-propyl-1-(3-trifluoromethylphenyl)-1,2,3,4-tetrahydropyrimidin-5-yl]-1H-pyrazol-1-yl]benzonitrile,
4-(5-(3-Ethyl-6-methyl-2,4-dioxo-1-(3-(trifluoromethyl)phenyl)-1,2,3,4-tetrahydropyrimidin-5-yl)-1H-pyrazol-1-yl)benzonitrile, 4-[5-[1-(3-Chlorophenyl)-3,6-dimethyl-2,4-dioxo-1,2,3, 4-tetrahydropyrimidin-5-yl]-1H-pyrazol-1-yl]benzonitrile,
4-(5-(3,6-Dimethyl-2,4-dioxo-1-m-tolyl-1,2,3,4-tetrahydropyrimidin-5-yl)-1H-pyrazol-1-yl)benzonitrile,
4-(5-(3-Isopropyl-6-methyl-2,4-dioxo-1-(3-(trifluoromethyl)phenyl)-1,2,3,4-tetrahydropyrimidin-5-yl)-1H-pyrazol-1-yl)benzonitrile,
4-(5-(6-Ethyl-3-methyl-2,4-dioxo-1-(3-(trifluoromethyl)phenyl)-1,2,3,4-tetrahydropyrimidin-5-yl)-1H-pyrazol-1-yl)benzonitrile,
(R)-4-(5-(3-(1-Hydroxypropan-2-yl)-6-methyl-2,4-dioxo-1-(3-(trifluoromethyl)phenyl)-1,2,3,4-tetrahydropyrimidin-5-yl)-1H-pyrazol-1-yl)benzonitrile,
4-(4-(3-Isopropyl-6-methyl-2,4-dioxo-1-(3-(trifluoromethyl)phenyl)-1,2,3,4-tetrahydropyrimidin-5-yl)-4H-1, 2,4-triazol-3-yl)benzonitrile,
(S)-4-(5-(2,4-Dioxo-3-(5-oxopyrrolidin-3-yl)1-(3-(trifluoromethyl)phenyl)-1,2,3,4-tetrahydropyrimidin-5-yl)-1H-pyrazol-1-yl)benzonitrile,
1-(4-Cyanophenyl)-5-(3-isopropyl-6-methyl-2,4-dioxo-1-(3-(trifluoromethyl)phenyl)-1,2,3,4-tetrahydropyrimidin-5-yl)-1H-pyrazole-4-carboxamide,
4-(Dimethylamino)butyl 1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-carboxylate,
(±)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonic acid,
(+)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonaic acid,
(−)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonaic acid,
(±)-1-(4-Cyanophenyl)-5-(3,6-dimethyl-2,4-dioxo-1-(3-trifluoromethylphienyl)-1,2,3,4-tetrahydropyrimidin-5-yl)-1H-pyrazole-4-sulfonamide,
(−)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide,
(+)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide,
(+)-1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide.0.5 IPA solvates,
(±)-1-(4-Cyanophenyl)-5-(3-ethyl-6-methyl-2,4-dioxo-1-(3-trifluoromethylphenyl)-1,2,3,4-tetrahydropyrimidin-5-yl)-1H-pyrazole-4-sulfonamide,
(+)-1-(4-Cyanophenyl)-5-(3-ethyl-6-methyl-2,4-dioxo-1-(3-trifluoromethylphenyl)-1,2,3,4-tetrahydropyrimidin-5-yl)-1H-pyrazole-4-sulfonamide,
N-(1-(4-Cyanophenyl)-5-(3,6-dimethyl-2,4-dioxo-1-(3-trifluoromethylphenyl)-1,2,3,4-tetrahydropyridin-5-yl)-1H-pyrazole-4-ylsulfonyl)pivalamine,
Butyl 1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-ylsulfonylcarbamate,
N-(1-(4-Cyanophenyl)-5-(3,6-dimethyl-2,4-dioxo-1-(3-trifluoromethylphenyl)-1,2,3,4-tetrahydropyrimidin-5-yl)-1H-pyrazole-4-ylsulfonyl)benzamide,
1-(4-Cyanophenyl)-5-(3,6-dimethyl-2,4-dioxo-1-(3-trifluoromethylphenyl)-1,2,3,4-tetrahydropyrimidin-5-yl)-N-(ethylcarbonyl)-1H-pyrazole-4-sulfonamide,
(±)-4-(5-(3,6-Dimethyl-2,4-dioxo-1-(3-trifluoromethylphenyl)-1,2,3,4-tetrahydropyrimidin-5-yl-4-(methylsulfonyl)-1H-pyrazol-1-yl)benzonitrile,
(+)-4-(5-(3,6-Dimethyl-2,4-dioxo-1-(3-trifluoromethylphenyl)-1,2,3,4-tetrahydropyrimidin-5-yl-4-(methylsulfonyl)-1H-pyrazol-1-yl)benzonitrile,
(±)-4-(5-(3-Isopropyl-6-methyl-2,4-dioxo-1-(3-trifluoromethylphenyl)-1,2,3,4-tetrahydropyrimidin-5-yl-4-(methylsulfonyl)-1H-pyrazol-1-yl)benzonitrile,
4-(5-(3-Ethyl-6-methyl-2,4-dioxo-1-(3-trifluoromethylphenyl)-1,2,3,4-tetrahydropyrimidin-5-yl)-4-(2-hydroxypropan-2-yl)-1H-pyrazol-1-yl)benzonitrile,
(R)-4-(5-(6-Methyl-2,4-dioxo-3-(pyrolidin-3-yl)-1-(3-trifluoromethylphenyl)-1,2,3,4-tetrahydropyrimidin-5-yl)-1H-pyrazol-1-yl)benzonitrile,
4-(5-(3,6-Dimethyl-2,4-dioxo-1-(3-trifluoromethylphenyl)-1,2,3,4-tetrahydropyrimidin-5-yl)-4-fluoro-1H-pyrazol-1-yl)benzonitrile,
4-(4-Chloro-5-(3,6-dimethyl-2,4-dioxo-1-(3-trifluoromethylphenyl)-1,2,3,4-tetrahydropyrimidin-5-yl)-1H-pyrazol-1-yl)benzonitrile,
1-(4-Cyanophenyl)-5-(3,6-dimethyl-2,4-dioxo-1-(3-trifluoromethyl)-1,2,3,4-tetrahydropyrimidin-5-yl)-1H-pyrazole-4-carbonitrile,
(R)-4-(5-(6-Methyl-3-(methanesulfonyl)propan-2-yl)-2, 4-dioxo-3-(1-oxopropane-2-yl)-1-(3-trifluoromethylphenyl)-1,2,3,4-tetrahydropyrimidin-5-yl)-1H-pyrazol-1-yl)benzonitrile,
(R)-2-(5-(1-(4-Cyanophenyl)-1H-pyrazol-5-yl)-4-methyl-2,6-dioxo-3-(3-trifluoromethylphenyl)-2,3-dihydropyrimidin-1(6H)-yl)propane-1-sulfonamide and
5-(4-Cyanophenyl)-4-(3-ethyl-6-methyl-2,4-dioxo-1-(3-trifluoromethylphenyl)-1,2,3,4-tetrahydropyrimidin-5-yl)-4H-1,2,4-triazole-3-carboxamide.

13. A method of treating inflammatory diseases or cancers, comprising the step of:
administering the compound according to claim 1 or physiologically acceptable salts thereof to a patient in need thereof.

14. A pharmaceutical composition for use in treatment or prophylaxis of inflammatory diseases or cancers comprising the compound according to claim 1 or physiologically acceptable salts thereof as active ingredient.

15. The compound according to claim 1, wherein the compound is 4-(5-(3,6-dimethyl-2,4-dioxo-1-(3-trifluoromethylphenyl)-1,2,3,4-tetrahydropyrimidin-5-yl)-1H-pyrazol-1-yl)benzonitrile or physiologically acceptable salts thereof.

16. The compound according to claim 1, wherein the compound is 1-(4-cyanophenyl)-5-(3-isopropyl-6-methyl-2,4-dioxo-1-(3-(trifluoromethyl)phenyl)-1,2,3,4-tetrahydropyrimidin-5-yl)-1H-pyrazole-4-carboxamide or physiologically acceptable salts thereof.

17. The compound according to claim 1, wherein the compound is (+)-1-(4-cyanophenyl)-5-(3,6-dimethyl-2,4-dioxo-1-(3-trifluoromethylphenyl)-1,2,3,4-tetrahydropyrimidin-5-yl)-1H-pyrazole-4-sulfonamide or physiologically acceptable salts thereof.

18. The compound according to claim 1, wherein the compound is (±)-1-(4-cyanophenyl)-5-(3-ethyl-6-methyl-2,4-dioxo-1-(3-trifluoromethylphenyl)-1,2,3,4-tetrahydropyrimidin-5-yl)-1H-pyrazole-4-sulfonamide or physiologically acceptable salts thereof.

19. The compound according to claim 1, wherein the compound is (+)-4-(5-(3,6-dimethyl-2,4-dioxo-1-(3-trifluoromethylphenyl)-1,2,3,4-tetrahydropyrimidin-5-yl-4-(methylsulfonyl)-1H-pyrazol-1-yl)benzonitrile or physiologically acceptable salts thereof.

20. The compound according to claim 1, wherein the compound is (±)-4-(5-(3-Isopropyl-6-methyl-2,4-dioxo-1-(3-trifluoromethylphenyl)-1,2,3,4-tetrahydropyrimidin-5-yl-4-(methylsulfonyl)-1H-pyrazol-1-yl)benzonitrile or physiologically acceptable salt thereof.

* * * * *